US010665792B2

(12) United States Patent
Bergmann et al.

(10) Patent No.: US 10,665,792 B2
(45) Date of Patent: May 26, 2020

(54) ORGANIC MOLECULES FOR USE IN OPTOELECTRONIC DEVICES

(71) Applicant: CYNORA GMBH, Bruchsal (DE)

(72) Inventors: Larissa Bergmann, Karlsruhe (DE); Daniel Zink, Bruchsal (DE)

(73) Assignee: CYNORA GMBH, Bruchsal (DE)

( * ) Notice: Subject to any disclaimer, the term of this patent is extended or adjusted under 35 U.S.C. 154(b) by 0 days.

(21) Appl. No.: 15/685,101

(22) Filed: Aug. 24, 2017

(65) Prior Publication Data
US 2018/0062085 A1 Mar. 1, 2018

(30) Foreign Application Priority Data

Aug. 24, 2016 (DE) .................... 10 2016 115 728
Oct. 19, 2016 (DE) .................... 10 2016 119 937
Feb. 24, 2017 (DE) .................... 10 2017 103 939
Mar. 22, 2017 (DE) .................... 10 2017 106 221

(51) Int. Cl.
*H01L 51/54* (2006.01)
*C09K 11/06* (2006.01)
*H01L 51/00* (2006.01)
*C07D 401/14* (2006.01)
*H01L 51/50* (2006.01)

(52) U.S. Cl.
CPC ........ *H01L 51/0072* (2013.01); *C07D 401/14* (2013.01); *C09K 11/06* (2013.01); *H01L 51/006* (2013.01); *H01L 51/5016* (2013.01); *C09K 2211/1029* (2013.01); *C09K 2211/1059* (2013.01); *Y02E 10/549* (2013.01)

(58) Field of Classification Search
CPC .. C07D 209/86; C07D 209/88; C07D 401/00; C07D 401/10; C07D 401/14; C07D 403/00; C07D 403/10; C07D 403/14; C07D 405/00; C07D 405/10; C07D 405/14; C07D 487/00; C07D 487/02; C07D 487/04; C07D 493/00; C07D 493/0204; C07D 519/00; C07D 493/02; C07D 493/04; C09K 11/06;
(Continued)

(56) References Cited

U.S. PATENT DOCUMENTS

2007/0190355 A1* 8/2007 Ikeda .................. C07D 239/26
428/690
2008/0145699 A1* 6/2008 Yabe .................... C07D 209/86
428/690
(Continued)

FOREIGN PATENT DOCUMENTS

JP 2003516421 A 5/2003
JP 2006199679 A 8/2006
(Continued)

OTHER PUBLICATIONS

Marie Lamothe et al., "Differentiation between Partial Agonists and Neutral 5-HT 1B Antagonists by Chemical Modulation of 3-[3-N(N,N-Dimethylamino)propyl]-4-hydroxy-N-[4-(pyridin-4-yl)phenyl]benzamide", American Chemical Society, 1997, pp. 3542-3550, vol. 40.

*Primary Examiner* — Andrew K Bohaty
(74) *Attorney, Agent, or Firm* — Ryan, Mason & Lewis, LLP

(57) ABSTRACT

The invention relates to an organic molecule, especially for use in optoelectronic components. The organic molecule contains
a first chemical unit having or consisting of a structure of formula I

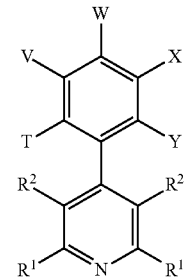

Formula I and
two second chemical units D each having or consisting of, identically or differently at each instance, a structure of formula II

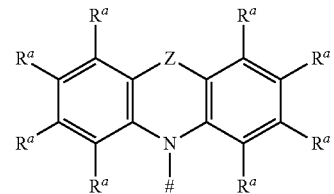

Formula II where the first chemical unit is joined to each of the two second chemical units D via a single bond;
where
T, V is independently an attachment point of the single bond between the chemical unit of formula I and a chemical unit D or H;
W, X, Y is independently an attachment point of the single bond between the chemical unit of formula I and a chemical unit D or selected from the group consisting of H, CN and CF$_3$;
where exactly one radical selected from W, X and Y is CN or CF$_3$ and exactly two radicals selected from the group consisting of T, V, W, X and Y are an attachment point of the single bond between the chemical unit according to formula I and a chemical unit D.

8 Claims, 23 Drawing Sheets

(58) Field of Classification Search
CPC ............ C09K 2211/00; C09K 2211/10; C09K 2211/1007; C09K 2211/1014; C09K 2211/1029; C09K 2211/1018; C09K 2211/1044; C09K 2211/1059; H01L 51/0032; H01L 51/0003; H01L 51/001; H01L 51/005; H01L 51/006; H01L 51/0067; H01L 51/0071; H01L 51/0072; H01L 51/0073; H01L 51/0074; H01L 51/0096; H01L 51/50; H01L 51/5012; H01L 51/5016; H01L 51/5071; H01L 51/5088; H01L 51/5096; H01L 51/5206; H01L 51/5221; H01L 2251/5376
USPC ....... 428/690, 691, 917, 411.4, 336; 427/58, 427/66; 313/500–512; 257/40, 88–104, 257/E51.001–E51.052; 252/301.16–301.35

See application file for complete search history.

(56) References Cited

U.S. PATENT DOCUMENTS

| | | | |
|---|---|---|---|
| 2009/0072727 A1* | 3/2009 | Takeda | C09K 11/06 313/504 |
| 2013/0306963 A1* | 11/2013 | Yamamoto | H01L 51/0085 257/40 |
| 2013/0313531 A1* | 11/2013 | Kaminaga | C07D 235/06 257/40 |
| 2015/0060791 A1 | 3/2015 | Shin et al. | |

FOREIGN PATENT DOCUMENTS

| | | | | |
|---|---|---|---|---|
| JP | 4474493 B1 | 6/2010 | | |
| JP | 4751955 B1 | 8/2011 | | |
| TW | 200631941 A1 | 9/2006 | | |
| TW | 201233775 A | 8/2012 | | |
| WO | WO-2005085387 A1 * | 9/2005 | ........... | C07D 239/26 |
| WO | 2012108881 A1 | 8/2012 | | |

* cited by examiner

ORGANIC MOLECULES FOR USE IN OPTOELECTRONIC DEVICES

CROSS-REFERENCE TO RELATED APPLICATIONS

This application claims priority to DE 10 2017 106 221.1 filed Mar. 22, 2017, DE 10 2017 103 939.2 filed Feb. 24, 2017, DE 10 2016 119 937.0 filed on Oct. 19, 2016 and DE 10 2016 115 728.7 filed on Aug. 24, 2016, the disclosures of which are incorporated by reference herein in their entireties.

FIELD OF INVENTION

The invention relates to purely organic molecules and to the use thereof in organic light-emitting diodes (OLEDs) and in other organic optoelectronic devices.

BACKGROUND

The problem addressed by the present invention was that of providing molecules suitable for use in optoelectronic devices.

The problem is solved by the invention, which provides a new class of organic molecules.

The organic molecules according to the invention are purely organic molecules, i.e. do not have any metal ions, and are thus delimited from the metal complexes known for use in organic optoelectronic devices.

BRIEF DESCRIPTION OF THE DRAWINGS

Exemplary embodiments of the present invention will be described below in more detail, with reference to the accompanying drawings, of which.

DETAILED DESCRIPTION OF EXEMPLARY EMBODIMENTS OF THE INVENTION

Figure 1:
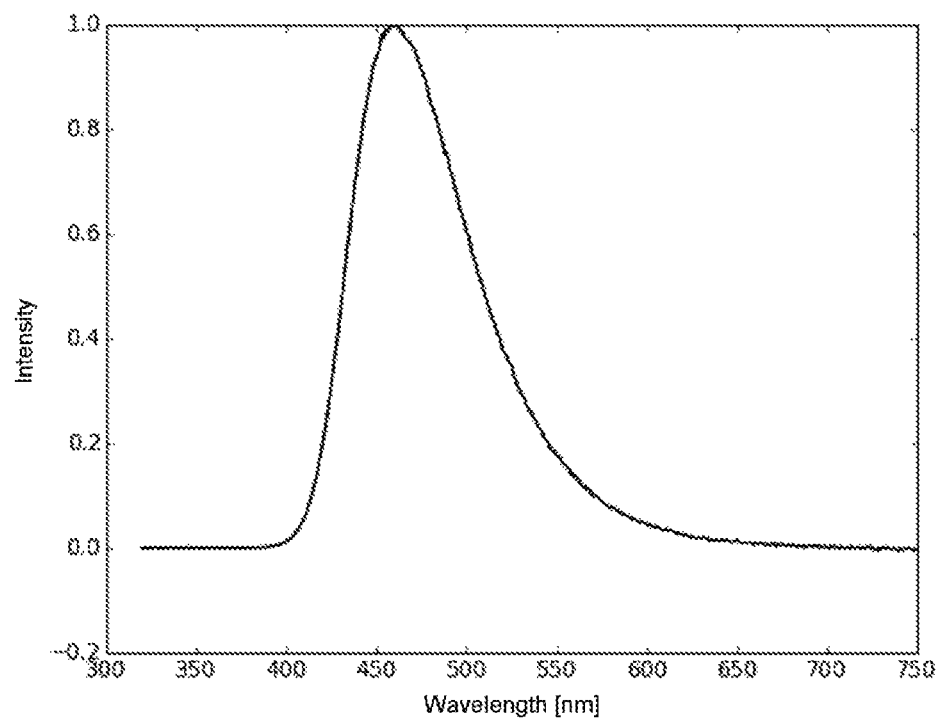
FIG. 1 is an emission spectrum of Example 1 (10% in PMMA).

Exemplary embodiments of the invention will now be discussed in further detail. This invention may, however, be embodied in many different forms and should not be construed as limited to the embodiments set forth herein.

The organic molecules according to the invention are notable for emissions in the blue, sky blue or green spectral region. The photoluminescence quantum yields of the organic molecules according to the invention are especially 20% or more. The molecules according to the invention especially exhibit thermally activated delayed fluorescence (TADF). The use of the molecules according to the invention in an optoelectronic device, for example an organic light-emitting diode (OLED), leads to higher efficiencies of the device. Corresponding OLEDs have higher stability than OLEDs with known emitter materials and a comparable colour.

The blue spectral region is understood here to mean the visible range of less than 470 nm, especially from 420 nm to 470 nm. The sky blue spectral region is understood here to mean the range from 470 nm to 499 nm. The green spectral region is understood here to mean the range from 500 nm to 599 nm. The emission maximum here is within the respective range.

The organic molecules contain a first chemical unit comprising or consisting of a structure of formula I:

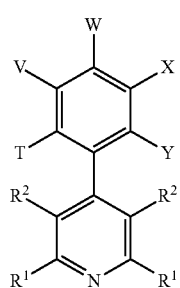

Formula I and two second chemical units D each comprising or consisting of, identically or differently at each instance, a structure of formula II

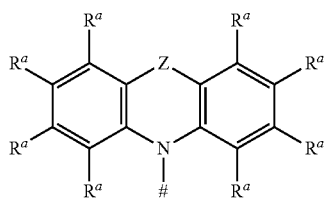

Formula II

In these molecules, the first chemical unit is joined to each of the two second chemical units D via a single bond.

T is an attachment point of the single bond between the first chemical unit and a second chemical unit D or H.

V is an attachment point of the single bond between the first chemical unit and a second chemical unit D or H.

W is an attachment point of the single bond between the first chemical unit and a second chemical unit D or is selected from the group consisting of H, CN and $CF_3$.

X is an attachment point of the single bond between the first chemical unit and a second chemical unit D or is selected from the group consisting of H, CN and $CF_3$.

Y is an attachment point of the single bond between the first chemical unit and a second chemical unit D or is selected from the group consisting of H, CN and $CF_3$.

# is an attachment point of the single bond between the respective second chemical unit D and the first chemical unit.

Z is the same or different at each instance and is a direct bond or selected from the group consisting of $CR^3R^4$, $C=CR^3R^4$, $C=O$, $C=NR^3$, $NR^3$, O, $SiR^3R^4$, S, $S(O)$ and $S(O)_2$.

$R^1$ and $R^2$ are the same or different at each instance and are H, deuterium, a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium, or an aromatic or heteroaromatic ring system which has 5 to 15 aromatic ring atoms and may be substituted in each case by one or more $R^6$ radicals.

$R^a$, $R^3$ and $R^4$ is the same or different at each instance and is H, deuterium, $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^5$ radicals, where one or more nonadjacent $CH_2$ groups may be replaced by $R^5C=CR^5$, $C≡C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^5$ radicals, or an aryloxy or heteroaryloxy group which has 5 to 60 aromatic ring atoms and may be substituted in each case by one or more $R^5$ radicals, or a diarylamino group, diheteroarylamino group or arylheteroarylamino group which has 10 to 40 aromatic ring atoms and may be substituted in each case by one or more $R^5$ radicals.

$R^5$ is the same or different at each instance and is H, deuterium, $N(R^6)_2$, OH, $Si(R^6)_3$, $B(OR^6)_2$, $OSO_2R^6$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^6$ radicals, where one or more nonadjacent $CH_2$ groups may be replaced by $R^6C=CR^6$, $C≡C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^6$ radicals, or an aryloxy or heteroaryloxy group which has 5 to 60 aromatic ring atoms and may be substituted in each case by one or more $R^6$ radicals, or a diarylamino group, diheteroarylamino group or arylheteroarylamino group which has 10 to 40 aromatic ring atoms and may be substituted in each case by one or more $R^6$ radicals.

$R^6$ is the same or different at each instance and is H, deuterium, OH, $CF_3$, CN, F, a linear alkyl, alkoxy or thioalkoxy group having 1 to 5 carbon atoms or a linear alkenyl or alkynyl group having 2 to 5 carbon atoms or a branched or cyclic alkyl, alkenyl, alkynyl, alkoxy or thioalkoxy group having 3 to 5 carbon atoms, where one or more hydrogen atoms may be replaced by deuterium, CN, $CF_3$ or $NO_2$; or an aromatic or heteroaromatic ring system having 5 to 60 aromatic ring atoms or an aryloxy or heteroaryloxy group having 5 to 60 aromatic ring atoms or a diarylamino group, diheteroarylamino group or arylheteroarylamino group having 10 to 40 aromatic ring atoms.

According to the invention, each of the $R^a$, $R^3$, $R^4$ or $R^5$ radicals together with one or more further $R^a$, $R^3$, $R^4$ or $R^5$ radicals may form a mono- or polycyclic, aliphatic, aromatic and/or benzofused ring system.

According to the invention, exactly one radical selected from W, X and Y is CN or $CF_3$ and exactly two radicals selected from the group consisting of T, V, W, X and Y are an attachment point of a single bond between the first chemical unit and a second chemical unit D.

In one embodiment of the organic molecule, $R^1$ and $R^2$ are the same or different at each instance and are H, methyl or phenyl.

In one embodiment of the organic molecule, W is CN.

In a further embodiment of the organic molecule, the chemical group D is the same or different at each instance and comprises a structure of the formula IIa or consists of a structure of the formula IIa:

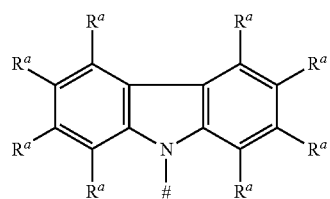

Formula IIa where the definitions for formula I and II are applicable to # and $R^a$.

In a further embodiment of the organic molecules according to the invention, the second chemical unit D independently comprises or consists of a structure selected from the group of the formula IIb, of the formula IIb-2, of the formula IIb-3 or of the formula IIb-4:

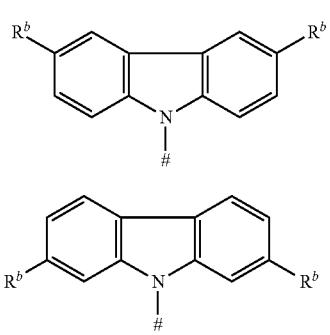

Formula IIb

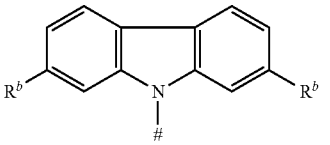

Formula IIb-2

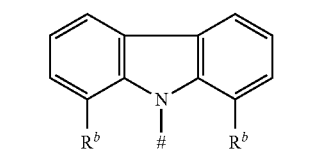

Formula IIb-3

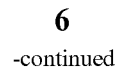

Formula IIb-4

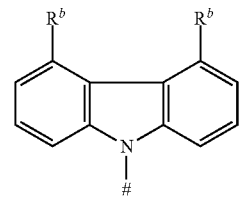

where
$R^b$ is the same or different at each instance and is $N(R^5)_2$, OH, $Si(R^5)_3$, $B(OR^5)_2$, $OSO_2R^5$, $CF_3$, CN, F, Br, I, a linear alkyl, alkoxy or thioalkoxy group having 1 to 40 carbon atoms or a linear alkenyl or alkynyl group having 2 to 40 carbon atoms or a branched or cyclic alkyl, alkenyl, alkynyl, alkoxy or thioalkoxy group having 3 to 40 carbon atoms, each of which may be substituted by one or more $R^5$ radicals, where one or more nonadjacent $CH_2$ groups may be replaced by $R^5C=CR^5$, $C\equiv C$, $Si(R^5)_2$, $Ge(R^5)_2$, $Sn(R^5)_2$, C=O, C=S, C=Se, $C=NR^5$, $P(=O)(R^5)$, SO, $SO_2$, $NR^5$, O, S or $CONR^5$, and where one or more hydrogen atoms may be replaced by deuterium, CN, $CF_3$ or $NO_2$; or an aromatic or heteroaromatic ring system which has 5 to 60 aromatic ring atoms and may be substituted in each case by one or more $R^5$ radicals, or an aryloxy or heteroaryloxy group which has 5 to 60 aromatic ring atoms and may be substituted in each case by one or more $R^5$ radicals, or a diarylamino group, diheteroarylamino group or arylheteroarylamino group which has 10 to 40 aromatic ring atoms and may be substituted in each case by one or more $R^5$ radicals. For the rest, the definitions given above are applicable.

In a further embodiment of the organic molecules according to the invention, the second chemical unit D independently comprises or consists of a structure selected from the group of the formula IIc, of the formula IIc-2, of the formula IIc-3 or of the formula IIc-4:

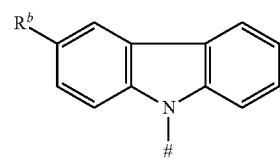

Formula IIc

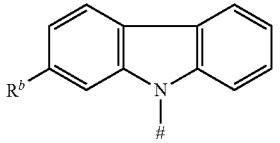

Formula IIc-2

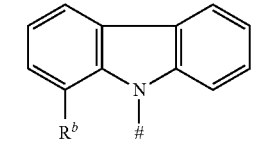

Formula IIc-3

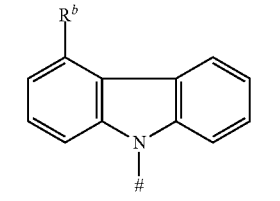

Formula IIc-4 where the definitions given above are applicable.

In a further embodiment of the organic molecules according to the invention, $R^b$ independently at each instance is selected from the group consisting of Me, $^iPr$, $^tBu$, CN, CF$_3$, Ph which may be substituted in each case by one or more radicals selected from Me, $^iPr$, $^tBu$, CN, CF$_3$ and Ph, pyridinyl which may be substituted in each case by one or more radicals selected from Me, $^iPr$, $^tBu$, CN, CF$_3$ and Ph, pyrimidinyl which may be substituted in each case by one or more radicals selected from Me, $^iPr$, $^tBu$, CN, CF$_3$ and Ph, carbazolyl which may be substituted in each case by one or more radicals selected from Me, $^iPr$, $^tBu$, CN, CF$_3$ and Ph, triazinyl which may be substituted in each case by one or more radicals selected from Me, $^iPr$, $^tBu$, CN, CF$_3$ and Ph, and N(Ph)$_2$.

The following are illustrative embodiments of the second chemical group D:

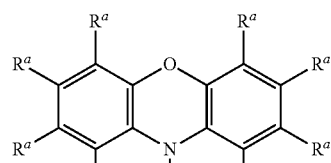

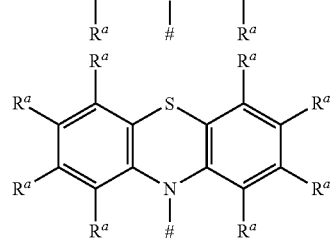

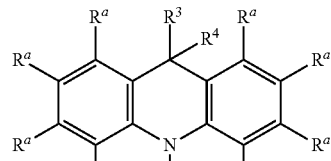

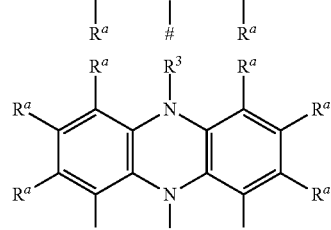

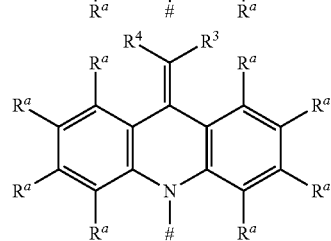

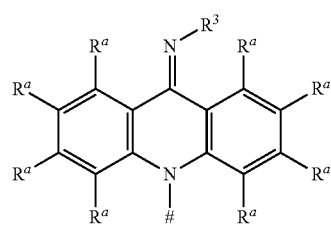

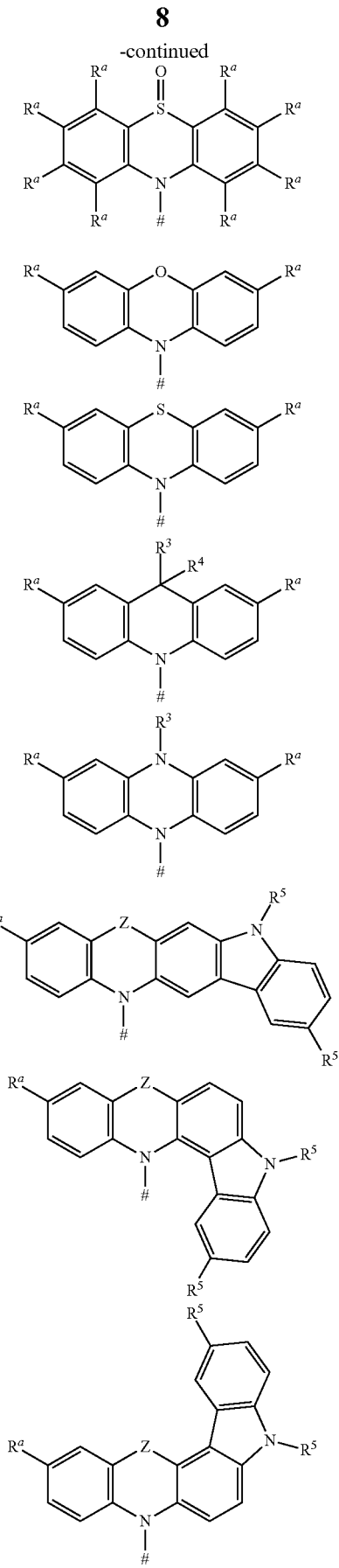

-continued
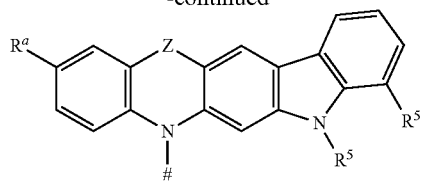
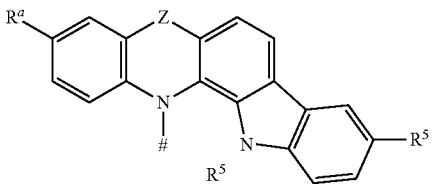
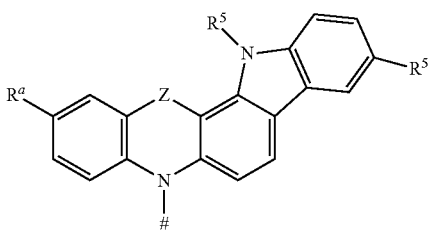
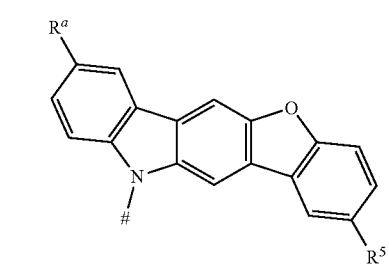
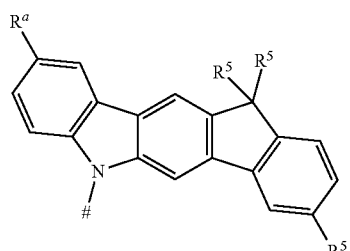
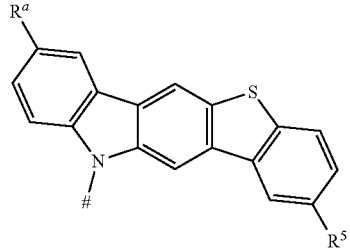
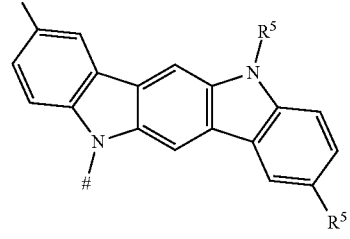
-continued
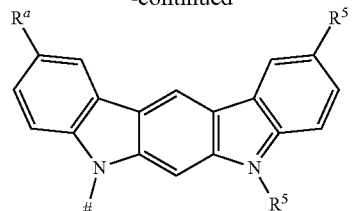
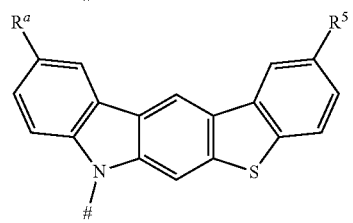
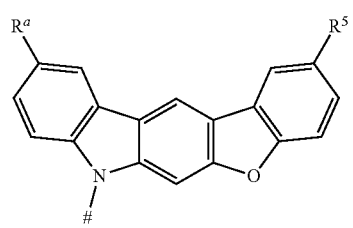
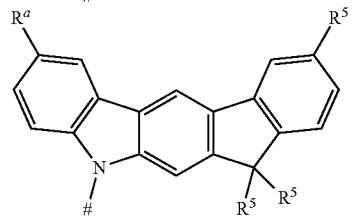
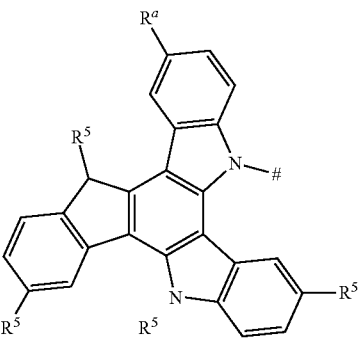
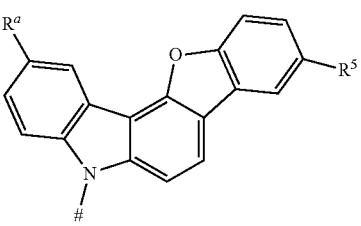
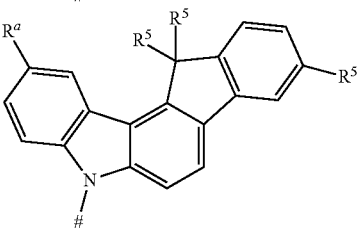

-continued

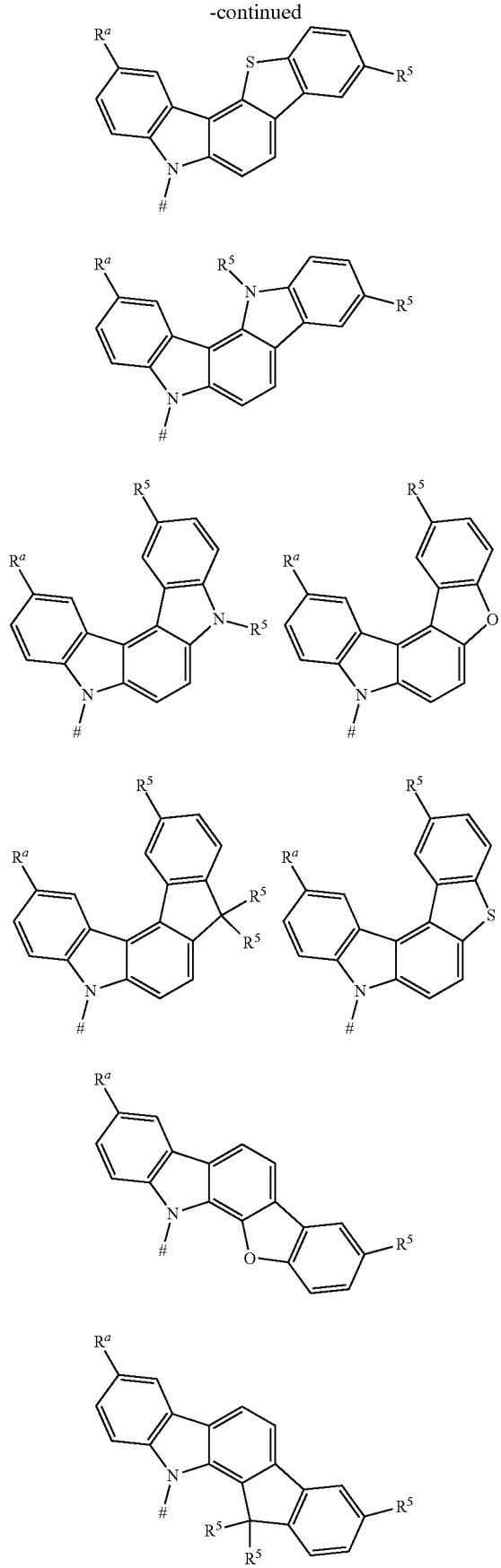

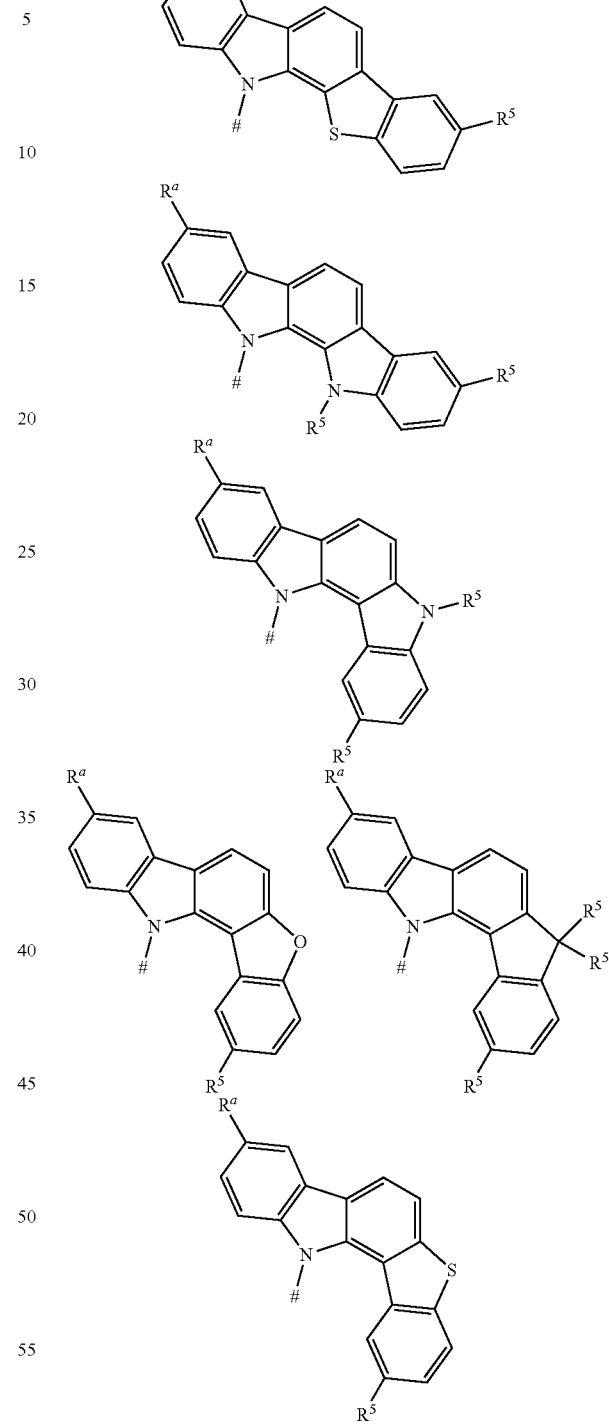

where the definitions given above are applicable to #, Z, $R^a$, $R^3$, $R^4$ and $R^5$. In one embodiment of the organic molecules according to the invention, the $R^5$ radical is the same or different at each instance and is selected from the group consisting of H, methyl, ethyl, phenyl and mesityl. In one embodiment, $R^a$ is the same or different at each instance and is selected from the group consisting of H, methyl (Me), i-propyl (CH(CH$_3$)$_2$) ($^i$Pr), t-butyl ($^t$Bu), phenyl (Ph), CN, CF$_3$ and diphenylamine (NPh$_2$).

In one embodiment, the organic molecules according to the invention comprise a structure of the formula III:

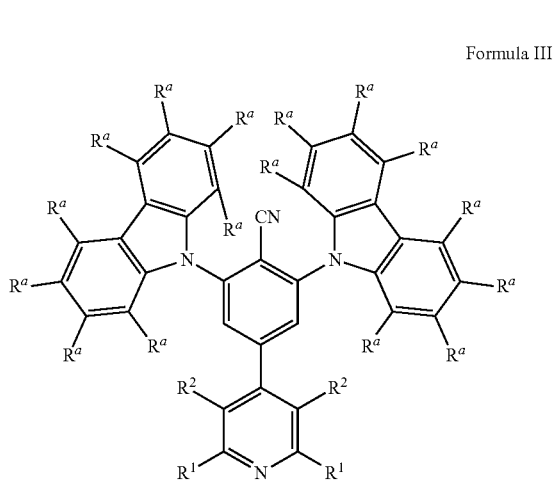

Formula III where the definitions given above are applicable.

In a further embodiment, the organic molecules according to the invention comprise a structure of the formula IIIa:

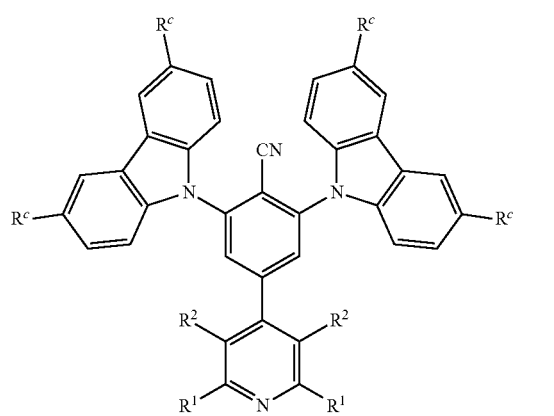

Formula IIIa where

R$^c$ independently at each instance is selected from the group consisting of Me, $^i$Pr, $^t$Bu, CN, CF$_3$, Ph which may be substituted in each case by one or more radicals selected from Me, $^i$Pr, $^t$Bu, CN, CF$_3$ and Ph, pyridinyl which may be substituted in each case by one or more radicals selected from Me, $^i$Pr, $^t$Bu, CN, CF$_3$ and Ph, pyrimidinyl which may be substituted in each case by one or more radicals selected from Me, $^i$Pr, $^t$Bu, CN, CF$_3$ and Ph, carbazolyl which may be substituted in each case by one or more radicals selected from Me, $^i$Pr, $^t$Bu, CN, CF$_3$ and Ph, triazinyl which may be substituted in each case by one or more radicals selected from Me, $^i$Pr, $^t$Bu, CN, CF$_3$ and Ph, and N(Ph)$_2$.

In a further embodiment, the organic molecules according to the invention comprise a structure of the formula IIIb:

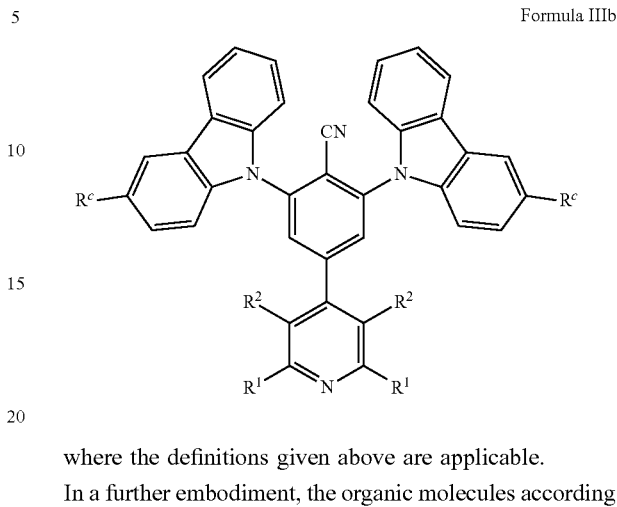

Formula IIIb where the definitions given above are applicable.

In a further embodiment, the organic molecules according to the invention comprise a structure of the formula IIIc:

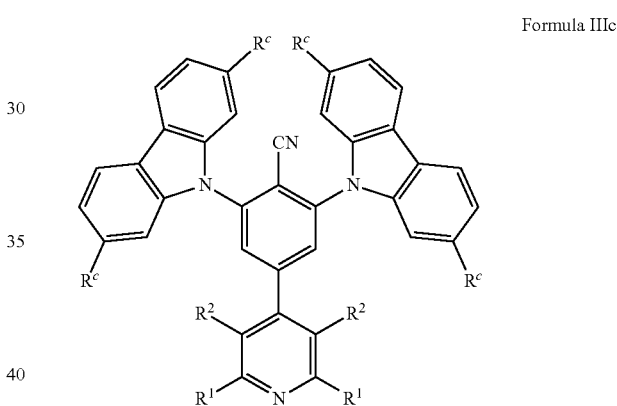

Formula IIIc where the definitions given above are applicable.

In a further embodiment, the organic molecules according to the invention comprise a structure of the formula IIId:

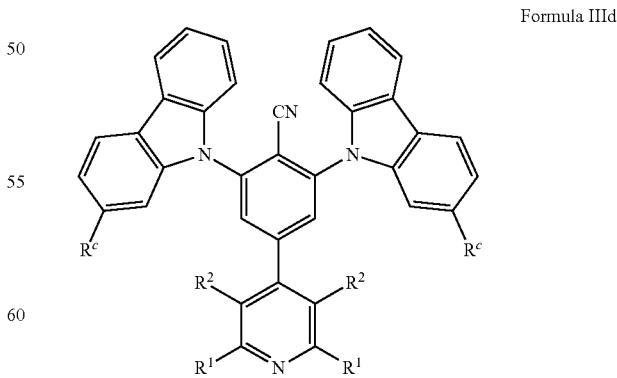

Formula IIId where the definitions given above are applicable.

In a further embodiment, the organic molecules according to the invention comprise a structure of the formula IIIe:

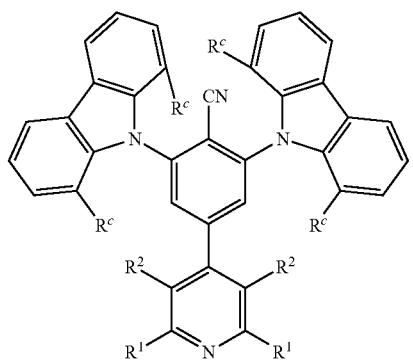

Formula IIIe where the definitions given above are applicable.

In a further embodiment, the organic molecules according to the invention comprise a structure of the formula IIIf:

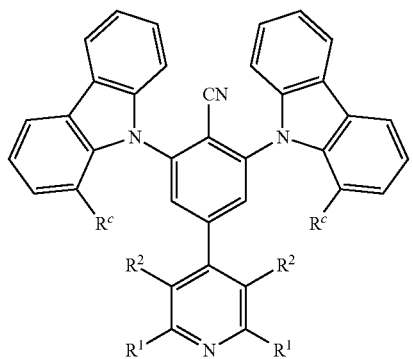

Formula IIIf where the definitions given above are applicable.

In a further embodiment, the organic molecules according to the invention comprise a structure of the formula IIIg:

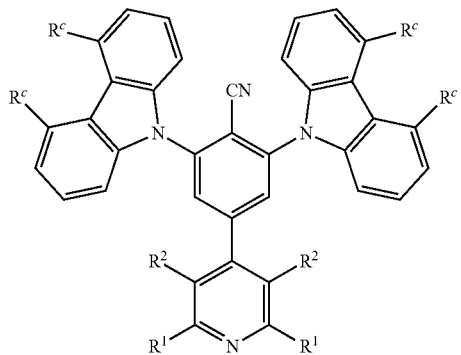

Formula IIIg where the definitions given above are applicable.

In a further embodiment, the organic molecules according to the invention comprise a structure of the formula IIIh:

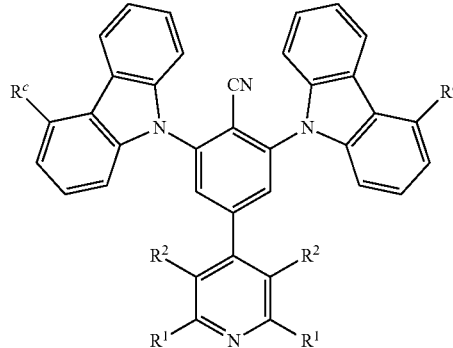

Formula IIIh where the definitions given above are applicable.

In one embodiment, the organic molecules according to the invention comprise a structure of the formula IV:

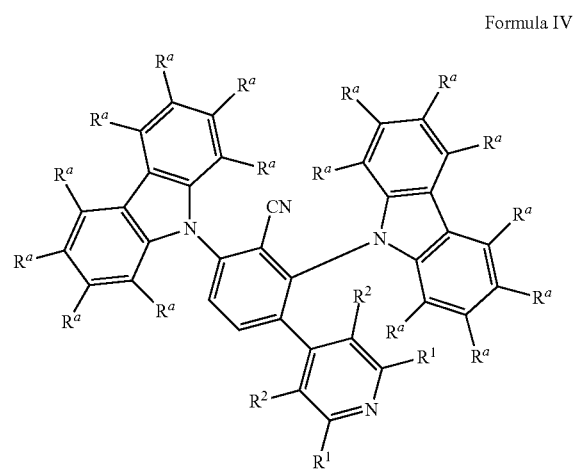

Formula IV where the definitions given above are applicable.

In a further embodiment, the organic molecules according to the invention comprise a structure of the formula IVa:

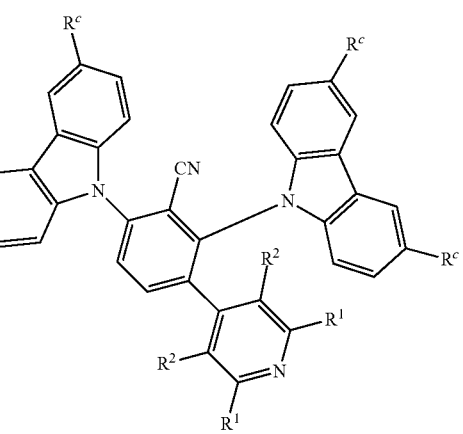

Formula IVa where the definitions given above are applicable.

In a further embodiment, the organic molecules according to the invention comprise a structure of the formula IVb:

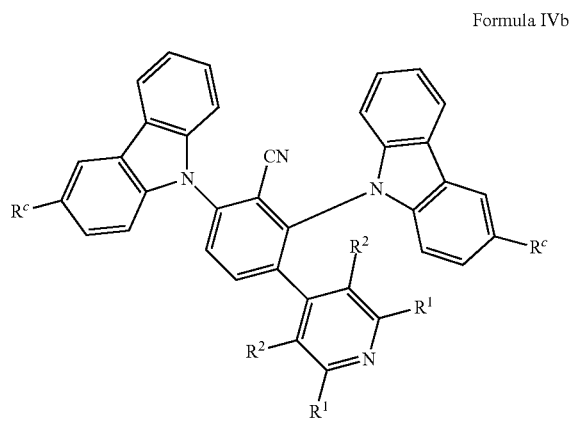

Formula IVb where the definitions given above are applicable.

In a further embodiment, the organic molecules according to the invention comprise a structure of the formula IVc:

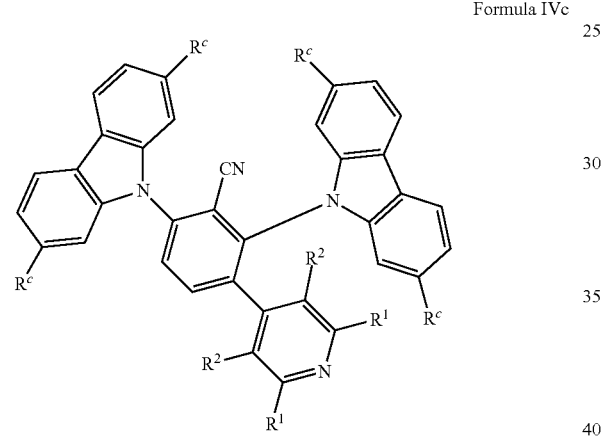

Formula IVc where the definitions given above are applicable.

In a further embodiment, the organic molecules according to the invention comprise a structure of the formula IVd:

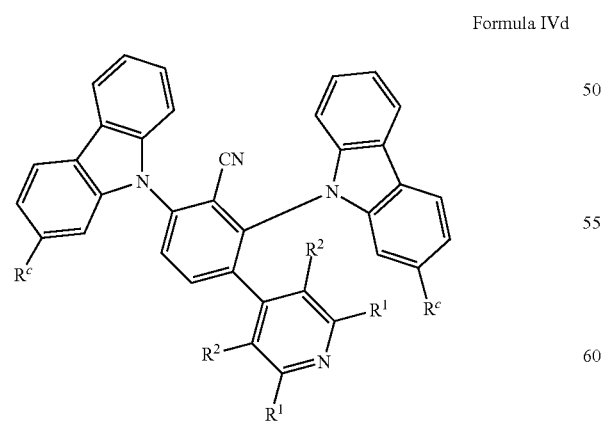

Formula IVd where the definitions given above are applicable.

In a further embodiment, the organic molecules according to the invention comprise a structure of the formula IVe:

Formula IVe where the definitions given above are applicable.

In a further embodiment, the organic molecules according to the invention comprise a structure of the formula IVf:

Formula IVf where the definitions given above are applicable.

In a further embodiment, the organic molecules according to the invention comprise a structure of the formula IVgf:

Formula IVg where the definitions given above are applicable.

In a further embodiment, the organic molecules according to the invention comprise a structure of the formula IVh:

Formula IVh

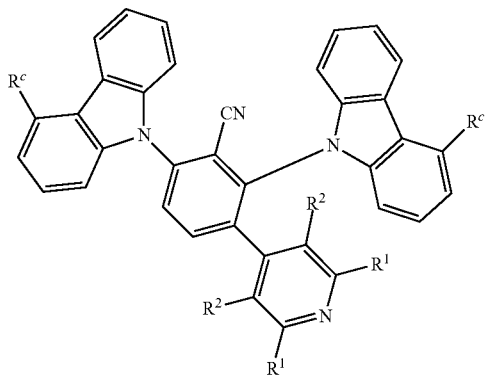

where the definitions given above are applicable.

In one embodiment, the organic molecules according to the invention comprise a structure of the formula V:

Formula V

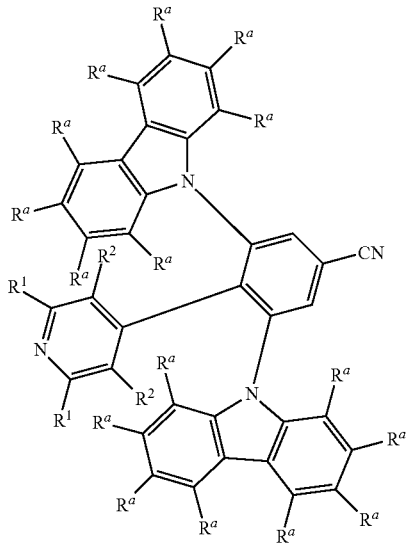

where the definitions given above are applicable.

In a further embodiment, the organic molecules according to the invention comprise a structure of the formula Va:

Formula Va

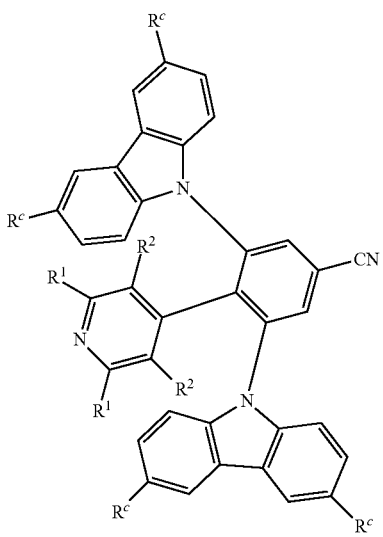

where the definitions given above are applicable.

In a further embodiment, the organic molecules according to the invention comprise a structure of the formula Vb:

Formula Vb

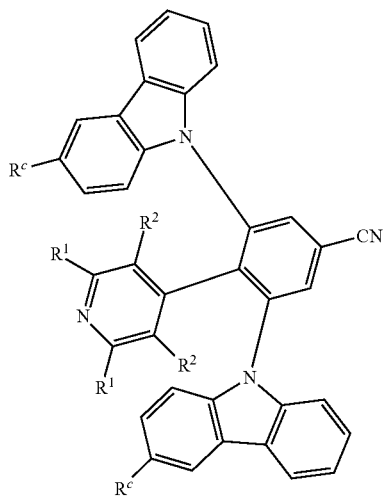

where the definitions given above are applicable.

In a further embodiment, the organic molecules according to the invention comprise a structure of the formula Vc:

Formula Vc

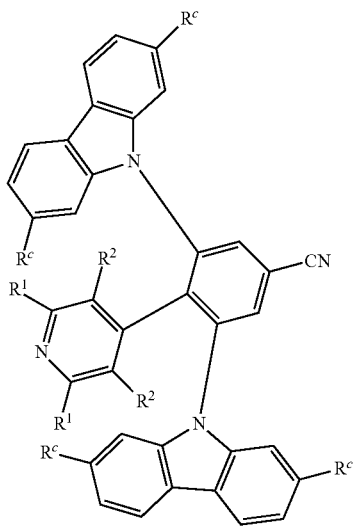

where the definitions given above are applicable.

In a further embodiment, the organic molecules according to the invention comprise a structure of the formula Vd:

Formula Vd

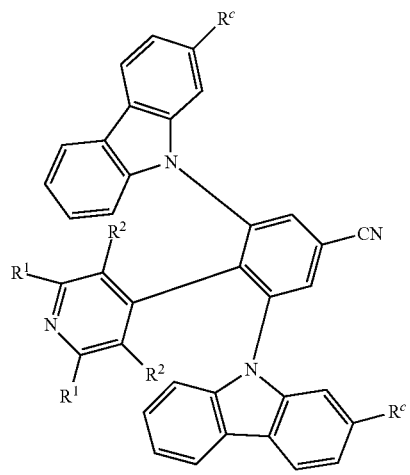

where the definitions given above are applicable.

In a further embodiment, the organic molecules according to the invention comprise a structure of the formula Ve:

Formula Ve

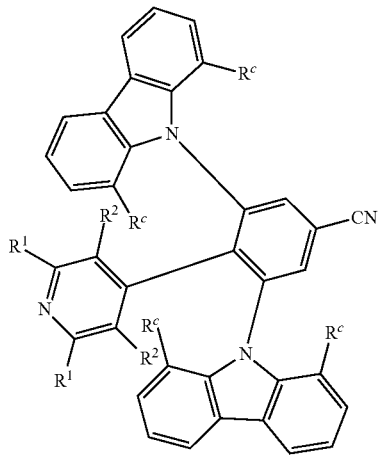

where the definitions given above are applicable.

In a further embodiment, the organic molecules according to the invention comprise a structure of the formula Vf:

Formula Vf

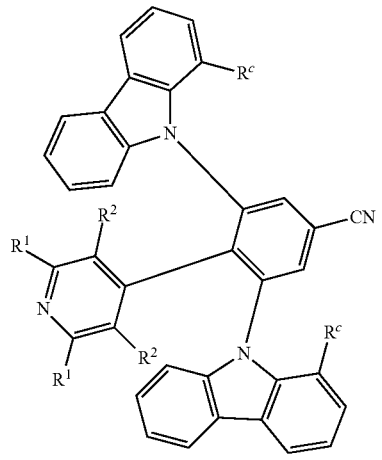

where the definitions given above are applicable.

In a further embodiment, the organic molecules according to the invention comprise a structure of the formula Vg:

Formula Vg

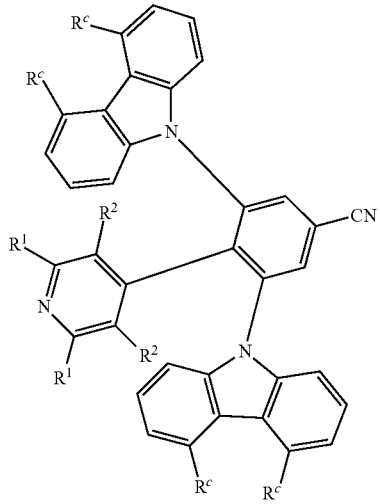

where the definitions given above are applicable.

In a further embodiment, the organic molecules according to the invention comprise a structure of the formula Vh:

Formula Vh

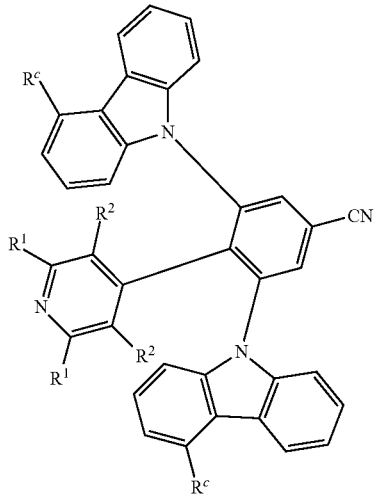

where the definitions given above are applicable.

In one embodiment, the organic molecules according to the invention comprise a structure of the formula VI:

Formula VI

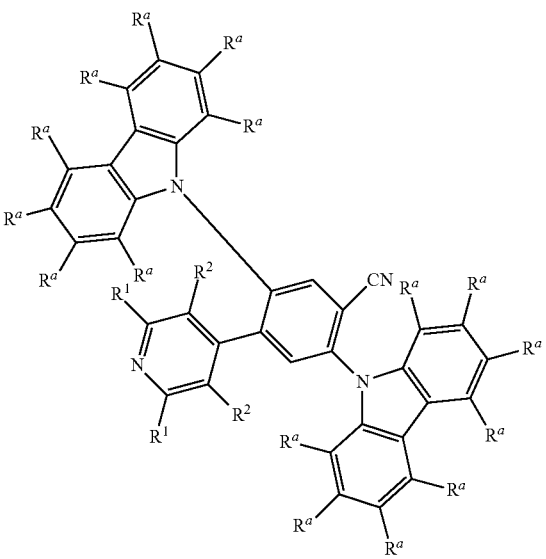

where the definitions given above are applicable.

In a further embodiment, the organic molecules according to the invention comprise a structure of the formula VIa:

Formula VIa

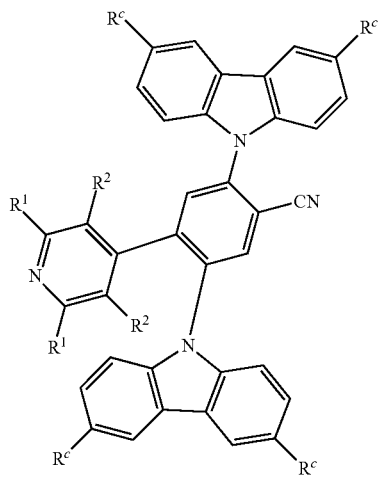

where the definitions given above are applicable.

In a further embodiment, the organic molecules according to the invention comprise a structure of the formula VIb:

Formula VIb

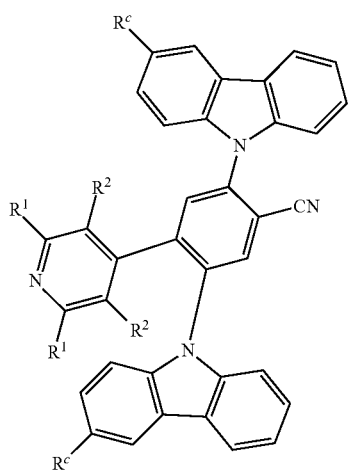

where the definitions given above are applicable.

In a further embodiment, the organic molecules according to the invention comprise a structure of the formula VIc:

Formula VIc

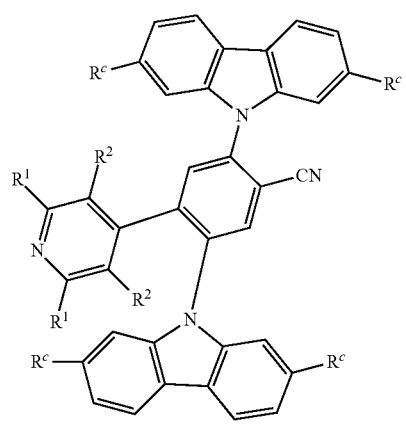

where the definitions given above are applicable.

In a further embodiment, the organic molecules according to the invention comprise a structure of the formula VId:

Formula VId

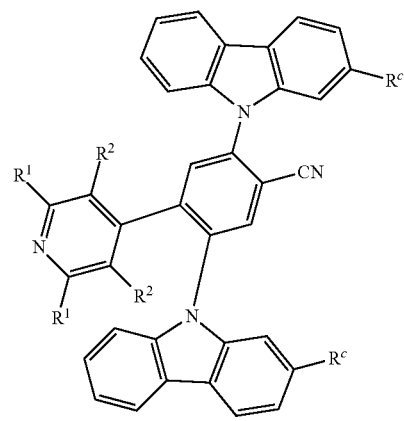

where the definitions given above are applicable.

In a further embodiment, the organic molecules according to the invention comprise a structure of the formula VIe:

Formula VIe

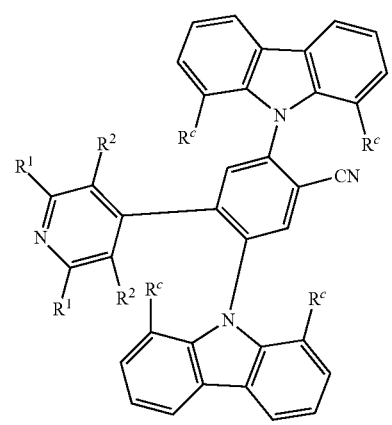

where the definitions given above are applicable.

In a further embodiment, the organic molecules according to the invention comprise a structure of the formula VIf:

Formula VIf

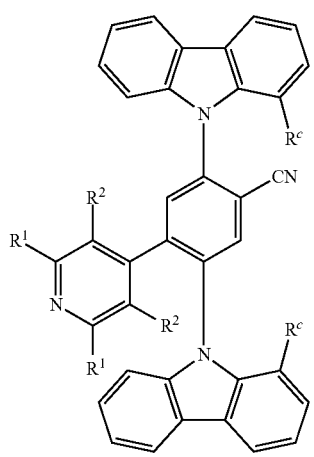

where the definitions given above are applicable.

In a further embodiment, the organic molecules according to the invention comprise a structure of the formula VIg:

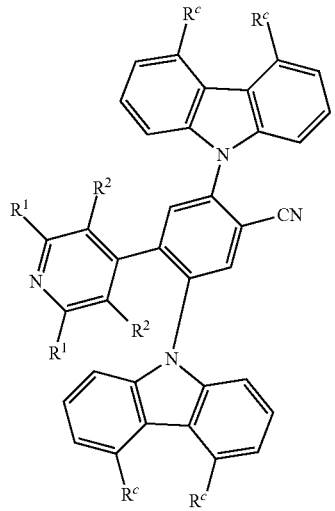

Formula VIg where the definitions given above are applicable.

In a further embodiment, the organic molecules according to the invention comprise a structure of the formula VIh:

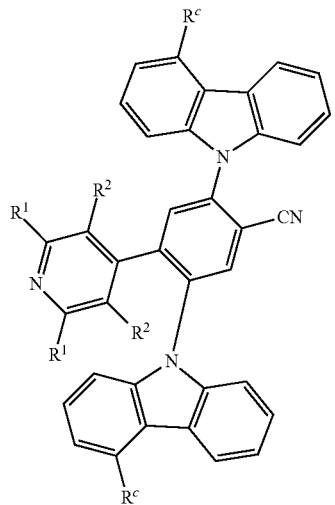

Formula VIh where the definitions given above are applicable.

In one embodiment, the organic molecules according to the invention comprise a structure of the formula VII:

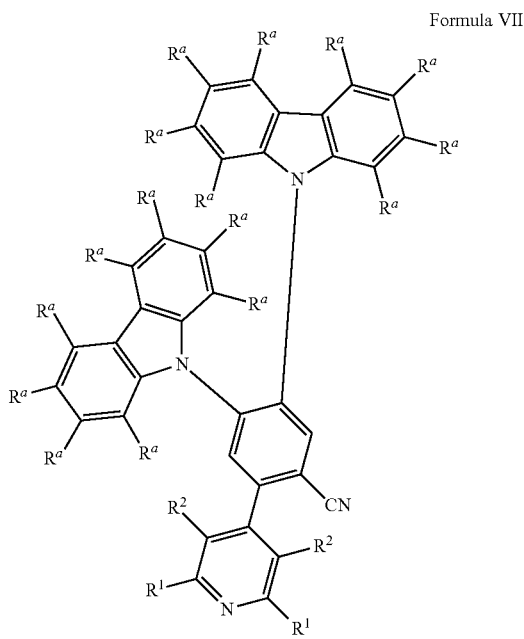

Formula VII where the definitions given above are applicable.

In a further embodiment, the organic molecules according to the invention comprise a structure of the formula VIIa:

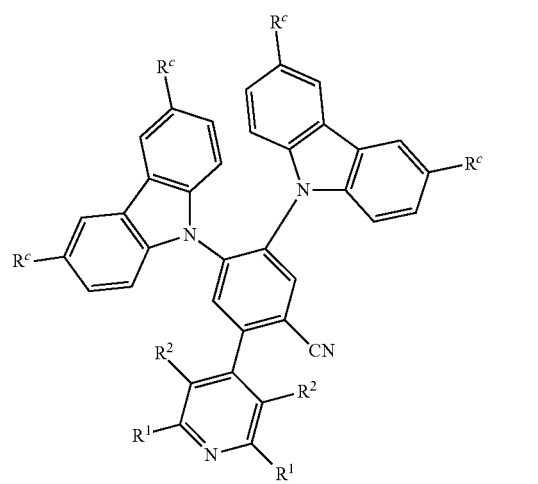

Formula VIIa where the definitions given above are applicable.

In a further embodiment, the organic molecules according to the invention comprise a structure of the formula VIIb:

Formula VIIb

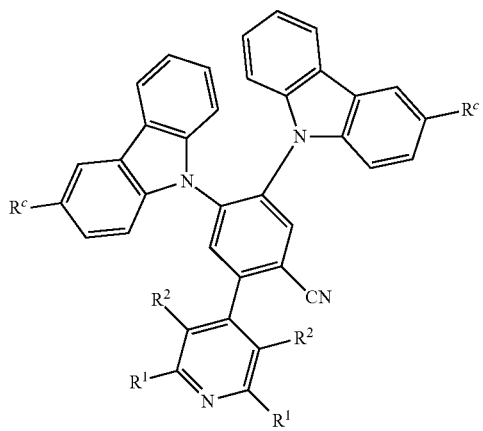

where the definitions given above are applicable.

In a further embodiment, the organic molecules according to the invention comprise a structure of the formula VIIc:

Formula VIIc

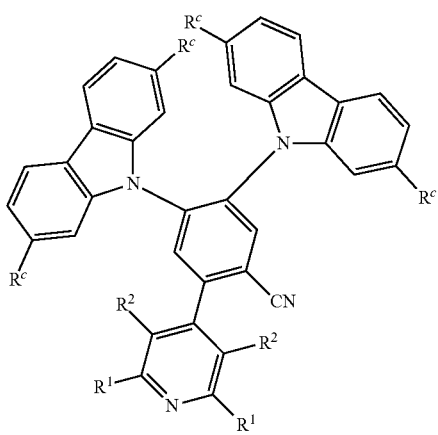

where the definitions given above are applicable.

In a further embodiment, the organic molecules according to the invention comprise a structure of the formula VIId:

Formula VIId

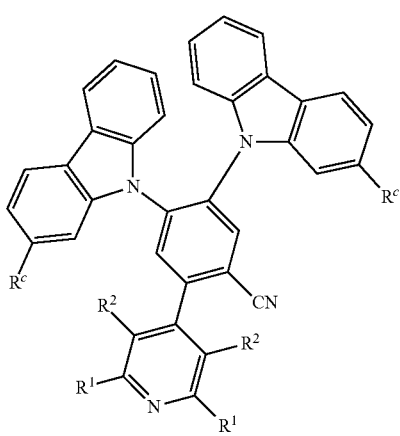

where the definitions given above are applicable.

In a further embodiment, the organic molecules according to the invention comprise a structure of the formula VIIe:

Formula VIIe

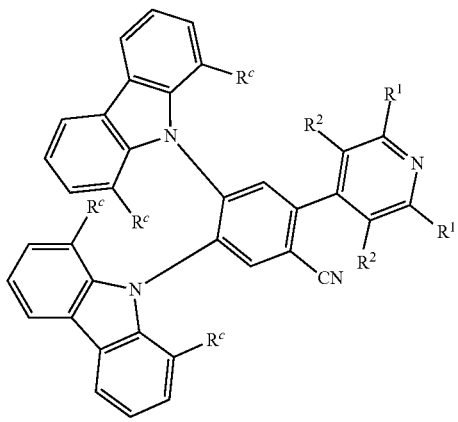

where the definitions given above are applicable.

In a further embodiment, the organic molecules according to the invention comprise a structure of the formula VIIf:

Formula VIIf

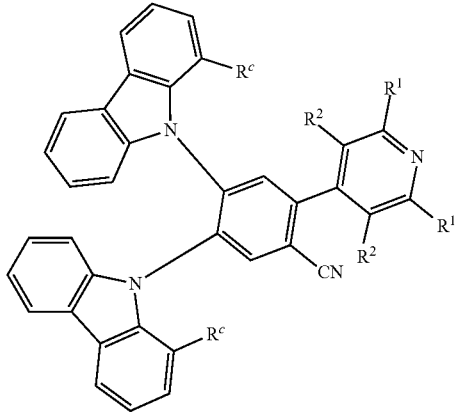

where the definitions given above are applicable.

In a further embodiment, the organic molecules according to the invention comprise a structure of the formula VIIg:

Formula VIIg

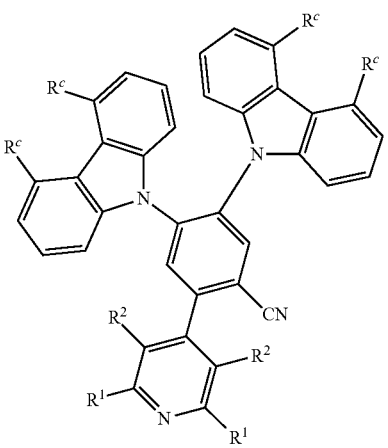

where the definitions given above are applicable.

In a further embodiment, the organic molecules according to the invention comprise a structure of the formula VIIh:

Formula VIIh

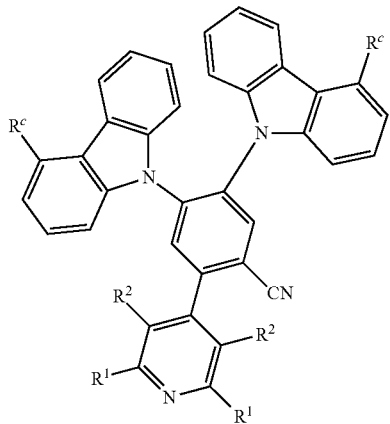

where the definitions given above are applicable.

In one embodiment, the organic molecules according to the invention comprise a structure of the formula VIII:

Formula VIII

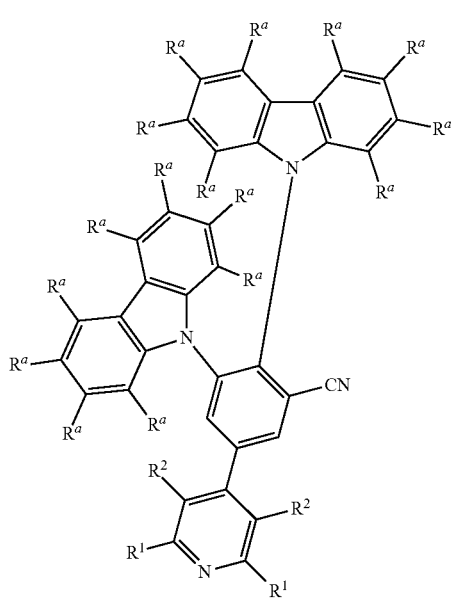

where the definitions given above are applicable.

In one embodiment of the organic molecules, $R^c$ independently at each instance is selected from the group consisting of CN, $CF_3$, Me, $^iPr$, $^tBu$, Ph which may be substituted in each case by one or more radicals selected from CN, $CF_3$, Me, $^iPr$, $^tBu$, CN, $CF_3$ and Ph, and carbazolyl which may be substituted in each case by one or more radicals selected from CN, $CF_3$, Me, $^iPr$, $^tBu$ and Ph.

In the context of this invention, an aryl group contains 6 to 60 aromatic ring atoms; a heteroaryl group contains 5 to 60 aromatic ring atoms, of which at least one is a heteroatom. The heteroatoms are especially N, O and/or S. If, in the description of particular embodiments of the invention, other definitions departing from the definition mentioned are given, for example with regard to the number of aromatic ring atoms or of heteroatoms present, these are applicable.

An aryl group or heteroaryl group is understood to mean a simple aromatic cycle, i.e. benzene, or a simple heteroaromatic cycle, for example pyridine, pyrimidine or thiophene, or a heteroaromatic polycycle, for example phenanthrene, quinoline or carbazole. A fused (annelated) aromatic or heteroaromatic polycycle in the context of the present application consists of two or more mutually condensed simple aromatic or heteroaromatic cycles.

An aryl or heteroaryl group which may be substituted in each case by the abovementioned radicals and which may be joined via any desired positions to the aromatic or heteroaromatic system is especially understood to mean groups derived from benzene, naphthalene, anthracene, phenanthrene, pyrene, dihydropyrene, chrysene, perylene, fluoranthene, benzanthracene, benzphenanthrene, tetracene, pentacene, benzopyrene, furan, benzofuran, isobenzofuran, dibenzofuran, thiophene, benzothiophene, isobenzothiophene, dibenzothiophene; pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, napthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,2,3,4-tetrazine, purine, pteridine, indolizine and benzothiadiazole or combinations of the groups mentioned.

A cyclic alkyl, alkoxy or thioalkoxy group is understood here to mean a monocyclic, bicyclic or polycyclic group.

In the context of the present invention, a $C_1$- to $C_{40}$-alkyl group in which individual hydrogen atoms or $CH_2$ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]-octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

One embodiment of the invention relates to organic molecules having a $\Delta E(S_1-T_1)$ value between the lowermost excited singlet state ($S_1$) and the triplet state ($T_1$) below it of not higher than 5000 cm$^{-1}$, especially not higher than 3000 cm$^{-1}$, or not higher than 1500 cm$^{-1}$ or 1000 cm$^{-1}$, and/or an emission lifetime of not more than 150 μs, especially of not more than 100 μs, of not more than 50 μs, or of not more than 10 μs, and/or a main emission band having a half-height width of less than 0.55 eV, especially less than 0.50 eV, less than 0.48 eV, or less than 0.45 eV.

The organic molecules according to the invention especially exhibit an emission maximum between 420 and 500 nm, between 430 and 480 nm, or between 450 and 470 nm.

In one embodiment, the molecules have a blue material index (BMI), the quotient of the PLQY (in %) and its CIE$_y$ colour coordinates of the light emitted by the molecule according to the invention, of greater than 150, especially of greater than 200, of greater than 250 or of greater than 300.

In a further aspect, the invention relates to a process for preparing an organic molecule according to the invention of the type described here (optionally with a further conversion), wherein a 3,5-R$^1$-substituted and 2,6-R$^2$-substituted 4-pyridineboronic acid or a corresponding 3,5-R$^1$-substituted and 2,6-R$^2$-substituted 4-pyridineboronic ester is used as reactant.

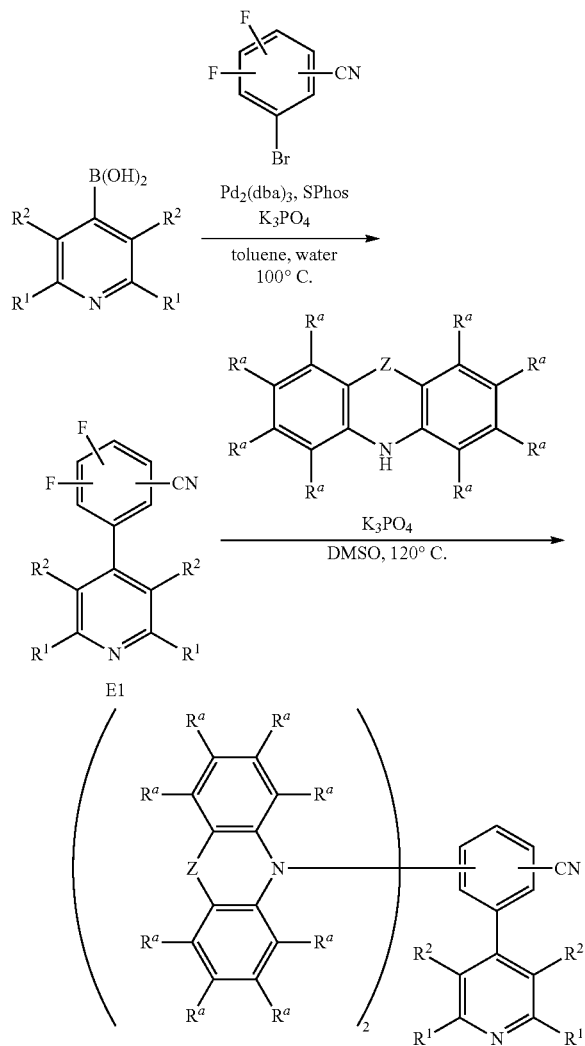

In the above scheme, in one embodiment, the chemical CN group is replaced by CF$_3$.

In one embodiment, a 3,5-R$^1$-substituted and 2,6-R$^2$-substituted 4-pyridineboronic acid or a corresponding 3,5-R$^1$-substituted and 2,6-R$^2$-substituted 4-pyridineboronic ester as reactant is reacted with a bromodifluorobenzonitrile in a palladium-catalysed cross-coupling reaction. It is possible here to use, by way of example, in accordance with the invention, 4-bromo-2,6-difluorobenzonitrile, 4-bromo-2,5-difluorobenzonitrile, 4-bromo-3,5-difluorobenzonitrile, 3-bromo-2,6-difluorobenzonitrile, 3-bromo-5,6-difluorobenzonitrile and 2-bromo-4,5-difluorobenzonitrile. The product is obtained by deprotonation of the corresponding amine, followed by nucleophilic substitution of the two fluorine groups. In this case, two nitrogen heterocycles are reacted with a reactant E1 in the manner of a nucleophilic aromatic substitution. Typical conditions include the use of a base, for example tribasic potassium phosphate or sodium hydride, in an aprotic polar solvent, for example dimethyl sulphoxide (DMSO) or N,N-dimethylformamide (DMF).

In a further aspect, the invention relates to the use of the organic molecules as luminescent emitters or as host material in an organic optoelectronic device, especially where the organic optoelectronic device is selected from the group consisting of:
  organic light-emitting diodes (OLEDs),
  light-emitting electrochemical cells,
  OLED sensors, especially in gas and vapour sensors not hermetically shielded from the outside,
  organic diodes,
  organic solar cells,
  organic transistors,
  organic field-effect transistors,
  organic lasers and
  down-conversion elements.

In a further aspect, the invention relates to a composition comprising or consisting of:
  (a) at least one organic molecule according to the invention, especially as emitter and/or host, and
  (b) at least one, i.e. one or more (such as 2, 3, 4, . . . ), emitter and/or host material(s) other than the organic molecule according to the invention, and
  (c) optionally one or more dyes and/or one or more organic solvents.

In one embodiment, the composition according to the invention consists of an organic molecule according to the invention and one or more host materials. The host material(s) especially has/have triplet ($T_1$) and singlet ($S_1$) energy levels at higher energy than the triplet ($T_1$) and singlet ($S_1$) energy levels of the organic molecule according to the invention. In one embodiment, the composition, as well as the organic molecule according to the invention, comprises an electron-dominant and a hole-dominant host material. The highest occupied orbital (HOMO) and the lowest unoccupied orbital (LUMO) of the hole-dominant host material are especially at higher energy than those of the electron-dominant host material. The HOMO of the hole-dominant host material is at lower energy than the HOMO of the organic molecule according to the invention, while the LUMO of the electron-dominant host material is at higher energy than the LUMO of the organic molecule according to the invention. In order to avoid exciplex formation between emitter and host material(s), the materials should be chosen such that the energy gaps between the respective orbitals are small. The gap between the LUMO of the electron-dominant host material and the LUMO of the organic molecule according to the invention is especially less than 0.5 eV, preferably less than 0.3 eV, even more preferably less than 0.2 eV. The gap between the HOMO of the hole-dominant host material and the HOMO of the organic molecule according to the invention is especially less than 0.5 eV, preferably less than 0.3 eV, even more preferably less than 0.2 eV.

In a further aspect, the invention relates to an organic optoelectronic device comprising an organic molecule according to the invention or a composition according to the invention. The organic optoelectronic device especially takes the form of a device selected from the group consisting of organic light-emitting diode (OLED); light-emitting electrochemical cell; OLED sensor, especially gas and vapour sensors that are not hermetically shielded from the outside; organic diode; organic solar cell; organic transistor; organic field effect transistor; organic laser and down-conversion element.

In one embodiment, an organic optoelectronic device comprises:
   a substrate,
   an anode and
   a cathode, where the anode or cathode has been applied to the substrate, and
   at least one light-emitting layer which is arranged between anode and cathode and comprises an organic molecule according to the invention is a further embodiment of the invention.

In one embodiment, the optoelectronic device is an organic light-emitting diode (OLED). A typical OLED has, for example, the following layer structure:
1. Substrate (carrier material)
2. Anode
3. Hole injection layer (HIL)
4. Hole transport layer (HTL)
5. Electron blocking layer (EBL)
6. Emitting layer (EML)
7. Hole blocking layer (HBL)
8. Electron transport layer (ETL)
9. Electron injection layer (EIL)
10. Cathode.

Individual layers here are present merely in an optional manner. In addition, two or more of these layers may be combined. And it is possible for individual layers to be present more than once in the component.

In one embodiment, at least one electrode of the organic component is translucent. "Translucent" refers here to a layer which is transparent to visible light. The translucent layer here may be clear and see-through, i.e. transparent, or at least partly light-absorbing and/or partly light-scattering, such that the translucent layer, for example, may also have a diffuse or milky appearance. More particularly, a layer referred to here as translucent is very substantially transparent, such that, in particular, the absorption of light is as low as possible.

In a further embodiment, the organic component, especially an OLED, comprises an inverted structure. It is a feature of the inverted structure that the cathode is on the substrate and the other layers are applied in a correspondingly inverted manner.
1. Substrate (carrier material)
2. Cathode
3. Electron injection layer (EIL)
4. Electron transport layer (ETL)
5. Hole blocking layer (HBL)
6. Emission layer/emitting layer (EML)
7. Electron blocking layer (EBL)
8. Hole transport layer (HTL)
9. Hole injection layer (HIL)
10. Anode Individual layers here are present merely in an optional manner. In addition, two or more of these layers may be combined. And it is also possible for individual layers to be present more than once in the component.

In one embodiment, in the inverted OLED, the anode layer of the typical structure, for example an ITO (indium tin oxide) layer, is connected as the cathode.

In a further embodiment, the organic component, especially an OLED, comprises a stacked structure. The individual OLEDs here are arranged one on top of another and not one alongside another as usual. A stacked structure can enable the generation of mixed light. For example, this structure can be used in the generation of white light, which is produced by forming the entire visible spectrum, typically by the combination of the emitted light from blue, green and red emitters. In addition, with practically the same efficiency and identical luminance, it is possible to achieve significantly longer lifetimes compared to standard OLEDs. For the stacked structure, it is optionally possible to use what is called a charge generation layer (CGL) between two OLEDs. This consists of an n-doped layer and a p-doped layer, the n-doped layer typically being applied closer to the anode.

In one embodiment—called a tandem OLED—two or more emission layers occur between the anode and cathode. In one embodiment, three emission layers are arranged one on top of another, where one emission layer emits red light, one emission layer emits green light and one emission layer emits blue light, and there are optionally further charge generation, blocker or transport layers applied between the individual emission layers. In a further embodiment, the respective emission layers are applied in a directly adjacent manner. In a further embodiment, there is one charge generation layer in each case between the emission layers. In addition, in an OLED, it is possible to combine directly adjacent emission layers and emission layers separated by charge generation layers.

It is also possible to arrange an encapsulation on top of the electrodes and the organic layers. The encapsulation may take the form, for example, of a glass lid or the form of a thin-film encapsulation.

The carrier material used in the optoelectronic device may, for example, be glass, quartz, plastic, metal, a silicon wafer or any other suitable solid or flexible, optionally transparent material. The carrier material may include, for example, one or more materials in the form of a layer, a film, a sheet or a laminate.

Anodes used in the optoelectronic device may, for example, be transparent conductive metal oxides, for example ITO (indium tin oxide), zinc oxide, tin oxide, cadmium oxide, titanium oxide, indium oxide or aluminium zinc oxide (AZO), $Zn_2SnO_4$, $CdSnO_3$, $ZnSnO_3$, $MgIn_2O_4$, $GaInO_3$, $Zn_2In_2O_5$ or $In_4Sn_3O_{12}$ or mixtures of different transparent conductive oxides.

HIL materials used may, for example, be PEDOT:PSS (poly-3,4-ethylenedioxythiophene:polystyrenesulphonic acid), PEDOT (poly-3,4-ethylenedioxythiophene), m-MTDATA (4,4',4''-tris[phenyl(m-tolyl)amino]triphenylamine), spiro-TAD (2,2',7,7'-tetrakis(N,N-diphenylamino)-9,9-spirobifluorene), DNTPD (4,4'-bis[N-[4-{N,N-bis(3-methylphenyl)amino}phenyl]-N-phenylamino]biphenyl), NPB (N,N'-bis-(1-naphthalenyl)-N,N'-bisphenyl-(1,1'-biphenyl)-4,4'-diamine), NPNPB (N,N'-diphenyl-N,N'-di-[4-(N,N-diphenylamino)phenyl]benzene), MeO-TPD (N,N,N',N'-tetrakis(4-methoxyphenyl)benzene), HAT-CN (1,4,5,8,9,11-hexaazatriphenylenehexacarbonitrile) or spiro-NPD (N,N'-diphenyl-N,N'-bis(1-naphthyl)-9,9'-spirobifluorene-2,7- diamine). By way of example, the layer thickness is 10-80 nm. In addition, it is possible to use small molecules (e.g. copper phthalocyanine (CuPc, e.g. thickness 10 nm)) or metal oxides, by way of example $MoO_3$, $V_2O_5$.

HTL materials used may be tertiary amines, carbazole derivatives, polystyrenesulphonic acid-doped polyethylenedioxythiophene, camphorsulphonic acid-doped polyaniline, poly-TPD (poly(4-butylphenyldiphenylamine), [alpha]-NPD (poly(4-butylphenyldiphenylamine)), TAPC (4,4'-cyclohexylidenebis[N,N-bis(4-methylphenyl)benzeneamine]), TCTA (tris(4-carbazoyl-9-ylphenyl)amine), 2-TNATA (4,4',4"-tris[2-naphthyl(phenyl)amino]triphenylamine), spiro-TAD, DNTPD, NPB, NPNPB, MeO-TPD, HAT-CN or TrisPcz (9,9'-diphenyl-6-(9-phenyl-9H-carbazol-3-yl)-9H,9'H-3,3'-bicarbazole). By way of example, the layer thickness is 10 nm to 100 nm.

The HTL may comprise a p-doped layer having an inorganic or organic dopant in an organic hole-conducting matrix. Inorganic dopants used may, for example, be transition metal oxides, for instance vanadium oxide, molybdenum oxide or tungsten oxide. Organic dopants used may, for example, be tetrafluorotetracyanoquinodimethane (F4-TCNQ), copper pentafluorobenzoate (Cu(I)pFBz) or transition metal complexes. By way of example, the layer thickness is 10 nm to 100 nm.

Electron blocker layer materials used may, for example, be mCP (1,3-bis(carbazol-9-yl)benzene), TCTA, 2-TNATA, mCBP (3,3-di(9H-carbazol-9-yl)biphenyl), tris-Pcz (9,9'-diphenyl-6-(9-phenyl-9H-carbazol-3-yl)-9H,9'H-3,3'-bicarbazole), CzSi (9-(4-tert-butylphenyl)-3,6-bis(triphenylsilyl)-9H-carbazole) or DCB (N,N'-dicarbazolyl-1,4-dimethylbenzene). By way of example, the layer thickness is 10 nm to 50 nm.

The emitter layer EML or emission layer consists of or comprises emitter material or a mixture including at least two emitter materials and optionally one or more host materials. Suitable host materials are, for example, mCP, TCTA, 2-TNATA, mCBP, CBP (4,4'-bis(N-carbazolyl)biphenyl), Sif87 (dibenzo[b,d]thiophen-2-yltriphenylsilane), Sif88 (dibenzo[b,d]thiophen-2-yl)diphenylsilane), 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole, 9-[3,5-bis(2-dibenzothio-phenyl)phenyl]-9H-carbazole, T2T (2,4,6-tris(biphenyl-3-yl)-1,3,5-triazine), T3T (2,4,6-tris(triphenyl-3-yl)-1,3,5-triazine), TST (2,4,6-tris(9,9'-spirobifluoren-2-yl)-1,3,5-triazine) and/or DPEPO (bis[2-((oxo)diphenylphosphino)phenyl]ether). In one embodiment, the EML contains 50%-80% by weight, preferably 60%-75% by weight, of a host material selected from the group consisting of CBP, mCP, mCBP, 9-[3-(dibenzofuran-2-yl)phenyl]-9H-carbazole, 9-[3-(dibenzofuran-2-yl)phenyl]-9H-carbazole, 9-[3-(dibenzothiophen-2-yl)phenyl]-9H-carbazole, 9-[3,5-bis(2-dibenzofuranyl)phenyl]-9H-carbazole and 9-[3,5-bis(2-dibenzothiophenyl)phenyl]-9H-carbazole; 10%-45% by weight, preferably 15%-30% by weight, of T2T and 5%-40% by weight, preferably 10%-30% by weight, of an organic molecule according to the invention as emitter. For emitter material which emits in the green or in the red or a mixture comprising at least two emitter materials, the standard matrix materials are suitable, such as CBP. For emitter material which emits in the blue or a mixture comprising at least two emitter materials, it is possible to use UHG matrix materials (ultra-high-energy gap materials) (see, for example, M. E. Thompson et al., Chem. Mater. 2004, 16, 4743), or other so-called wide-gap matrix materials. By way of example, the layer thickness is 10 nm to 250 nm.

The hole blocker layer HBL may include, for example, BCP (2,9-dimethyl-4,7-diphenyl-1,10-phenanthroline=bathocuproin), bis(2-methyl-8-hydroxyquinolinato)-(4-phenylphenolato)-aluminium(III) (BAlq), NBphen (2,9-bis(naphthalen-2-yl)-4,7-diphenyl-1,10-phenanthroline), Alq3 (aluminium tris(8-hydroxyquinoline)), T2T, TSPO1 (diphenyl-4-triphenylsilylphenylphosphine oxide) or TCB/TCP (1,3,5-tris(N-carbazolyl)benzene/1,3,5-tris(carbazol)-9-yl)benzene). By way of example, the layer thickness is 10 nm to 50 nm.

The electron transport layer ETL may include, for example, materials based on $AlQ_3$, TSPO1, NBPhen, BPyTP2 (2,7-di(2,2'-bipyridin-5-yl)triphenyl), Sif87, Sif88, BmPyPhB (1,3-bis[3,5-di(pyridin-3-yl)phenyl]benzene) or BTB (4,4'-bis[2-(4,6-diphenyl-1,3,5-triazinyl)]-1,1'-biphenyl). By way of example, the layer thickness is 10 nm to 200 nm.

Materials used in a thin electron injection layer EIL may, for example, be CsF, LiF, 8-hydroxyquinolinolatolithium (Liq), $Li_2O$, $BaF_2$, MgO or NaF.

Materials used in the cathode layer may be metals or alloys, for example Al, Al>AlF, Ag, Pt, Au, Mg, Ag:Mg. Typical layer thicknesses are 100 nm to 200 nm. In particular, one or more metals that are stable under air and/or self-passivating, for example through formation of a thin protective oxide layer, are used.

Suitable materials for encapsulation are, for example, aluminium oxide, vanadium oxide, zinc oxide, zirconium oxide, titanium oxide, hafnium oxide, lanthanum oxide, tantalum oxide.

In one embodiment of the organic optoelectronic device according to the invention, the organic molecule according to the invention is used as emission material in a light-emitting layer EML, where it is used either in the form of a pure layer or in combination with one or more host materials.

One embodiment of the invention relates to organic optoelectronic devices having an external quantum efficiency (EQE) at 1000 $cd/m^2$ of greater than 5%, especially of greater than 8%, especially of greater than 10%, or of greater than 13%, or of greater than 16% and especially of greater than 20%, and/or an emission maximum at a wavelength between 420 nm and 500 nm, especially between 430 nm and 490 nm, or between 440 nm and 480 nm and especially between 450 nm and 470 nm, and/or an LT80 value at 500 $cd/m^2$ of greater than 30 h, especially of greater than 70 h, or of greater than 100 h, or of greater than 150 h and especially of greater than 200 h.

The proportion by mass of the organic molecule according to the invention in the emitter layer EML, in a further embodiment in a light-emitting layer in optical light-emitting devices, especially in OLEDs, is between 1% and 80%. In one embodiment of the organic optoelectronic device according to the invention, the light-emitting layer is applied to a substrate, preferably with application of an anode and a cathode to the substrate and application of the light-emitting layer between the anode and cathode.

The light-emitting layer, in one embodiment, may have exclusively an organic molecule according to the invention in 100% concentration, with the anode and the cathode applied to the substrate, and the light-emitting layer applied between the anode and cathode.

In one embodiment of the organic optoelectronic device according to the invention, a hole- and electron-injecting layer has been applied between the anode and cathode, and a hole- and electron-transporting layer between the hole- and electron-injecting layer, and the light-emitting layer between the hole- and electron-transporting layer.

The organic optoelectronic device, in a further embodiment of the invention, comprises: a substrate, an anode, a cathode and at least one hole- and one electron-injecting layer, and at least one hole- and one electron-transporting layer, and at least one light-emitting layer comprising an organic molecule according to the invention and one or more host materials, the triplet ($T_1$) and singlet ($S_1$) energy levels of which are at higher energy than the triplet ($T_1$) and singlet ($S_1$) energy levels of the organic molecule, with the anode and cathode applied to the substrate, and the hole- and electron-injecting layer applied between the anode and cathode, and the hole- and electron-transporting layer applied between the hole- and electron-injecting layer, and the light-emitting layer applied between the hole- and electron-transporting layer.

In a further aspect, the invention relates to a process for producing an optoelectronic component. This is done using an organic molecule according to the invention. In one embodiment, the production process encompasses the processing of the organic molecule according to the invention by means of a vacuum evaporation method or from a solution.

The invention also includes a process for producing an optoelectronic device according to the invention, in which at least one layer of the optoelectronic device
- is coated by a sublimation method,
- is coated by an OVPD (organic vapour phase deposition) method,
- is coated by a carrier gas sublimation, and/or
- is produced from solution or by a printing method.

In the production of the optoelectronic device according to the invention, known methods are used. In general, the layers are applied individually to a suitable substrate in successive deposition process steps. In the gas phase deposition, it is possible to employ the commonly used methods, such as thermal evaporation, chemical gas phase deposition (CVD), physical gas phase deposition (PVD). For active-matrix OLED (AMOLED) displays, deposition is effected on an AMOLED backplane as substrate.

Alternatively, it is possible to apply layers from solutions or dispersions in suitable solvents.

Illustrative suitable coating methods are spin-coating, dip-coating and jet printing methods.

The individual layers can be produced in accordance with the invention either via the same coating method or via different coating methods in each case.

EXAMPLES

General synthesis scheme I

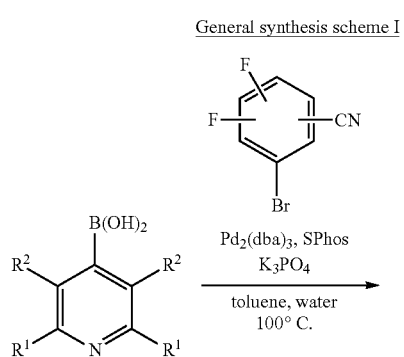

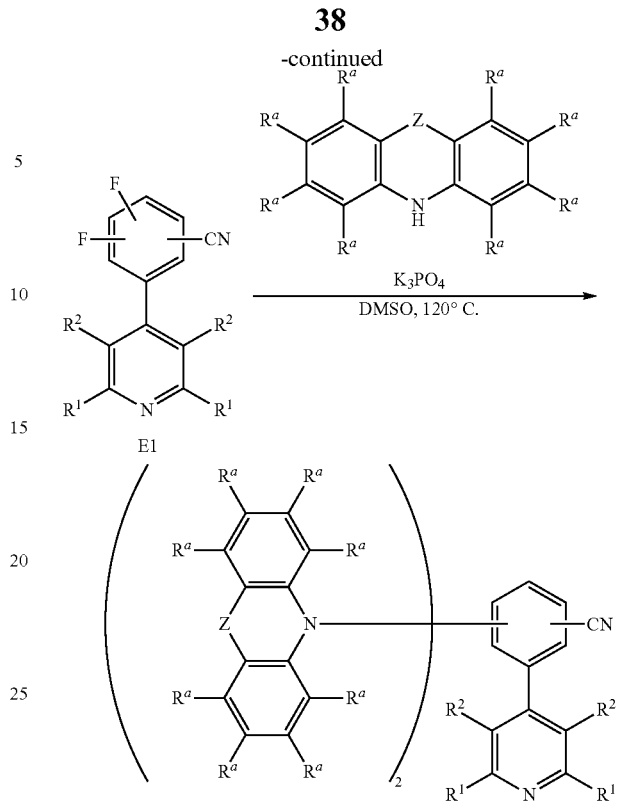

General Synthesis Method GM1

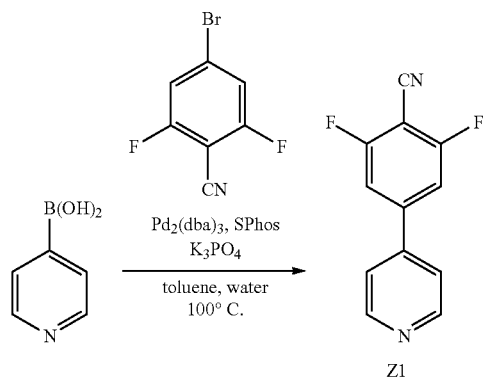

4-Pyridineboronic acid (1.80 equivalents), 4-bromo-2,6-difluorobenzonitrile (1.00 equivalent), Pd$_2$(dba)$_3$ (0.02 equivalent), 2-dicyclohexylphosphino-2',6'-dimethoxybiphenyl (SPhos) (0.08 equivalent) and tribasic potassium phosphate (3.00 equivalents) are stirred under nitrogen in a toluene/water mixture (ratio 6:1) at 100° C. for 16 h. Subsequently, the reaction mixture is added to 600 ml of saturated sodium chloride solution and extracted with ethyl acetate (2×300 ml). The combined organic phases are washed with saturated sodium chloride solution and dried over MgSO$_4$, and the solvent is removed. The resulting crude product is purified by flash chromatography and the product is obtained in solid form.

It is also possible in accordance with the invention to use a corresponding boronic ester rather than a boronic acid.

General Synthesis Method GM2

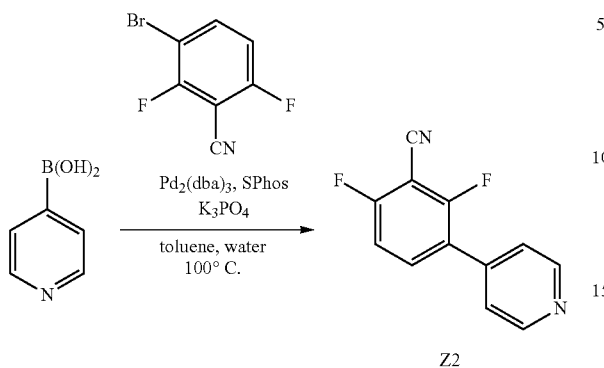

The synthesis of Z2 is effected analogously to GM1, by reaction of 4-pyridineboronic acid with 3-bromo-2,6-difluorobenzonitrile.

General Synthesis Method GM3

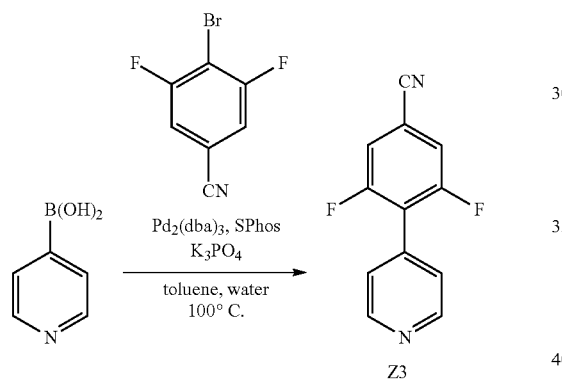

The synthesis of Z3 is effected analogously to GM1, by reaction of 4-pyridineboronic acid with 4-bromo-3,5-difluorobenzonitrile.

General Synthesis Method GM4

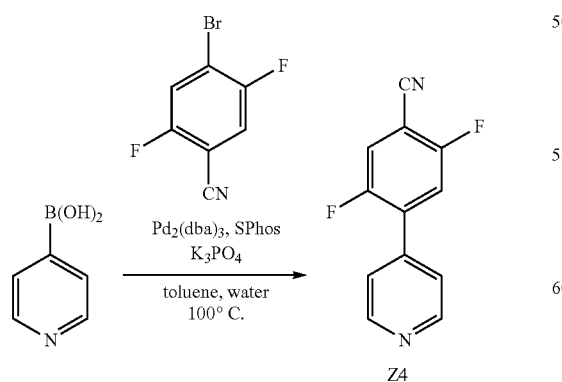

The synthesis of Z4 is effected analogously to GM1, by reaction of 4-pyridineboronic acid with 4-bromo-2,5-difluorobenzonitrile.

General Synthesis Method GM5

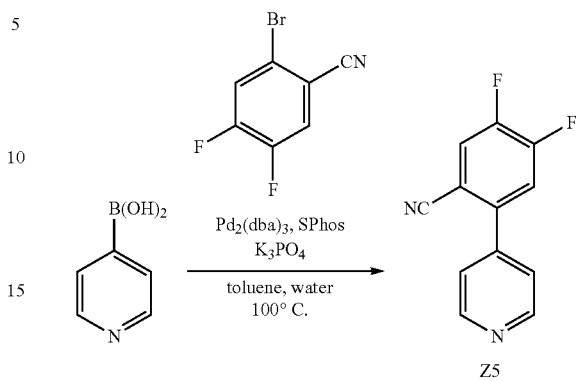

The synthesis of Z5 is effected analogously to GM1, by reaction of 4-pyridineboronic acid with 2-bromo-4,5-difluorobenzonitrile.

General Synthesis Method GM6

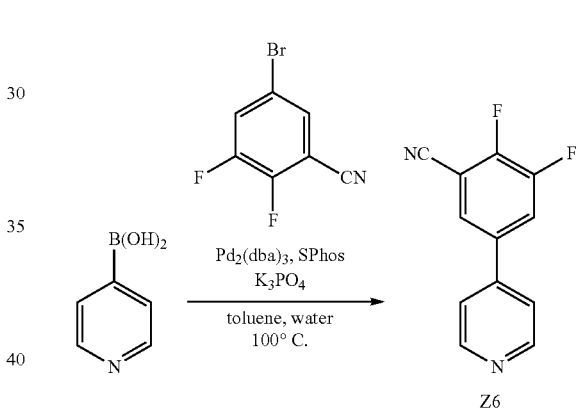

The synthesis of Z6 is effected analogously to GM1, by reaction of 4-pyridineboronic acid with 3-bromo-5,6-difluorobenzonitrile.

General Synthesis Method GM7

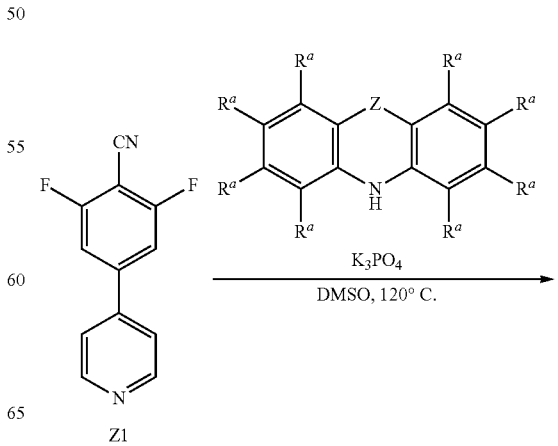

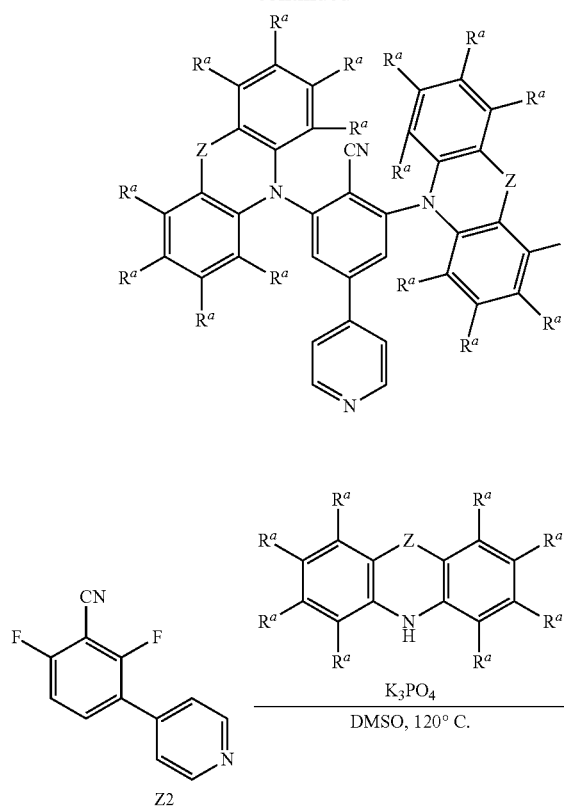
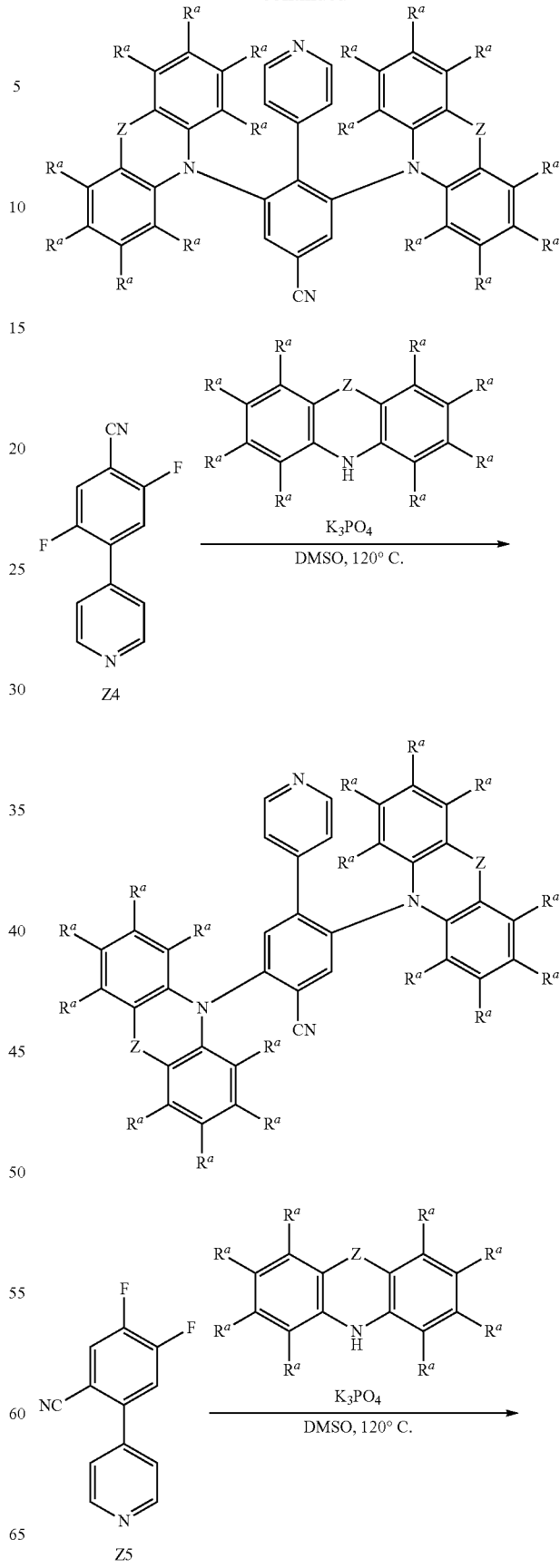

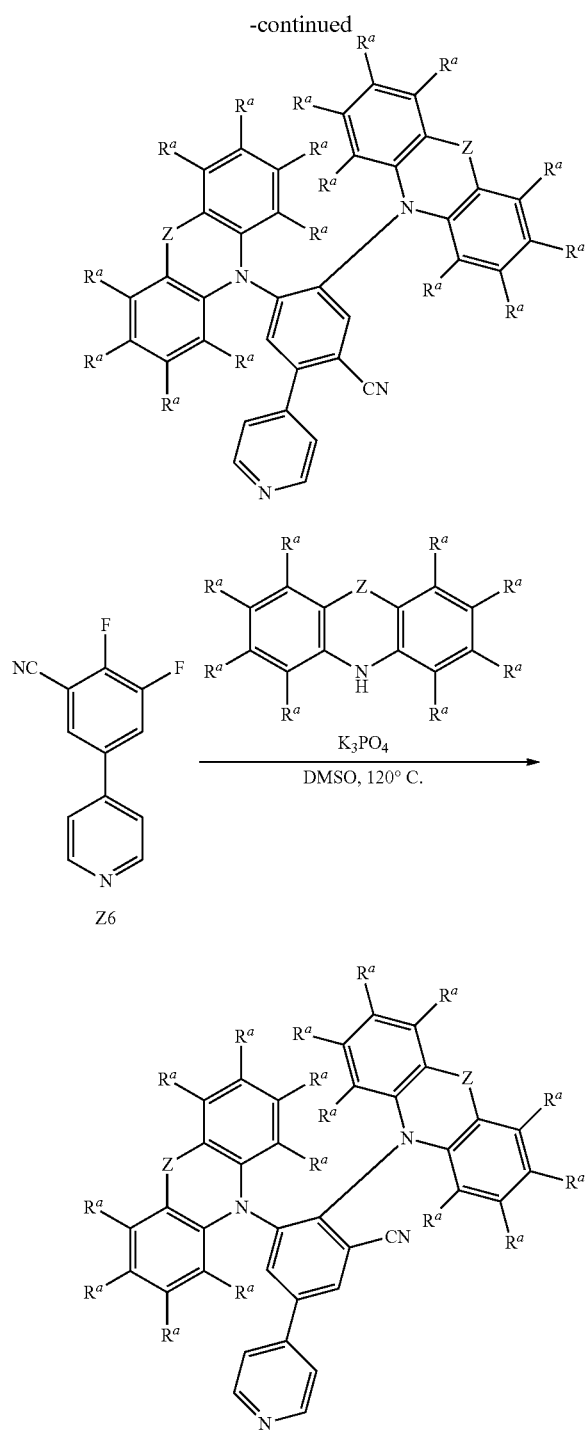

Z1, Z2, Z3, Z4, Z5 or Z6 (1.00 equivalent of each), the appropriate donor molecule D-H (2.00 equivalents) and tribasic potassium phosphate (4.00 equivalents) are suspended in DMSO under nitrogen and stirred at 110° C. (16 h). Subsequently, the reaction mixture is added to saturated sodium chloride solution and extracted three times with dichloromethane. The combined organic phases are washed twice with saturated sodium chloride solution and dried over magnesium sulphate, and the solvent is then removed. The crude product was finally purified by recrystallization from toluene or by flash chromatography. The product is obtained in solid form.

In order to obtain the corresponding $R^1$- and/or $R^2$-substituted products, a correspondingly substituted 4-pyridineboronic acid is used instead of 4-pyridineboronic acid.

Specifically, D-H corresponds to a 3,6-substituted carbazole (e.g. 3,6-dimethylcarbazole, 3,6-diphenylcarbazole, 3,6-di-tert-butylcarbazole), a 2,7-substituted carbazole (e.g. 2,7-dimethylcarbazole, 2,7-diphenylcarbazole, 2,7-di-tert-butylcarbazole), a 1,8-substituted carbazole (e.g. 1,8-dimethylcarbazole, 1,8-diphenylcarbazole, 1,8-di-tert-butylcarbazole), a 1-substituted carbazole (e.g. 1-methylcarbazole, 1-phenylcarbazole, 1-tert-butylcarbazole), a 2-substituted carbazole (e.g. 2-methylcarbazole, 2-phenylcarbazole, 2-tert-butylcarbazole) or a 3-substituted carbazole (e.g. 3-methylcarbazole, 3-phenylcarbazole, 3-tert-butylcarbazole). It is especially possible to use a halocarbazole, especially 3-bromocarbazole or 3,6-dibromocarbazole, as D-H, which is converted in a subsequent reaction, for example, to a corresponding boronic acid, for example (carbazol-3-yl) boronic acid, or to a corresponding boronic ester, for example (carbazol-3-yl)boronic ester, by way of example by reaction with bis(pinacol)boronic ester (CAS No. 73183-34-3). In a subsequent reaction, it is possible to introduce one or more $R^a$ radicals which are used in the form of the halogenated reactant $R^a$Hal, preferably $R^a$—Cl and $R^a$—Br, in place of the boronic acid group or the boronic ester group via a coupling reaction. Alternatively, one or more $R^a$ radicals can be introduced by reaction of the previously introduced halocarbazole with boronic acids of the $R^a$ radical ($R^a$—B(OH)$_2$) or corresponding boronic esters.

Photophysical Measurements
Pretreatment of Optical Glassware

All glassware (cuvettes and substrates made from quartz glass, diameter: 1 cm) was cleaned after each use: Three rinses each time with dichloromethane, acetone, ethanol, demineralized water, placing in 5% Hellmanex solution for 24 h, thorough rinsing-out with demineralized water. For drying, the optical glassware was blown dry with nitrogen.

Sample Preparation, Film: Spin-Coating
Instrument: Spin150, SPS euro.
Sample concentration corresponded to 10 mg/ml, made up in toluene or chlorobenzene.
Programme: 1) 3 s at 400 rpm; 2) 20 s at 1000 rpm at 1000 rpm/s. 3) 10 s at 4000 rpm at 1000 rpm/s. After coating, the films were dried at 70° C. under air on an LHG precision hotplate for 1 min.

Photoluminescence Spectroscopy and TCSPC

Steady-state emission spectroscopy was conducted with a Horiba Scientific fluorescence spectrometer, model: Fluoro-Max-4, equipped with a 150 W xenon arc lamp, excitation and emission monochromators and a Hamamatsu R928 photomultiplier tube, and also a "time-correlated single-photon counting" (TCSPC) option. Emission and excitation spectra were corrected by means of standard correction curves.

The emission decay times were likewise measured with this system using the TCSPC method with the FM-2013 accessories and a TCSPC hub from Horiba Yvon Jobin. Excitation sources:
NanoLED 370 (wavelength: 371 nm, pulse duration: 1.1 ns)
NanoLED 290 (wavelength: 294 nm, pulse duration: <1 ns)
SpectraLED 310 (wavelength: 314 nm)
SpectraLED 355 (wavelength: 355 nm).

The evaluation (exponential fitting) was effected with the DataStation software package and the DAS 6 evaluation software. The fit was reported by the chi-squared method $$c^2 = \sum_{k=1}^{i} \frac{(e_i - o_i)^2}{e_i}$$

with $e_i$: parameter predicted by the fit and $o_i$: parameter measured.

Determination of Quantum Efficiency

The photoluminescence quantum yield (PLQY) was measured by means of an Absolute PL Quantum Yield Measurement C9920-03G system from Hamamatsu Photonics. This consists of a 150 W xenon gas discharge lamp, automatically adjustable Czerny-Turner monochromators (250-950 nm) and an Ulbricht sphere with highly reflective Spectralon coating (a Teflon derivative), connected via a glass fibre cable to a PMA-12 multichannel detector with a BT (back-thinned) CCD chip having 1024×122 pixels (size 24×24 µm). The quantum efficiency and the CIE coordinates were evaluated with the aid of the U6039-05 software, version 3.6.0.

The emission maximum is reported in nm, the quantum yield φ in %, and the CIE colour coordinates as x,y values.

The photoluminescence quantum yield was determined according to the following protocol:

1) Performance of quality assurance: The reference material used is anthracene in ethanol with known concentration.

2) Determining the excitation wavelength: First of all, the absorption maximum of the organic molecule was determined and it was excited therewith.

3) Performance of sample analysis:

The absolute quantum yield of degassed solutions and films was determined under a nitrogen atmosphere.

The calculation was effected within the system according to the following equation:

$$\Phi_{PL} = \frac{n_{photon,\ emitted}}{n_{photon,\ absorbed}} = \frac{\int \frac{\lambda}{hc}[Int_{emitted}^{sample}(\lambda) - Int_{absorbed}^{sample}(\lambda)]d\lambda}{\int \frac{\lambda}{hc}[Int_{emitted}^{reference}(\lambda) - Int_{absorbed}^{reference}(\lambda)]d\lambda}$$

with the photon count $n_{photon}$ and the intensity Int.

Production and characterization of organic electroluminescent devices from the gas phase With the organic molecules according to the invention, it is possible to create OLED devices by means of vacuum sublimation methodology.

These as yet unoptimized OLEDs can be characterized in a standard manner; for this purpose, the electroluminescent spectra, the external quantum efficiency (measured in %) as a function of brightness, calculated from the light detected by the photodiode, the electroluminescence spectra and the current are recorded.

HPLC-MS:

HPLC-MS spectroscopy was measured with an Agilent HPLC system (1100 series) connected to an MS detector (Thermo LTQ XL). For the HPLC, an Eclipse Plus C18 column from Agilent with a particle size of 3.5 µm, a length of 150 mm and an internal diameter of 4.6 mm was used. No pre-column was employed and operation was effected at room temperature with the solvents acetonitrile, water and tetrahydrofuran in these concentrations:

| Solvent A: | H$_2$O (90%) | MeCN (10%) |
| Solvent B: | H$_2$O (10%) | MeCN (90%) |
| Solvent C: | THF (100%) | |

An injection volume of 15 µl and a concentration of 10 µg/ml with this gradient was employed:

| Flow rate [ml/min] | Time [min] | A [%] | B [%] | C [%] | Pressure [bar] |
| --- | --- | --- | --- | --- | --- |
| 0.3 | 0 | 80 | 20 | — | 115 |
| 0.3 | 5 | 80 | 20 | — | 115 |
| 0.3 | 14 | 0 | 90 | 10 | 65 |
| 0.3 | 25 | 0 | 90 | 10 | 65 |
| 0.3 | 26 | 80 | 20 | — | 115 |
| 0.3 | 33 | 80 | 20 | — | 115 |

The sample was ionized by APCI (atmospheric pressure chemical ionization).

Example 1

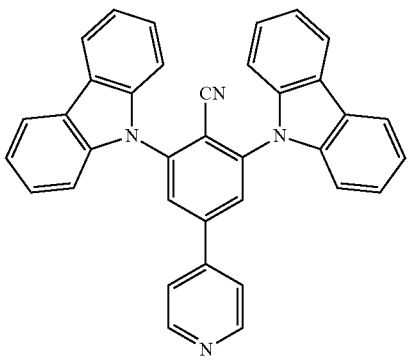 [SMILES: N#Cc1c(-n2c3ccccc3c3ccccc32)cc(-c2ccncc2)cc1-n1c2ccccc2c2ccccc21]

Example 1 was prepared according to GM1 (62% yield) and GM7 (91% yield).

MS (HPLC-MS), m/z (retention time): 510, (6.18 min)

FIG. 1 shows the emission spectrum of Example 1 (10% in PMMA). The emission maximum is at 460 nm. The photoluminescence quantum yield (PLQY) is 74% and the half-height width is 0.43 eV.

Example 2

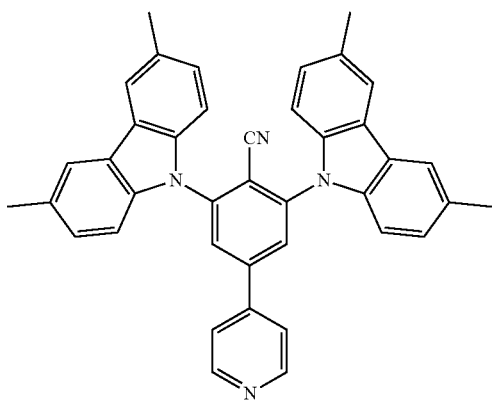

Example 2 was prepared according to GM1 (62% yield) and GM7 (90% yield).

MS (HPLC-MS), m/z (retention time): 566, (13.78 min)

Figure 2:
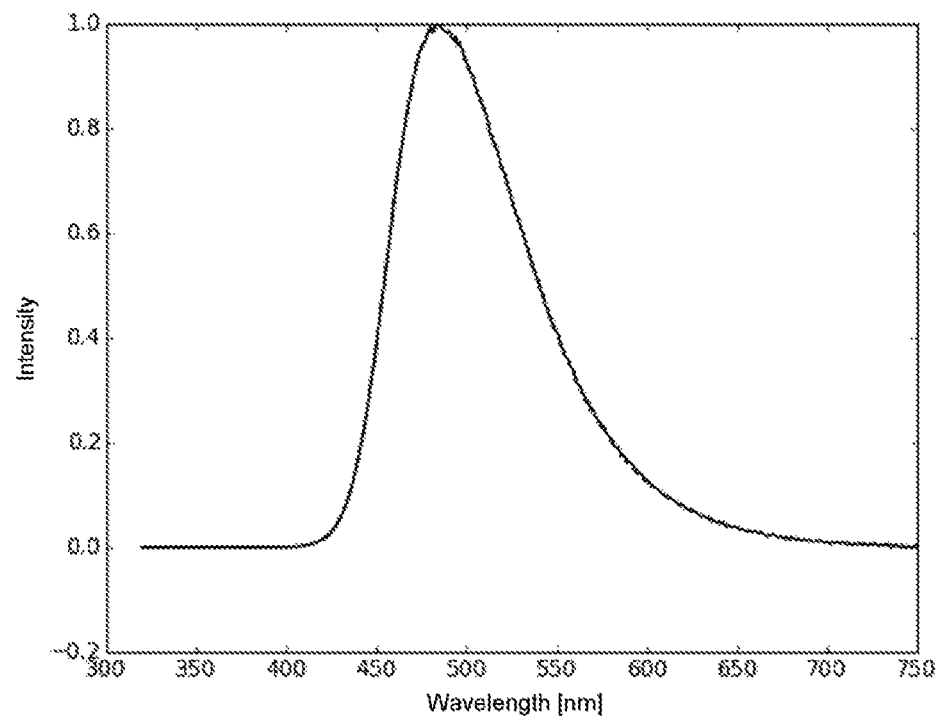
FIG. 2 is an emission spectrum of Example 2 (10% in PMMA).

FIG. 2 shows the emission spectrum of Example 2 (10% in PMMA). The emission maximum is at 485 nm. The photoluminescence quantum yield (PLQY) is 75% and the half-height width is 0.43 eV. The emission decay time is 8 µs.

Example 3

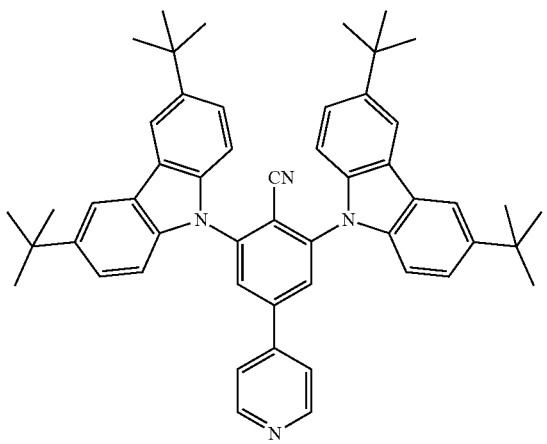 [SMILES: CC(C)(C)c1ccc2c(c1)c1cc(C(C)(C)C)ccc1n2-c1cc(-c2ccncc2)cc(-n2c3ccc(C(C)(C)C)cc3c3cc(C(C)(C)C)ccc32)c1C#N]

Example 3 was prepared according to GM1 (62% yield) and GM7 (25% yield).

MS (HPLC-MS), m/z (retention time): 734, (21.78 min)
$R_f$=0.17 (cyclohexane/ethyl acetate 5:1).

Figure 3:
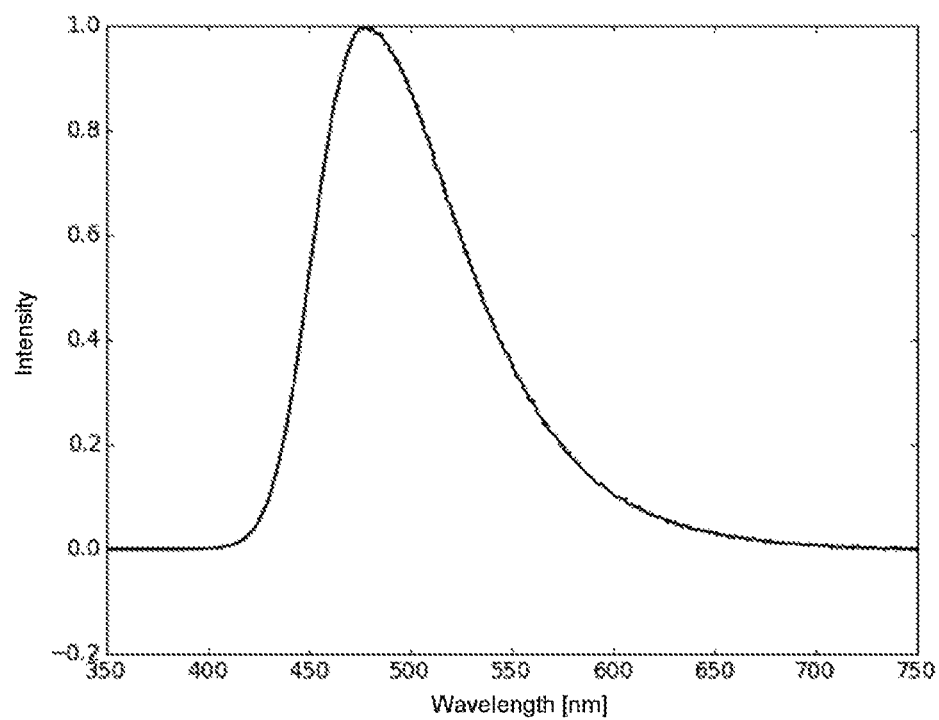
FIG. 3 is an emission spectrum of Example 3 (10% in PMMA).

FIG. 3 shows the emission spectrum of Example 3 (10% in PMMA). The emission maximum is at 478 nm. The photoluminescence quantum yield (PLQY) is 72% and the half-height width is 0.44 eV. The emission decay time is 12 µs.

Example 4

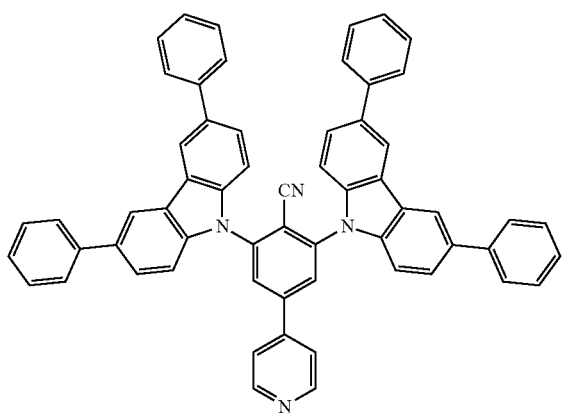

Example 4 was prepared according to GM1 (62% yield) and GM7 (74% yield).

MS (HPLC-MS), m/z (retention time): 814, (18.61 min)
$R_f$=0.1 (cyclohexane/ethyl acetate 5:1).

Figure 4:
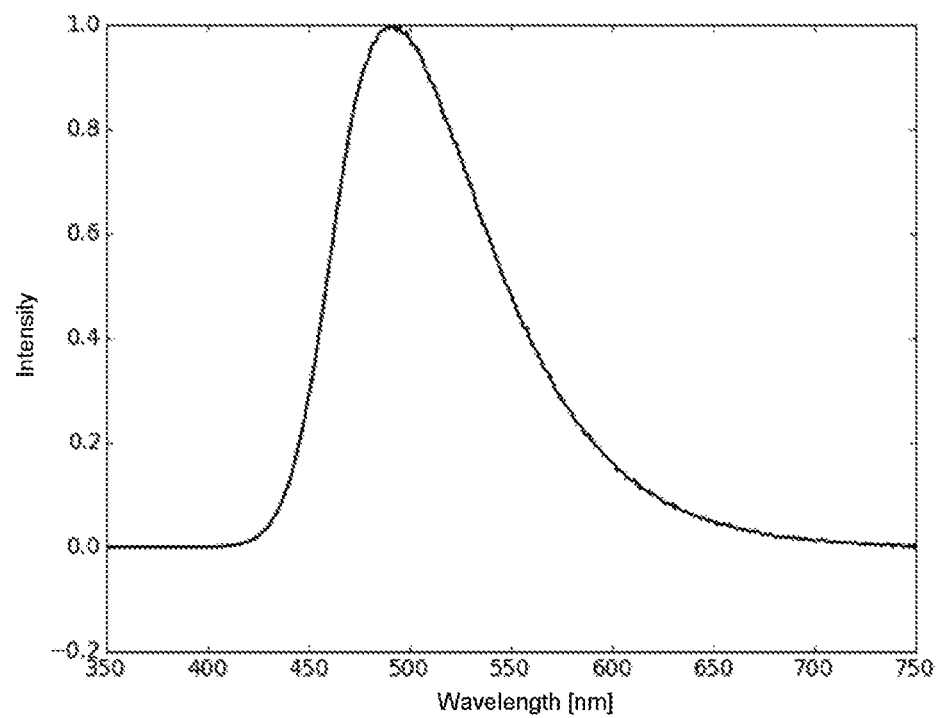
FIG. 4 is an emission spectrum of Example 4 (10% in PMMA).

FIG. 4 shows the emission spectrum of Example 4 (10% in PMMA). The emission maximum is at 489 nm. The photoluminescence quantum yield (PLQY) is 73% and the half-height width is 0.44 eV. The emission decay time is 5 µs.

Example 5

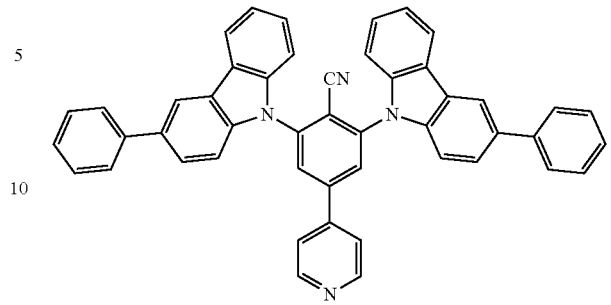

Example 5 was prepared according to GM1 (62% yield) and GM7 (66% yield).

MS (HPLC-MS), m/z (retention time): 662, (15.12 min)
$R_f$=0.07 (cyclohexane/ethyl acetate 5:1).

Figure 5:
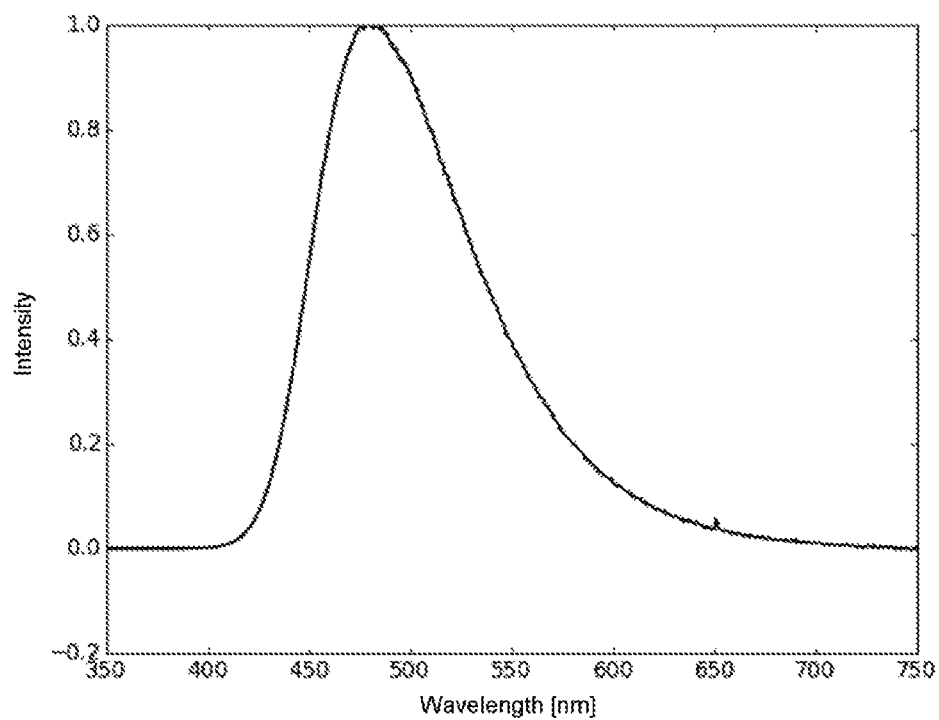
FIG. 5 is an emission spectrum of Example 5 (10% in PMMA).

FIG. 5 shows the emission spectrum of Example 5 (10% in PMMA). The emission maximum is at 483 nm. The photoluminescence quantum yield (PLQY) is 69% and the half-height width is 0.46 eV. The emission decay time is 13 µs.

Example 6

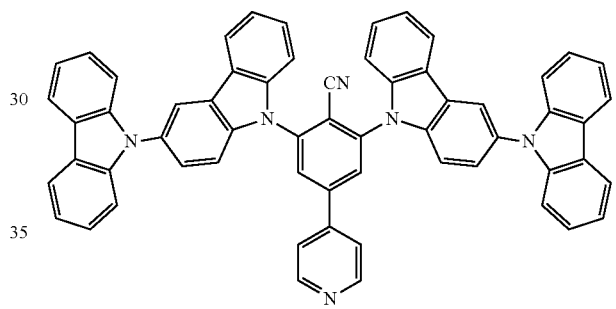

Example 6 was prepared according to GM1 (62% yield) and GM7 (81% yield).

MS (HPLC-MS), m/z (retention time): 840, (8.23 min)
$R_f$=0.24 (cyclohexane/ethyl acetate 5:1).

Figure 6:
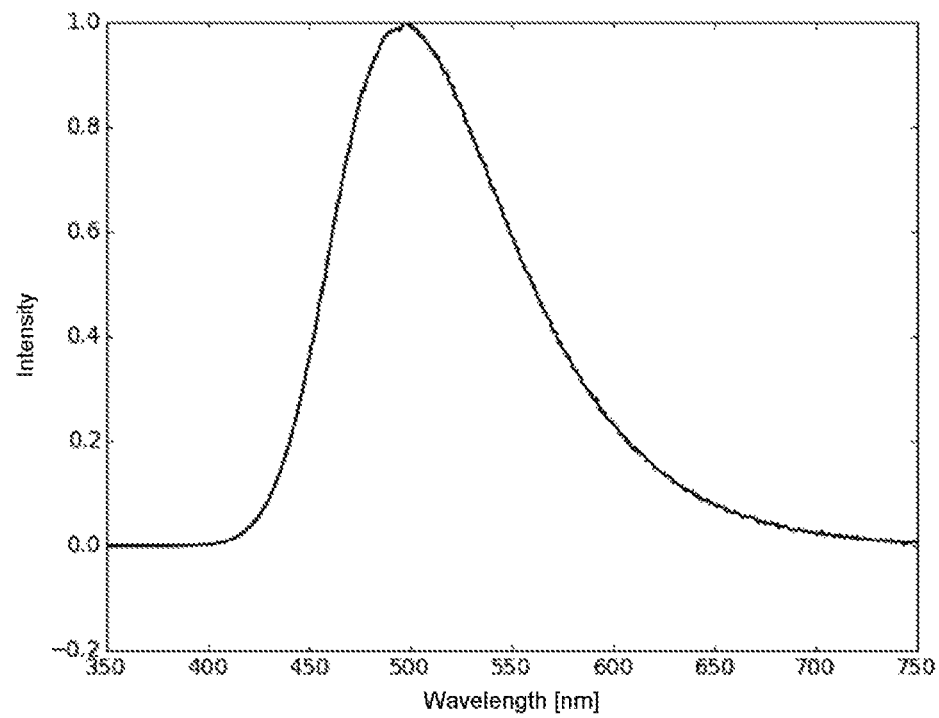
FIG. 6 is an emission spectrum of Example 6 (10% in PMMA).

FIG. 6 shows the emission spectrum of Example 6 (10% in PMMA). The emission maximum is at 497 nm. The photoluminescence quantum yield (PLQY) is 52% and the half-height width is 0.50 eV. The emission decay time is 9 µs.

Example 7

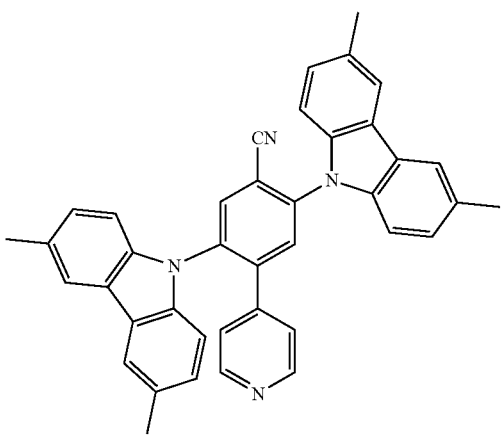

Example 7 was prepared according to GM4 (40% yield) and GM7 (73% yield).

MS (HPLC-MS), m/z (retention time): 566, (15.39 min)

$R_f$=0.27 (cyclohexane/ethyl acetate 5:1).

Figure 7:
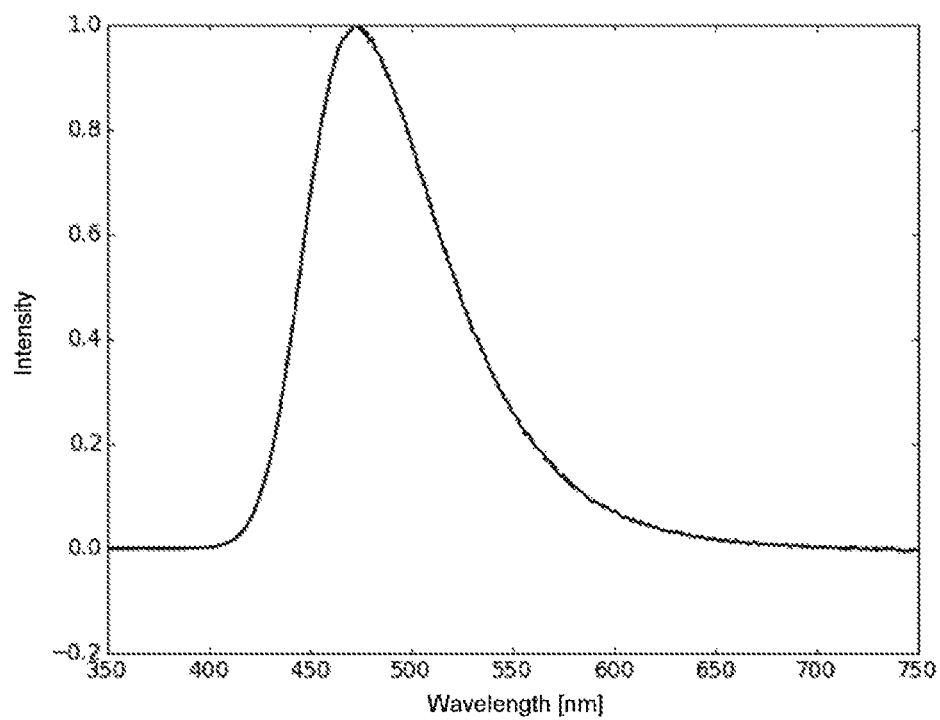
FIG. 7 is an emission spectrum of Example 7 (10% in PMMA).

FIG. 7 shows the emission spectrum of Example 7 (10% in PMMA). The emission maximum is at 472 nm. The photoluminescence quantum yield (PLQY) is 84% and the half-height width is 0.42 eV.

Example 8

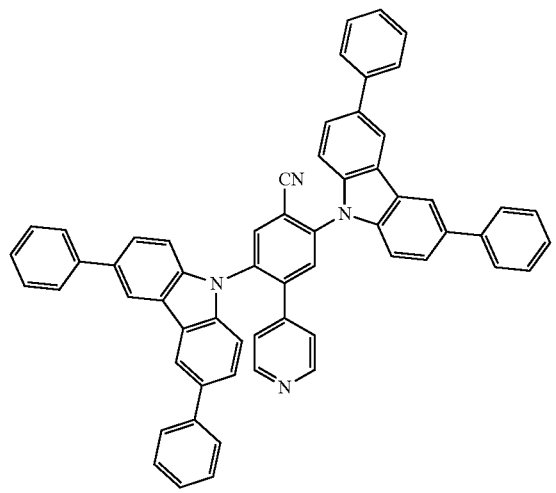 [SMILES: N#Cc1cc(-n2c3ccc(-c4ccccc4)cc3c3cc(-c4ccccc4)ccc32)c(-c2ccncc2)cc1-n1c2ccc(-c3ccccc3)cc2c2cc(-c3ccccc3)ccc21]

Example 8 was prepared according to GM4 (40% yield) and GM7 (57% yield).

MS (HPLC-MS), m/z (retention time): 814, (19.46 min)

$R_f$=0.26 (cyclohexane/ethyl acetate 5:1).

Figure 8:
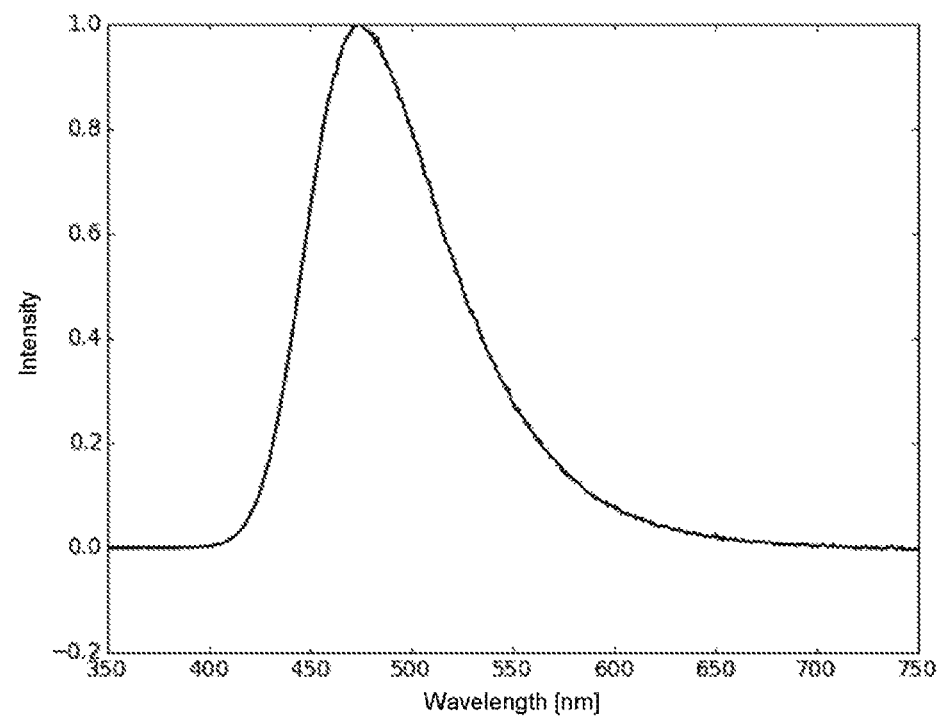
FIG. 8 is an emission spectrum of Example 8 (10% in PMMA).

FIG. 8 shows the emission spectrum of Example 8 (10% in PMMA). The emission maximum is at 475 nm. The photoluminescence quantum yield (PLQY) is 84% and the half-height width is 0.43 eV.

Example 9

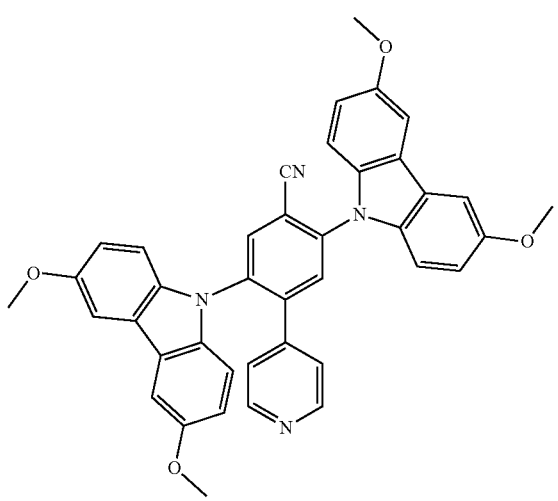

Example 9 was prepared according to GM4 (40% yield) and GM7 (74% yield).

MS (HPLC-MS), m/z (retention time): 630, (4.93 min)

$R_f$=0.05 (cyclohexane/ethyl acetate 5:1).

Figure 9:
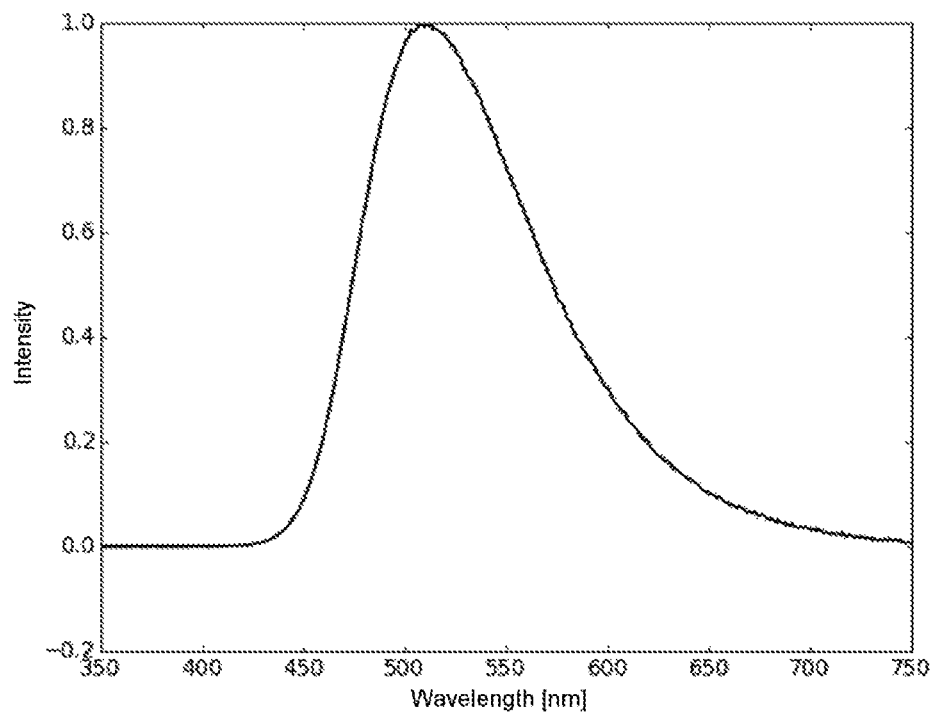
FIG. 9 is an emission spectrum of Example 9 (10% in PMMA).

FIG. 9 shows the emission spectrum of Example 9 (10% in PMMA). The emission maximum is at 511 nm. The photoluminescence quantum yield (PLQY) is 41% and the half-height width is 0.46 eV.

Example 10

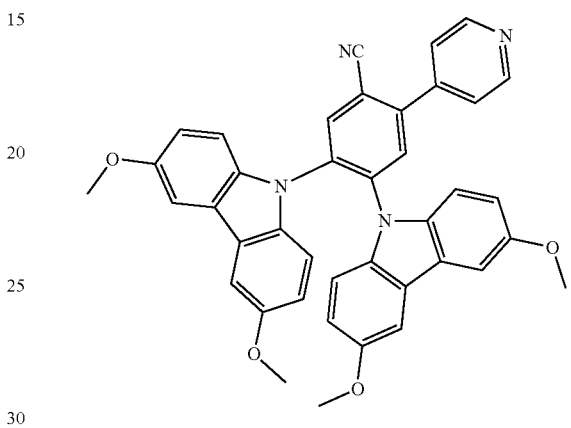

Example 10 was prepared according to GM5 (41% yield) and GM7 (32% yield).

MS (HPLC-MS), m/z (retention time): 630, (4.29 min)

Figure 10:
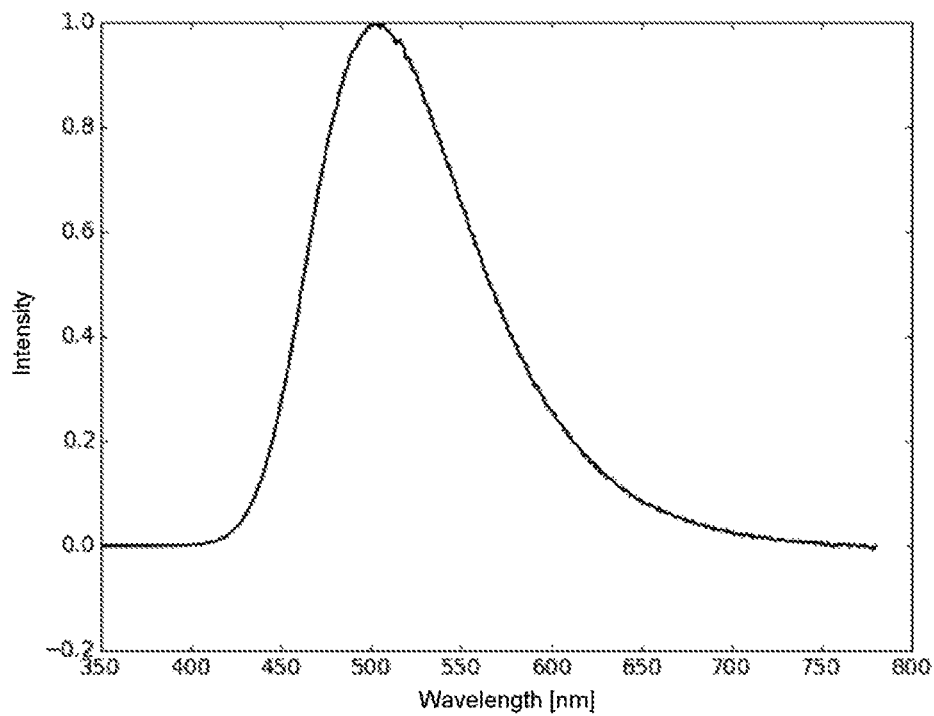
FIG. 10 is an emission spectrum of Example 10 (10% in PMMA).

FIG. 10 shows the emission spectrum of Example 10 (10% in PMMA). The emission maximum is at 501 nm. The photoluminescence quantum yield (PLQY) is 59% and the half-height width is 0.49 eV.

Example 11

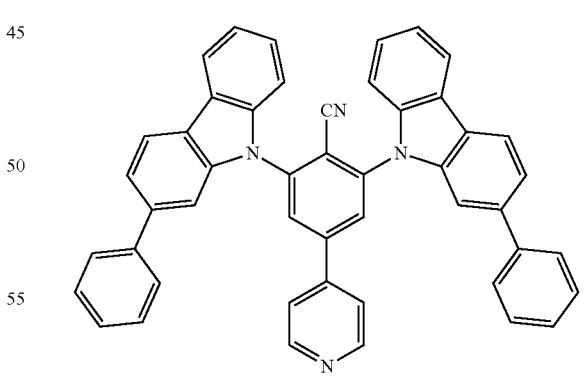

Example 11 was prepared according to GM1 (62% yield) and GM7 (78% yield).

MS (HPLC-MS), m/z (retention time): 662, (14.14 min)

Figure 11:
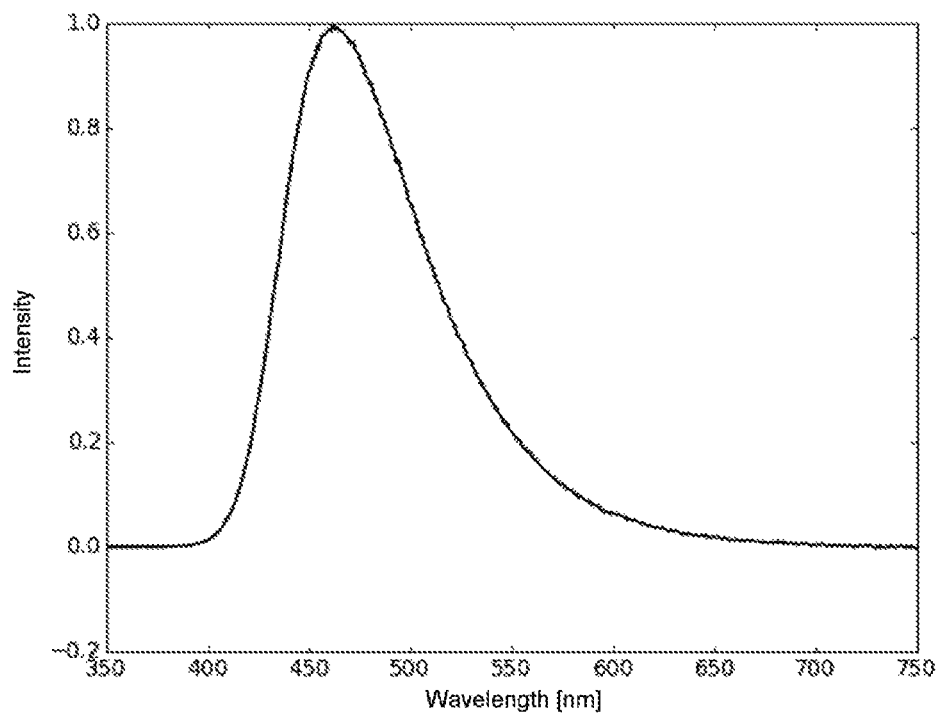
FIG. 11 is an emission spectrum of Example 11 (10% in PMMA).

FIG. 11 shows the emission spectrum of Example 11 (10% in PMMA). The emission maximum is at 462 nm. The photoluminescence quantum yield (PLQY) is 55% and the half-height width is 0.45 eV.

Example 12

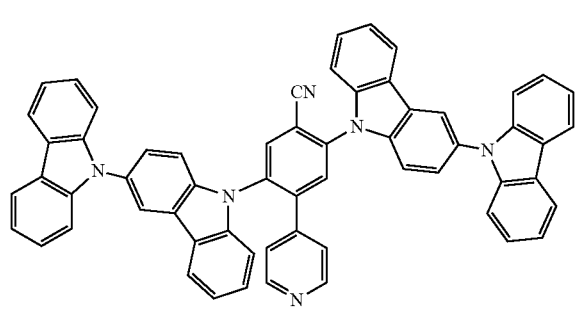 [SMILES: N#Cc1cc(-n2c3ccccc3c3cc(-n4c5ccccc5c5ccccc54)ccc32)c(-c2ccncc2)cc1-n1c2ccccc2c2cc(-n3c4ccccc4c4ccccc43)ccc21]

Example 12 was prepared according to GM4 (40% yield) and GM7 (38% yield).

MS (HPLC-MS), m/z (retention time): 841, (20.13 min)

Figure 12:
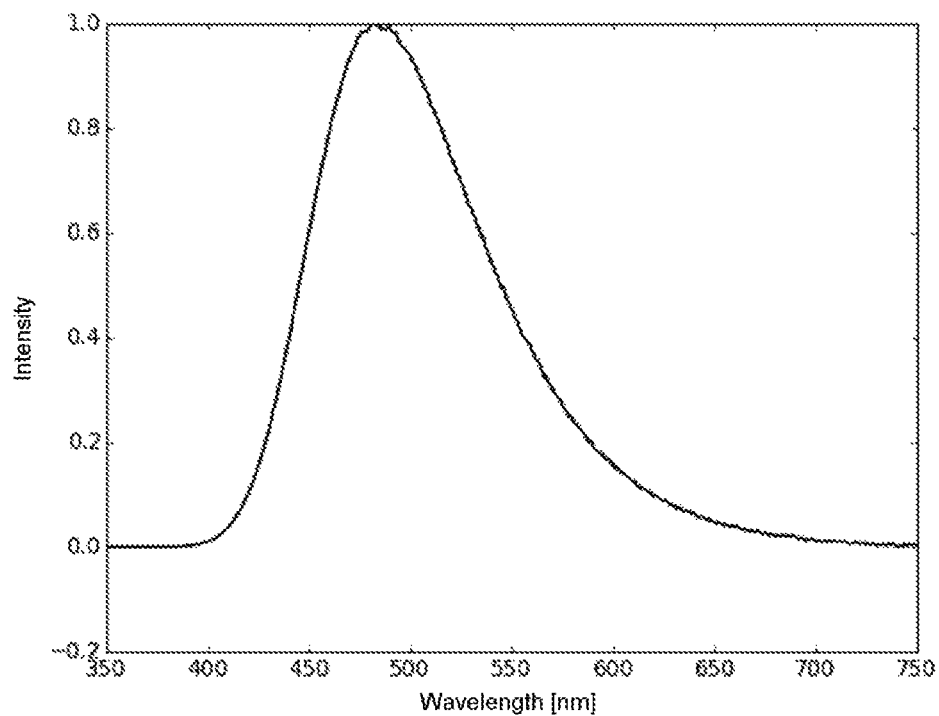
FIG. 12 is an emission spectrum of Example 12 (10% in PMMA).

FIG. 12 shows the emission spectrum of Example 12 (10% in PMMA). The emission maximum is at 482 nm. The photoluminescence quantum yield (PLQY) is 61% and the half-height width is 0.51 eV.

Example 13

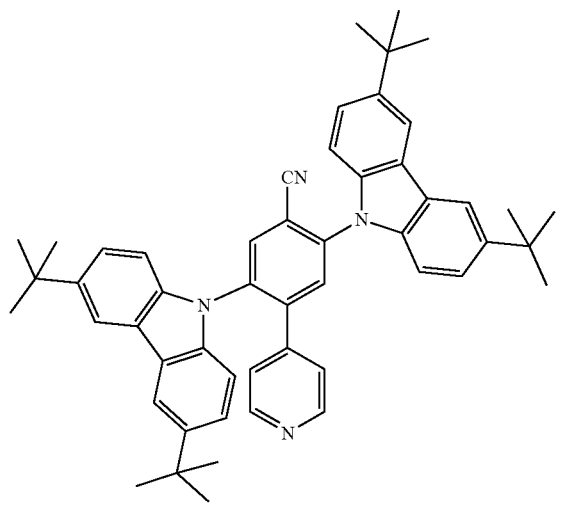 [SMILES: CC(C)(C)c1ccc2c(c1)c1cc(C(C)(C)C)ccc1n2-c1cc(-c2ccncc2)c(-n2c3ccc(C(C)(C)C)cc3c3cc(C(C)(C)C)ccc32)cc1C#N]

Example 13 was prepared according to GM4 (40% yield) and GM7 (52% yield).

MS (HPLC-MS), m/z (retention time): 735, (23.35 min)

Figure 13:
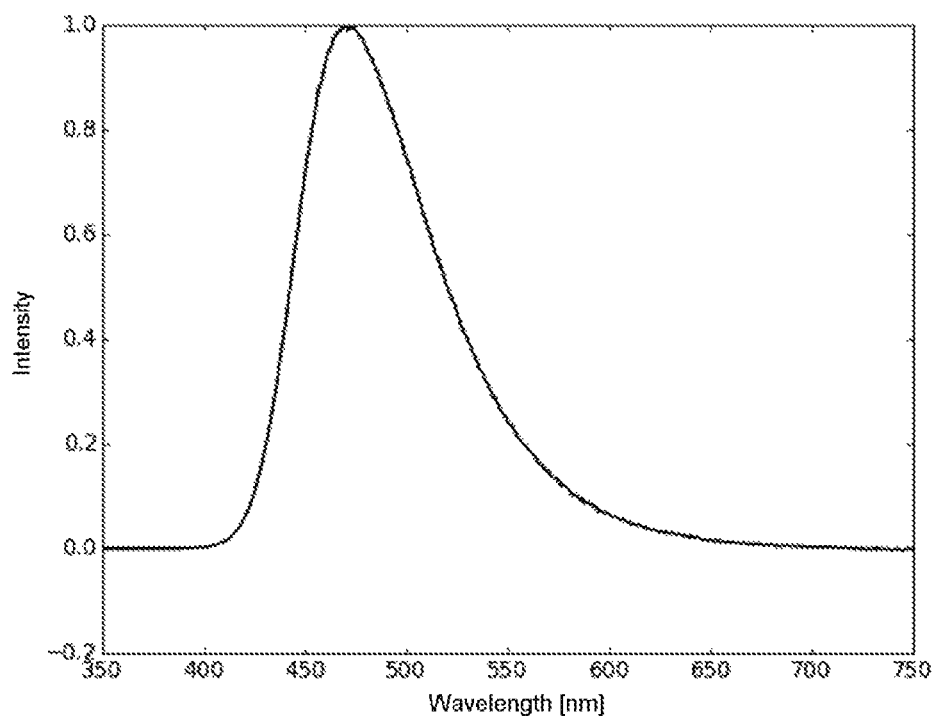
FIG. 13 is an emission spectrum of Example 13 (10% in PMMA).

FIG. 13 shows the emission spectrum of Example 13 (10% in PMMA). The emission maximum is at 471 nm. The photoluminescence quantum yield (PLQY) is 81% and the half-height width is 0.42 eV.

Example 14

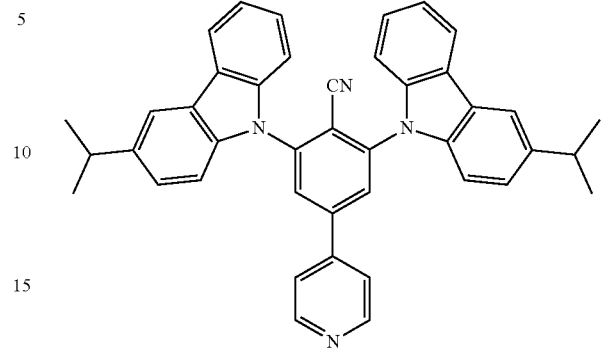

Example 14 was prepared according to GM4 (40% yield) and GM7 (66% yield).

MS (HPLC-MS), m/z (retention time): 623, (6.65 min)

Figure 14:
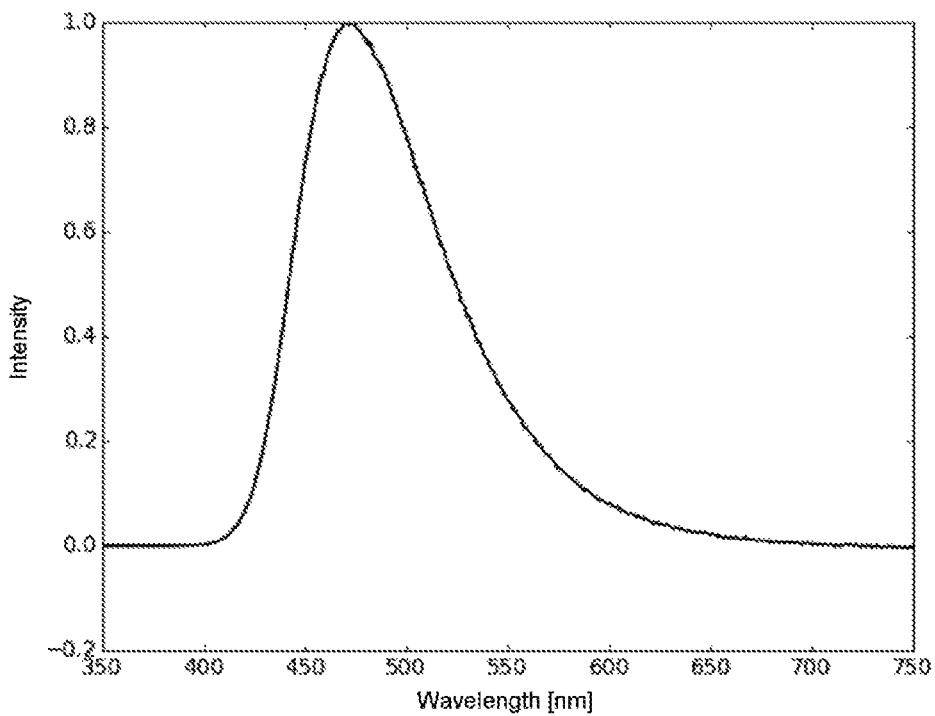
FIG. 14 is an emission spectrum of Example 14 (10% in PMMA).

FIG. 14 shows the emission spectrum of Example 14 (10% in PMMA). The emission maximum is at 474 nm. The photoluminescence quantum yield (PLQY) is 75% and the half-height width is 0.44 eV. The emission decay time is 38 µs.

Example 15

Example 15 was prepared according to GM1 (62% yield) and GM7 (72% yield).

Figure 15:
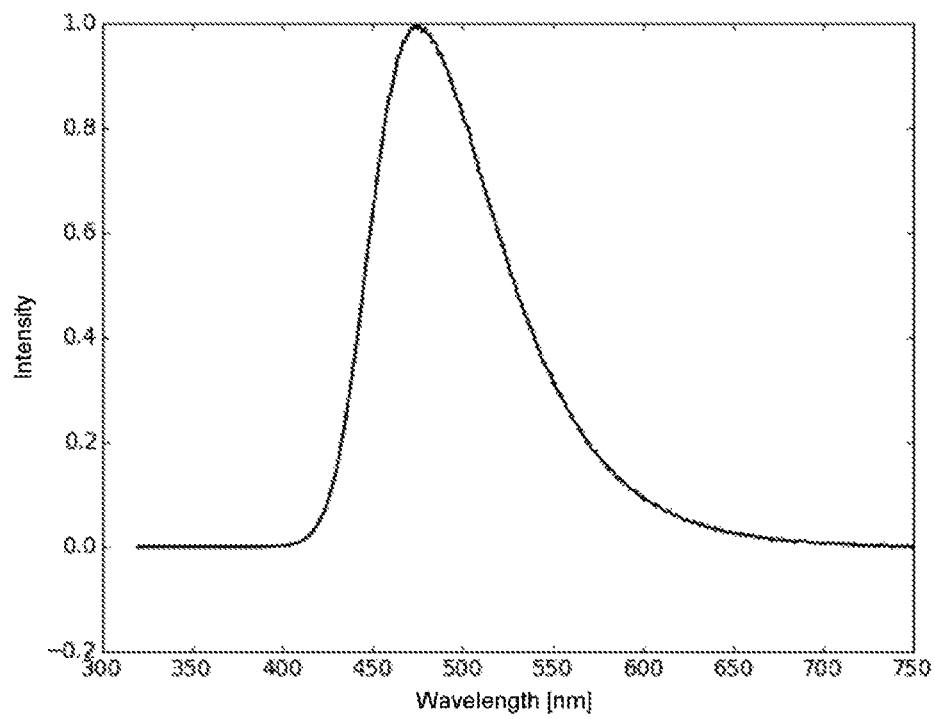
FIG. 15 is an emission spectrum of Example 15 (10% in PMMA).

FIG. 15 shows the emission spectrum of Example 15 (10% in PMMA). The emission maximum is at 475 nm. The photoluminescence quantum yield (PLQY) is 48% and the half-height width is 0.44 eV. The emission decay time is 24 µs.

Example 16

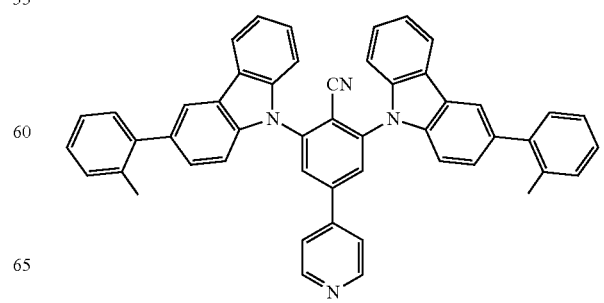

Example 16 was prepared according to GM1 (62% yield) and GM7 (29% yield).

Figure 16:
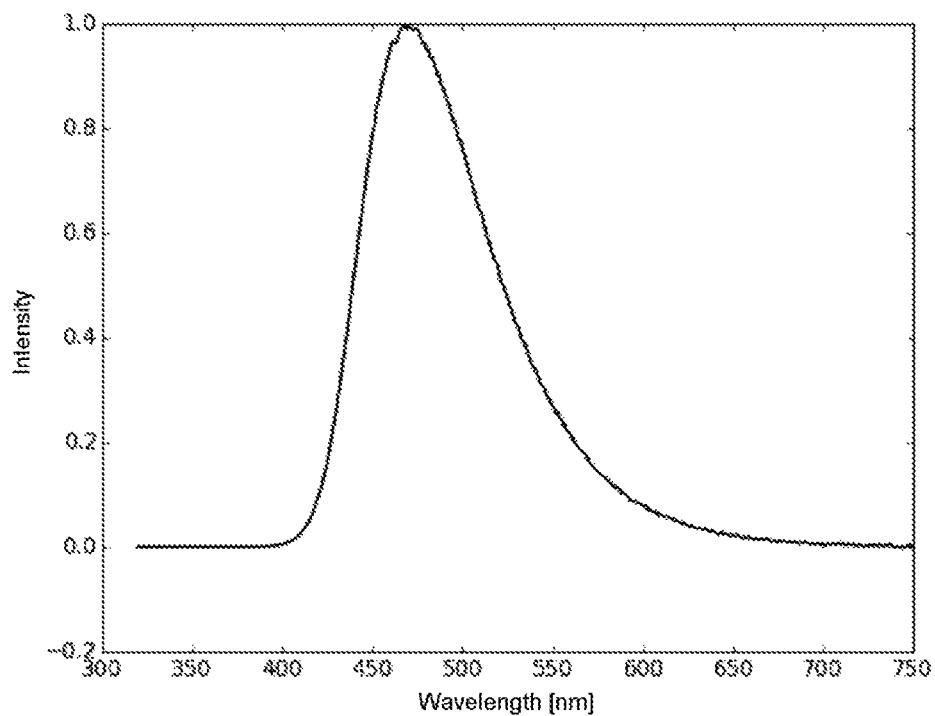
FIG. 16 is an emission spectrum of Example 16 (10% in PMMA).

FIG. 16 shows the emission spectrum of Example 16 (10% in PMMA). The emission maximum is at 470 nm. The photoluminescence quantum yield (PLQY) is 65% and the half-height width is 0.45 eV. The emission decay time is 56 µs.

Example 17

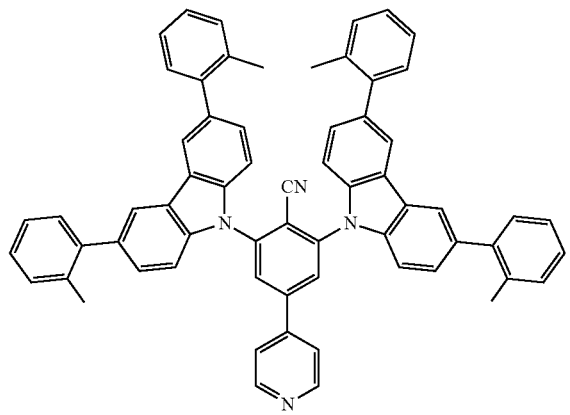 [SMILES: Cc1ccccc1-c1ccc2c(c1)c1cc(-c3ccccc3C)ccc1n2-c1cc(-c2ccncc2)cc(-n2c3ccc(-c4ccccc4C)cc3c3cc(-c4ccccc4C)ccc32)c1C#N]

Example 17 was prepared according to GM1 (62% yield) and GM7 (51% yield).

Figure 17:
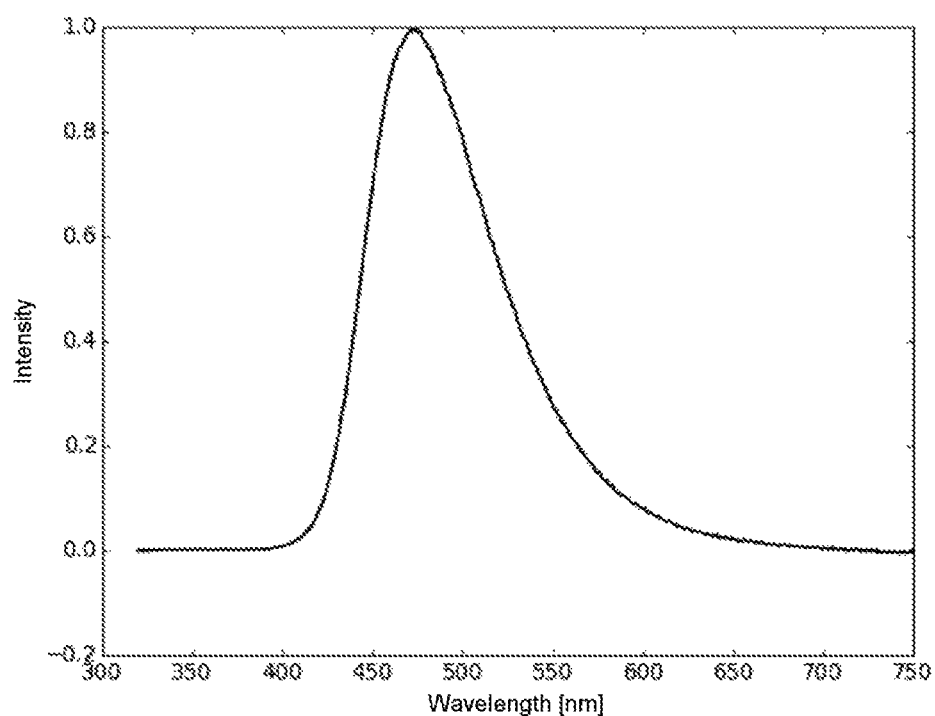
FIG. 17 is an emission spectrum of Example 17 (10% in PMMA).

FIG. 17 shows the emission spectrum of Example 17 (10% in PMMA). The emission maximum is at 476 nm. The photoluminescence quantum yield (PLQY) is 66% and the half-height width is 0.43 eV. The emission decay time is 23 µs.

Example 18

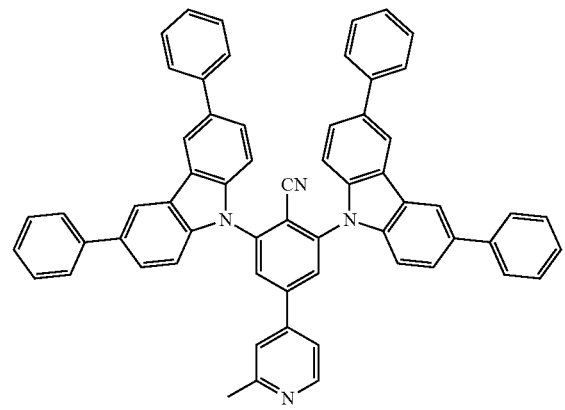 [SMILES: Cc1cc(-c2cc(-n3c4ccc(-c5ccccc5)cc4c4cc(-c5ccccc5)ccc43)c(C#N)c(-n3c4ccc(-c5ccccc5)cc4c4cc(-c5ccccc5)ccc43)c2)ccn1]

Example 18 was prepared with a 2-methyl-4-pyridineboronic acid instead of a 4-pyridine-boronic acid according to GM1 (36% yield) and GM7 (90% yield).

Figure 18:
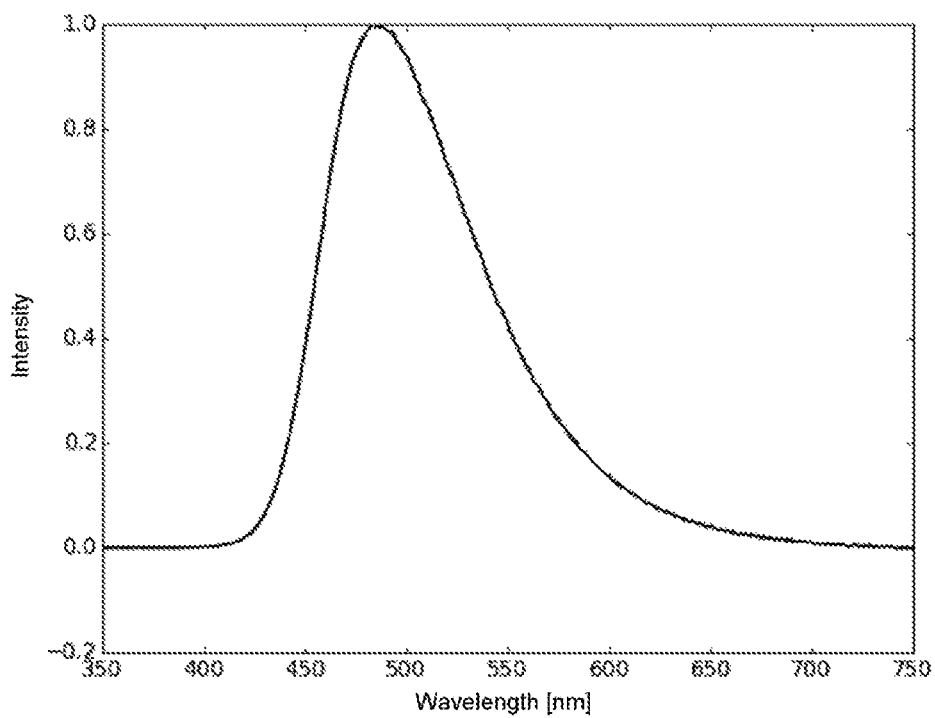
FIG. 18 is an emission spectrum of Example 18 (10% in PMMA).

FIG. 18 shows the emission spectrum of Example 18 (10% in PMMA). The emission maximum is at 483 nm. The photoluminescence quantum yield (PLQY) is 71% and the half-height width is 0.44 eV. The emission decay time is 5 µs.

Example 19

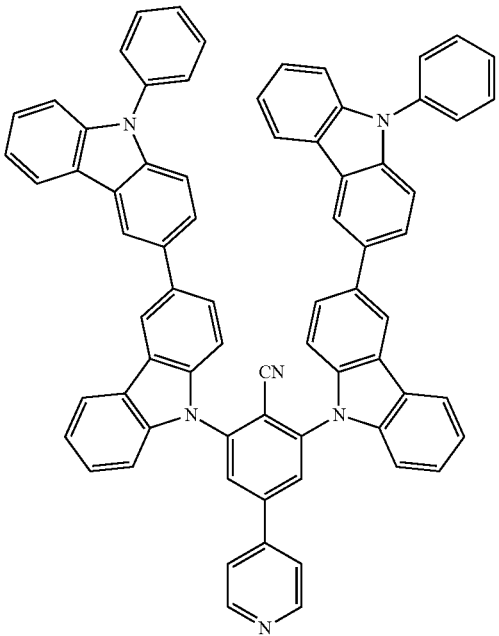 [SMILES: N#Cc1c(-n2c3ccccc3c3cc(-c4ccc5c(c4)c4ccccc4n5-c4ccccc4)ccc32)cc(-c2ccncc2)cc1-n1c2ccccc2c2cc(-c3ccc4c(c3)c3ccccc3n4-c3ccccc3)ccc21]

Example 19 was prepared according to GM1 (62% yield) and GM7 (88% yield).

Figure 19:
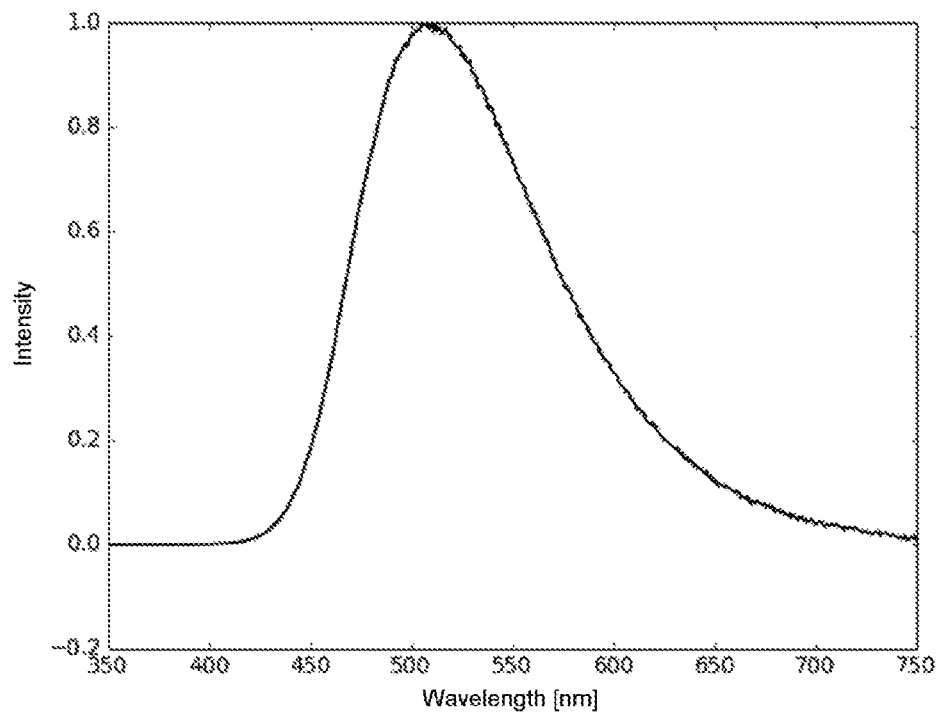
FIG. 19 is an emission spectrum of Example 19 (10% in PMMA).

FIG. 19 shows the emission spectrum of Example 19 (10% in PMMA). The emission maximum is at 510 nm. The photoluminescence quantum yield (PLQY) is 38% and the half-height width is 0.50 eV. The emission decay time is 3 µs.

Example 20

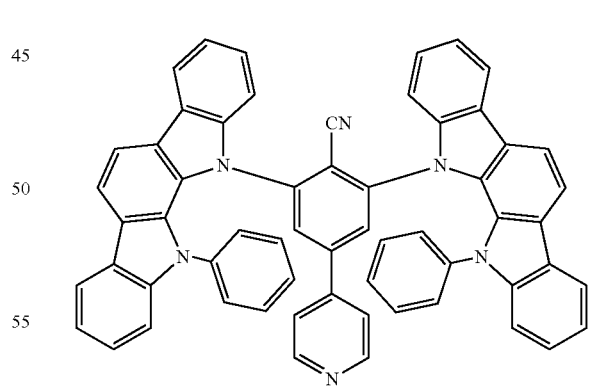

Example 20 was prepared according to GM1 (62% yield) and GM7 (9% yield).

Figure 20:
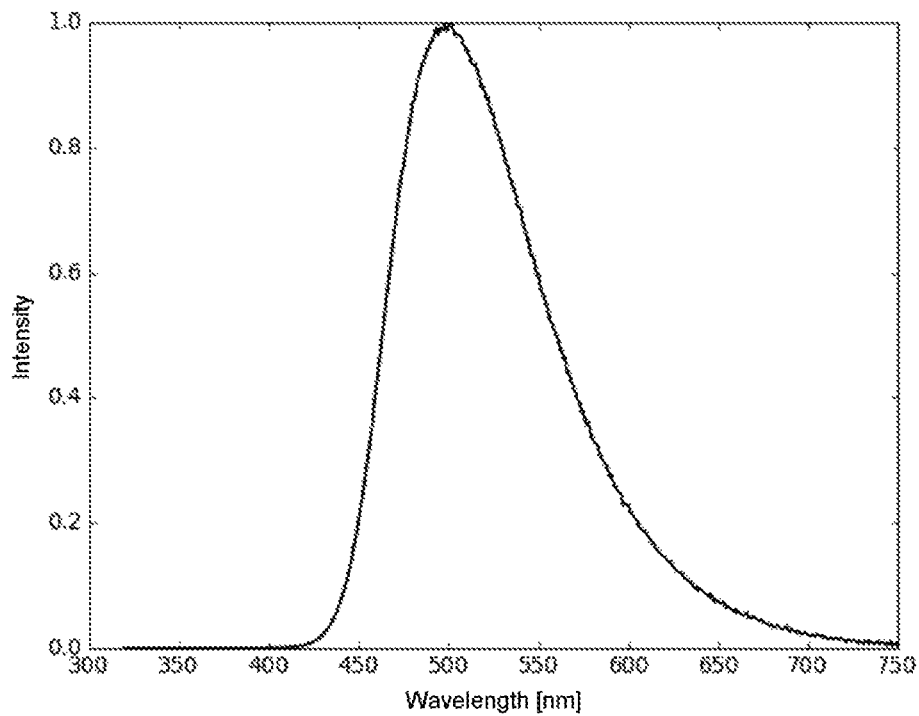
FIG. 20 is an emission spectrum of Example 20 (10% in PMMA).

FIG. 20 shows the emission spectrum of Example 20 (10% in PMMA). The emission maximum is at 498 nm. The photoluminescence quantum yield (PLQY) is 40% and the half-height width is 0.46 eV. The emission decay time is 4 µs.

Example 21

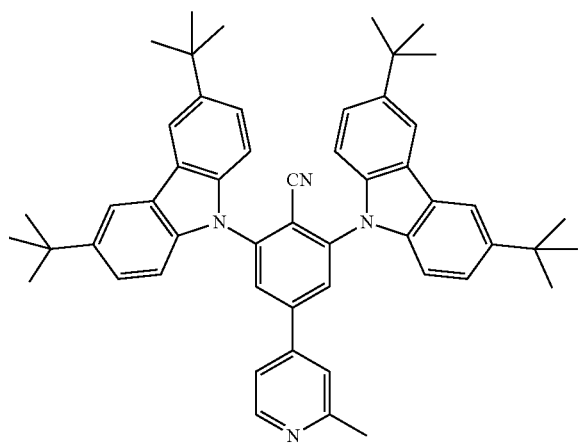 [SMILES: Cc1cc(-c2cc(-n3c4ccc(C(C)(C)C)cc4c4cc(C(C)(C)C)ccc43)c(C#N)c(-n3c4ccc(C(C)(C)C)cc4c4cc(C(C)(C)C)ccc43)c2)ccn1]

Example 21 was prepared with a 2-methyl-4-pyridineboronic acid instead of a 4-pyridine-boronic acid according to GM1 (36% yield) and GM7 (71% yield).

Figure 21:
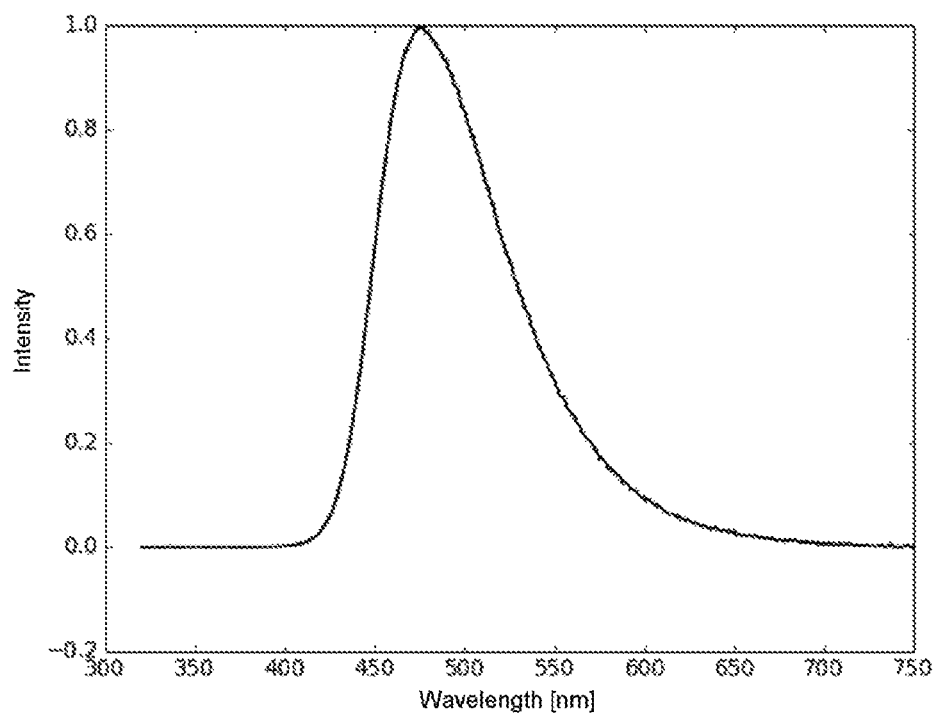
FIG. 21 is an emission spectrum of Example 21 (10% in PMMA).

FIG. 21 shows the emission spectrum of Example 21 (10% in PMMA). The emission maximum is at 477 nm. The photoluminescence quantum yield (PLQY) is 74% and the half-height width is 0.43 eV. The emission decay time is 14 µs.

Example 22

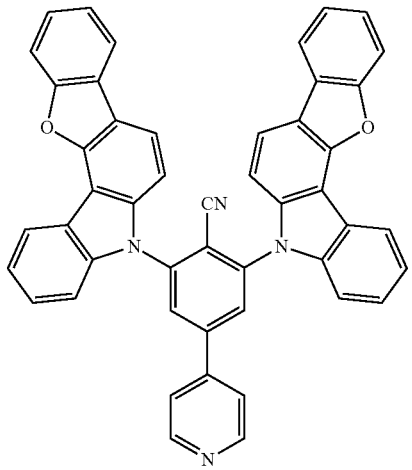 [SMILES: N#Cc1c(-n2c3ccccc3c3c4oc5ccccc5c4ccc32)cc(-c2ccncc2)cc1-n1c2ccccc2c2c3oc4ccccc4c3ccc21]

Example 22 was prepared according to GM1 (62% yield) and GM7 (73% yield).

Figure 22:
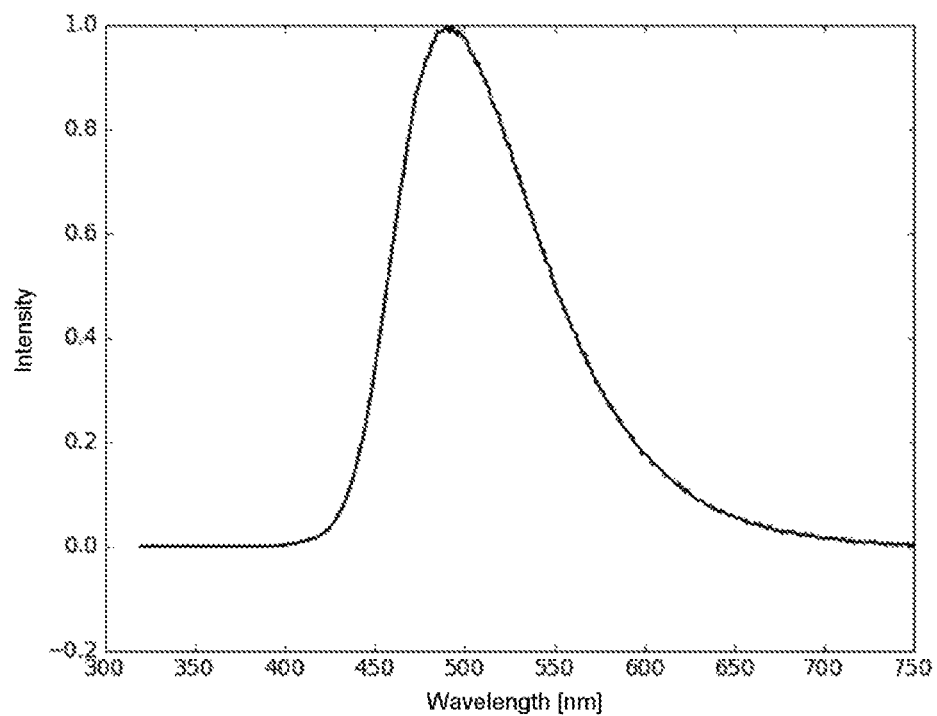
FIG. 22 is an emission spectrum of Example 22 (10% in PMMA).

FIG. 22 shows the emission spectrum of Example 22 (10% in PMMA). The emission maximum is at 493 nm. The photoluminescence quantum yield (PLQY) is 63% and the half-height width is 0.46 eV. The emission decay time is 5 µs.

Example 23

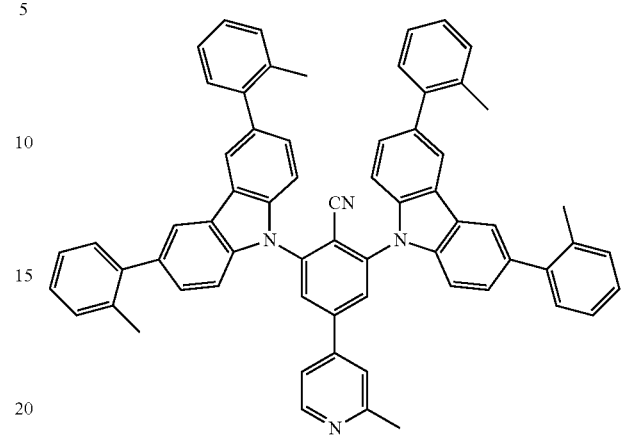

Example 23 was prepared with a 2-methyl-4-pyridineboronic acid instead of a 4-pyridine-boronic acid according to GM1 (36% yield) and GM7 (86% yield).

Figure 23:
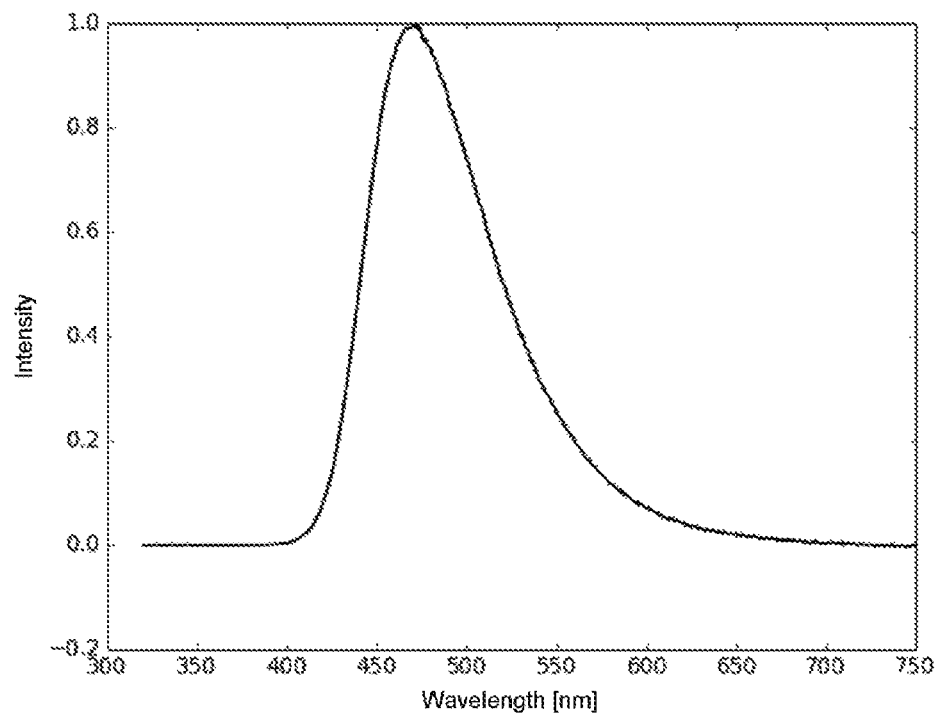
FIG. 23 is an emission spectrum of Example 23 (10% in PMMA).

FIG. 23 shows the emission spectrum of Example 23 (10% in PMMA). The emission maximum is at 472 nm. The photoluminescence quantum yield (PLQY) is 76% and the half-height width is 0.43 eV. The emission decay time is 35 µs.

Example 24

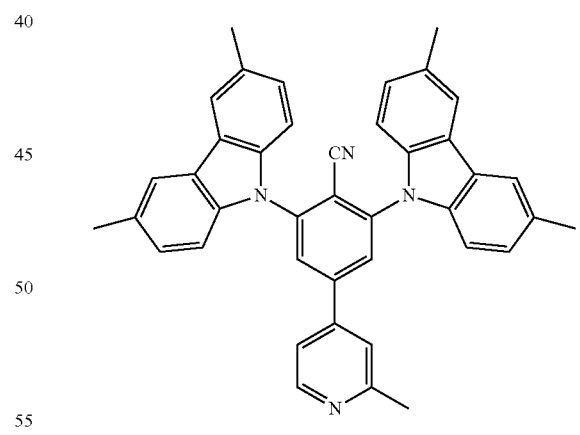

Example 24 was prepared with a 2-methyl-4-pyridineboronic acid instead of a 4-pyridine-boronic acid according to GM1 (36% yield) and GM7 (99% yield).

Figure 24:
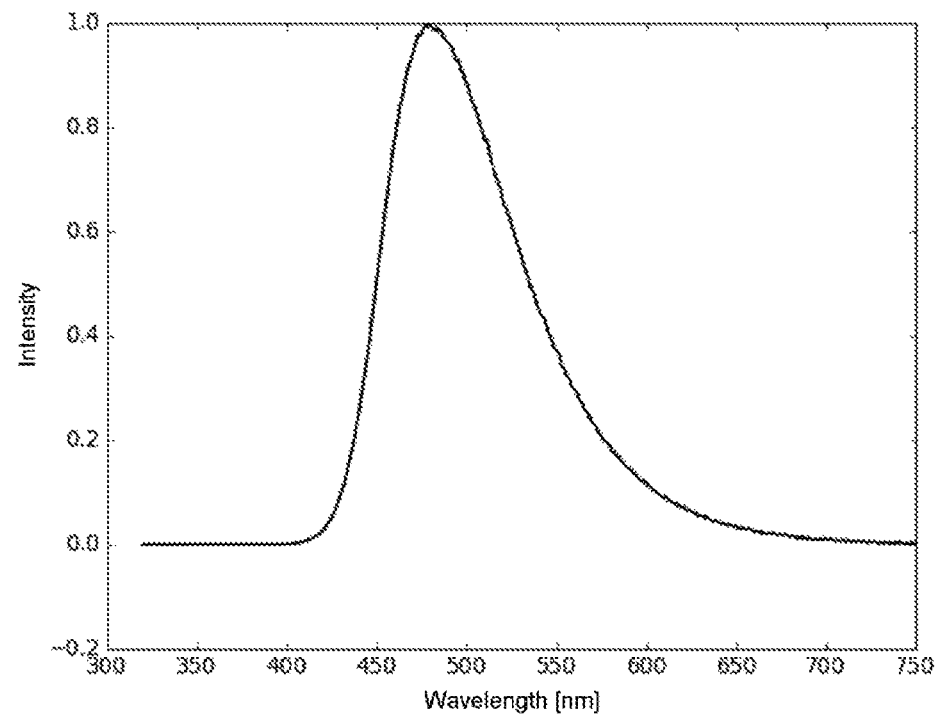
FIG. 24 is an emission spectrum of Example 24 (10% in PMMA).

FIG. 24 shows the emission spectrum of Example 24 (10% in PMMA). The emission maximum is at 477 nm. The photoluminescence quantum yield (PLQY) is 65% and the half-height width is 0.44 eV. The emission decay time is 12 µs.

Example 25

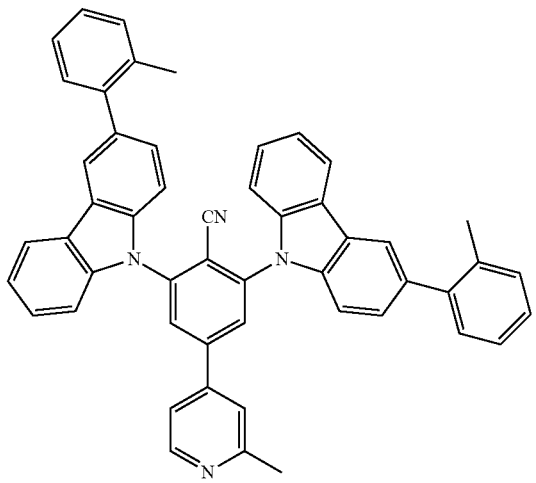 [SMILES: Cc1cc(-c2cc(-n3c4ccccc4c4cc(-c5ccccc5C)ccc43)c(C#N)c(-n3c4ccccc4c4cc(-c5ccccc5C)ccc43)c2)ccn1]

Example 25 was prepared with a 2-methyl-4-pyridineboronic acid instead of a 4-pyridine-boronic acid according to GM1 (36% yield) and GM7 (42% yield).

Figure 25:
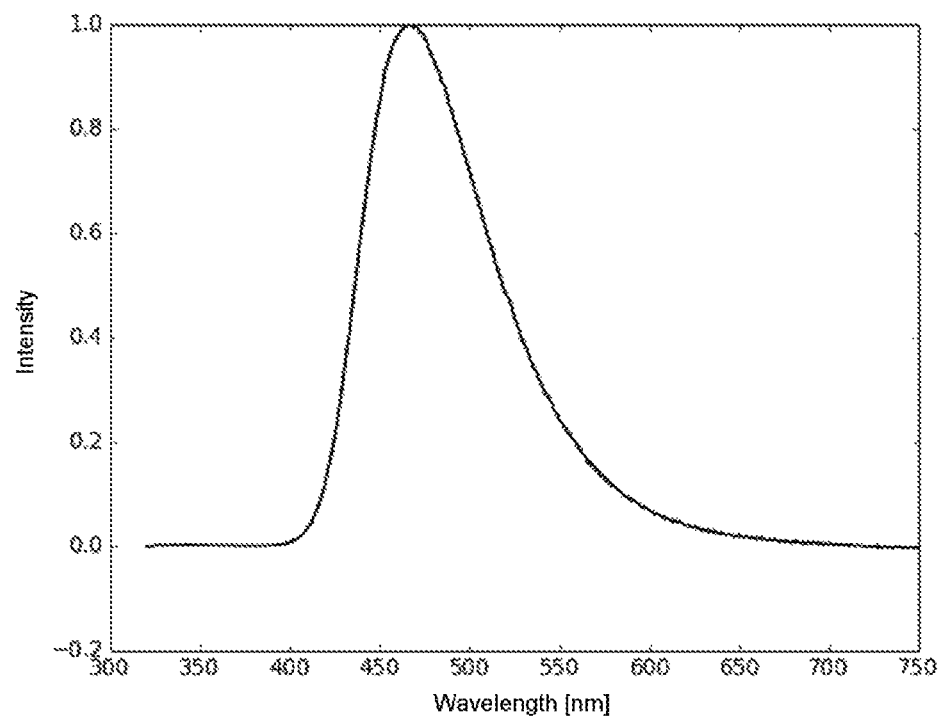
FIG. 25 is an emission spectrum of Example 25 (10% in PMMA).

FIG. 25 shows the emission spectrum of Example 25 (10% in PMMA). The emission maximum is at 466 nm. The photoluminescence quantum yield (PLQY) is 76% and the half-height width is 0.45 eV. The emission decay time is 73 μs.

Example 26

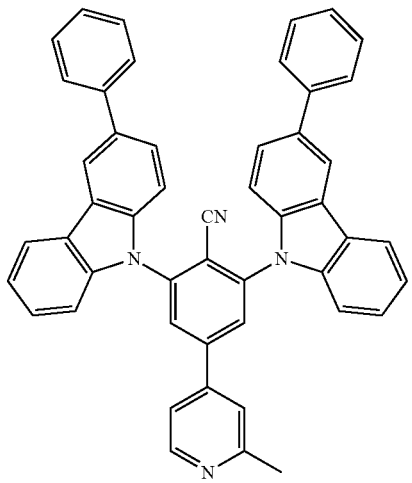 [SMILES: Cc1cc(-c2cc(-n3c4ccccc4c4cc(-c5ccccc5)ccc43)c(C#N)c(-n3c4ccccc4c4cc(-c5ccccc5)ccc43)c2)ccn1]

Example 26 was prepared with a 2-methyl-4-pyridineboronic acid instead of a 4-pyridine-boronic acid according to GM1 (36% yield) and GM7 (78% yield).

Figure 26:
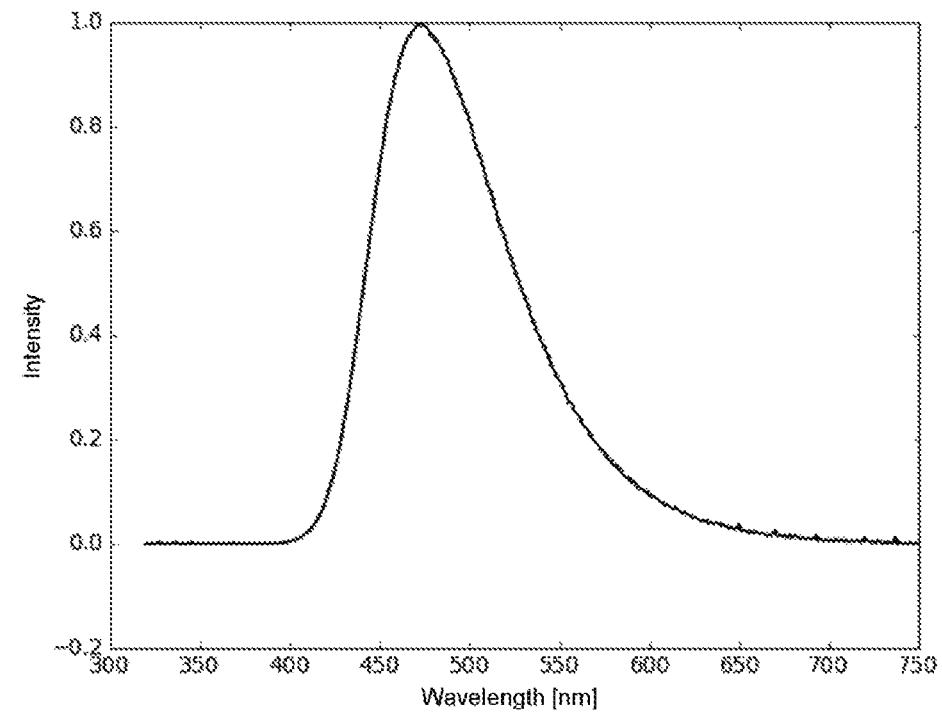
FIG. 26 is an emission spectrum of Example 26 (10% in PMMA).

FIG. 26 shows the emission spectrum of Example 26 (10% in PMMA). The emission maximum is at 473 nm. The photoluminescence quantum yield (PLQY) is 71% and the half-height width is 0.46 eV. The emission decay time is 65 μs.

Example 27

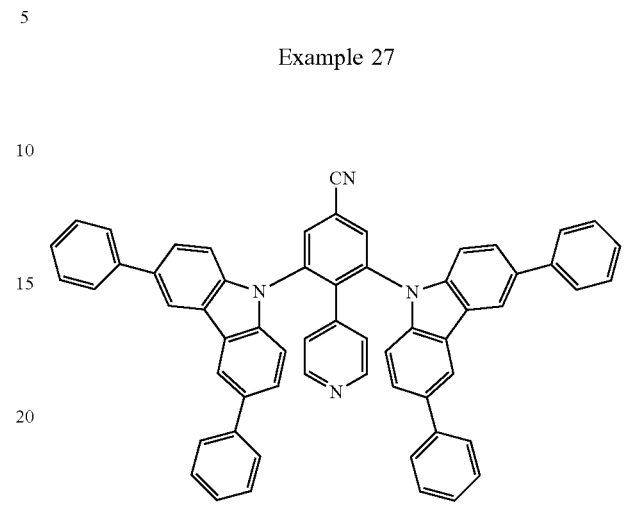

Example 27 was prepared according to GM3 (10% yield) and GM7 (2% yield).

Figure 27:
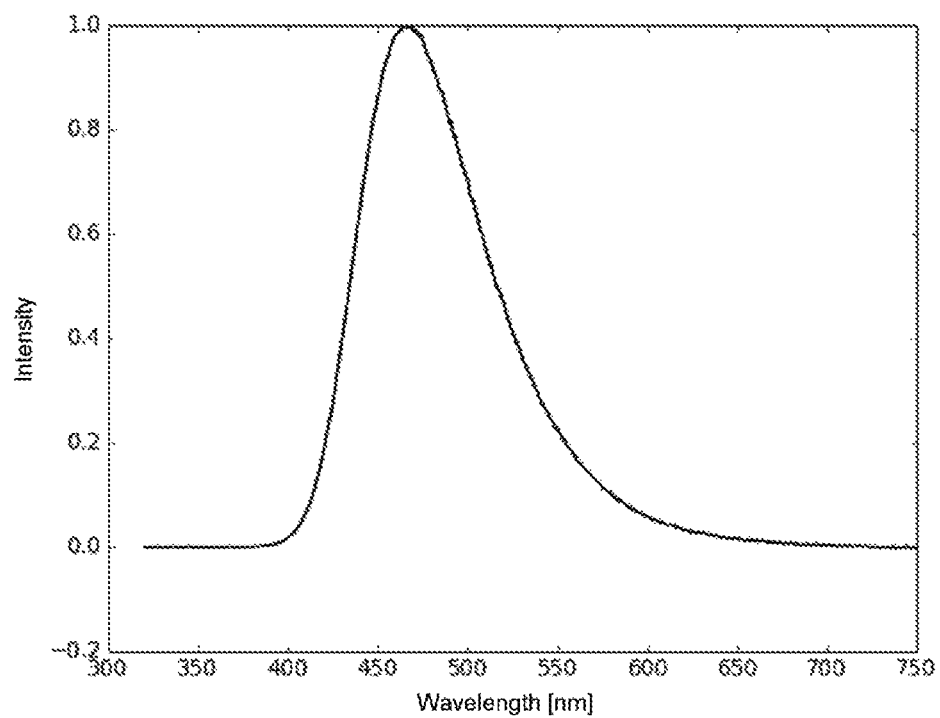
FIG. 27 is an emission spectrum of Example 27 (10% in PMMA).

FIG. 27 shows the emission spectrum of Example 27 (10% in PMMA). The emission maximum is at 467 nm. The photoluminescence quantum yield (PLQY) is 68% and the half-height width is 0.45 eV.

Example 28

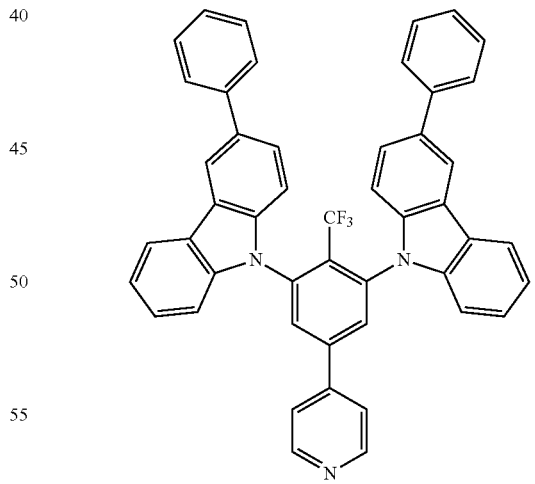

Example 28 was prepared according to GM1 (62% yield) and GM7 (23% yield).

Figure 28:
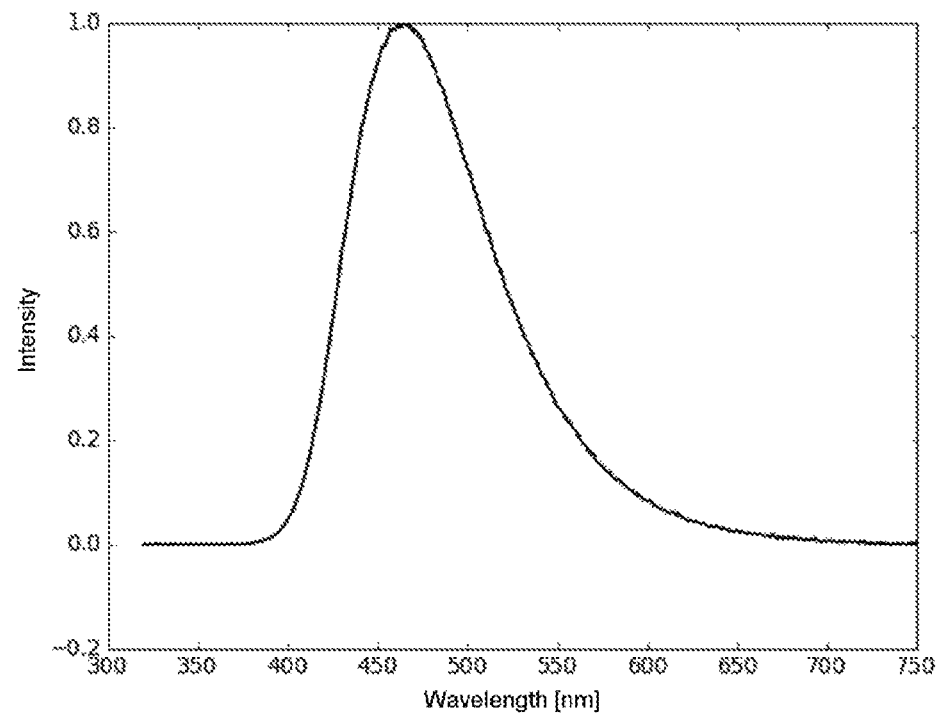
FIG. 28 is an emission spectrum of Example 28 (10% in PMMA).

FIG. 28 shows the emission spectrum of Example 28 (10% in PMMA). The emission maximum is at 465 nm. The photoluminescence quantum yield (PLQY) is 33% and the half-height width is 0.52 eV.

Example 29

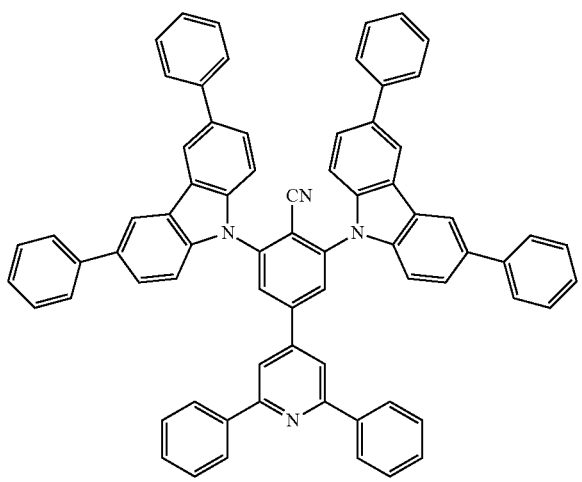 [SMILES: N#Cc1c(-n2c3ccc(-c4ccccc4)cc3c3cc(-c4ccccc4)ccc32)cc(-c2cc(-c3ccccc3)nc(-c3ccccc3)c2)cc1-n1c2ccc(-c3ccccc3)cc2c2cc(-c3ccccc3)ccc21]

Example 29 was prepared by the reaction of 2,6-dichloro-4-iodopyridine (1.0 equivalent) with a 4-cyano-3,5-difluorobenzeneboronic ester (1.1 equivalents) under reaction conditions analogous to GM1 (80% yield), subsequent reaction with phenylboronic acid (2.5 equivalents) in a 1,4-dioxane/water mixture (10:1 ratio) at 100° C. and a reaction time of 24 h (38% yield) and subsequent reaction according to GM7 (71% yield).

Figure 29:
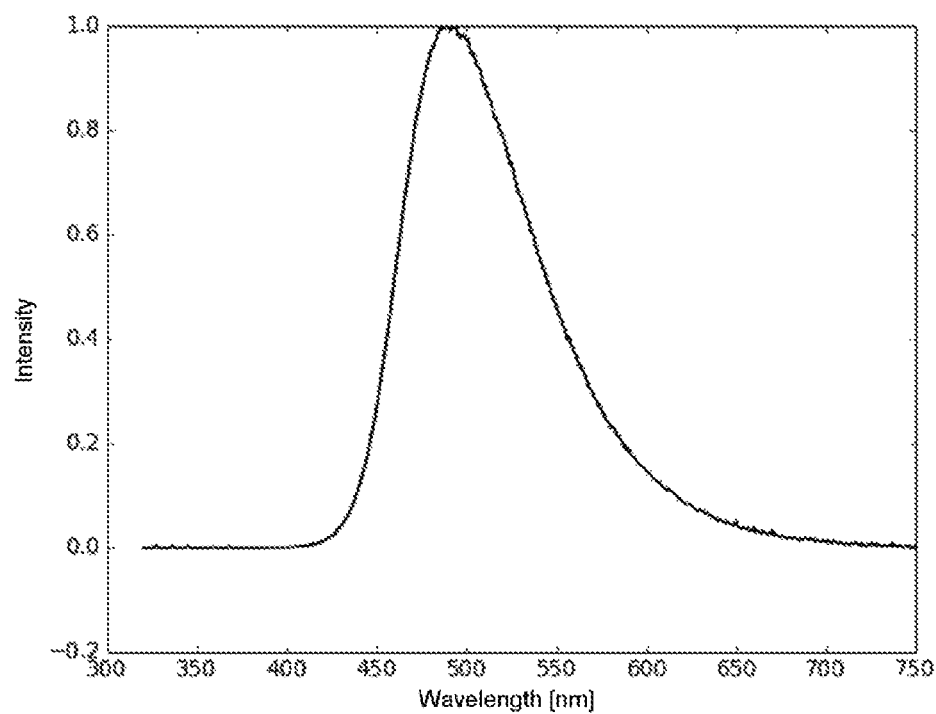
FIG. 29 is an emission spectrum of Example 29 (10% in PMMA).

FIG. 29 shows the emission spectrum of Example 29 (10% in PMMA). The emission maximum is at 492 nm. The photoluminescence quantum yield (PLQY) is 76% and the half-height width is 0.43 eV. The emission decay time is 6 µs.

Example 30

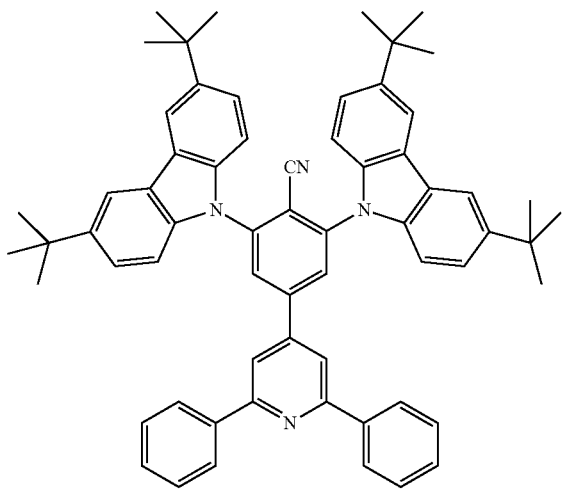 [SMILES: CC(C)(C)c1ccc2c(c1)c1cc(C(C)(C)C)ccc1n2-c1cc(-c2cc(-c3ccccc3)nc(-c3ccccc3)c2)cc(-n2c3ccc(C(C)(C)C)cc3c3cc(C(C)(C)C)ccc32)c1C#N]

Example 30 was prepared by the reaction of 2,6-dichloro-4-iodopyridine (1.0 equivalent) with a 4-cyano-3,5-difluorobenzeneboronic ester (1.1 equivalents) under reaction conditions analogous to GM1 (80% yield), subsequent reaction with phenylboronic acid (2.5 equivalents) in a 1,4-dioxane/water mixture (10:1 ratio) at 100° C. and a reaction time of 24 h (38% yield) and subsequent reaction according to GM7 (25% yield).

Figure 30:
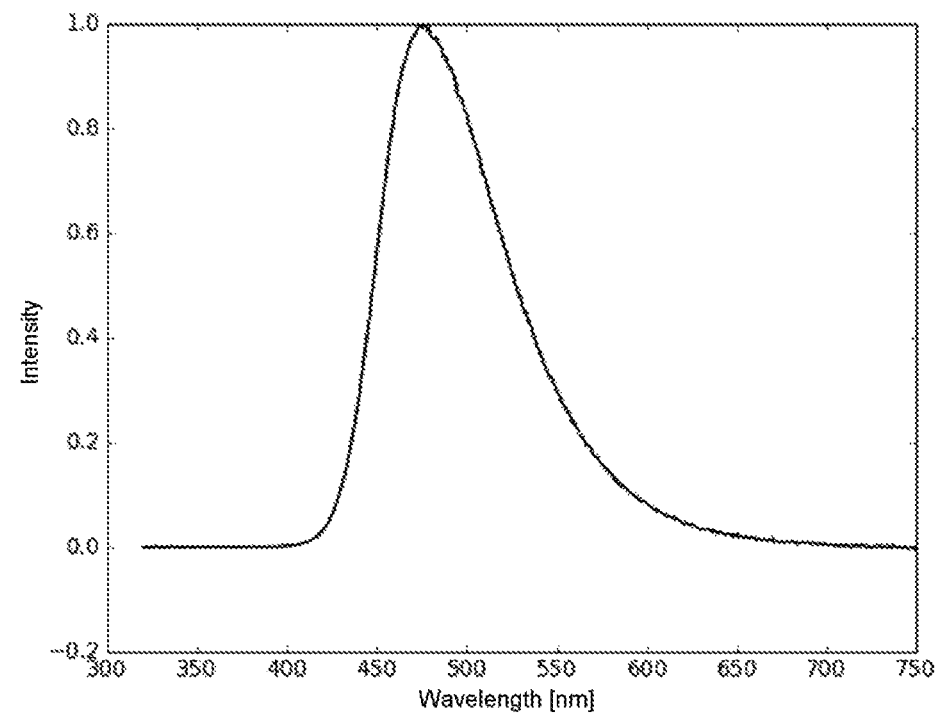
FIG. 30 is an emission spectrum of Example 30 (10% in PMMA).

FIG. 30 shows the emission spectrum of Example 30 (10% in PMMA). The emission maximum is at 474 nm. The photoluminescence quantum yield (PLQY) is 81% and the half-height width is 0.42 eV. The emission decay time is 27 µs.

Example 31

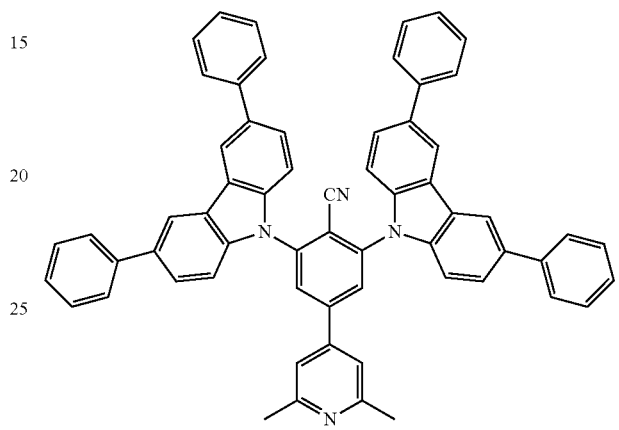

Example 31 was prepared by the reaction of 4-bromo-2,6-dimethylpyridine (1.0 equivalent) with a 4-cyano-3,5-difluorobenzeneboronic ester (1.3 equivalents) under reaction conditions analogous to GM1 (45% yield) and subsequent reaction according to GM7 (15% yield).

Figure 31:
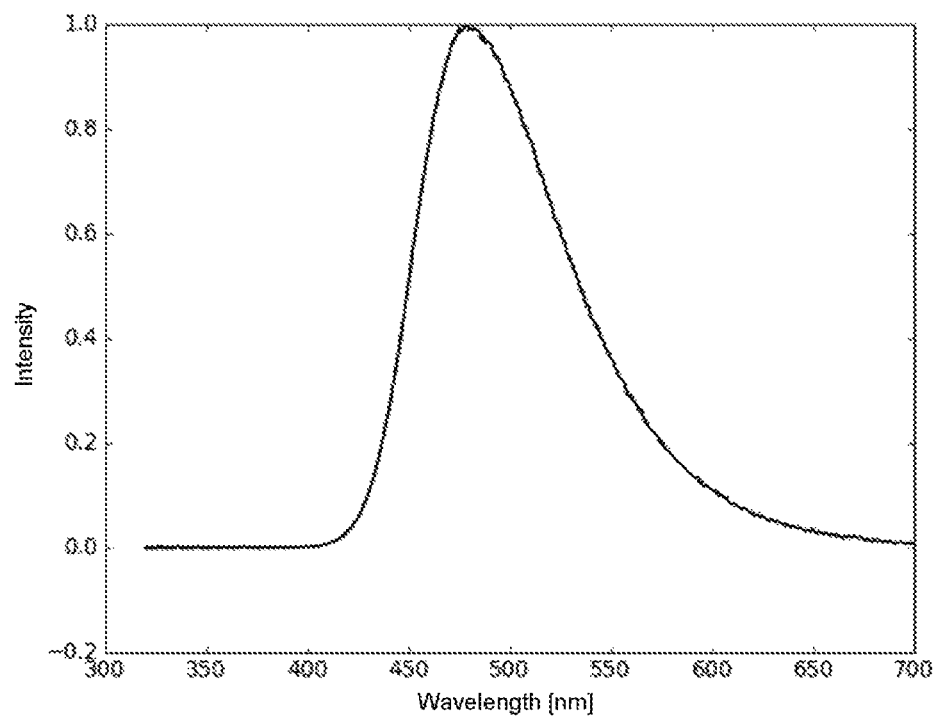
FIG. 31 is an emission spectrum of Example 31 (10% in PMMA).

FIG. 31 shows the emission spectrum of Example 31 (10% in PMMA). The emission maximum is at 479 nm. The photoluminescence quantum yield (PLQY) is 72% and the half-height width is 0.44 eV. The emission decay time is 18 µs.

Example 32

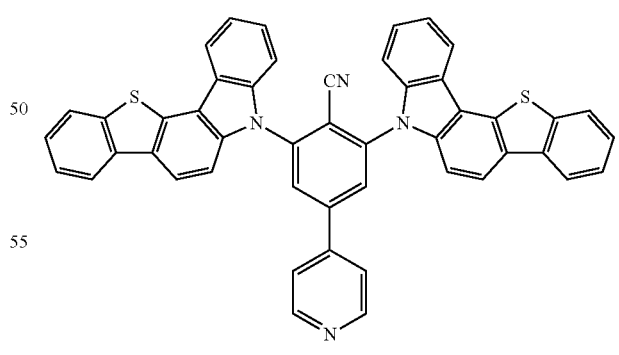

Example 32 was prepared according to GM1 (62% yield) and GM7 (41% yield).

Figure 32:
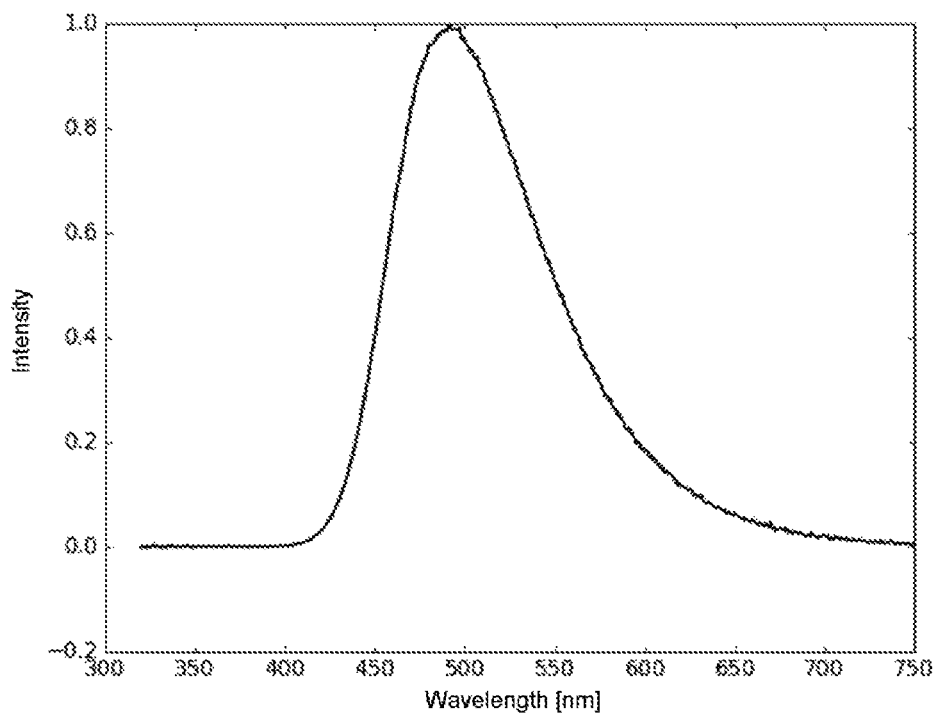
FIG. 32 is an emission spectrum of Example 32 (10% in PMMA).

FIG. 32 shows the emission spectrum of Example 32 (10% in PMMA). The emission maximum is at 491 nm. The photoluminescence quantum yield (PLQY) is 52% and the half-height width is 0.48 eV. The emission decay time is 12 µs.

Example 33

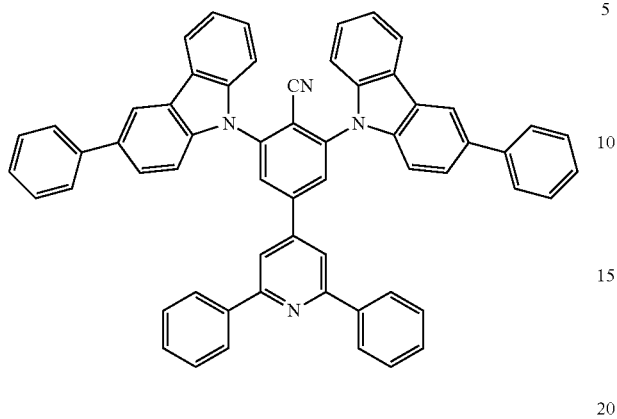

Example 33 was prepared by the reaction of 2,6-dichloro-4-iodopyridine (1.0 equivalent) with a 4-cyano-3,5-difluorobenzeneboronic ester (1.1 equivalents) under reaction conditions analogous to GM1 (65% yield), subsequent reaction with phenylboronic acid (2.5 equivalents) in a 1,4-dioxane/water mixture (10:1 ratio) at 100° C. and a reaction time of 24 h (96% yield) and subsequent reaction according to GM7 (57% yield).

Figure 33:
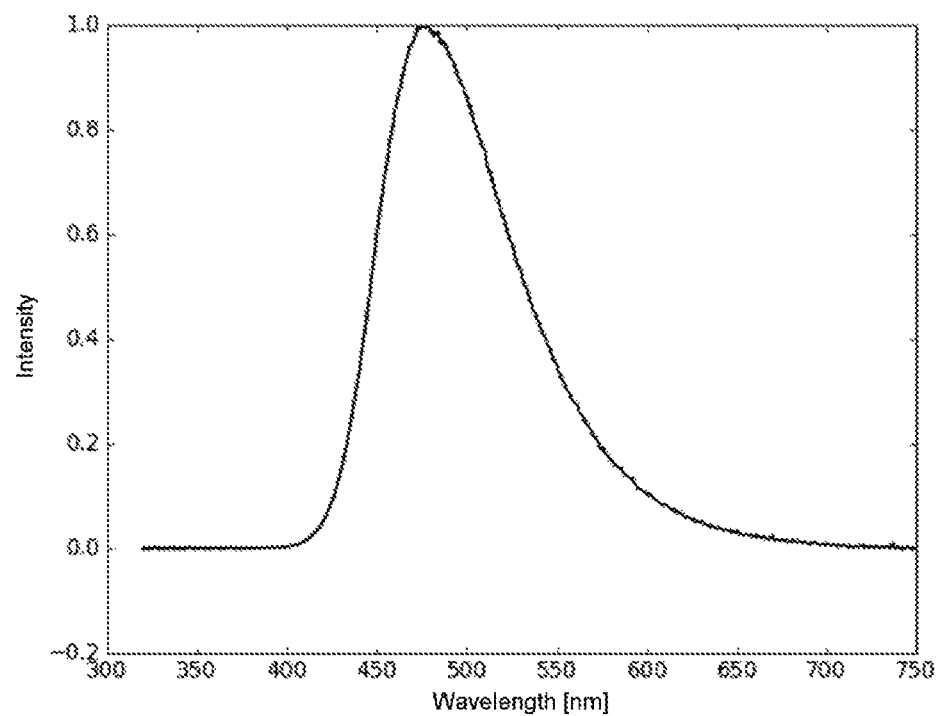
FIG. 33 is an emission spectrum of Example 33 (10% in PMMA).

FIG. 33 shows the emission spectrum of Example 33 (10% in PMMA). The emission maximum is at 476 nm. The photoluminescence quantum yield (PLQY) is 71% and the half-height width is 0.45 eV. The emission decay time is 186 μs.

Example 34

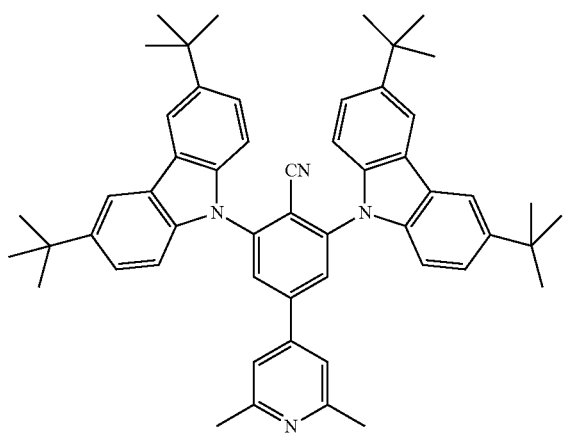 [SMILES: Cc1cc(-c2cc(-n3c4ccc(C(C)(C)C)cc4c4cc(C(C)(C)C)ccc43)c(C#N)c(-n3c4ccc(C(C)(C)C)cc4c4cc(C(C)(C)C)ccc43)c2)cc(C)n1]

Example 34 was prepared by the reaction of 4-bromo-2,6-dimethylpyridine (1.0 equivalent) with a 4-cyano-3,5-difluorobenzeneboronic ester (1.3 equivalents) under reaction conditions analogous to GM1 (45% yield) and subsequent reaction according to GM7 (50% yield).

Figure 34:
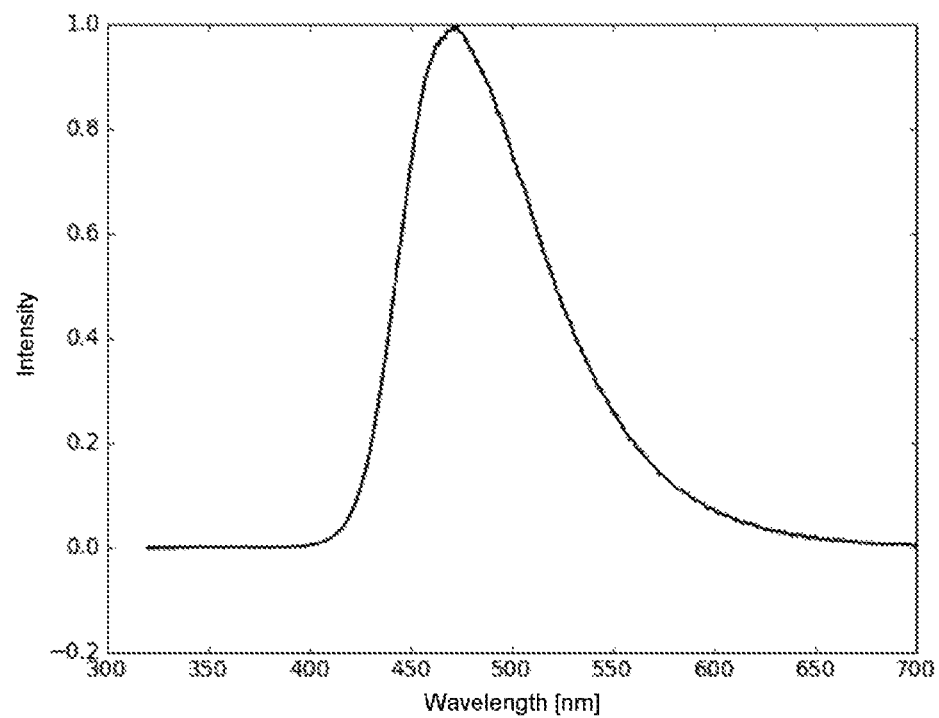
FIG. 34 is an emission spectrum of Example 34 (10% in PMMA).

FIG. 34 shows the emission spectrum of Example 34 (10% in PMMA). The emission maximum is at 471 nm. The photoluminescence quantum yield (PLQY) is 72% and the half-height width is 0.42 eV. The emission decay time is 22 μs.

Example 35

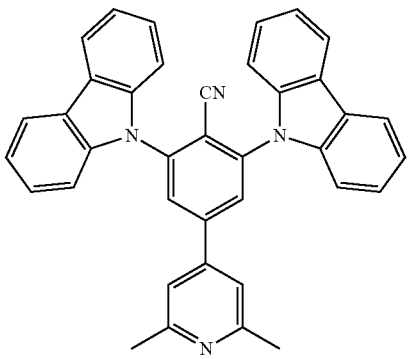 [SMILES: Cc1cc(-c2cc(-n3c4ccccc4c4ccccc43)c(C#N)c(-n3c4ccccc4c4ccccc43)c2)cc(C)n1]

Example 35 was prepared by the reaction of 4-bromo-2,6-dimethylpyridine (1.0 equivalent) with a 4-cyano-3,5-difluorobenzeneboronic ester (1.3 equivalents) under reaction conditions analogous to GM1 (45% yield) and subsequent reaction according to GM7 (43% yield).

Figure 35:
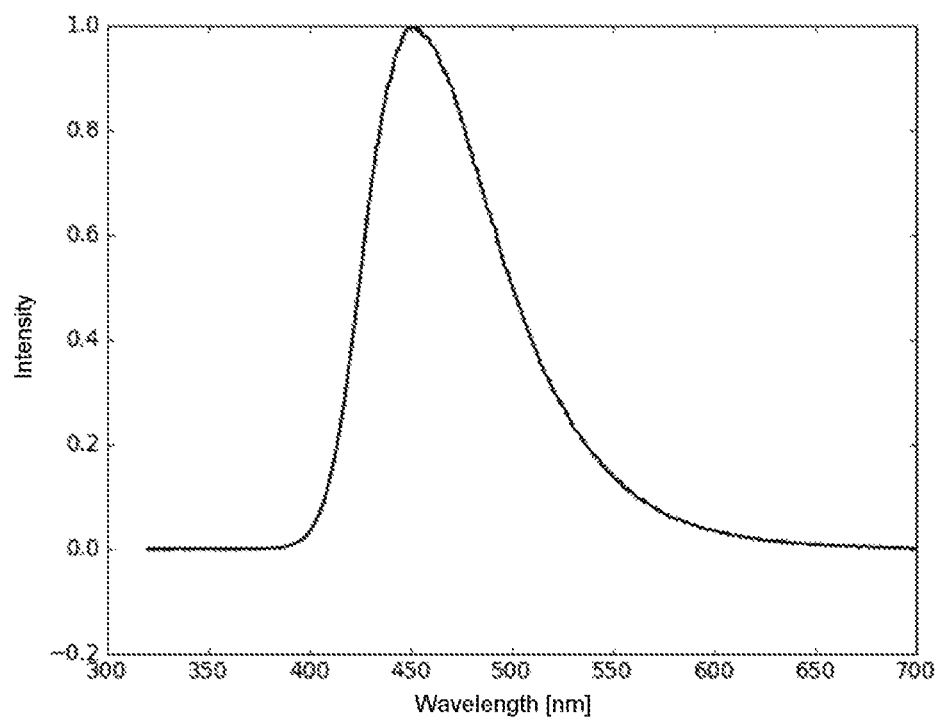
FIG. 35 is an emission spectrum of Example 35 (10% in PMMA).

FIG. 35 shows the emission spectrum of Example 35 (10% in PMMA). The emission maximum is at 450 nm. The photoluminescence quantum yield (PLQY) is 62% and the half-height width is 0.44 eV.

Example 36

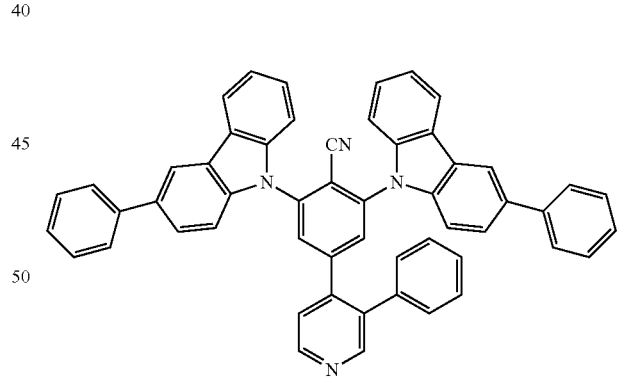

Example 36 was prepared by the reaction of 4-chloro-3-phenylpyridine (1.0 equivalent) with a 4-cyano-3,5-difluorobenzeneboronic ester (1.1 equivalents) under reaction conditions analogous to GM1 (77% yield) and subsequent reaction according to GM7 (37% yield).

Figure 36:
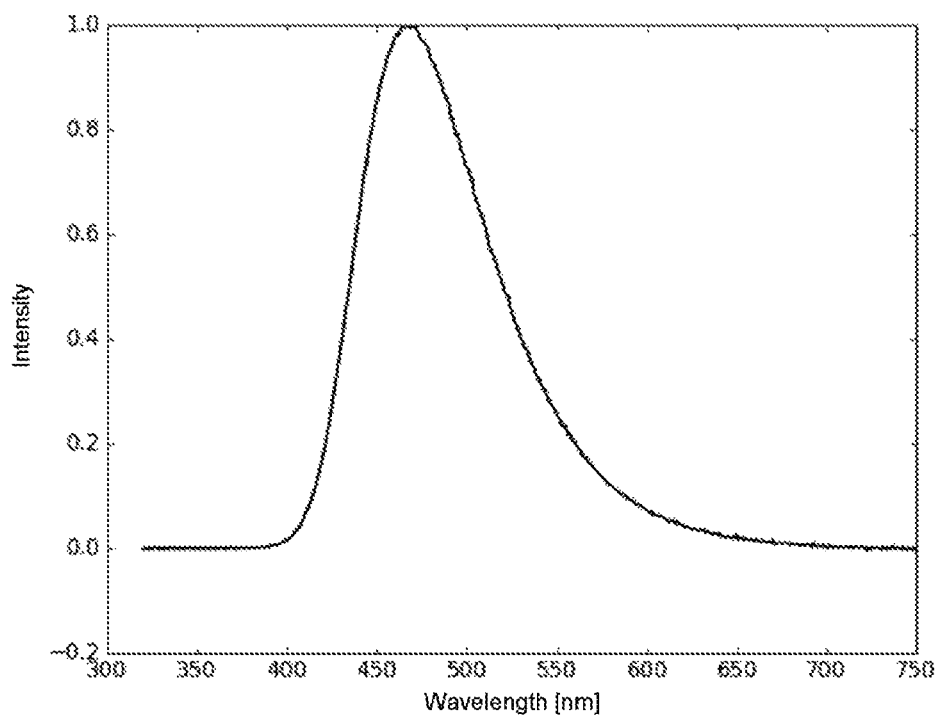
FIG. 36 is an emission spectrum of Example 36 (10% in PMMA).

FIG. 36 shows the emission spectrum of Example 36 (10% in PMMA). The emission maximum is at 468 nm. The photoluminescence quantum yield (PLQY) is 55% and the half-height width is 0.47 eV. The emission decay time is 272 μs.

Example 37

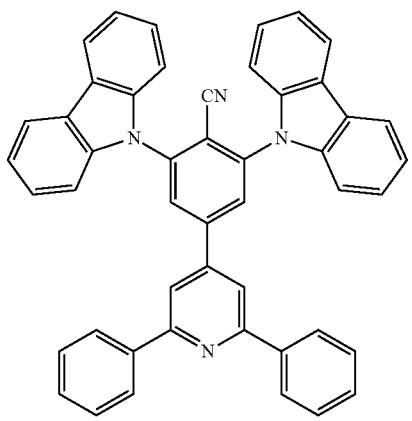 [SMILES: N#Cc1c(-n2c3ccccc3c3ccccc32)cc(-c2cc(-c3ccccc3)nc(-c3ccccc3)c2)cc1-n1c2ccccc2c2ccccc21]

Example 37 was prepared by the reaction of 2,6-dichloro-4-iodopyridine (1.0 equivalent) with a 4-cyano-3,5-difluorobenzeneboronic ester (1.1 equivalents) under reaction conditions analogous to GM1 (65% yield), subsequent reaction with phenylboronic acid (2.5 equivalents) in a 1,4-dioxane/water mixture (10:1 ratio) at 100° C. and a reaction time of 24 h (96% yield) and subsequent reaction according to GM7 (17% yield).

Figure 37:
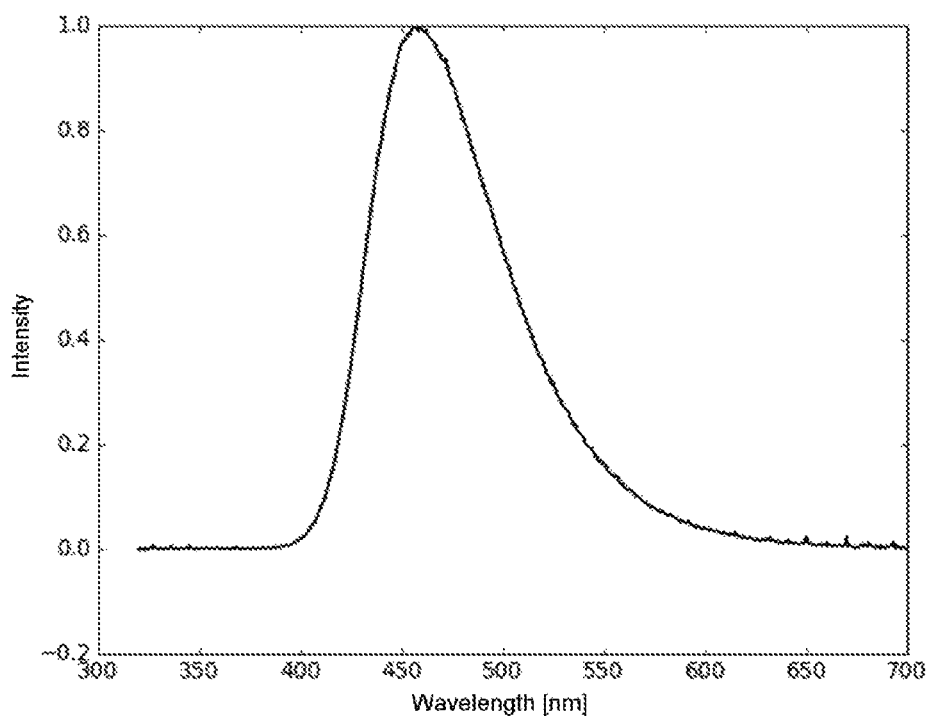
FIG. 37 is an emission spectrum of Example 37 (10% in PMMA).

FIG. 37 shows the emission spectrum of Example 37 (10% in PMMA). The emission maximum is at 457 nm. The photoluminescence quantum yield (PLQY) is 62% and the half-height width is 0.43 eV.

Example 38

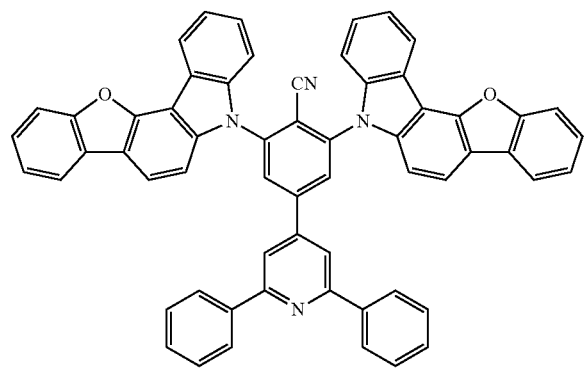 [SMILES: N#Cc1c(-n2c3ccccc3c3c4oc5ccccc5c4ccc32)cc(-c2cc(-c3ccccc3)nc(-c3ccccc3)c2)cc1-n1c2ccccc2c2c3oc4ccccc4c3ccc21]

Example 38 was prepared by the reaction of 2,6-dichloro-4-iodopyridine (1.0 equivalent) with a 4-cyano-3,5-difluorobenzeneboronic ester (1.1 equivalents) under reaction conditions analogous to GM1 (65% yield), subsequent reaction with phenylboronic acid (2.5 equivalents) in a 1,4-dioxane/water mixture (10:1 ratio) at 100° C. and a reaction time of 24 h (96% yield) and subsequent reaction according to GM7 (45% yield).

Figure 38:
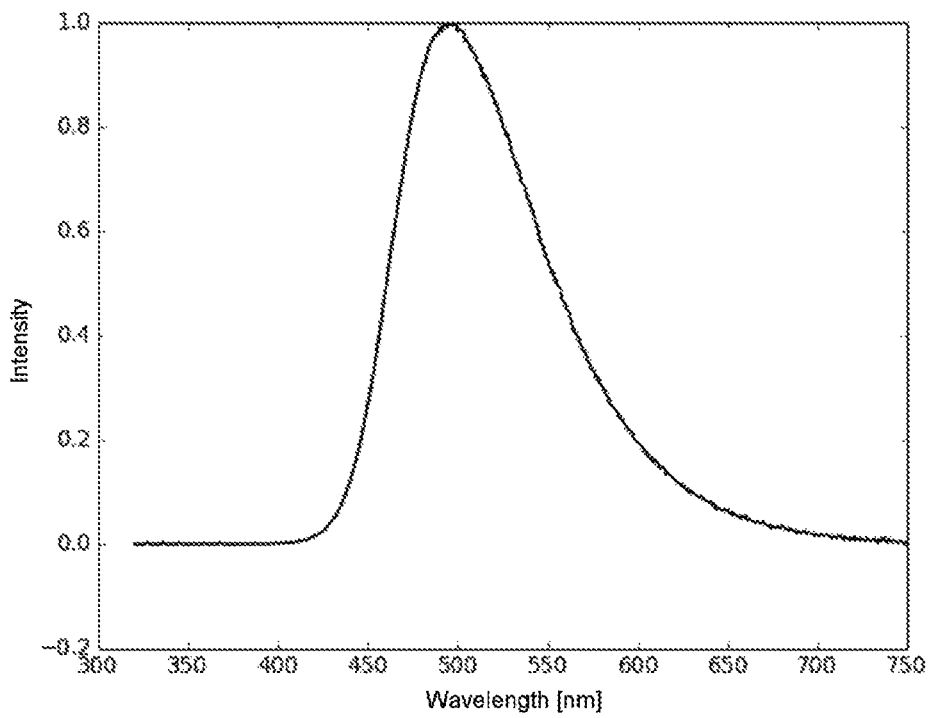
FIG. 38 is an emission spectrum of Example 38 (10% in PMMA).

FIG. 38 shows the emission spectrum of Example 38 (10% in PMMA). The emission maximum is at 496 nm. The photoluminescence quantum yield (PLQY) is 61% and the half-height width is 0.46 eV. The emission decay time is 6 μs.

Example 39

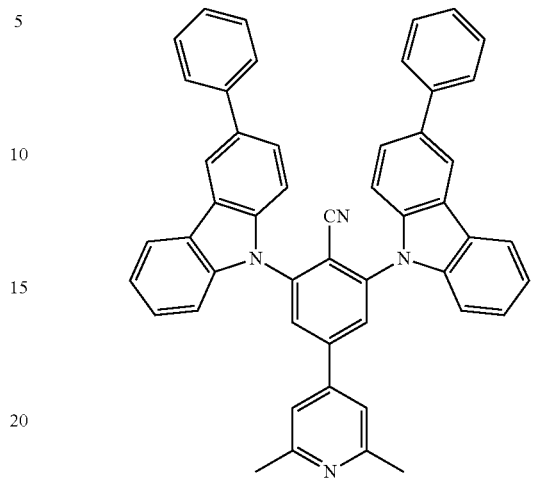

Example 39 was prepared by the reaction of 4-bromo-2,6-dimethylpyridine (1.0 equivalent) with a 4-cyano-3,5-difluorobenzeneboronic ester (1.3 equivalents) under reaction conditions analogous to GM1 (45% yield) and subsequent reaction according to GM7 (14% yield).

Figure 39:
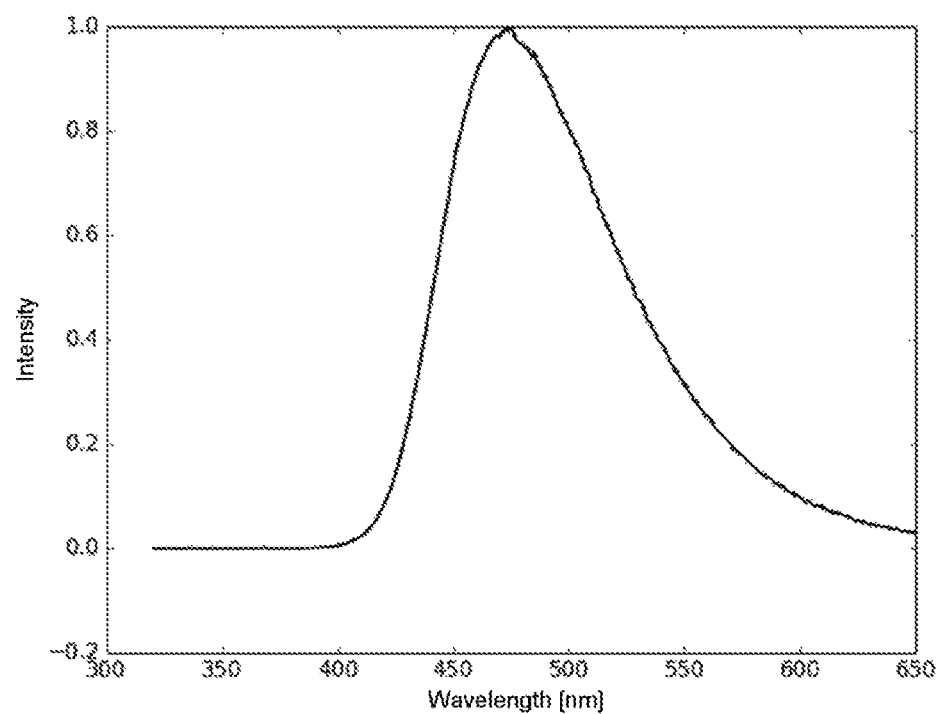
FIG. 39 is an emission spectrum of Example 39 (10% in PMMA).

FIG. 39 shows the emission spectrum of Example 39 (10% in PMMA). The emission maximum is at 475 nm. The photoluminescence quantum yield (PLQY) is 60% and the half-height width is 0.46 eV. The emission decay time is 34 μs.

Example 40

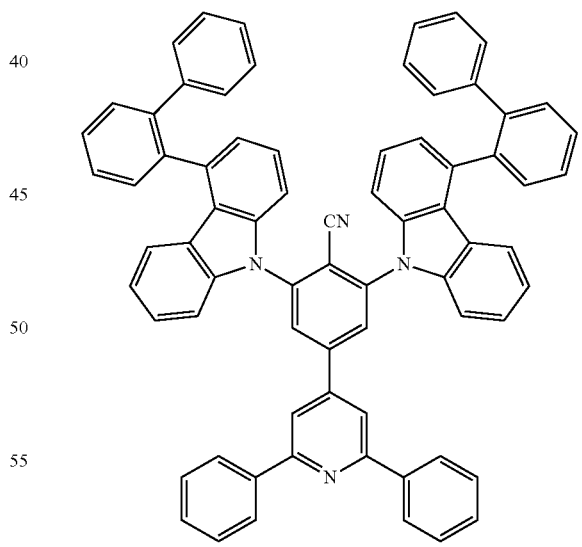

Example 40 was prepared by the reaction of 2,6-dichloro-4-iodopyridine (1.0 equivalent) with a 4-cyano-3,5-difluorobenzeneboronic ester (1.1 equivalents) under reaction conditions analogous to GM1 (65% yield), subsequent reaction with phenylboronic acid (2.5 equivalents) in a 1,4-dioxane/water mixture (10:1 ratio) at 100° C. and a reaction time of 24 h (96% yield) and subsequent reaction according to GM7 (20% yield).

Figure 40:
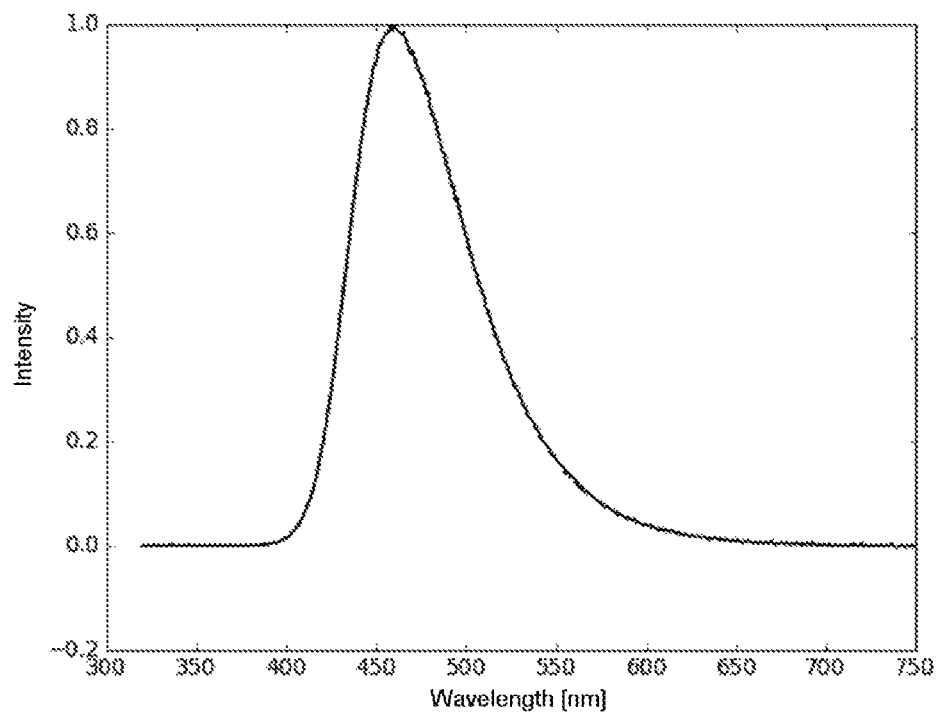
FIG. 40 is an emission spectrum of Example 40 (10% in PMMA).

FIG. 40 shows the emission spectrum of Example 40 (10% in PMMA). The emission maximum is at 460 nm. The photoluminescence quantum yield (PLQY) is 58% and the half-height width is 0.43 eV.

Example 41

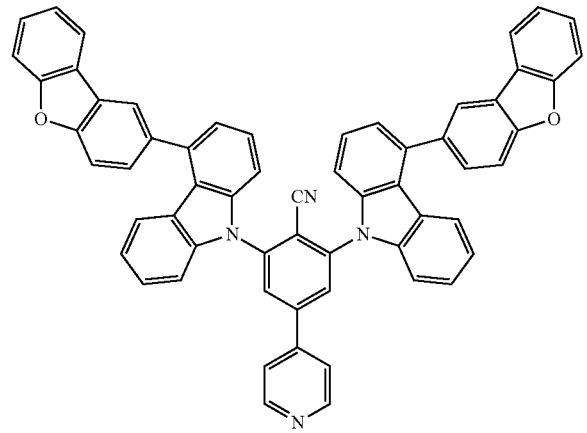 [SMILES: N#Cc1c(-n2c3ccccc3c3c(-c4ccc5oc6ccccc6c5c4)cccc32)cc(-c2ccncc2)cc1-n1c2ccccc2c2c(-c3ccc4oc5ccccc5c4c3)cccc21]

Example 41 was prepared according to GM1 (62% yield) and GM7 (35% yield).

Figure 41:
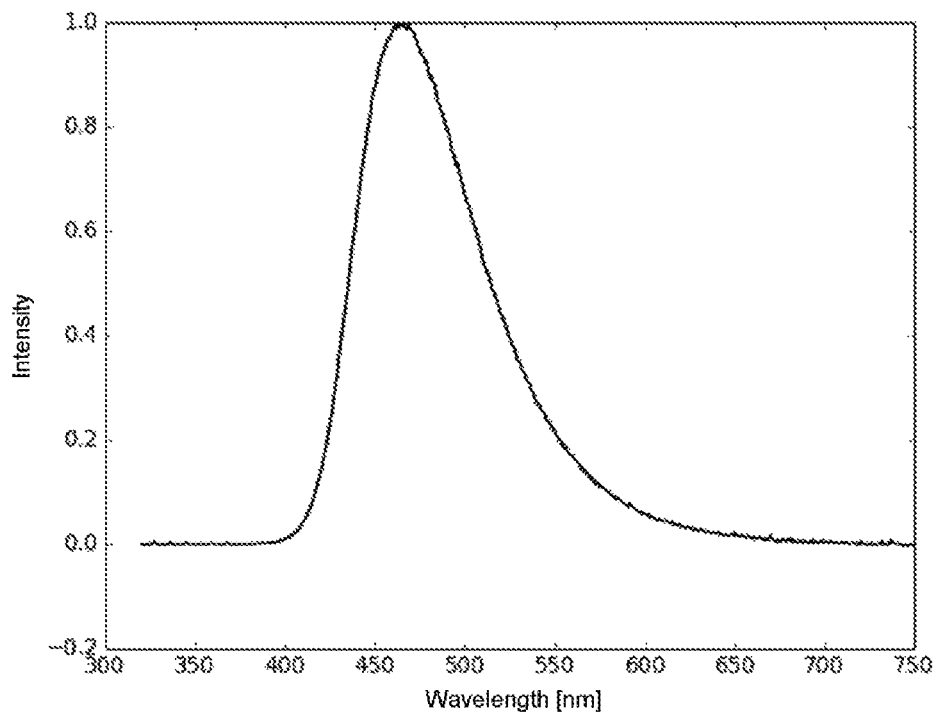
FIG. 41 is an emission spectrum of Example 41 (10% in PMMA).

FIG. 41 shows the emission spectrum of Example 41 (10% in PMMA). The emission maximum is at 465 nm. The photoluminescence quantum yield (PLQY) is 69% and the half-height width is 0.44 eV.

Example 42

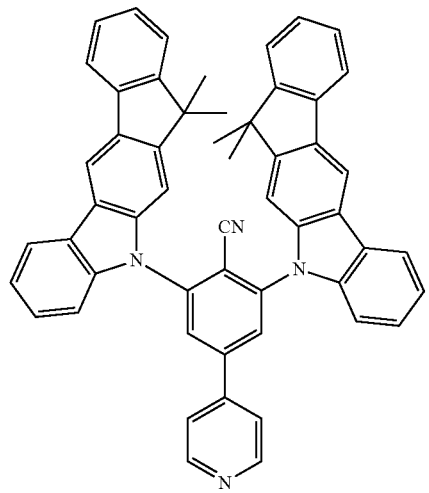 [SMILES: CC1(C)c2ccccc2-c2cc3c4ccccc4n(-c4cc(-c5ccncc5)cc(-n5c6ccccc6c6cc7c(cc65)C(C)(C)c5ccccc5-7)c4C#N)c3cc21]

Example 42 was prepared according to GM1 (62% yield) and GM7 (87% yield).

Figure 42:
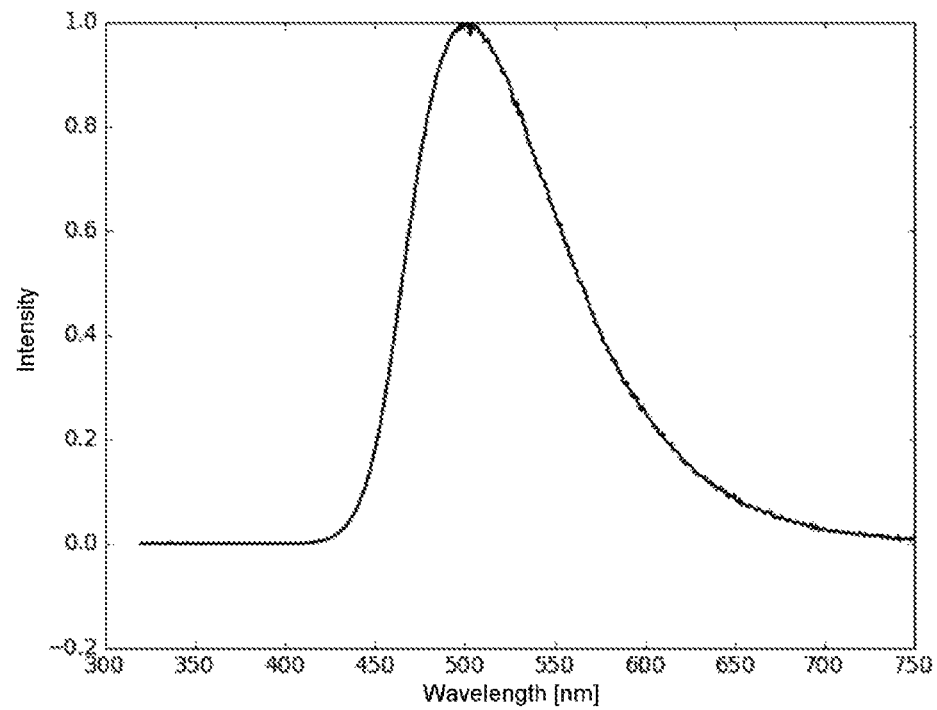
FIG. 42 is an emission spectrum of Example 42 (10% in PMMA).

FIG. 42 shows the emission spectrum of Example 42 (10% in PMMA). The emission maximum is at 501 nm. The photoluminescence quantum yield (PLQY) is 47% and the half-height width is 0.48 eV. The emission decay time is 4 μs.

Example 43

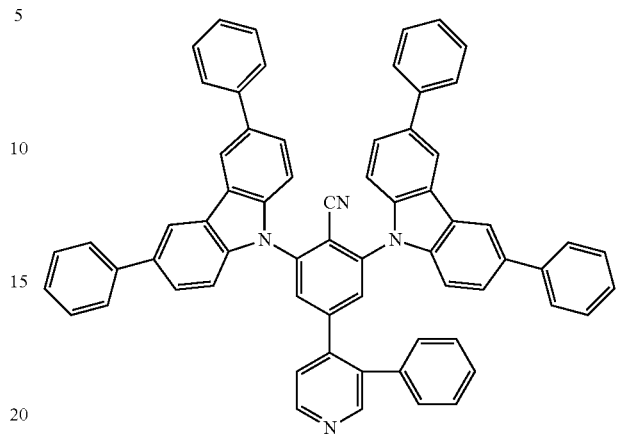

Example 43 was prepared by the reaction of 4-chloro-3-phenylpyridine (1.0 equivalent) with a 4-cyano-3,5-difluorobenzeneboronic ester (1.1 equivalents) under reaction conditions analogous to GM1 (77% yield) and subsequent reaction according to GM7 (43% yield).

Figure 43:
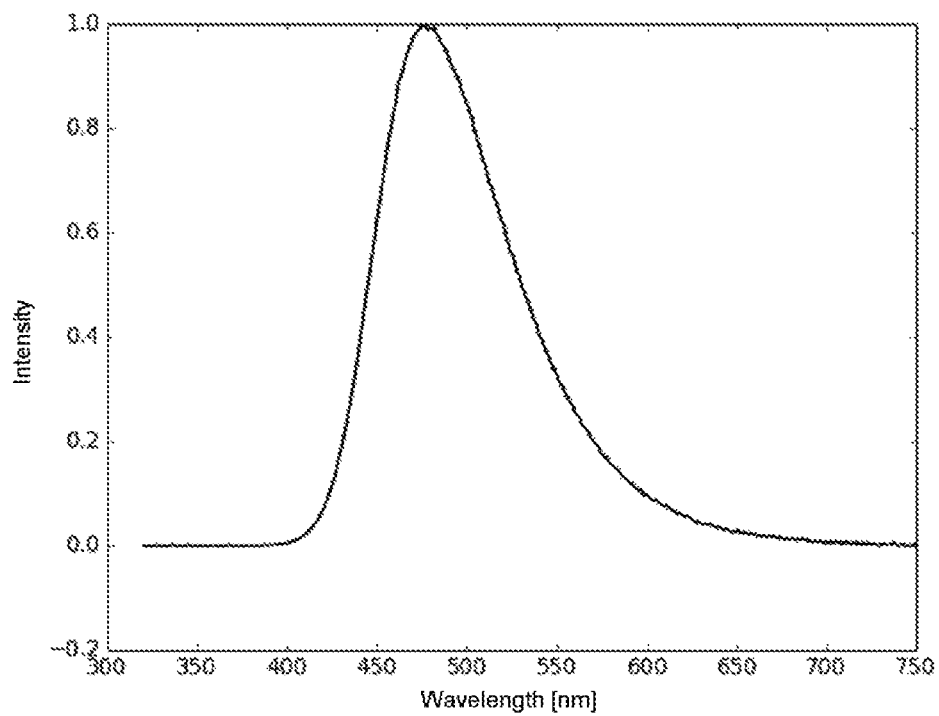
FIG. 43 is an emission spectrum of Example 43 (10% in PMMA).

FIG. 43 shows the emission spectrum of Example 43 (10% in PMMA). The emission maximum is at 475 nm. The photoluminescence quantum yield (PLQY) is 63% and the half-height width is 0.45 eV. The emission decay time is 24 μs.

Example 44

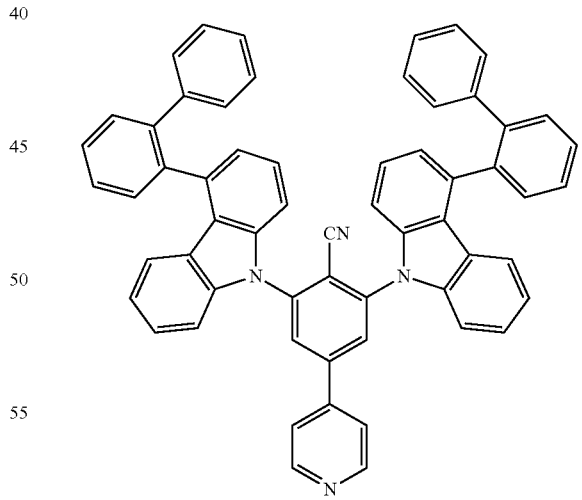

Example 44 was prepared according to GM1 (62% yield) and GM7 (42% yield).

Figure 44:
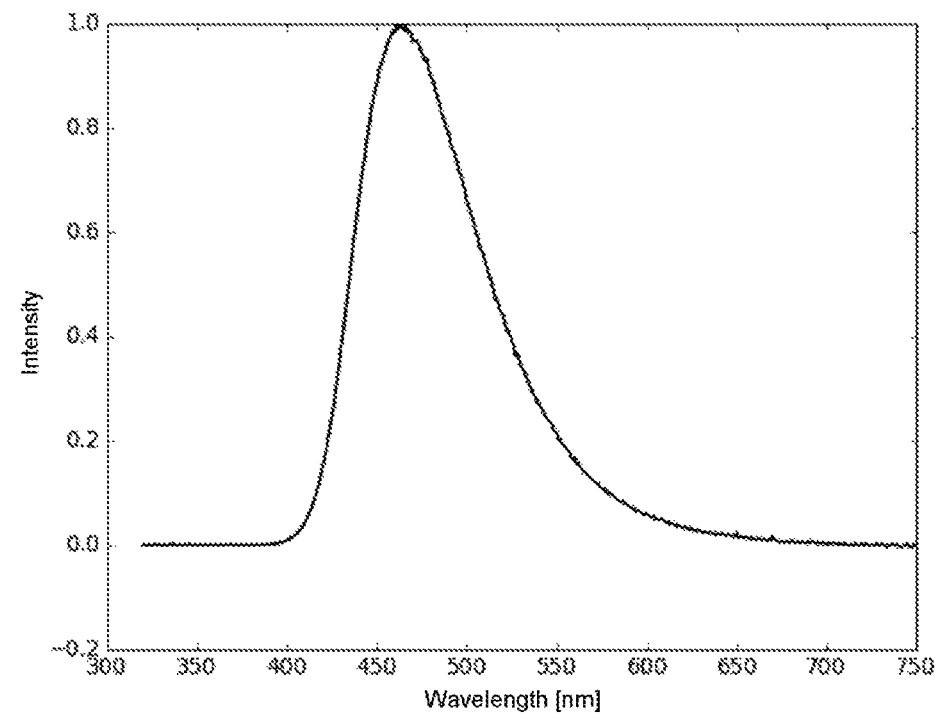
FIG. 44 is an emission spectrum of Example 44 (10% in PMMA).

FIG. 44 shows the emission spectrum of Example 44 (10% in PMMA). The emission maximum is at 466 nm. The photoluminescence quantum yield (PLQY) is 51% and the half-height width is 0.44 eV.

Example 45

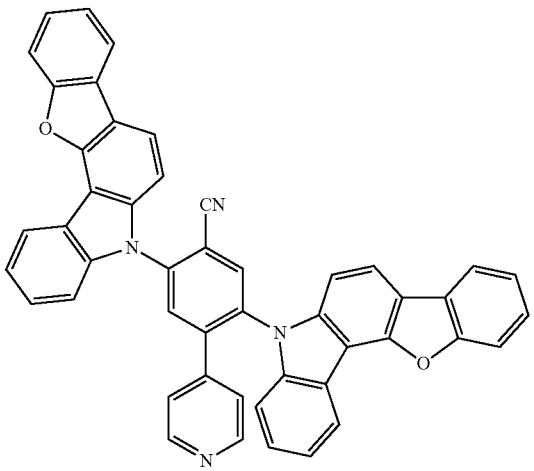 [SMILES: N#Cc1cc(-n2c3ccccc3c3c4oc5ccccc5c4ccc32)c(-c2ccncc2)cc1-n1c2ccccc2c2c3oc4ccccc4c3ccc21]

Example 45 was prepared according to GM4 (40% yield) and GM7 (74% yield).

Figure 45:
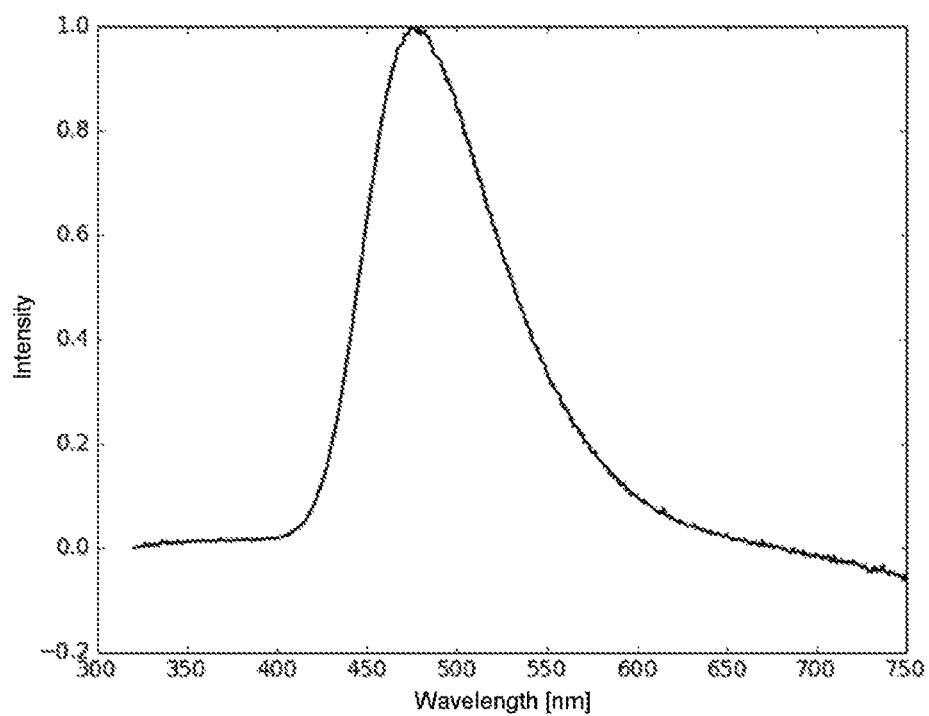
FIG. 45 is an emission spectrum of Example 45 (10% in PMMA).

FIG. 45 shows the emission spectrum of Example 45 (10% in PMMA). The emission maximum is at 474 nm. The photoluminescence quantum yield (PLQY) is 53% and the half-height width is 0.46 eV. The emission decay time is 189 µs.

Comparative Example 1

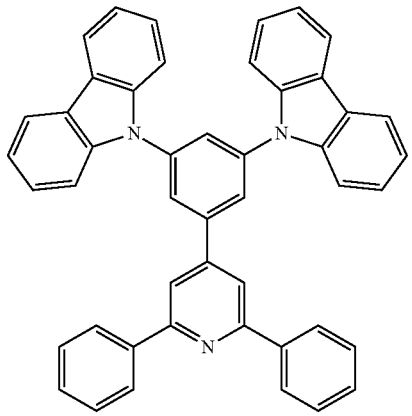 [SMILES: c1ccc(-c2cc(-c3cc(-n4c5ccccc5c5ccccc54)cc(-n4c5ccccc5c5ccccc54)c3)cc(-c3ccccc3)n2)cc1]

Comparative Example 1 was prepared and the emission spectrum of Comparative Example 1 (10% in PMMA) was measured. The emission maximum is at 387 nm. The photoluminescence quantum yield (PLQY) is 11% and the emission decay time is 6 ns. The low PLQY and the short emission decay time show that Comparative Example 1 is not a TADF emitter.

Example D1

Molecule 2 was tested in an OLED component ("component D1") with the following structure (proportion of the molecule according to the invention in the emission layer is reported in percent by mass):

| Layer | Thickness | D1 |
|---|---|---|
| 7 | 100 nm | Al |
| 6 | 2 nm | Liq |
| 5 | 40 nm | NBPhen |
| 4 | 20 nm | 2 (10%):mCBP |
| 3 | 10 nm | TCTA |
| 2 | 80 nm | NPB |
| 1 | 130 nm | ITO |
| Substrate | | glass |

| | Maximum values | at 1000 cd/m$^2$ |
|---|---|---|
| Power efficiency: | 40.9 ± 0.4 lm/W | 22.4 ± 0.1 lm/W |
| Current efficiency: | 40.3 ± 0.4 cd/A | 27.7 ± 0.1 cd/A |
| External quantum yield (EQE): | 19.2 ± 0.2% | 13.2 ± 0.1% |

The emission maximum is at 480 nm; CIEx was determined as 0.19 and CIEy: 0.33 at 6 V.

Example D2

Molecule 3 was tested in the OLED component D2 with the following structure (proportion of the molecule according to the invention and the two host molecules in the emission layer is reported in percent by mass in each case):

| Layer | Thickness | Material |
|---|---|---|
| 9 | 100 nm | Al |
| 8 | 2 nm | Liq |
| 7 | 30 nm | NBPhen |
| 6 | 10 nm | T2T |
| 5 | 20 nm | 3 (10%):9-[3,5-bis(2-dibenzofuranyl)phenyl]-9H-carbazole (70%):T2T (20%) |
| 4 | 10 nm | 9-[3,5-bis(2-dibenzofuranyl)phenyl]-9H-carbazole |
| 3 | 10 nm | TCTA |
| 2 | 80 nm | NPB |
| 1 | 130 nm | ITO |
| Substrate | | glass |

The emission maximum is at 475 nm; CIEx was determined as 0.18 and CIEy: 0.34 at 6 V.

The EQE at 1000 cd/m$^2$ is 19.4±0.3% and the LT80 at 500 cd/m$^2$ is 79 h.

Example D3

Molecule 3 was tested in the OLED component D3 with the following structure (proportion of the molecule according to the invention and the host molecule in the emission layer is reported in percent by mass in each case):

| Layer | Thickness | Material |
|---|---|---|
| 8 | 100 nm | Al |
| 7 | 2 nm | Liq |
| 6 | 40 nm | NBPhen |
| 5 | 20 nm | 3 (20%):9-[3,5-bis(2-dibenzofuranyl)-phenyl]-9H-carbazole (80%) |
| 4 | 5 nm | 9-[3,5-bis(2-dibenzofuranyl)phenyl]-9H-carbazole |
| 3 | 10 nm | TCTA |
| 2 | 75 nm | NPB |

-continued

| Layer | Thickness | Material |
|---|---|---|
| 1 | 130 nm | ITO |
| Substrate | | glass |

The emission maximum is at 475 nm; CIEx was determined as 0.19 and CIEy: 0.35 at 6 V.

The EQE at 1000 cd/m² is 15.1±0.1% and the LT80 at 500 cd/m² is 187 h.

A further OLED component comprises the following structure:

| Layer | Thickness | Material |
|---|---|---|
| 9 | 100 nm | Al |
| 8 | 2 nm | Liq |
| 7 | 30 nm | NBPhen |
| 6 | 10 nm | T2T |
| 5 | 20 nm | Example 3 (20%):mCBP (60%):T2T (20%) |
| 4 | 10 nm | mCBP |
| 3 | 10 nm | TCTA |
| 2 | 80 nm | NPB |
| 1 | 130 nm | ITO |
| Substrate | | glass |

A further OLED component comprises the following structure:

| Layer | Thickness | Material |
|---|---|---|
| 9 | 100 nm | Al |
| 8 | 2 nm | Liq |
| 7 | 30 nm | NBPhen |
| 6 | 10 nm | T2T |
| 5 | 20 nm | Example 5 (20%):mCBP (60%):T2T (20%) |
| 4 | 10 nm | mCBP |
| 3 | 10 nm | TCTA |
| 2 | 80 nm | NPB |
| 1 | 130 nm | ITO |
| Substrate | | glass |

Example D4

Molecule 26 was tested in the OLED component D4 with the following structure (proportion of the molecule according to the invention and the two host molecules in the emission layer is reported in percent by mass in each case):

| Layer | Thickness | Material |
|---|---|---|
| 8 | 100 nm | Al |
| 7 | 2 nm | Liq |
| 6 | 40 nm | NBPhen |
| 5 | 20 nm | 26 (10%):mCBP (75%):T2T (15%) |
| 4 | 5 nm | mCBP |
| 3 | 10 nm | TCTA |
| 2 | 75 nm | NPB |
| 1 | 130 nm | ITO |
| Substrate | | glass |

The emission maximum is at 472 nm; CIEx was determined as 0.18 and CIEy: 0.27 at 6 V.

The EQE at 1000 cd/m² is 10.6±0.2% and the LT80 at 500 cd/m² is 37 h.

Example D5

Molecule 5 was tested in the OLED component D5 with the following structure (proportion of the molecule according to the invention and the host molecule in the emission layer is reported in percent by mass in each case):

| Layer | Thickness | Material |
|---|---|---|
| 7 | 100 nm | Al |
| 6 | 2 nm | Liq |
| 5 | 40 nm | NBPhen |
| 4 | 20 nm | 5 (20%):9-[3-(dibenzothiophen-2-yl)phenyl]-9H-carbazole (80%) |
| 3 | 10 nm | TCTA |
| 2 | 140 nm | NPB |
| 1 | 130 nm | ITO |
| Substrate | | glass |

The emission maximum is at 480 nm; CIEx was determined as 0.21 and CIEy: 0.39 at 6 V.

The EQE at 1000 cd/m² is 13.3±0.2% and the LT80 at 500 cd/m² is 233 h.

Example D6

Molecule 3 was tested in OLED component D6 having the following structure (proportion of the molecule according to the invention and the two host molecules in the emission layer is reported in percent by mass in each case):

| Layer | Thickness | Material |
|---|---|---|
| 8 | 100 nm | Al |
| 7 | 2 nm | Liq |
| 6 | 40 nm | NBPhen |
| 5 | 30 nm | 3 (10%):9-[3,5-bis(2-dibenzofuranyl)phenyl]-9H-carbazole (70%):T2T (20%) |
| 4 | 8 nm | 9-[3,5-bis(2-dibenzofuranyl)phenyl]-9H-carbazole |
| 3 | 10 nm | TCTA |
| 2 | 62 nm | NPB |
| 1 | 50 nm | ITO |
| Substrate | | glass |

The emission maximum is at 480 nm; CIEx was determined as 0.16 and CIEy: 0.34 at 6 V.

The EQE at 1000 cd/m² is 22.3±0.2% and the LT80 at 500 cd/m² is 580 h.

Example D7

Molecule 22 was tested in the OLED component D7 with the following structure (proportion of the molecule according to the invention and the host molecule in the emission layer is reported in percent by mass in each case):

| Layer | Thickness | Material |
|---|---|---|
| 9 | 100 nm | Al |
| 8 | 2 nm | Liq |
| 7 | 40 nm | NBPhen |
| 6 | 10 nm | 22 (10%):9-[3,5-bis(2-dibenzofuranyl)-phenyl]-9H-carbazole (90%) |
| 5 | 10 nm | TCTA |
| 4 | 110 nm | NPB |
| 3 | 5 nm | HAT-CN |
| 2 | 50 nm | PEDOT:PSS |
| 1 | 130 nm | ITO |
| Substrate | | glass |

The emission maximum is at 486 nm; CIEx was determined as 0.22 and CIEy: 0.41 at 6 V.

The EQE at 1000 cd/m² is 11.0±0.3% and the LT80 at 500 cd/m² is 152 h.

Example D8

Molecule 43 was tested in OLED component D7 having the following structure (proportion of the molecule according to the invention and the host molecule in the emission layer is reported in percent by mass in each case):

| Layer | Thickness | Material |
|---|---|---|
| 10 | 100 nm | Al |
| 9 | 2 nm | Liq |
| 8 | 40 nm | NBPhen |
| 7 | 30 nm | 43 (10%):mCBP (70%):T2T (20%) |
| 6 | 10 nm | mCBP |
| 5 | 10 nm | TCTA |
| 4 | 100 nm | NPB |
| 3 | 5 nm | HAT-CN |
| 2 | 50 nm | PEDOT:PSS |
| 1 | 130 nm | ITO |
| Substrate | | glass |

The emission maximum is at 477 nm; CIEx was determined as 0.16 and CIEy: 0.28 at 6 V.

The EQE at 1000 cd/m² is 11.1±0.4% and the LT80 at 500 cd/m² is 37 h.

Further Examples of Molecules According to the Invention:

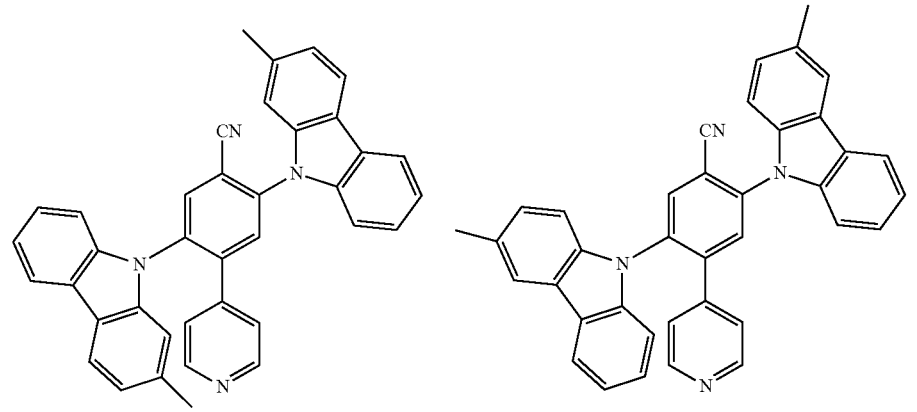

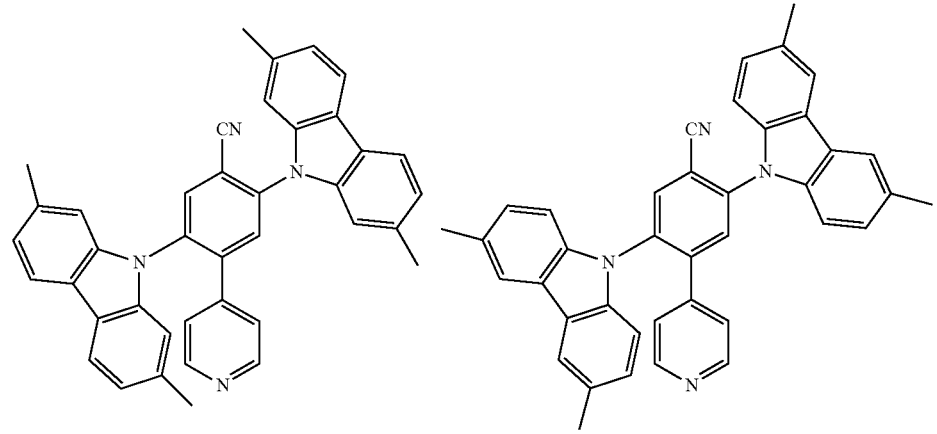

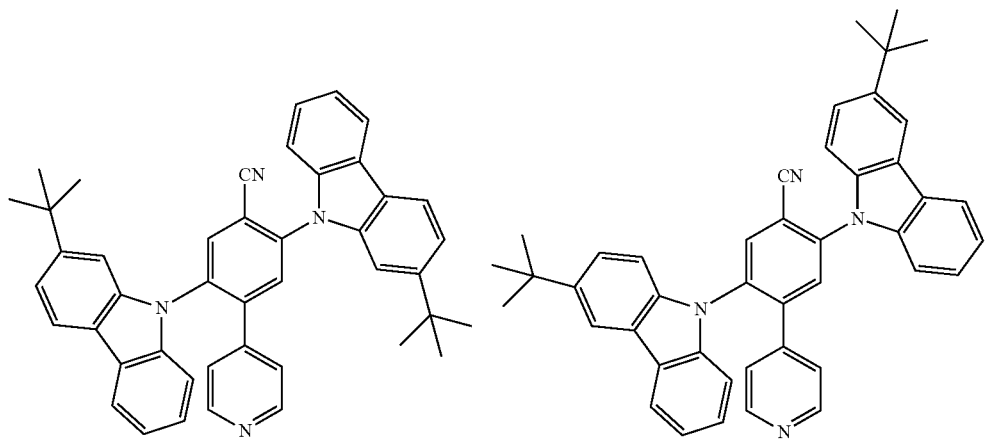

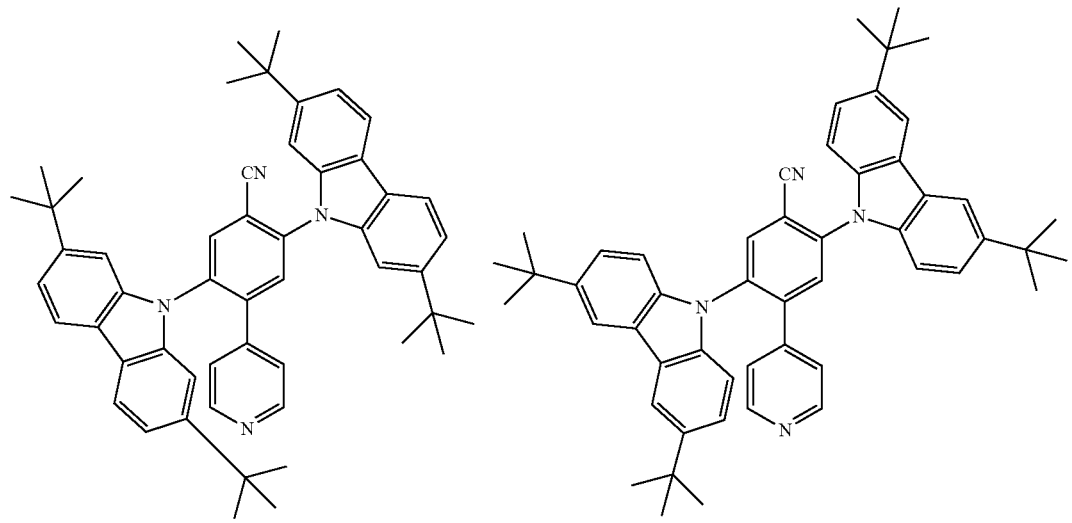
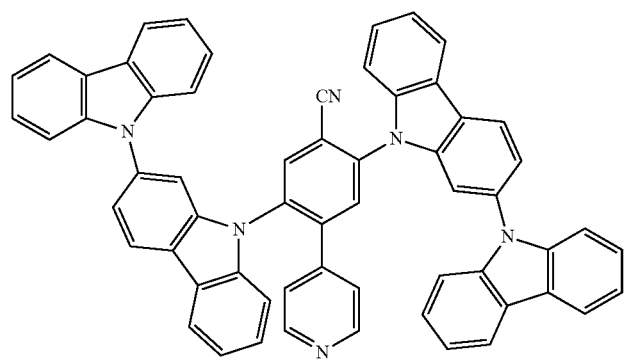
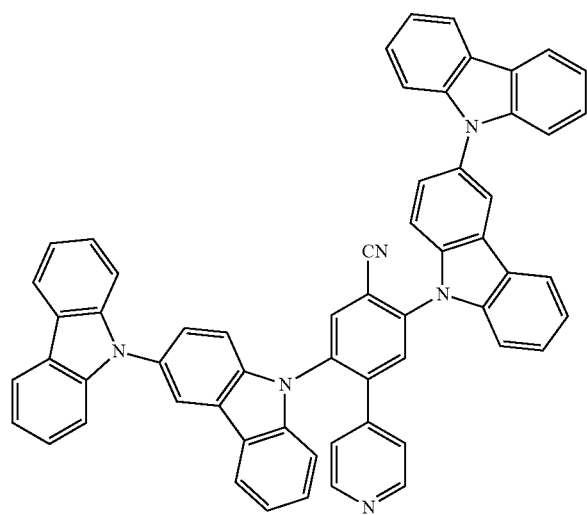

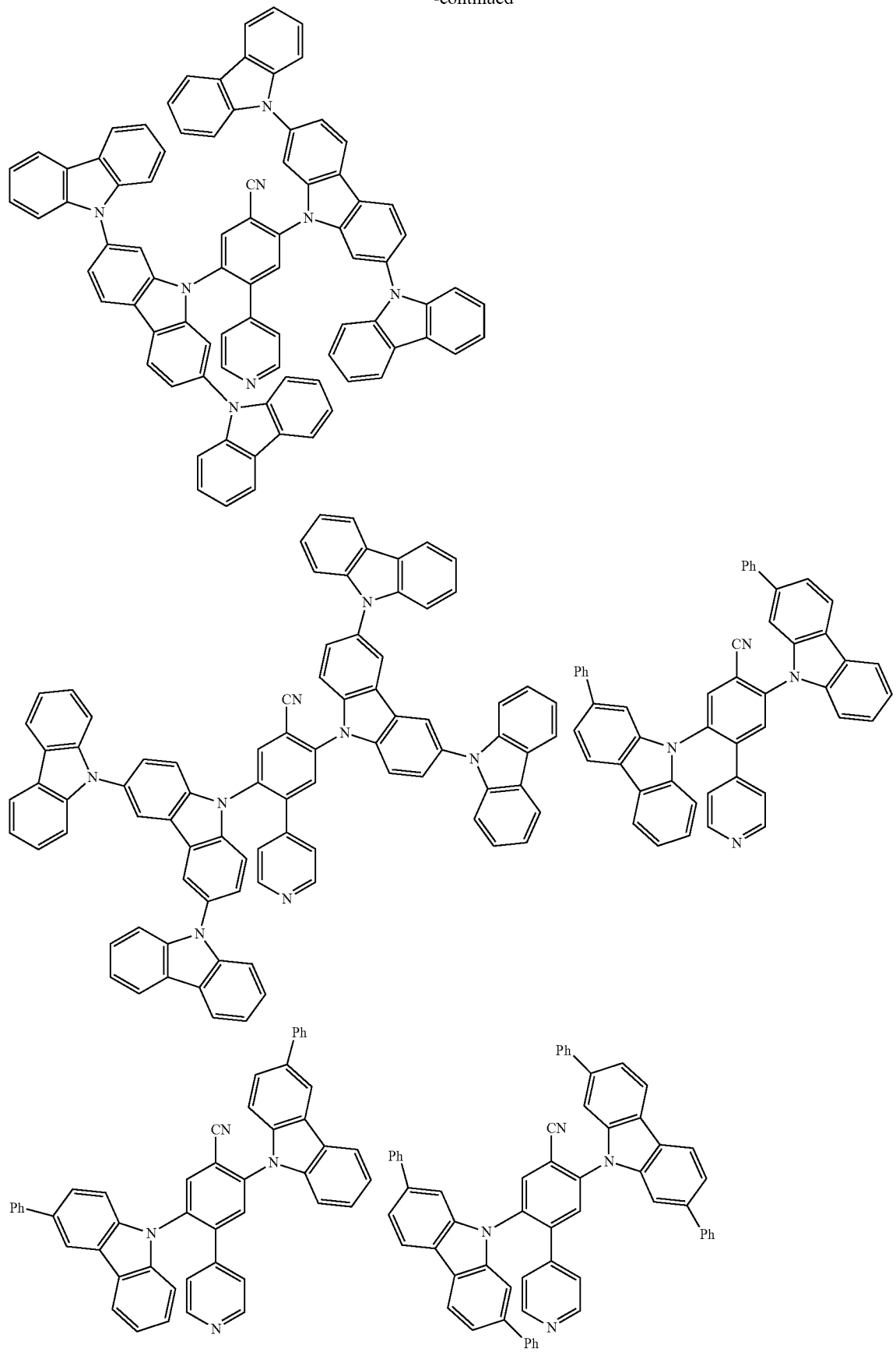

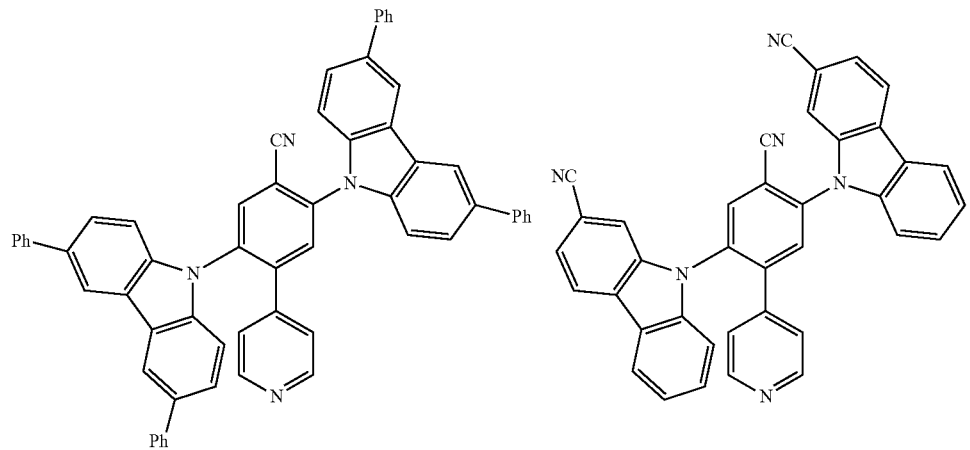
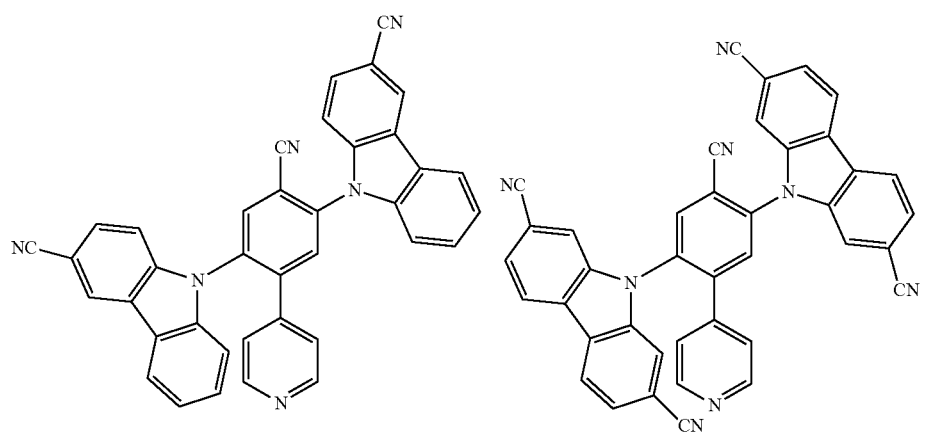
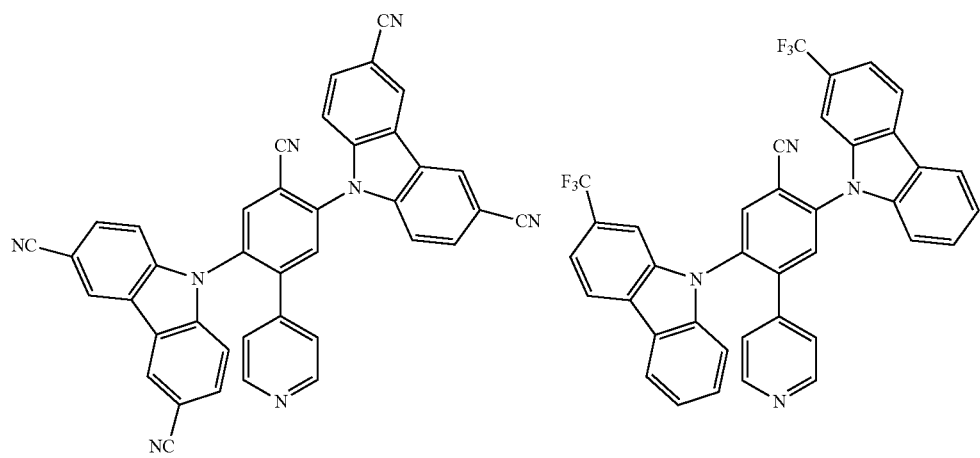

-continued
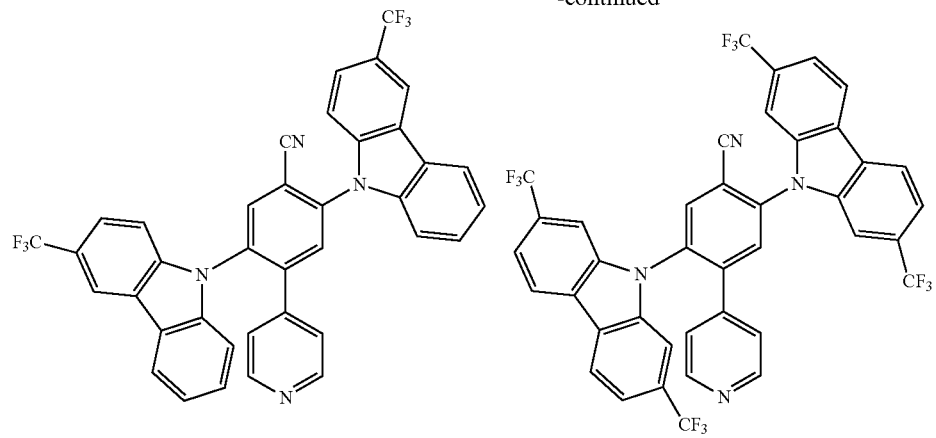
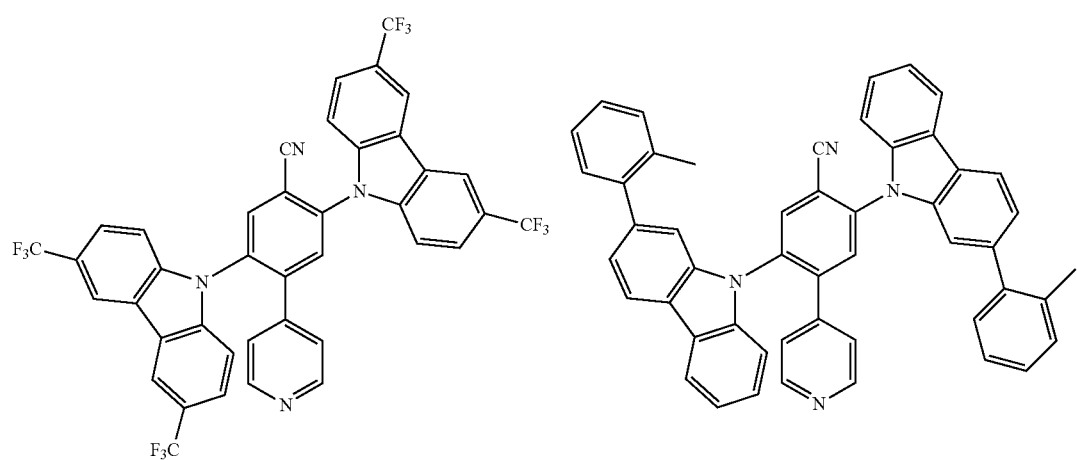
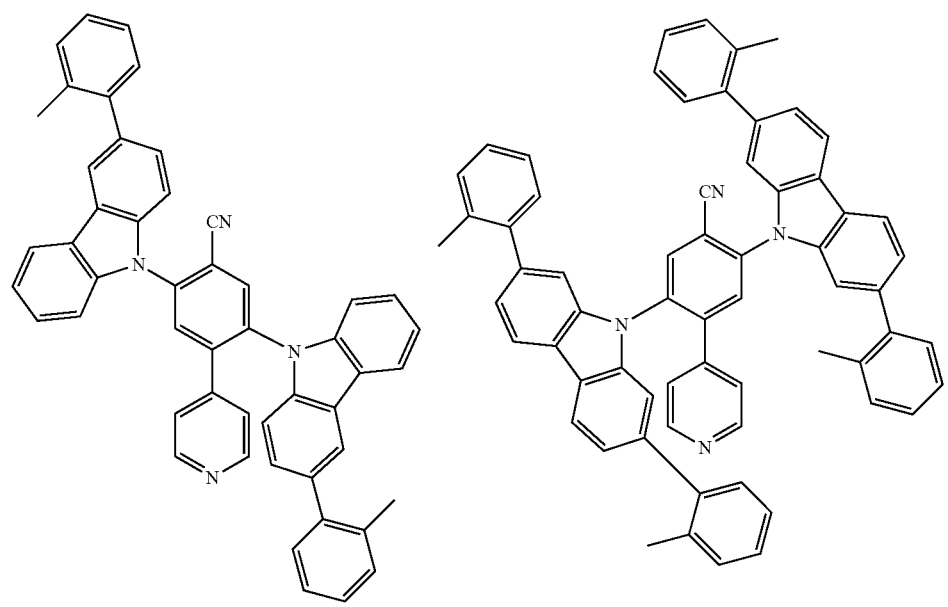

-continued
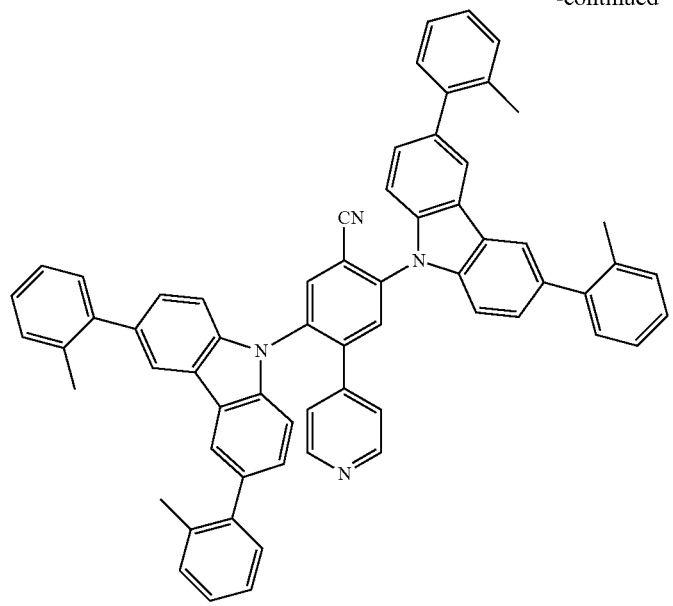
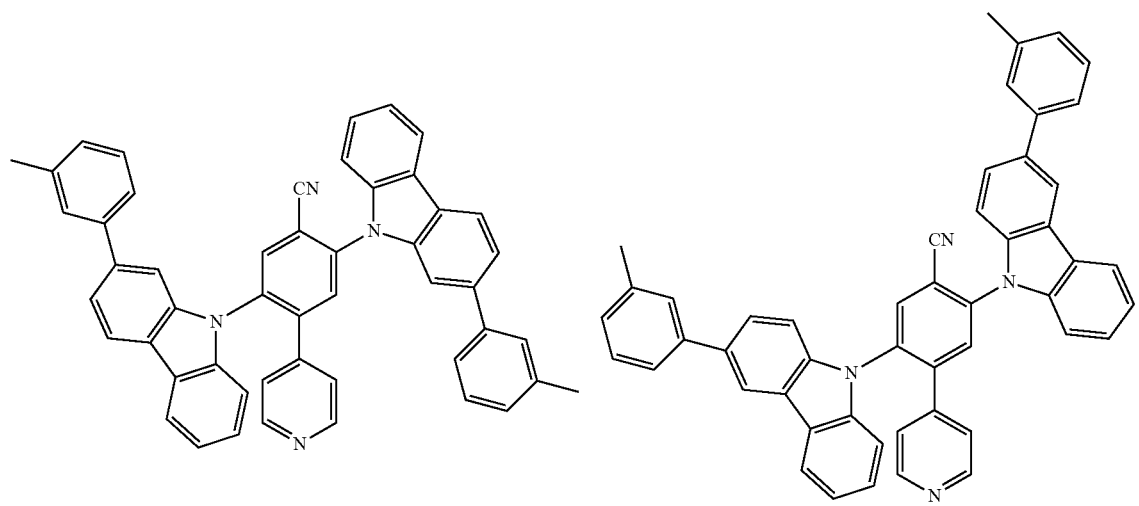
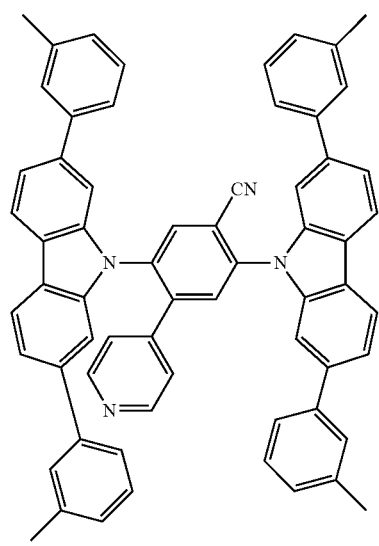

-continued
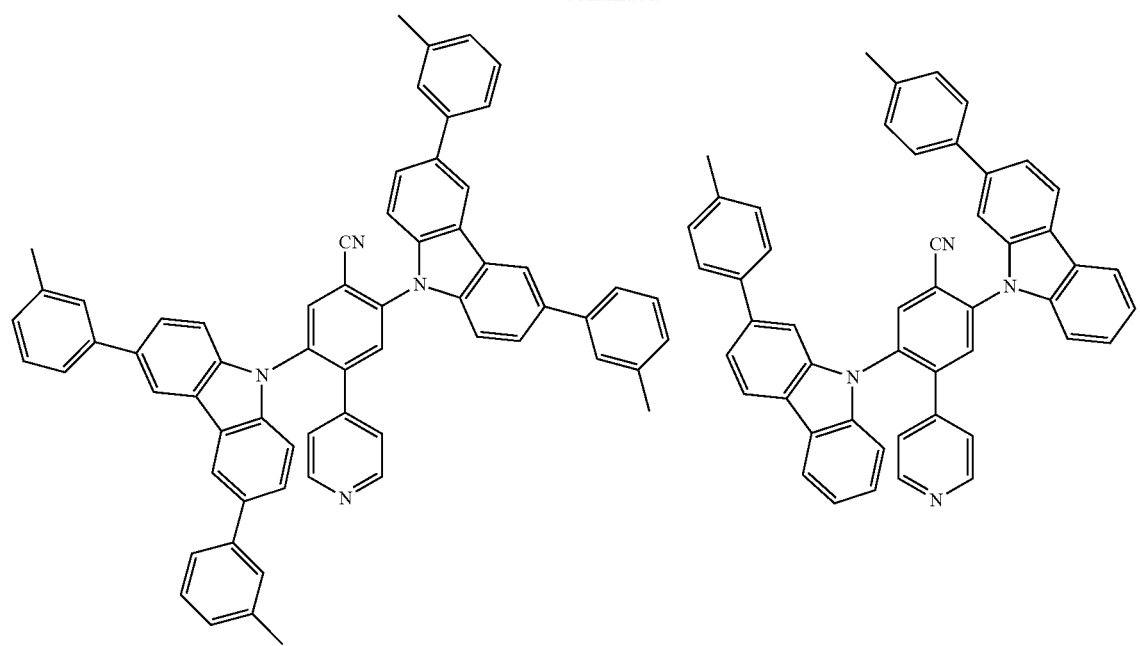
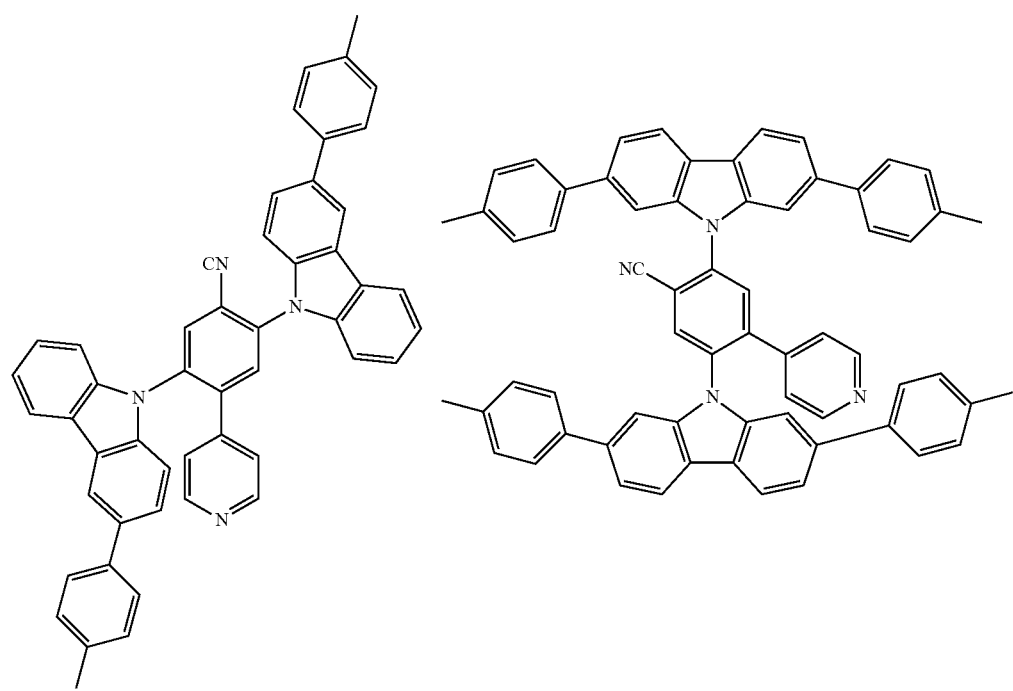

-continued
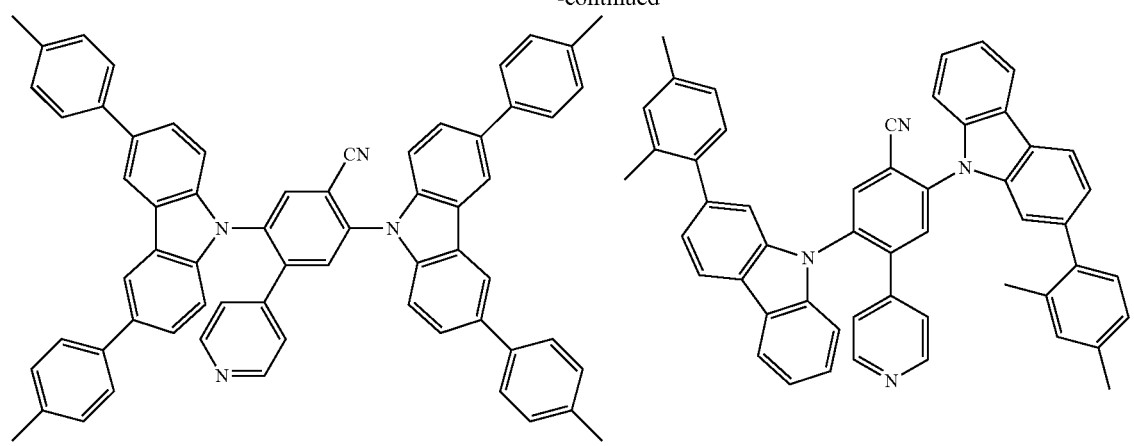
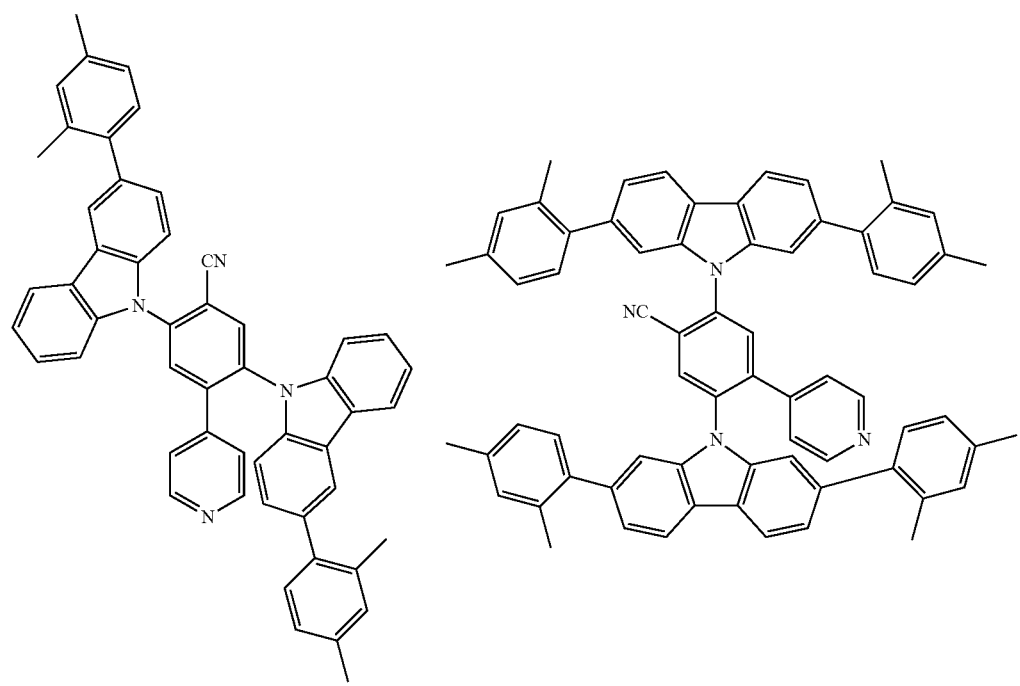

-continued
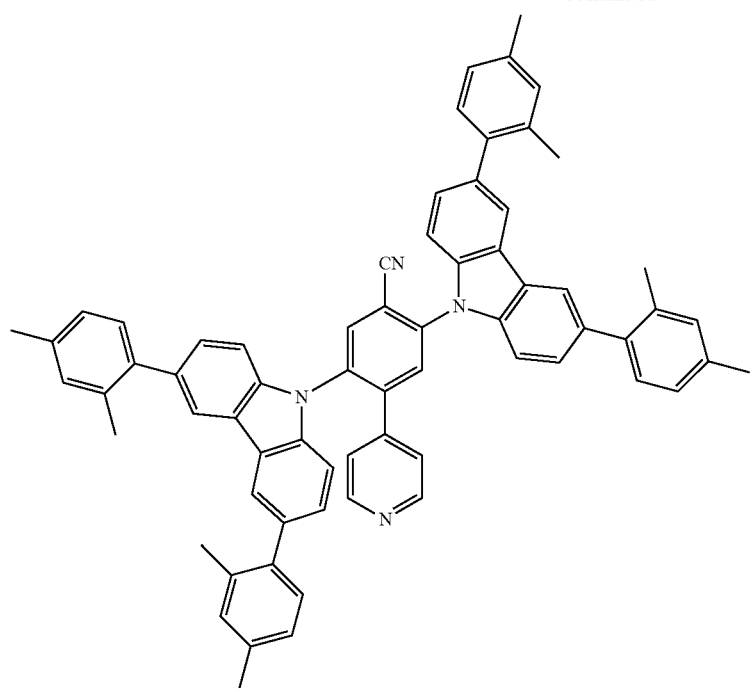
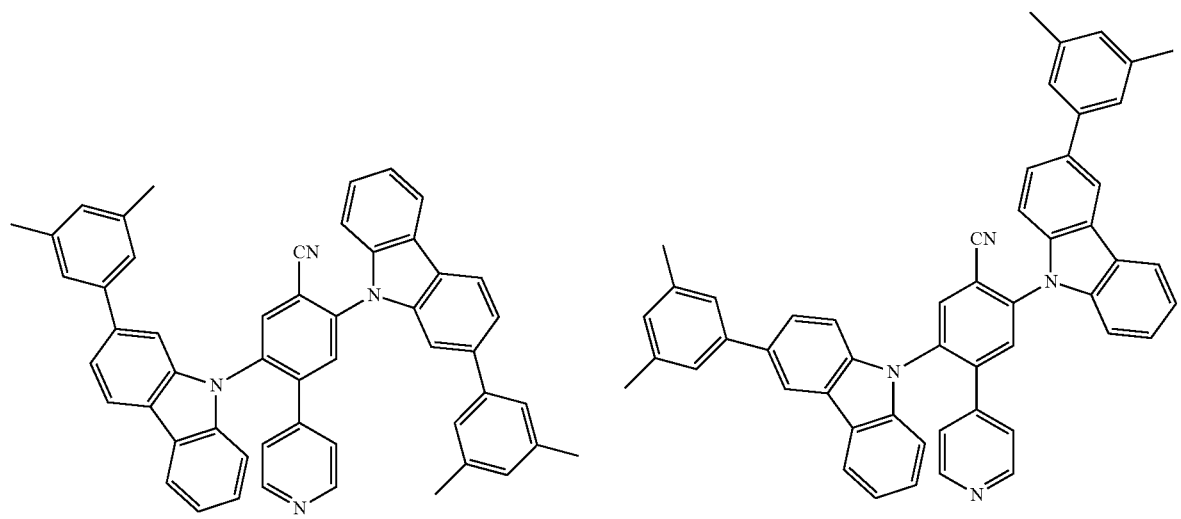
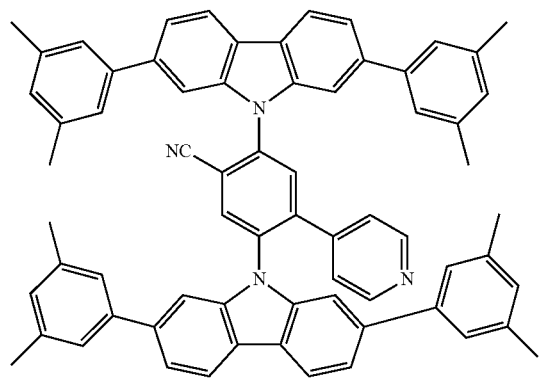

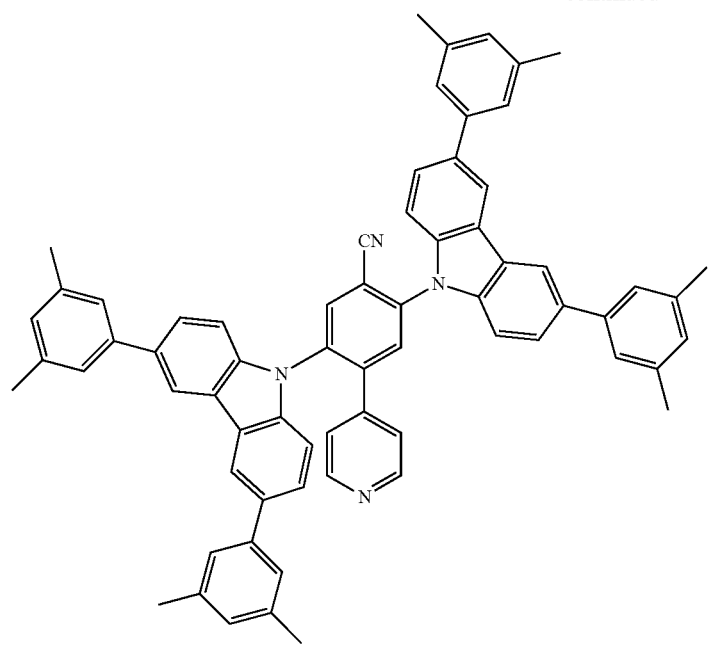
-continued
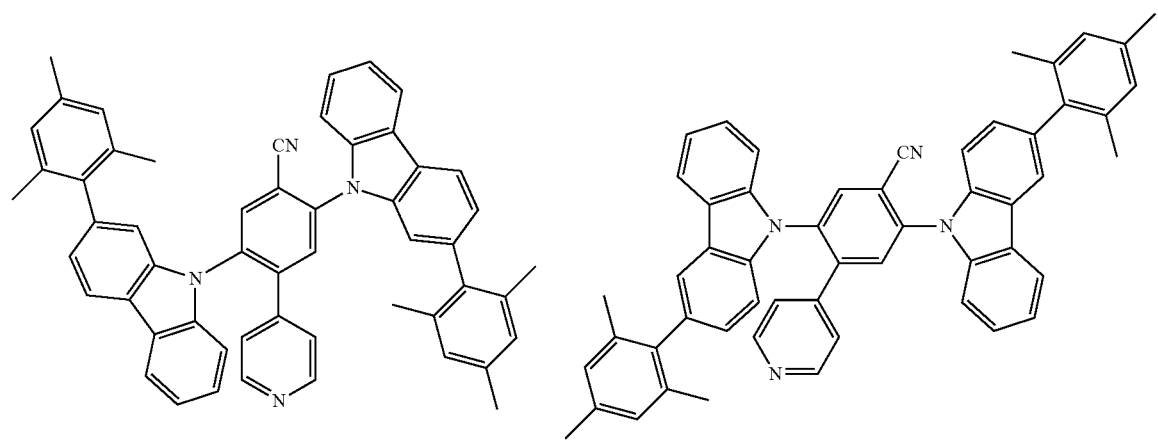

91 92
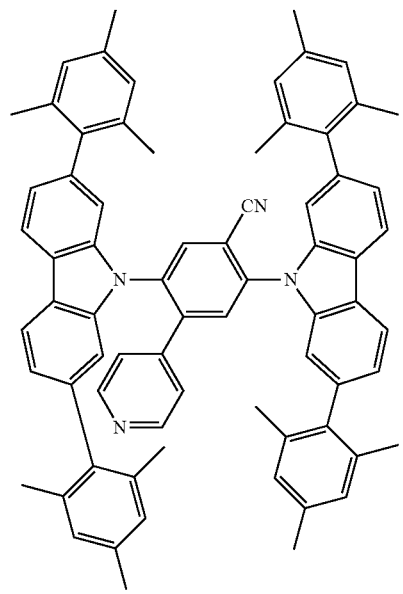
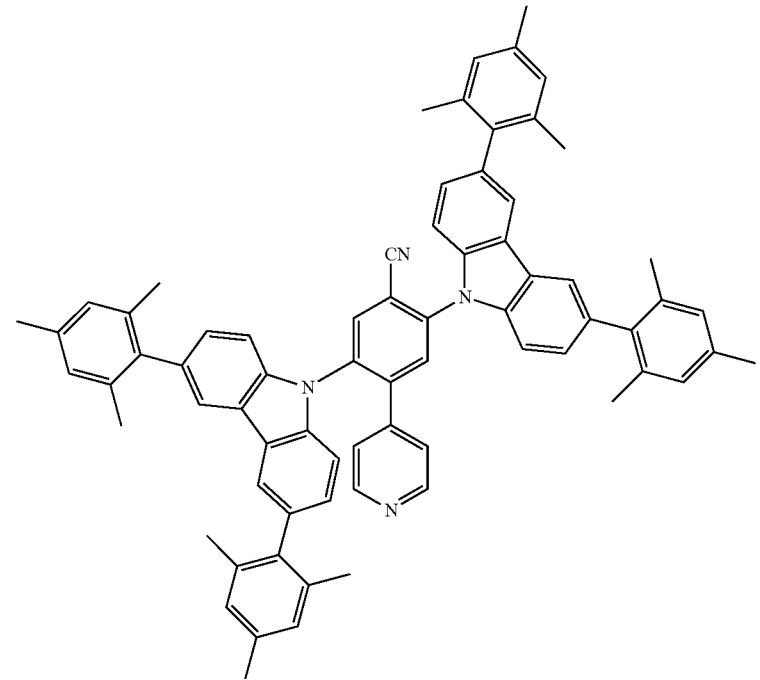
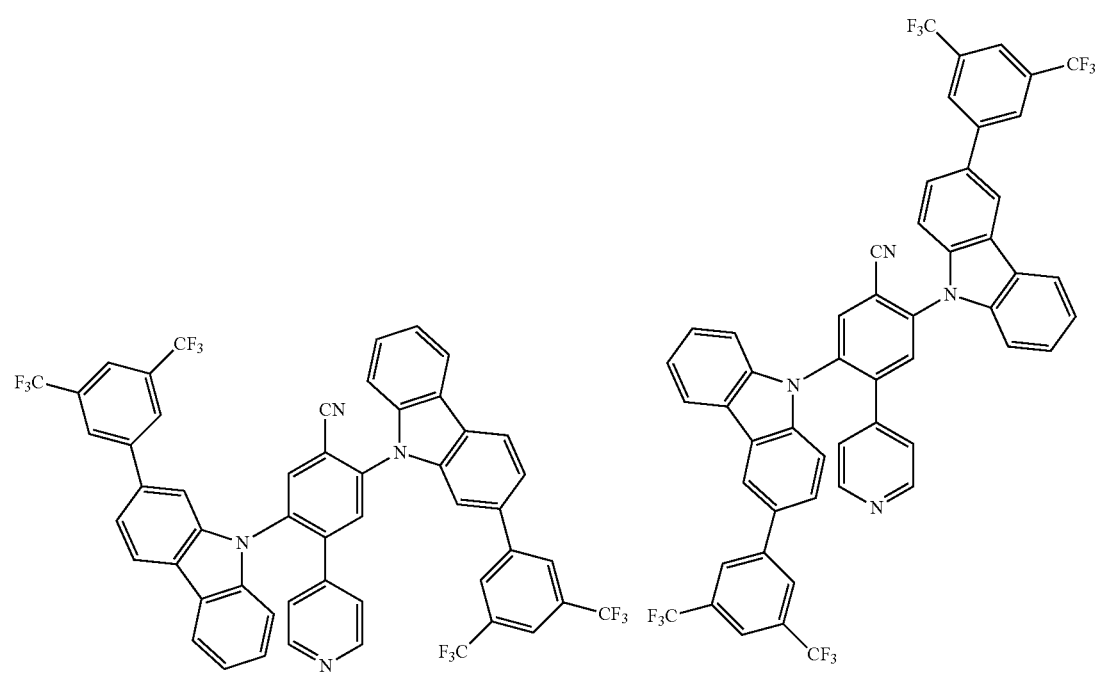

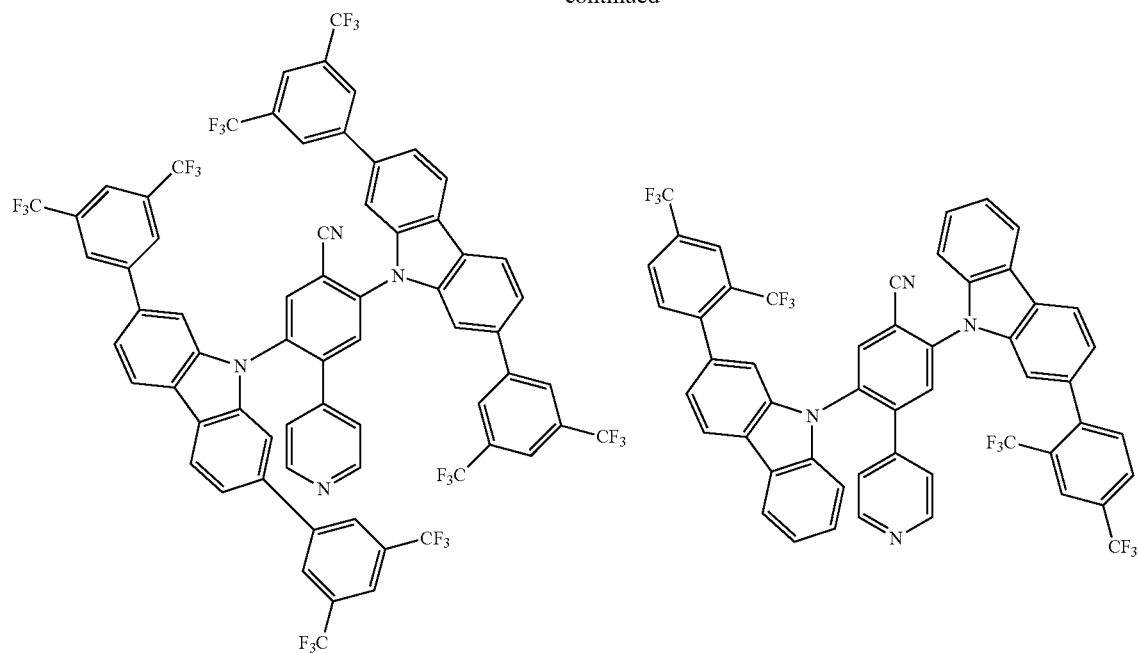
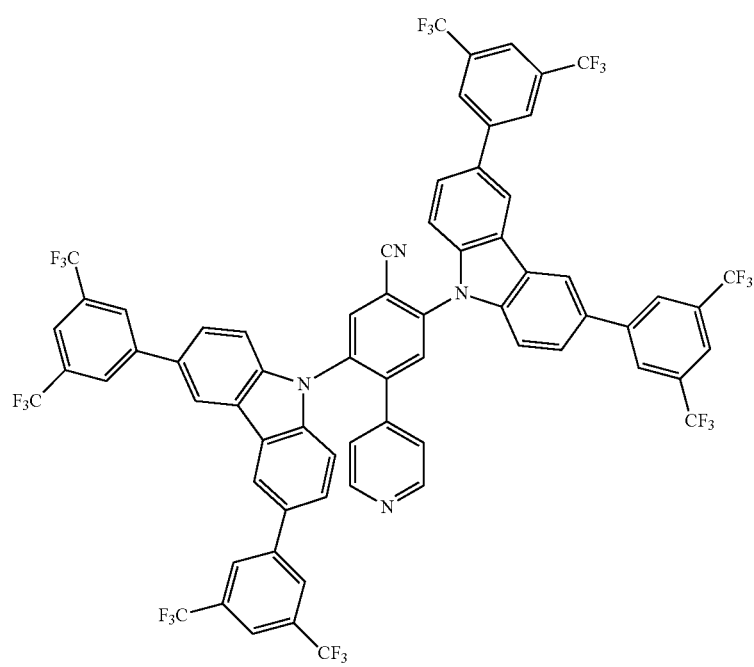

-continued
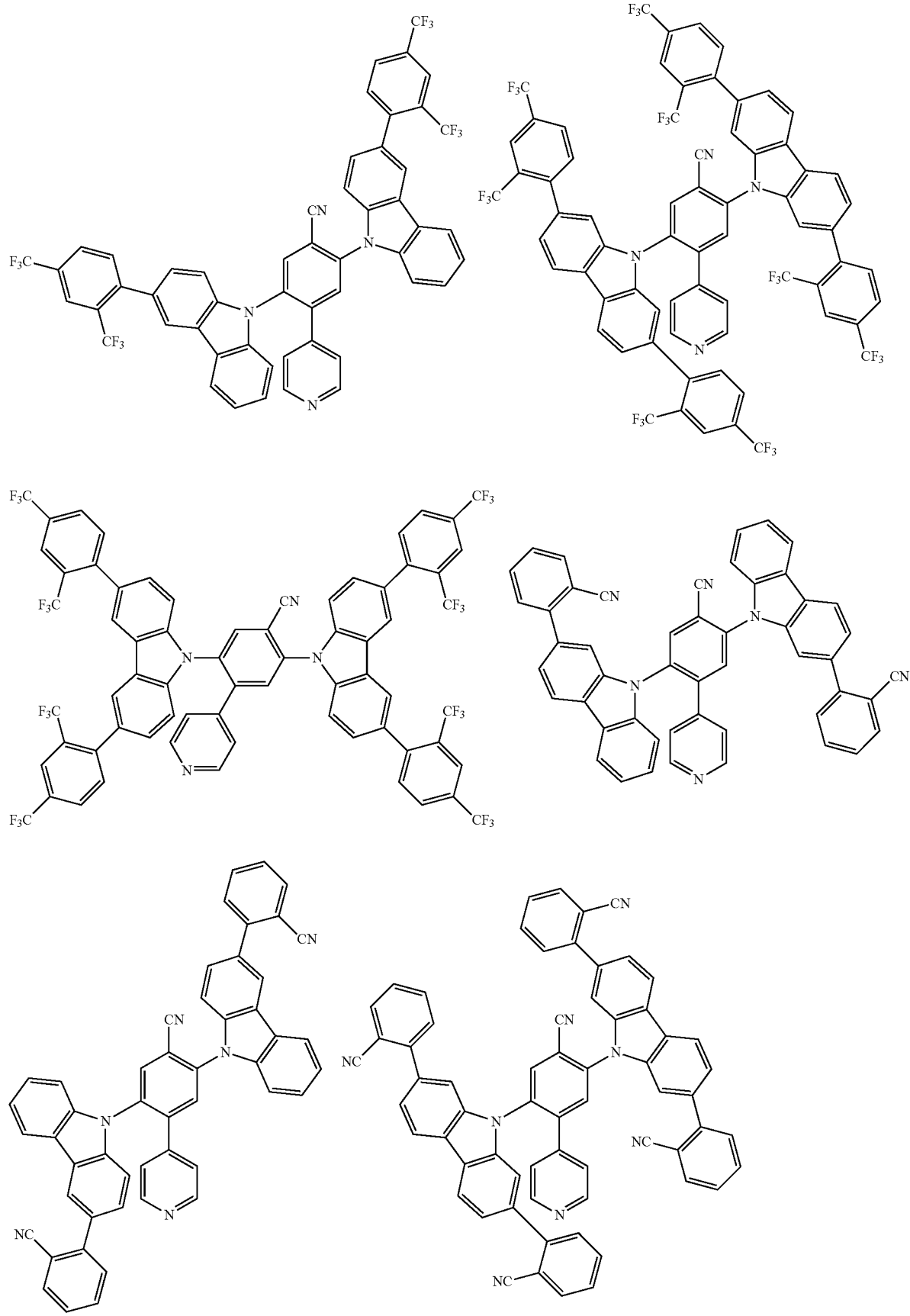

97 98
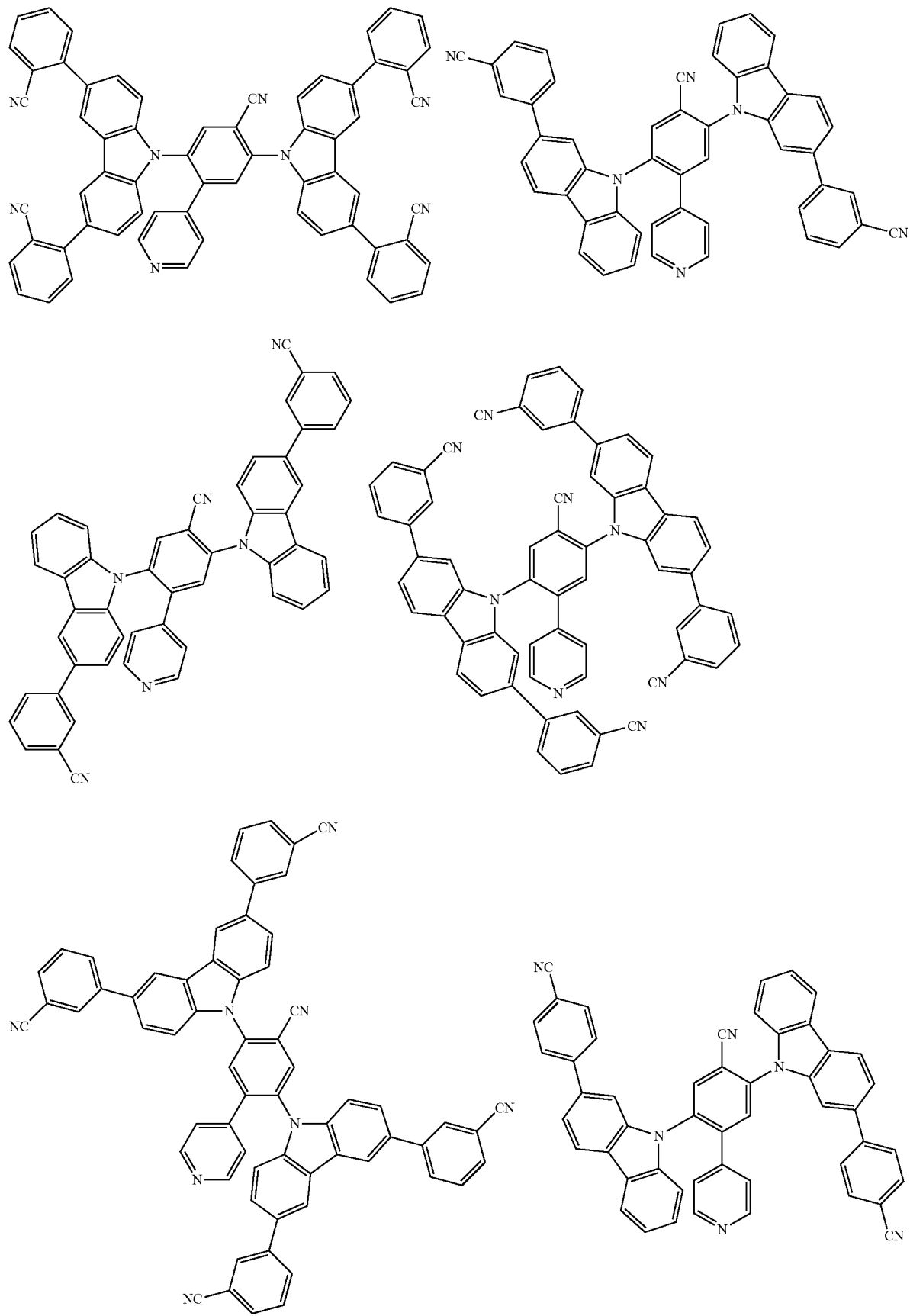
-continued

-continued
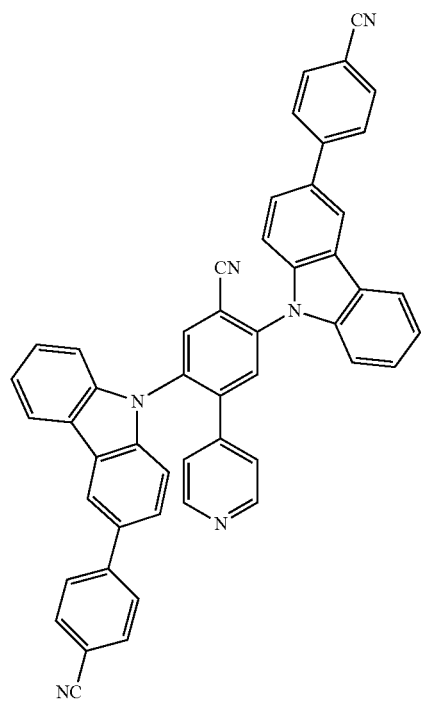
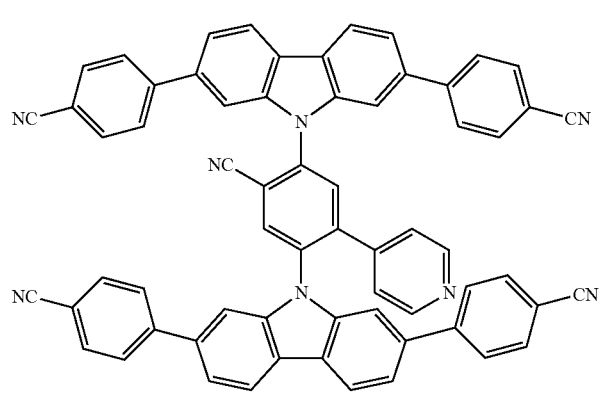
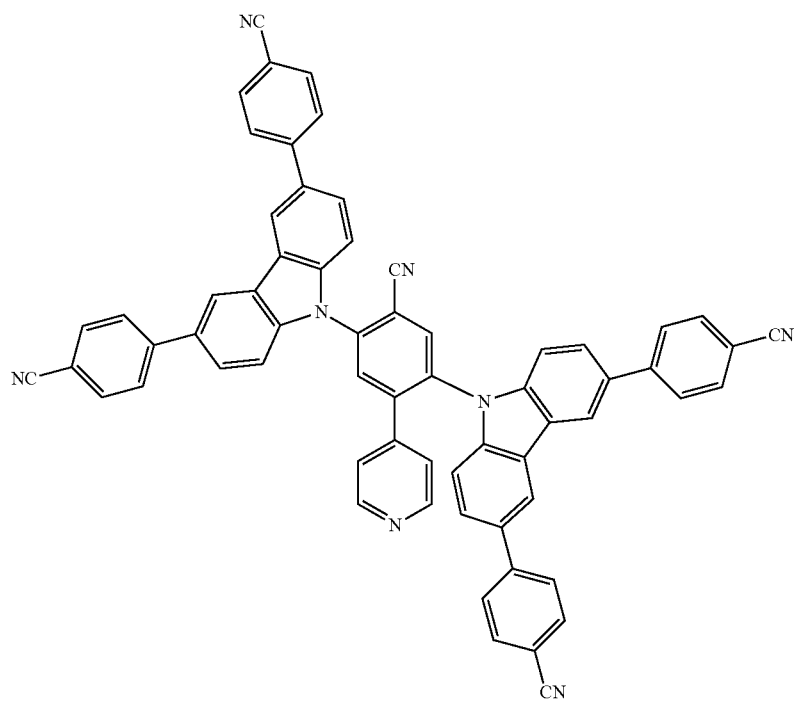

101
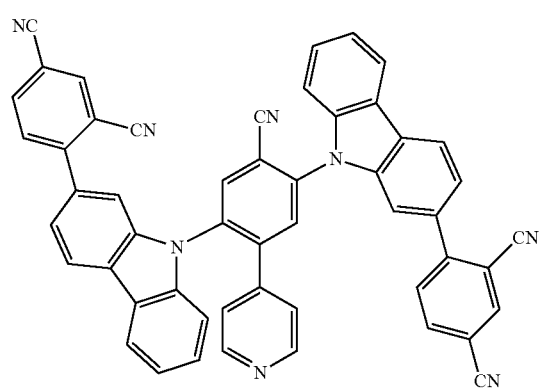
102
-continued
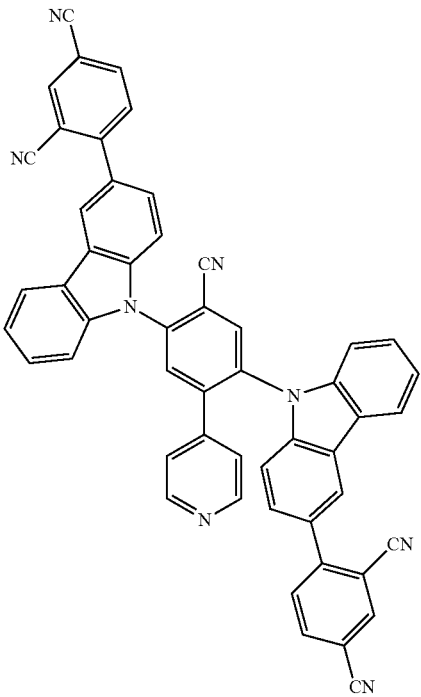
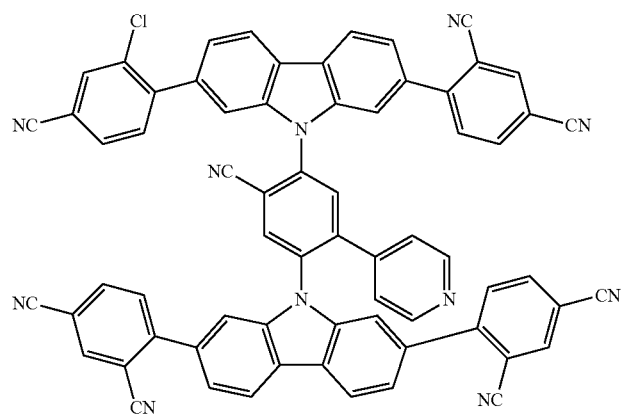
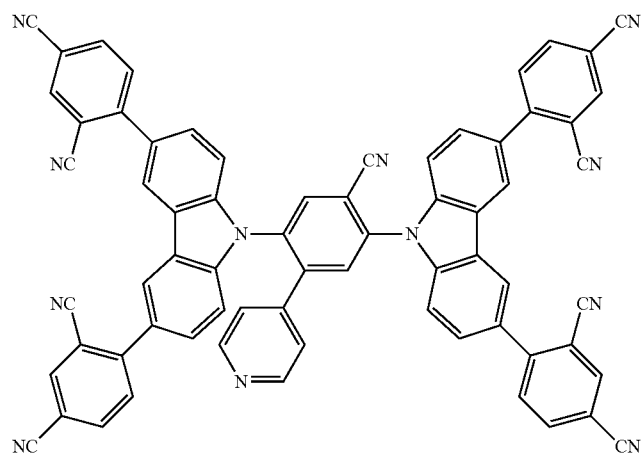

103
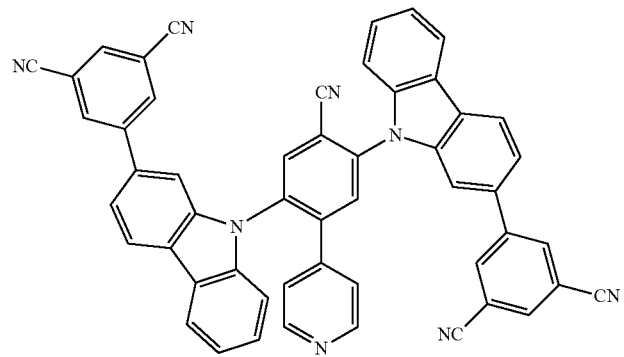
104
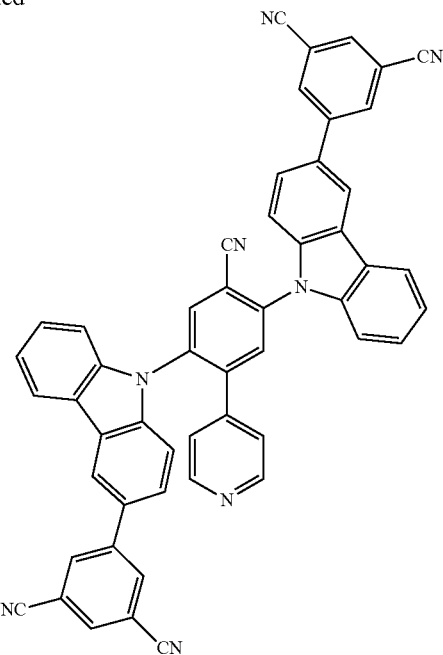
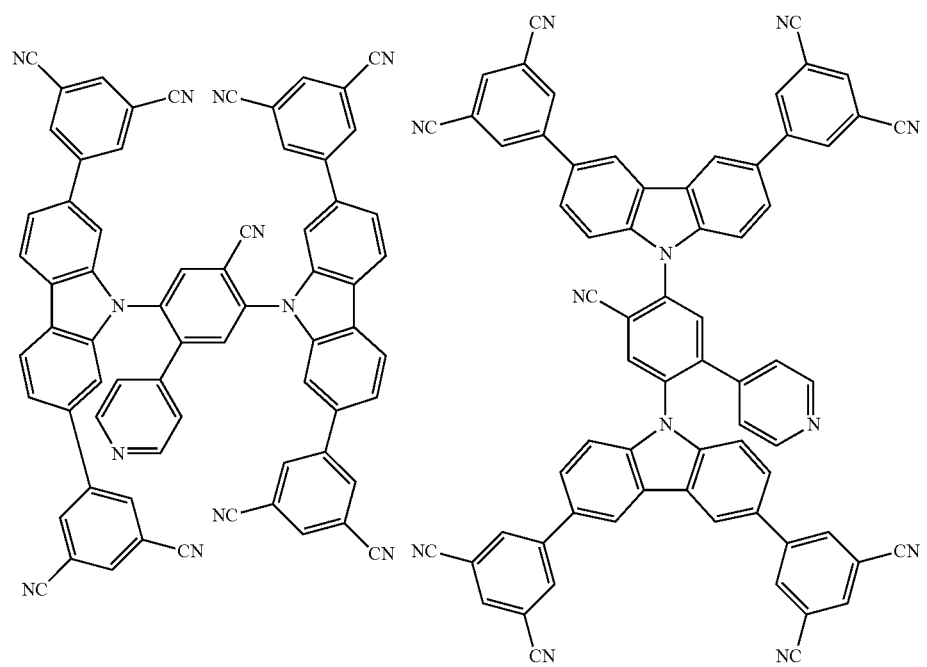

-continued
105
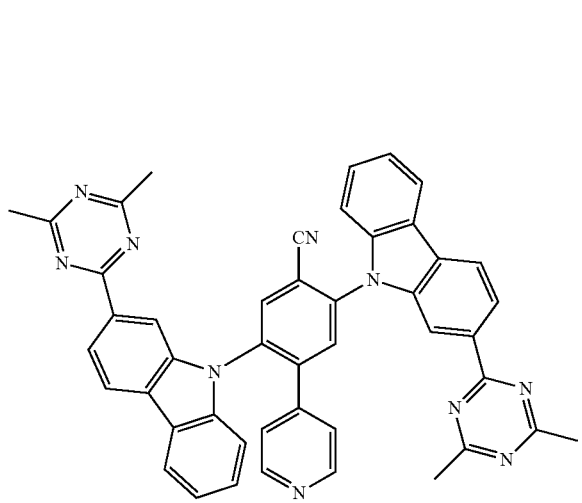
106
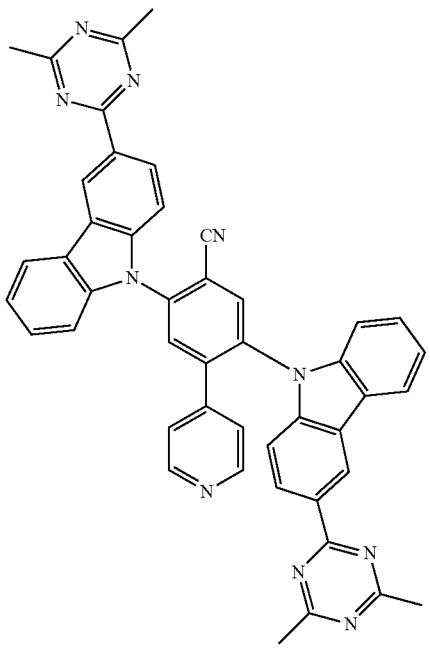
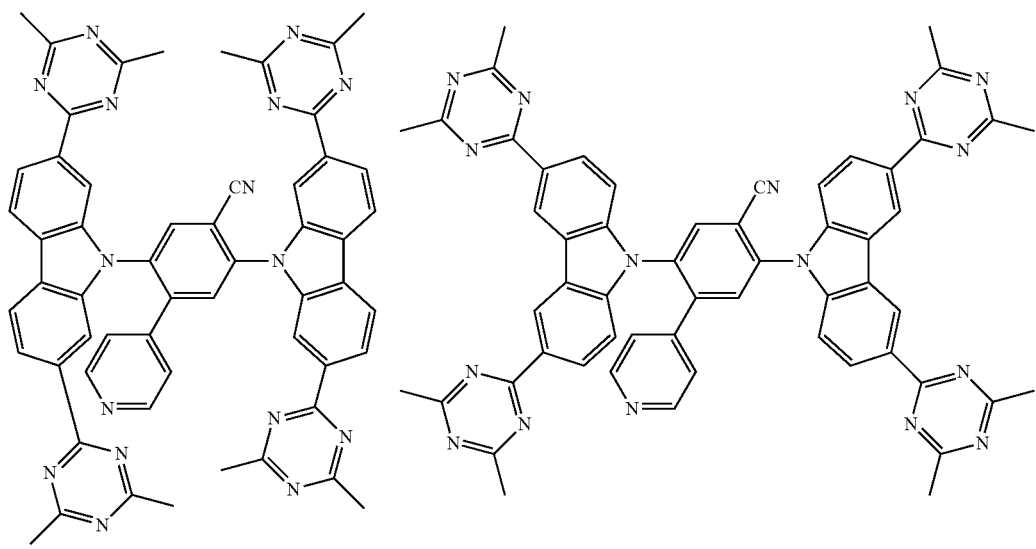
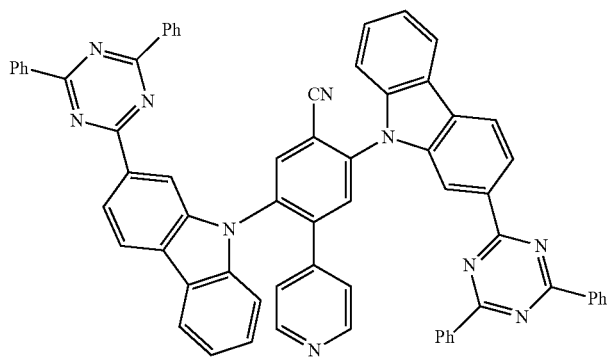

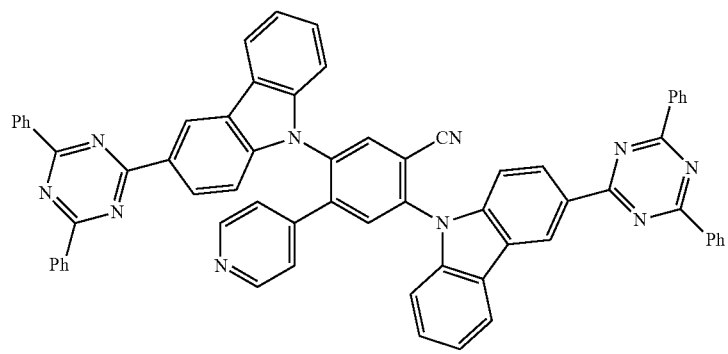
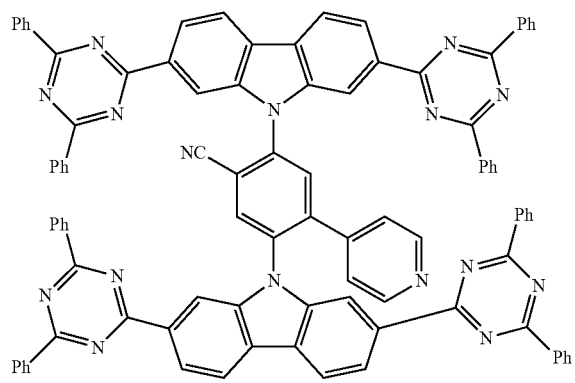
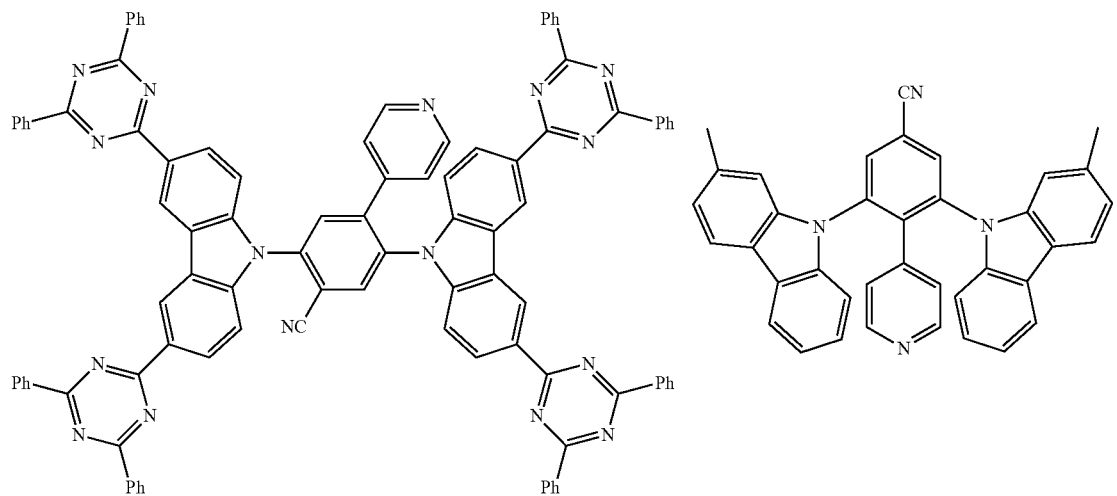
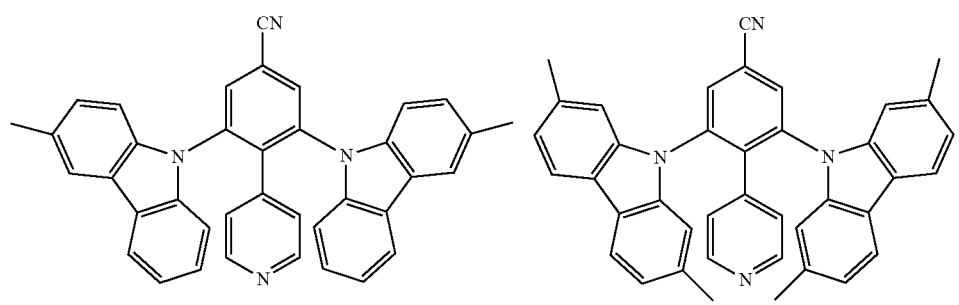

109
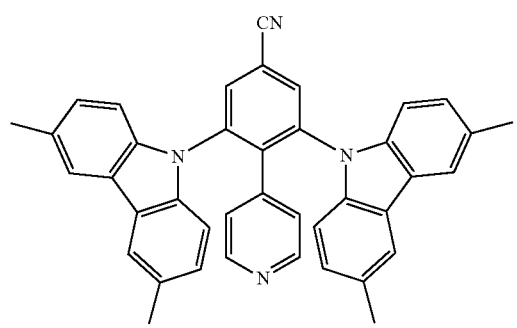
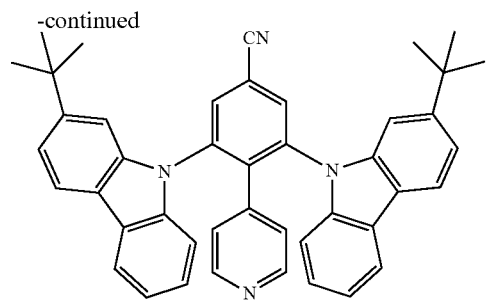
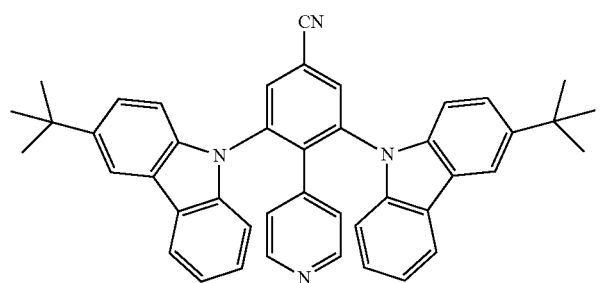
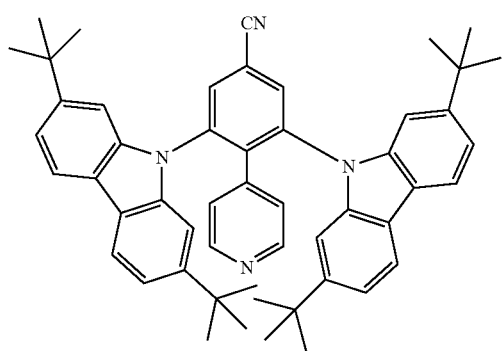
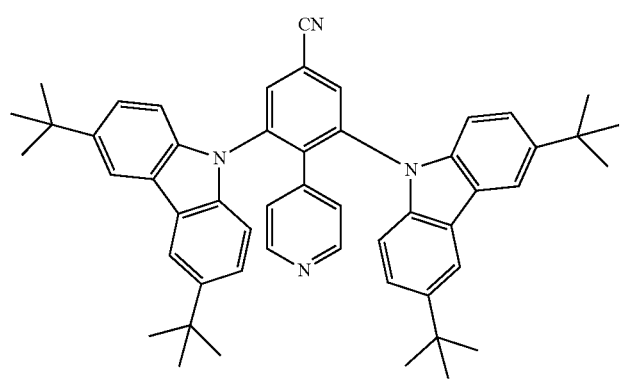
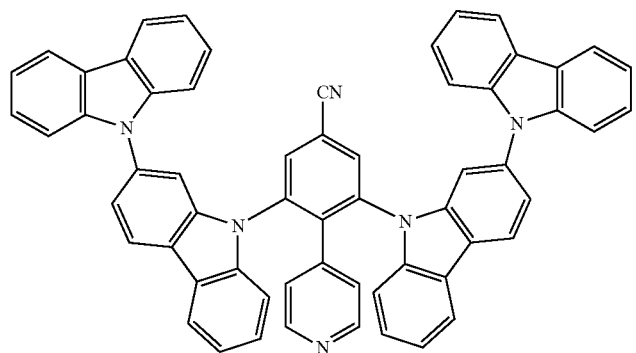
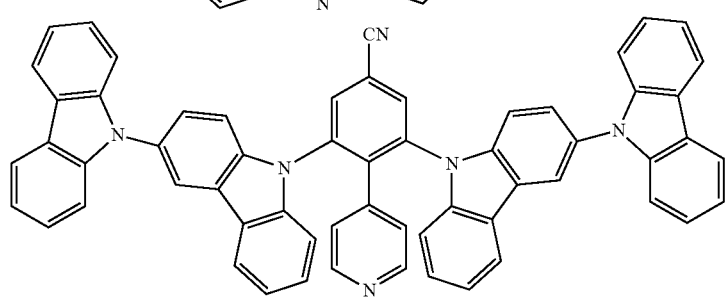
110
-continued 111
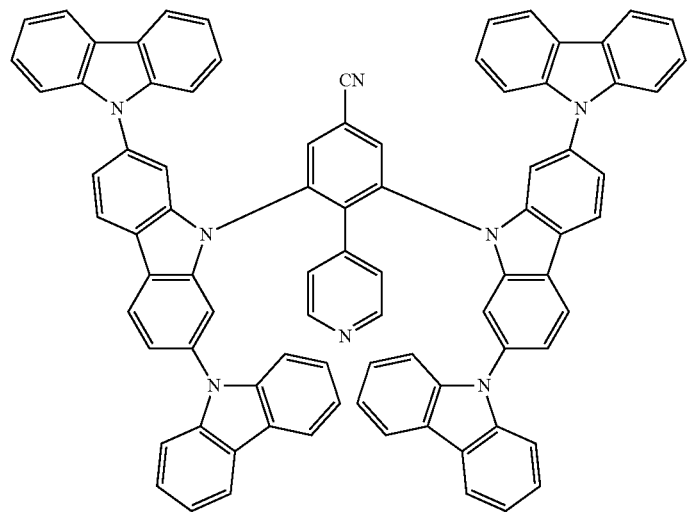
112
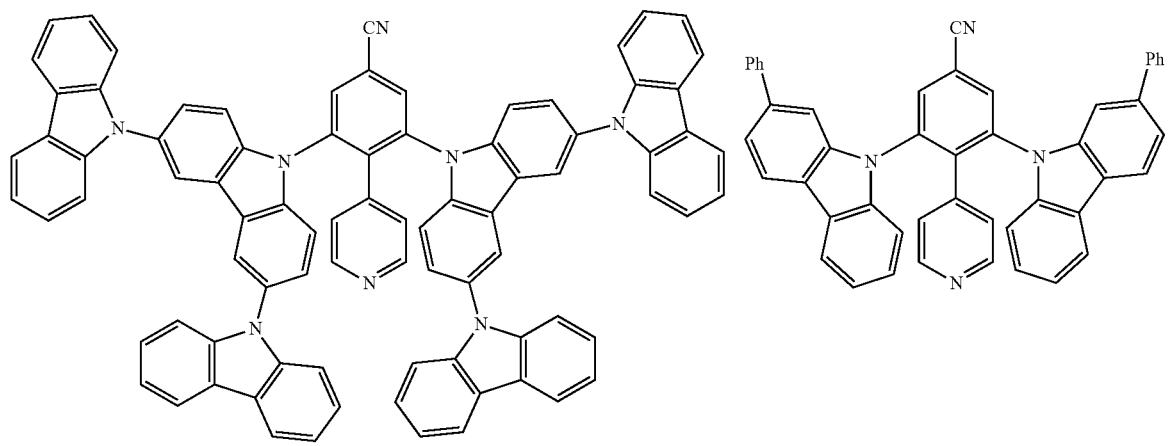
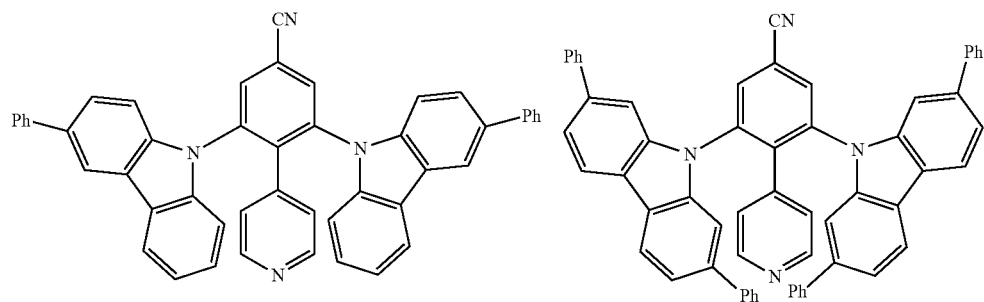
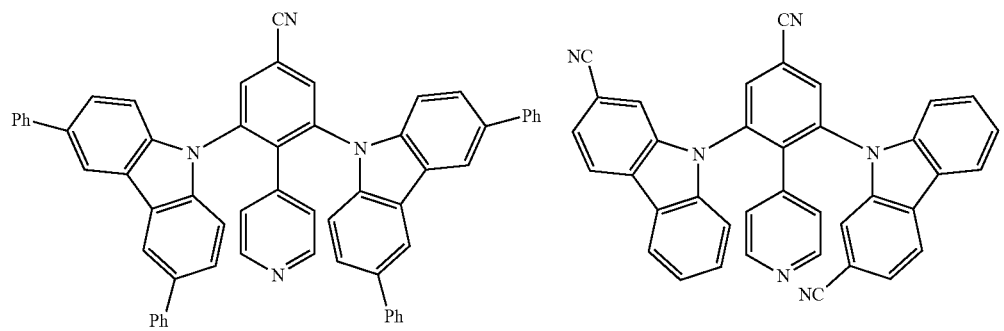

-continued
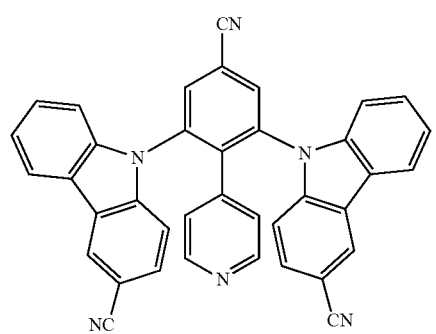
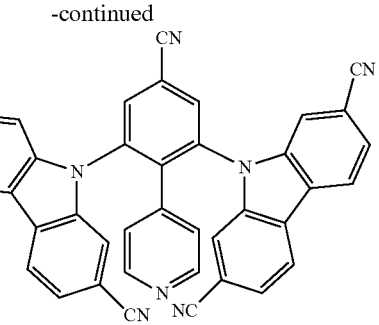
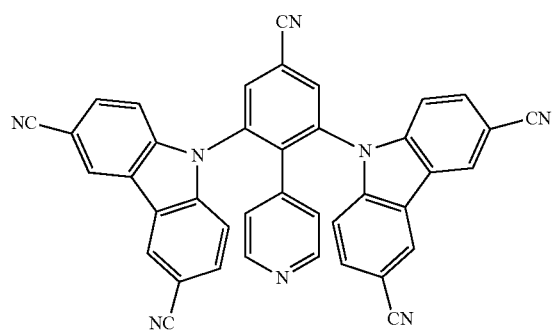
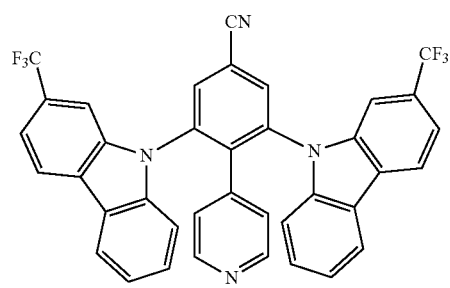
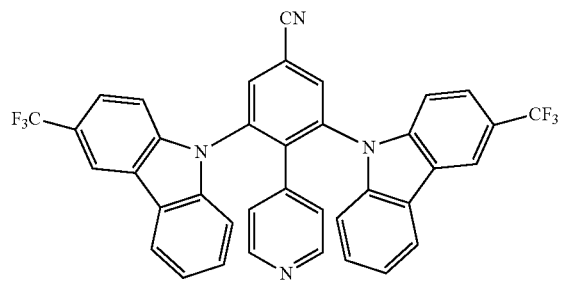
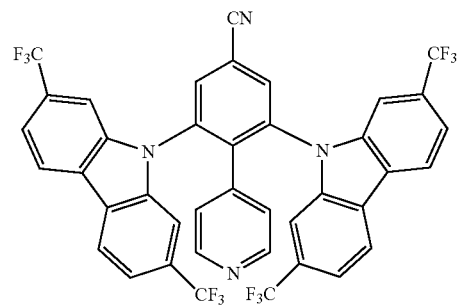
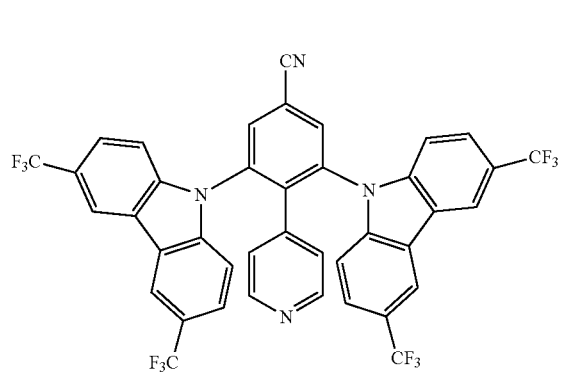
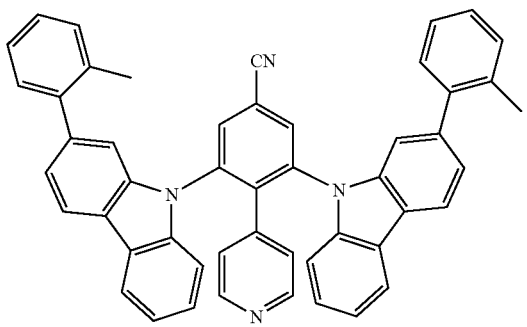

-continued
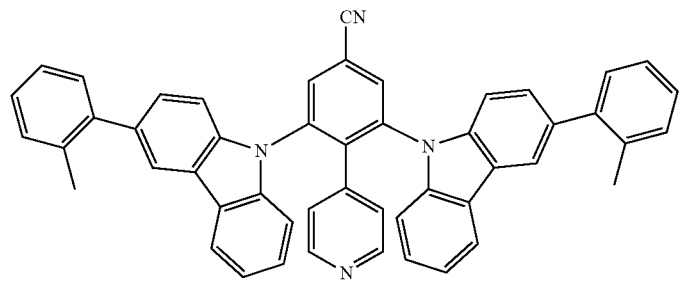
115
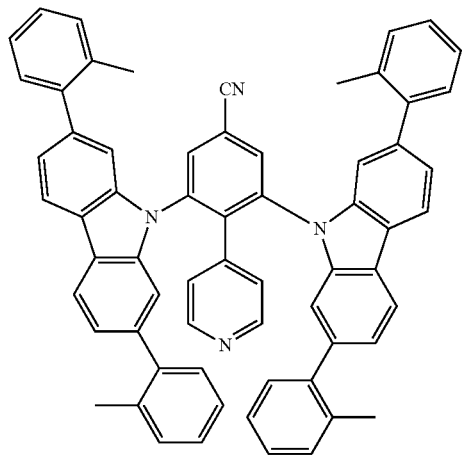
116
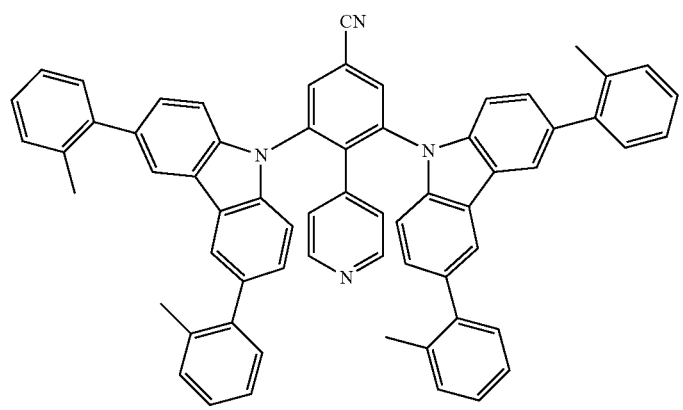
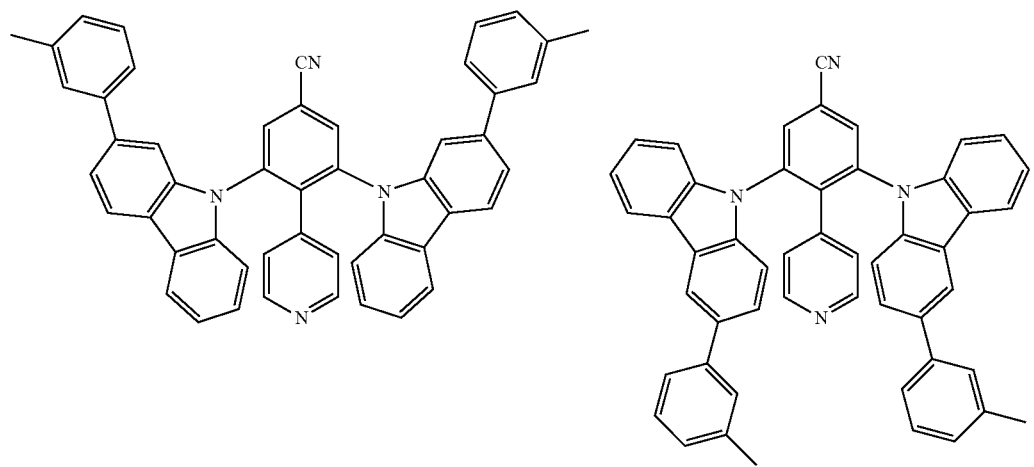

-continued
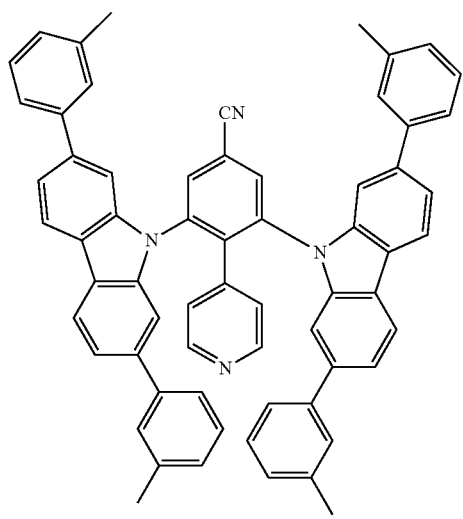
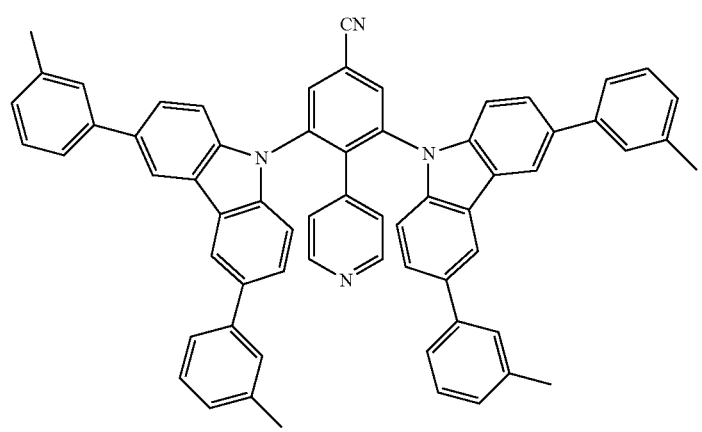
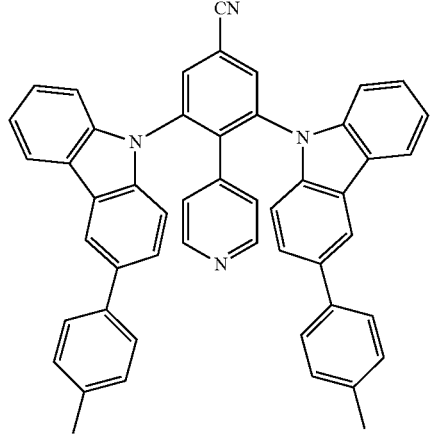
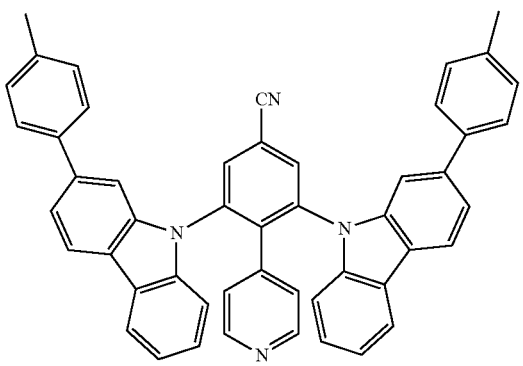
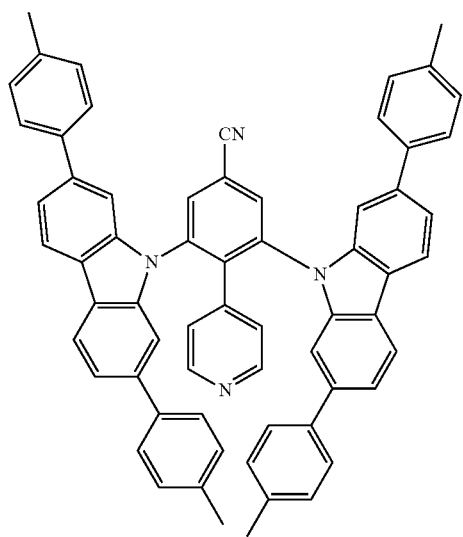
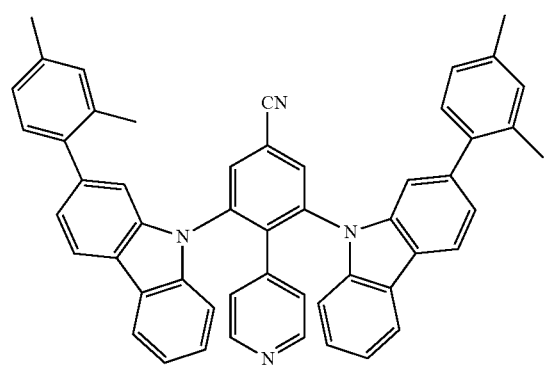

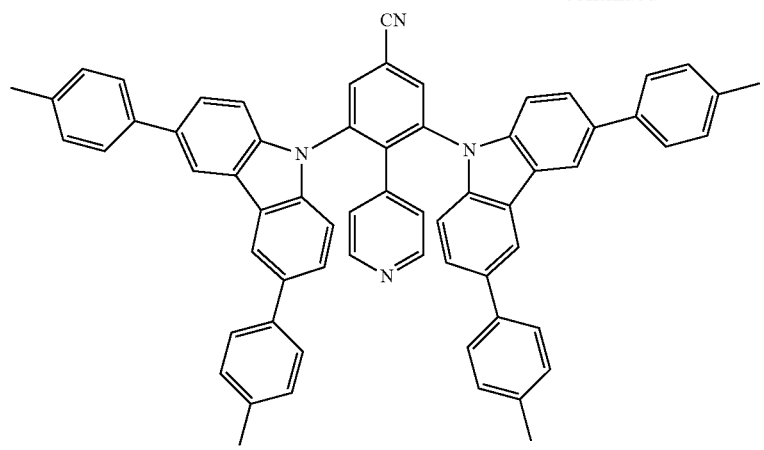
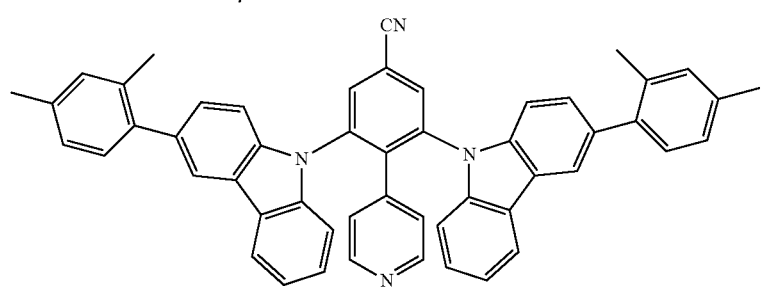
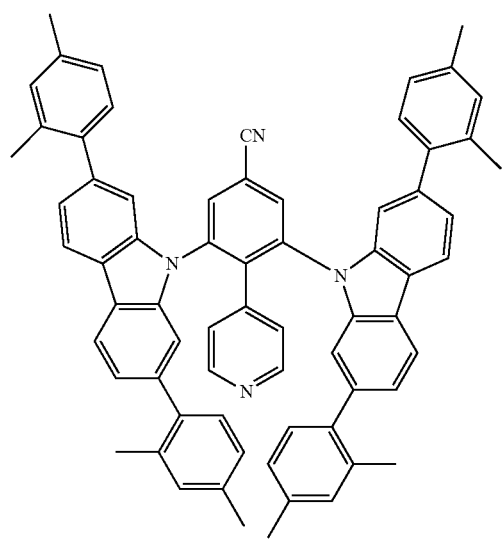
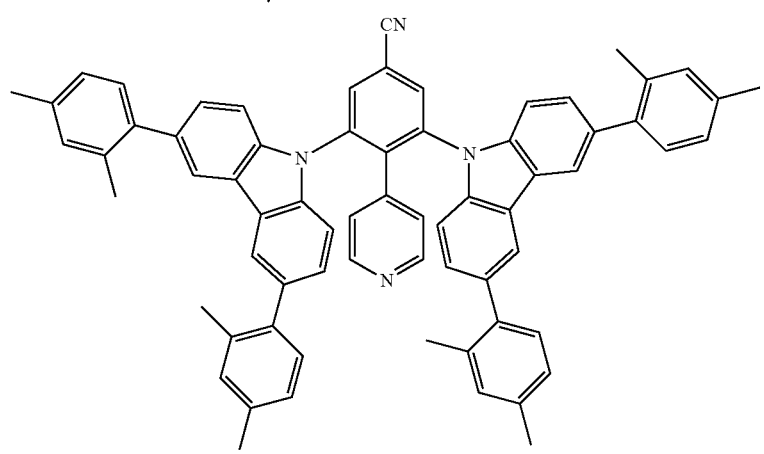

-continued
121
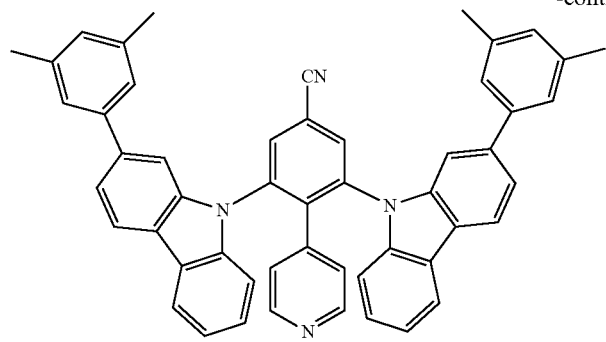
122
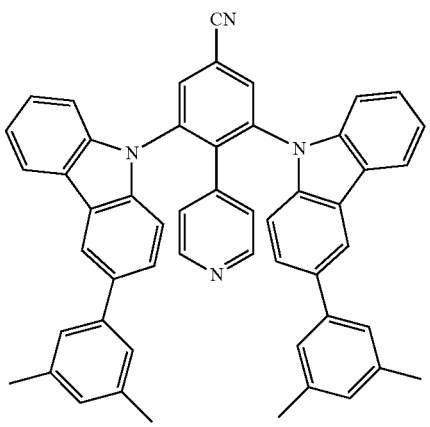
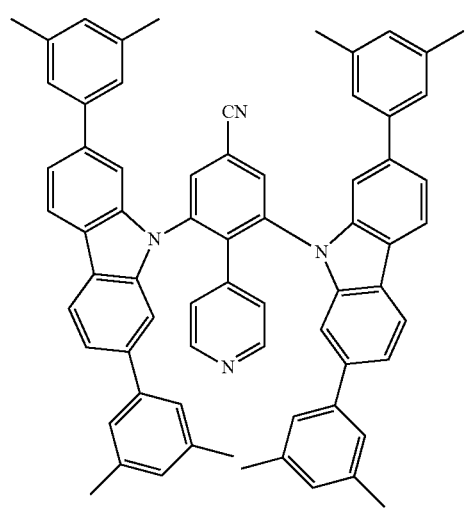
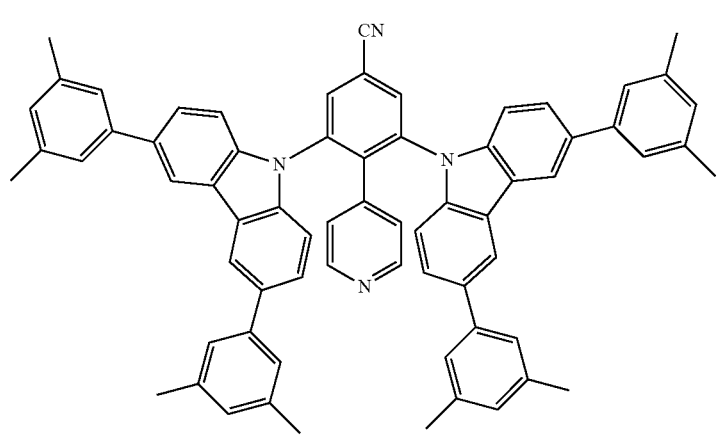
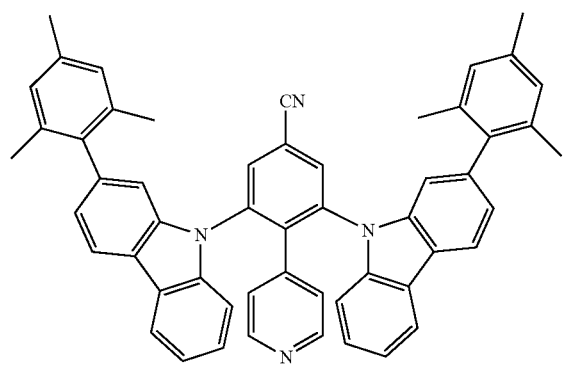
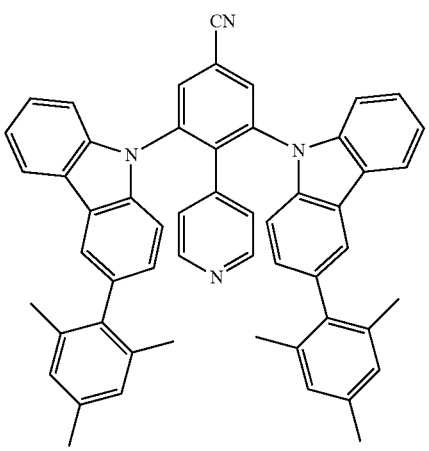

123
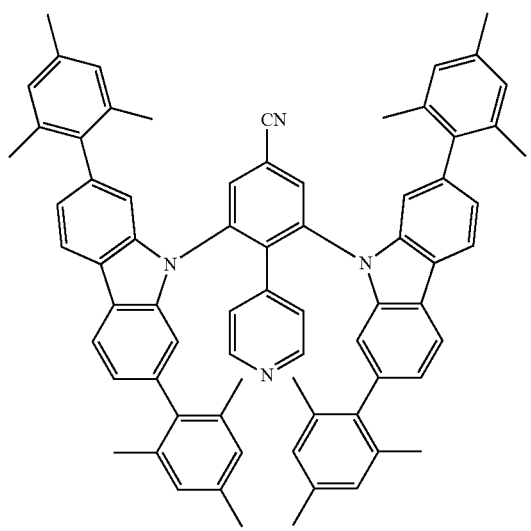
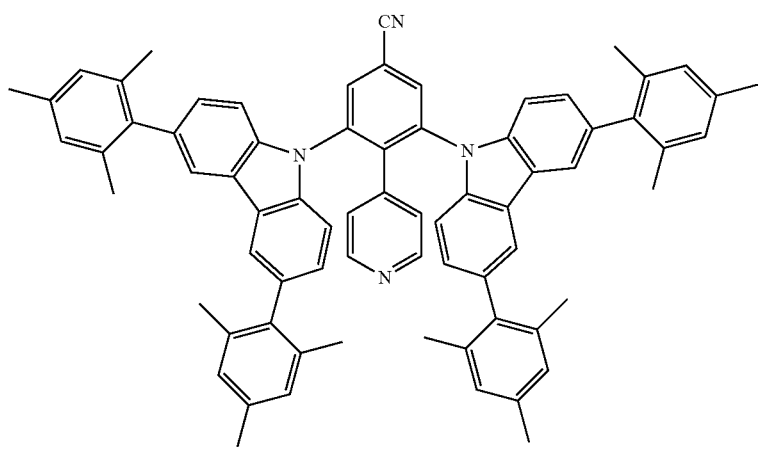
124
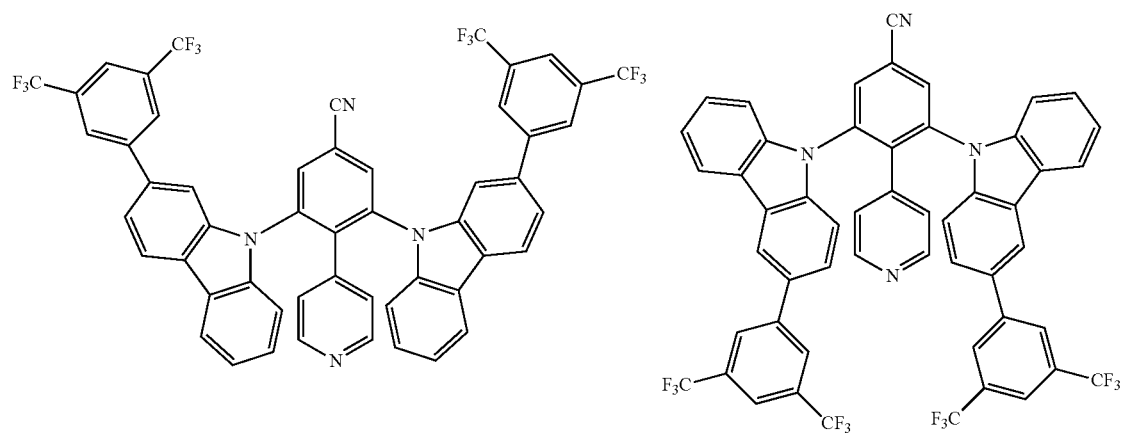

125
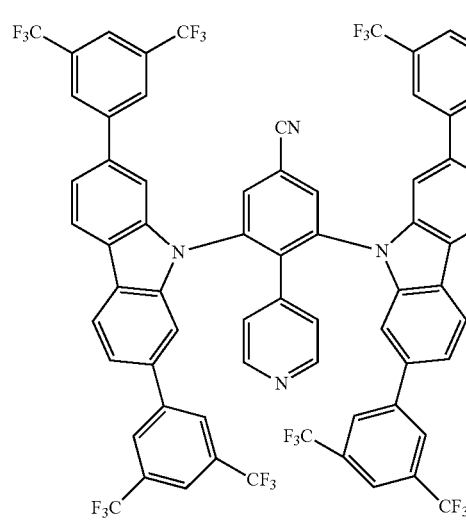
126
-continued
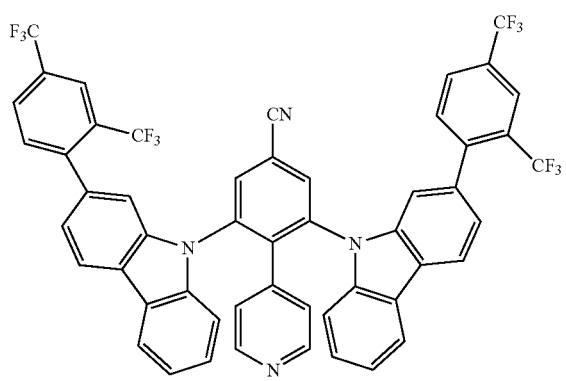
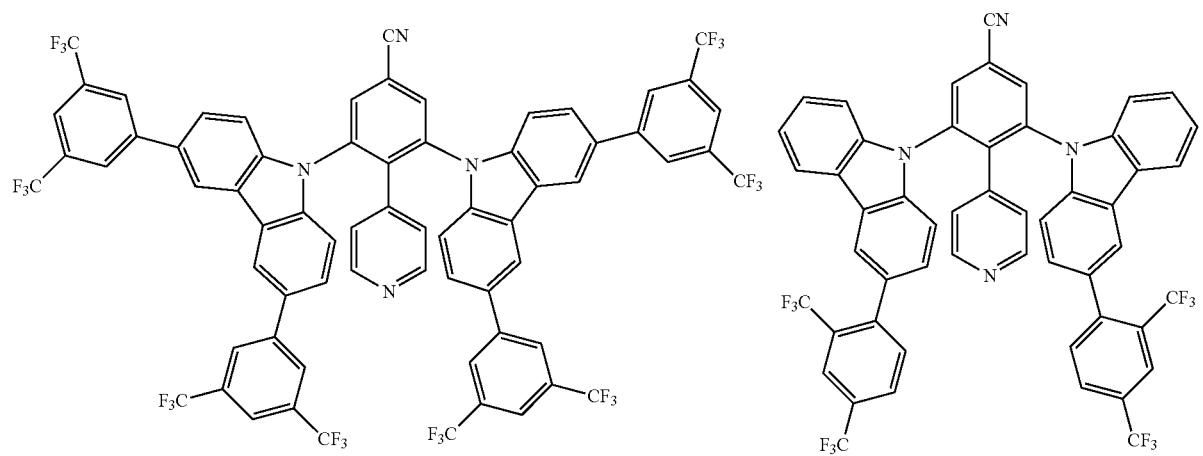
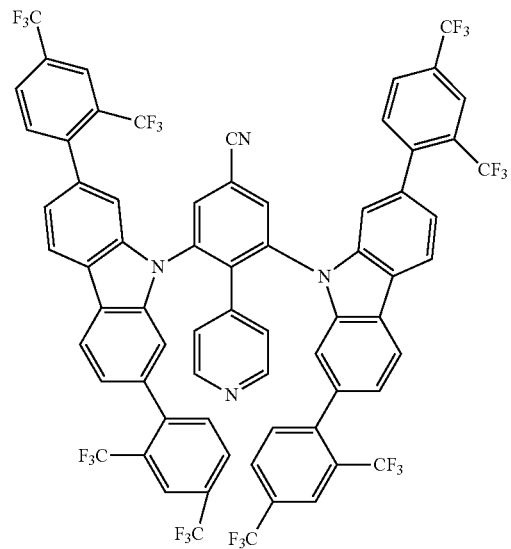

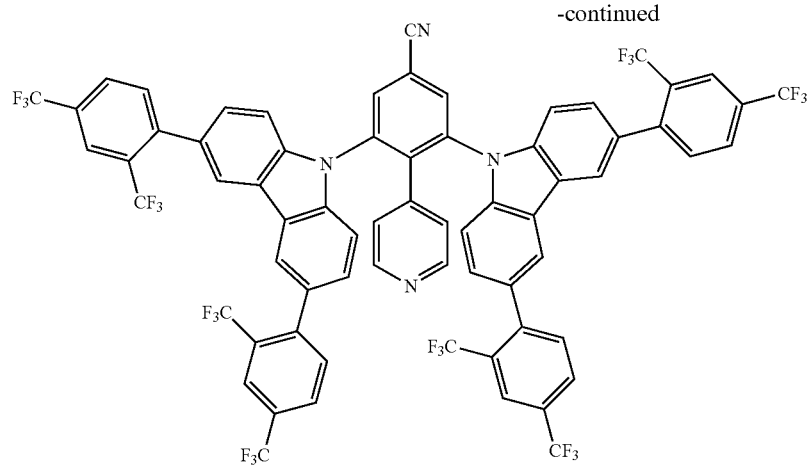
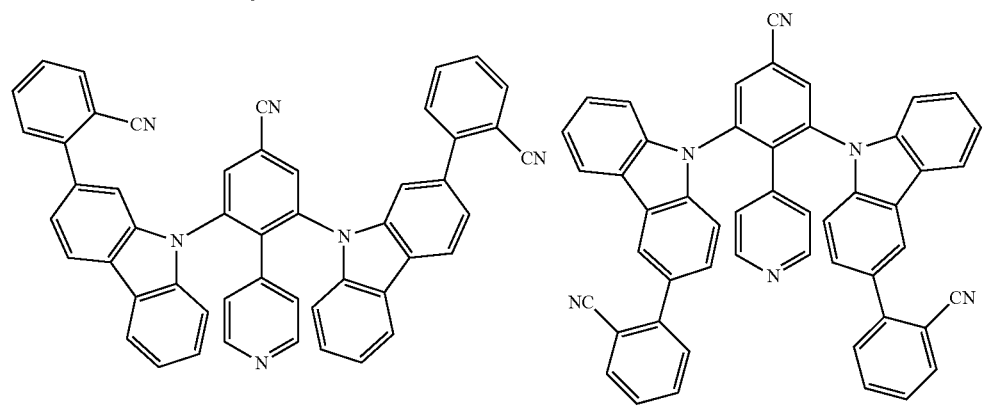
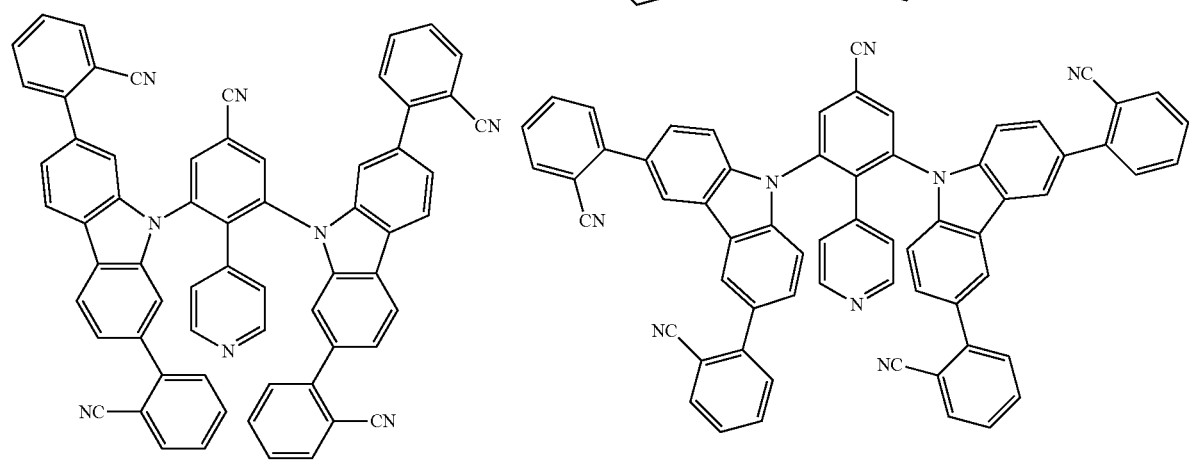
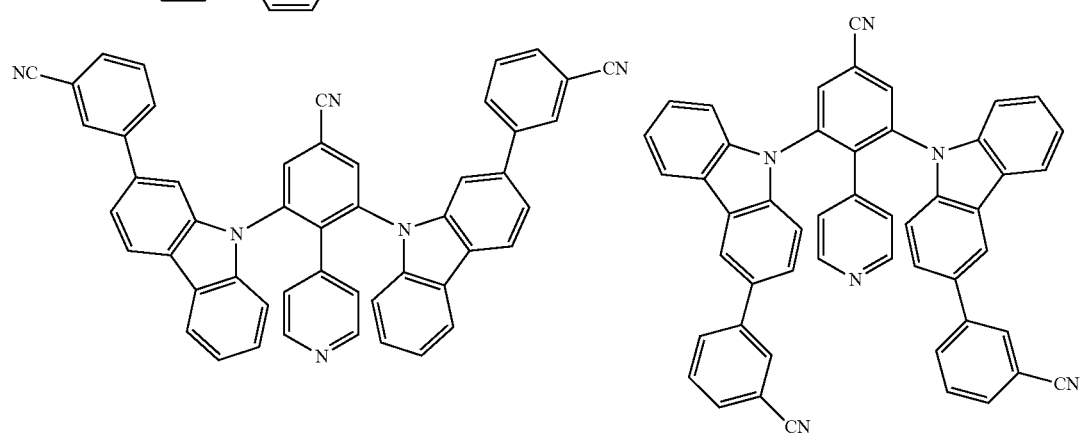

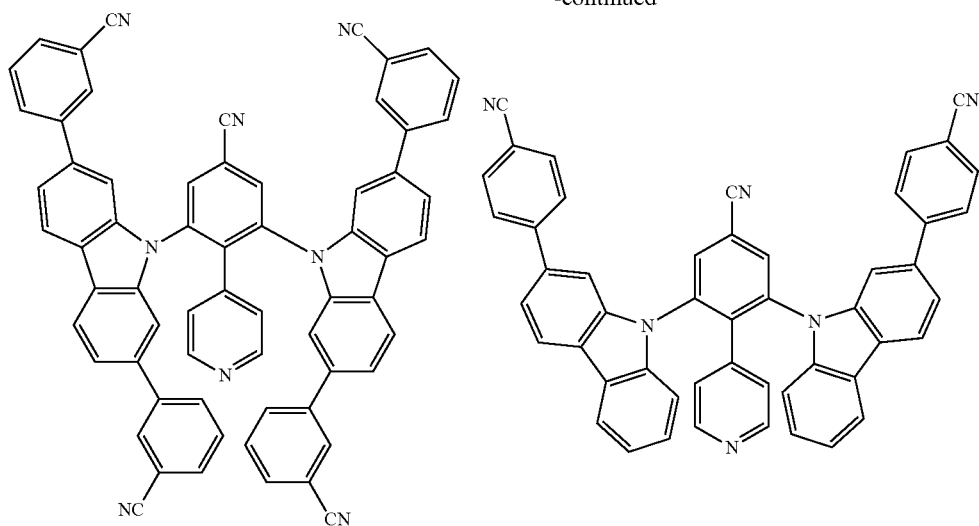
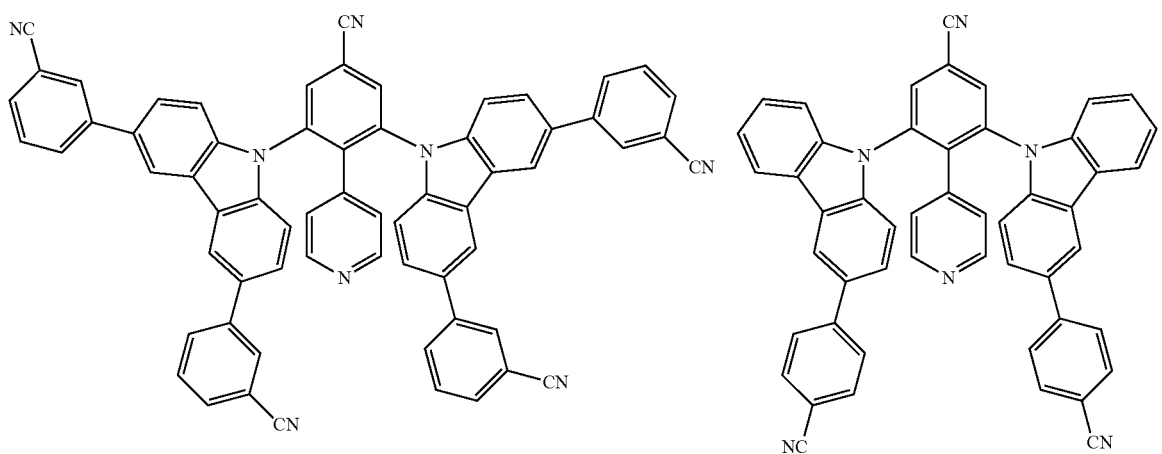
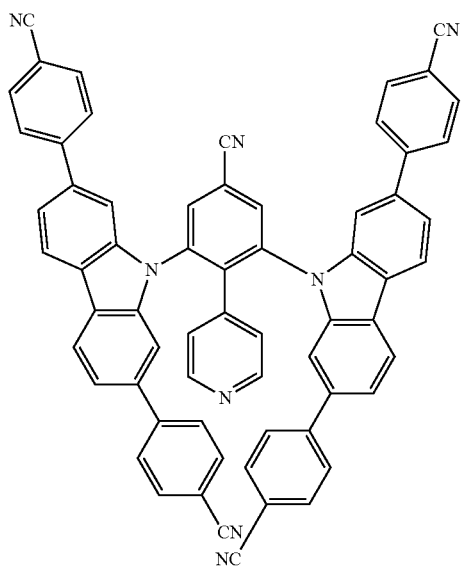

-continued
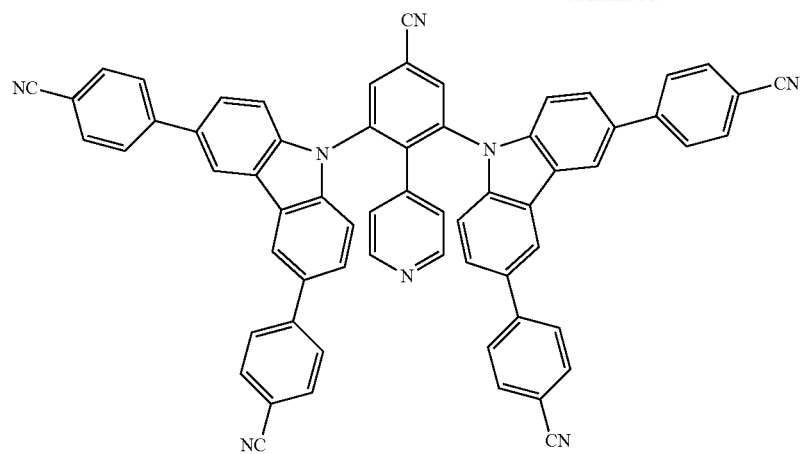
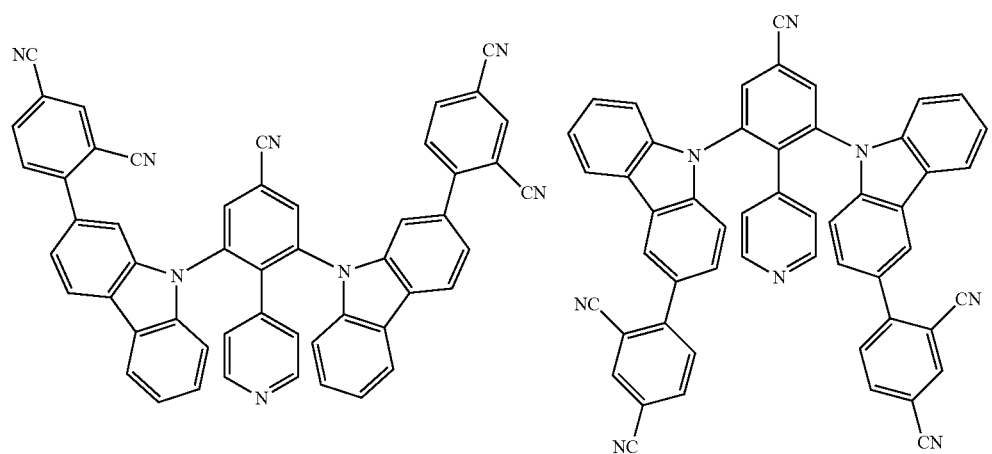
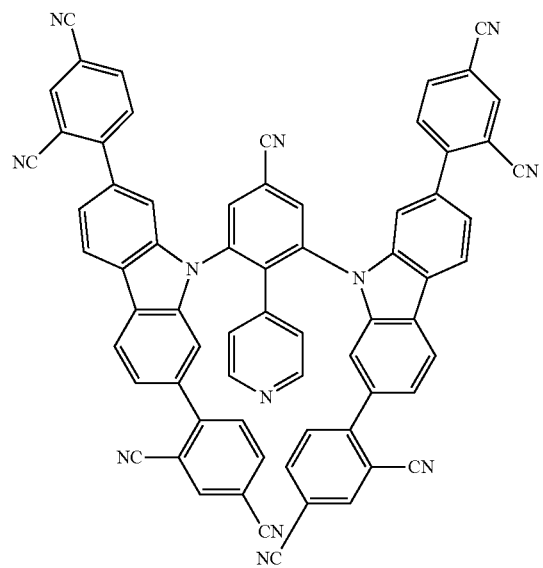

-continued
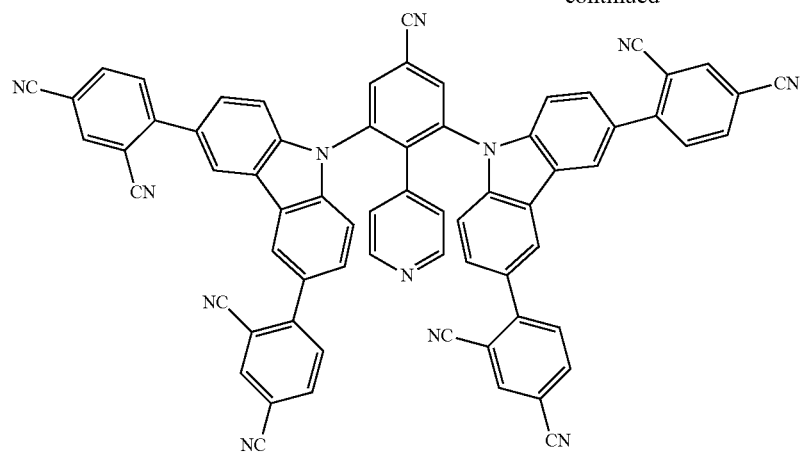
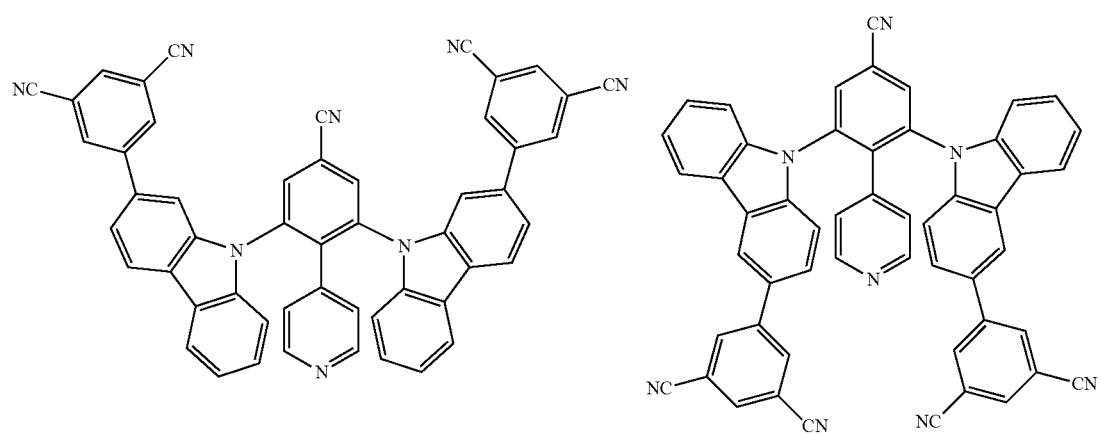
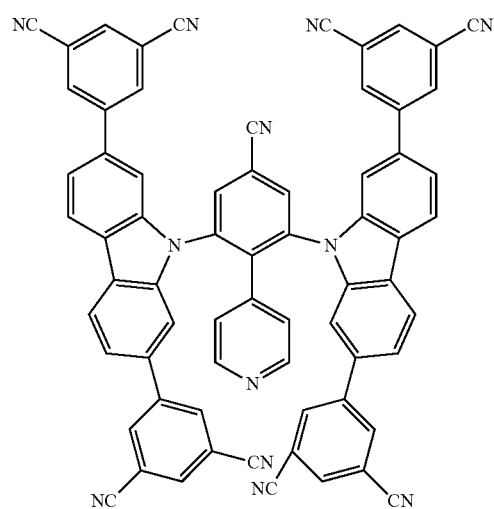

-continued
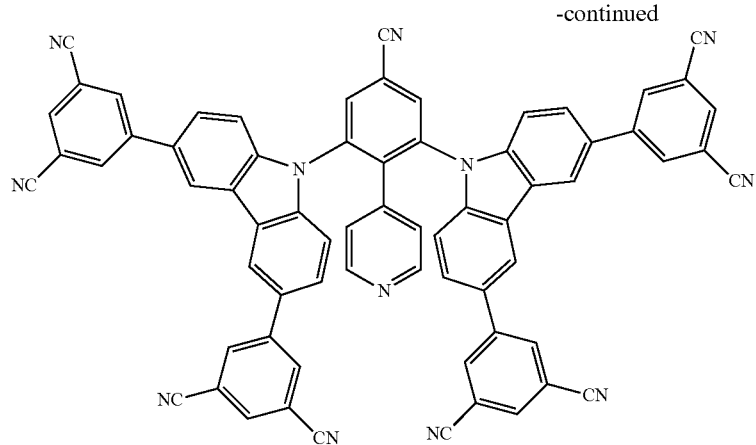
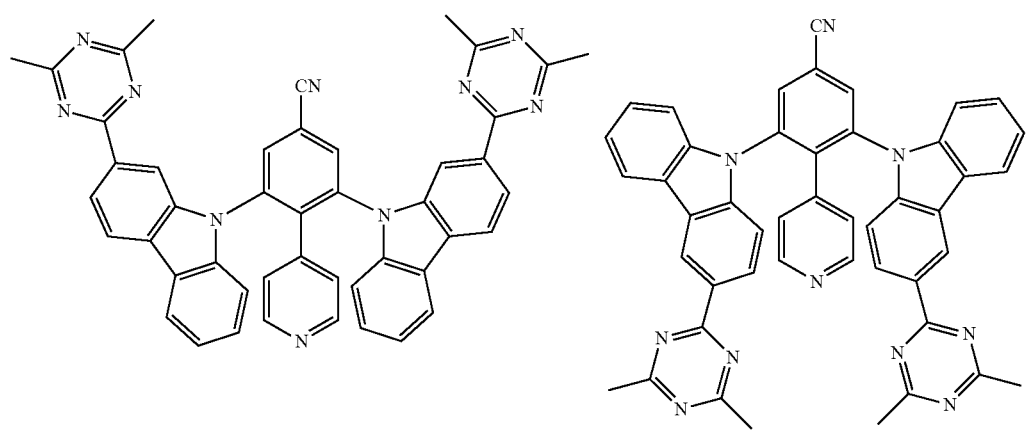
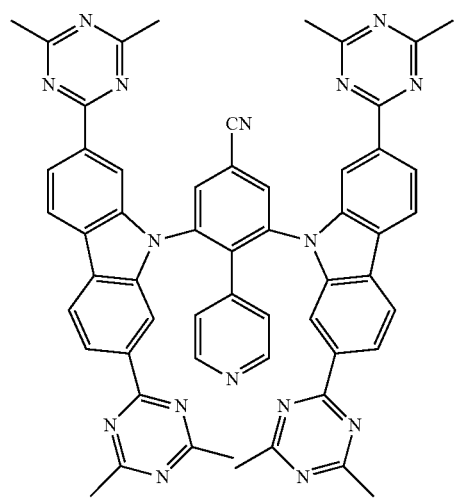

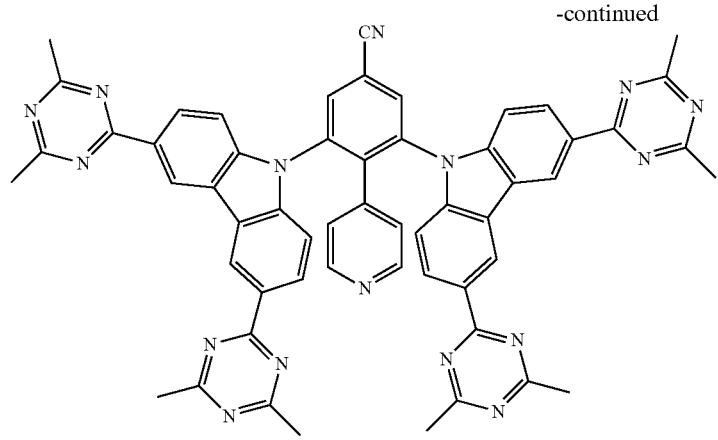
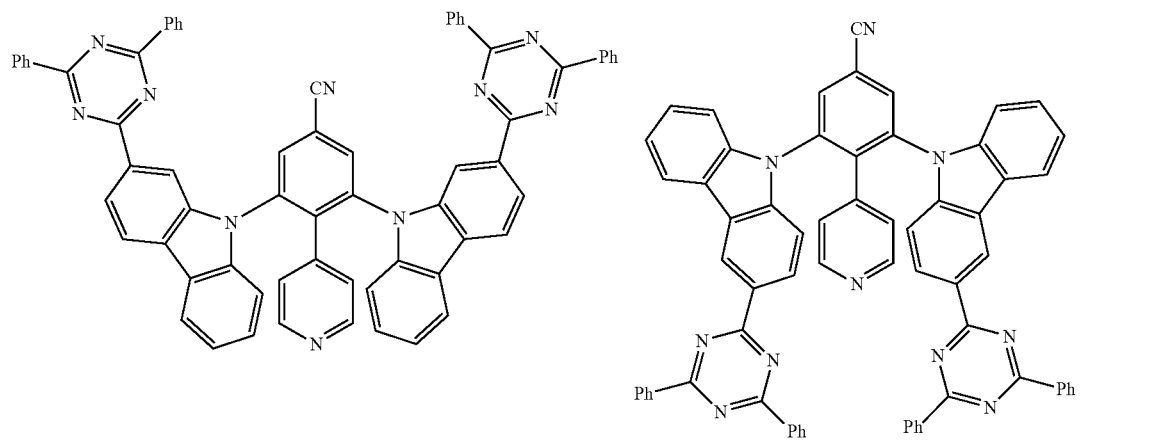
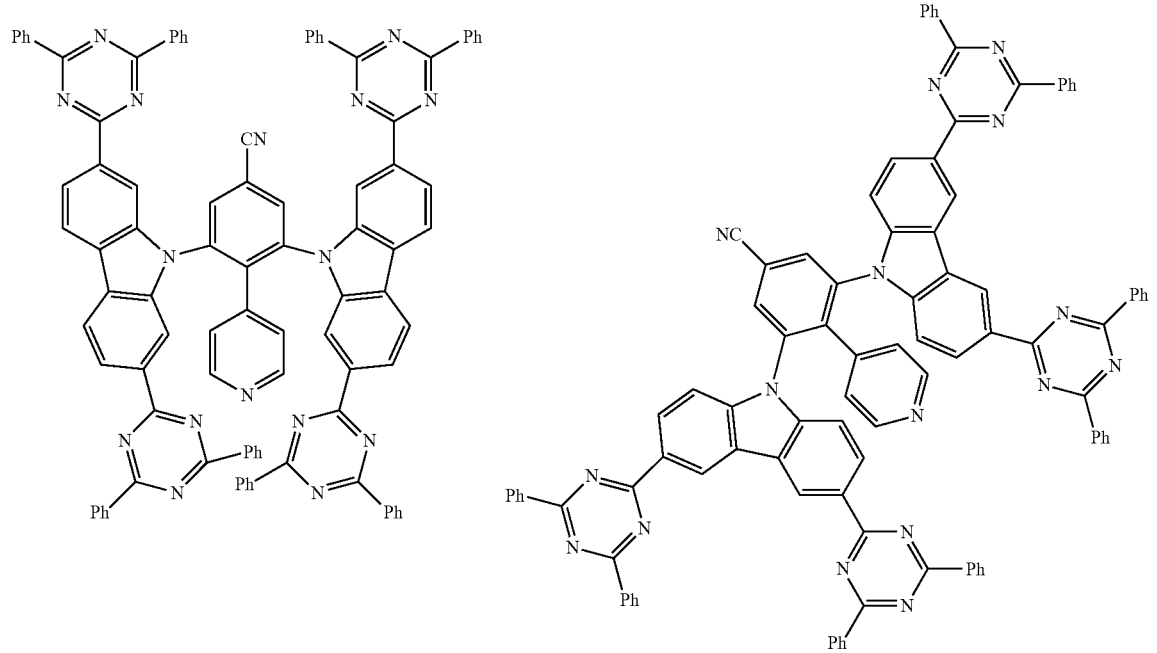

-continued
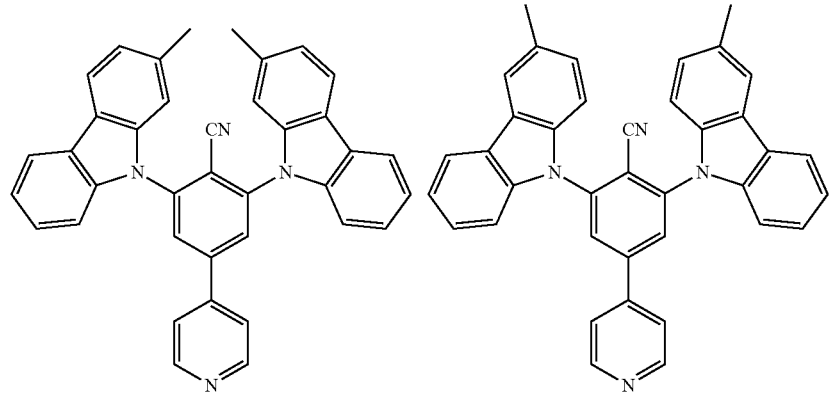
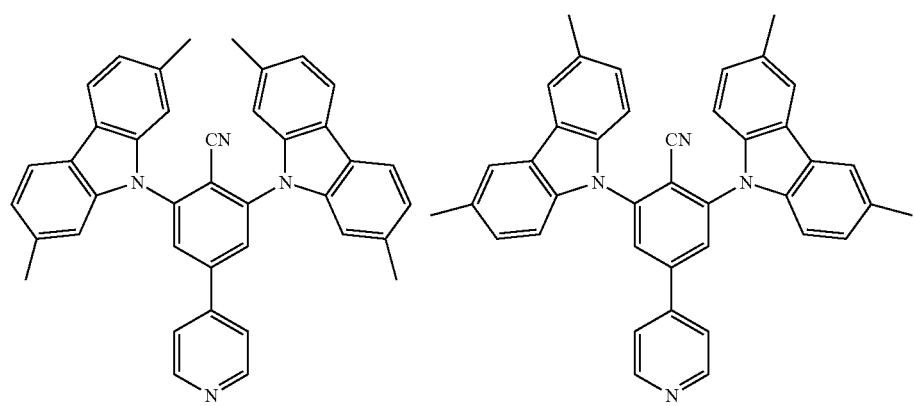
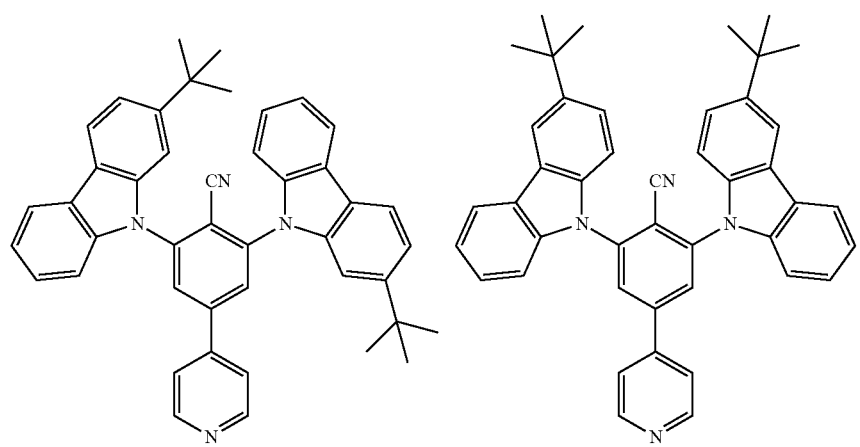
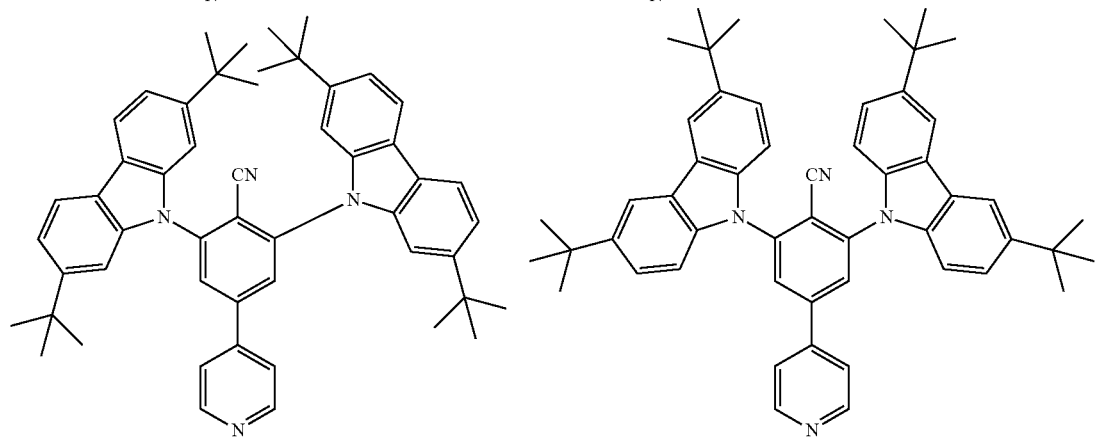

141
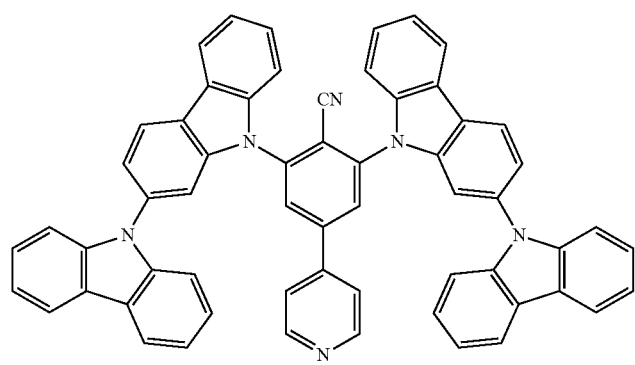
142
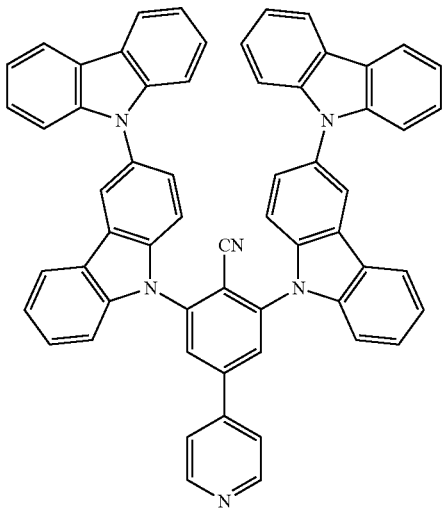
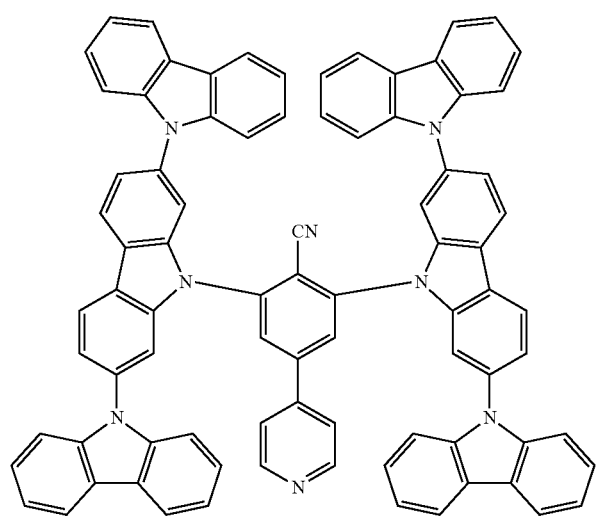
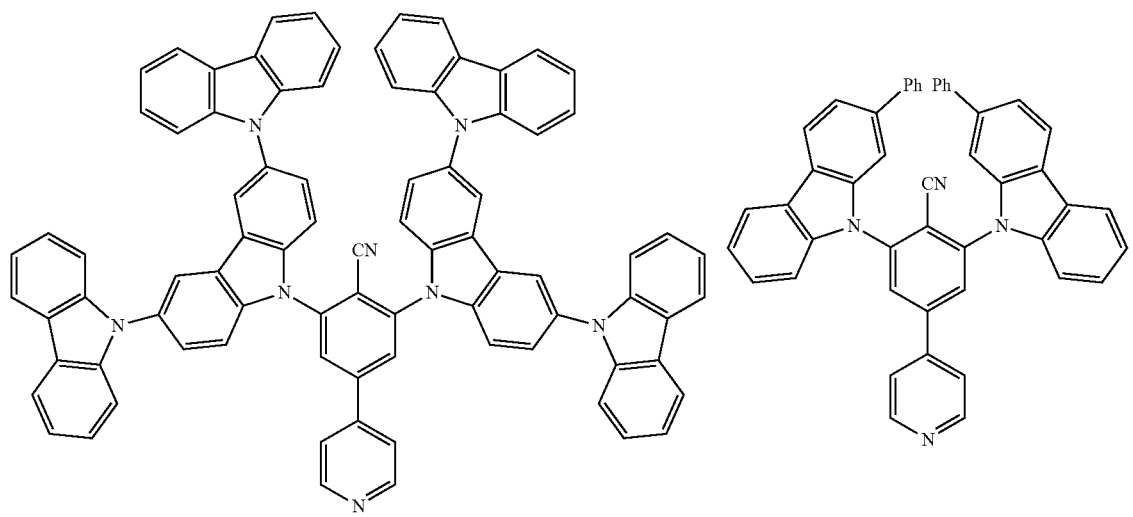

-continued
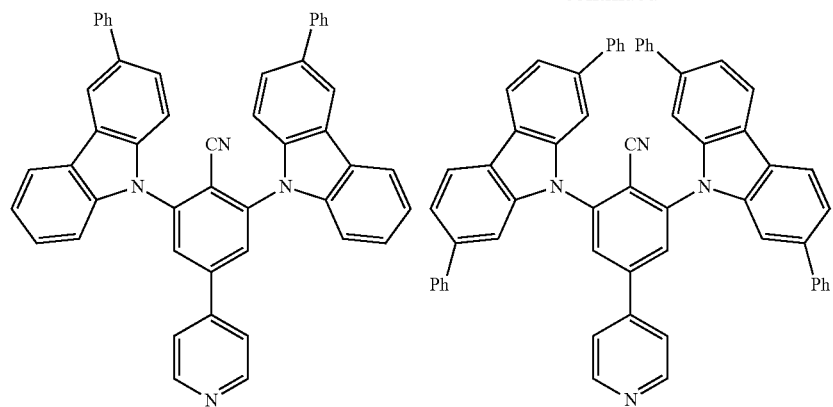
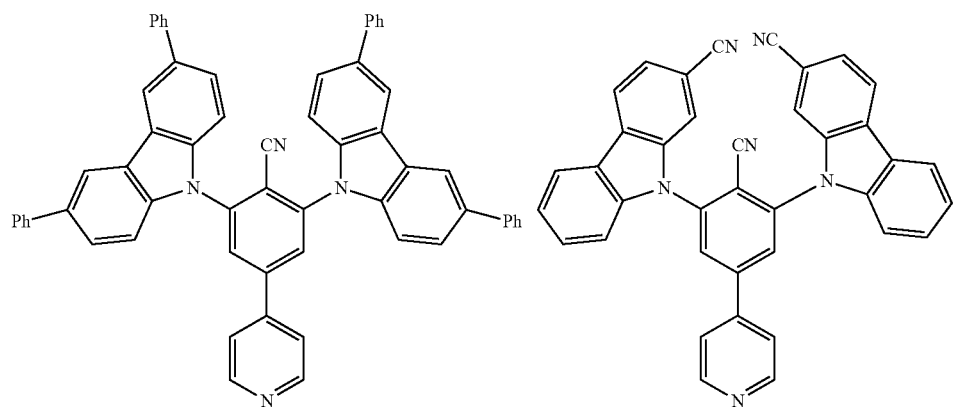
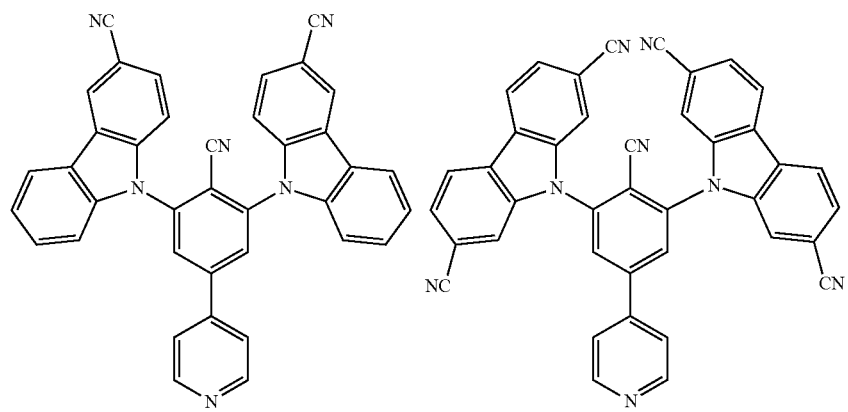
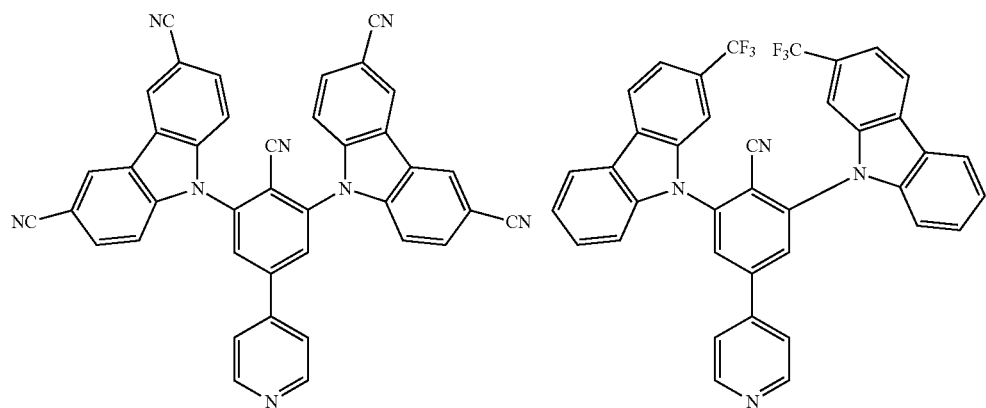

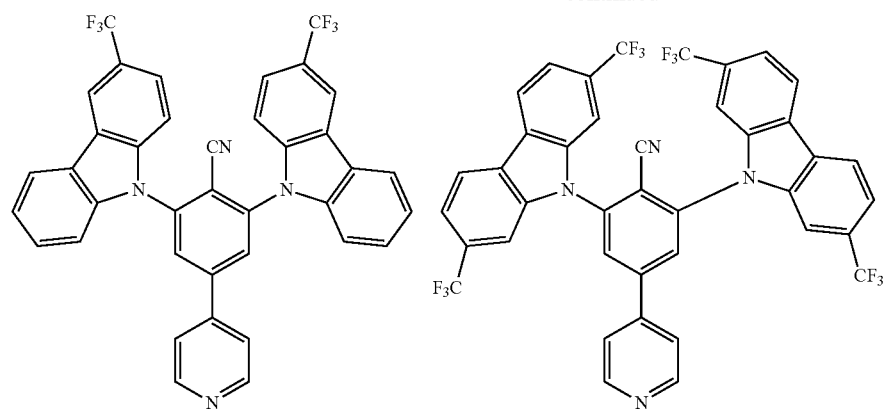
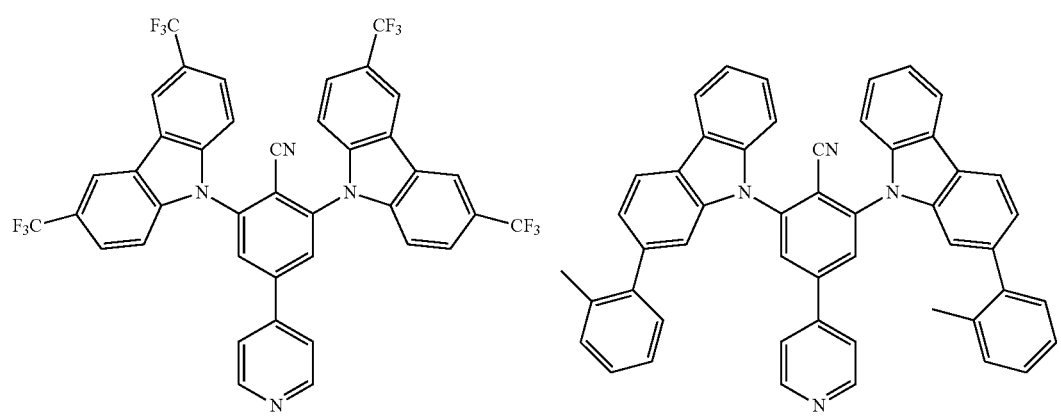
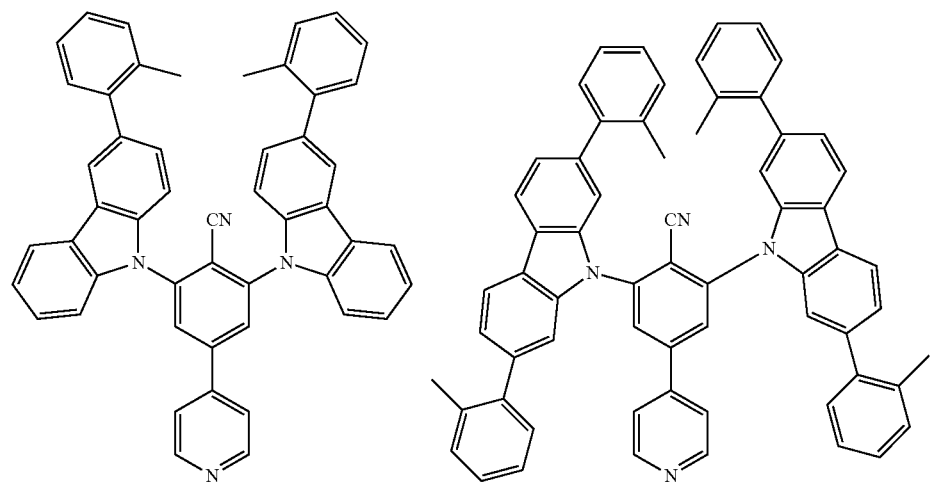

147 148
-continued
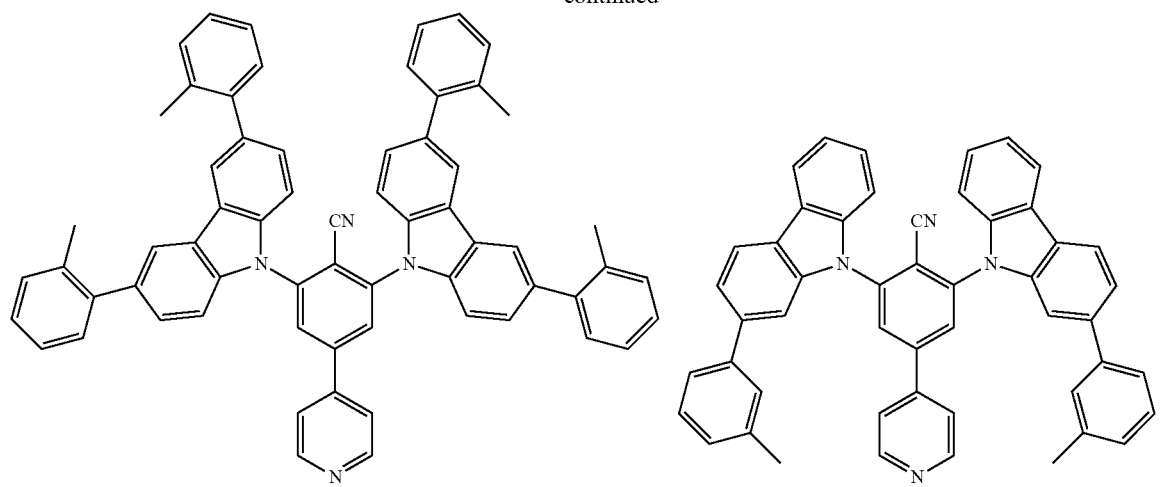
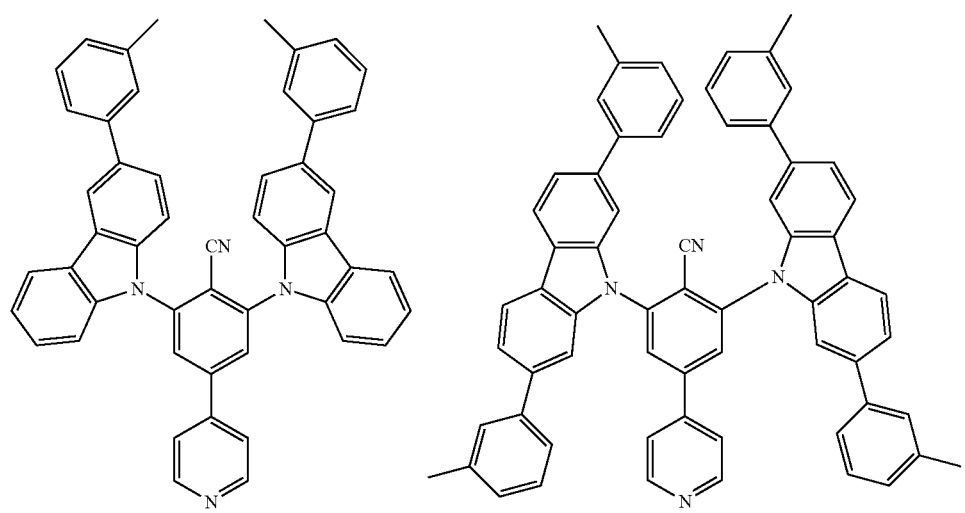
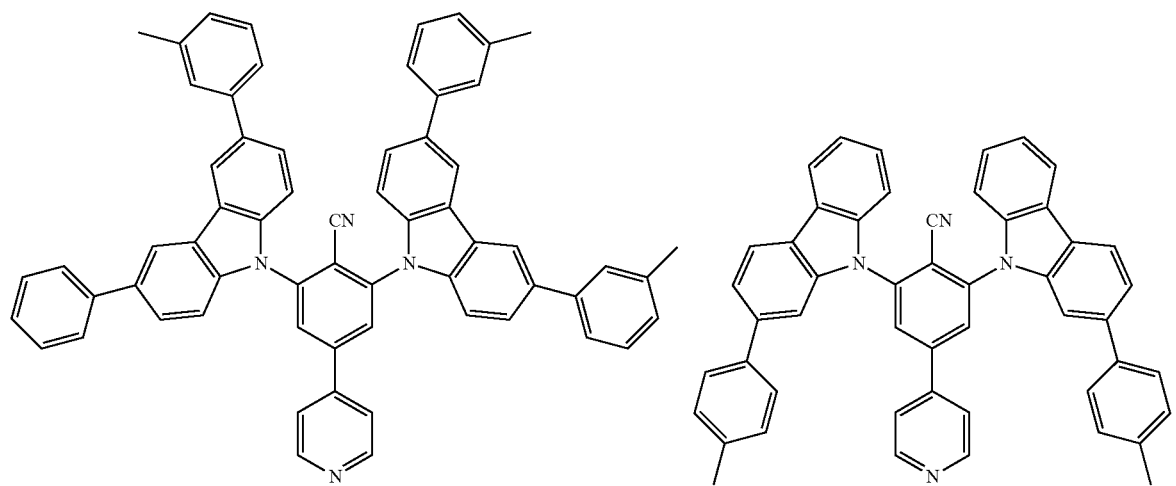

-continued
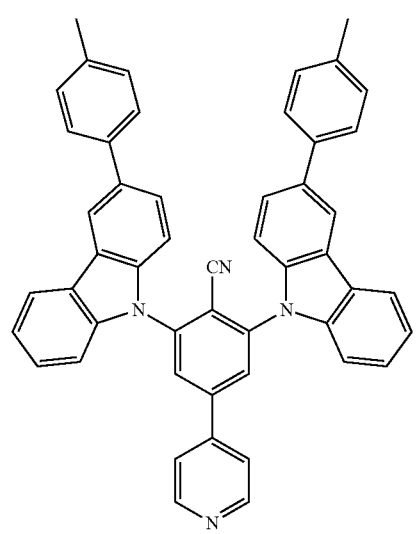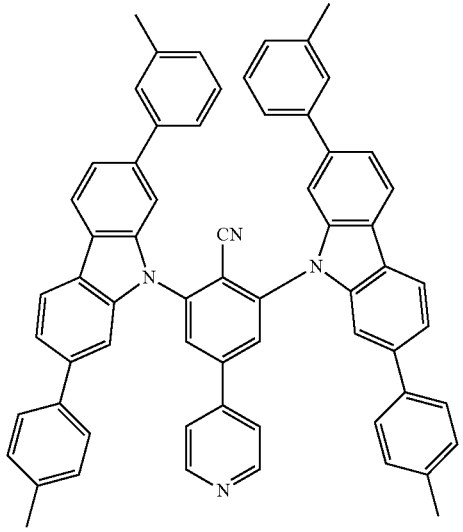
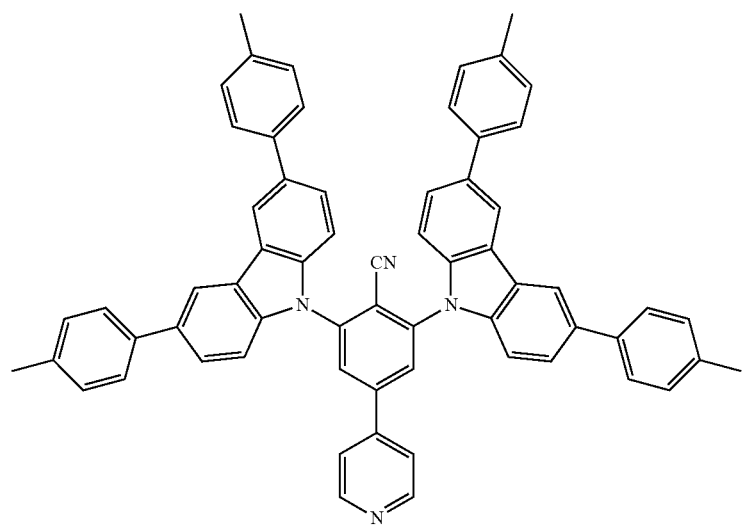
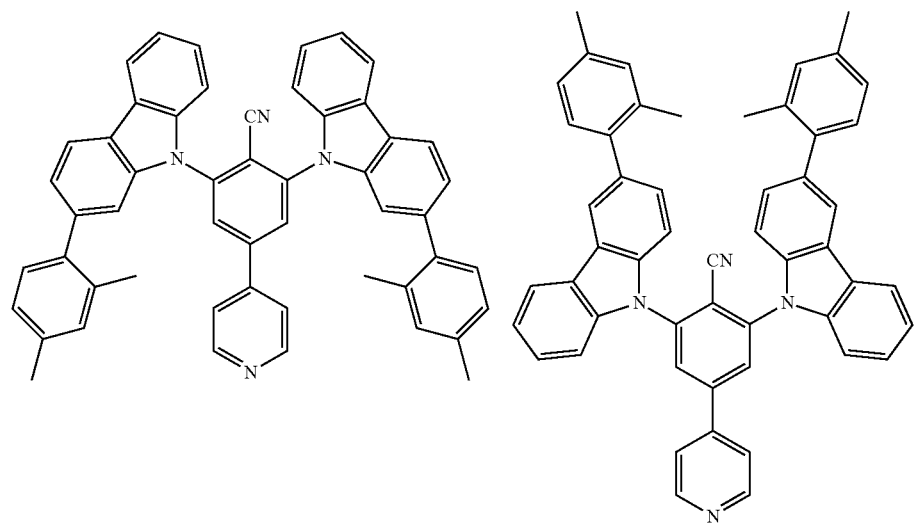

151
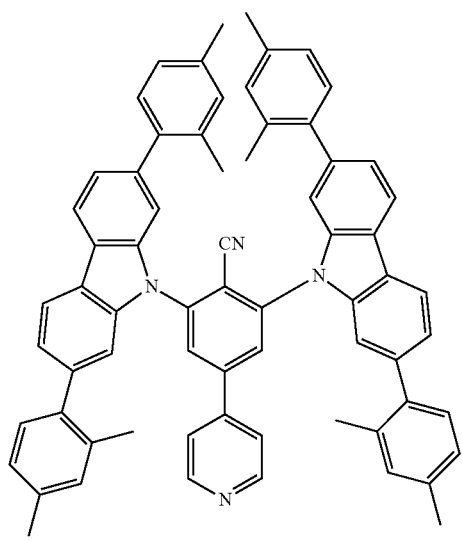
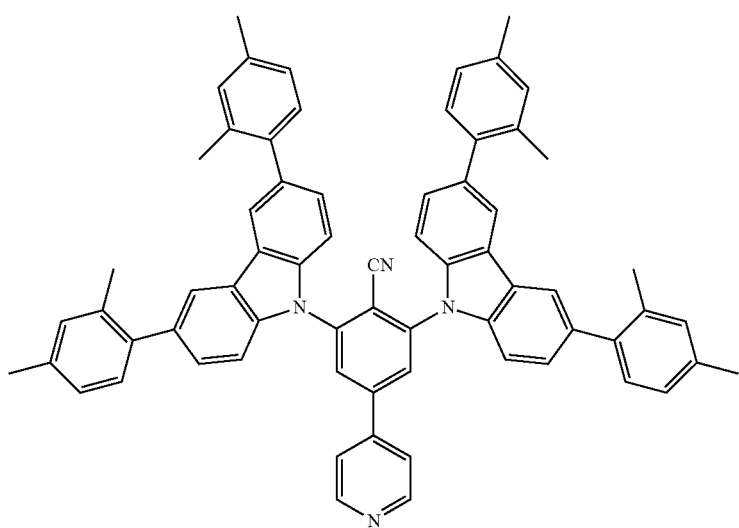
152
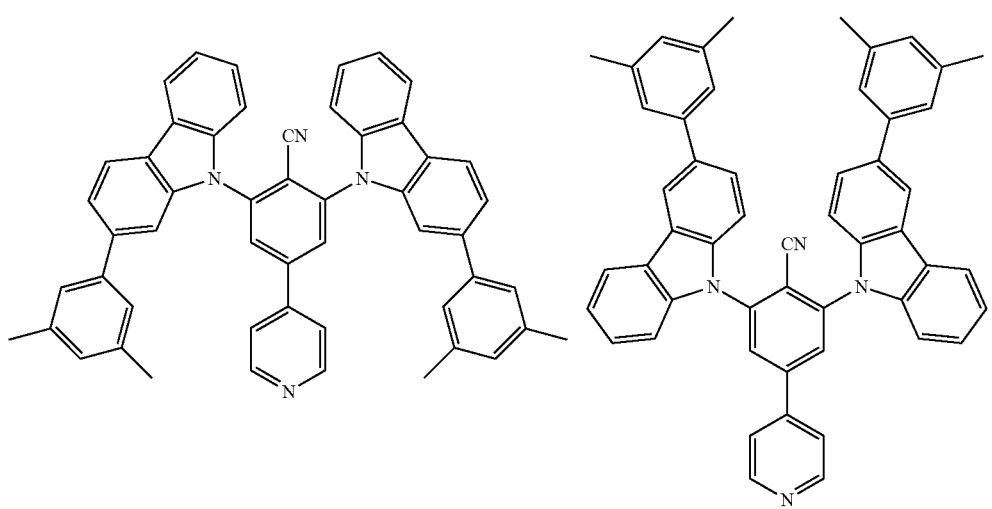

153
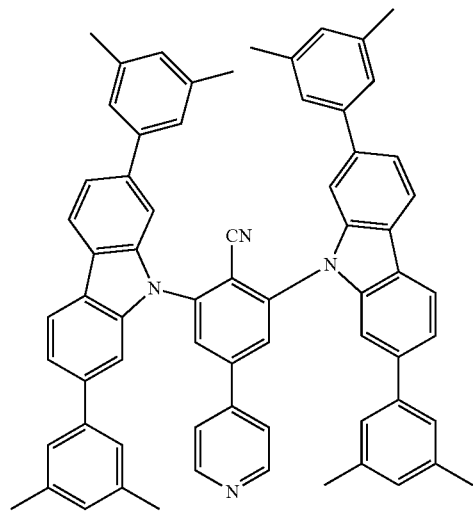
154
-continued
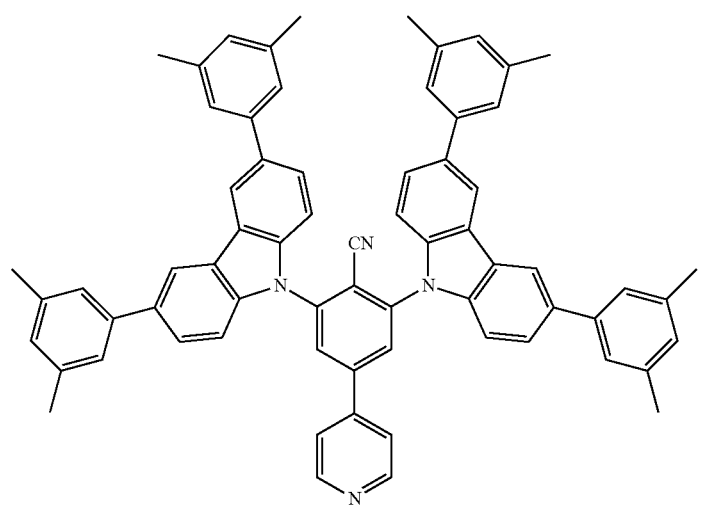
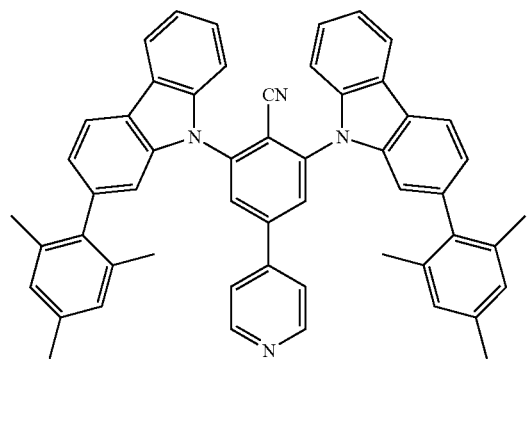
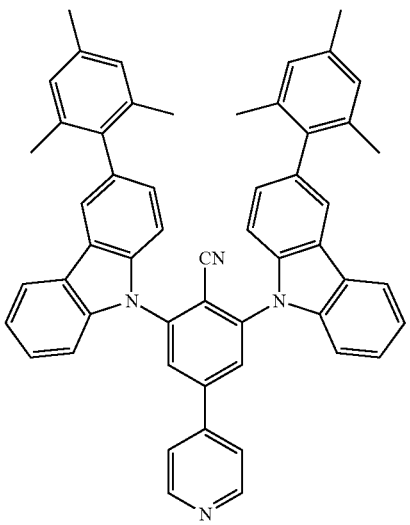
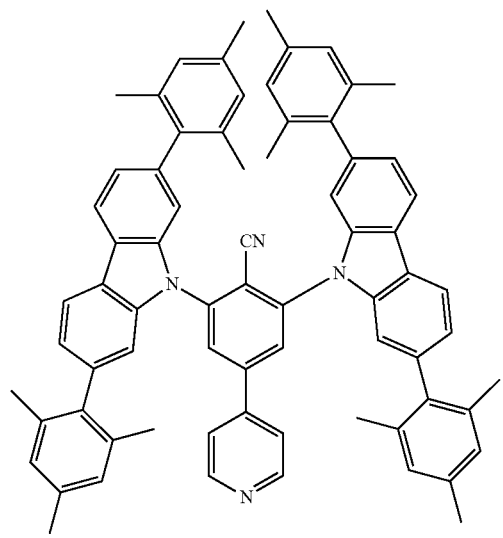

155 156
-continued
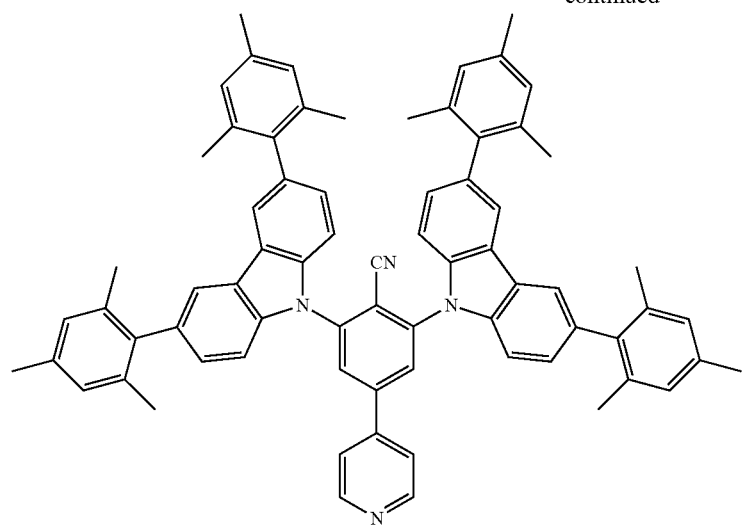
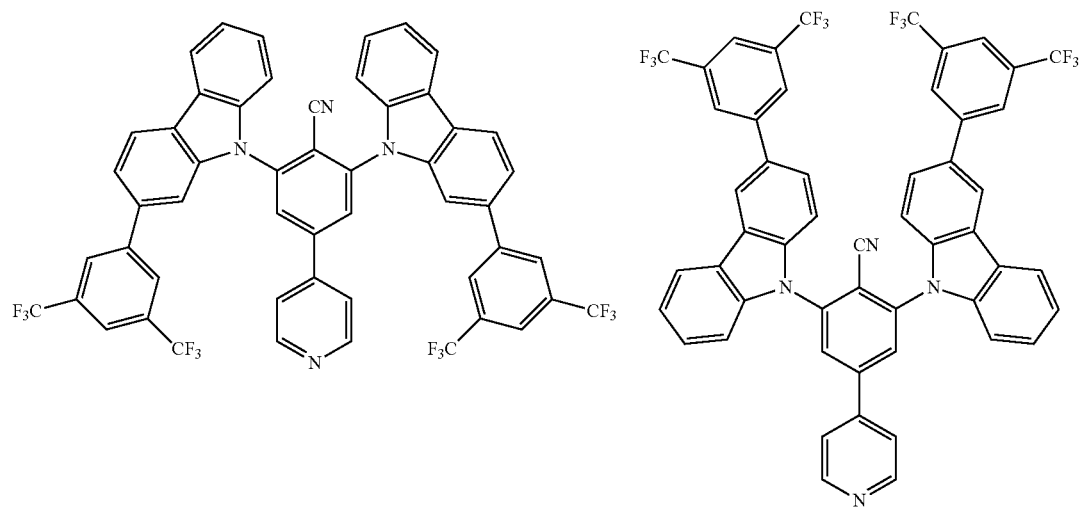
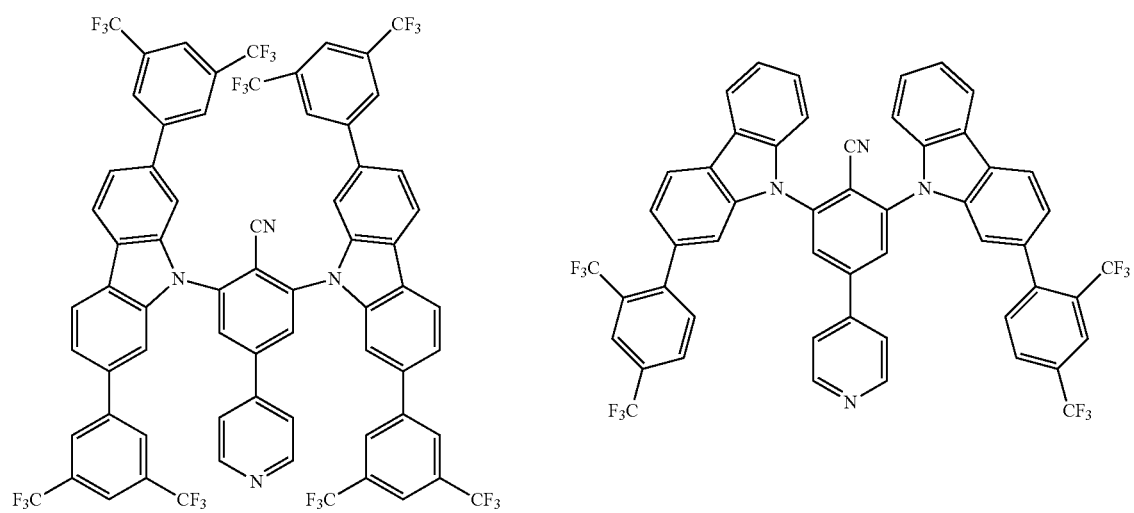

-continued
157
158
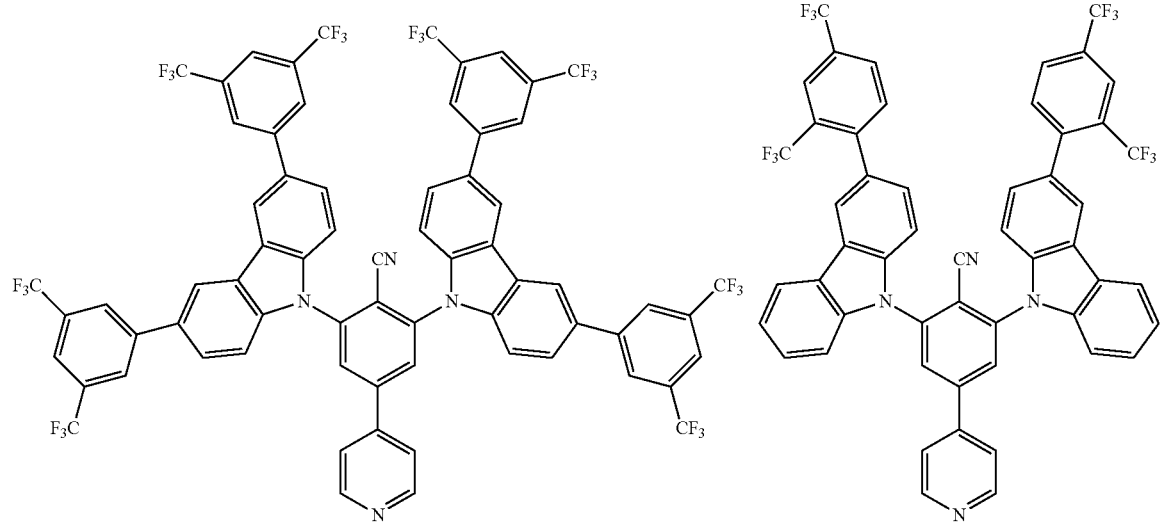
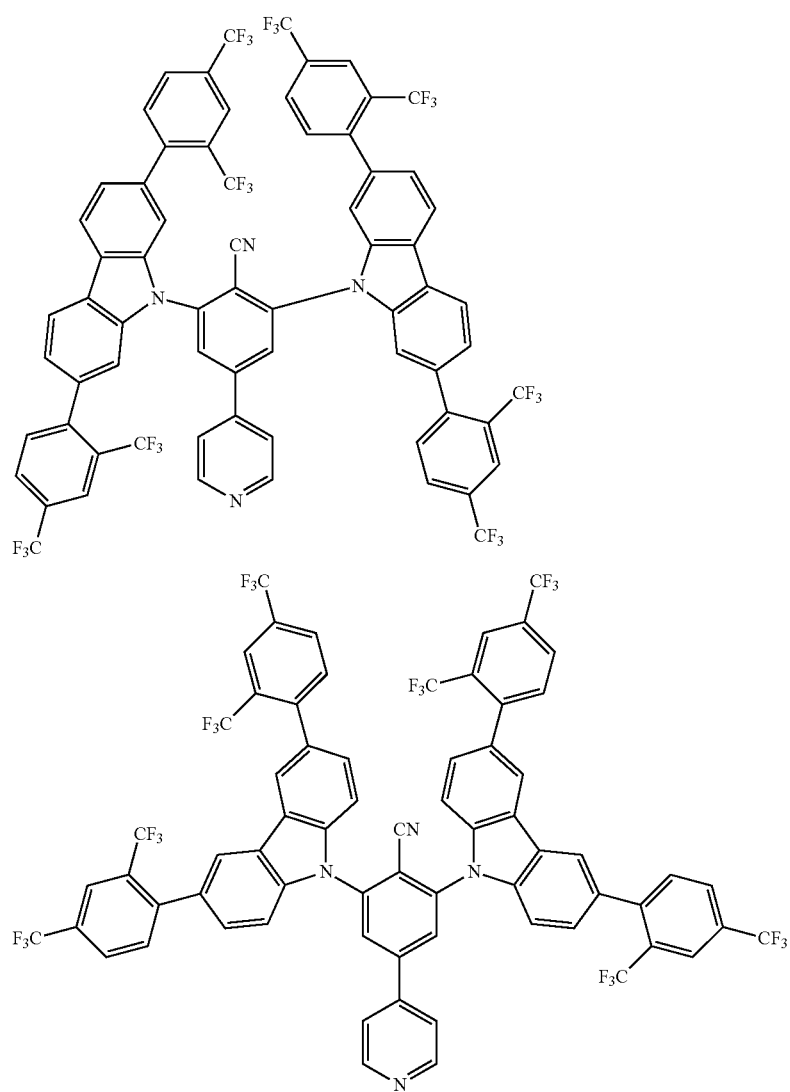

159    160
-continued
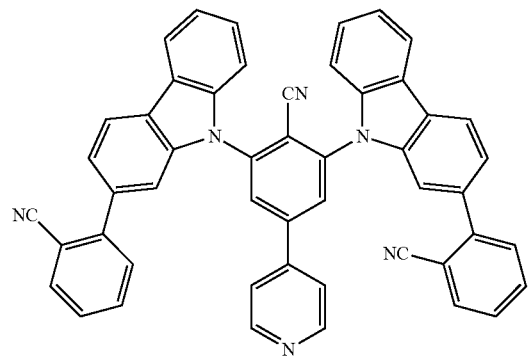
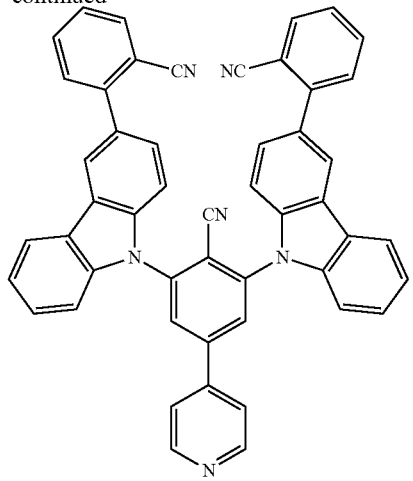
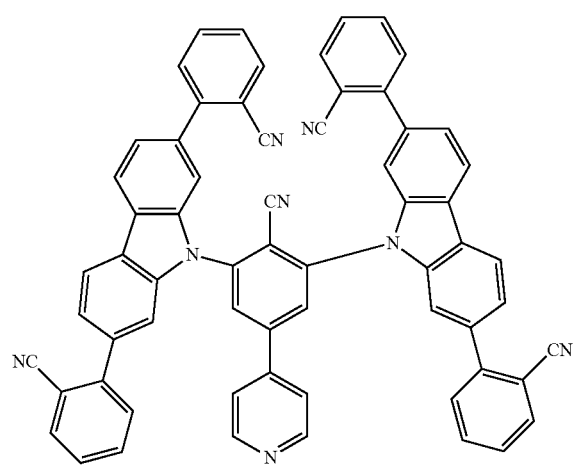
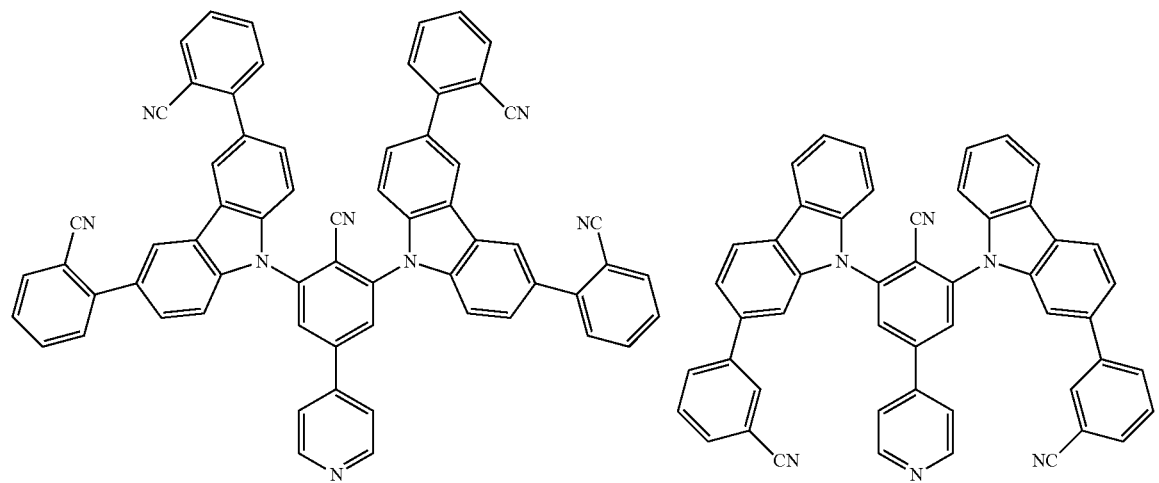

-continued
161
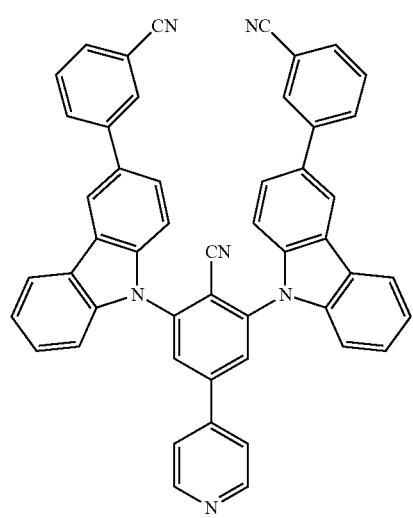
162
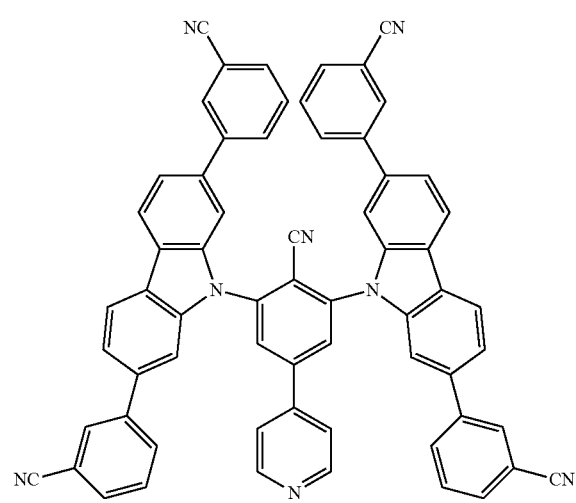
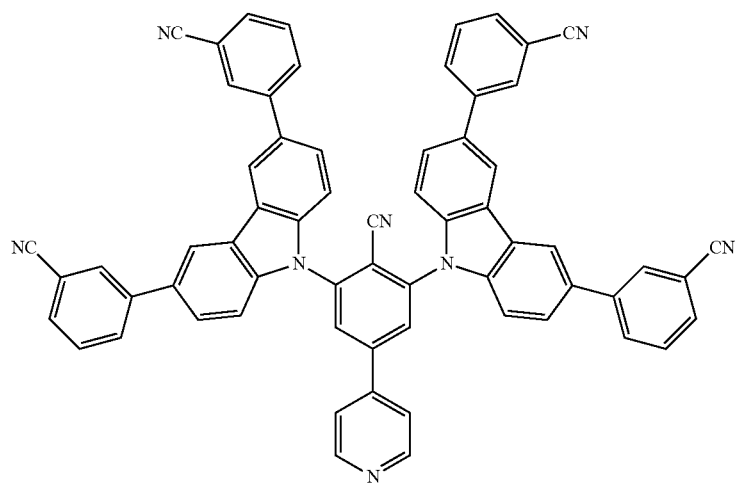
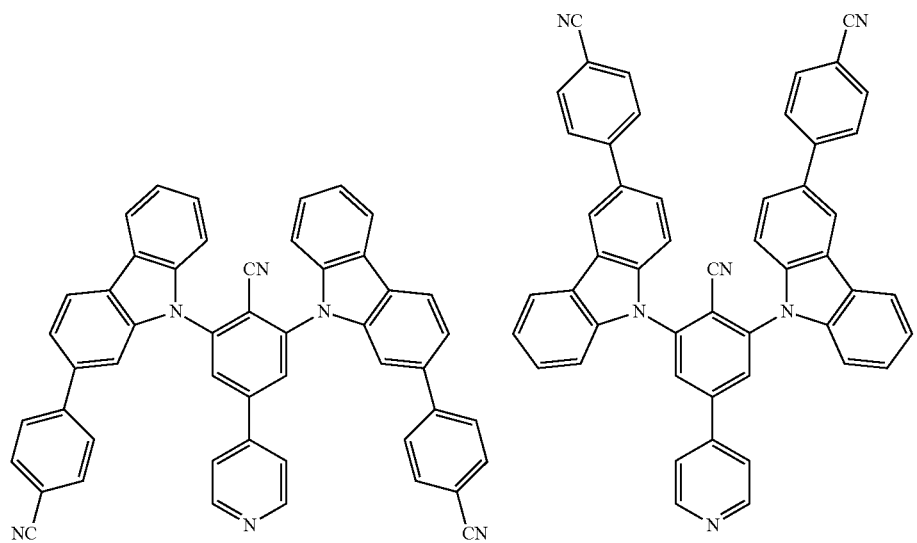

-continued
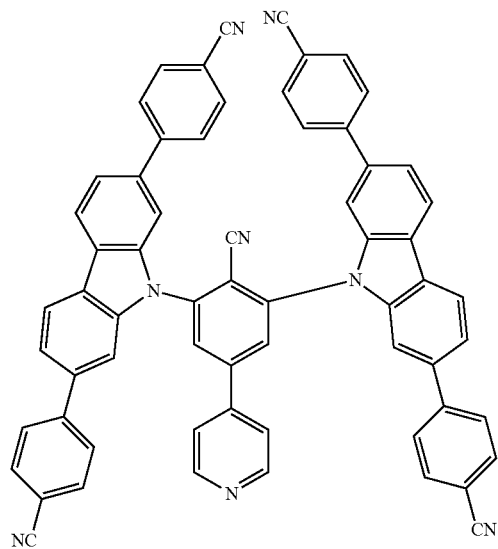
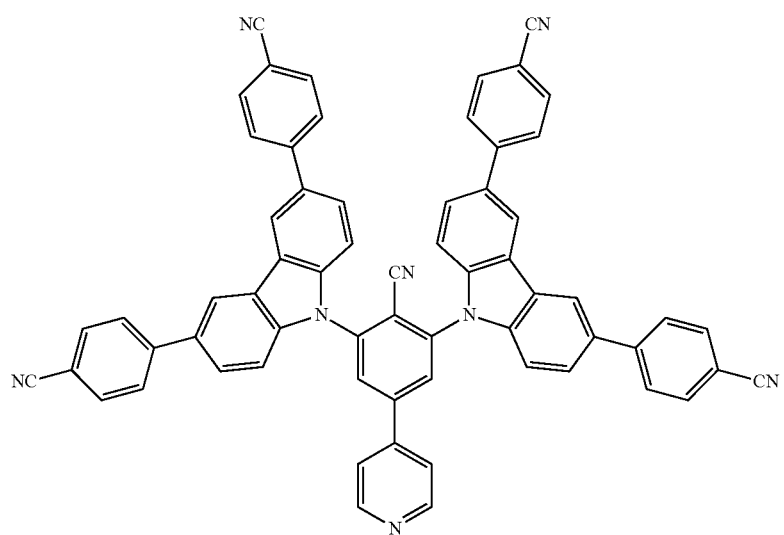
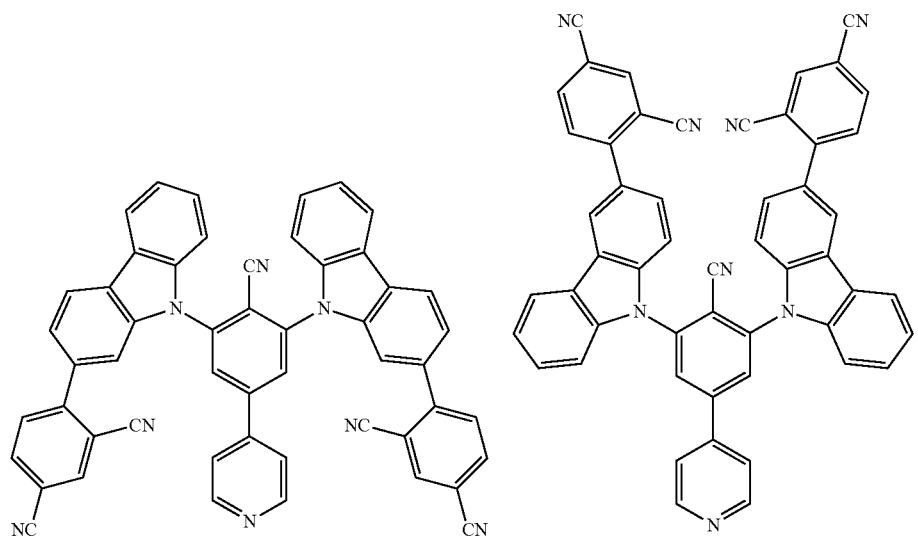

165
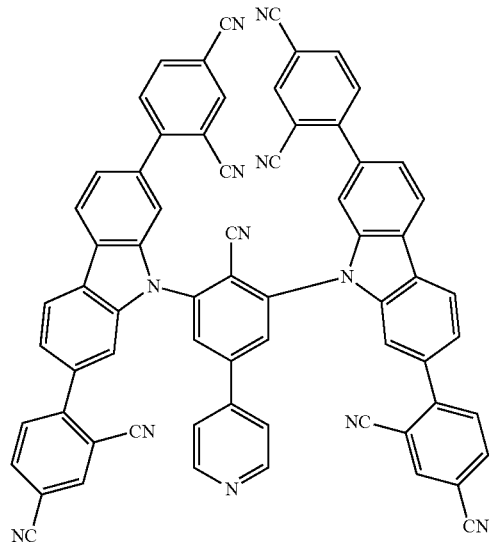
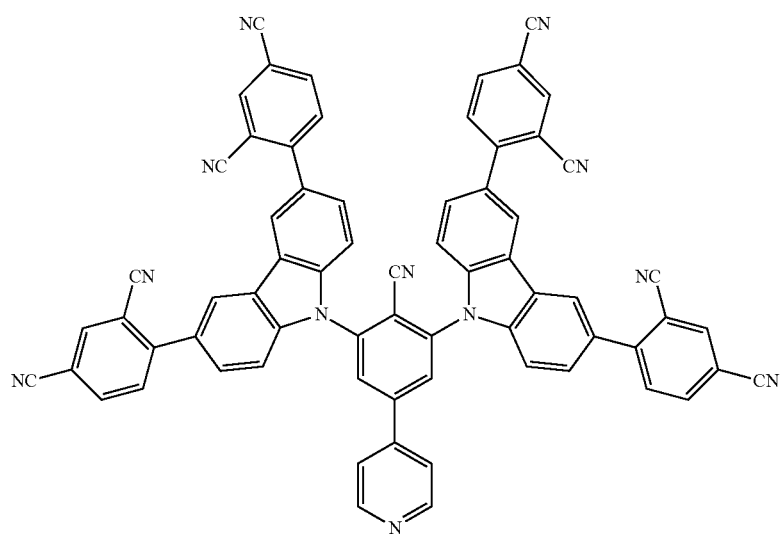
166
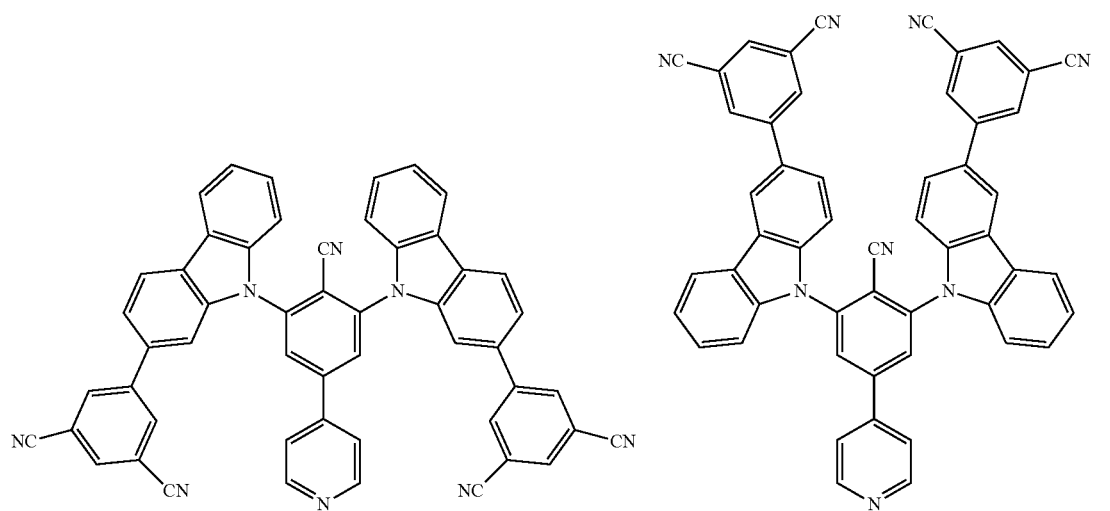

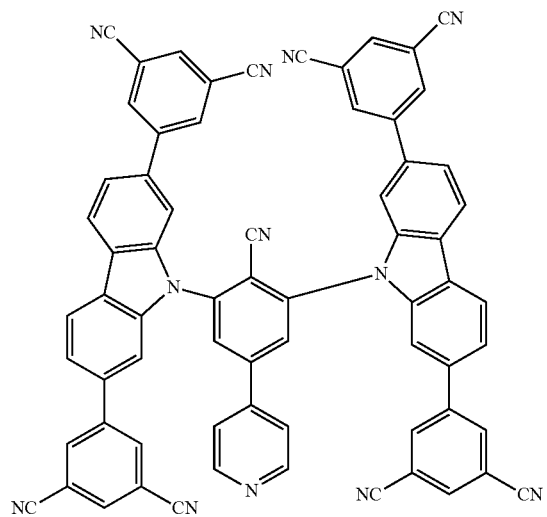
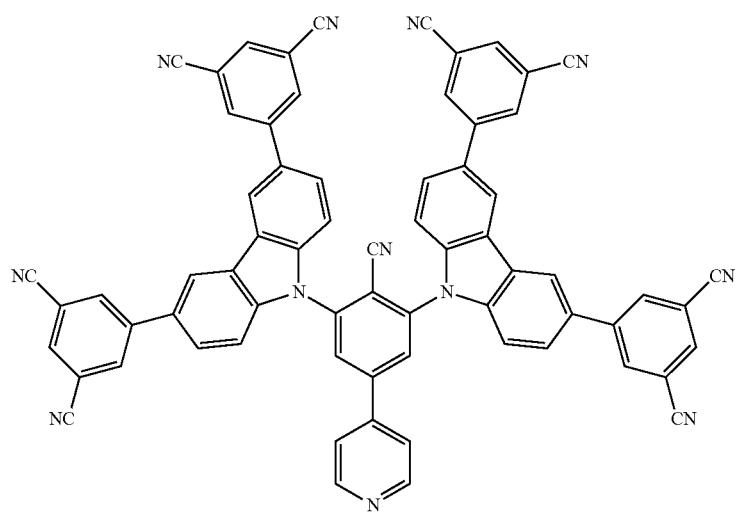
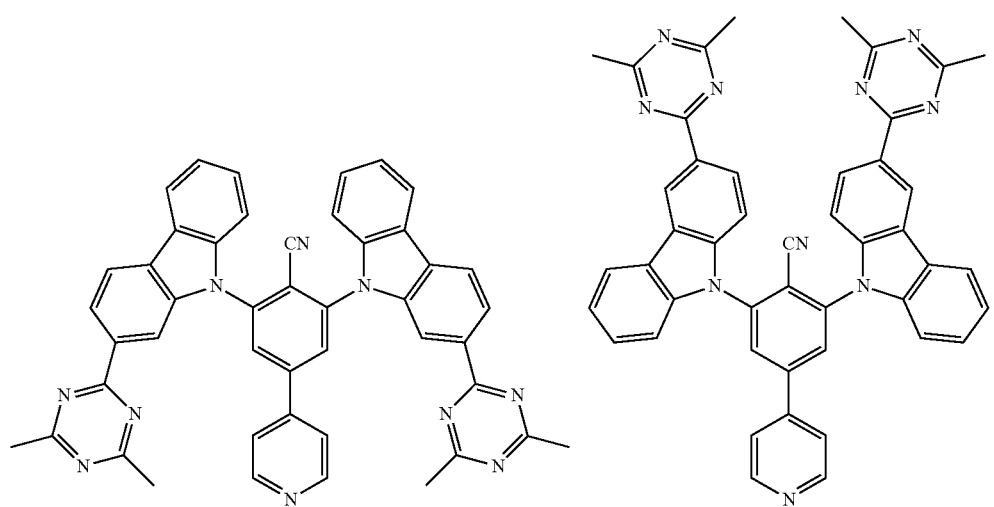

-continued
169
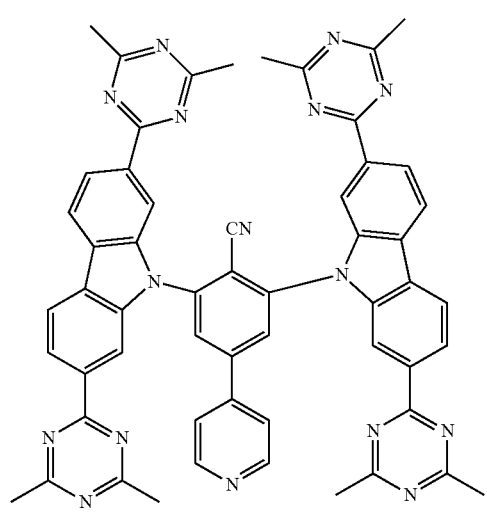
170
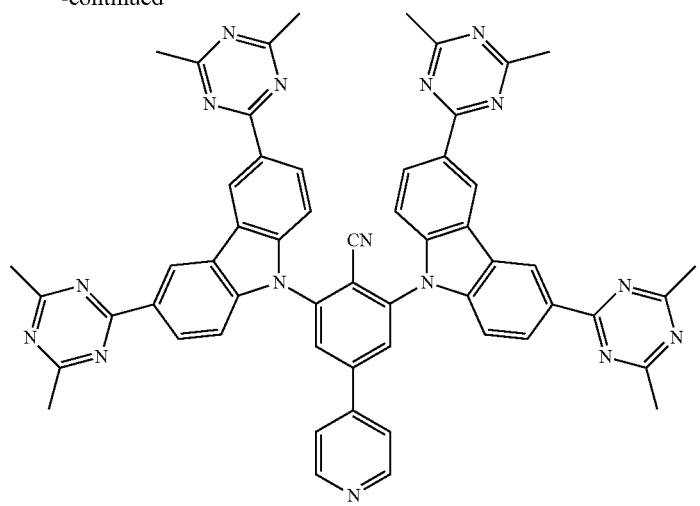
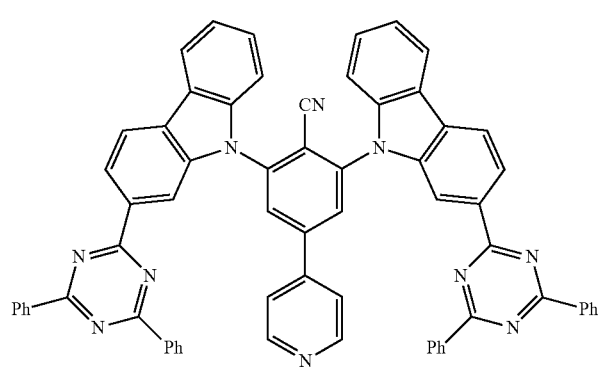
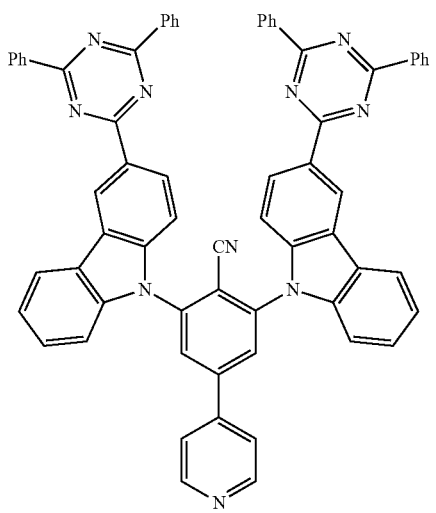
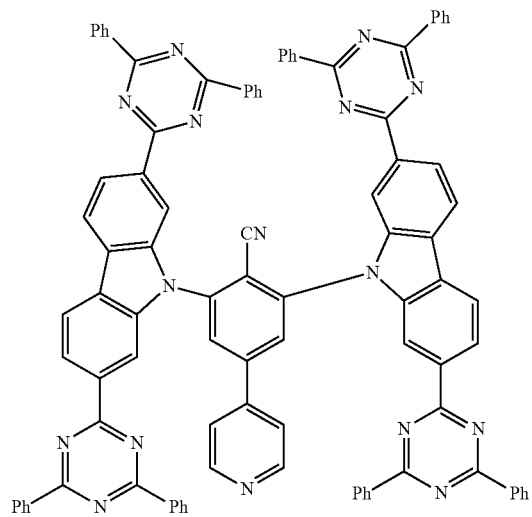

-continued
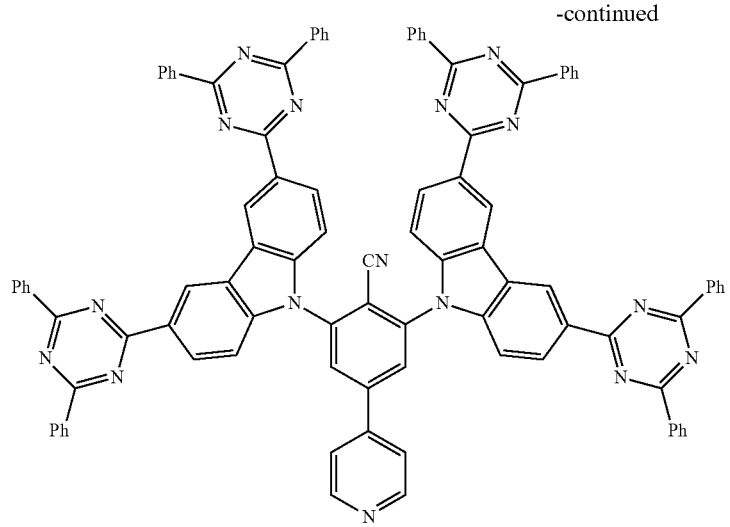
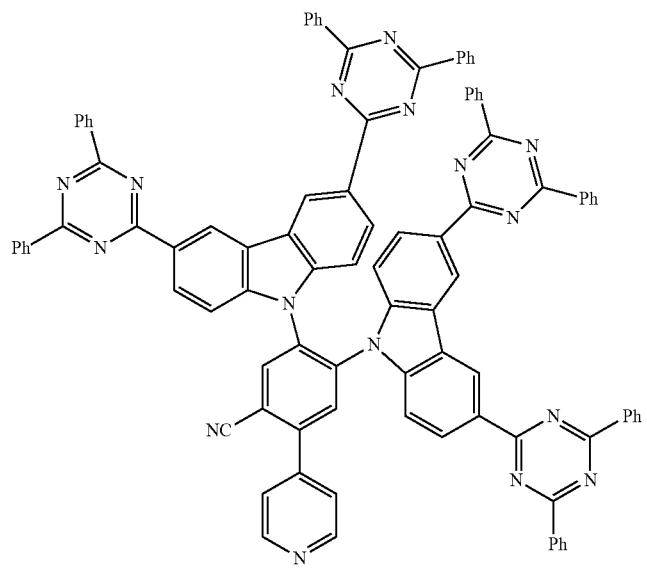
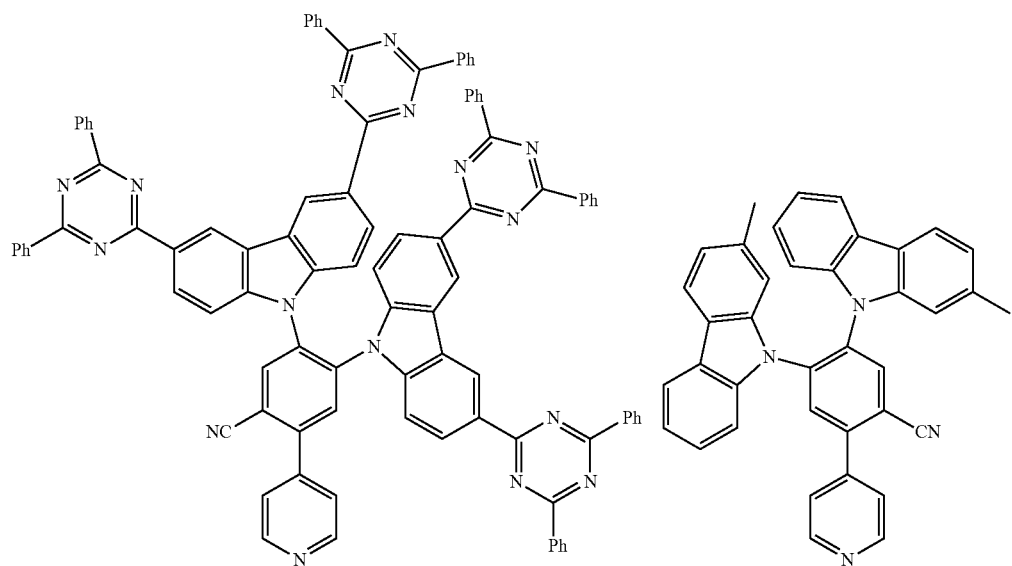

173 174
-continued
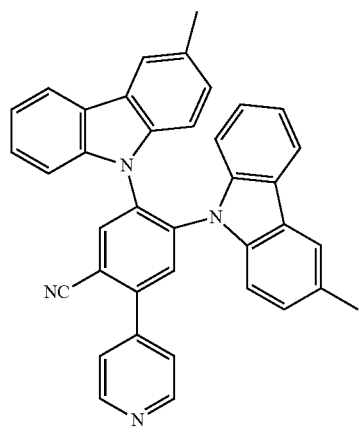
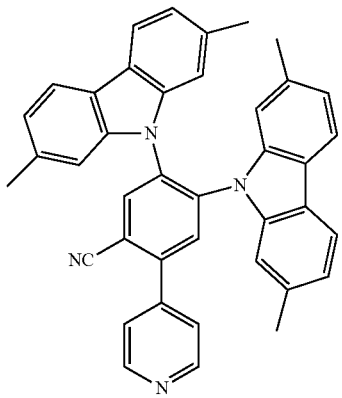
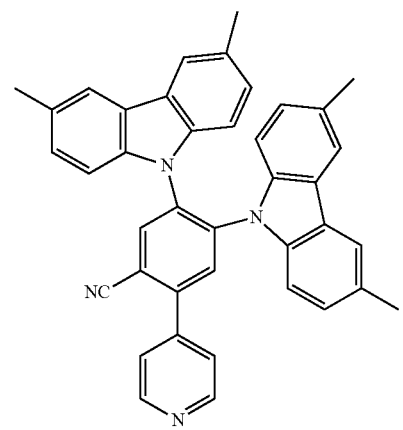
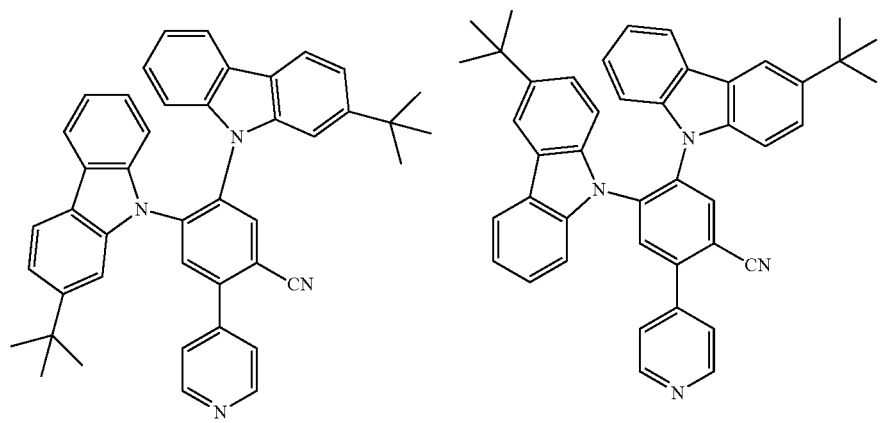
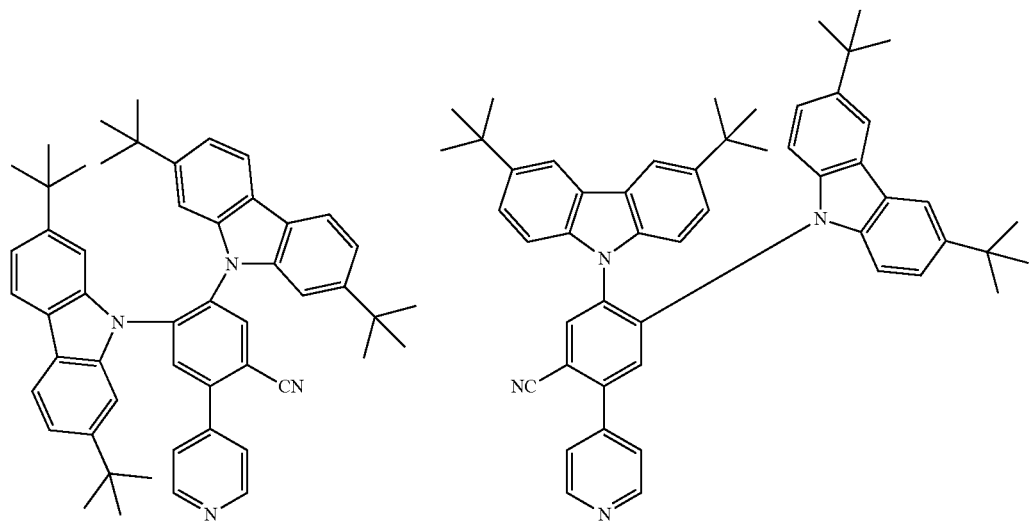

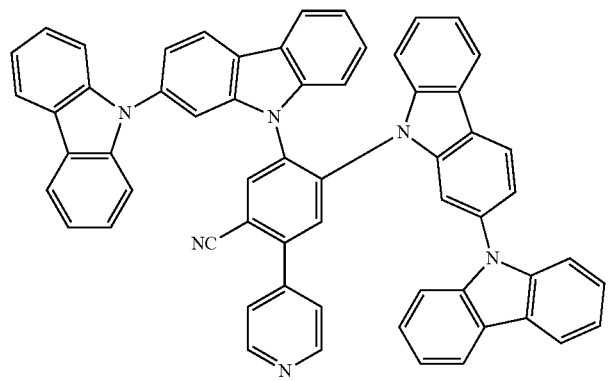
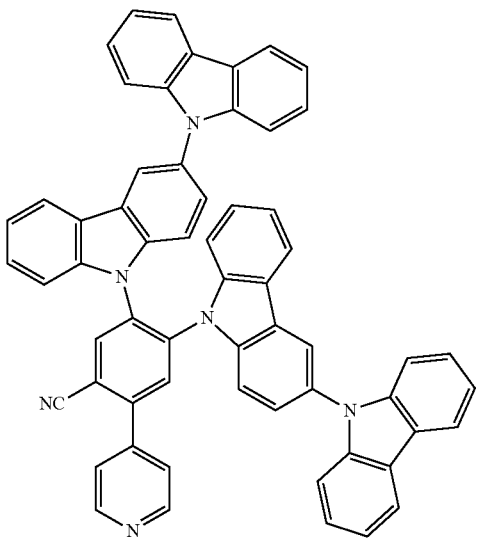
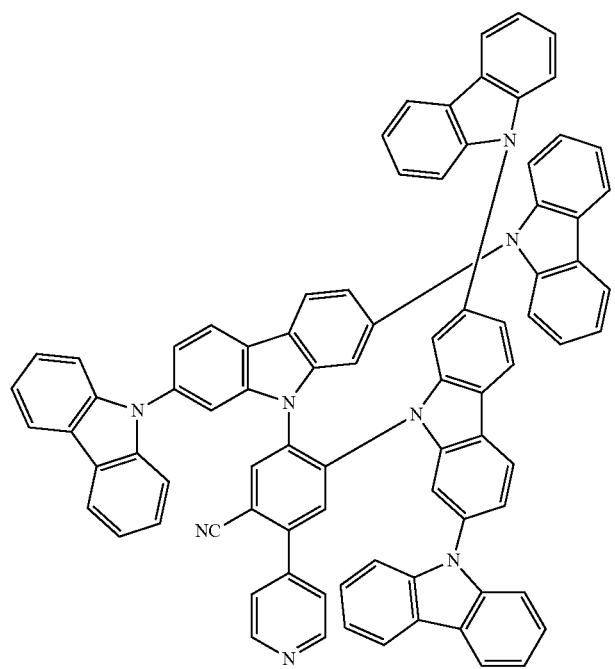

177 178
-continued
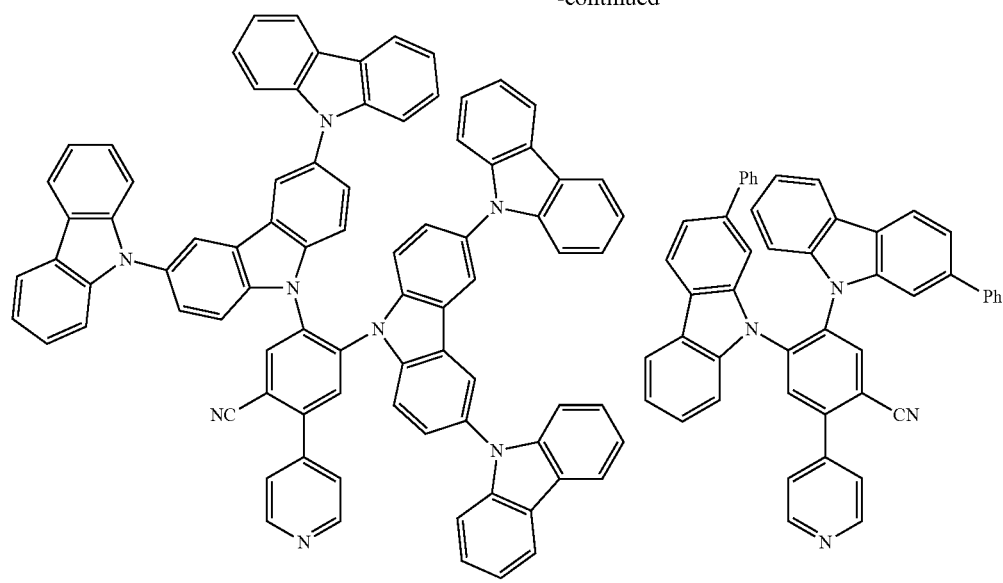
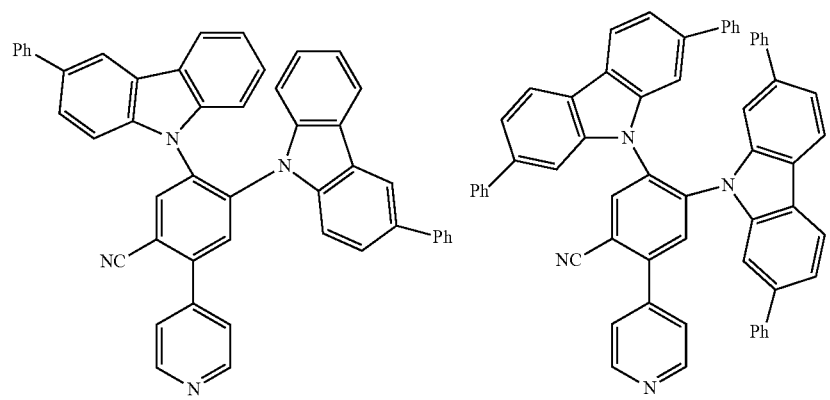
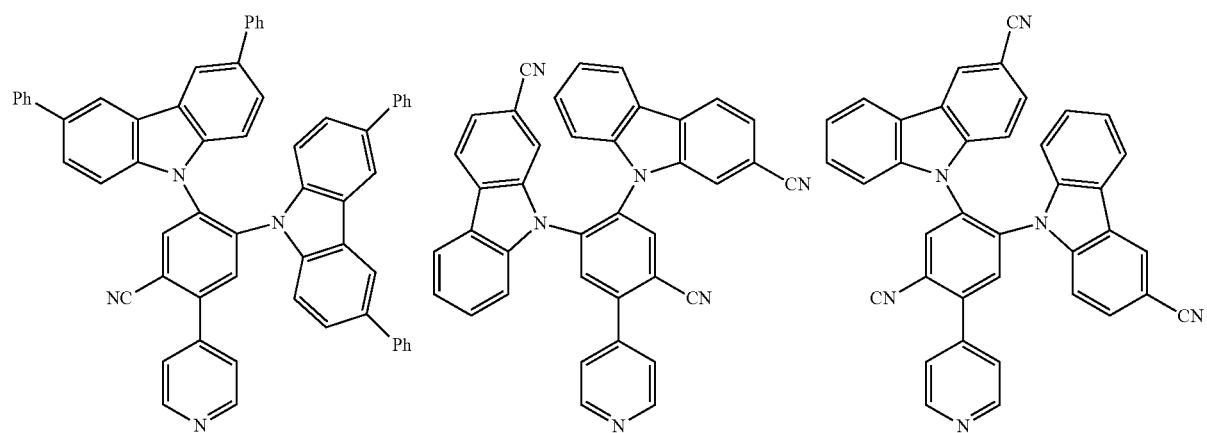

-continued
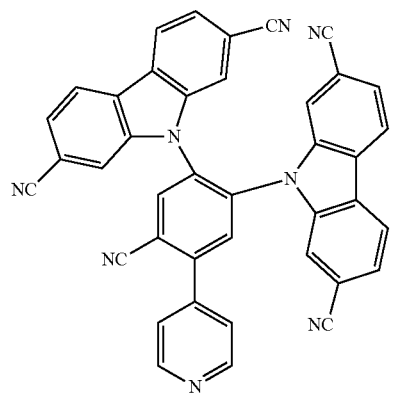
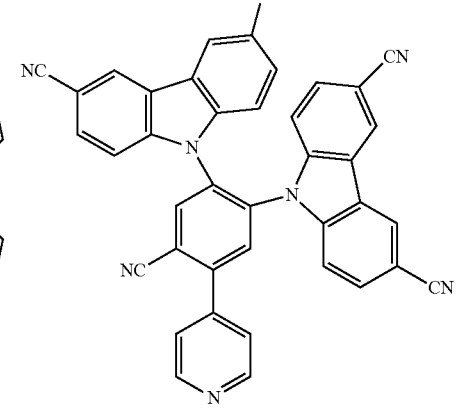
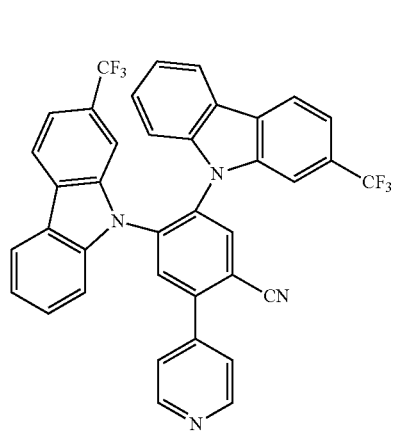
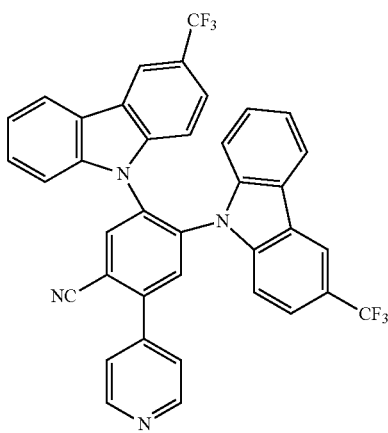
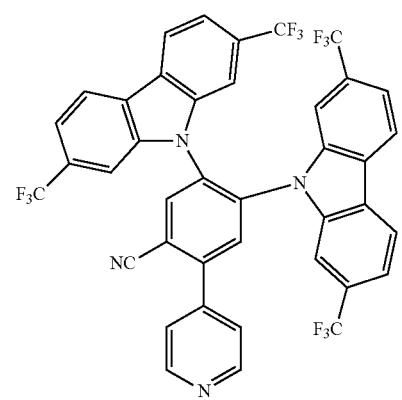
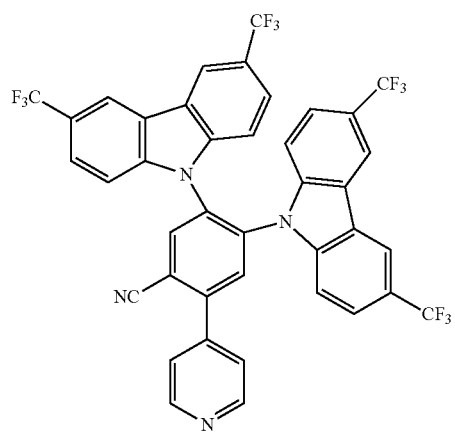
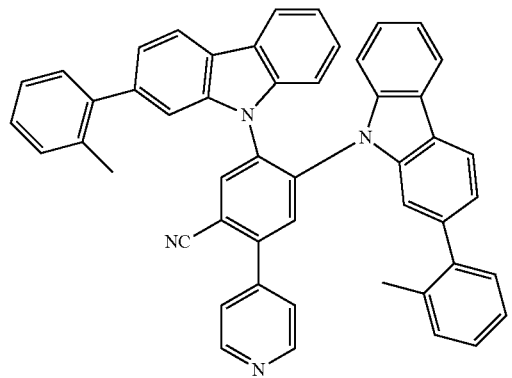

-continued
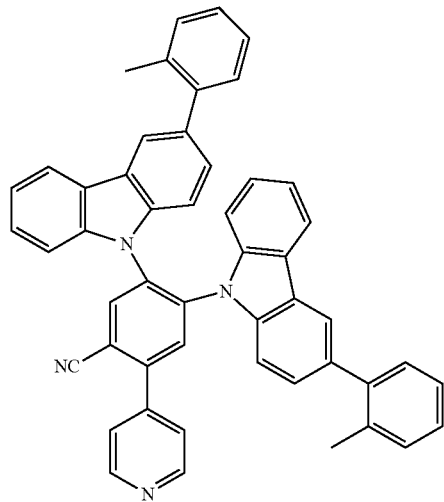
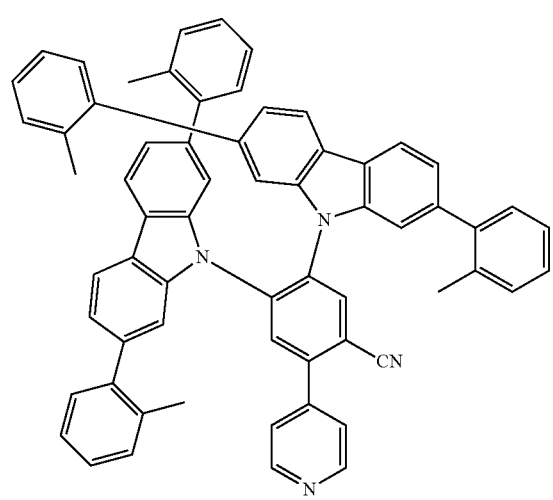
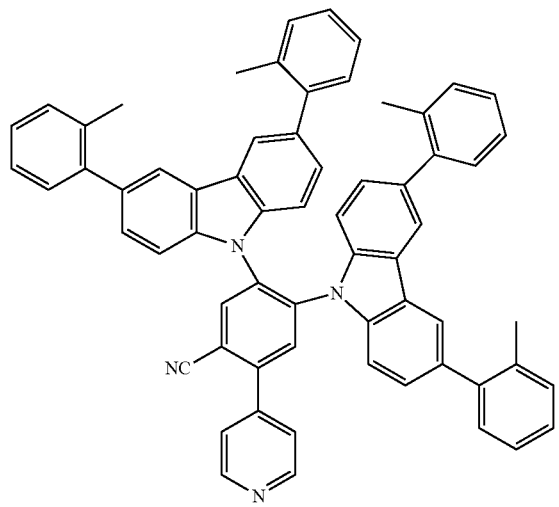
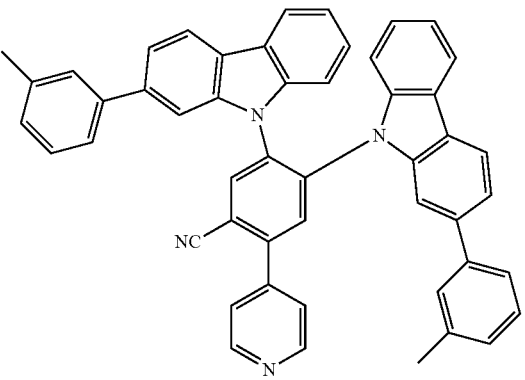
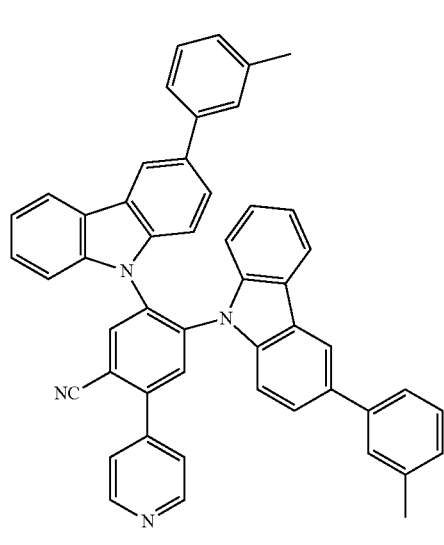
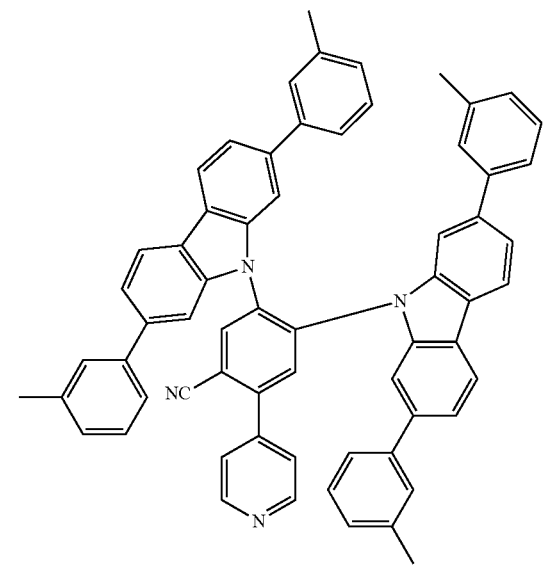

183 184
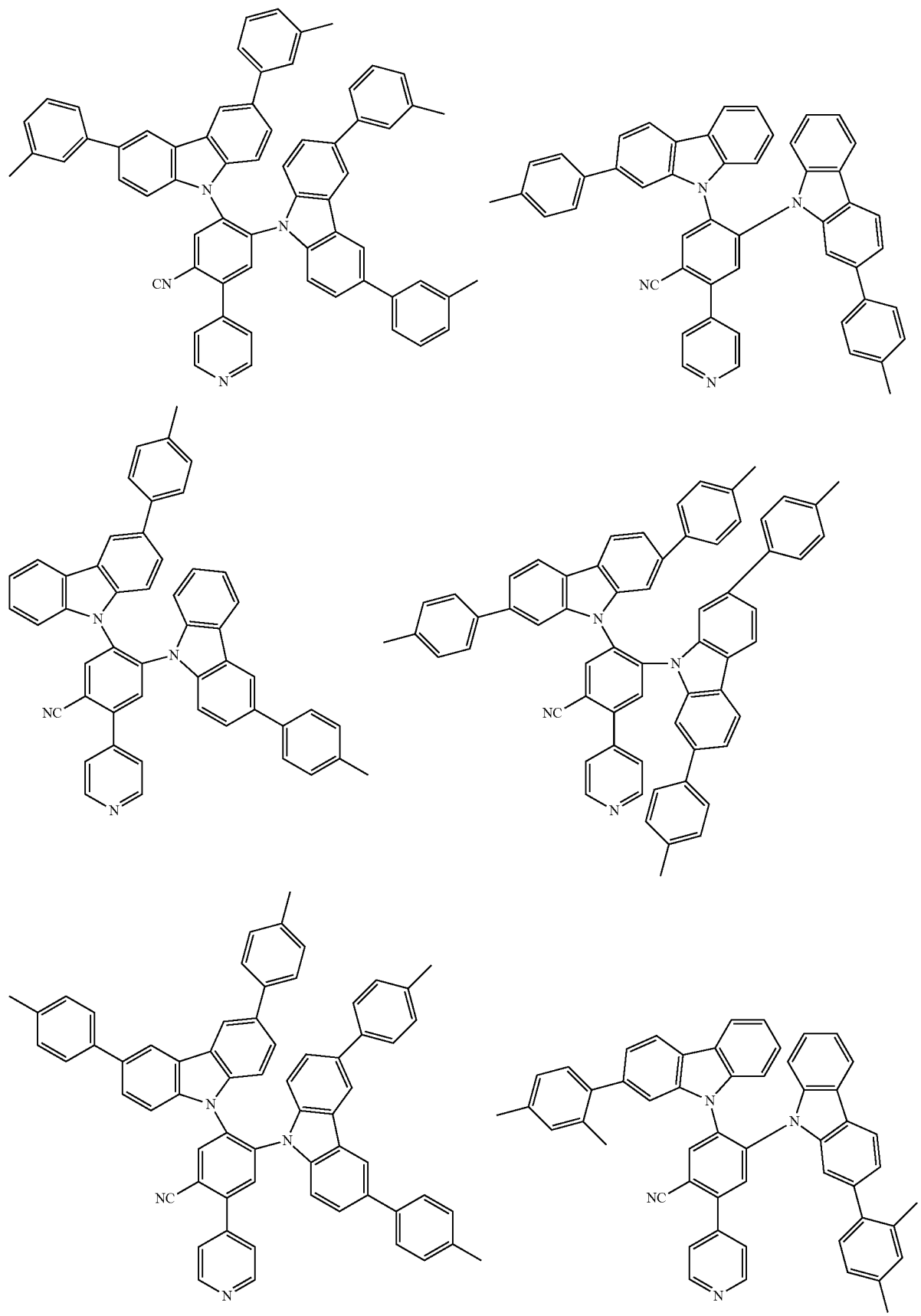
-continued

185
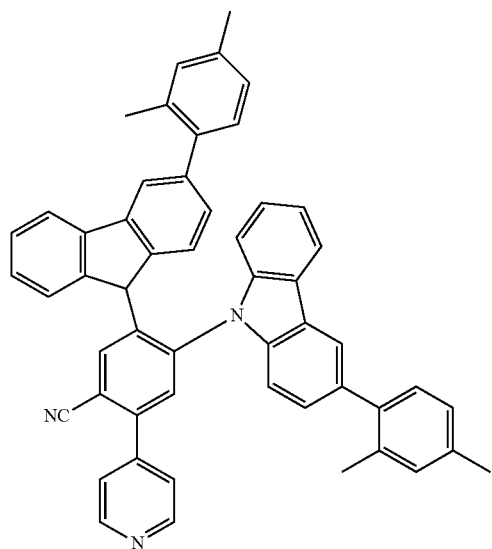
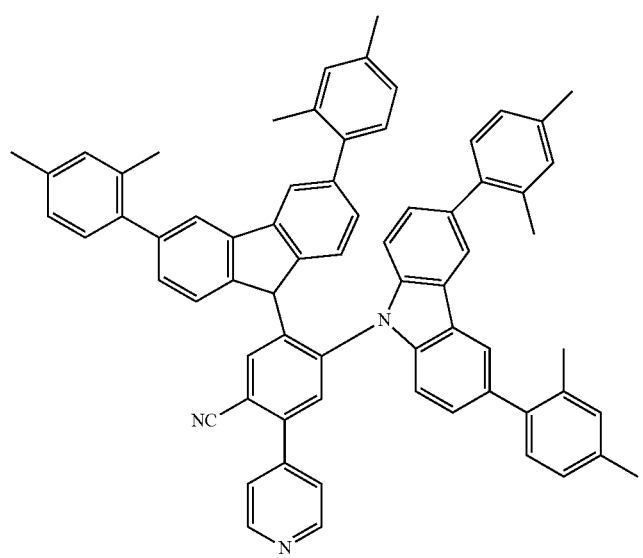
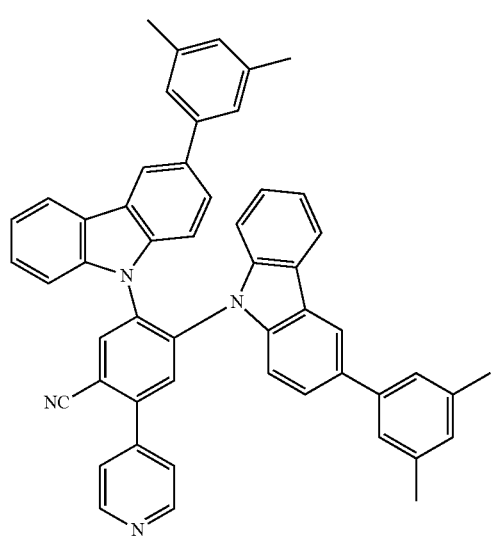
-continued
186
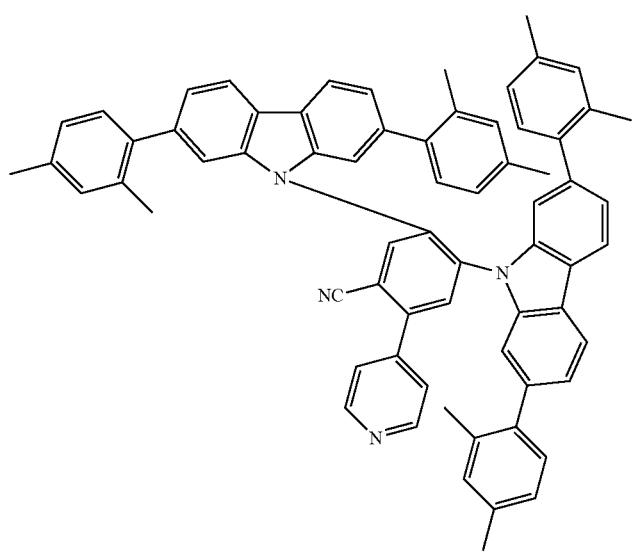
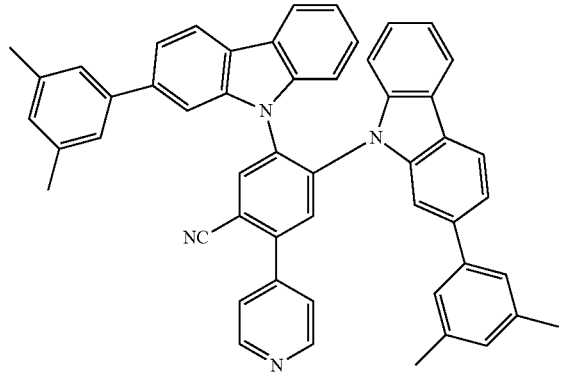
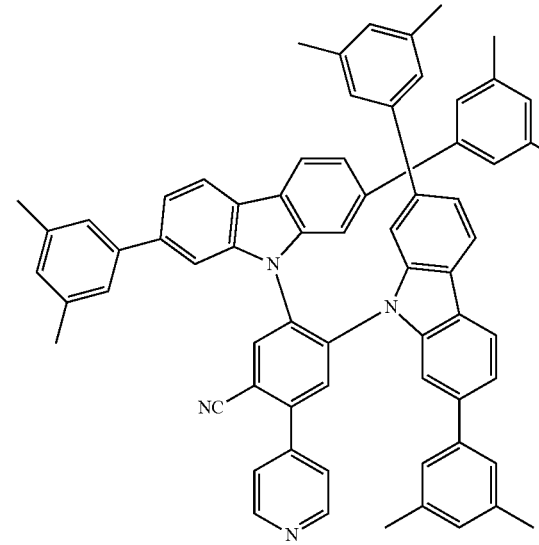

187 188
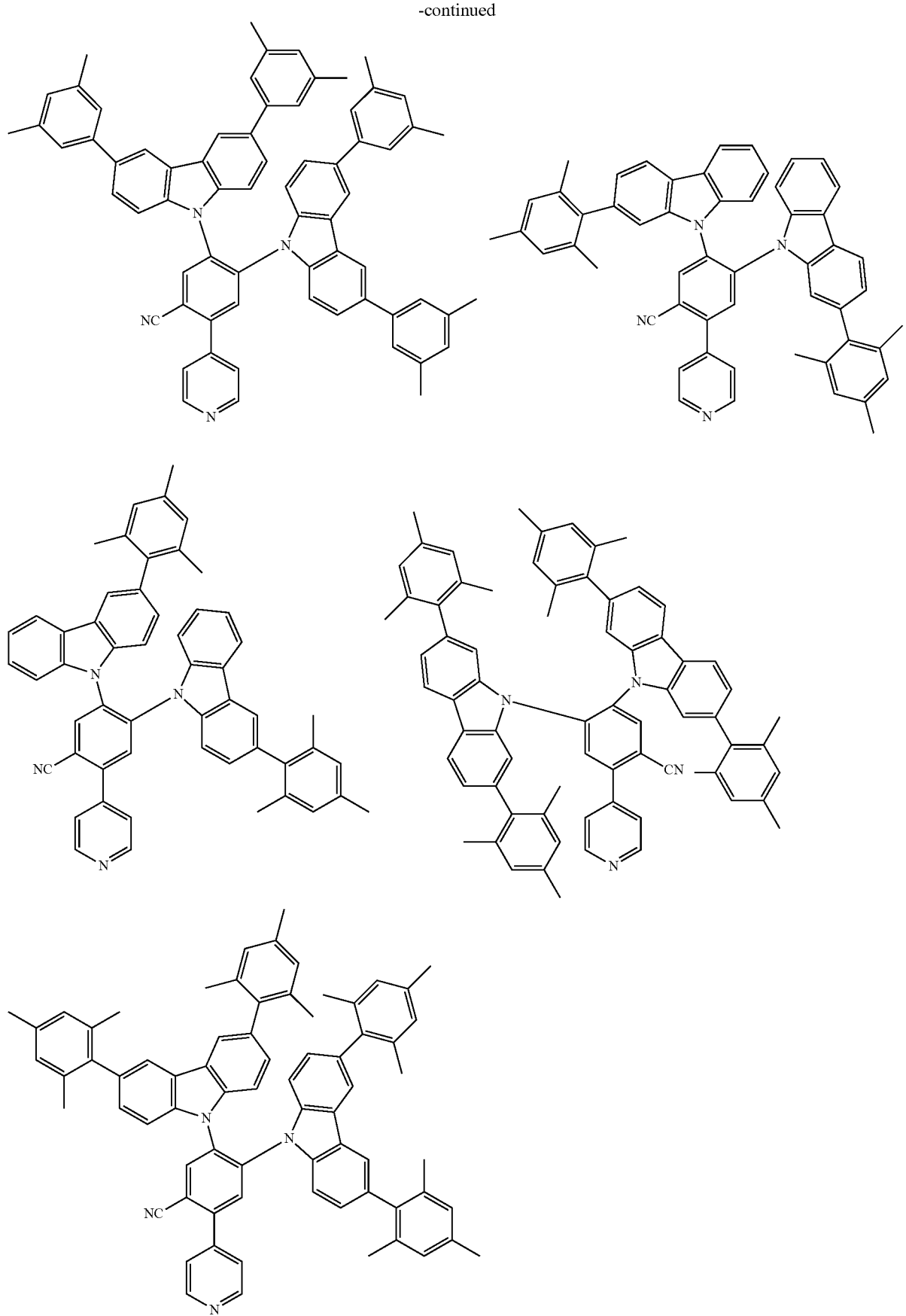

-continued
| 189 | 190 |
|---|---|
| 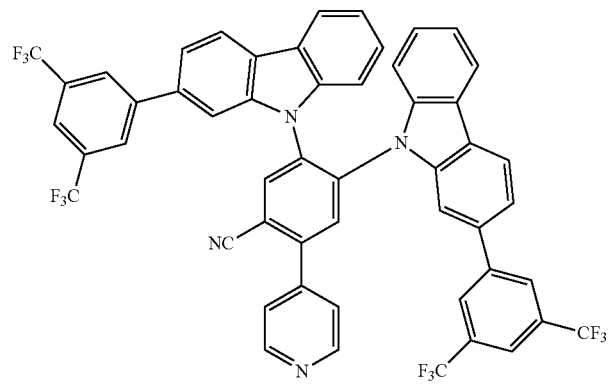 | 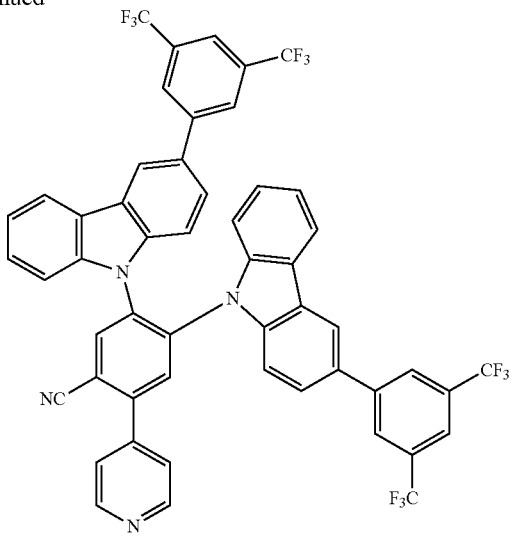 |
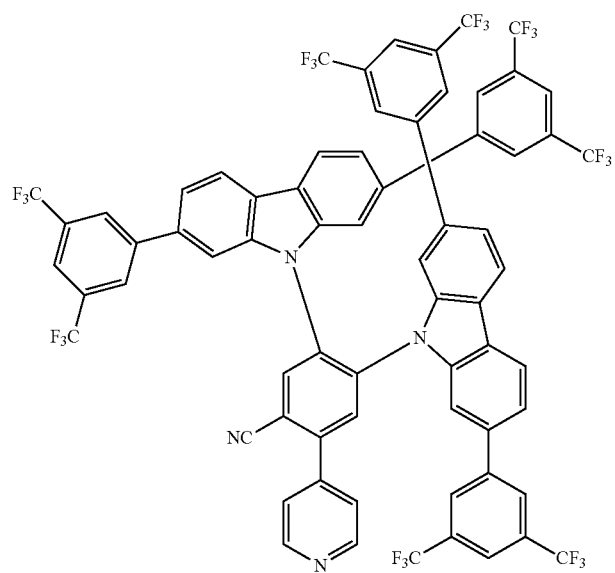
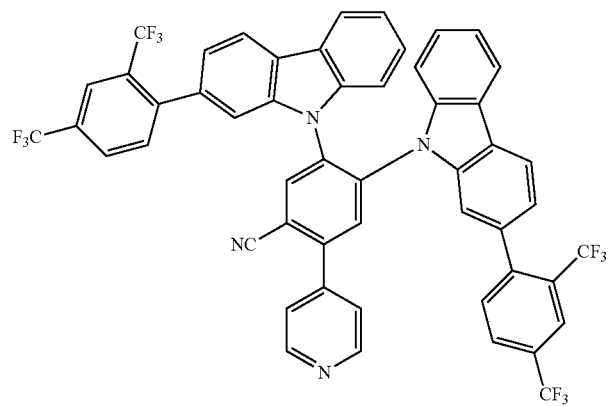

-continued
191
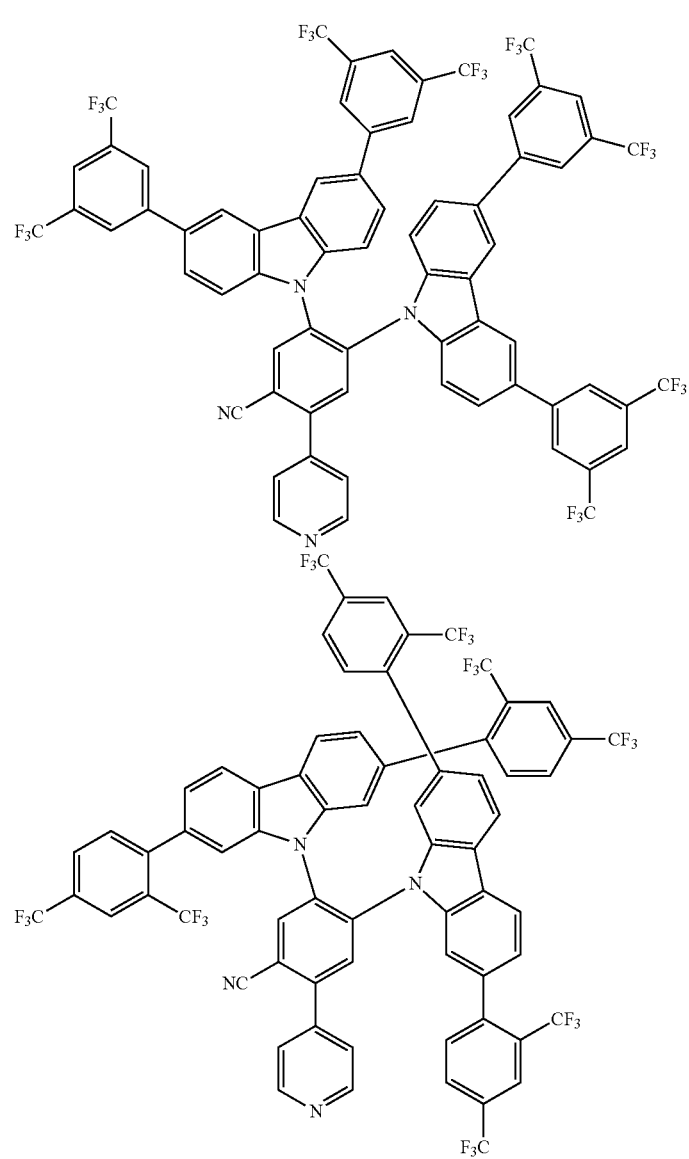
192
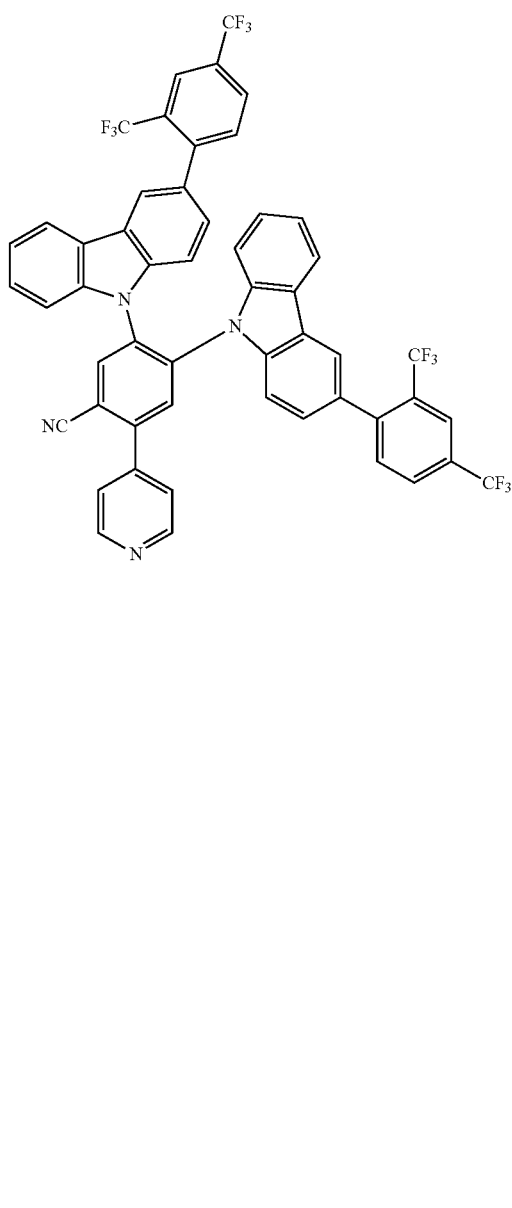

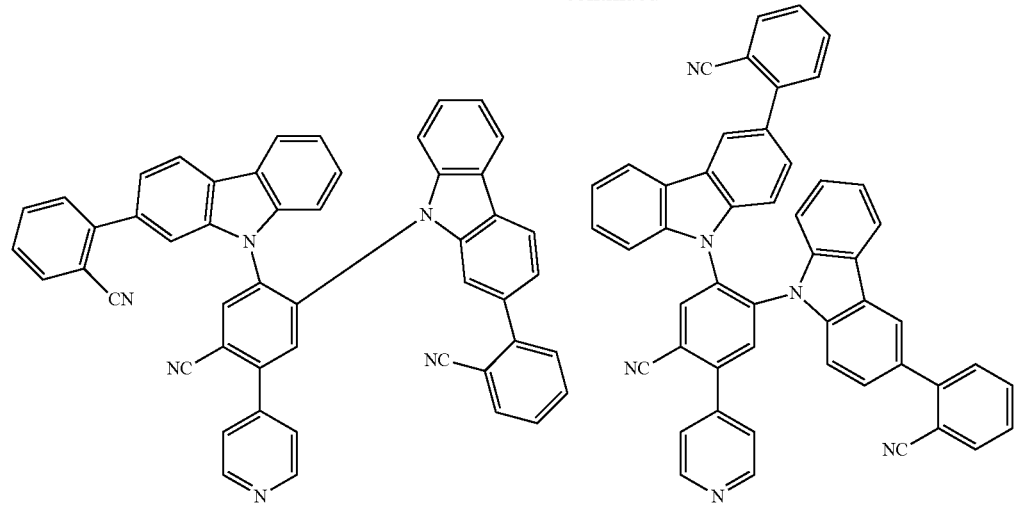
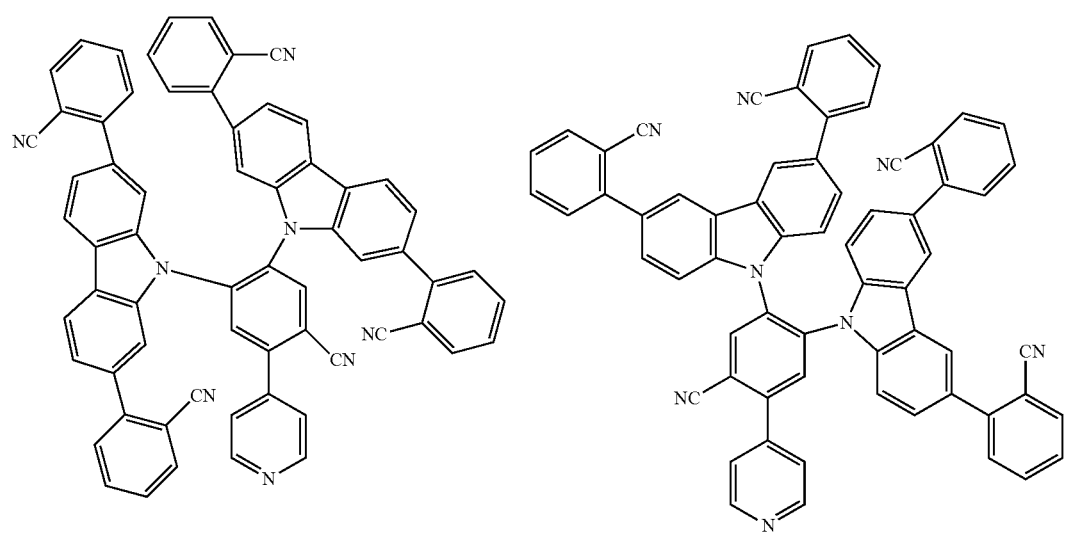
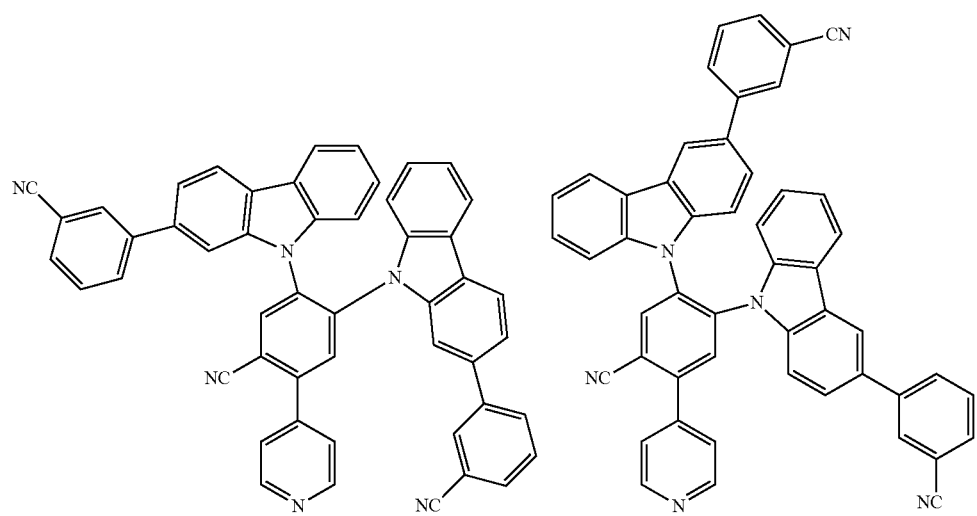

-continued
195
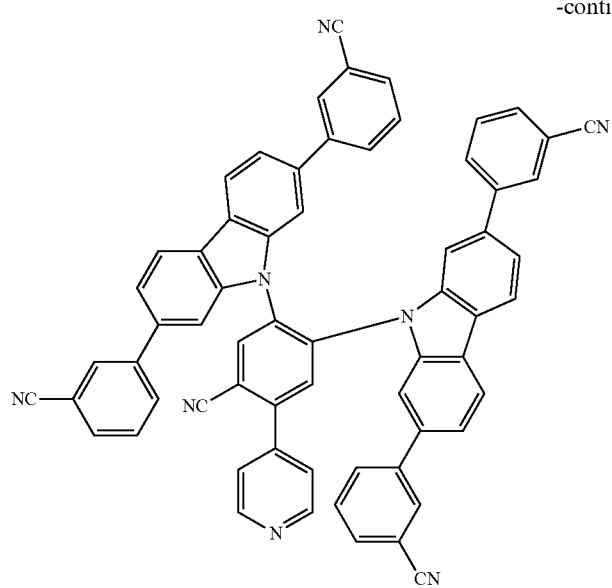
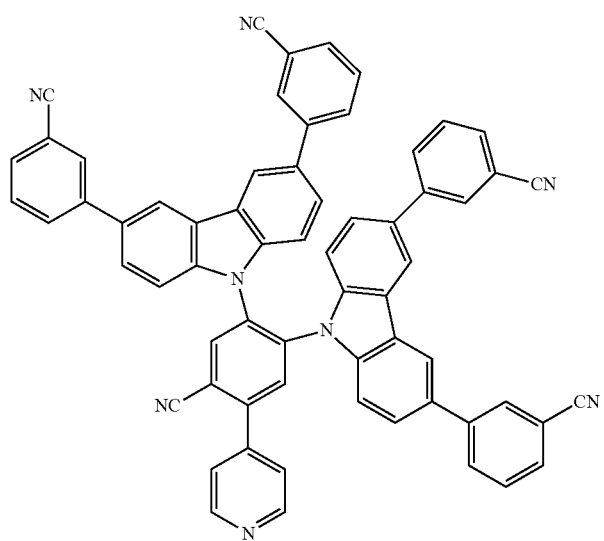
196
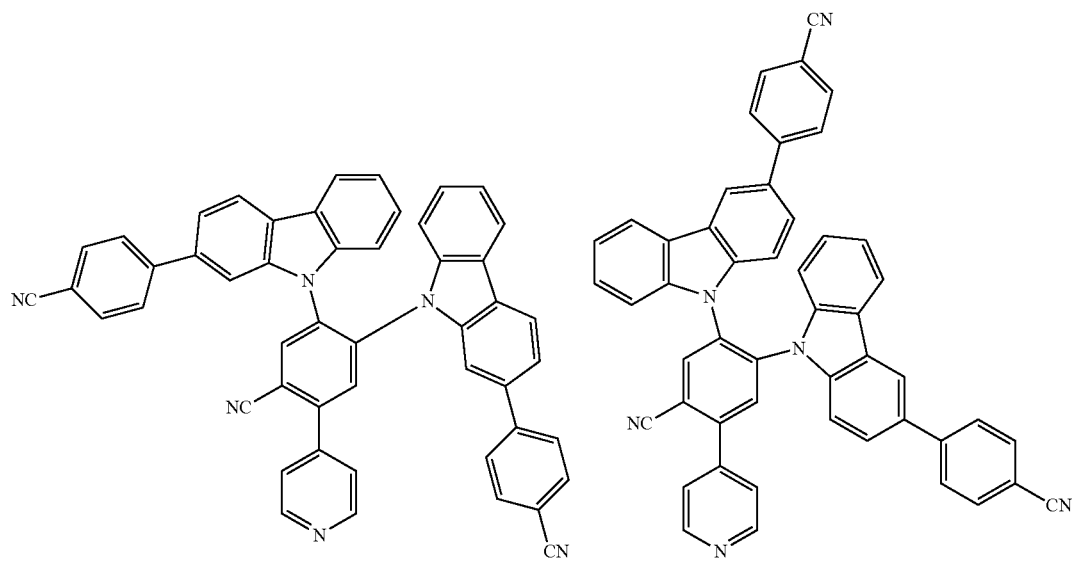

-continued
197
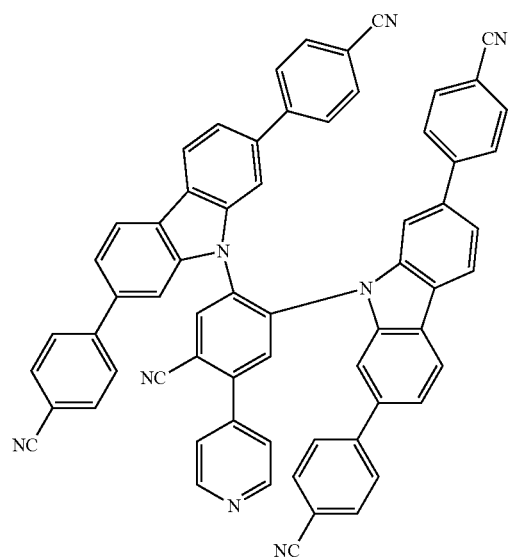
198
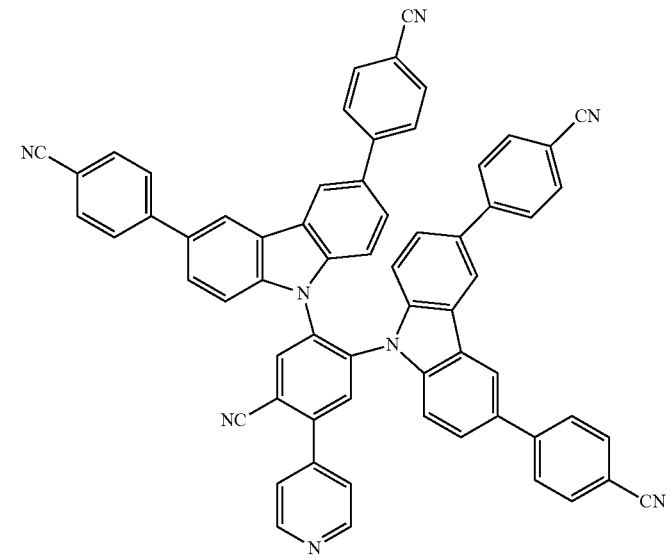
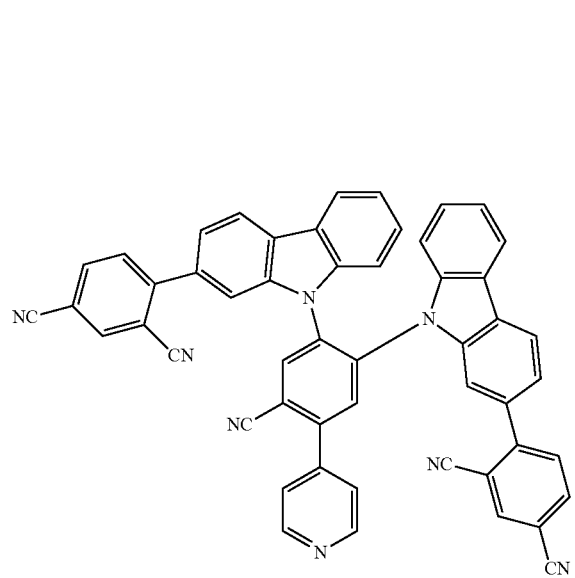
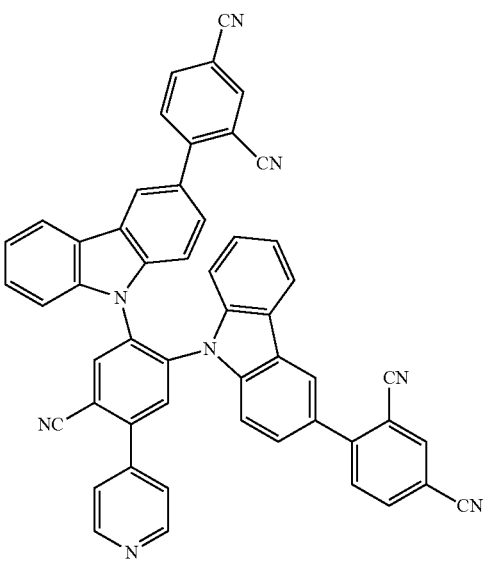

-continued
199
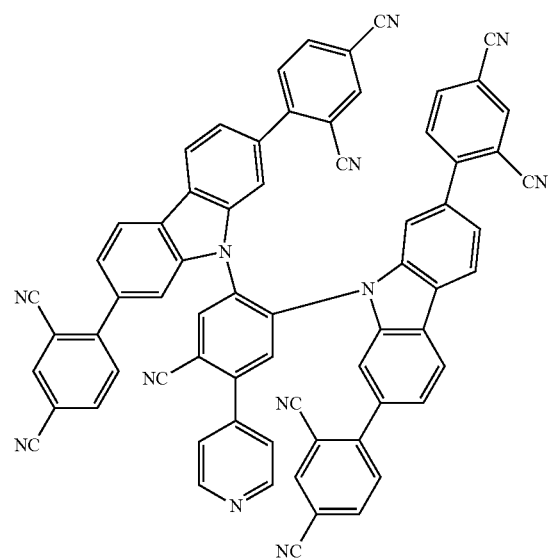
200
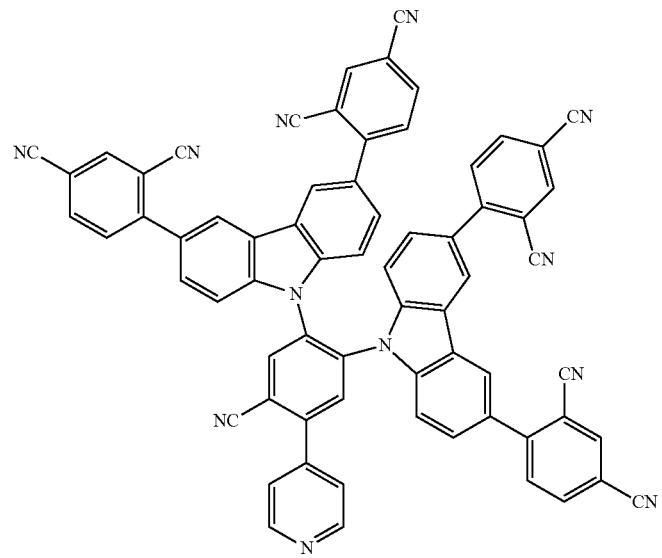
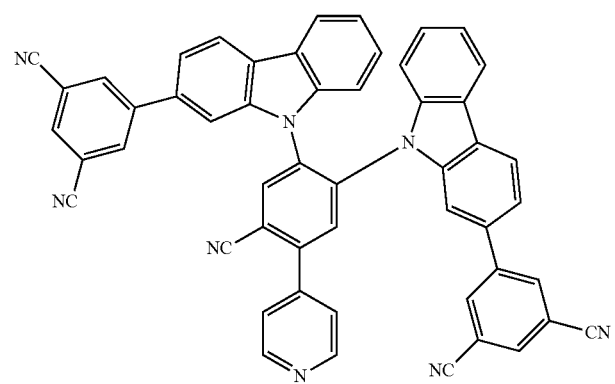
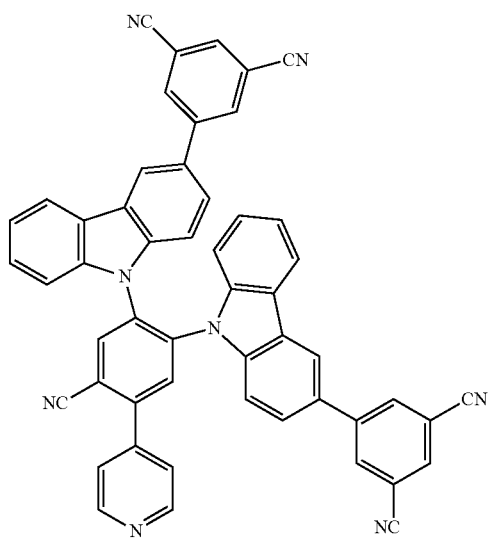

201
-continued
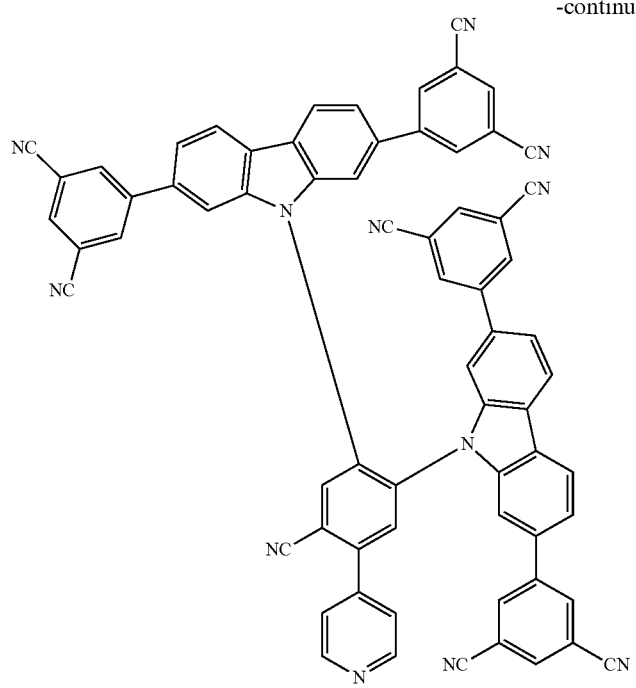
202
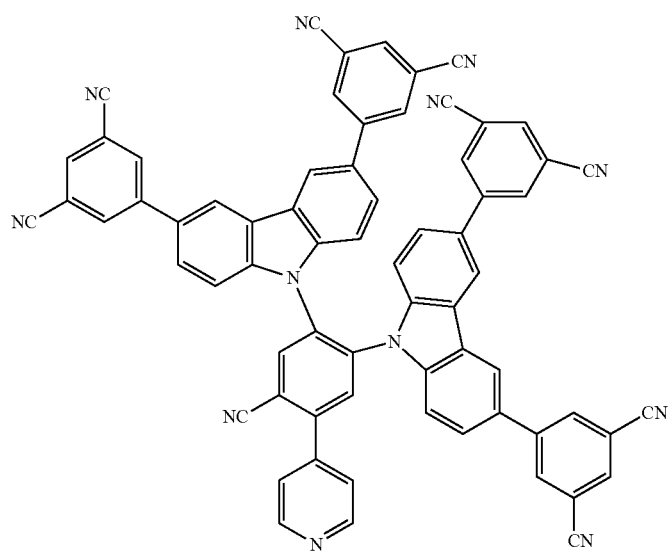

-continued
203
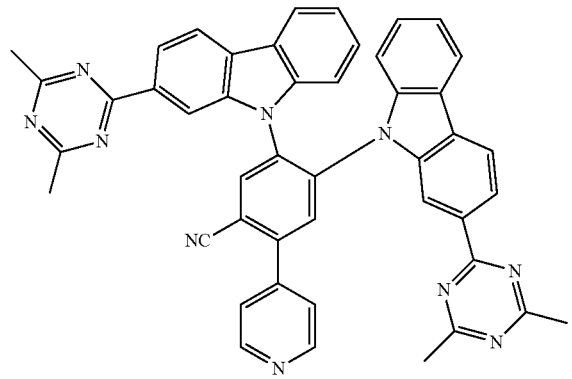
204
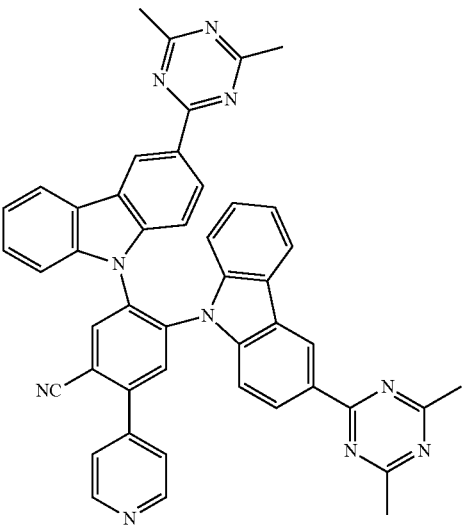
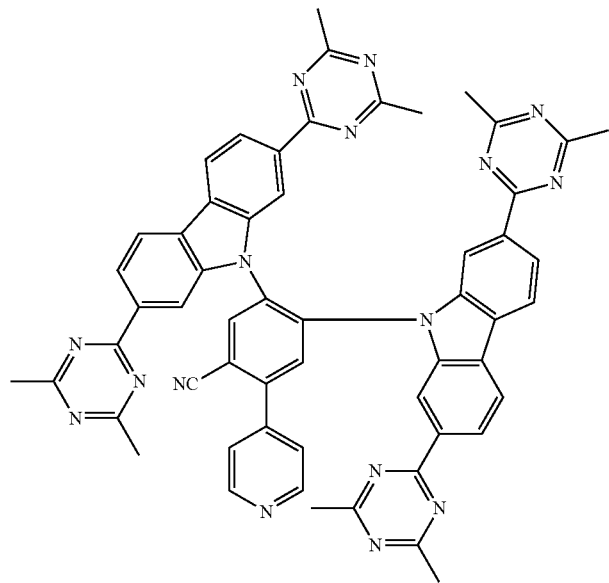
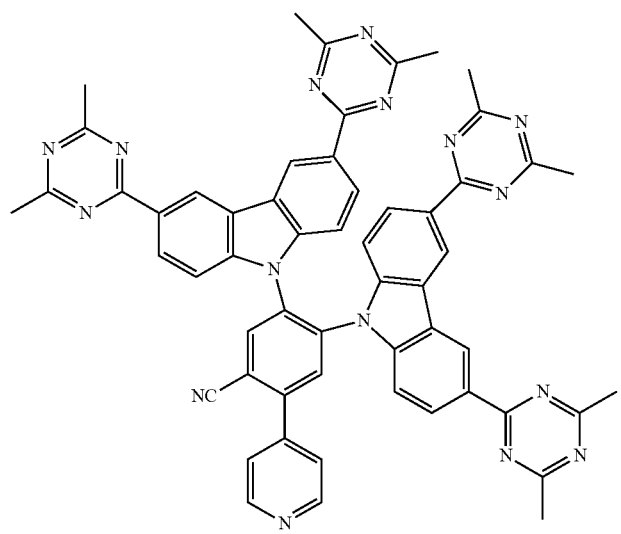

-continued
205
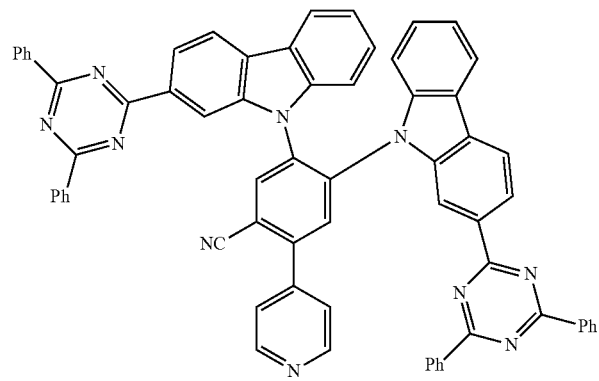
206
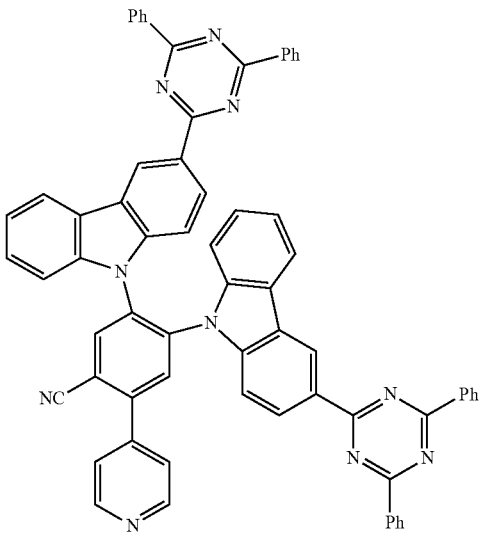
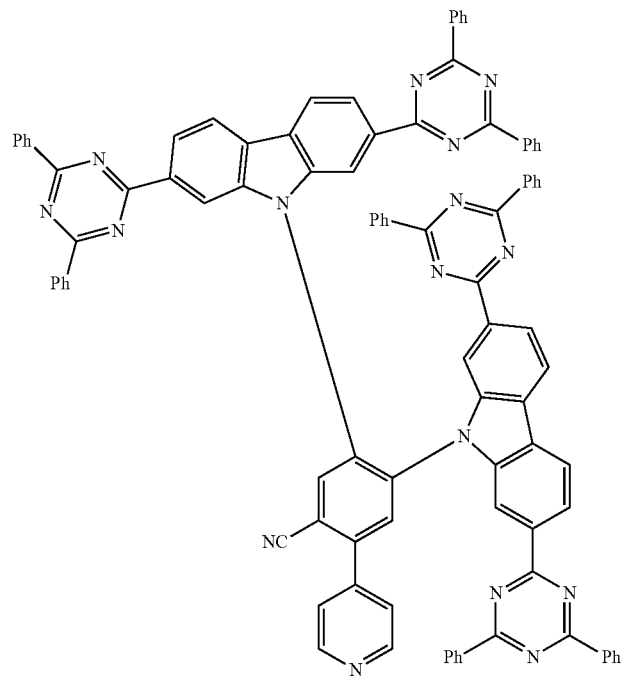
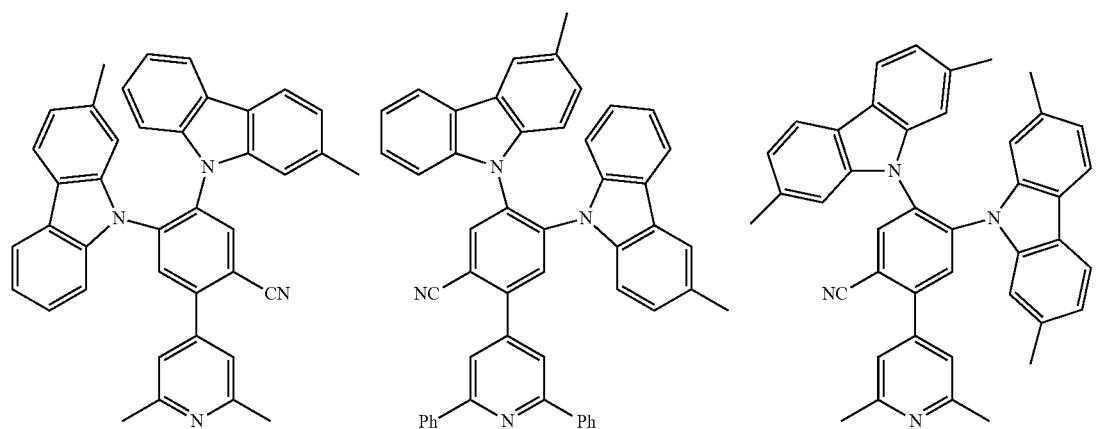

-continued
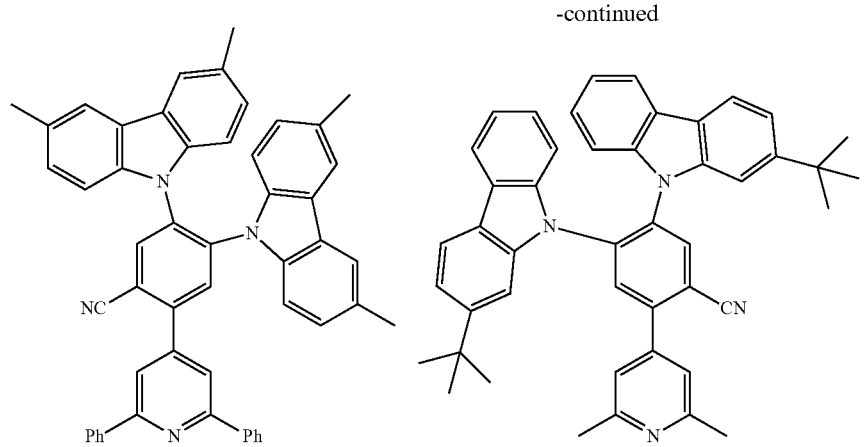
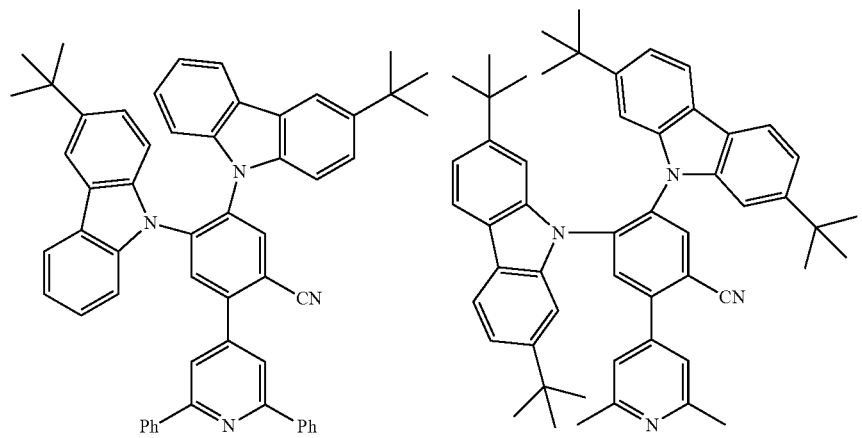
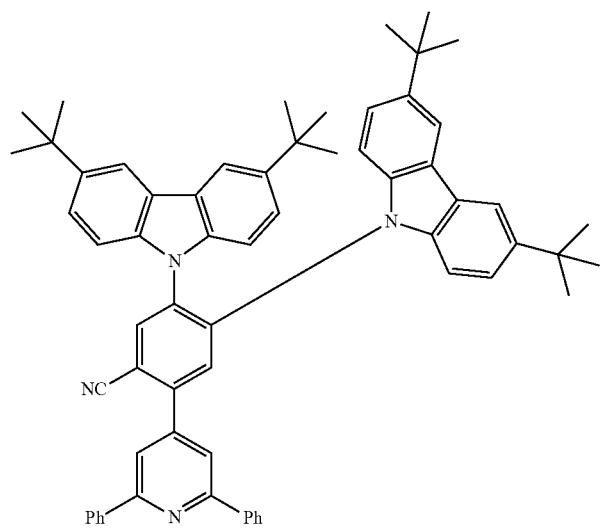

209 210
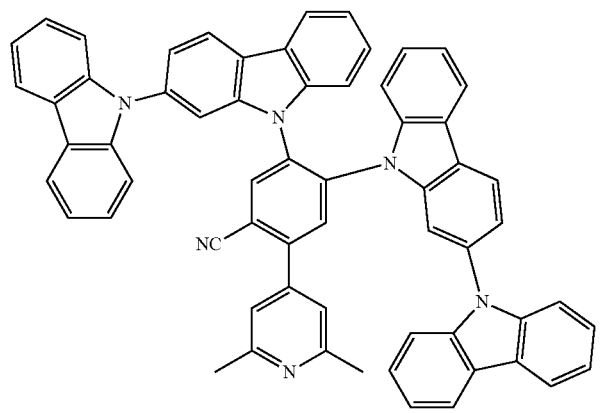 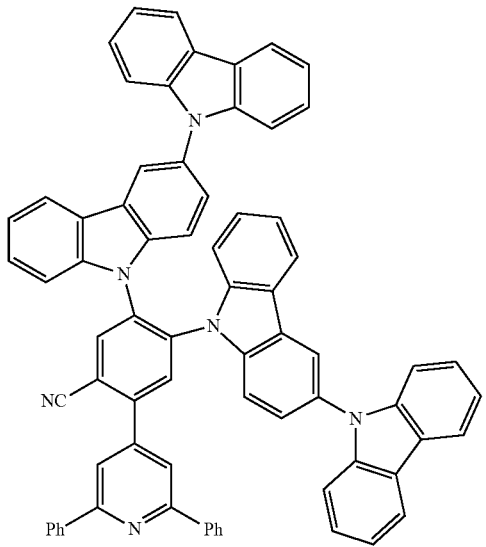
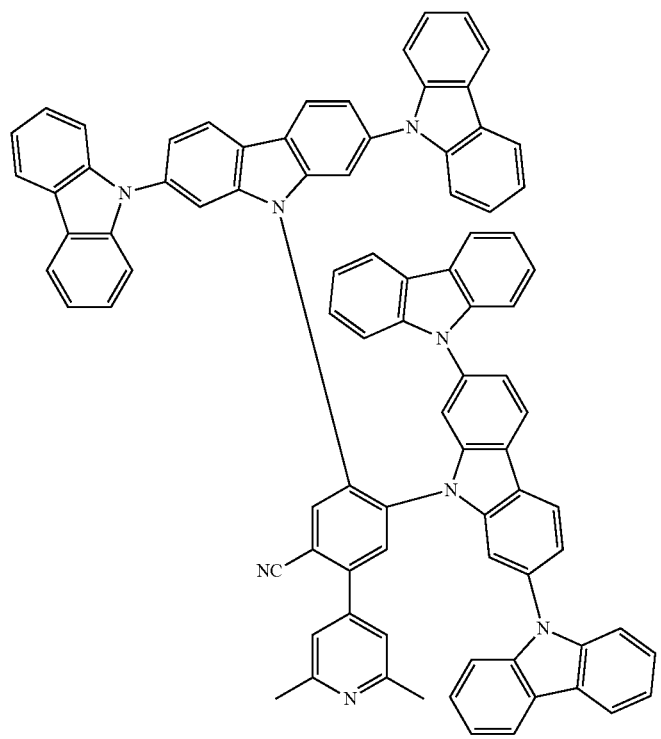

-continued
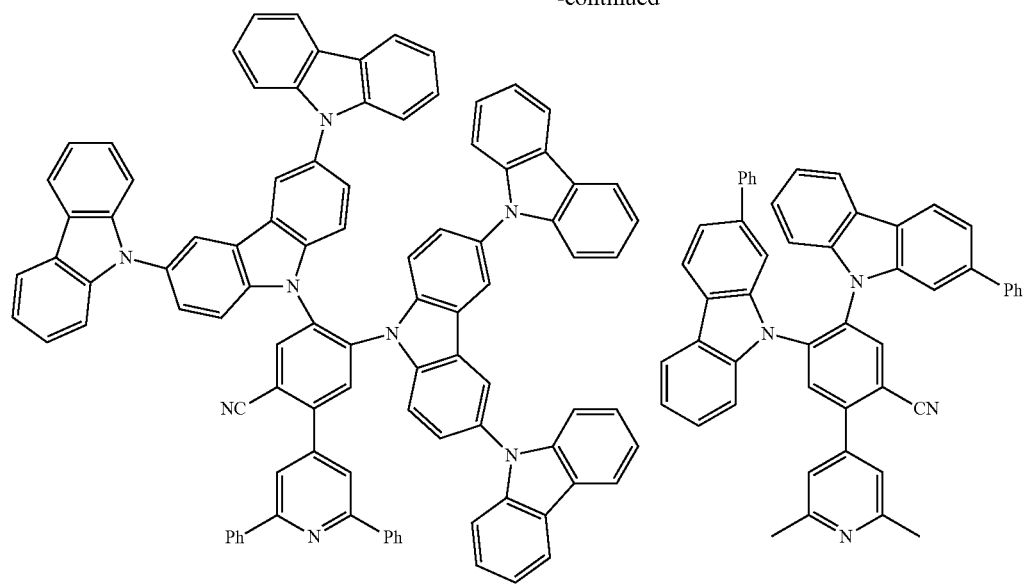
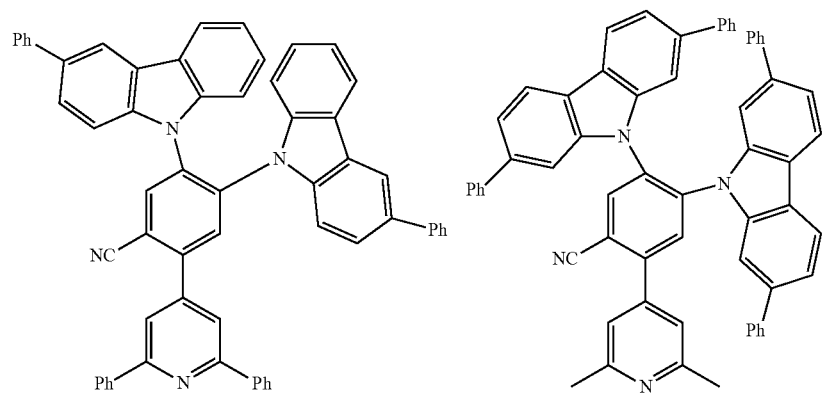
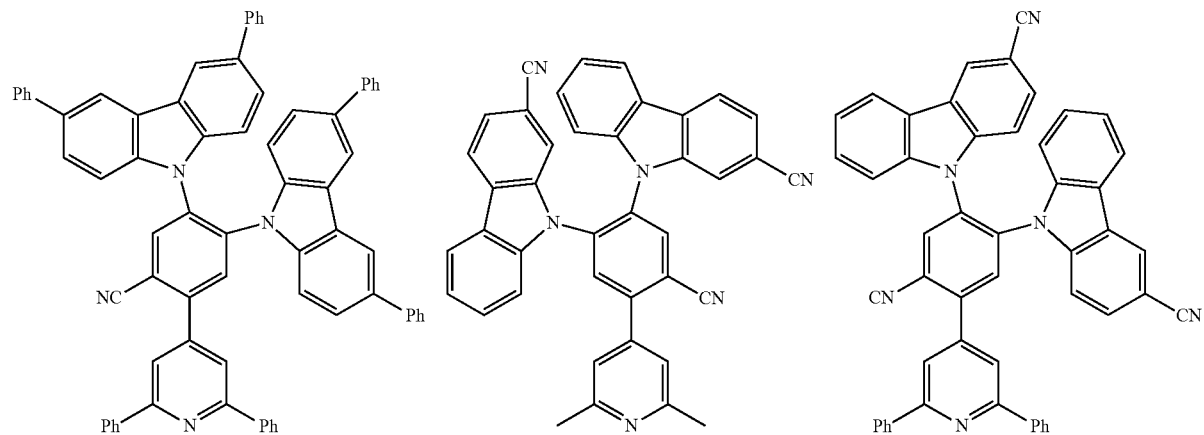

213
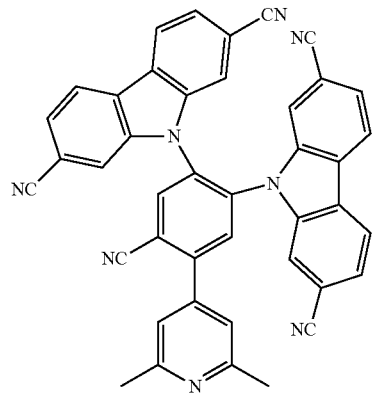
-continued
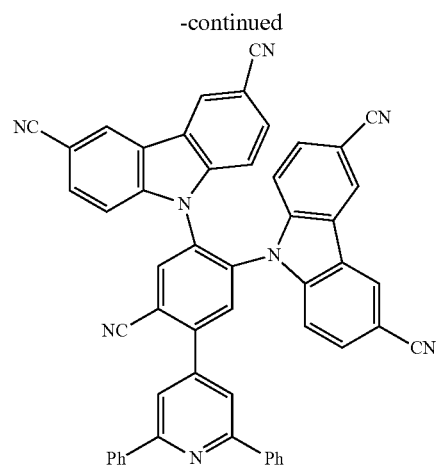
214
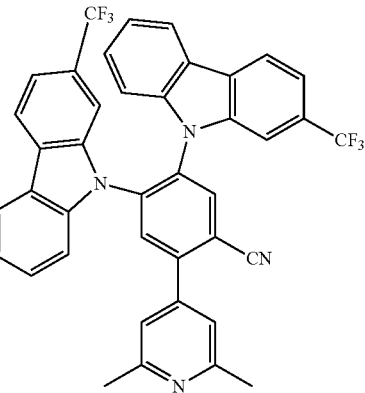
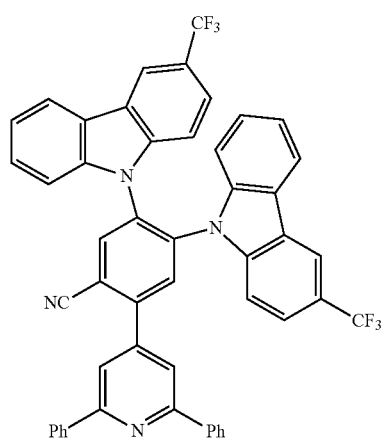
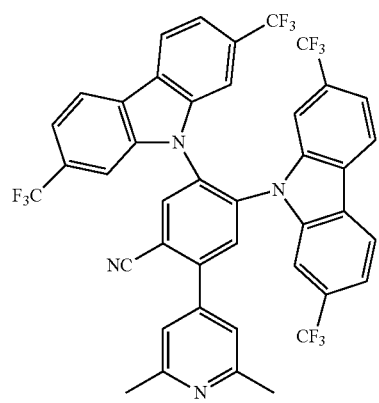
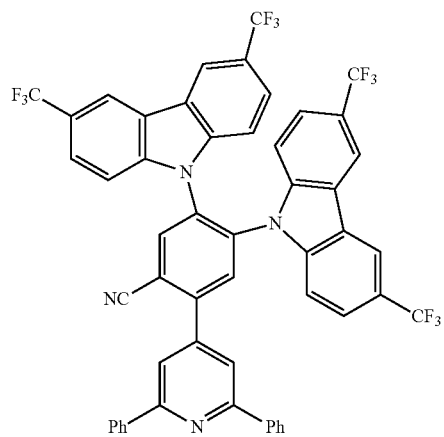
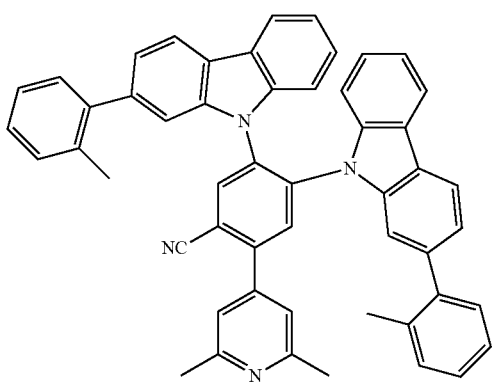

-continued
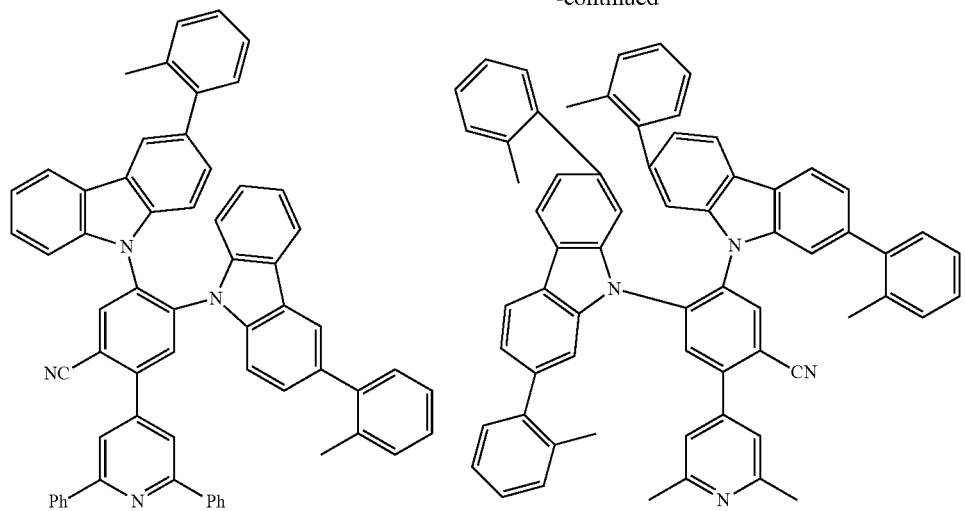
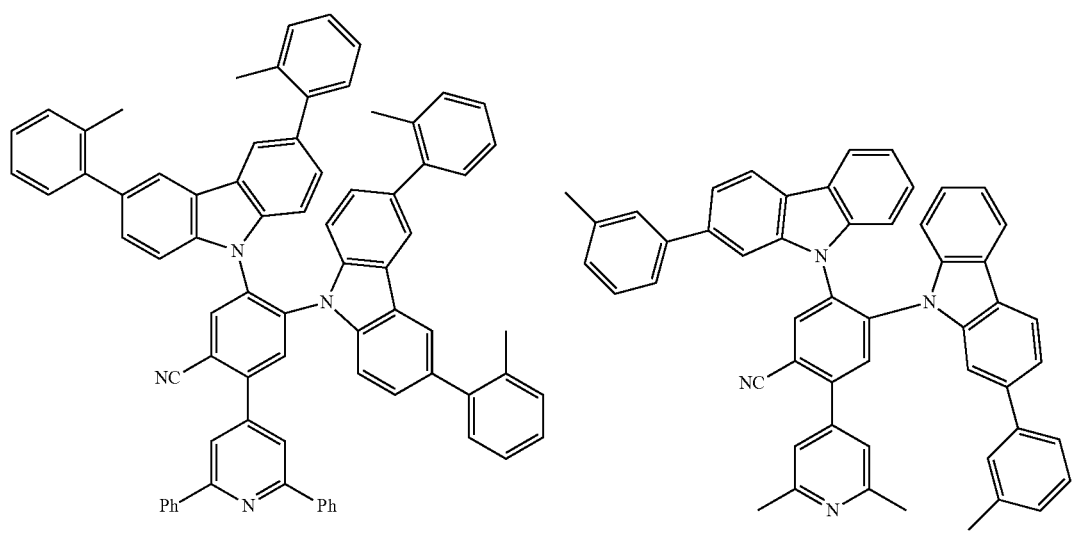
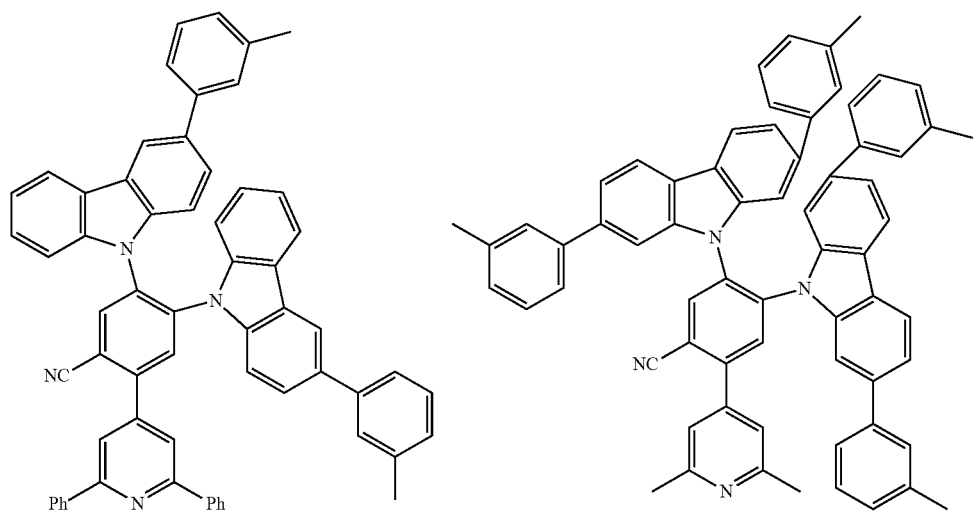

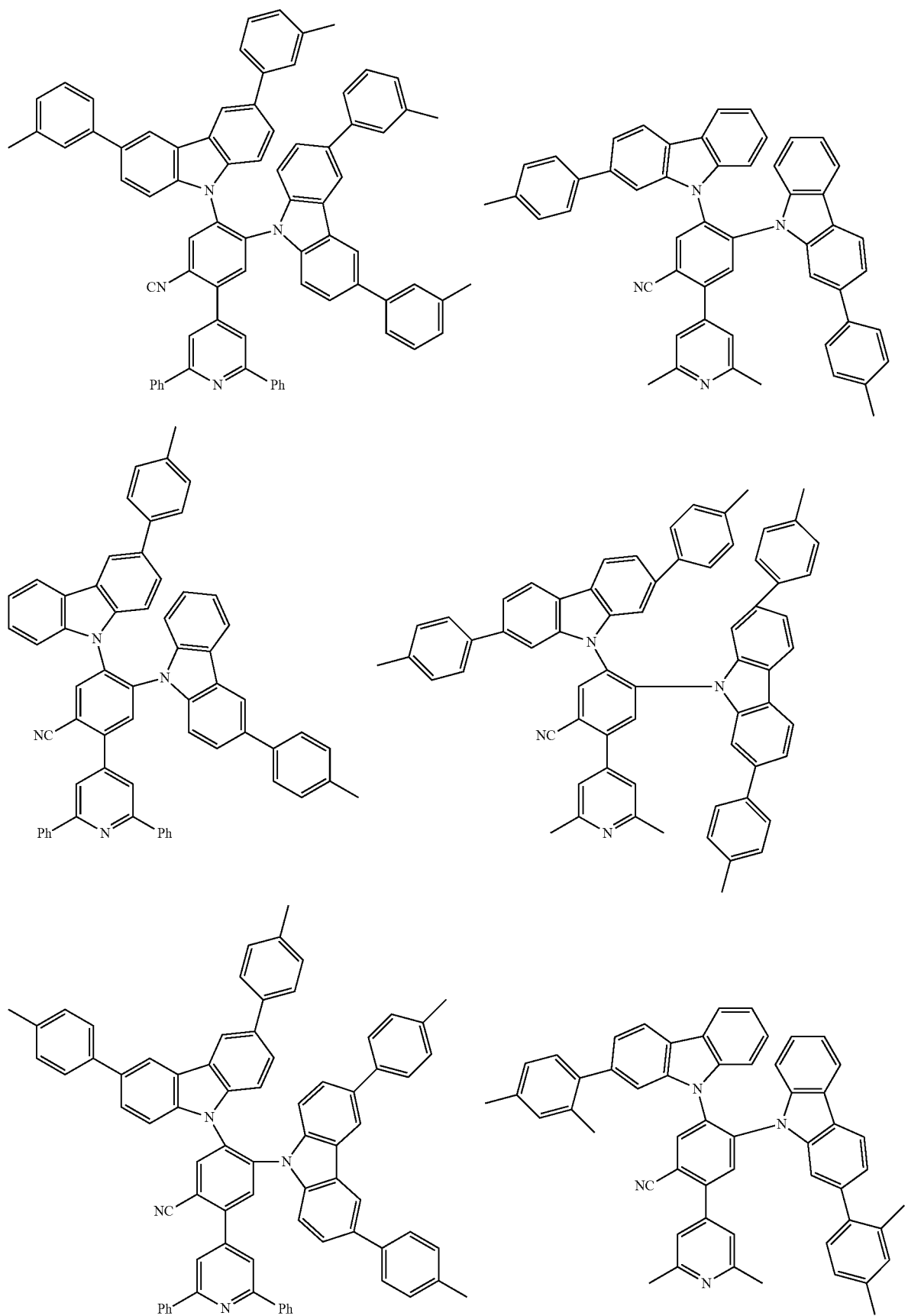

219
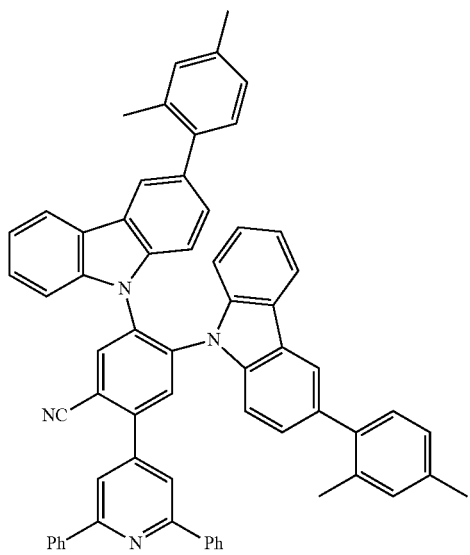
220
-continued
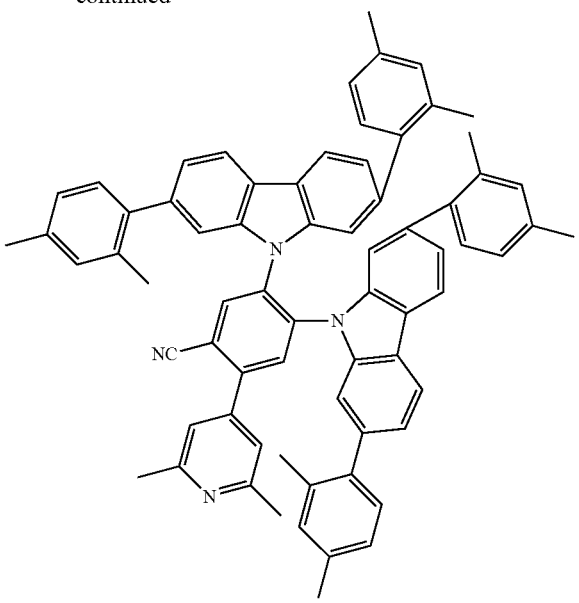
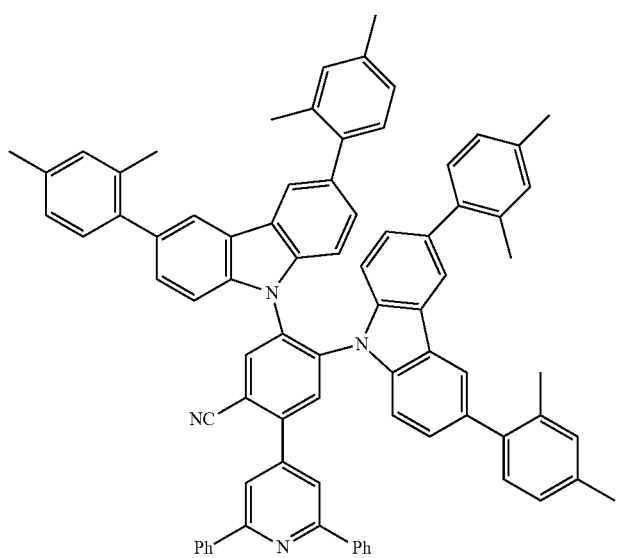
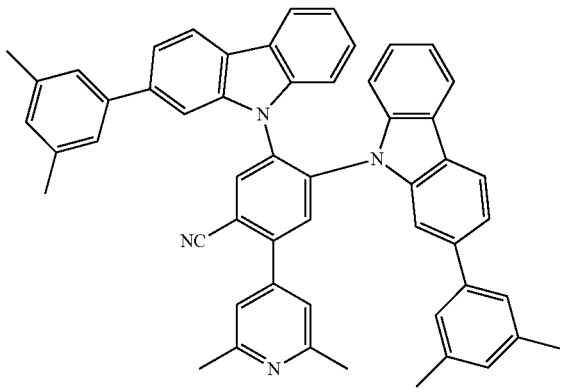
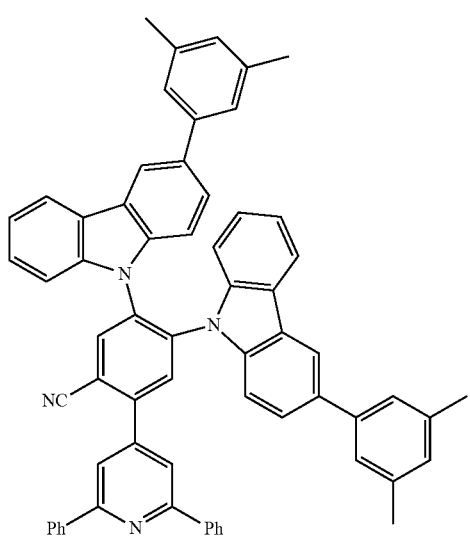
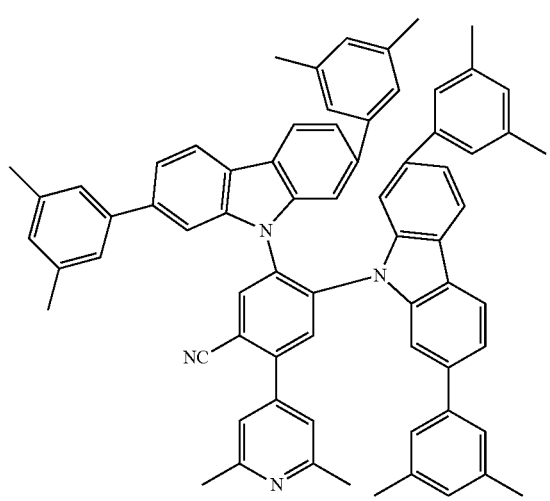

-continued
221
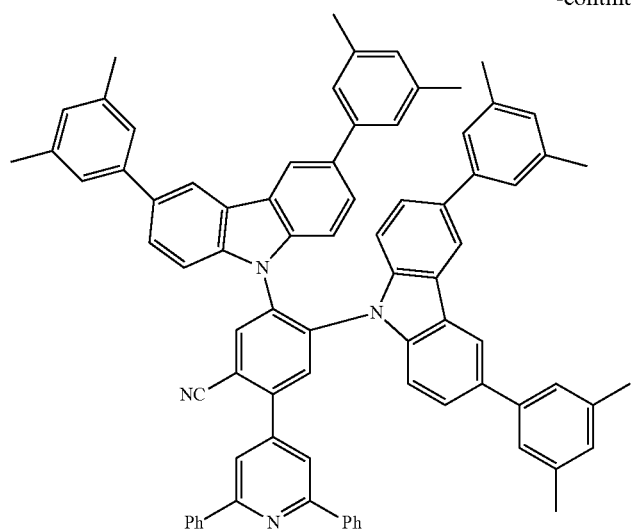
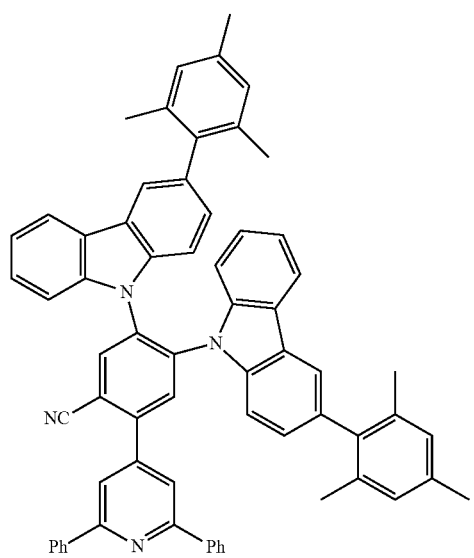
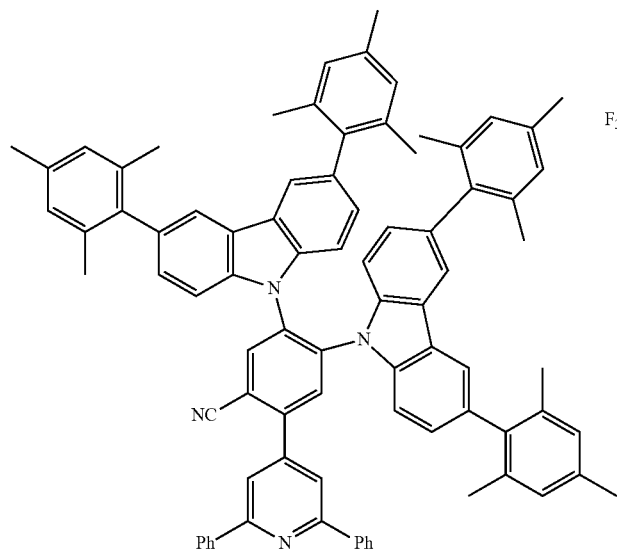
222
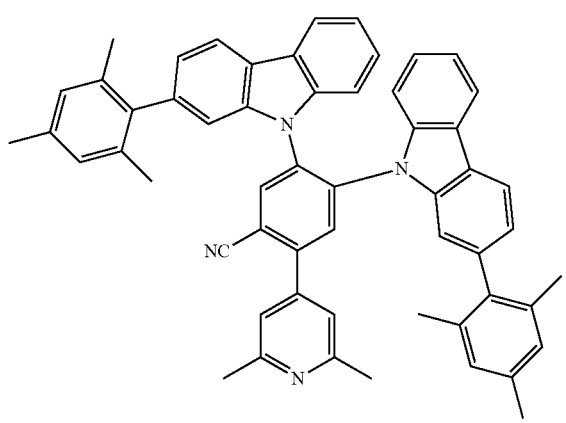
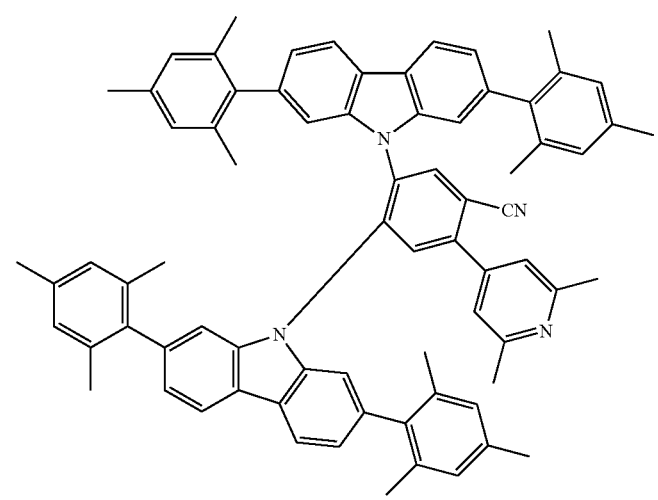
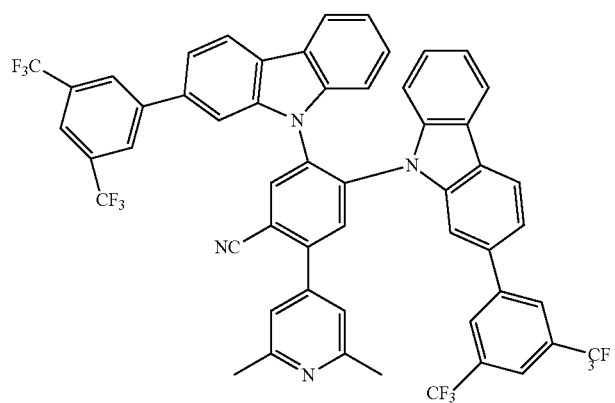

-continued
223
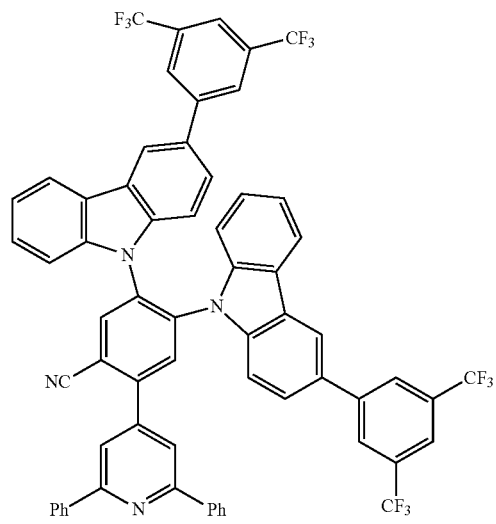
224
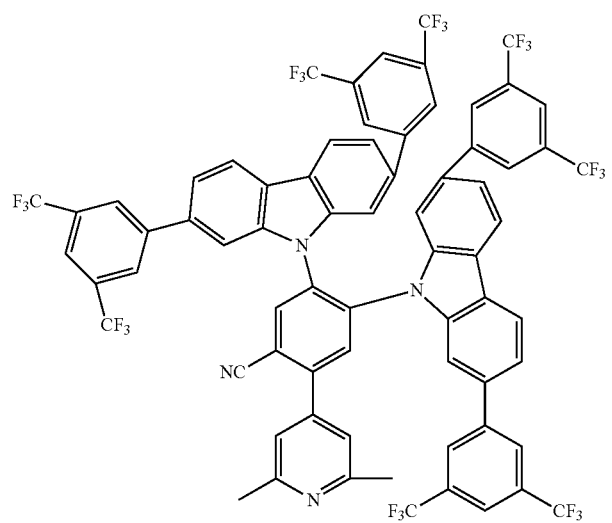
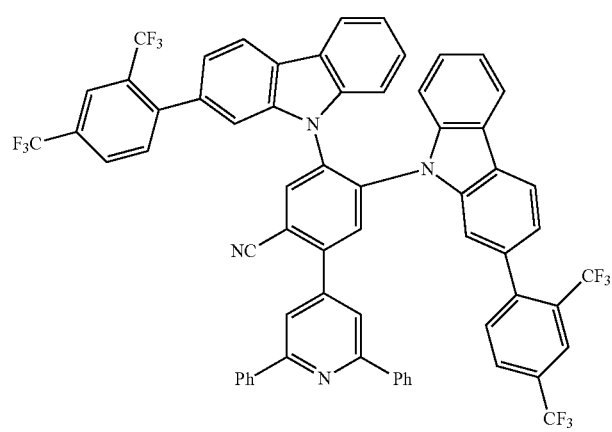
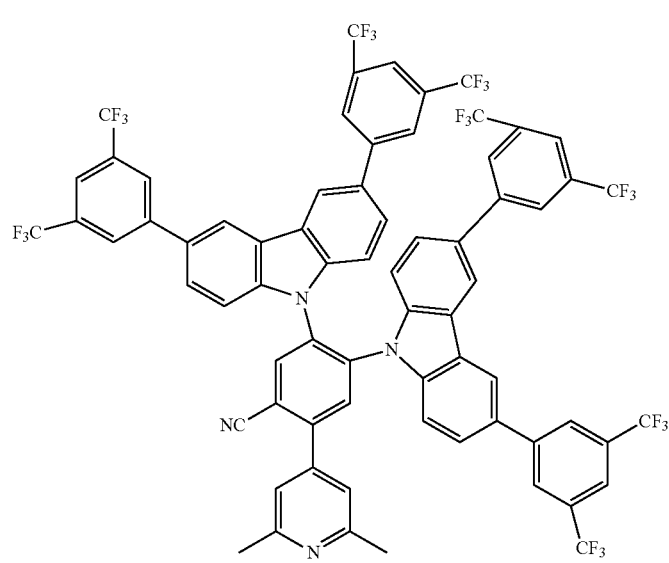
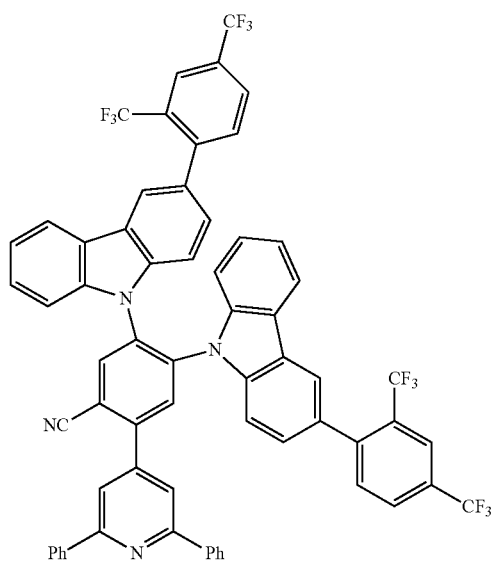

-continued
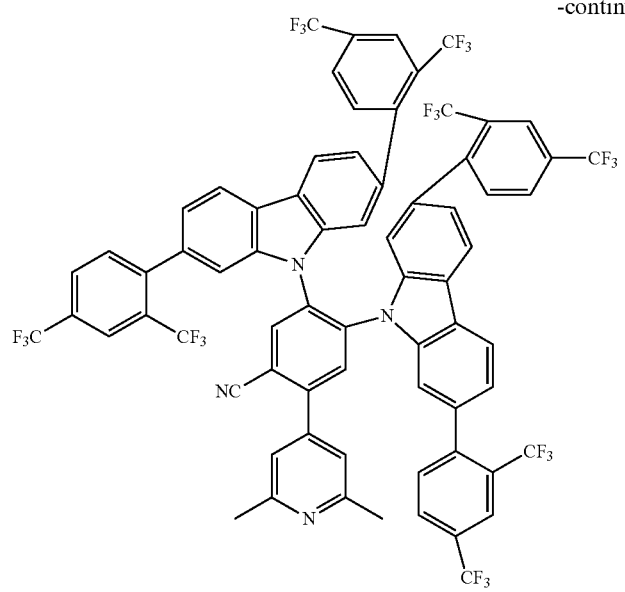
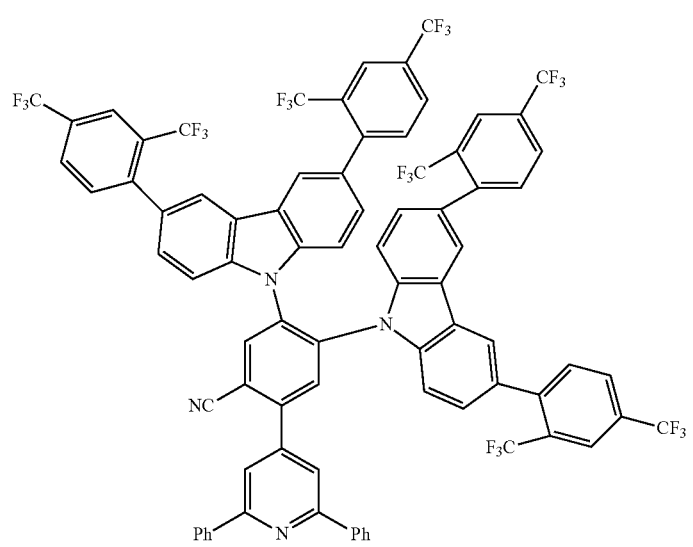
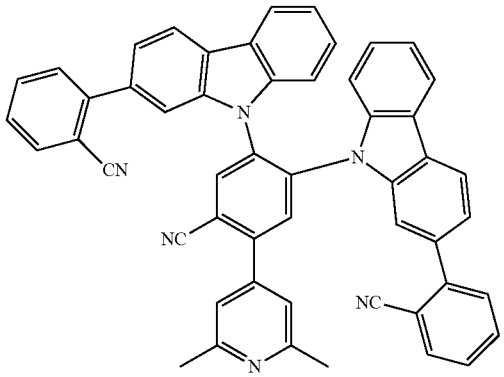
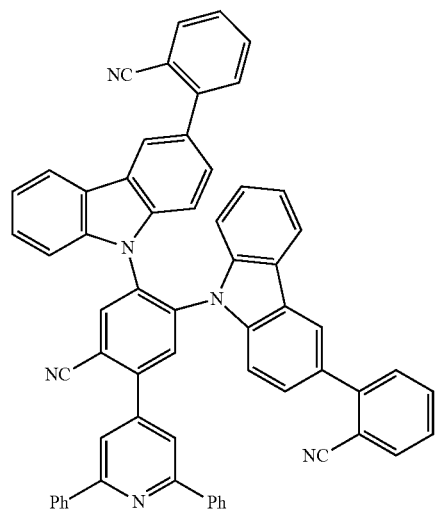
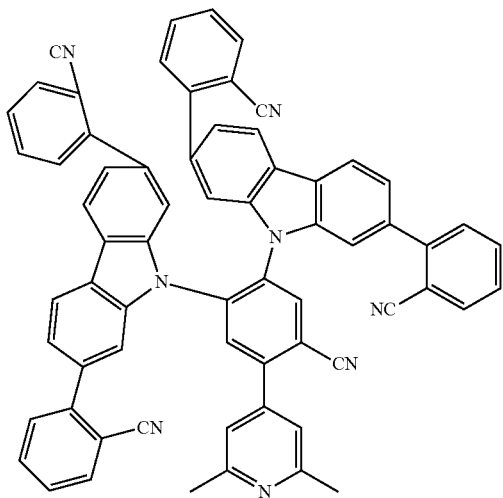

227
-continued
228
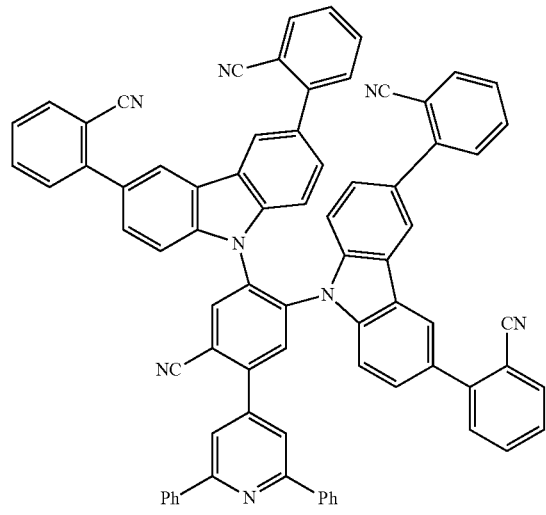
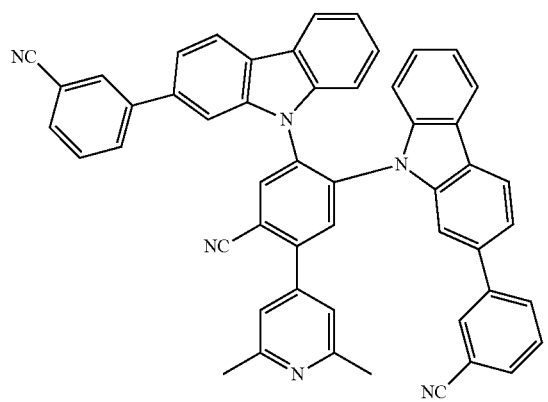
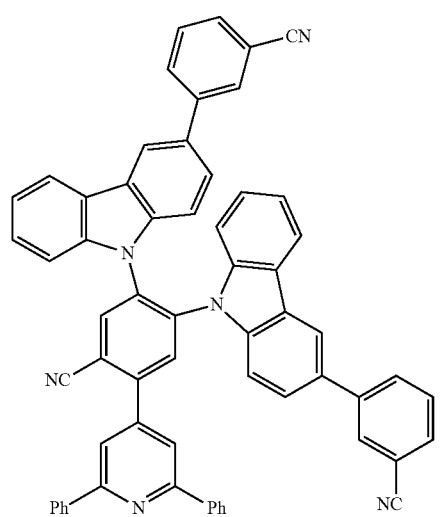
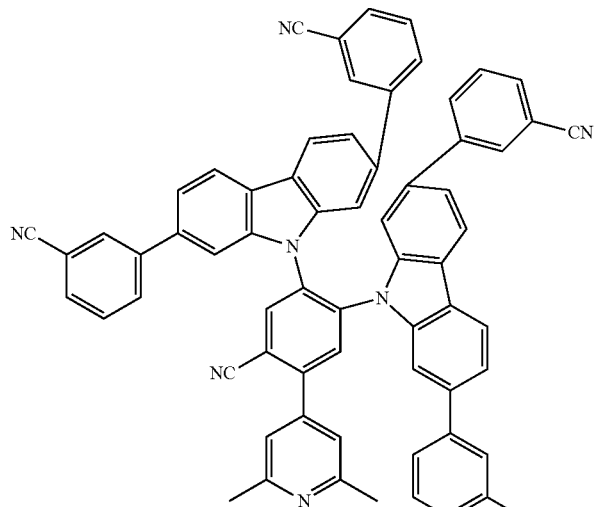
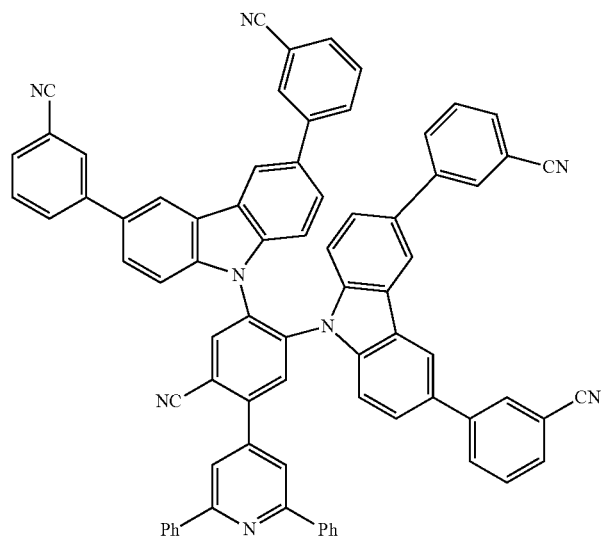
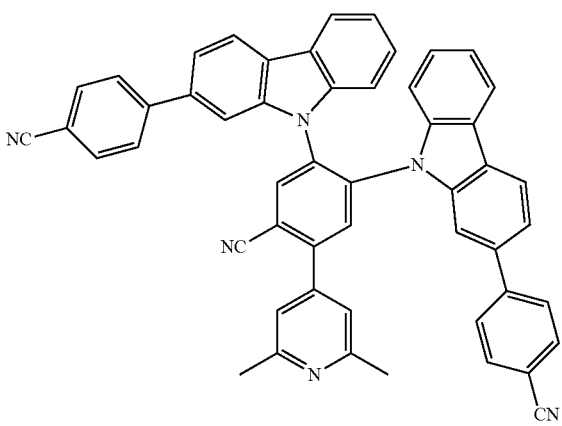

-continued
229
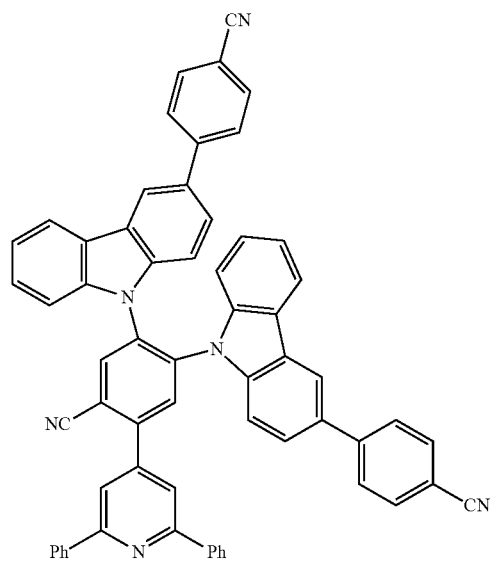
230
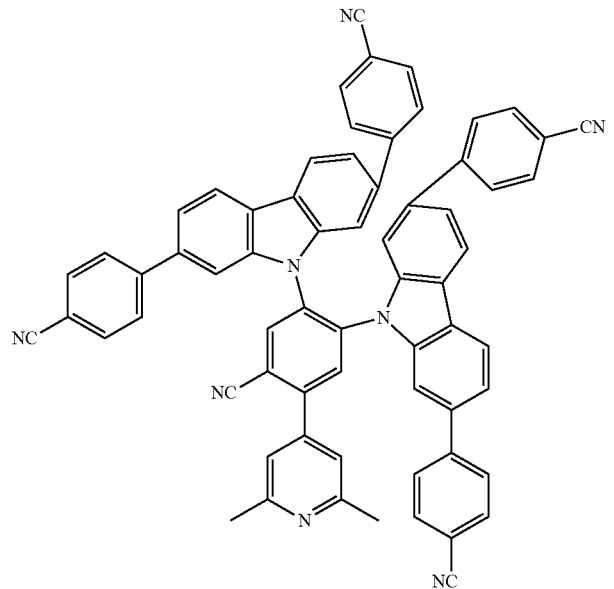
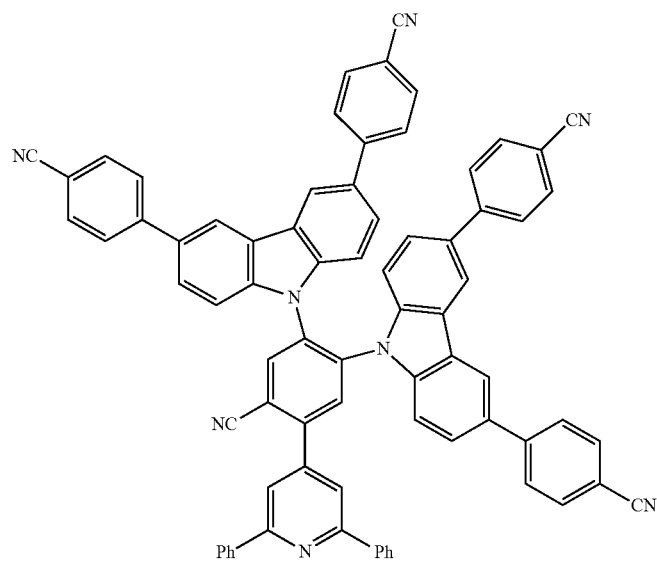

231
232
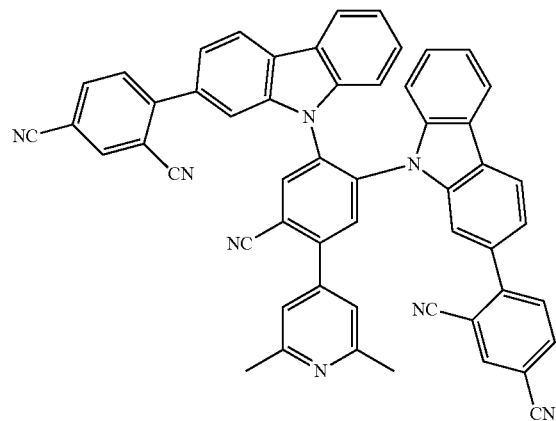
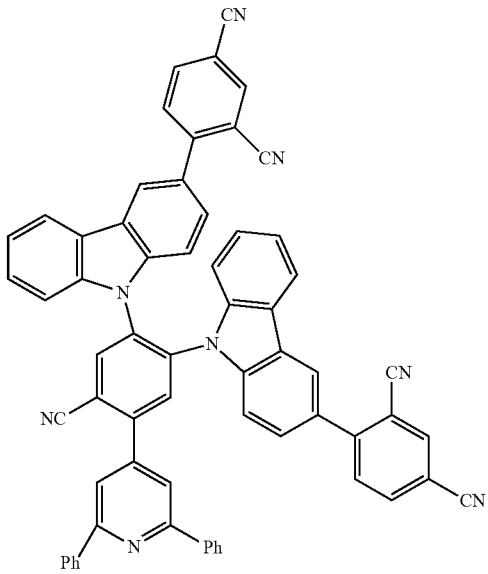
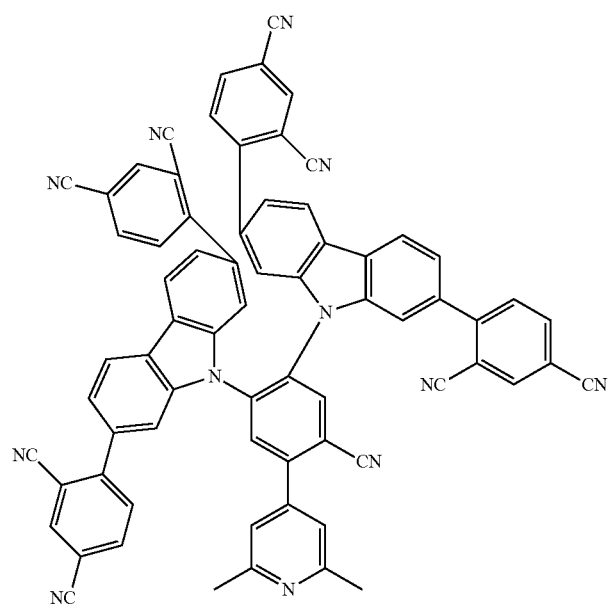

233
234
-continued
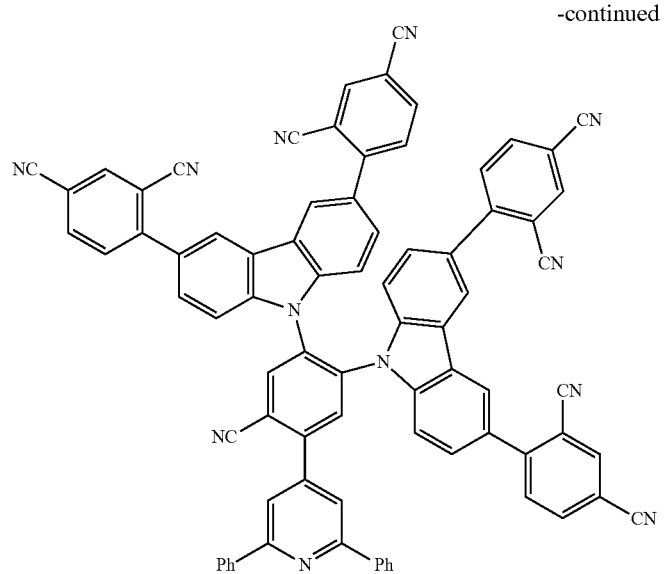
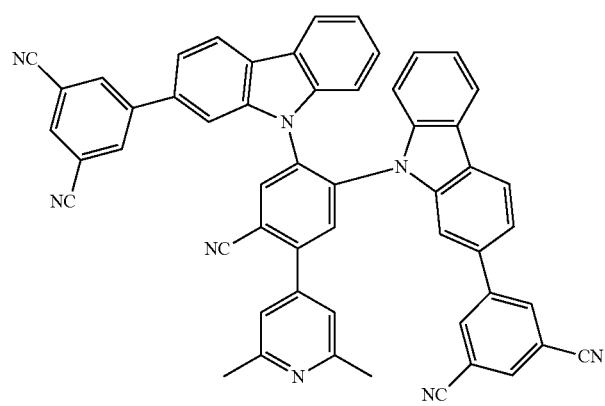
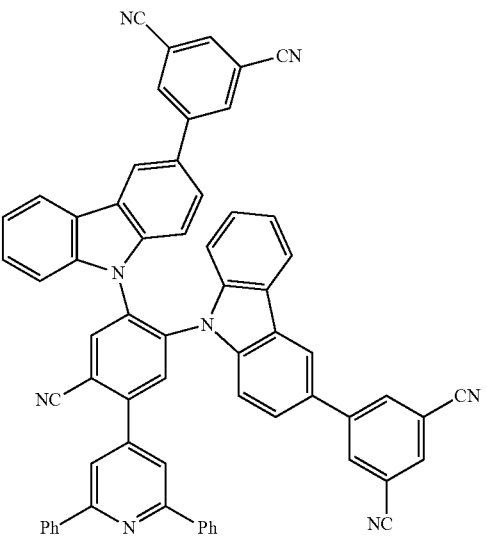
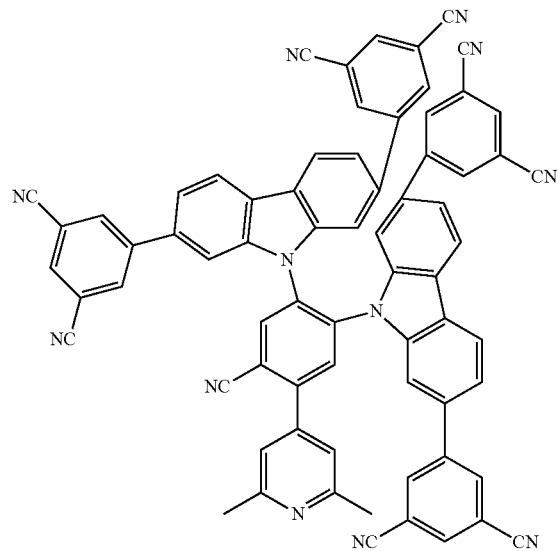

235 236
-continued
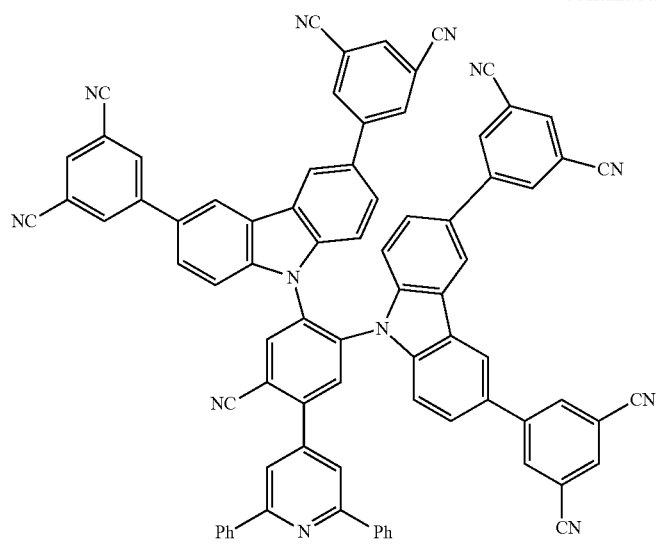
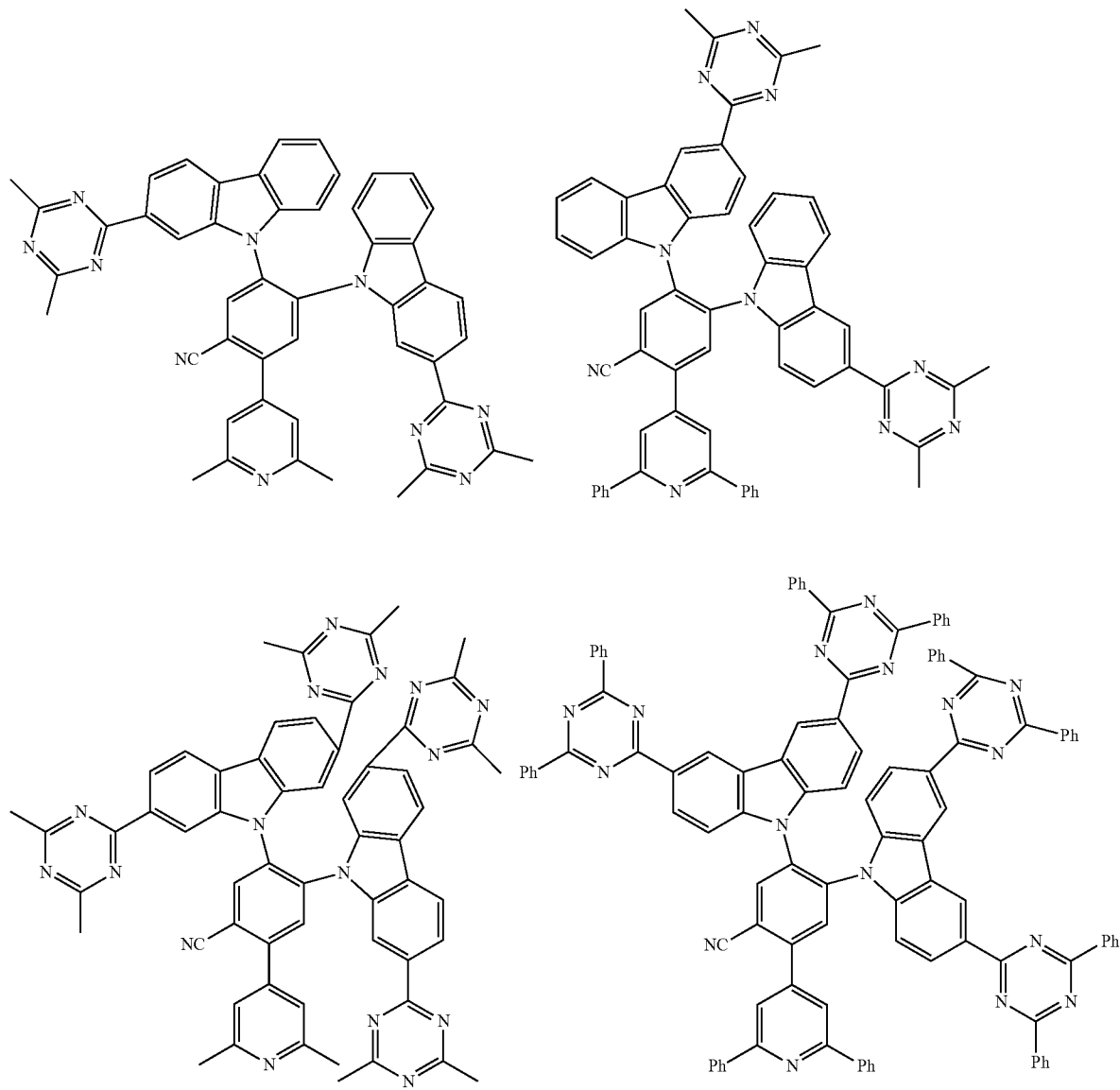

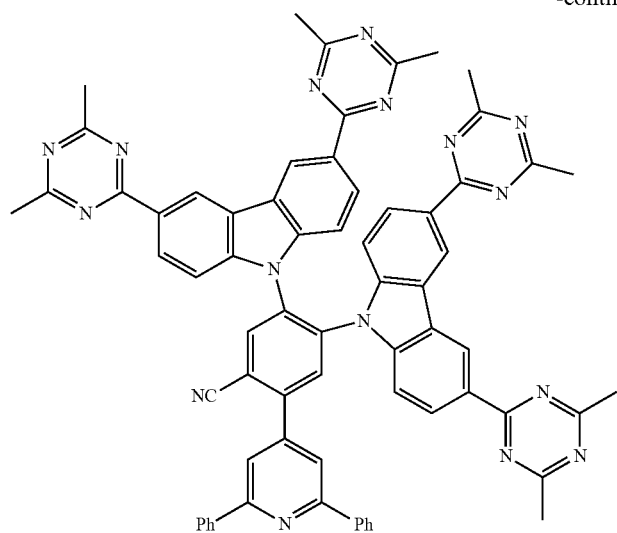
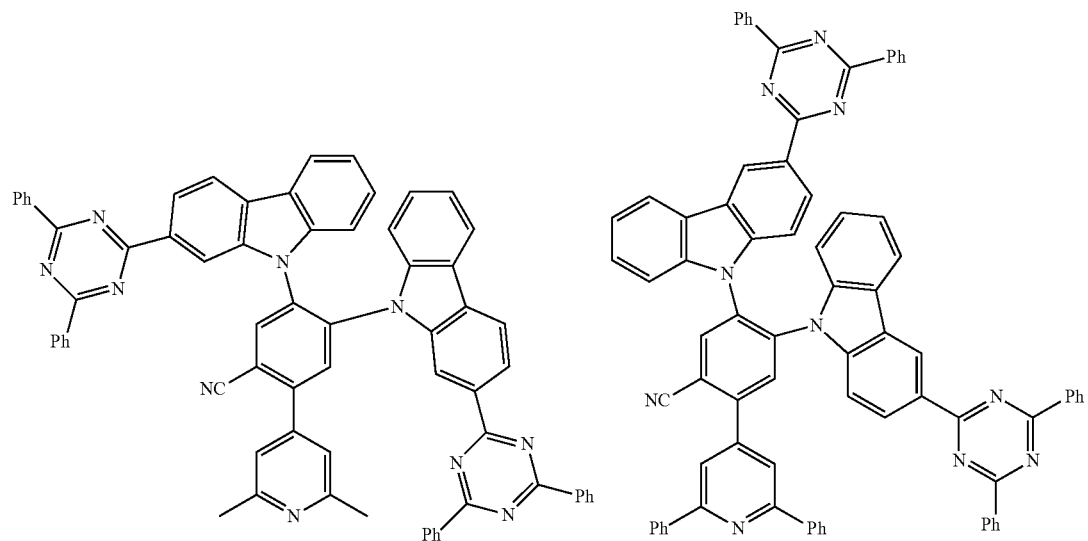
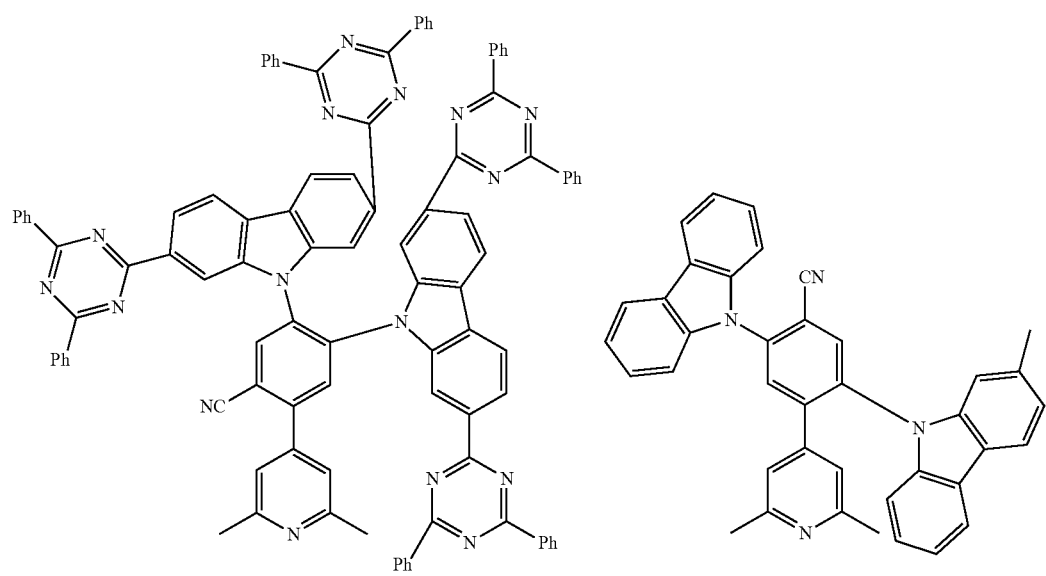

-continued
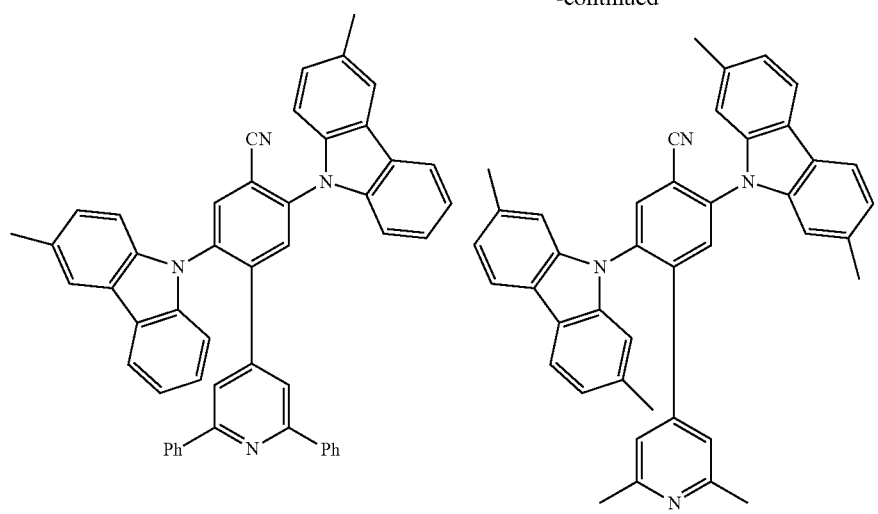
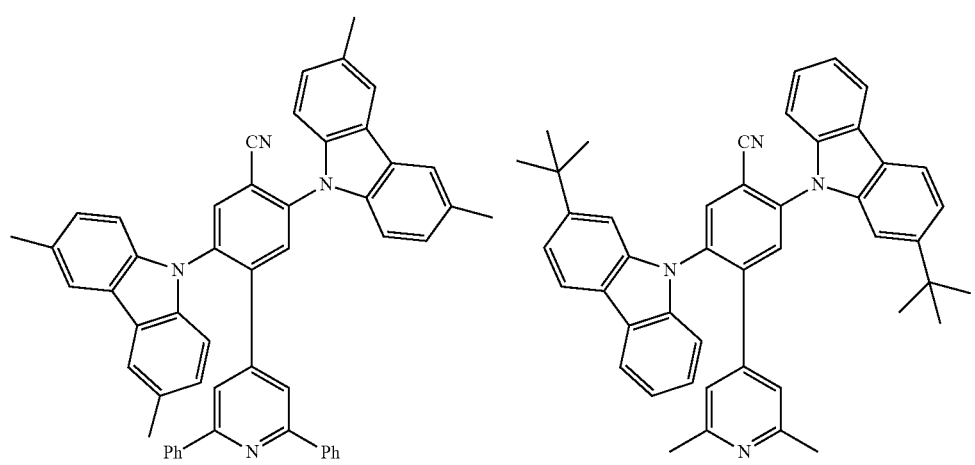
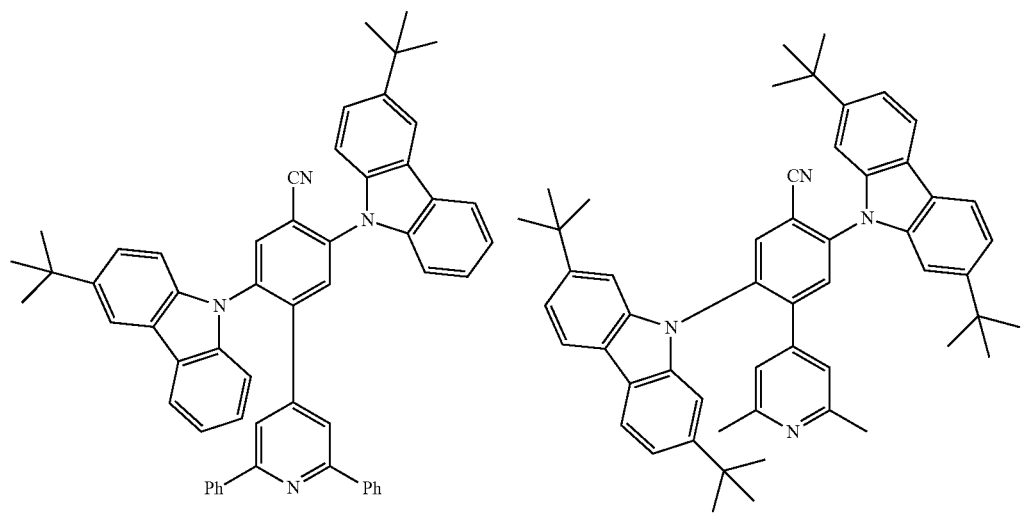

-continued
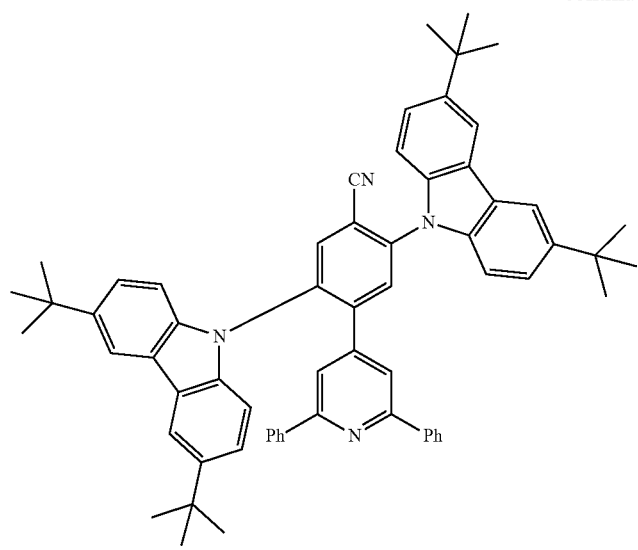
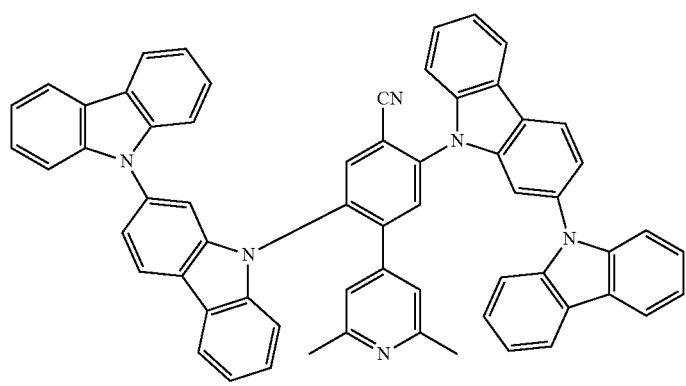
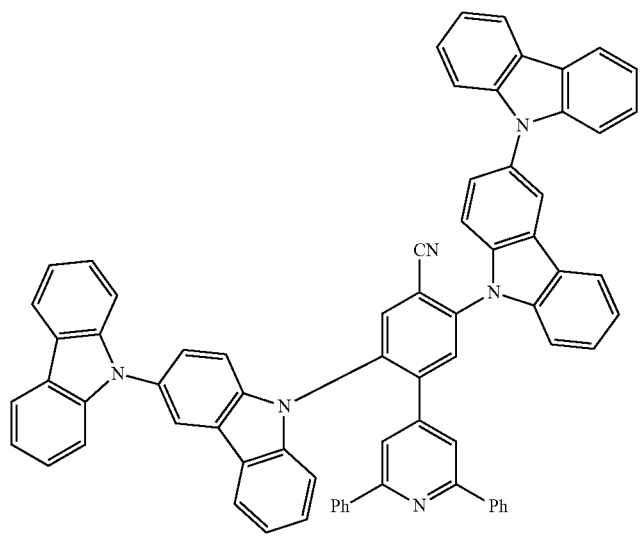

-continued
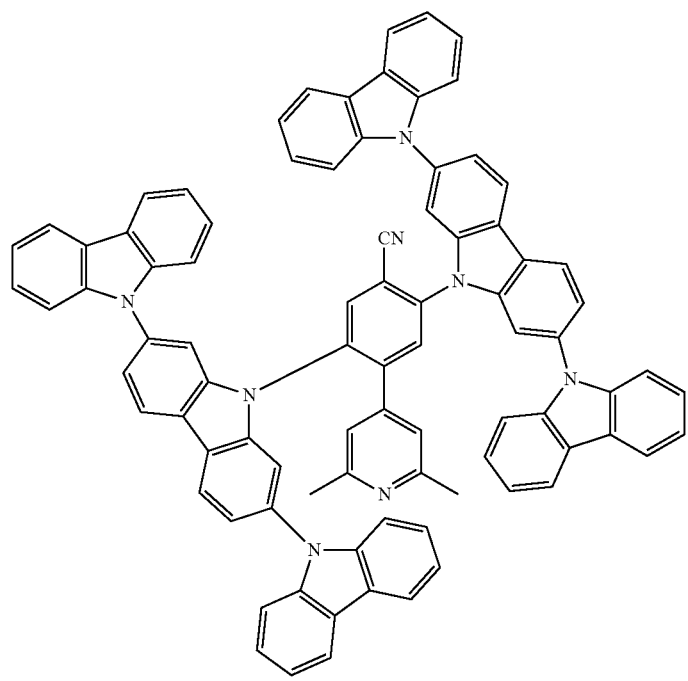 [SMILES: Cc1cc(-c2cc(-n3c4cc(-n5c6ccccc6c6ccccc65)ccc4c4ccc(-n5c6ccccc6c6ccccc65)cc43)c(C#N)cc2-n2c3cc(-n4c5ccccc5c5ccccc54)ccc3c3ccc(-n4c5ccccc5c5ccccc54)cc32)cc(C)n1]
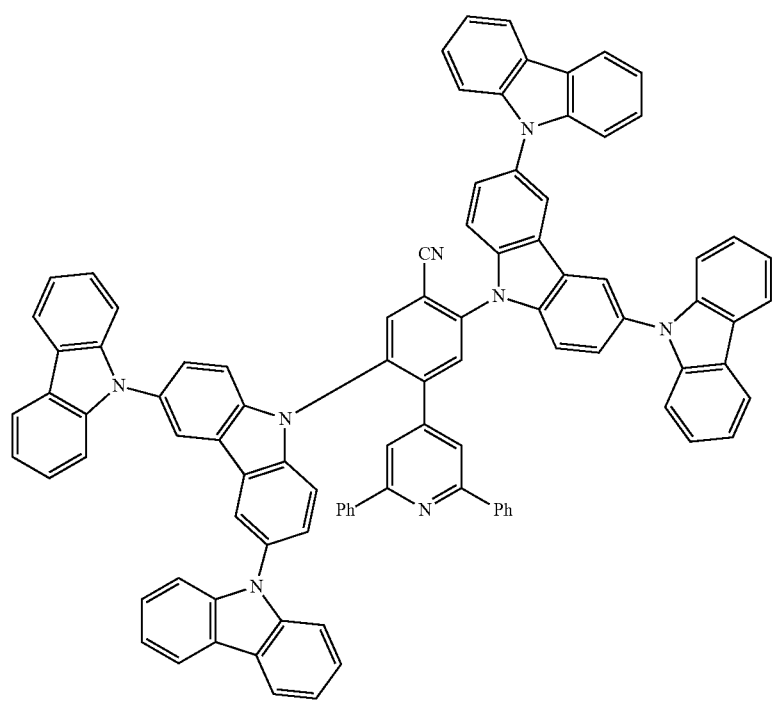

-continued
245
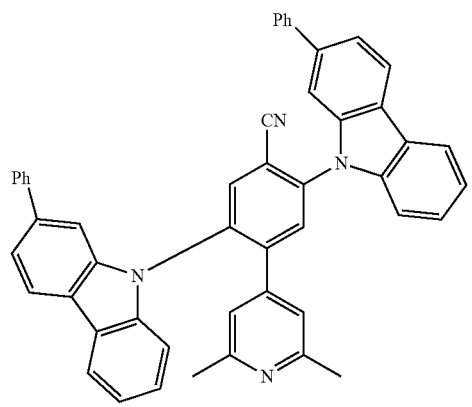
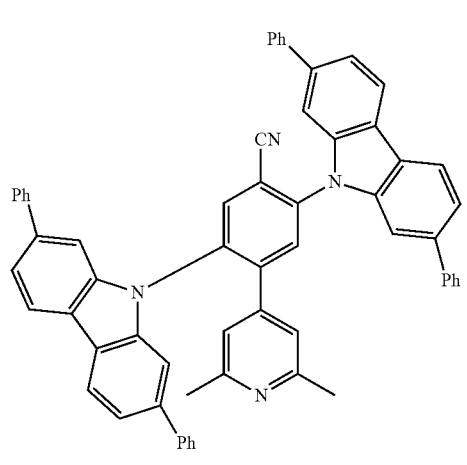
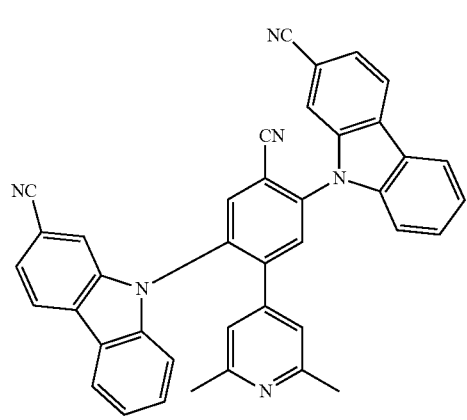
246
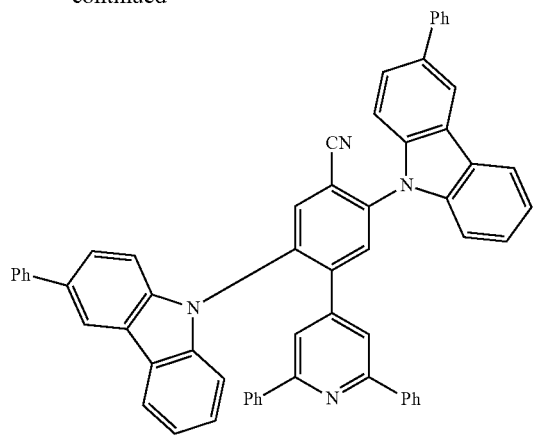
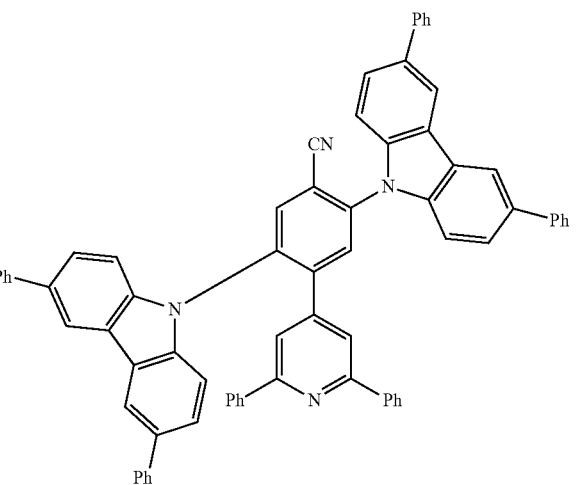
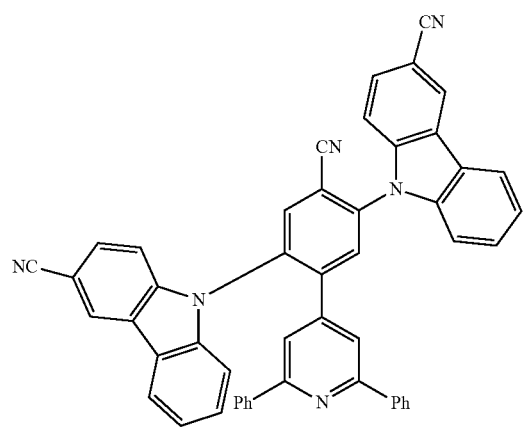

-continued
247
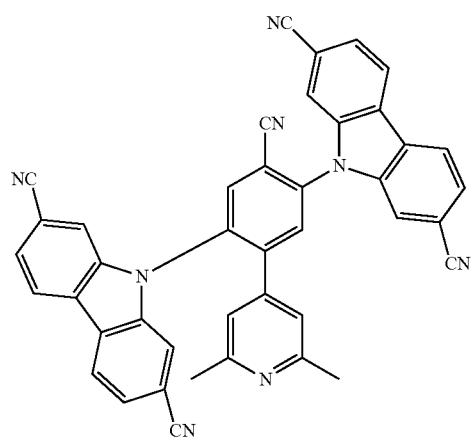
248
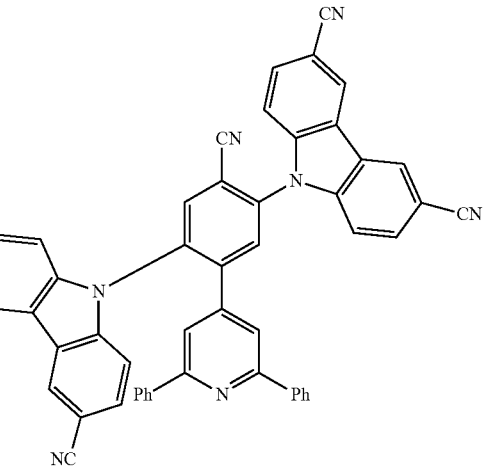
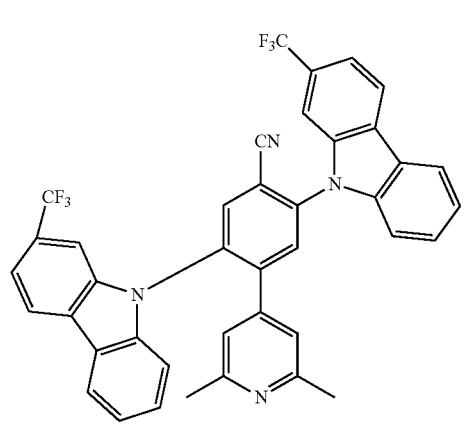
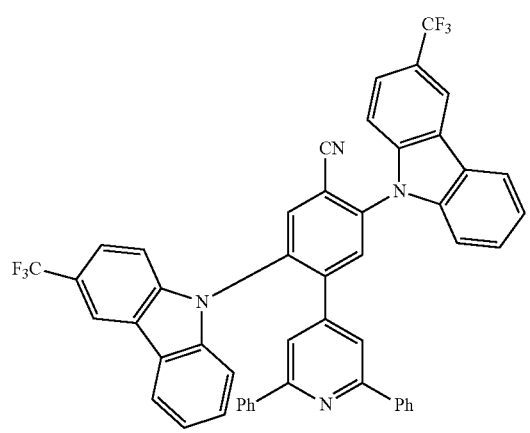
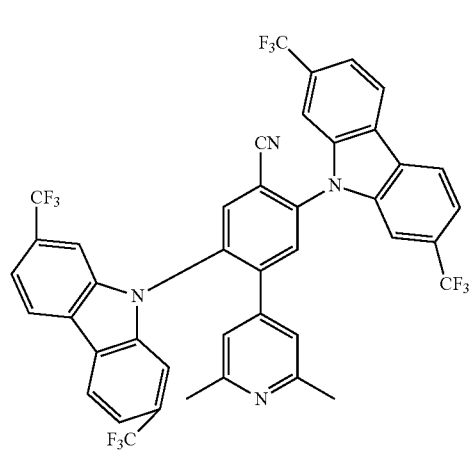
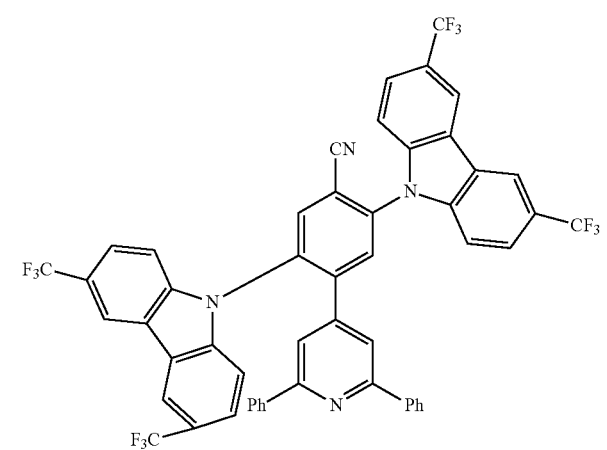

-continued
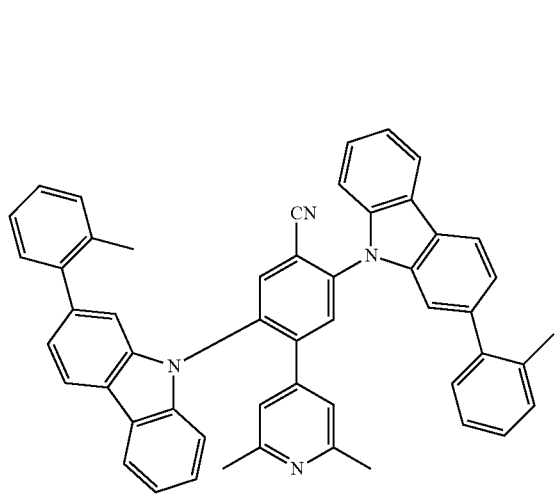
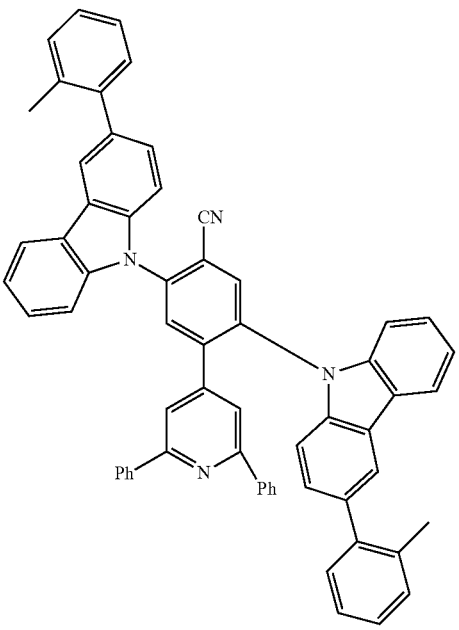
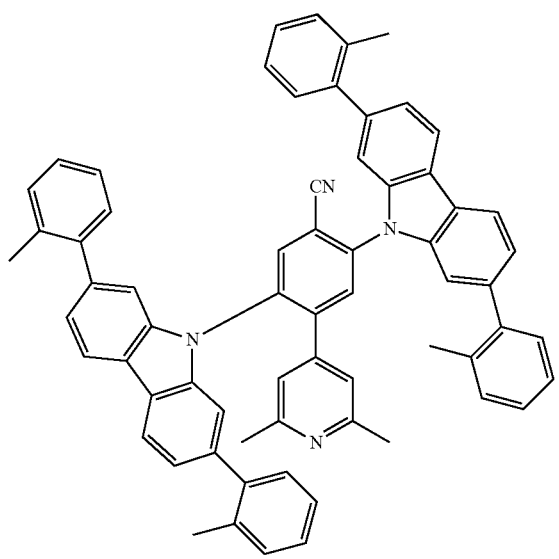

-continued
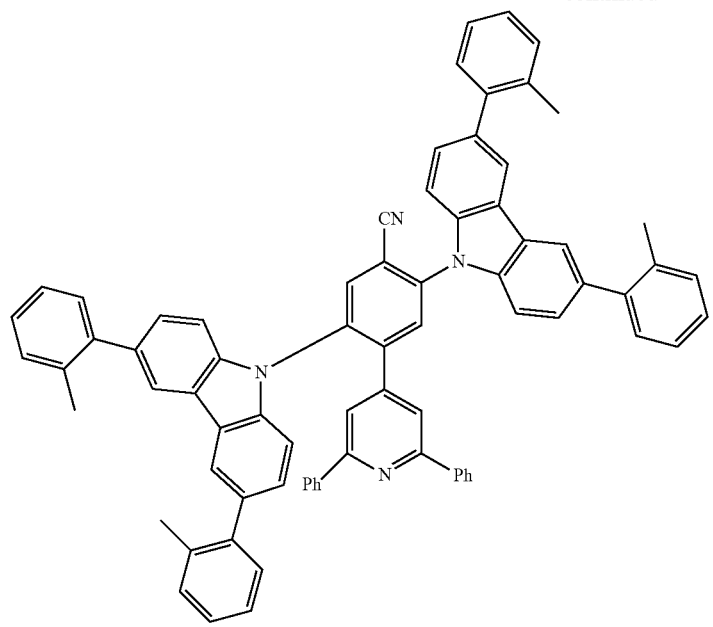
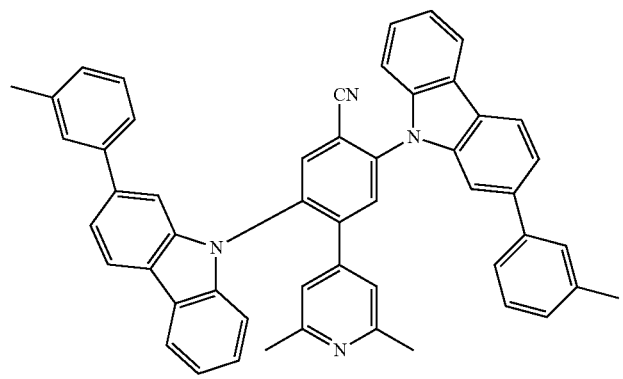
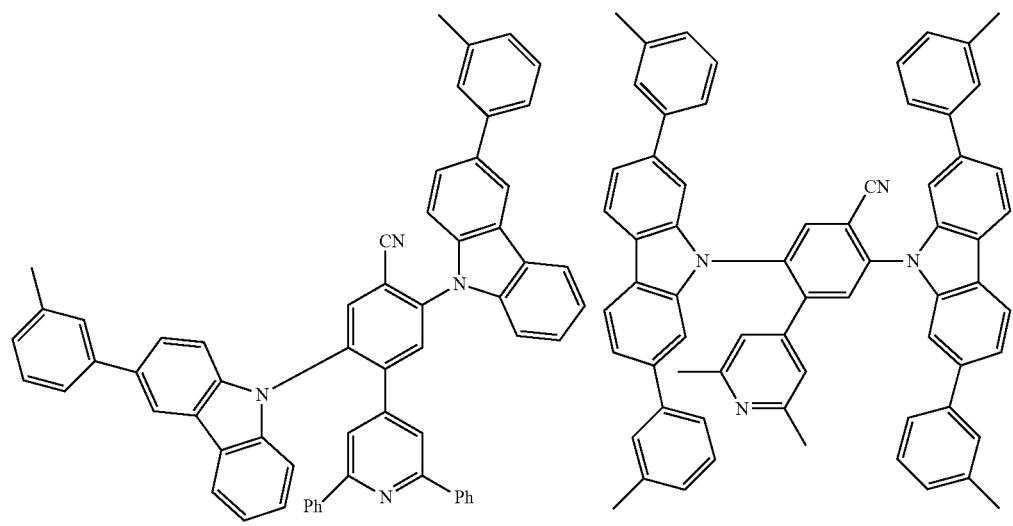

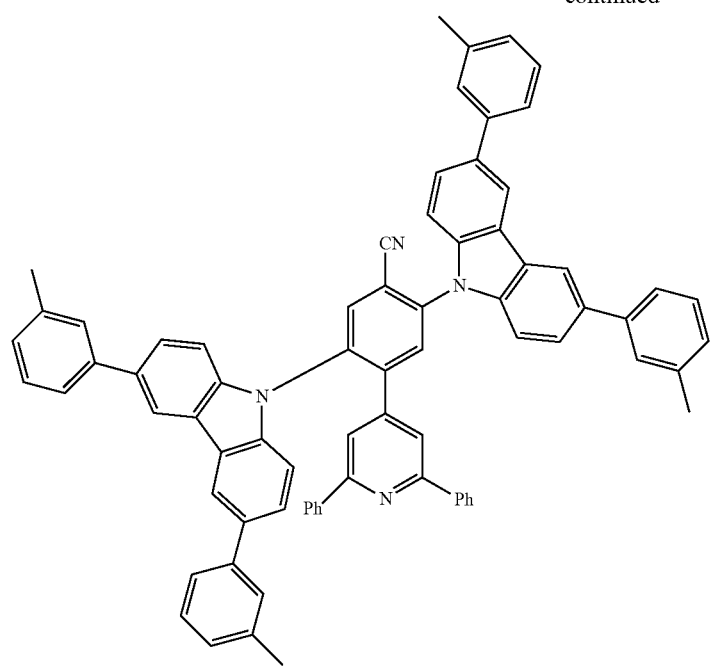
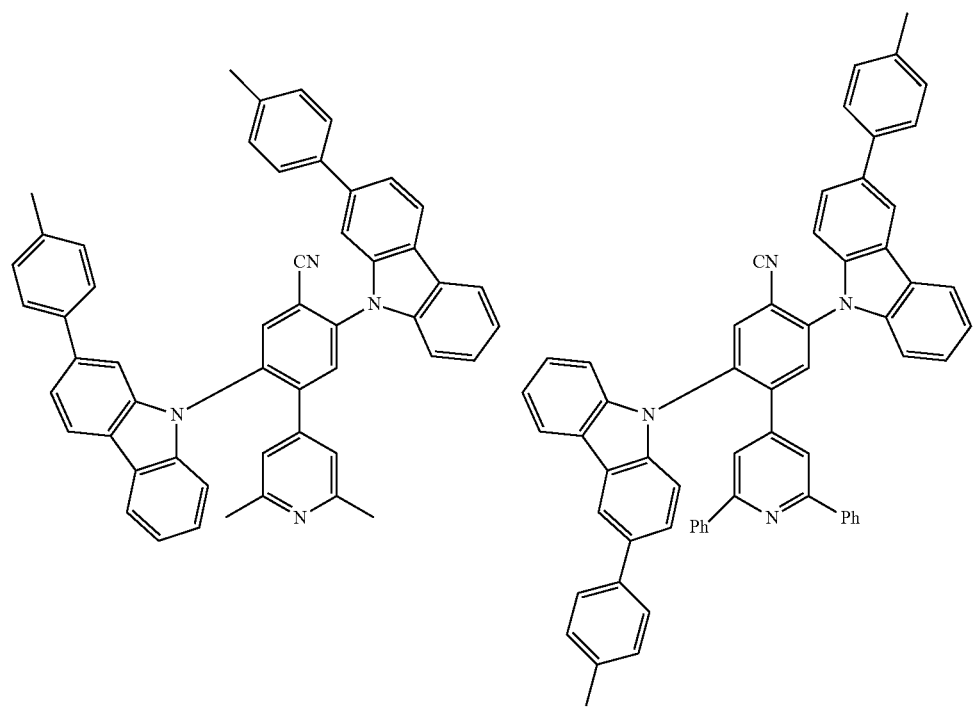

255
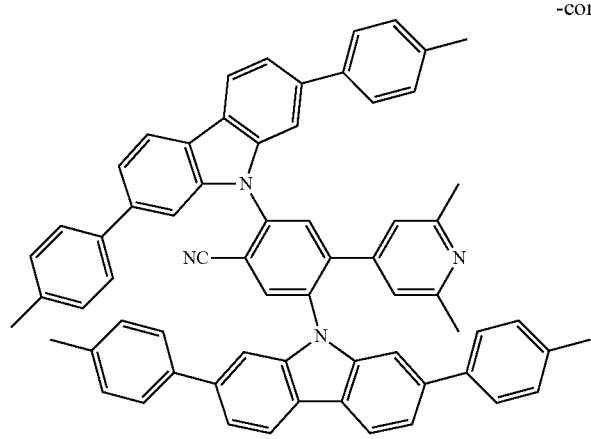
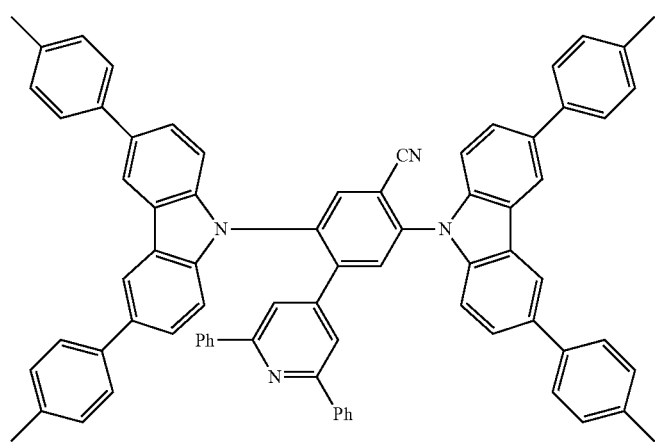
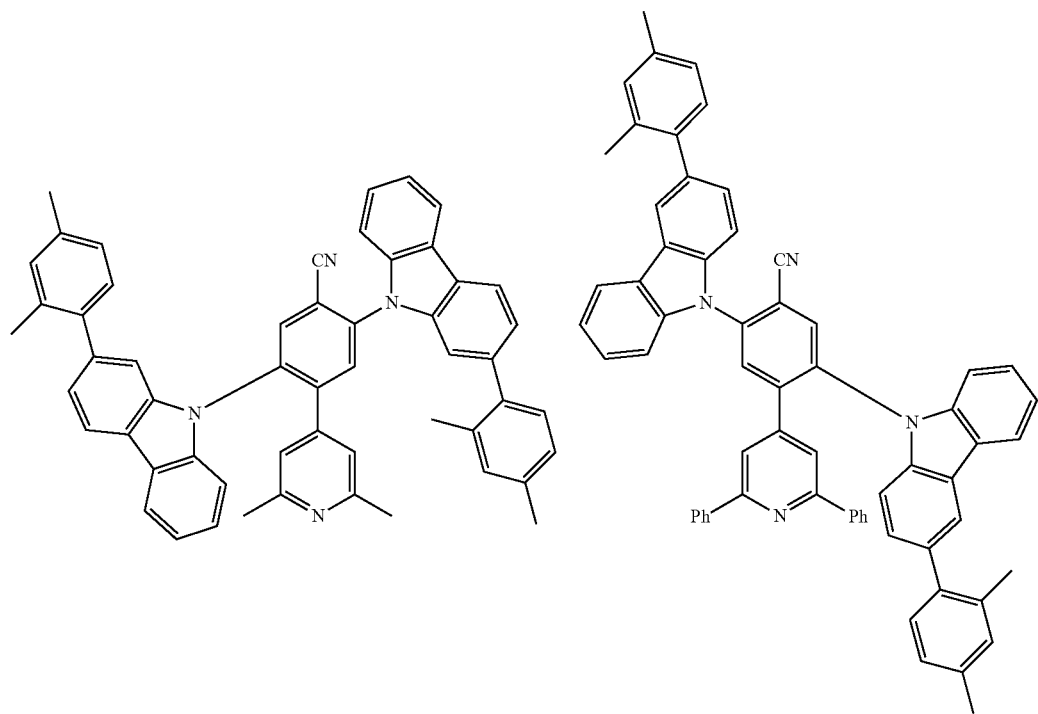

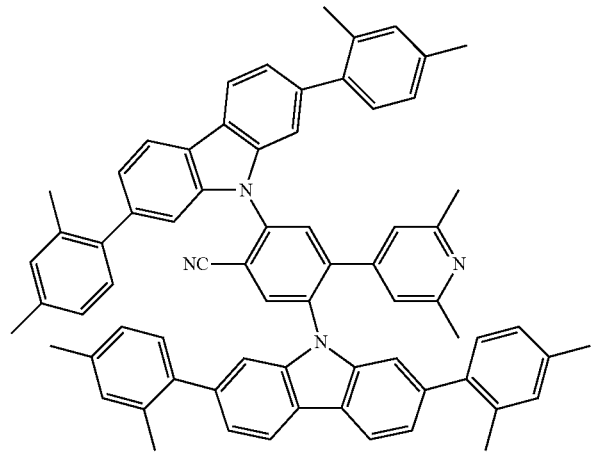
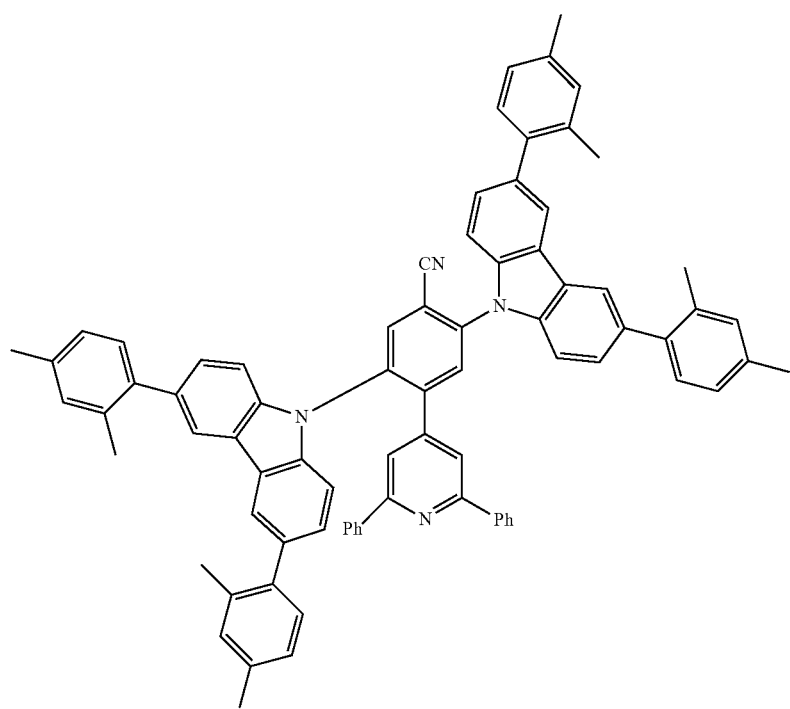
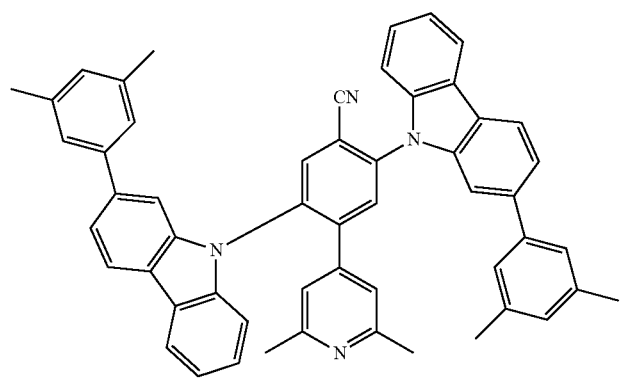

259 260
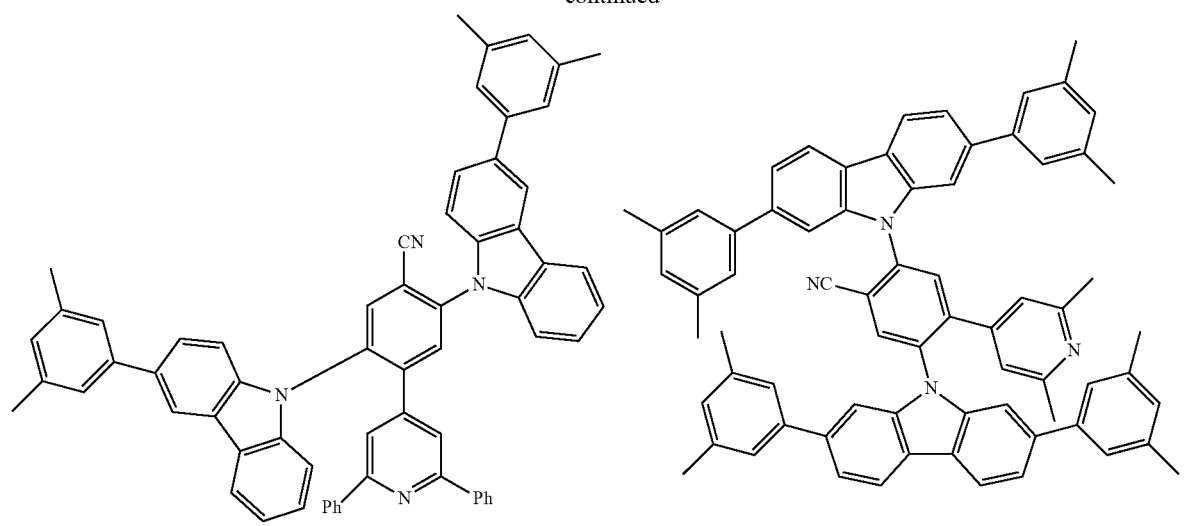
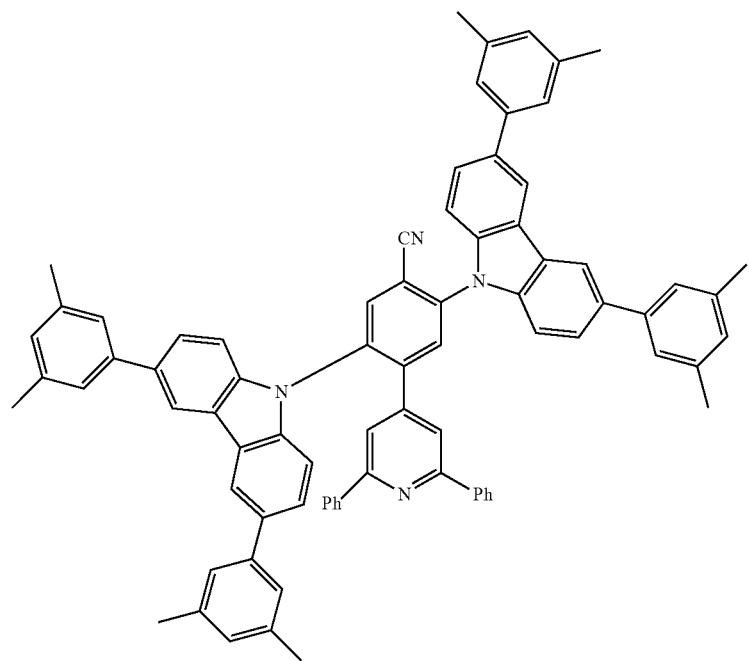
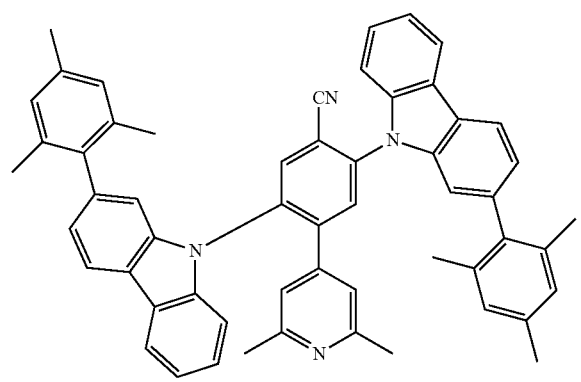

261 262
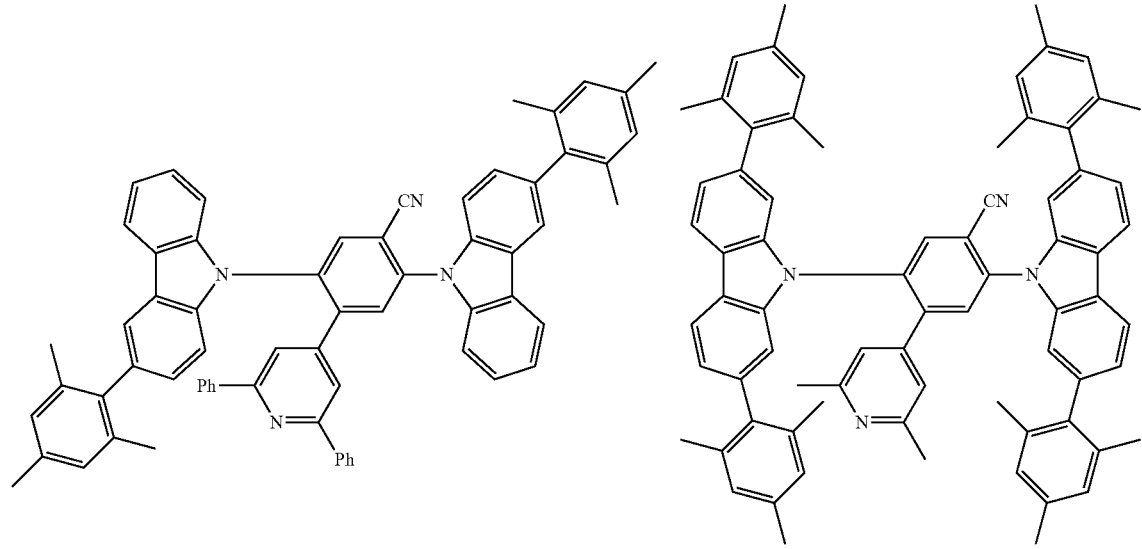
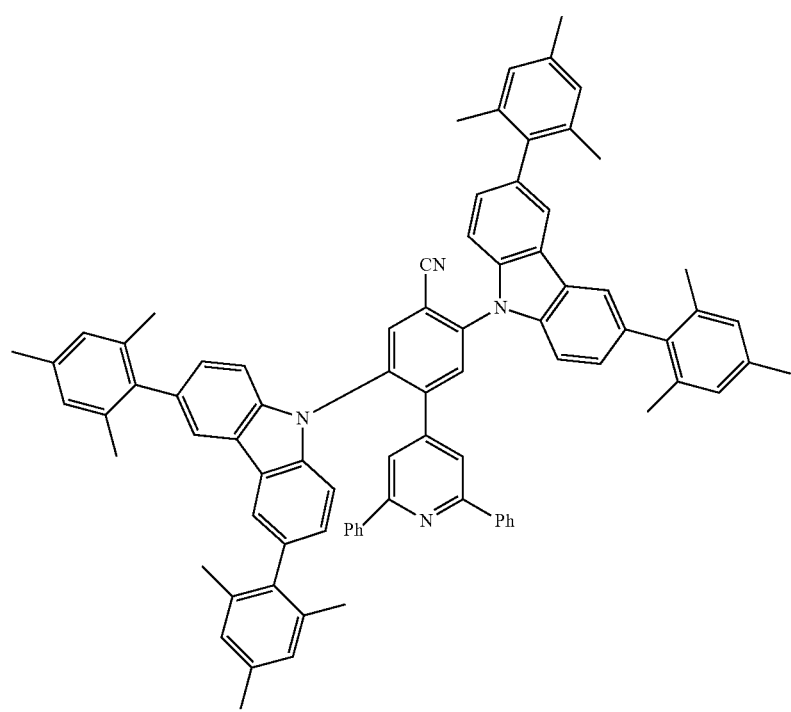

263
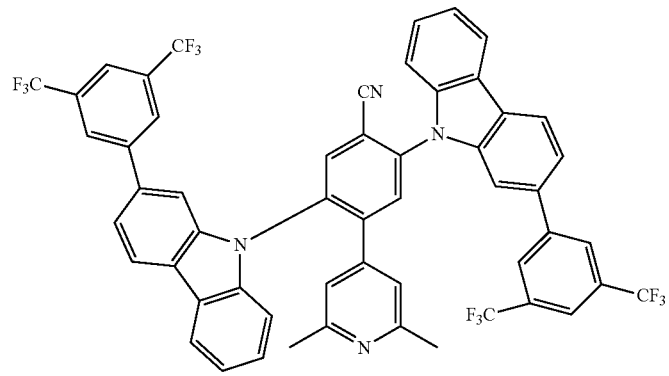
-continued
264
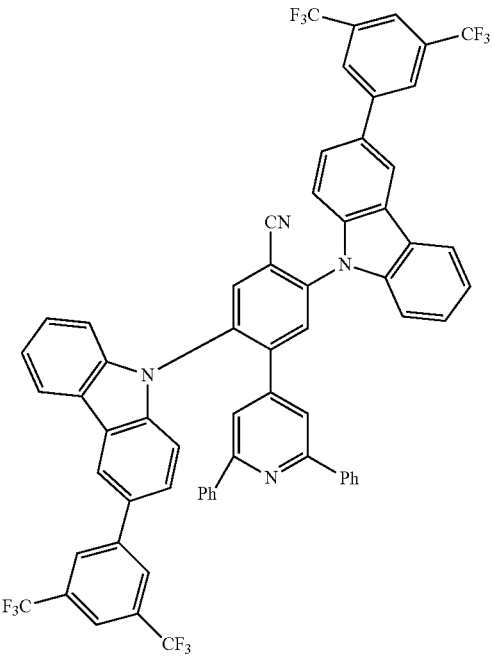
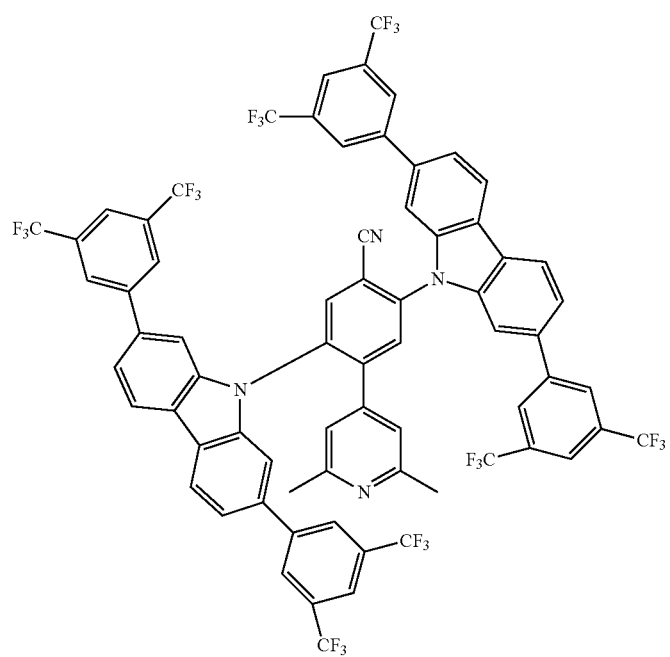
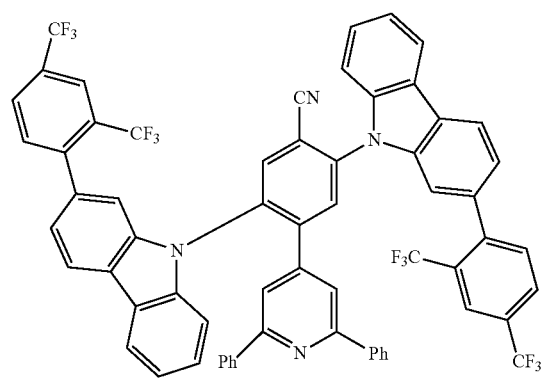

-continued
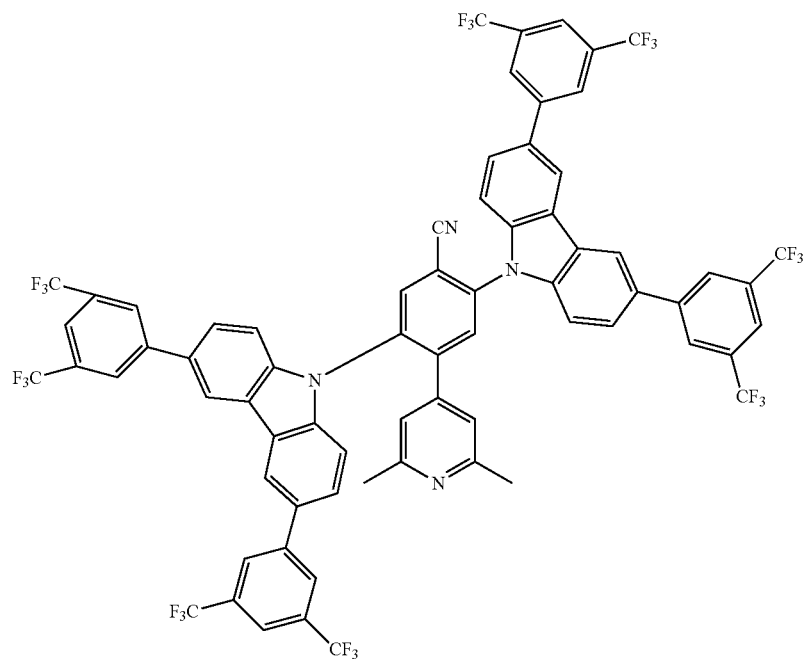
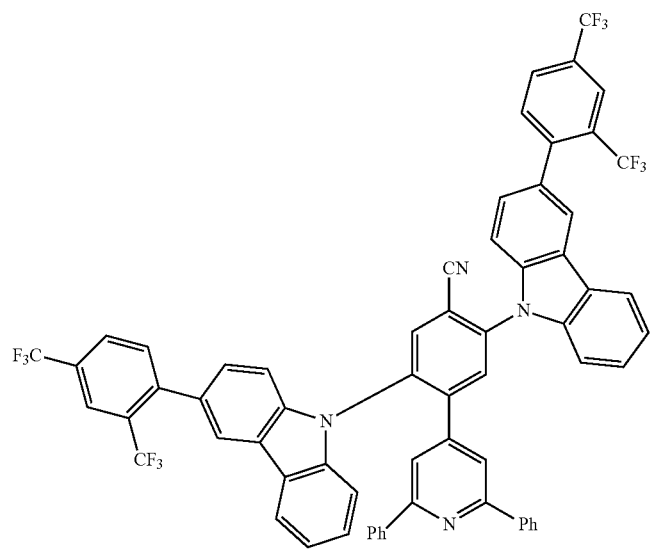

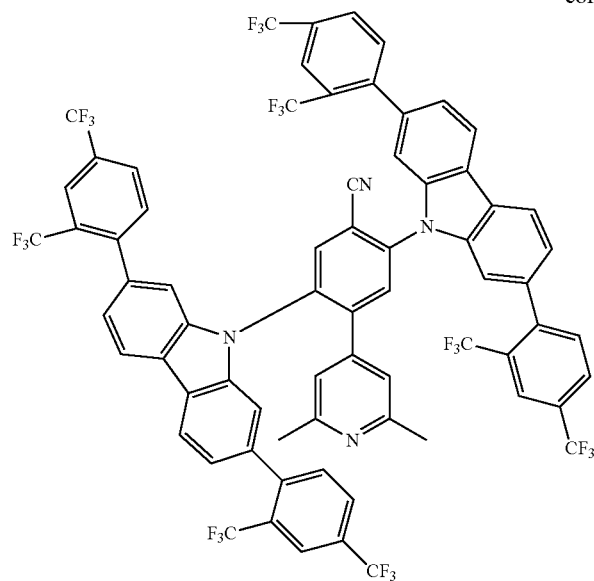
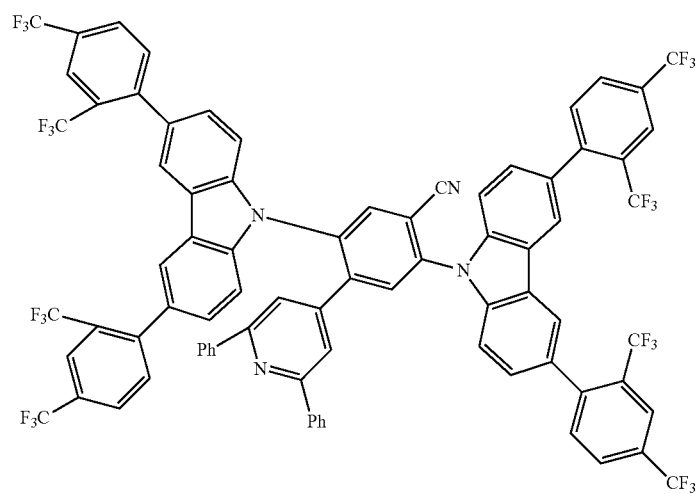
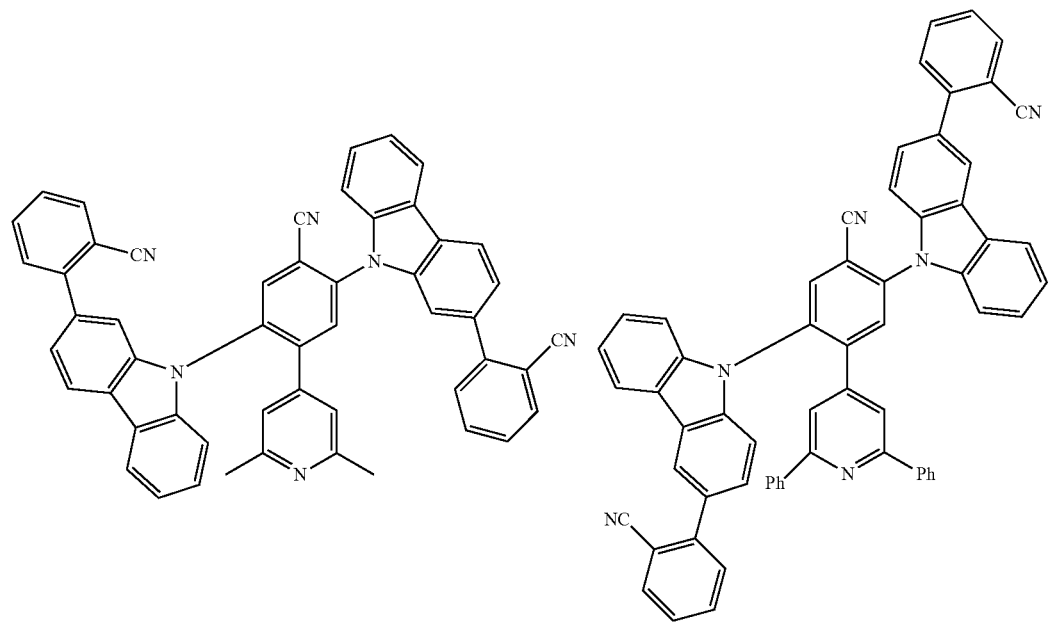

-continued
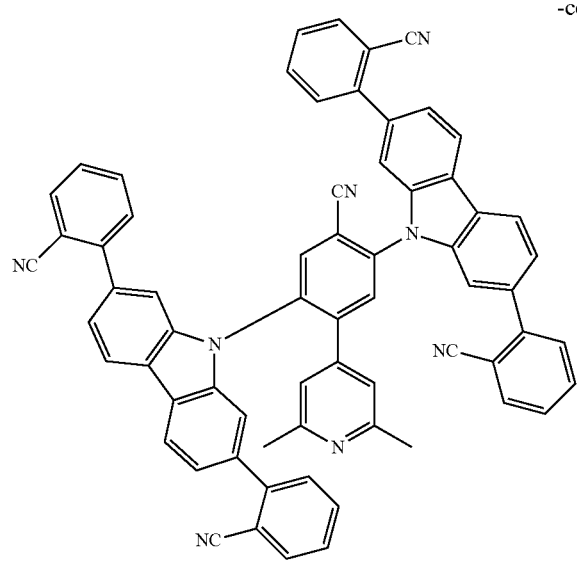
269
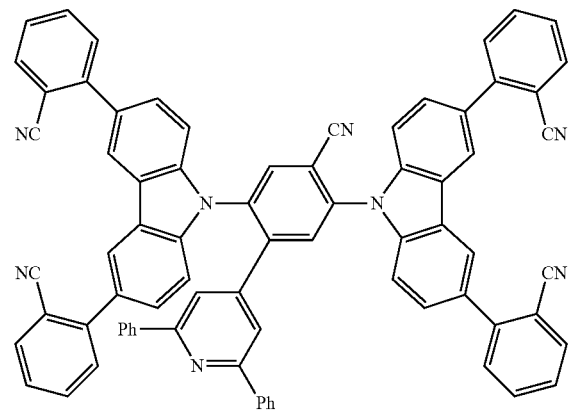
270
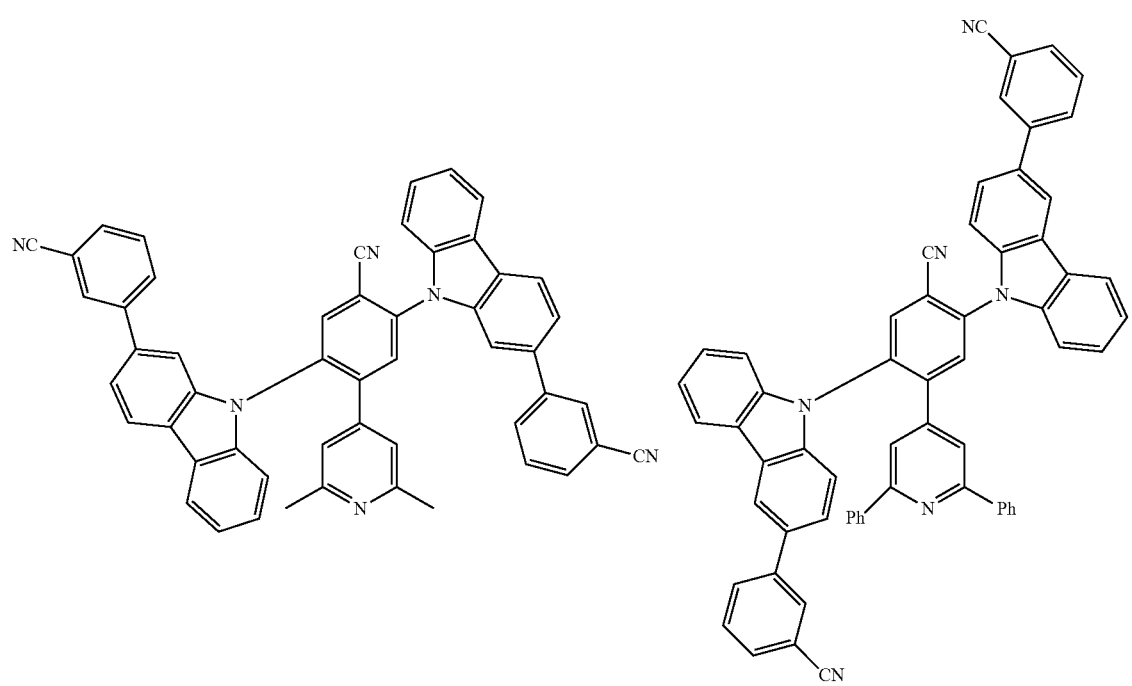

271  272
-continued
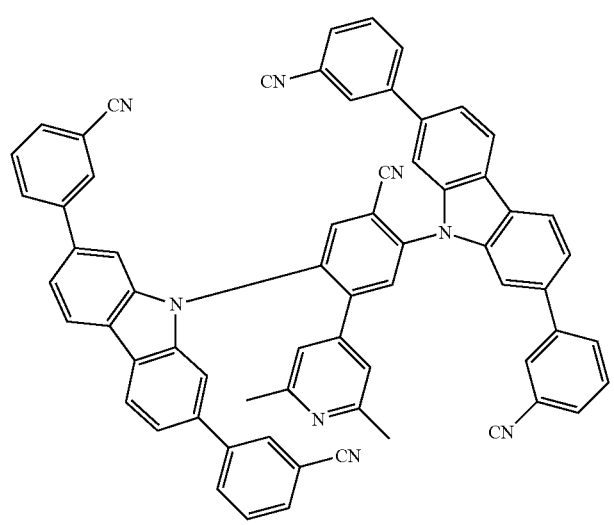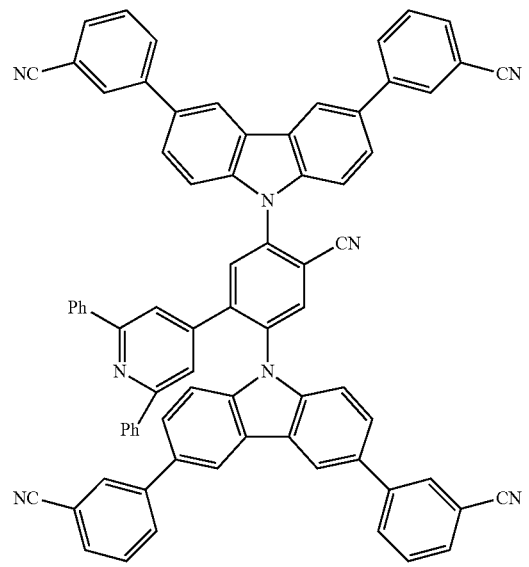
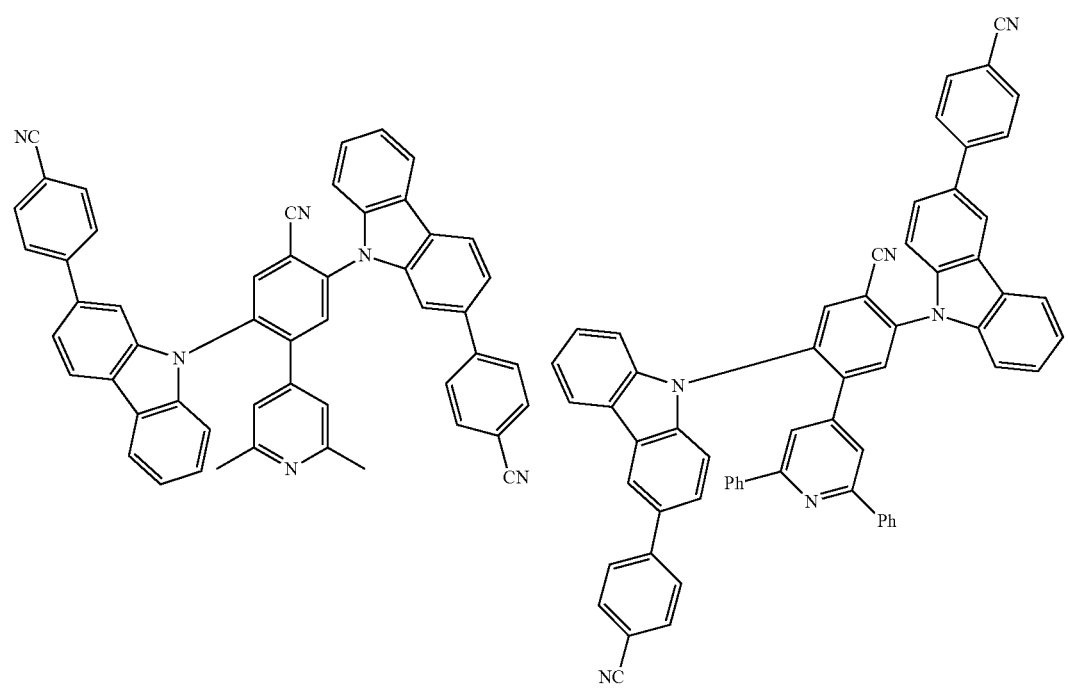

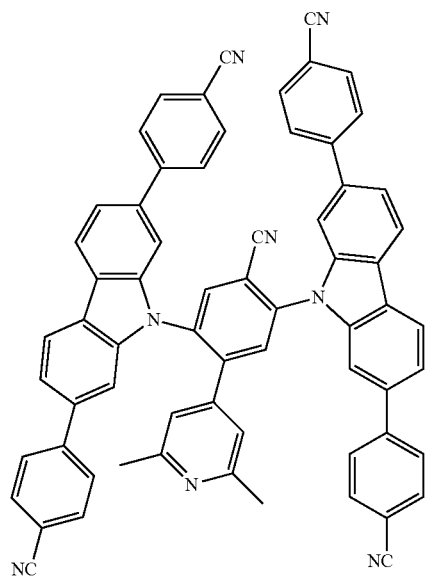
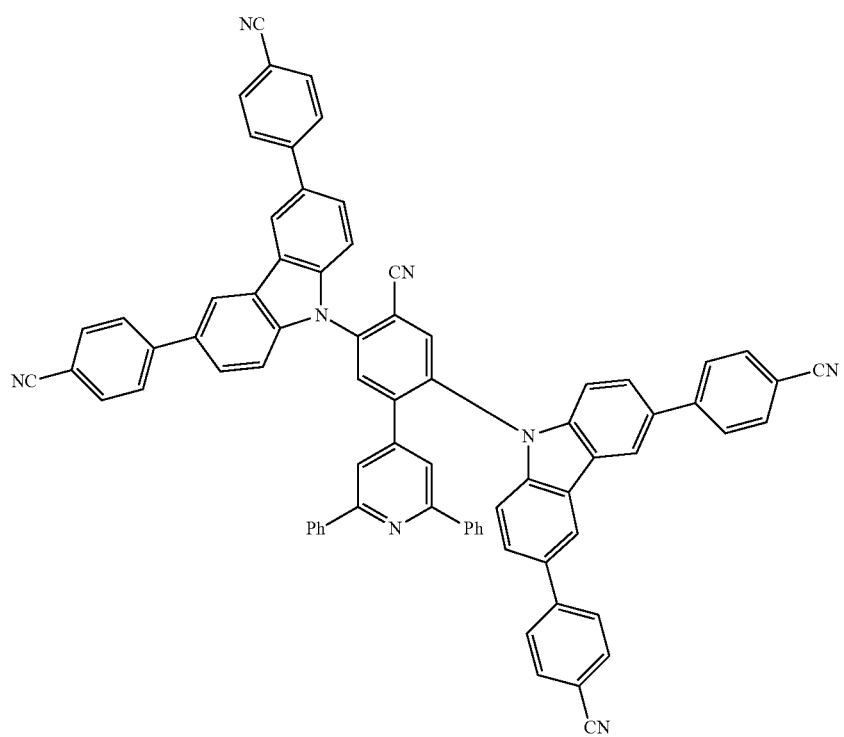

-continued
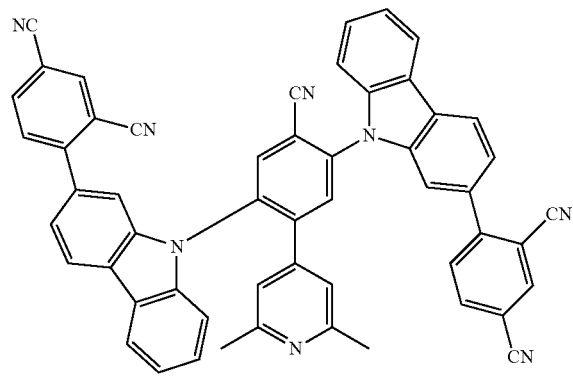
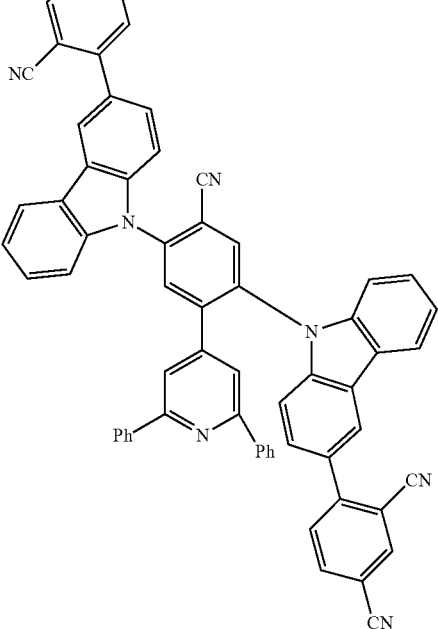
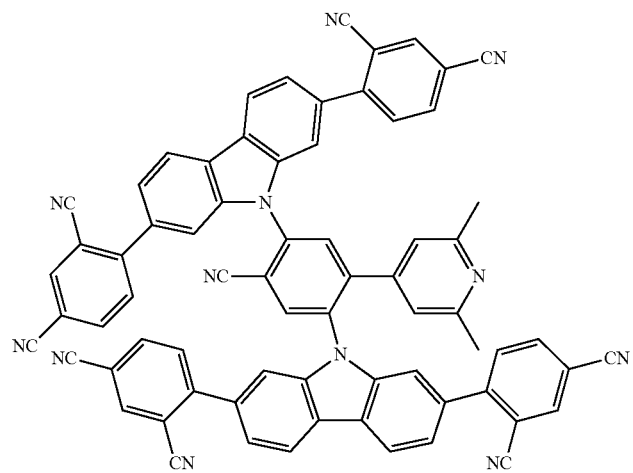
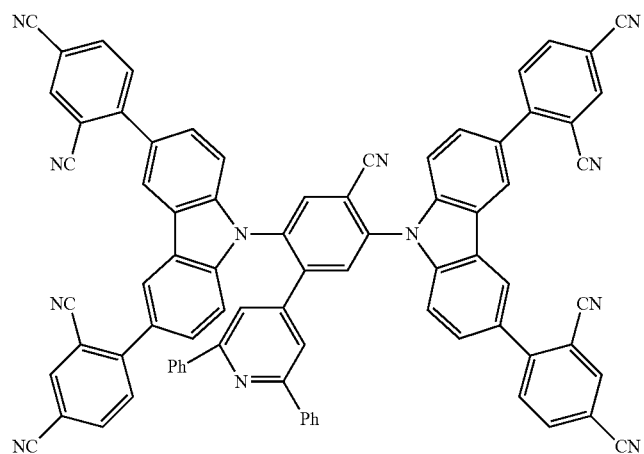

277 278
-continued
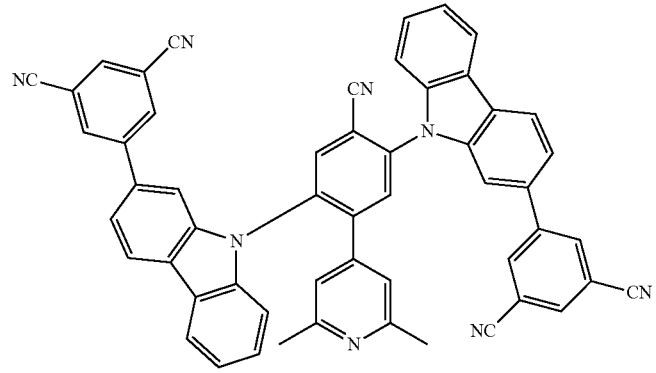
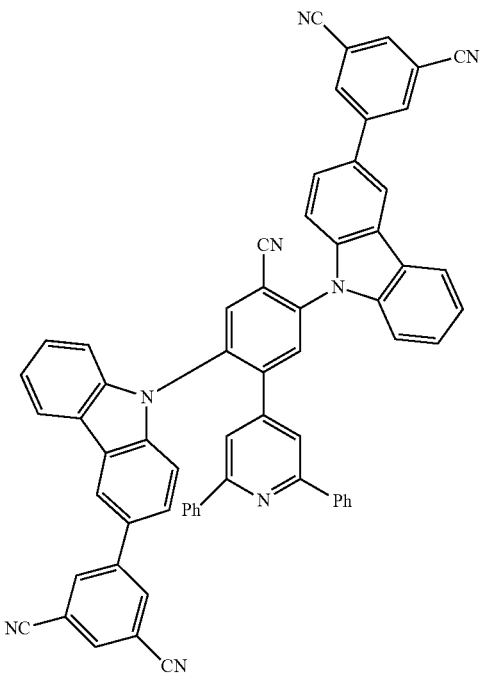
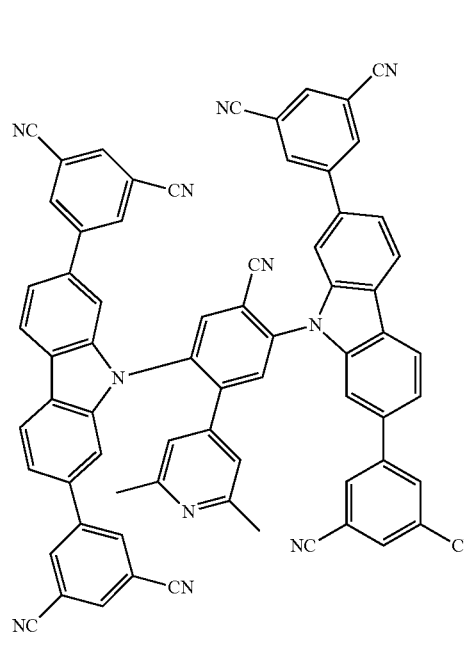
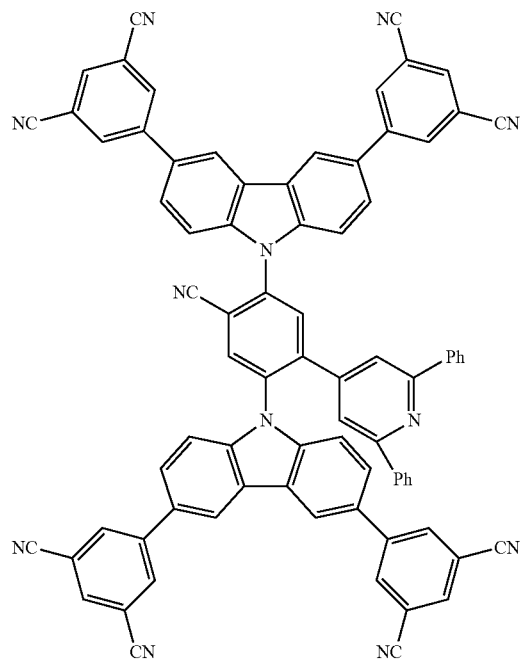

-continued
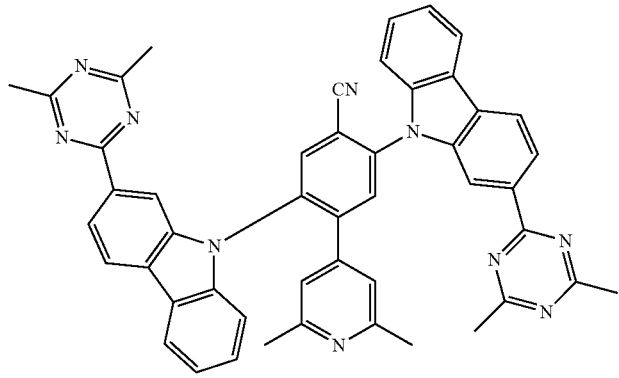
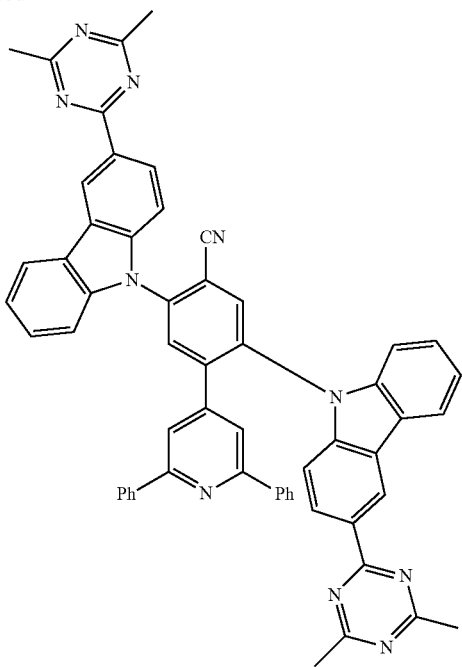
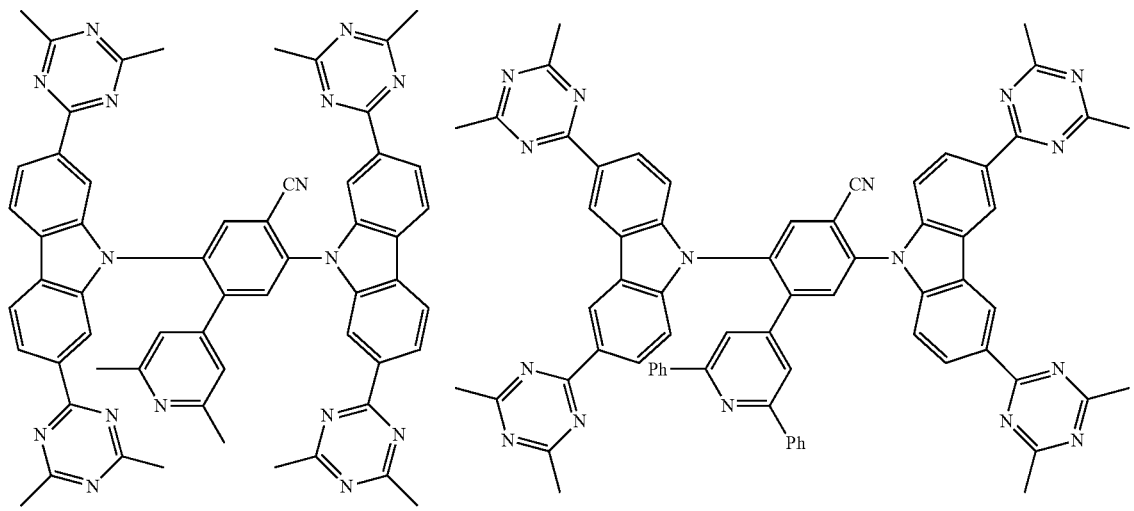
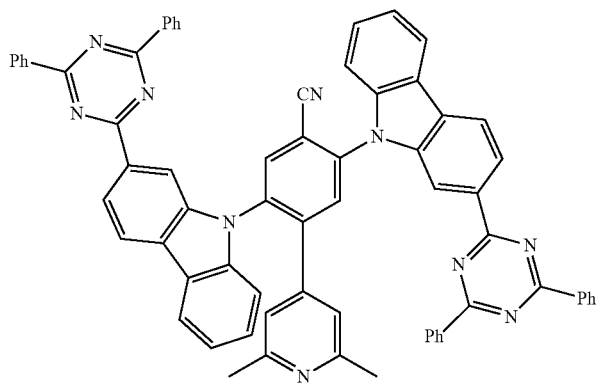

-continued
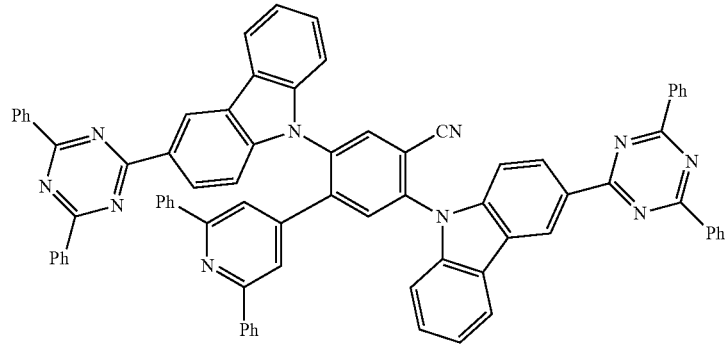
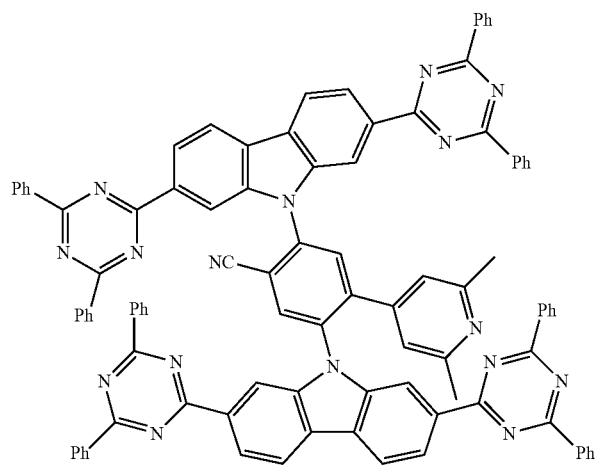
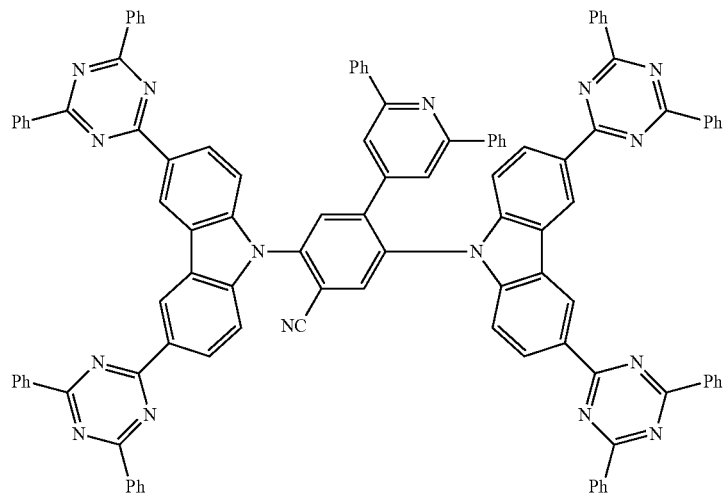
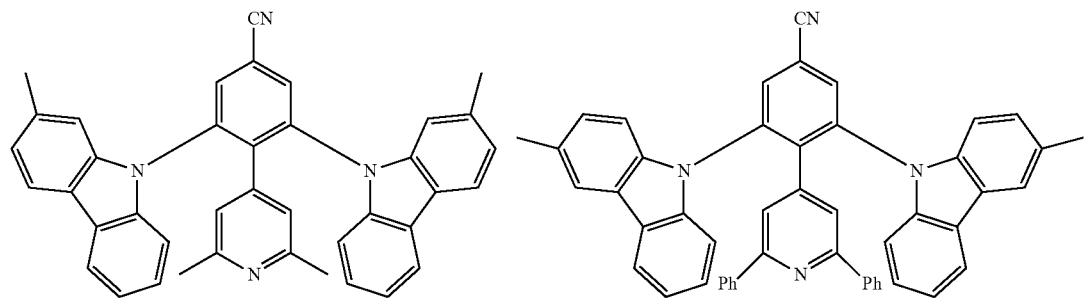

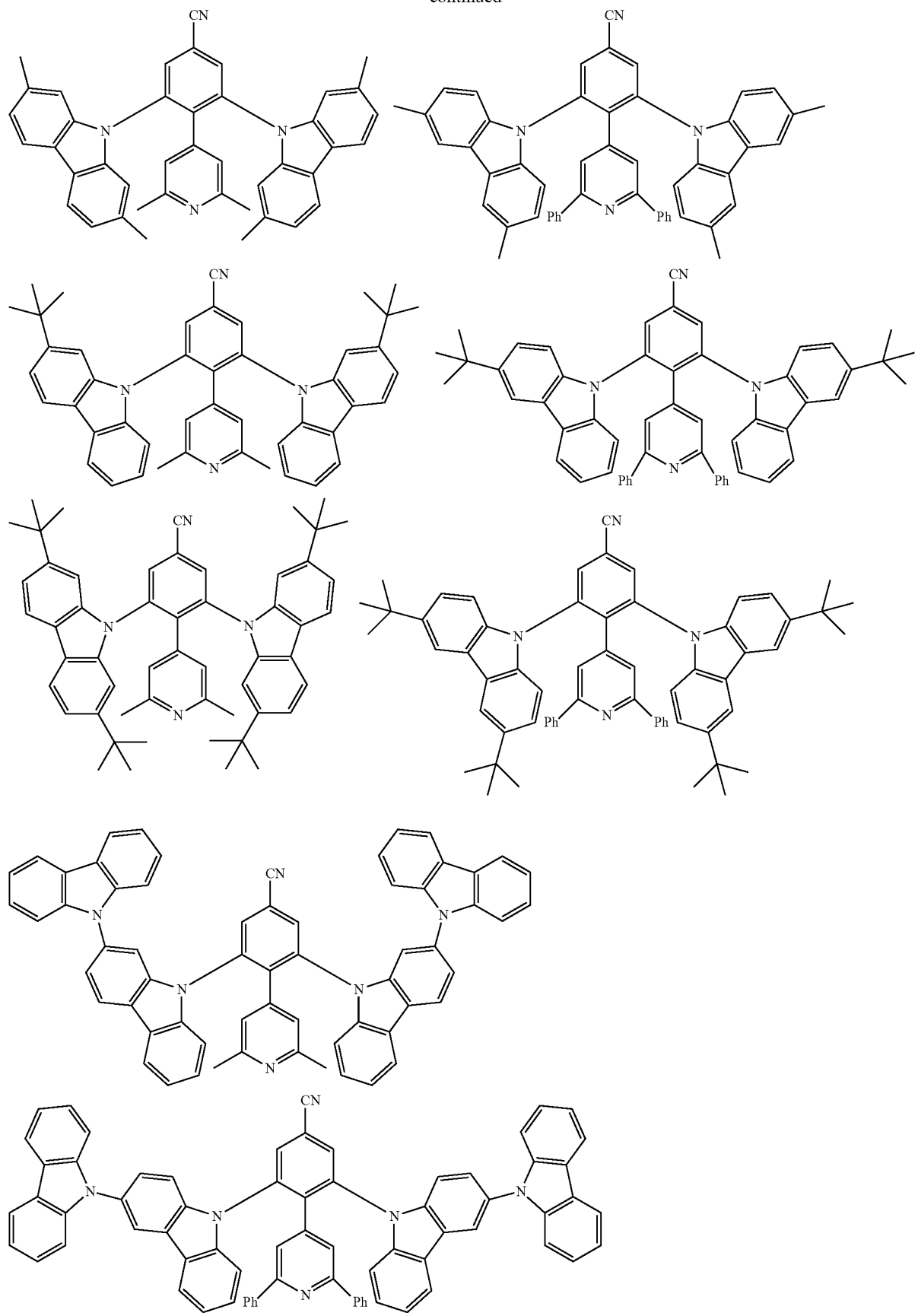

-continued
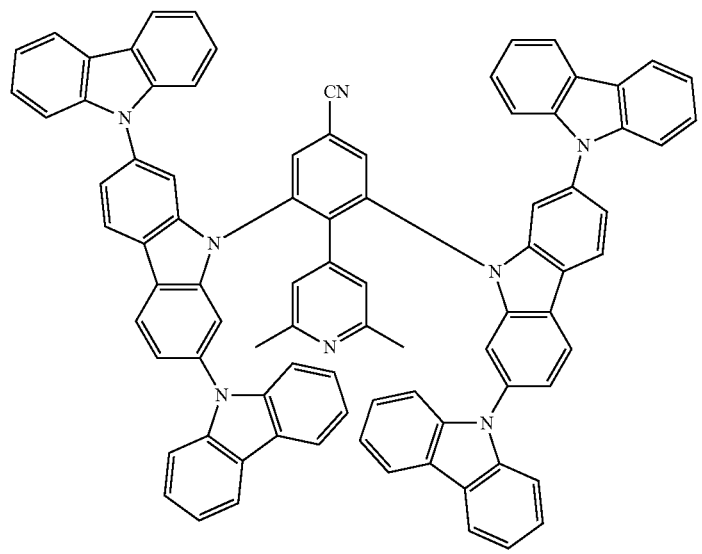
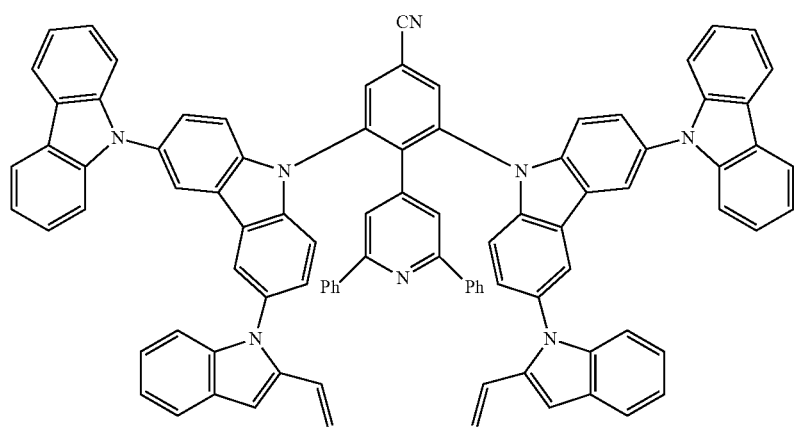
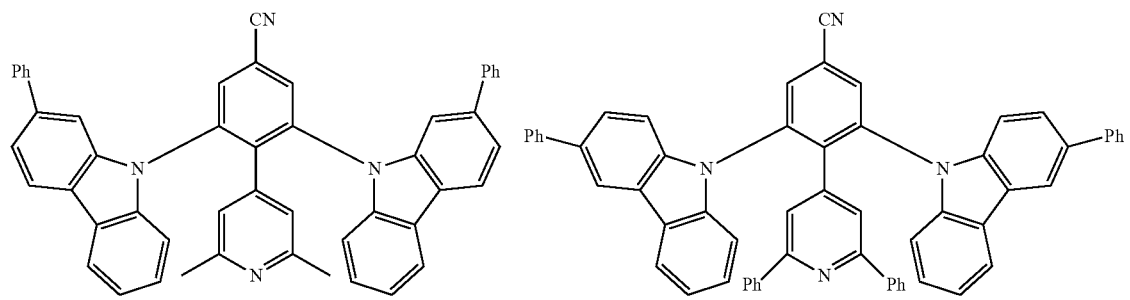
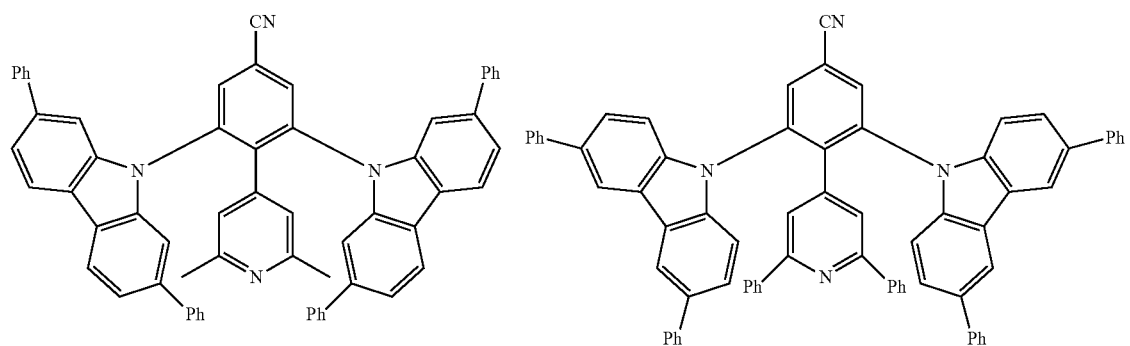

-continued
287
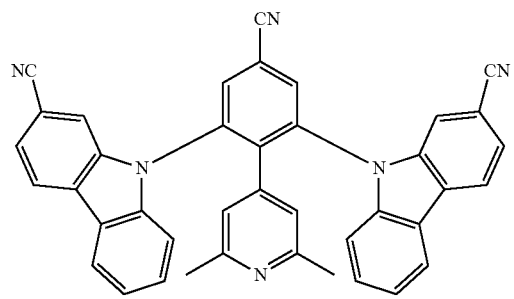
288
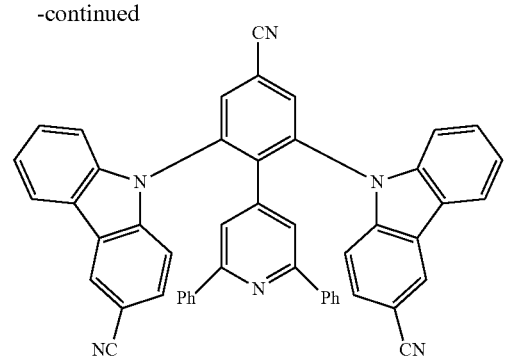
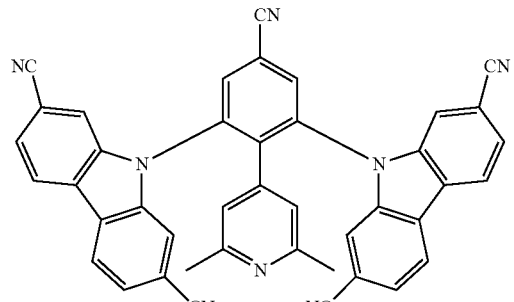
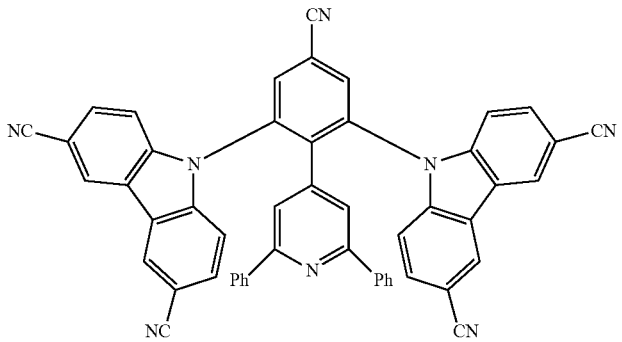
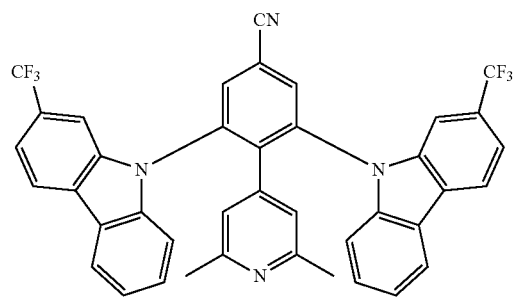
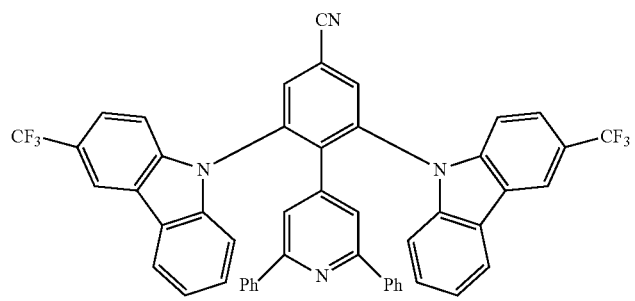
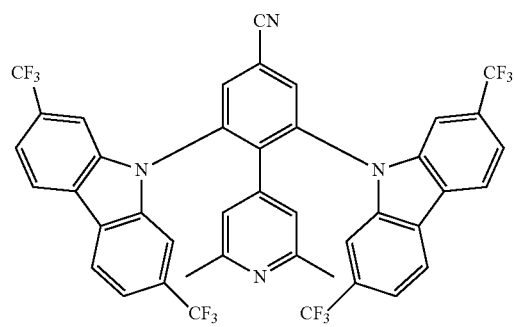
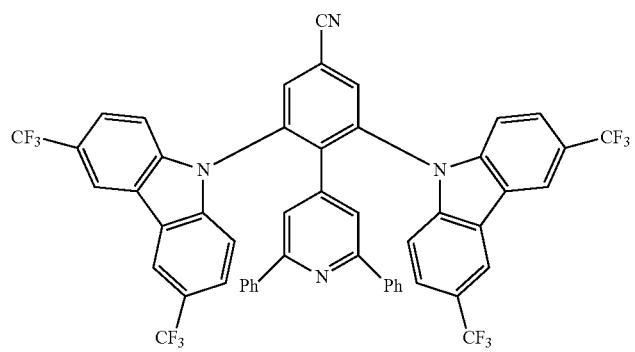
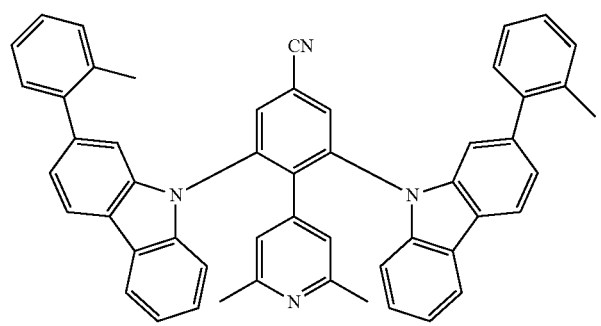

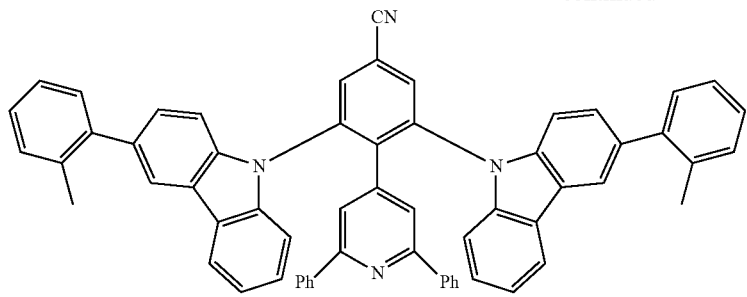
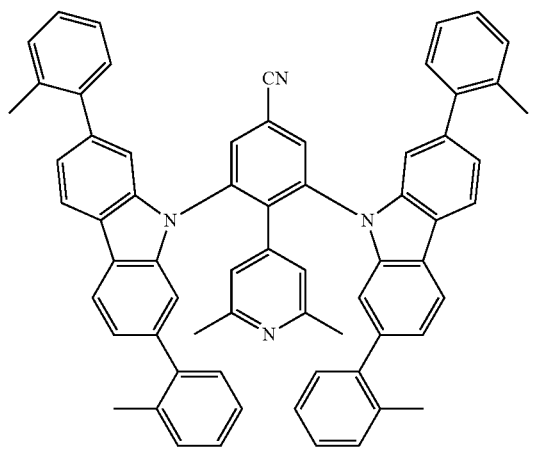
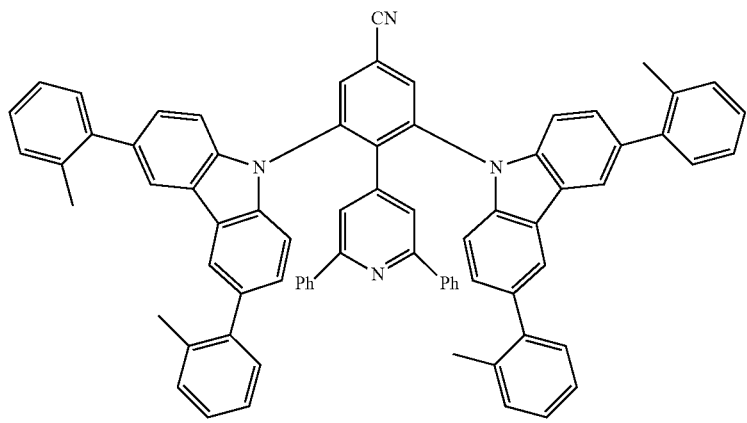
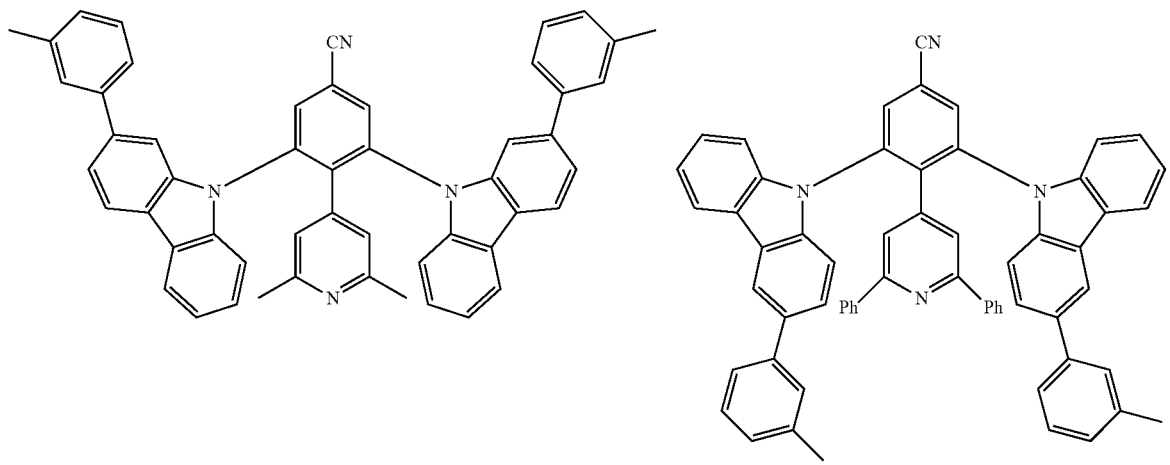

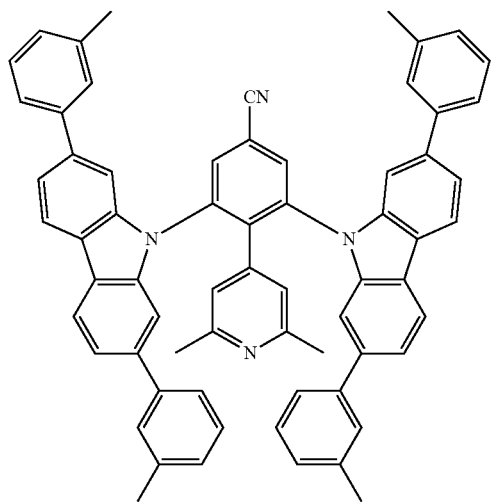
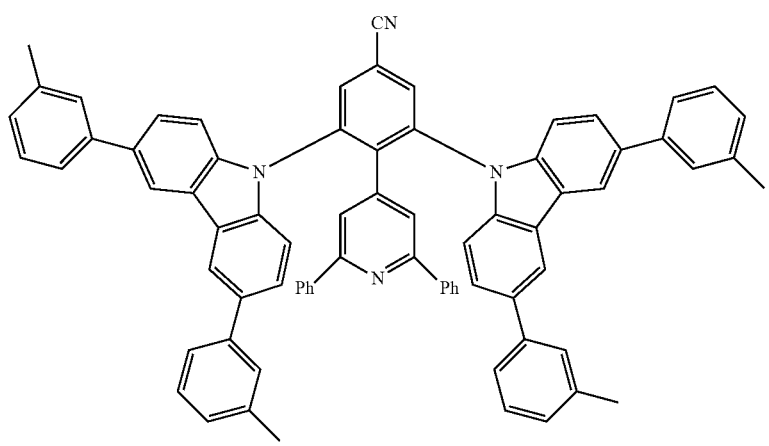
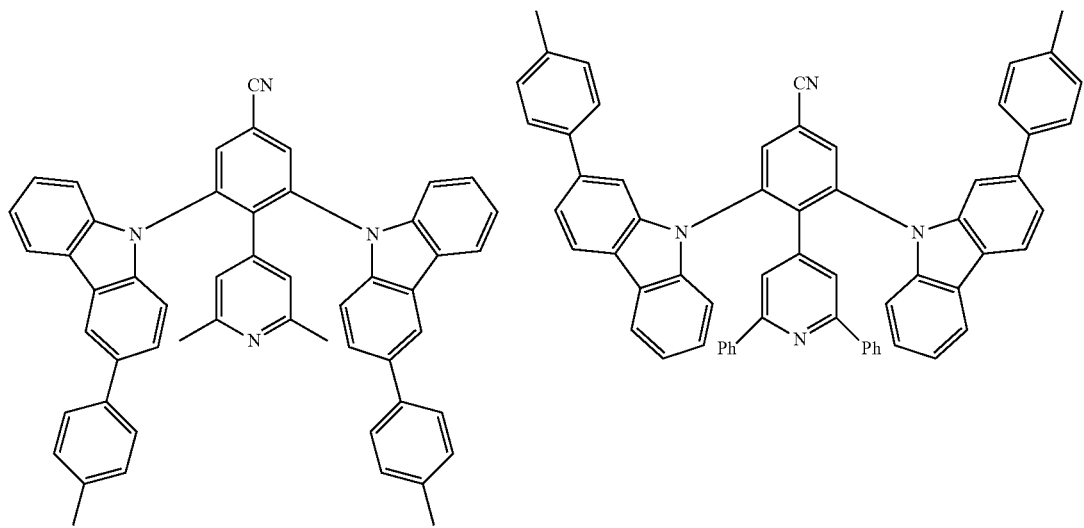

293 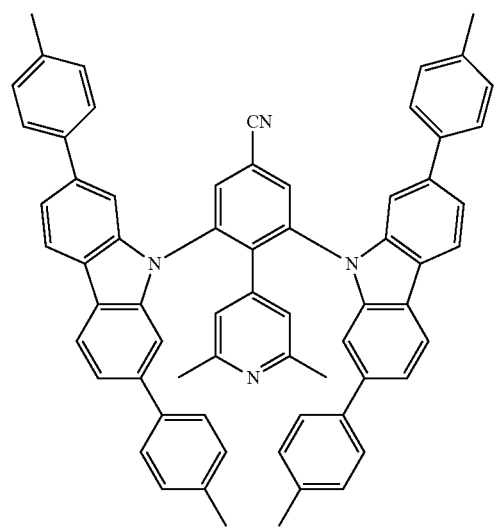
294 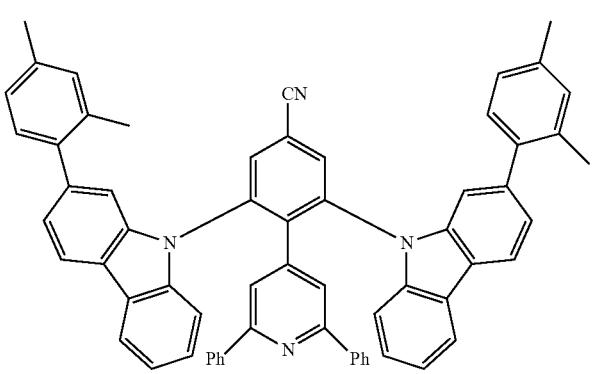
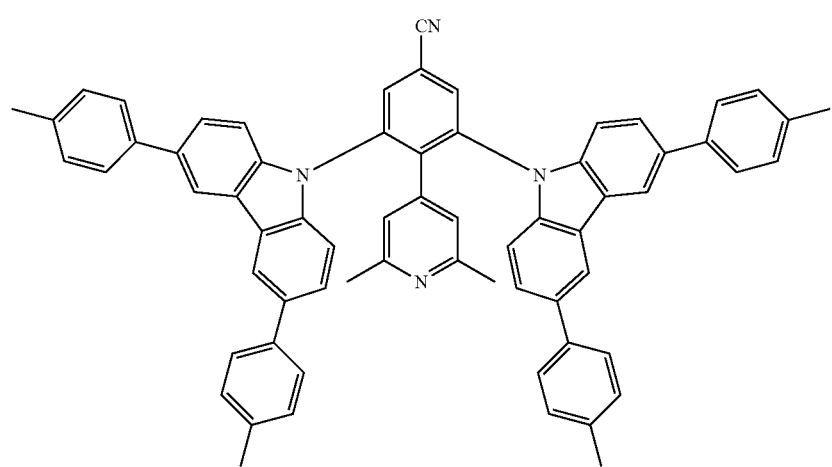
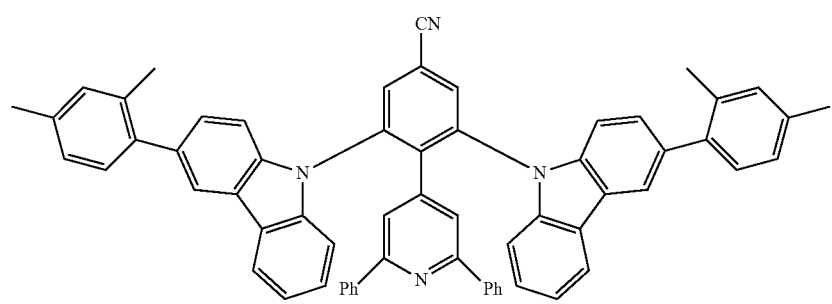

-continued
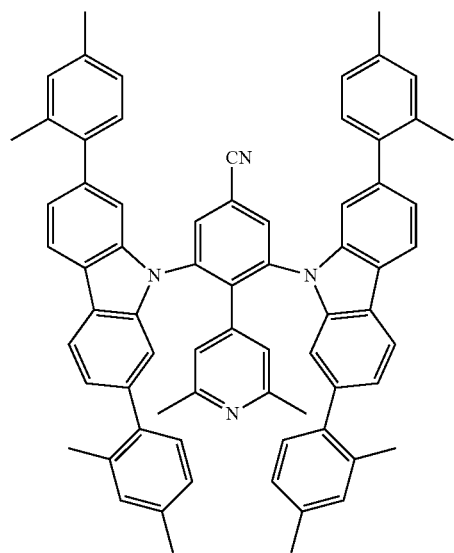
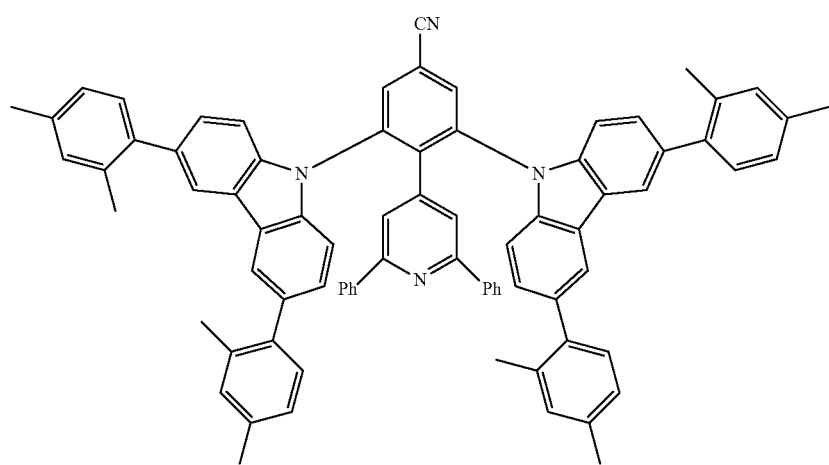
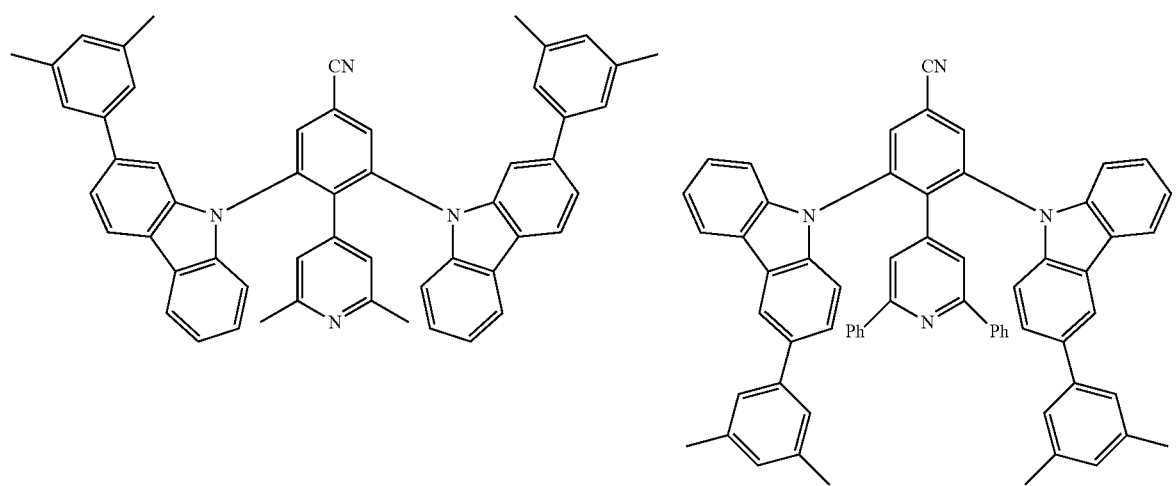

297
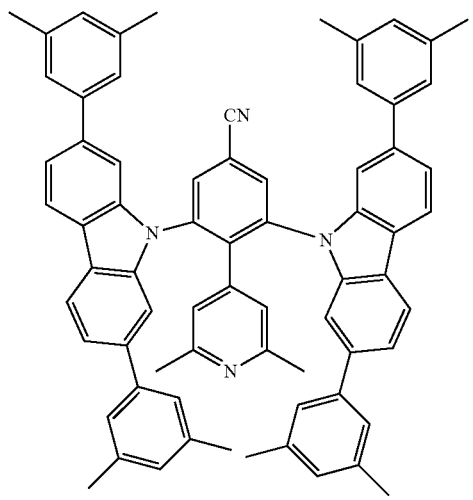
298
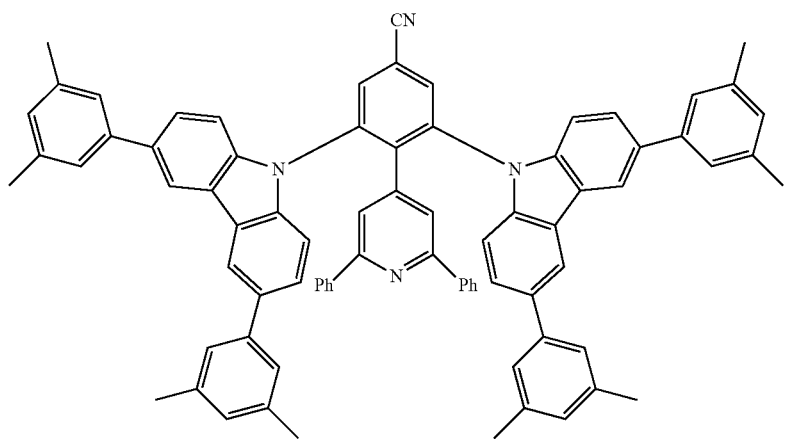
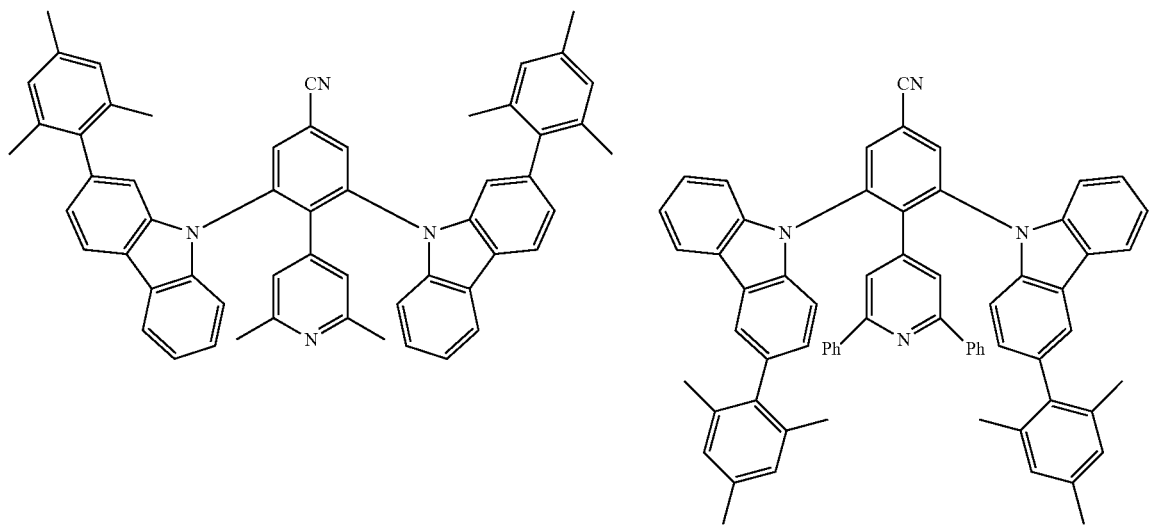

-continued
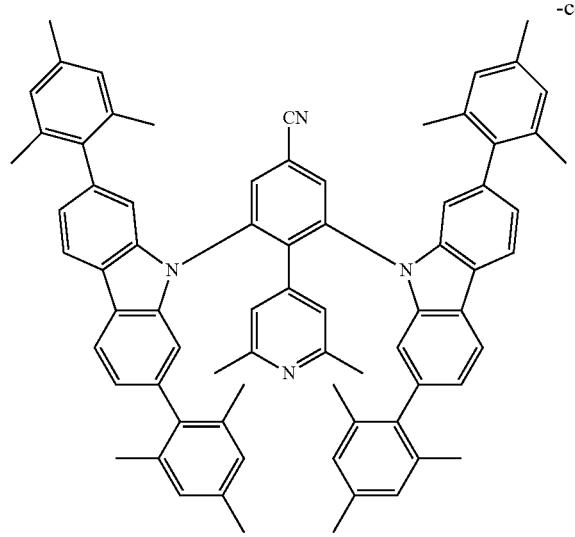
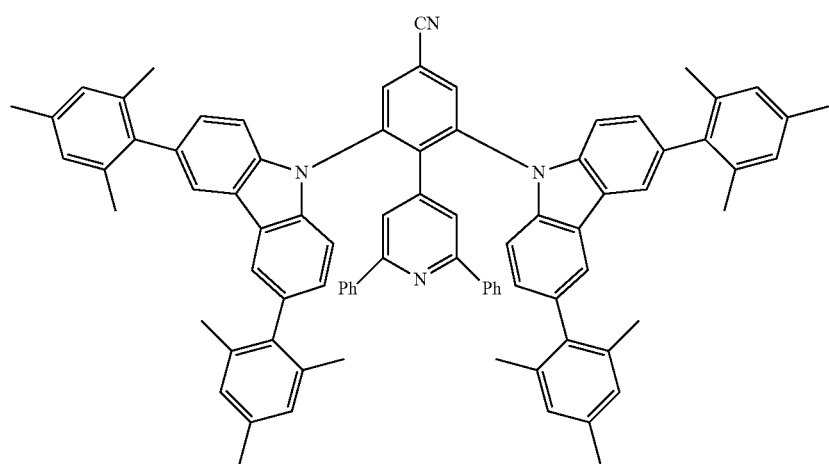
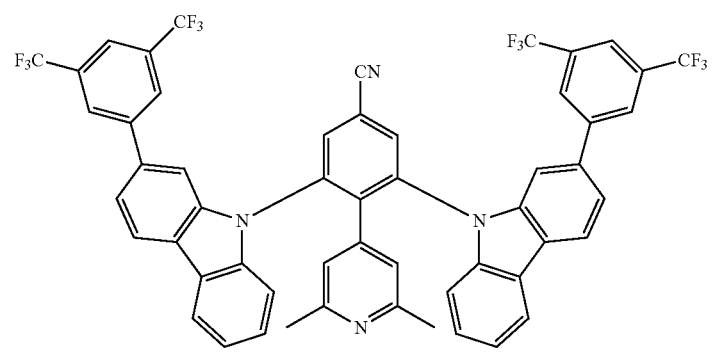

301
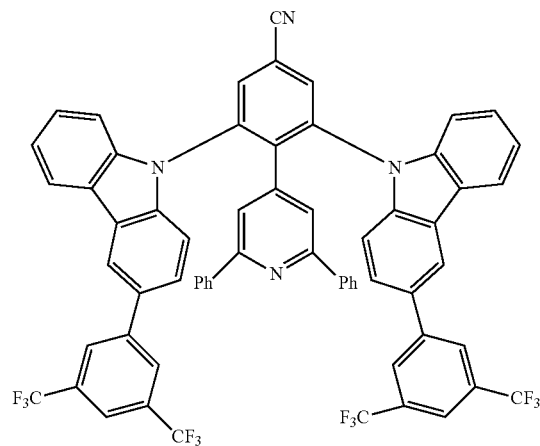
302
-continued
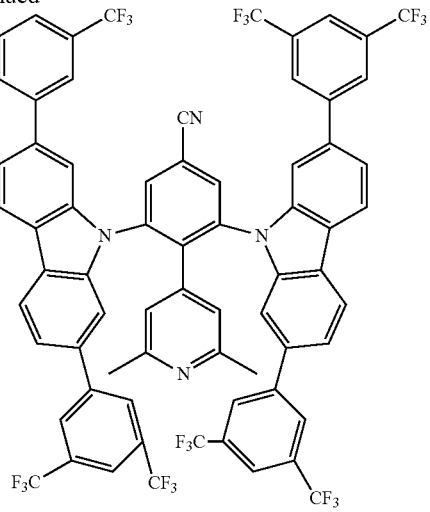
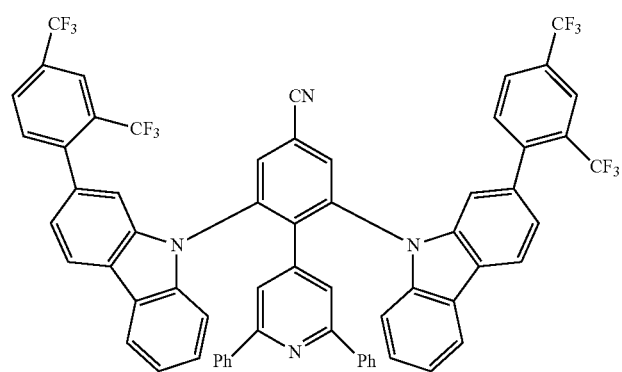
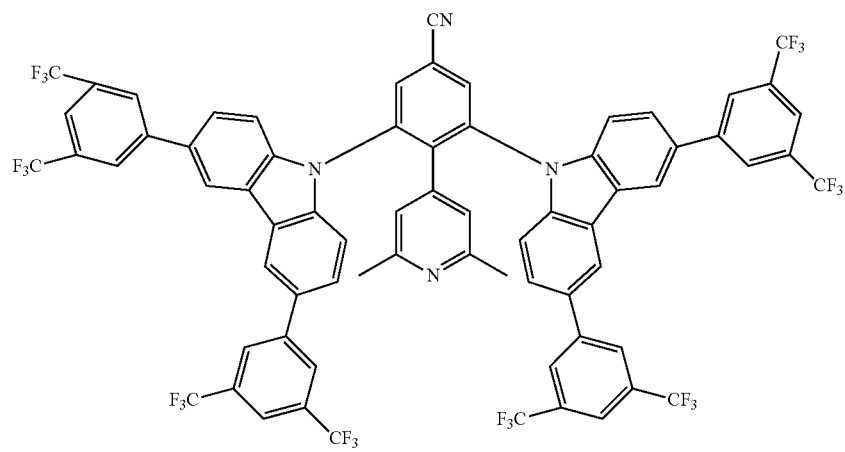

303
304
-continued
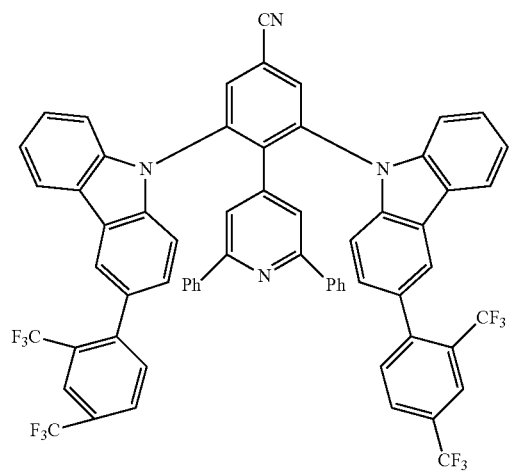
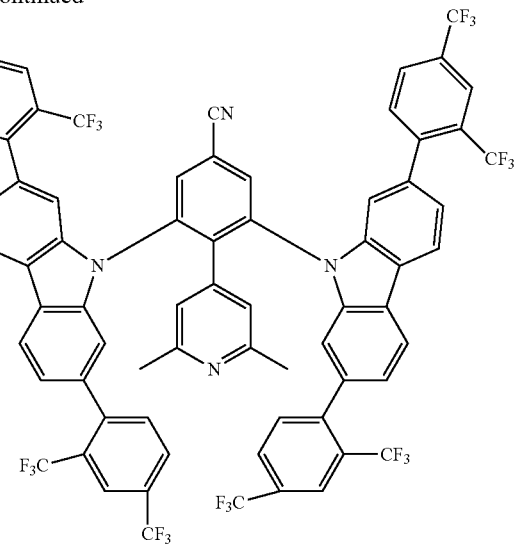
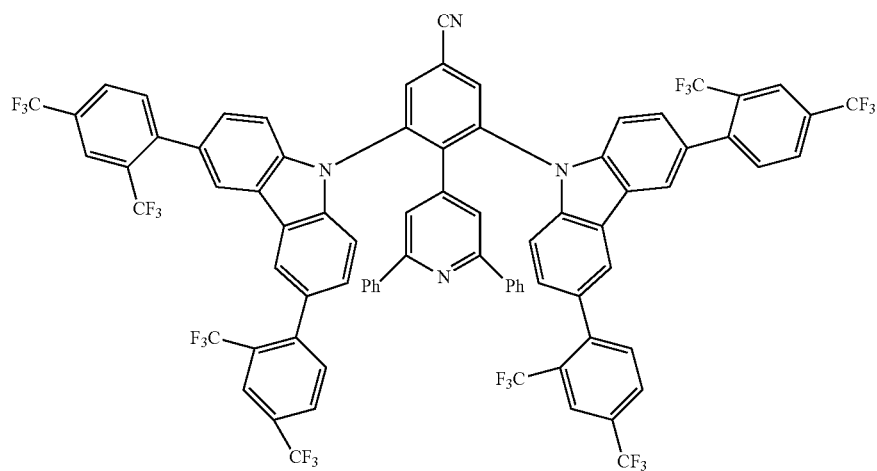
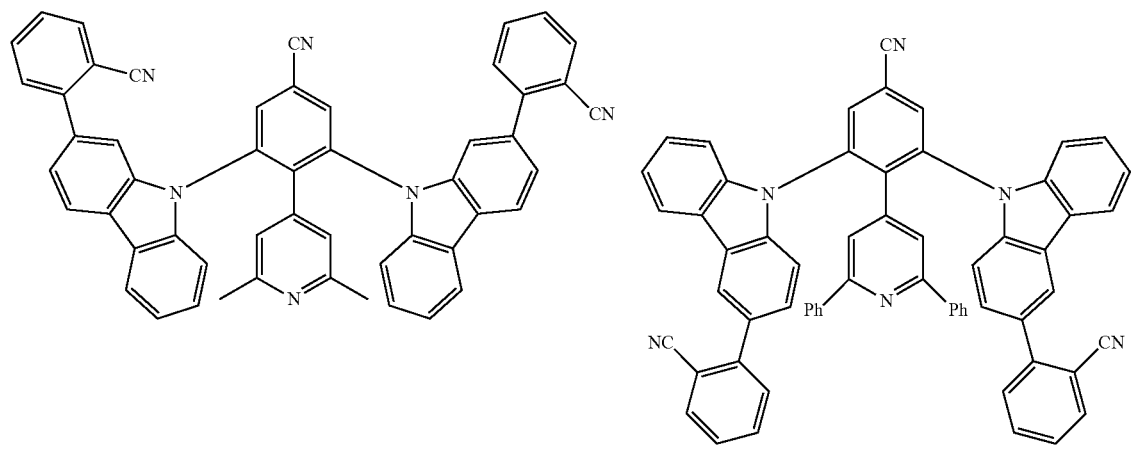

-continued
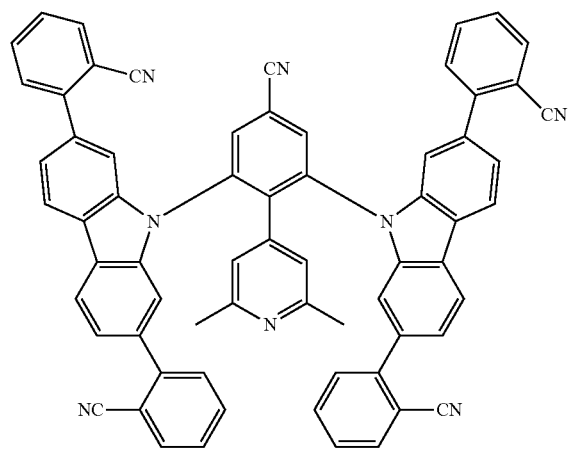
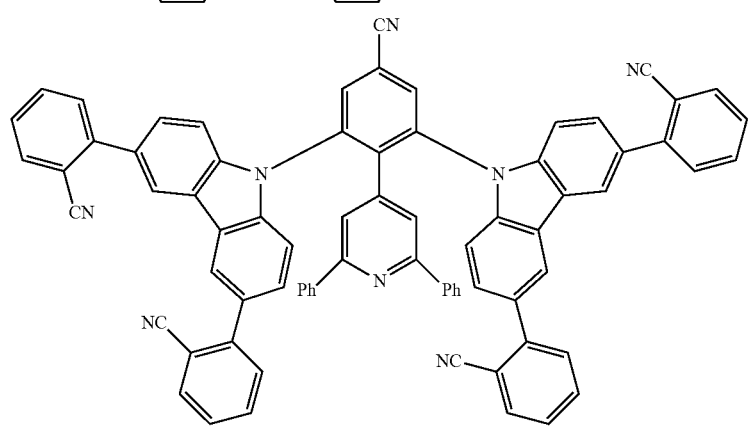
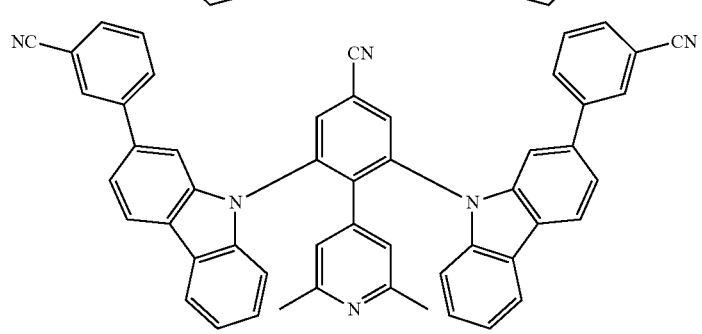
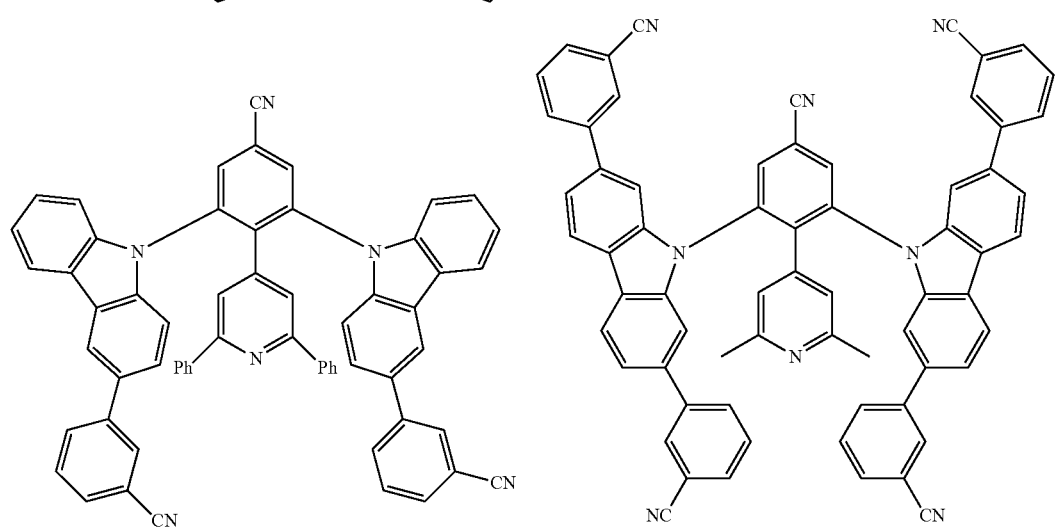

-continued
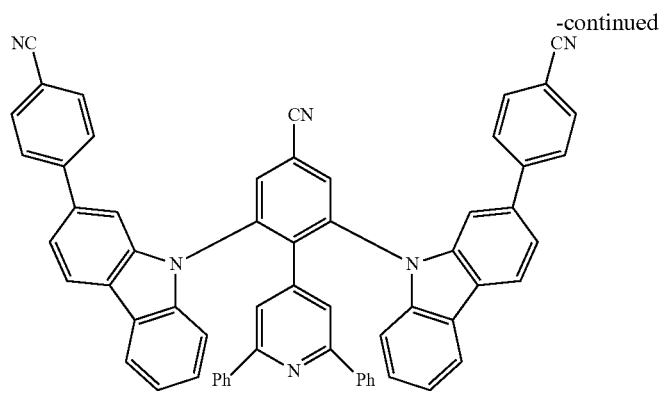
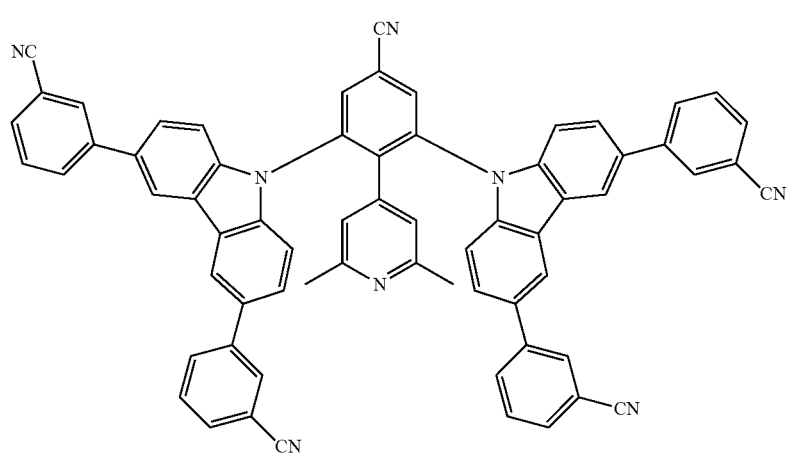
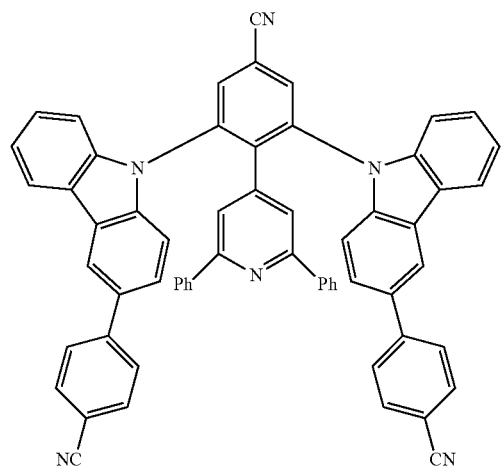

309
310
-continued
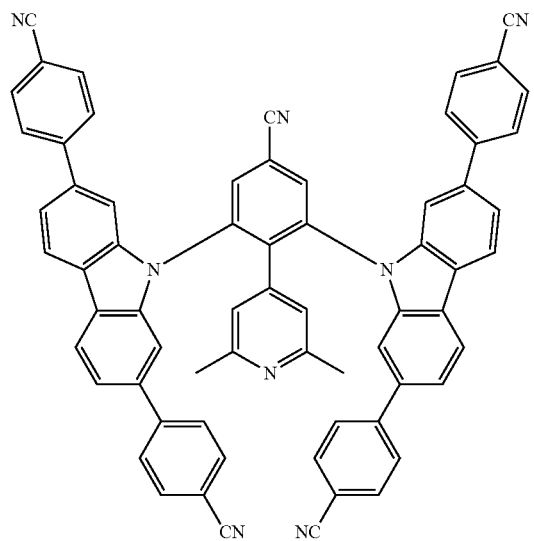
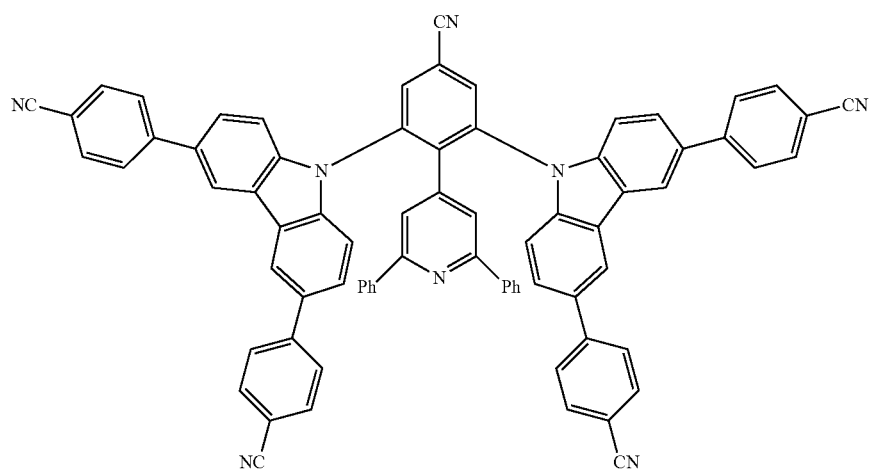
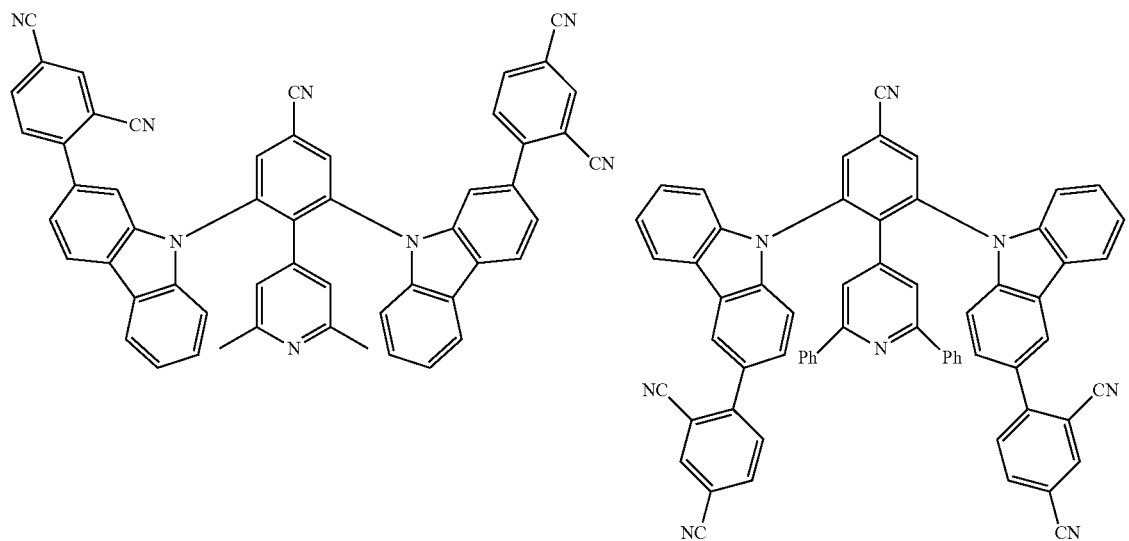

311
-continued
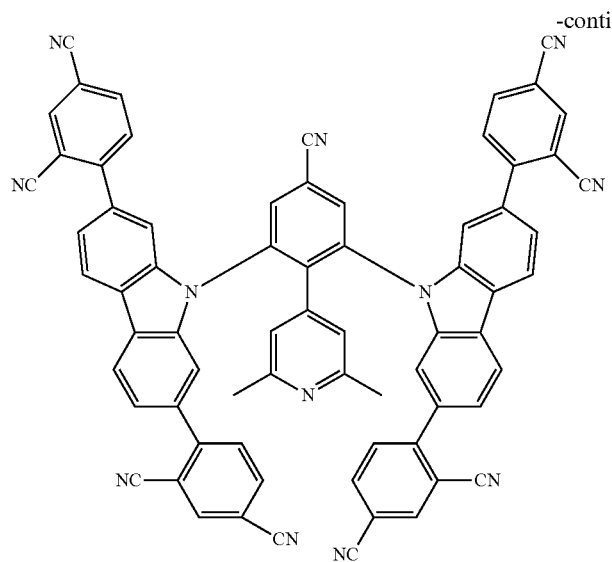
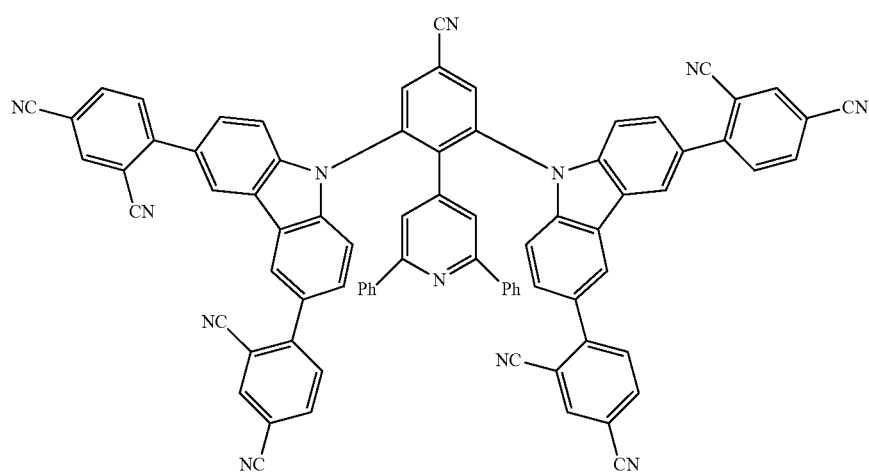
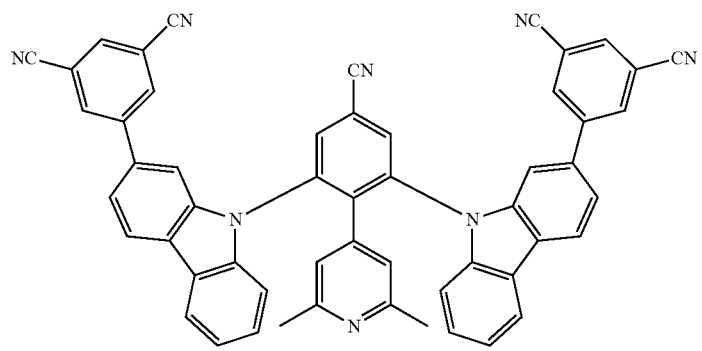
312

-continued
313
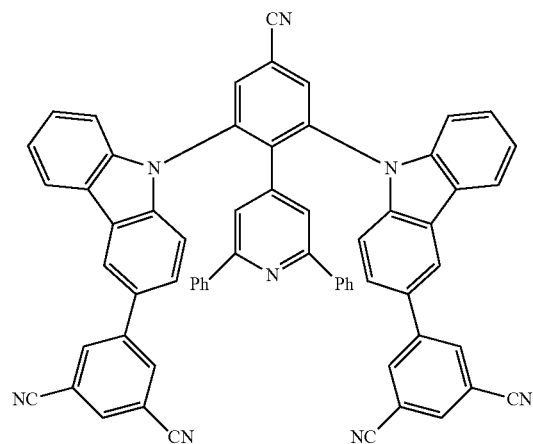
314
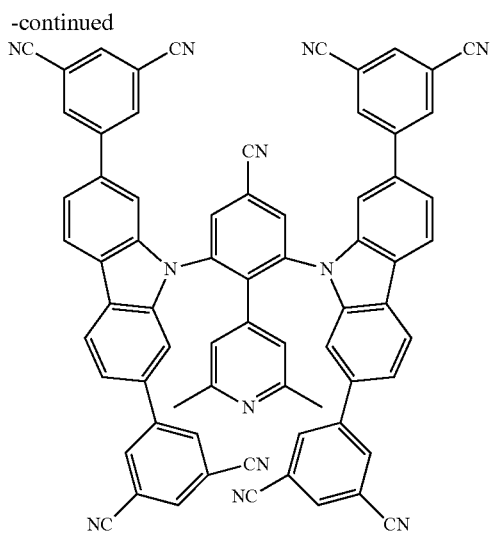
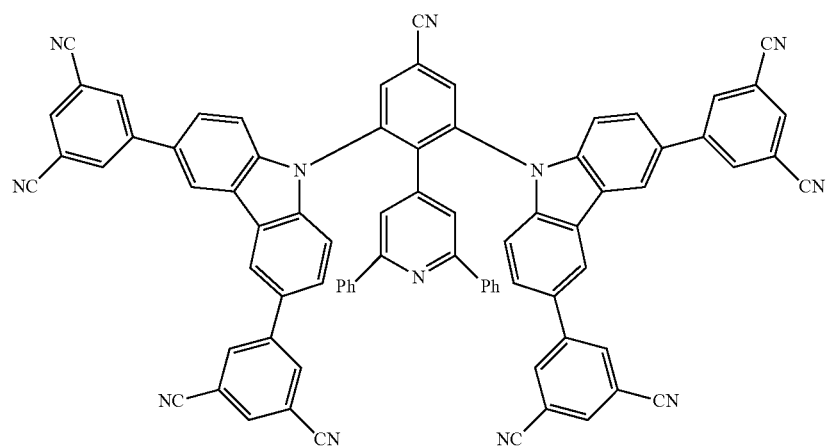
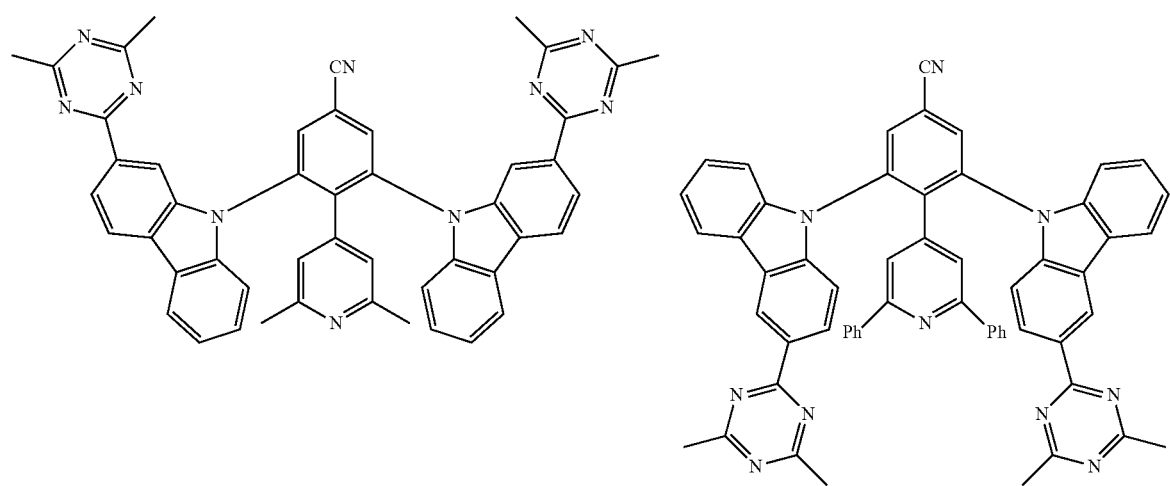

-continued
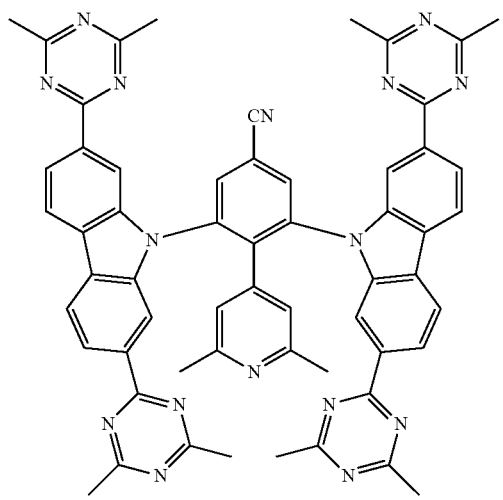
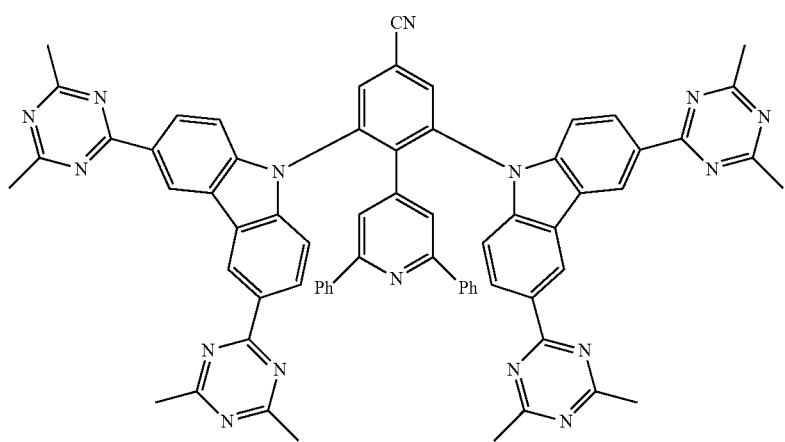
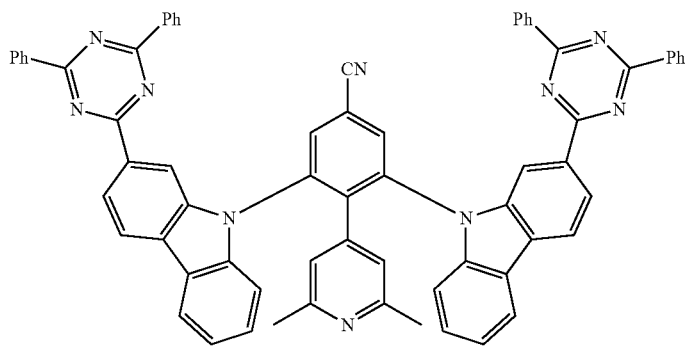

317
318
-continued
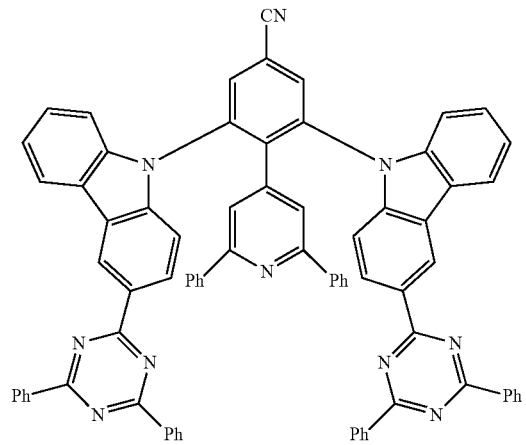
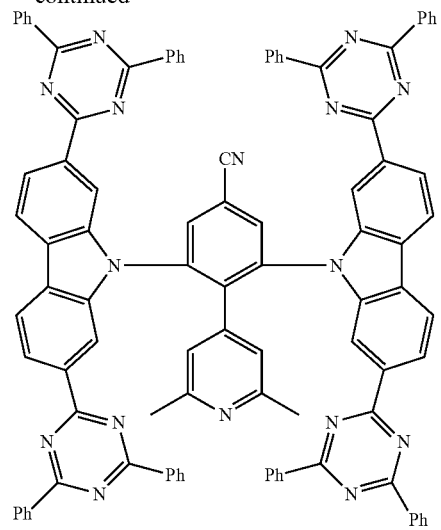
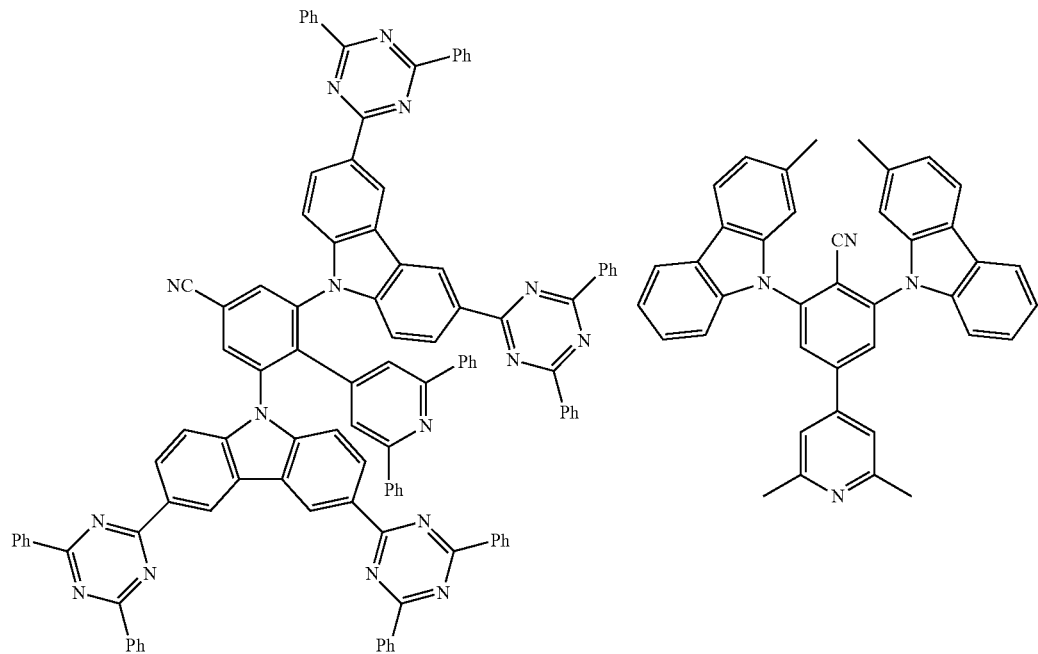
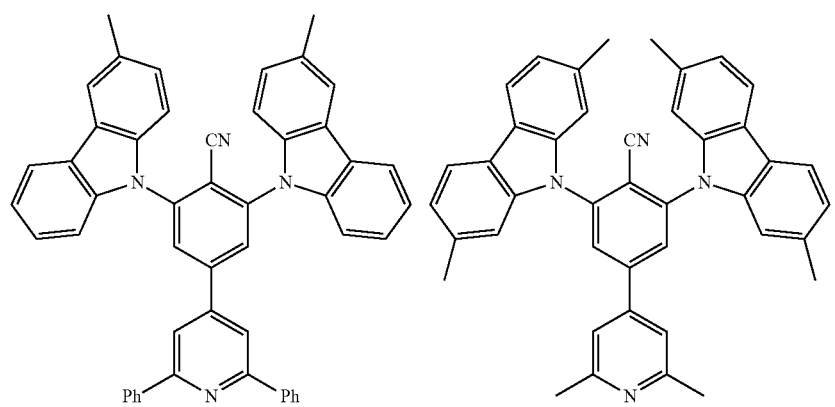

319
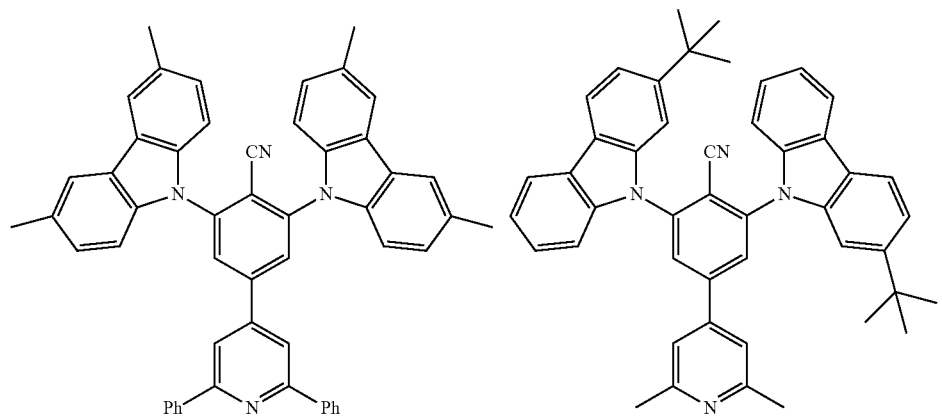
-continued
320
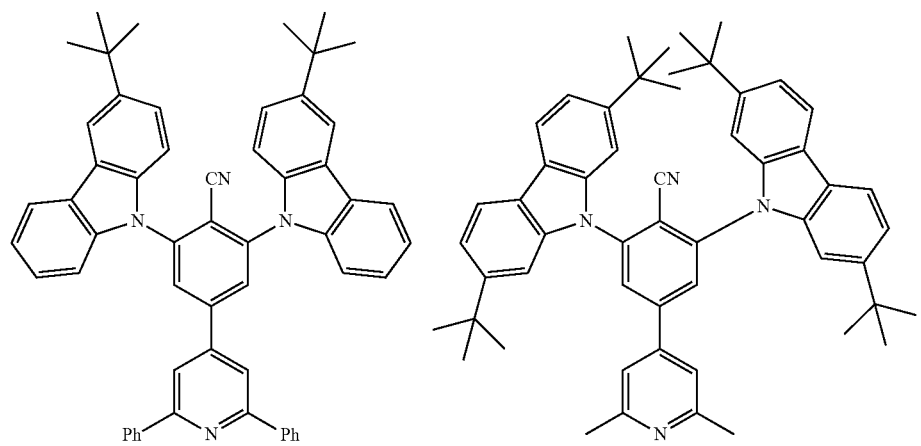
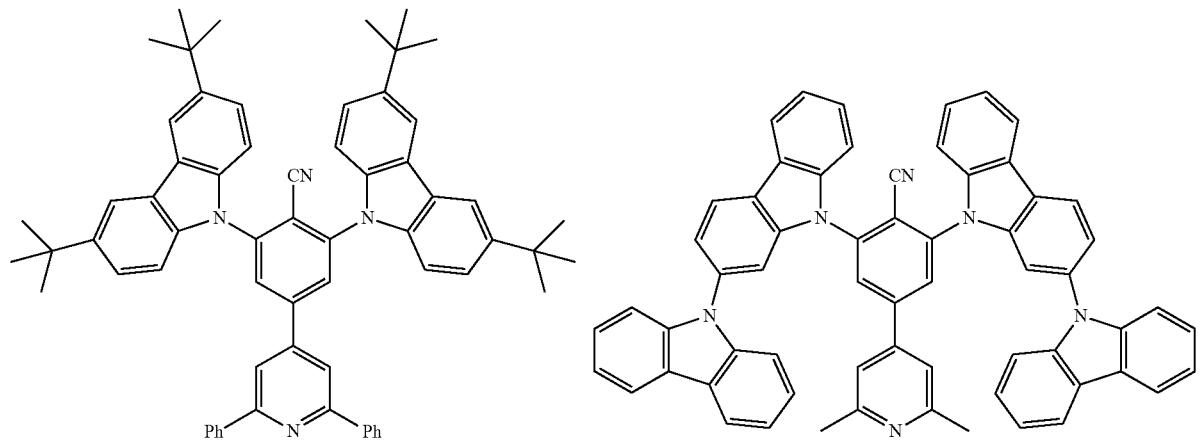

-continued
321
322
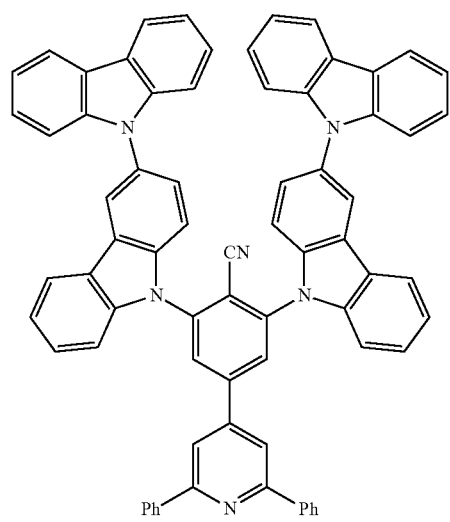
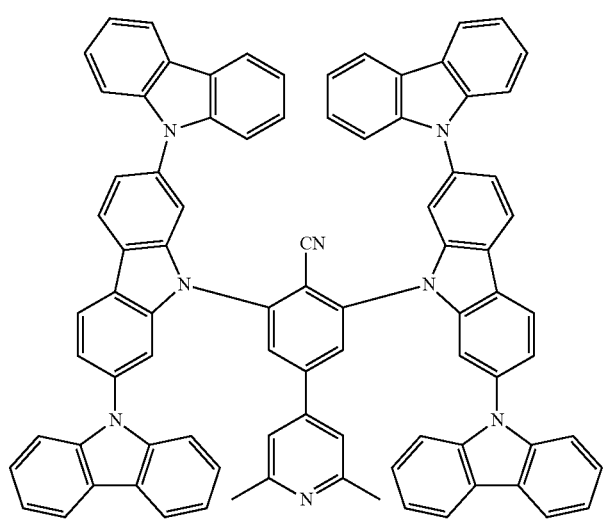
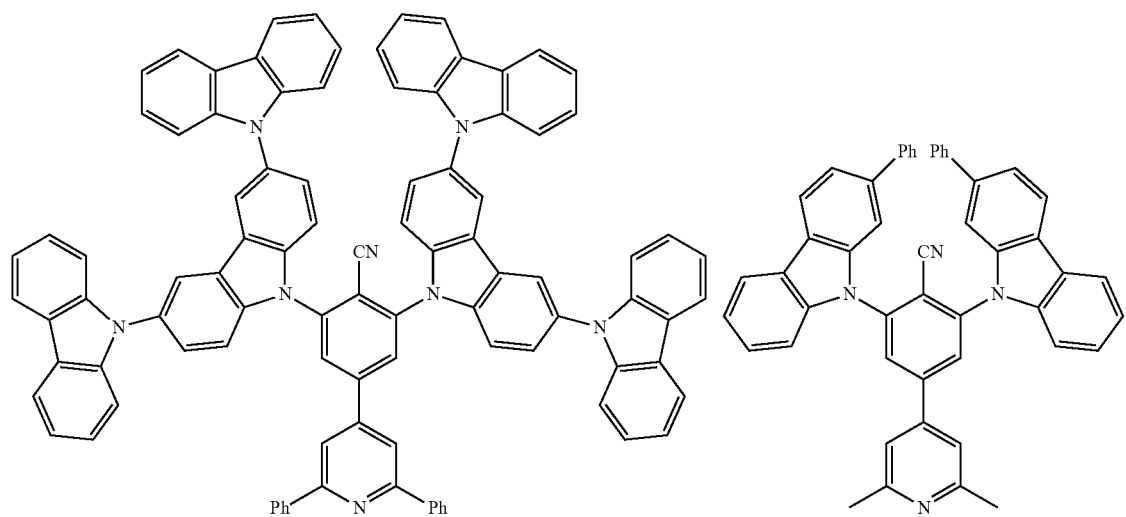
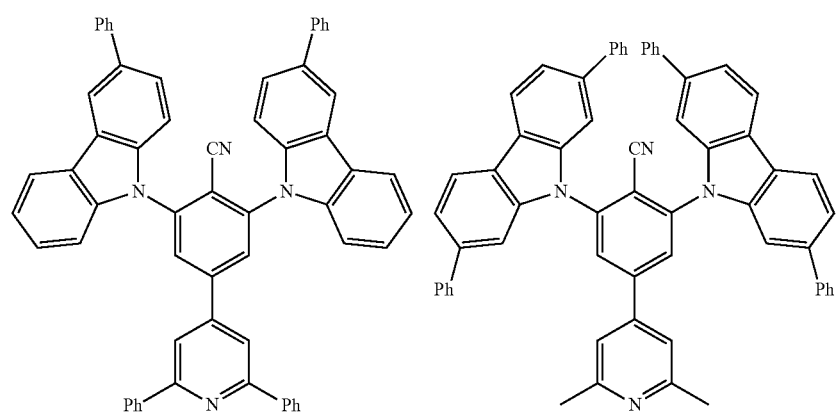

-continued
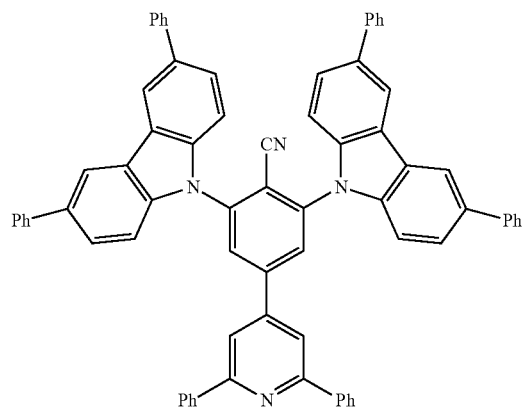
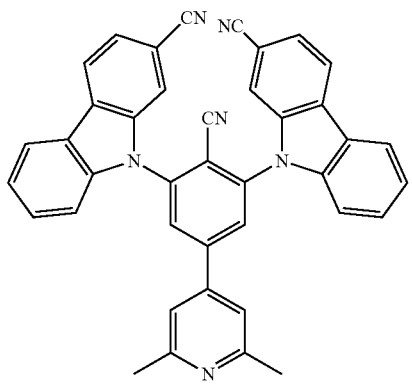
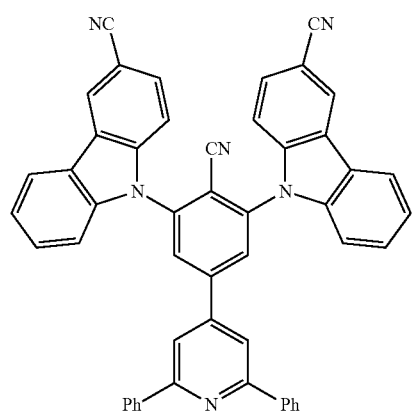
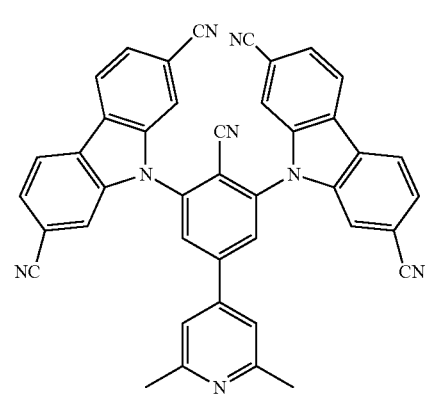
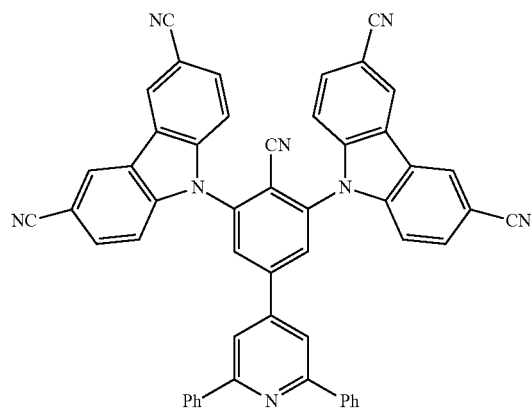
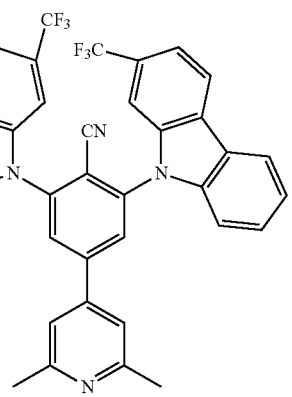
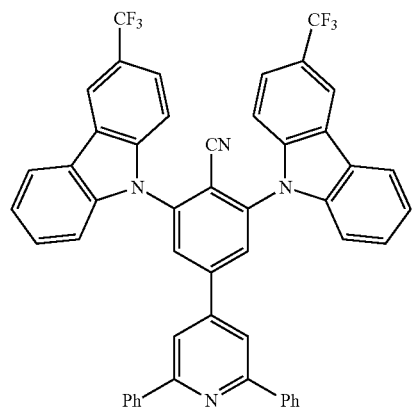
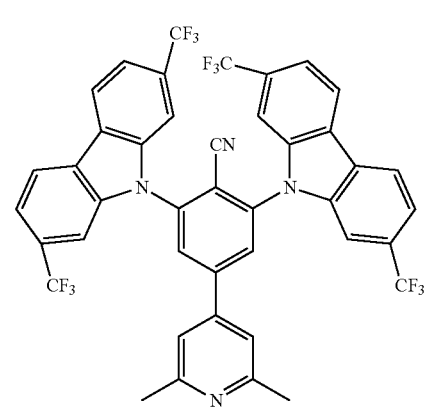

-continued
325
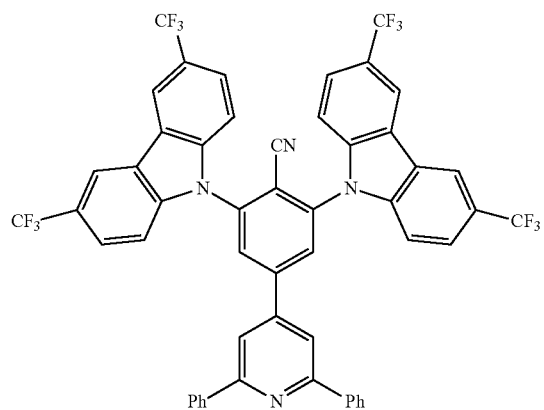
326
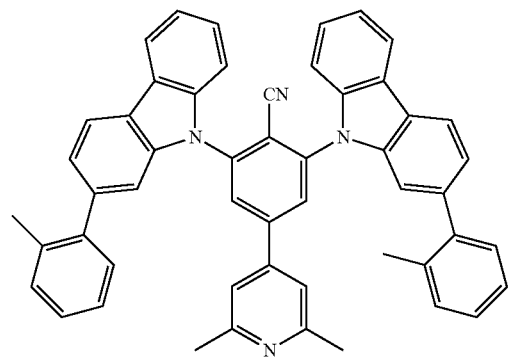
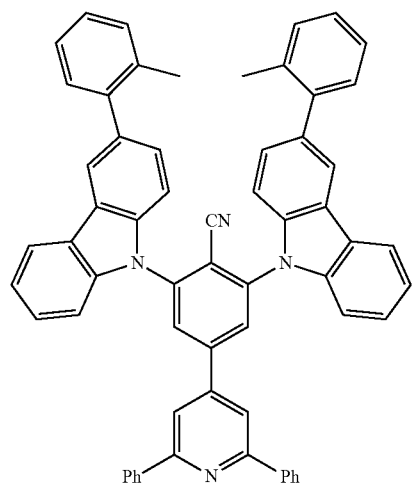
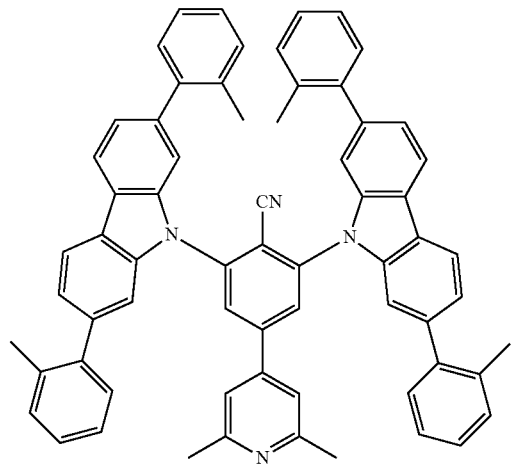
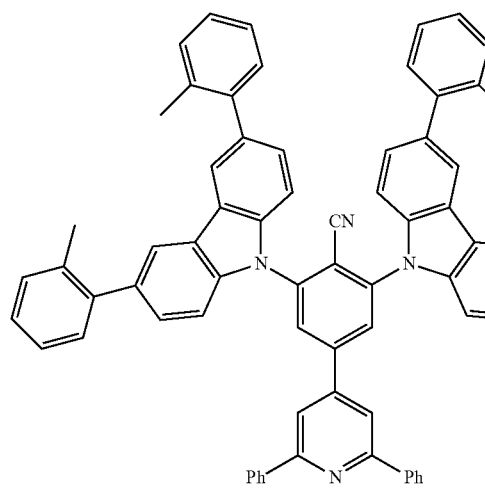
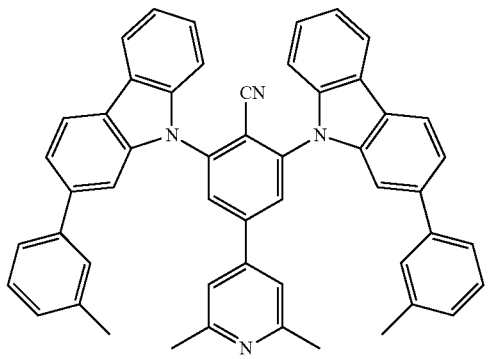

-continued
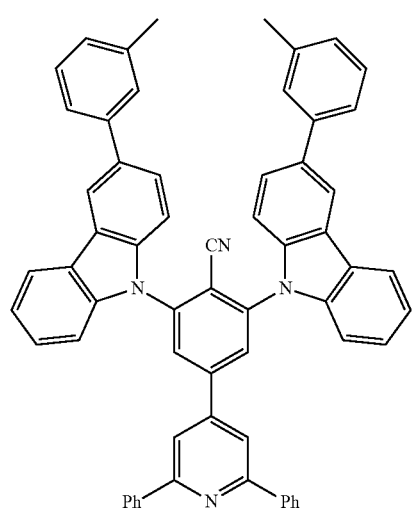
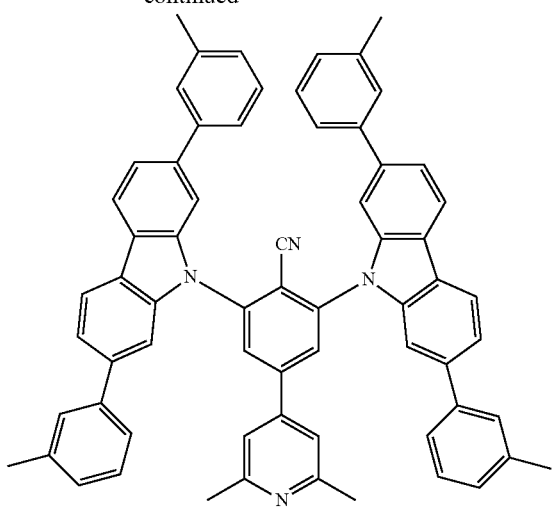
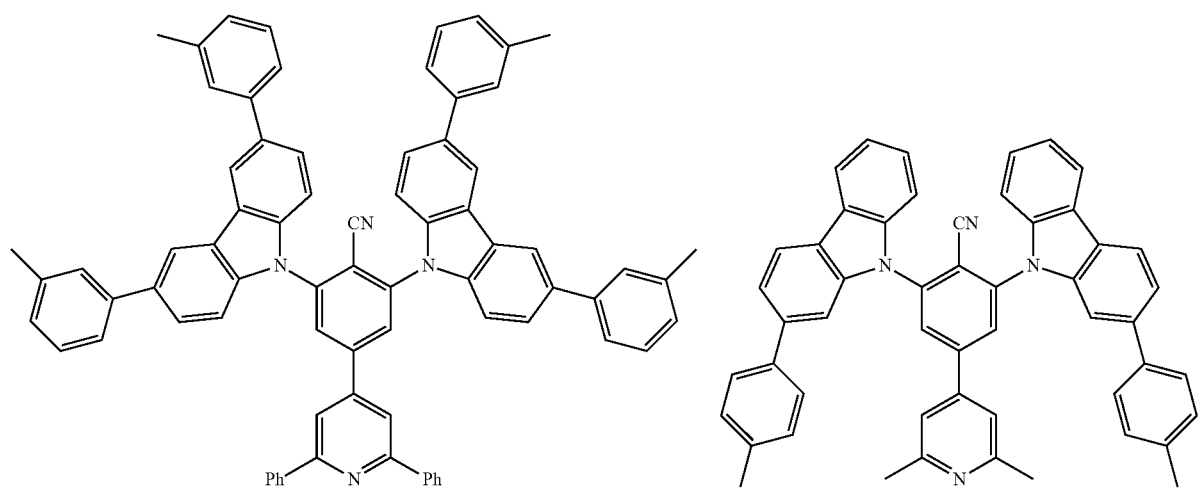
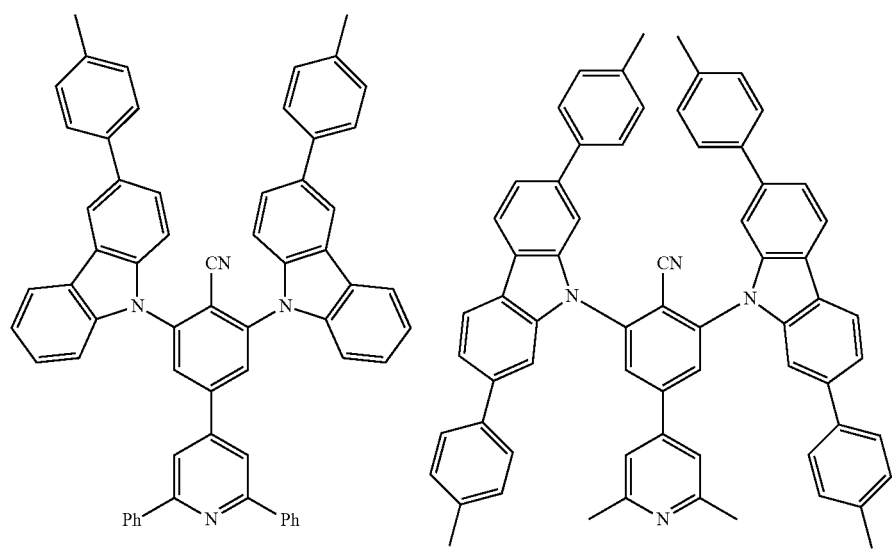

-continued
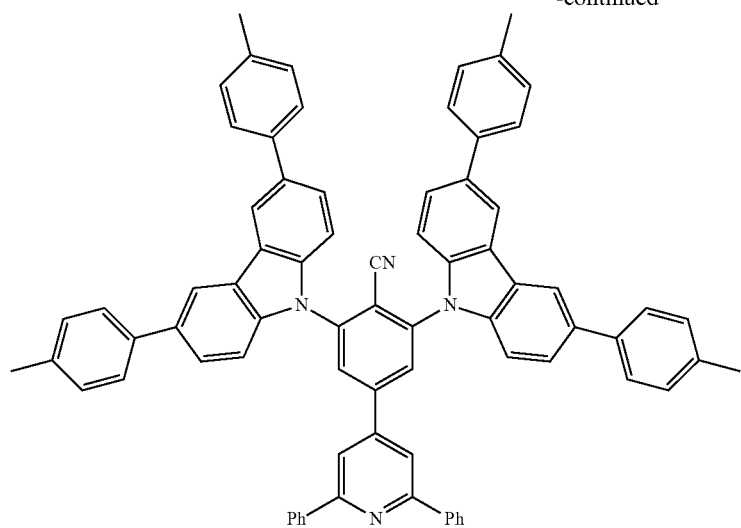
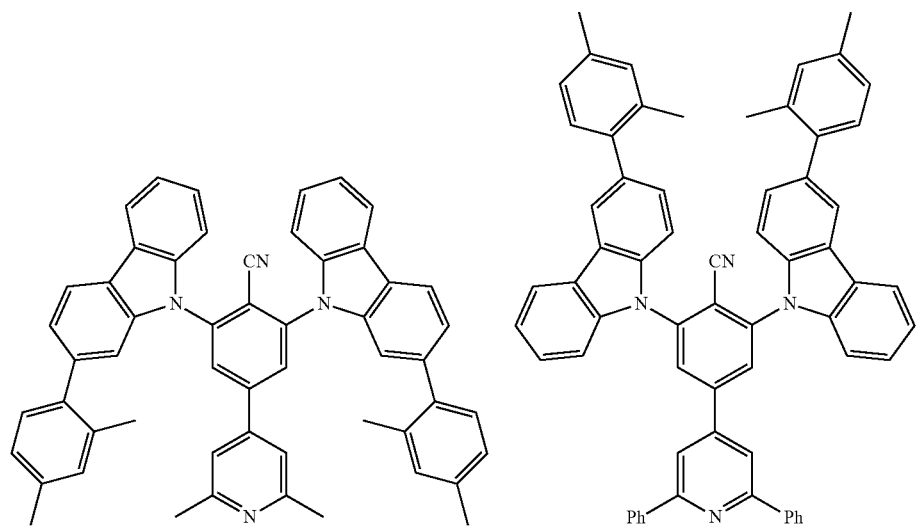
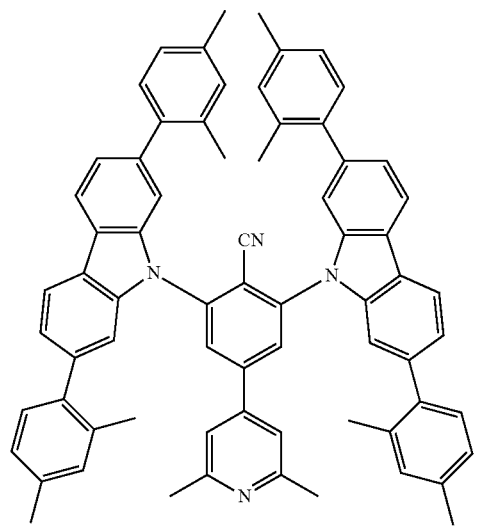

331
332
-continued
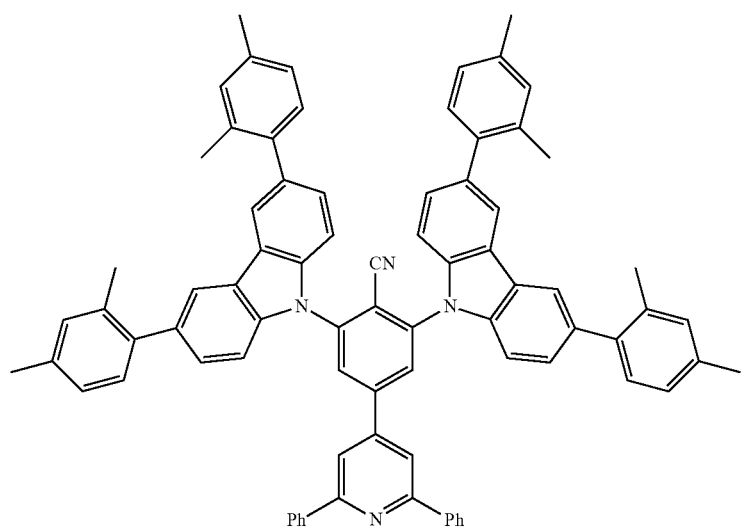
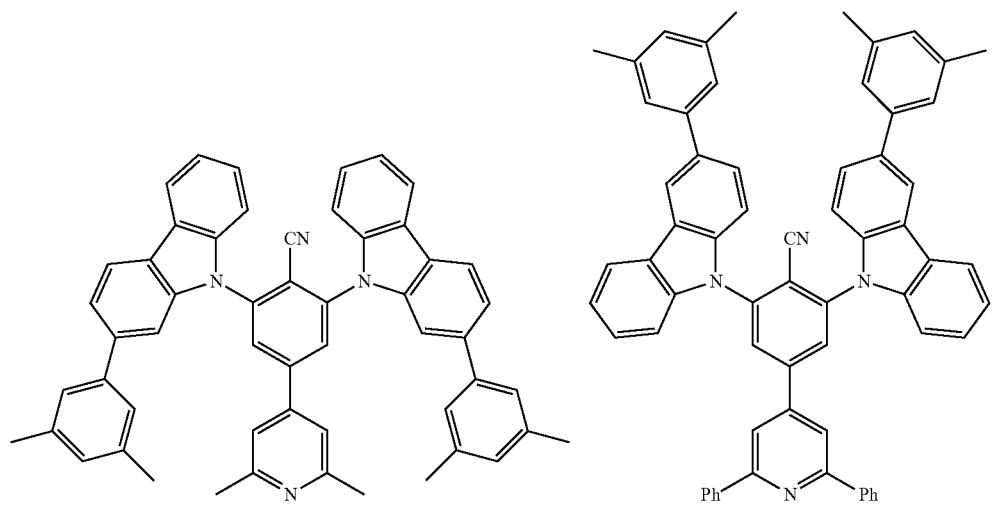
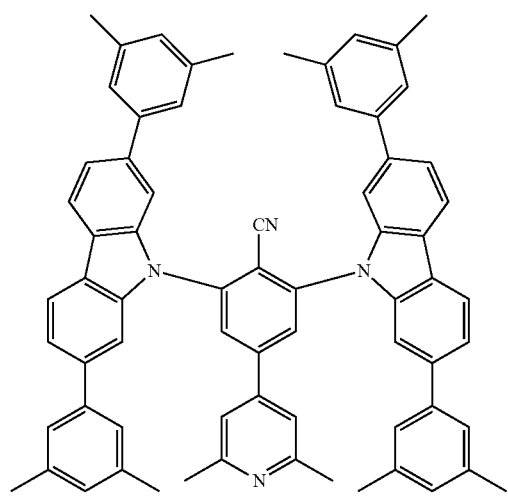

-continued
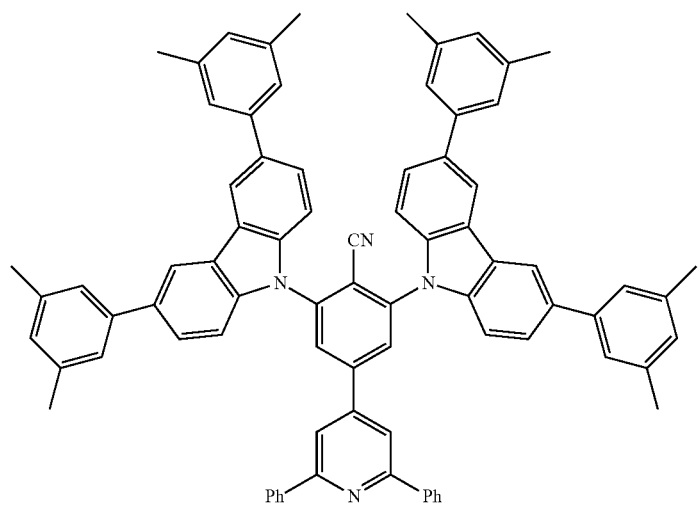
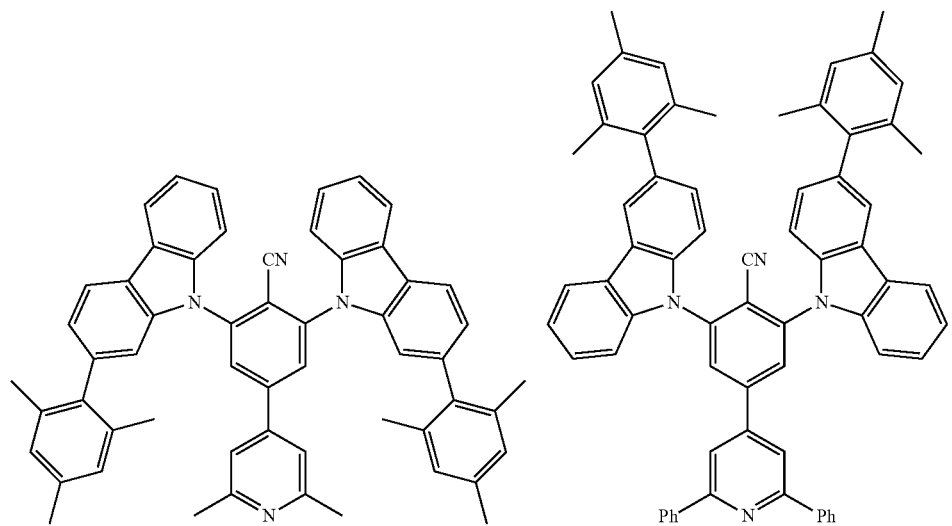
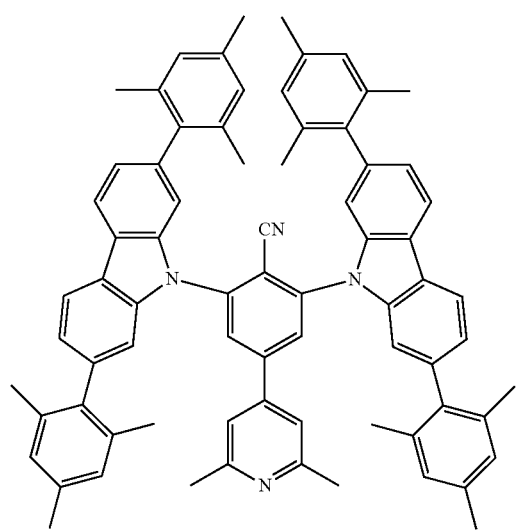

335
-continued
336
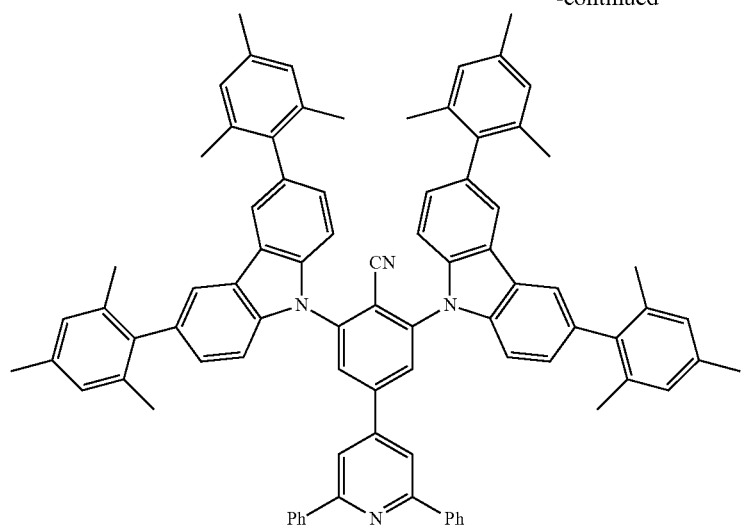
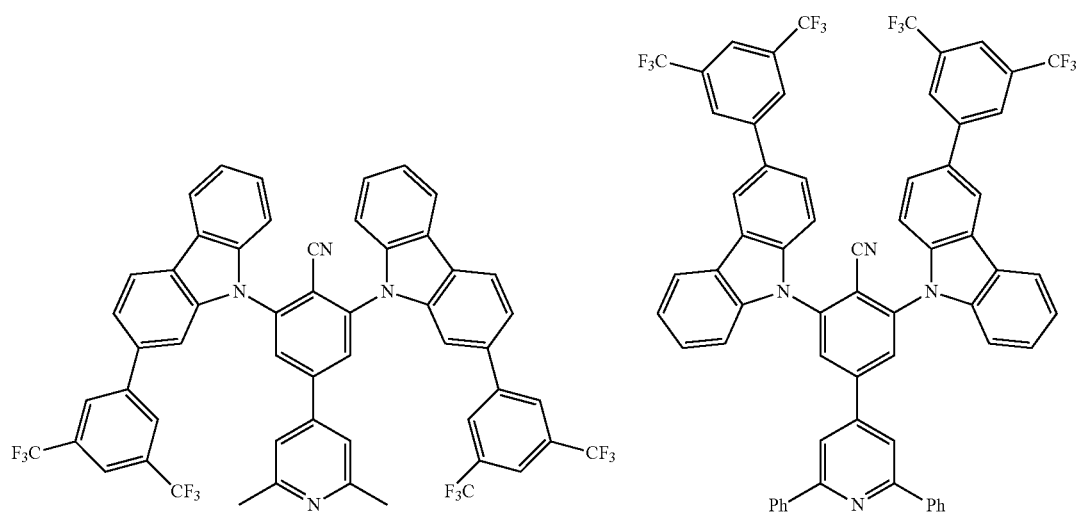
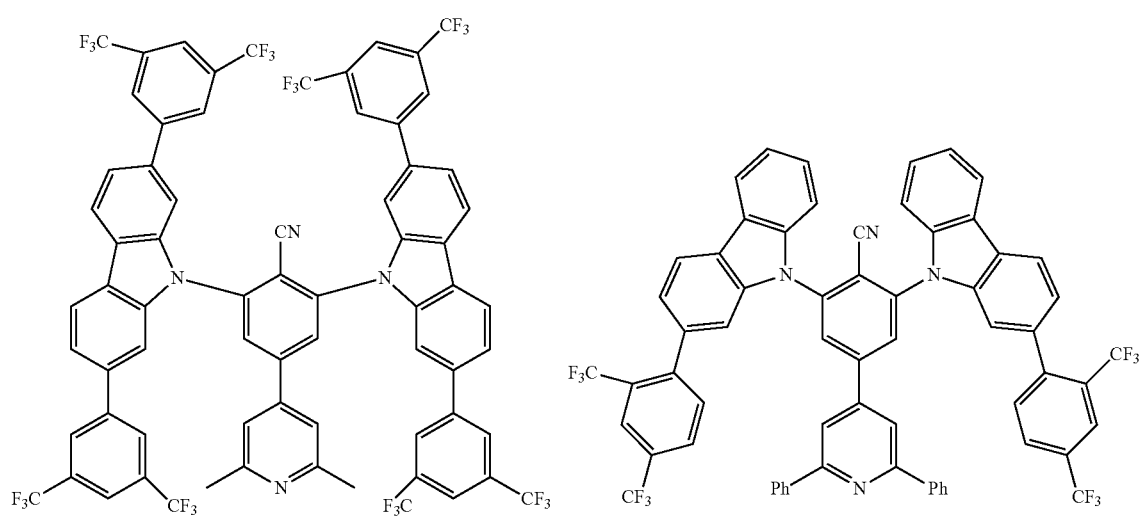

-continued
337
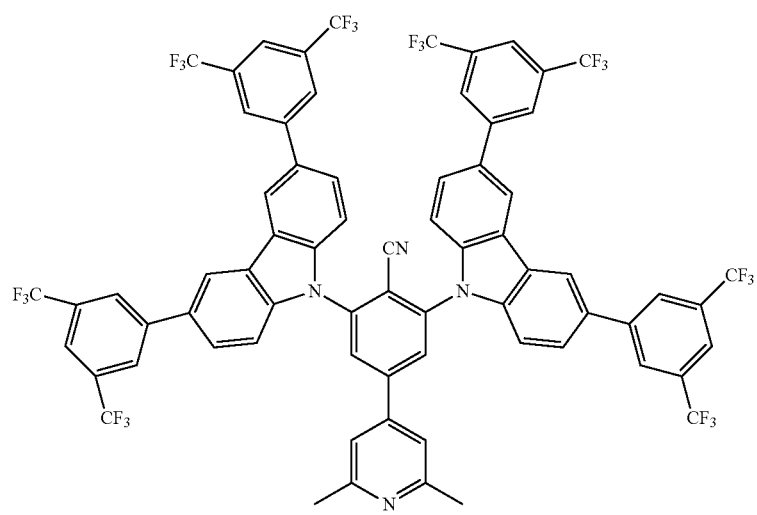
338
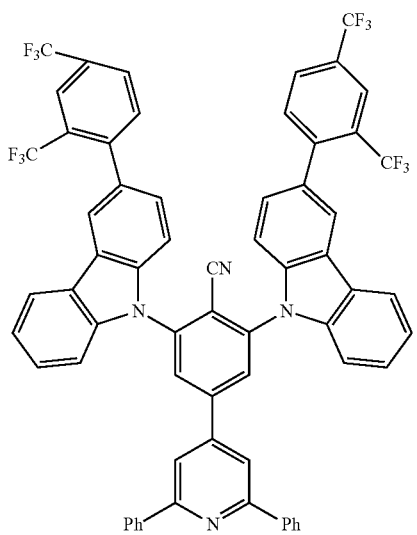
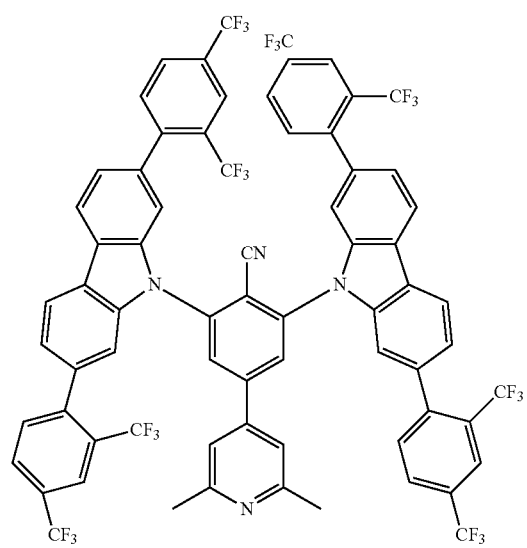
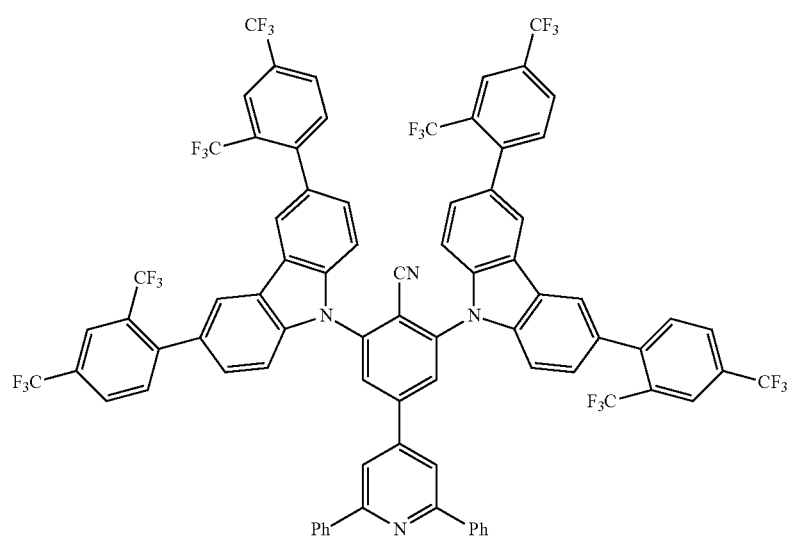

-continued
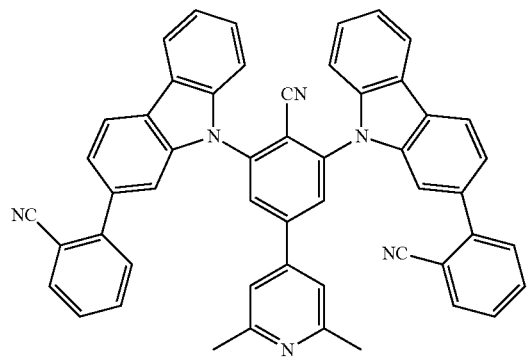
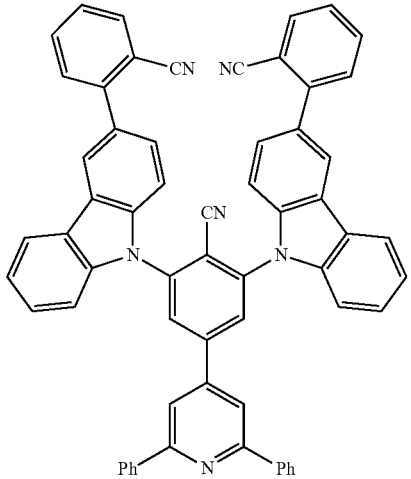
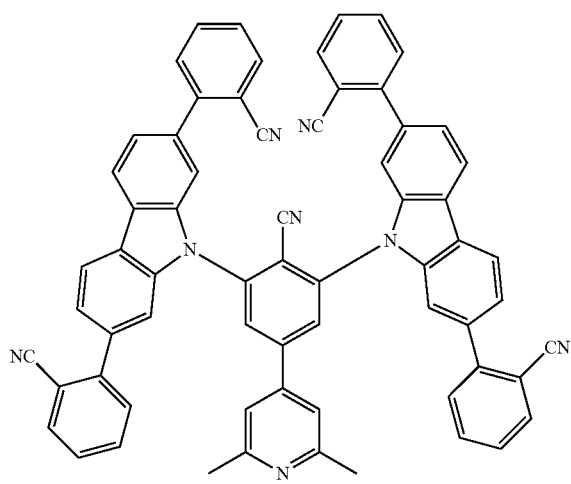
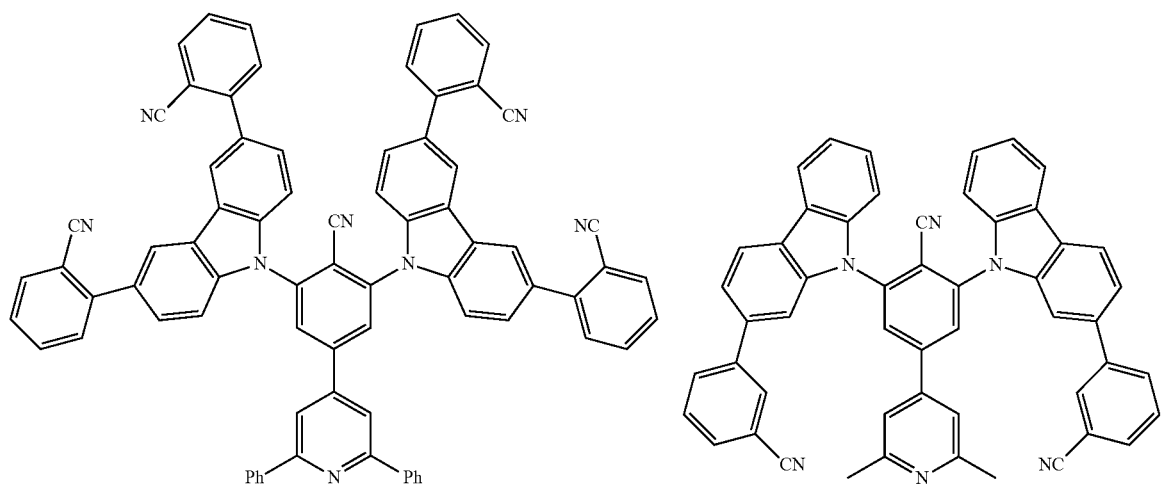

-continued
341
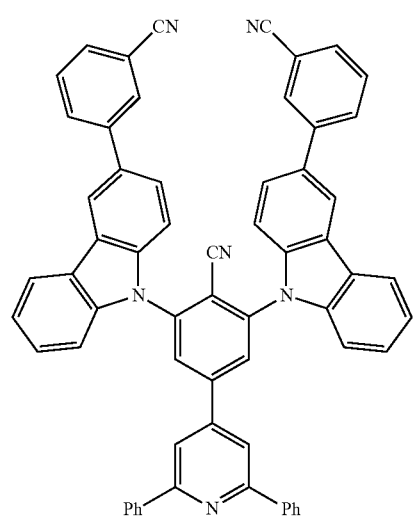
342
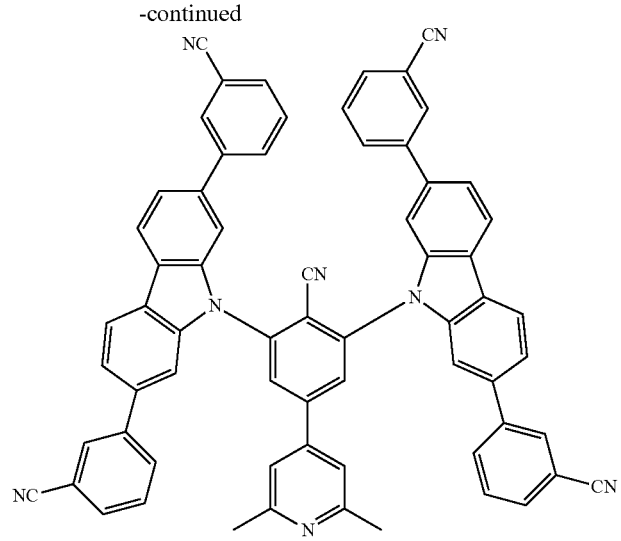
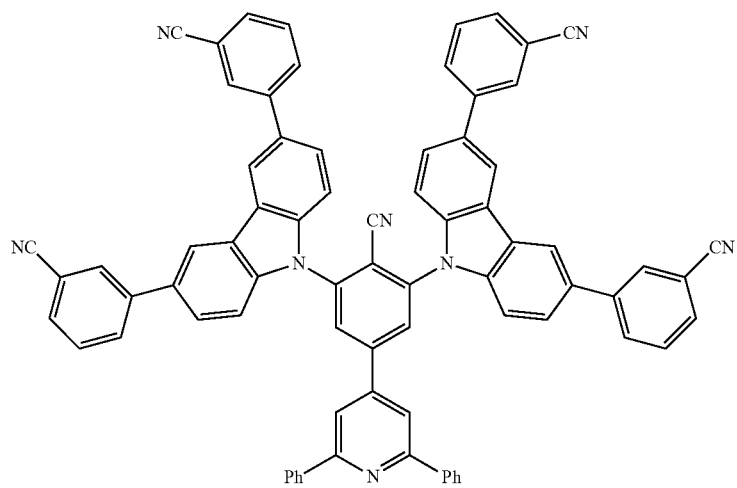
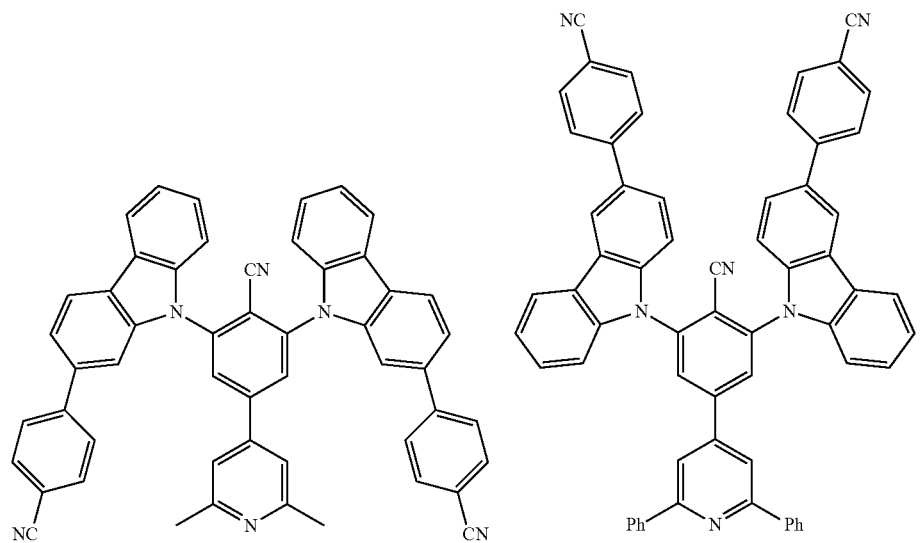

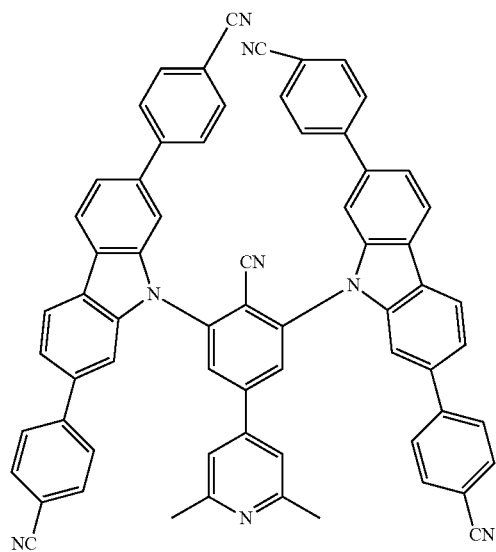
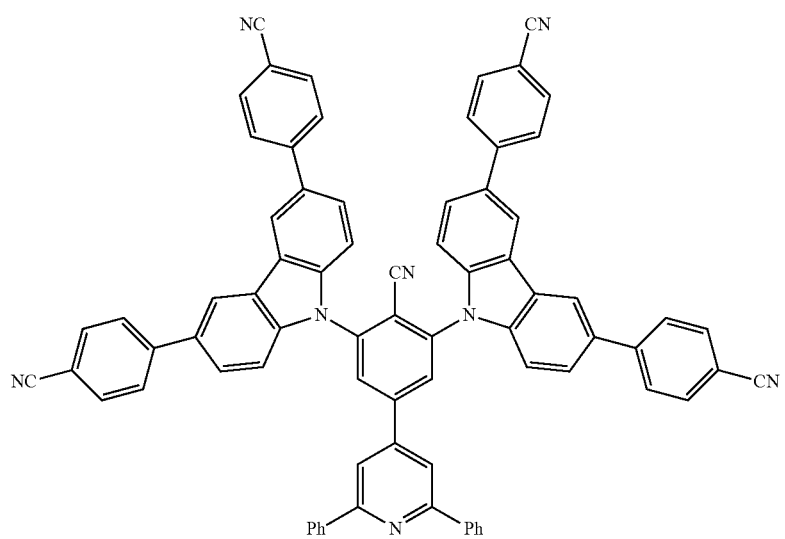
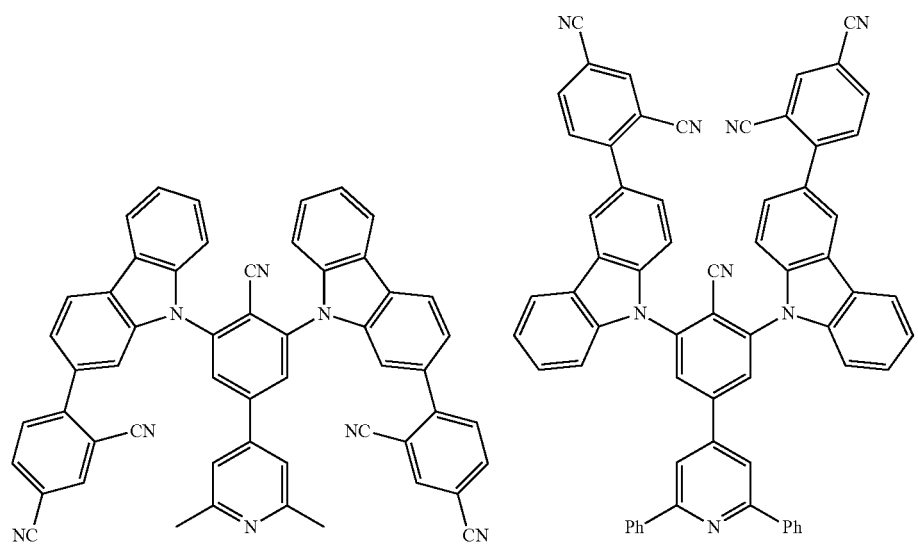

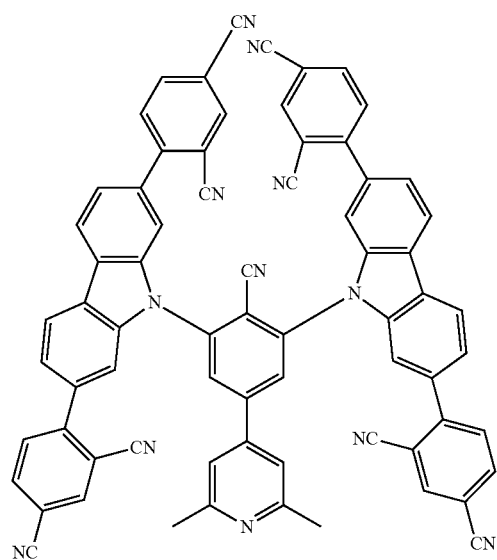
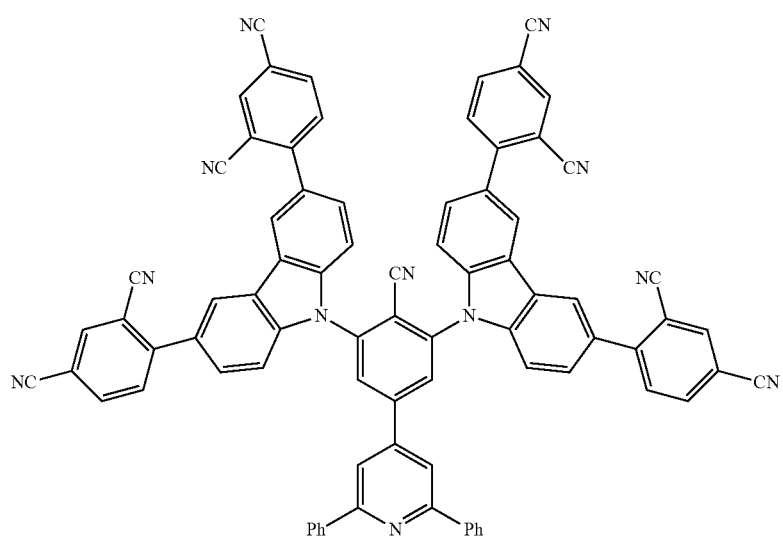
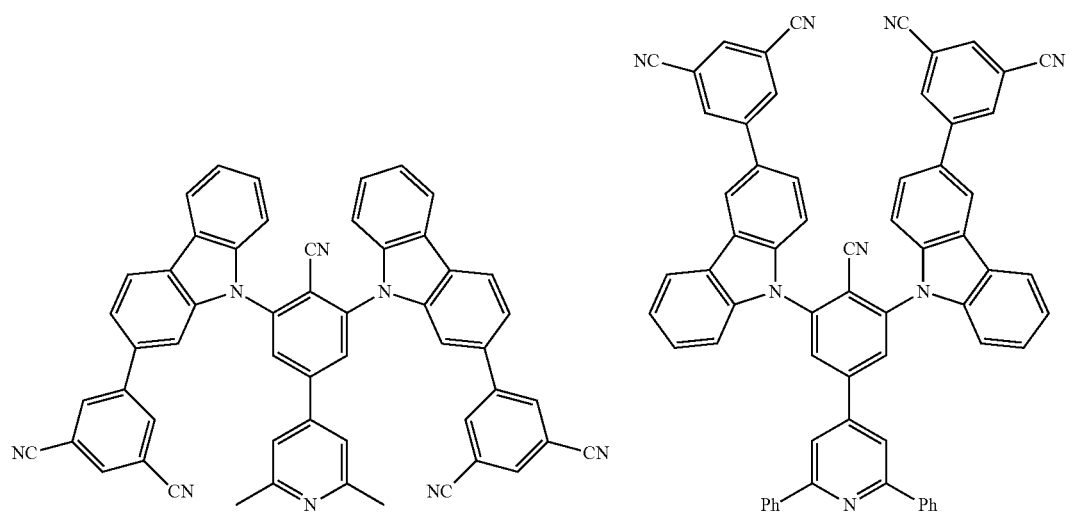

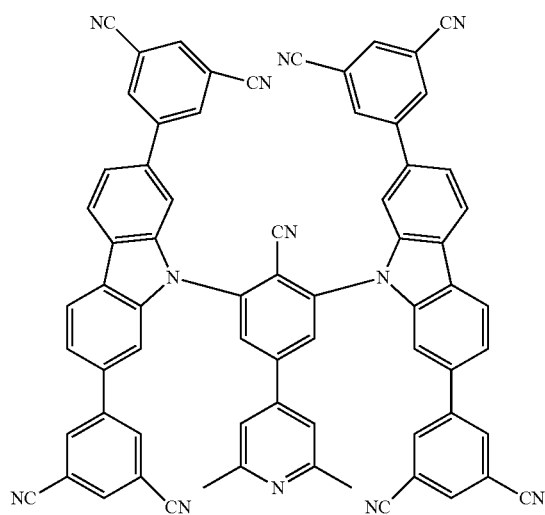
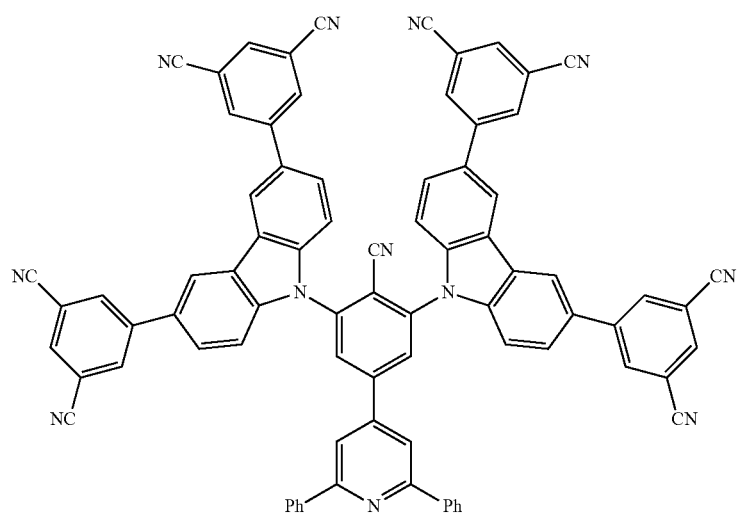
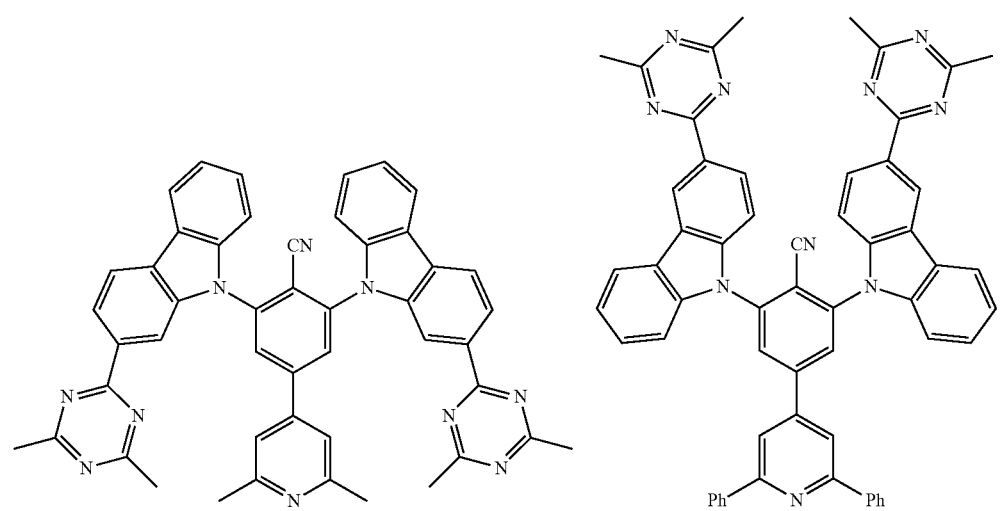

-continued
| 349 | 350 |
|---|---|
| 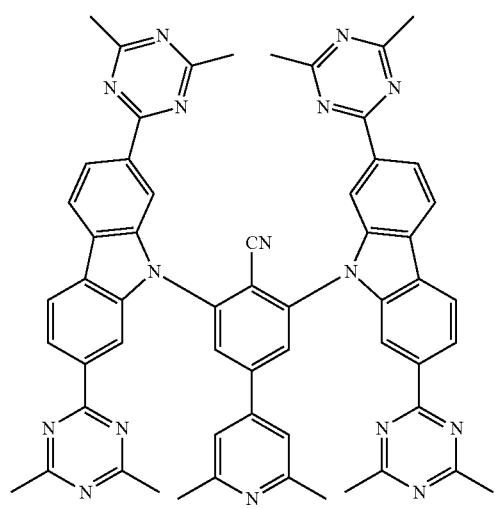 | 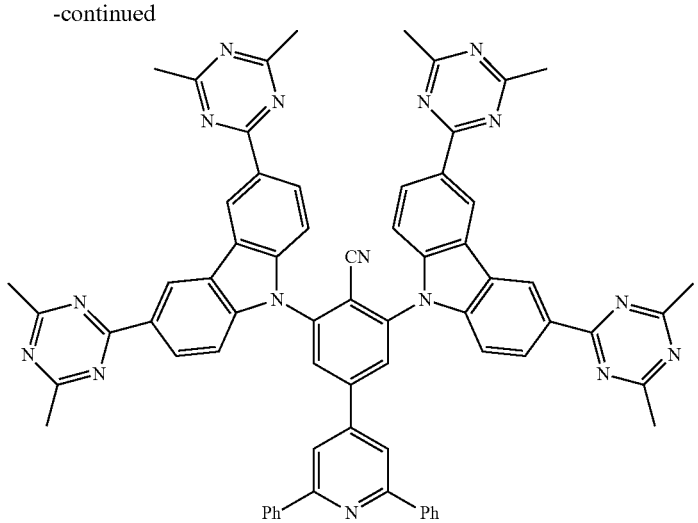 |
| 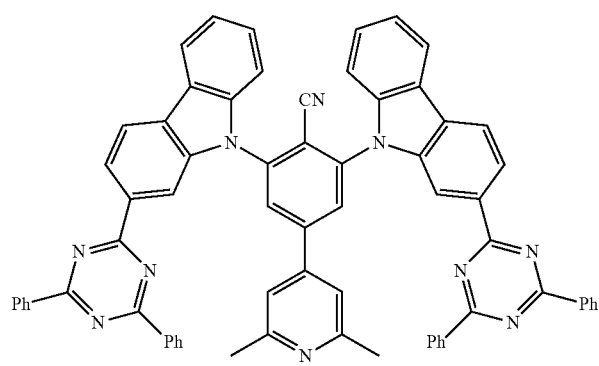 | 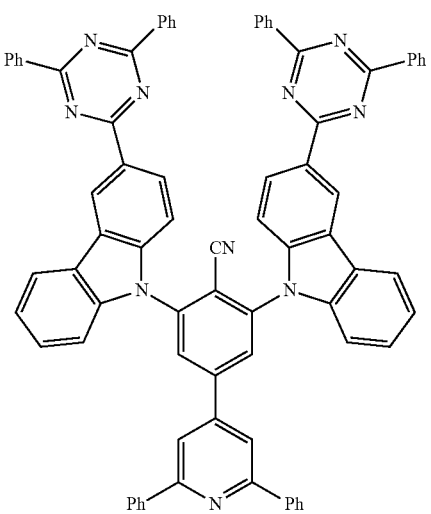 |
| 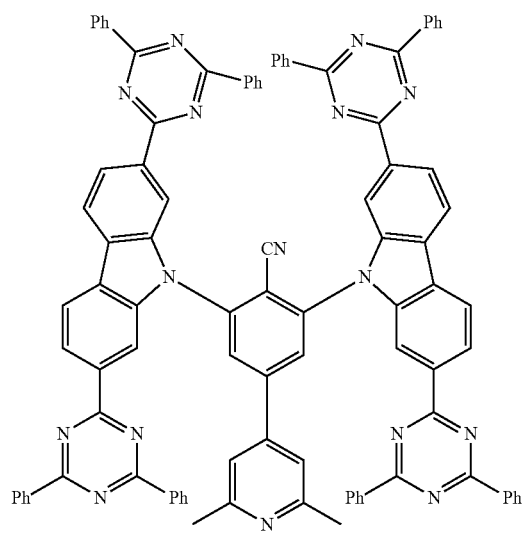 | |

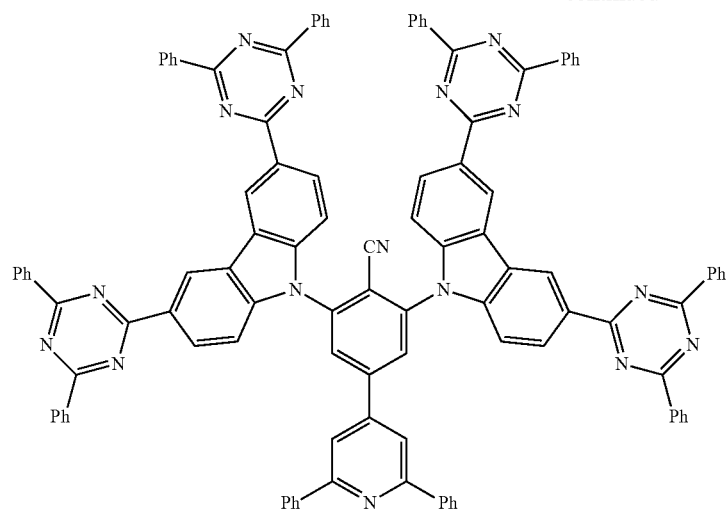 [SMILES: N#Cc1c(-n2c3ccc(-c4nc(-c5ccccc5)nc(-c5ccccc5)n4)cc3c3cc(-c4nc(-c5ccccc5)nc(-c5ccccc5)n4)ccc32)cc(-c2cc(-c3ccccc3)nc(-c3ccccc3)c2)cc1-n1c2ccc(-c3nc(-c4ccccc4)nc(-c4ccccc4)n3)cc2c2cc(-c3nc(-c4ccccc4)nc(-c4ccccc4)n3)ccc21]
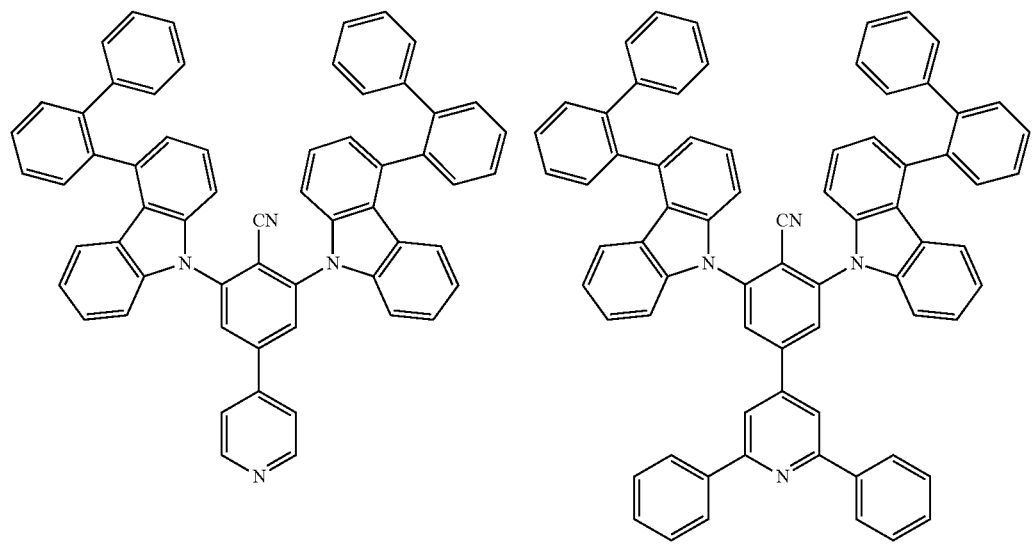
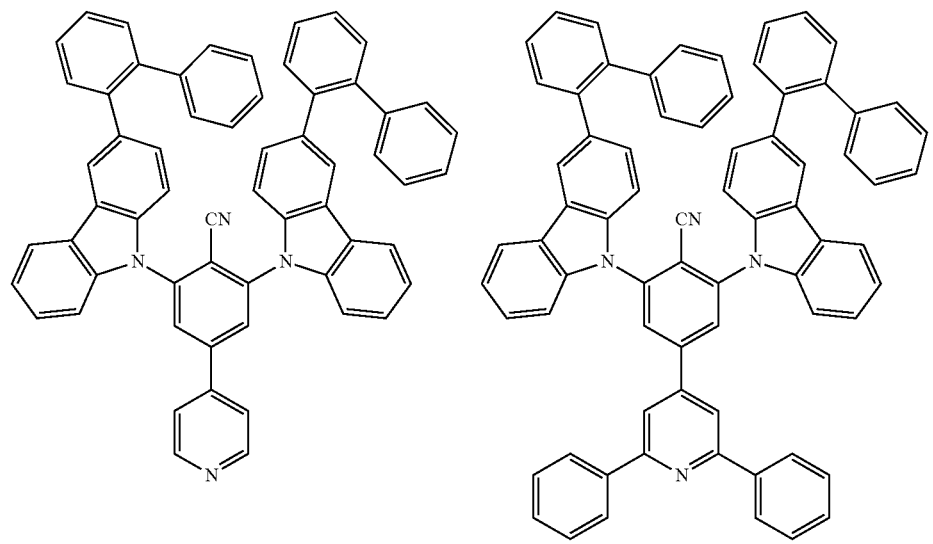

-continued
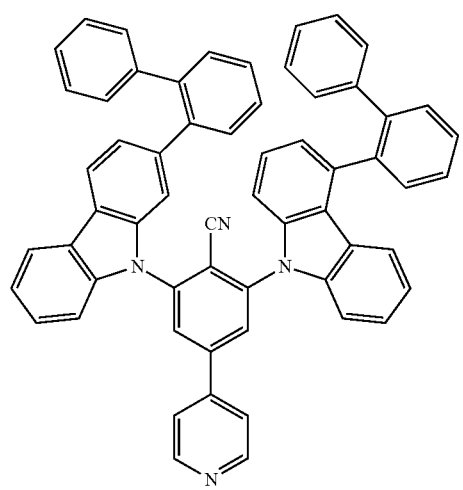
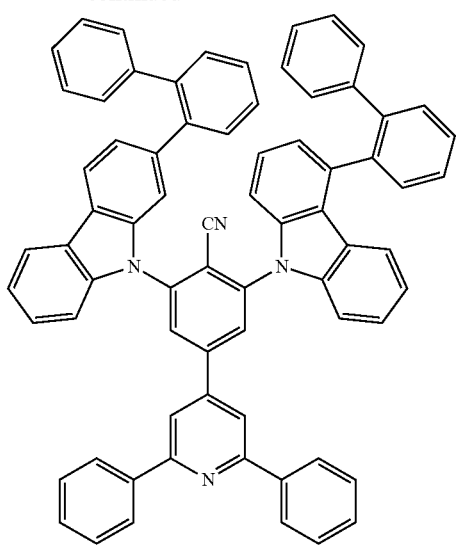
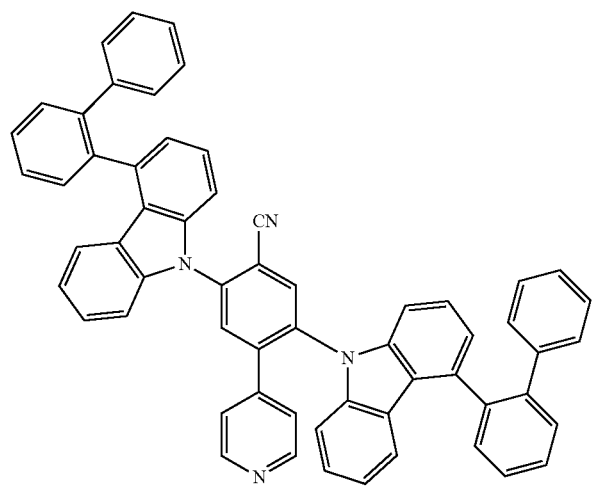
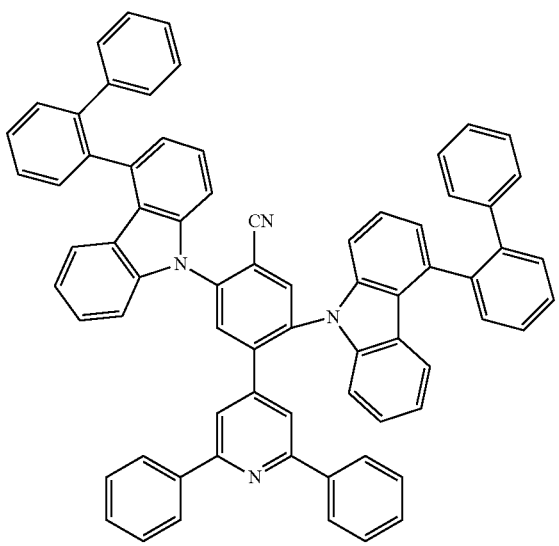
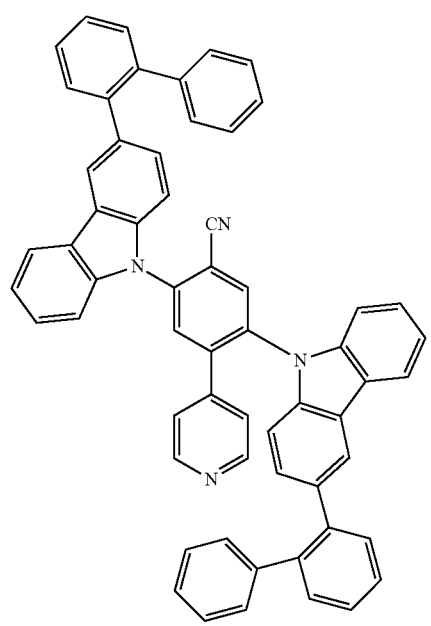
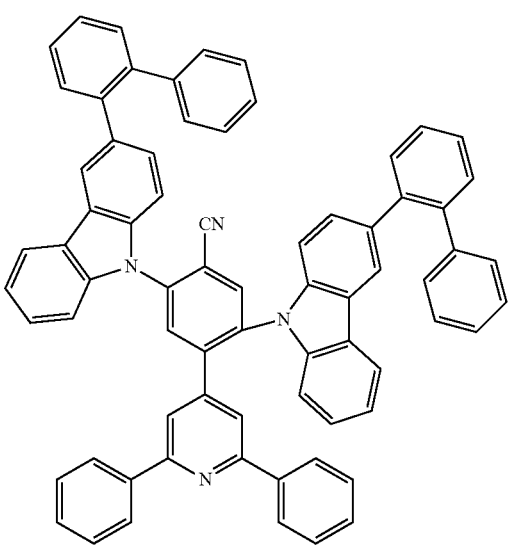

-continued
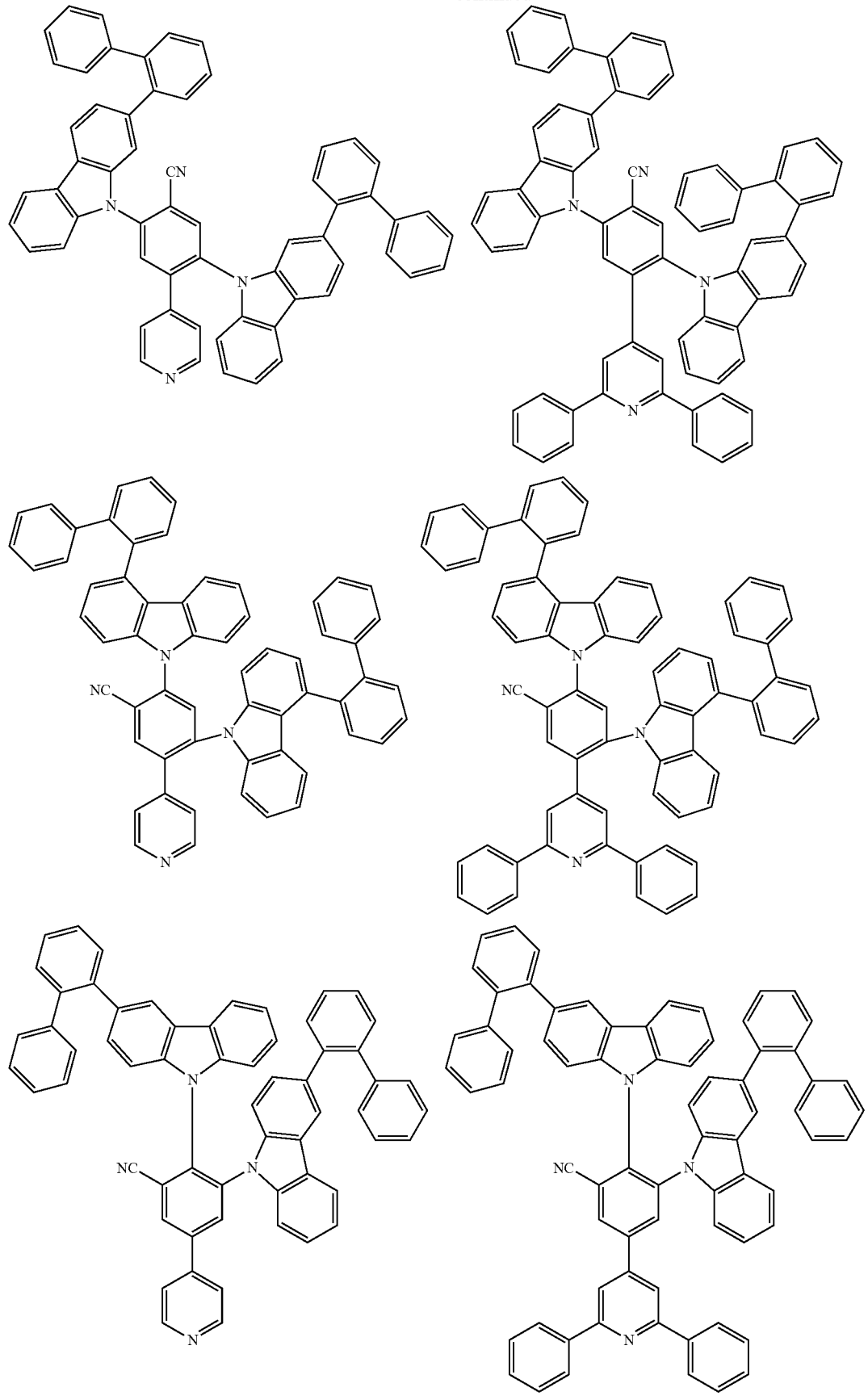

357
358
-continued
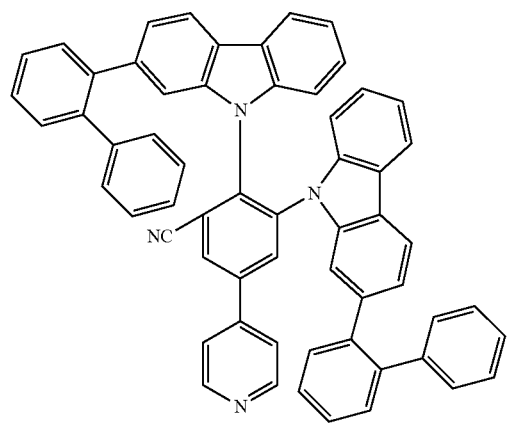
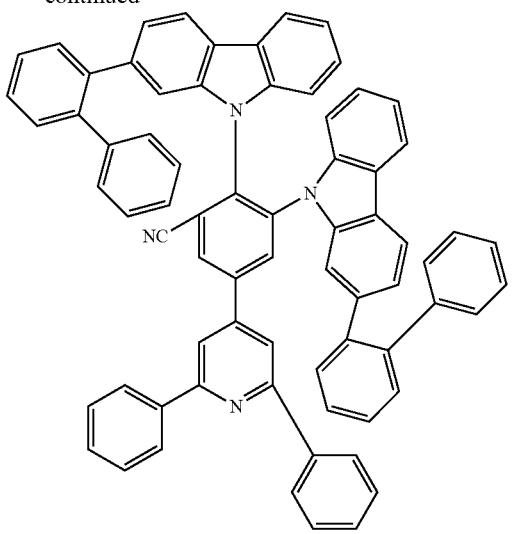
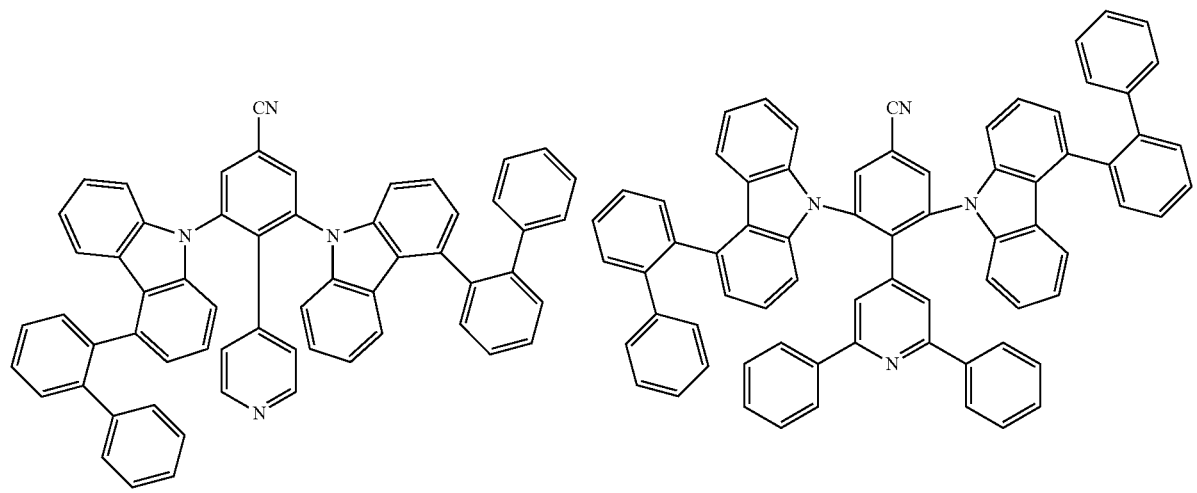
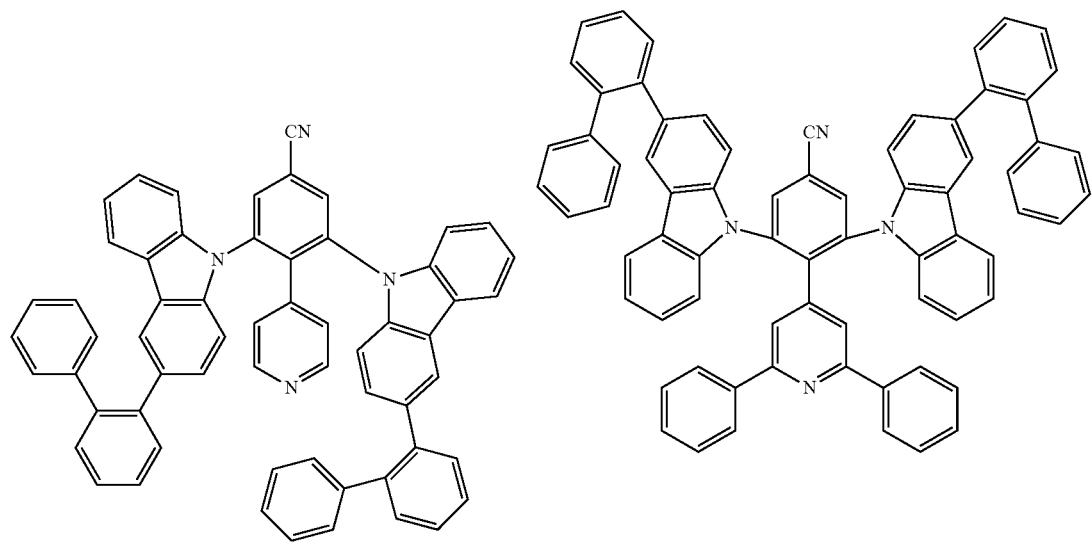

359            360
-continued
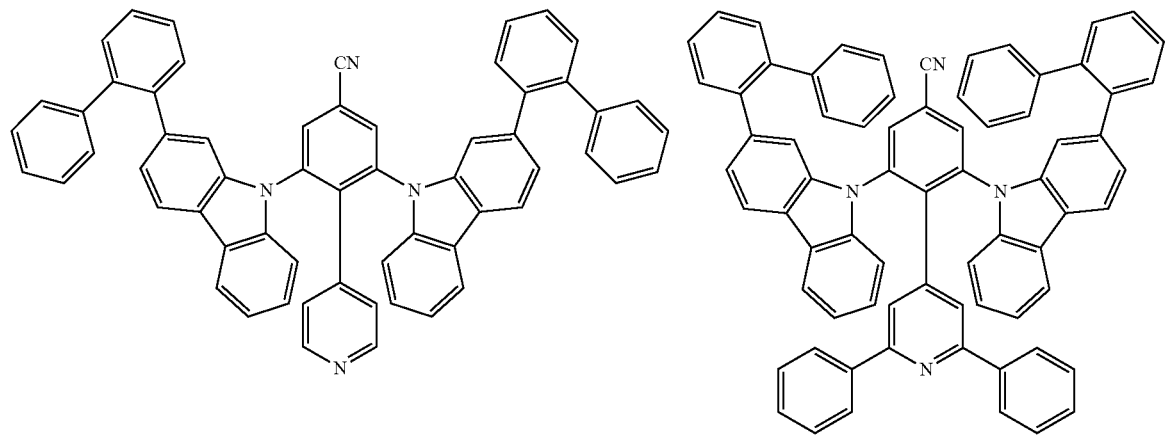
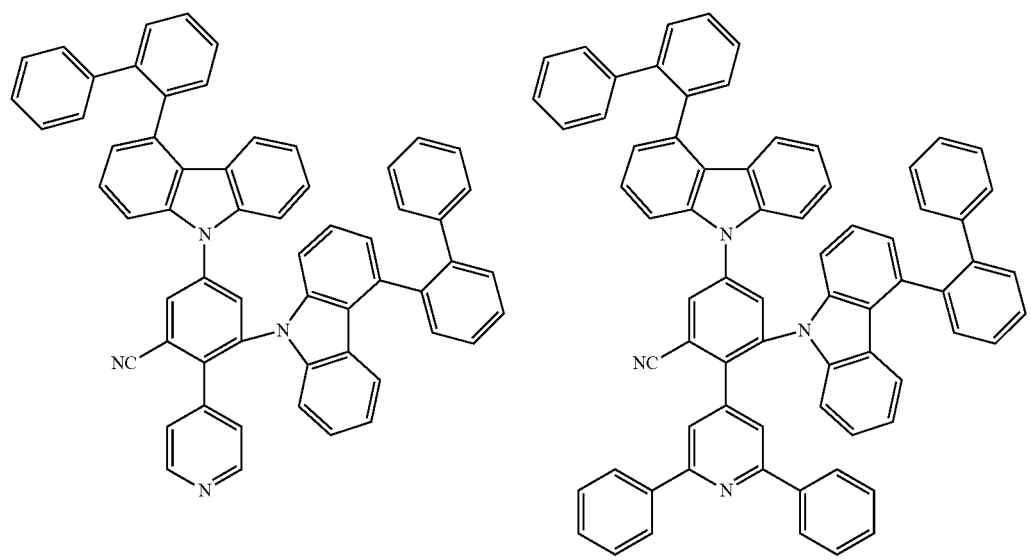
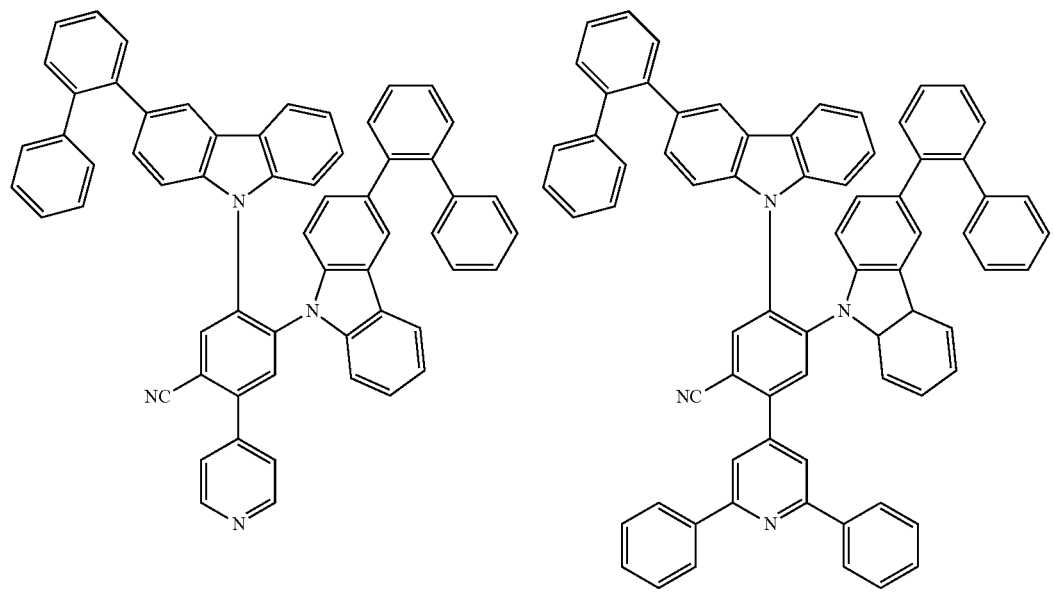

361
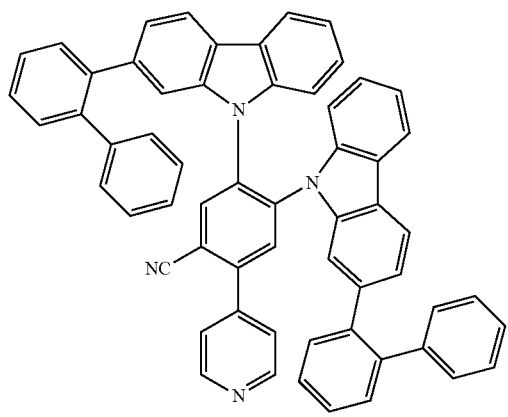
-continued
362
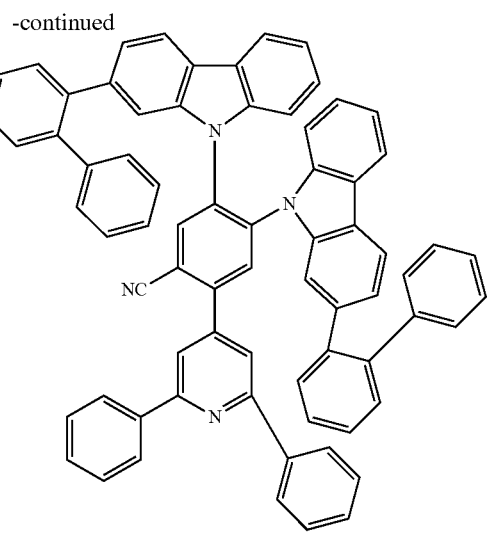
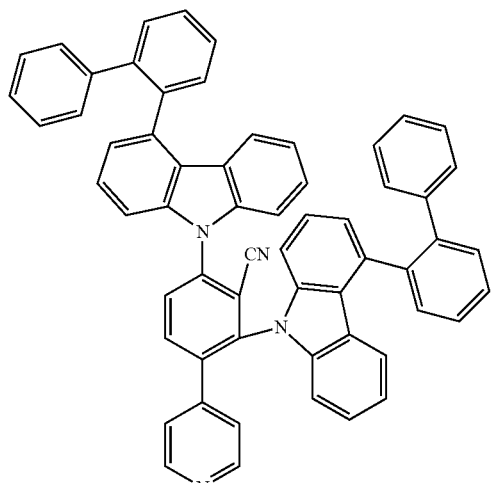
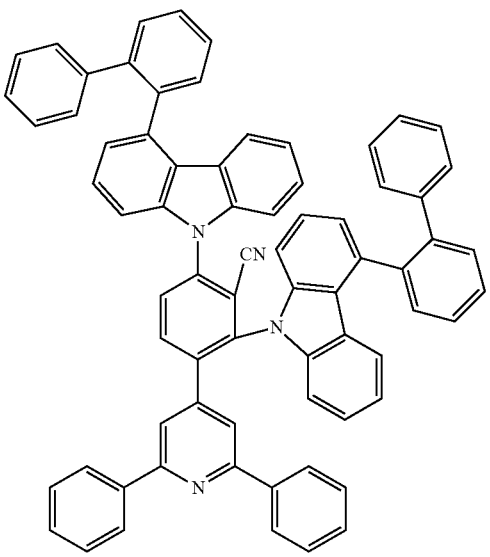
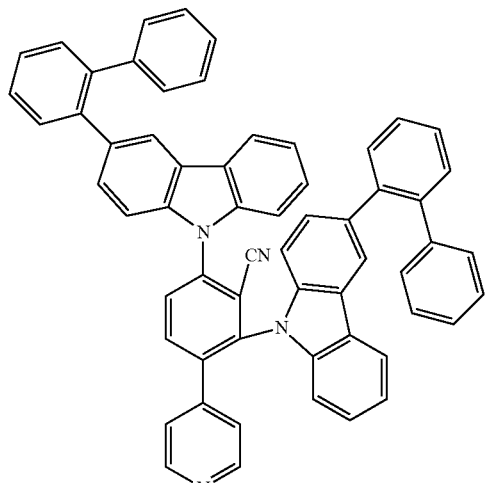
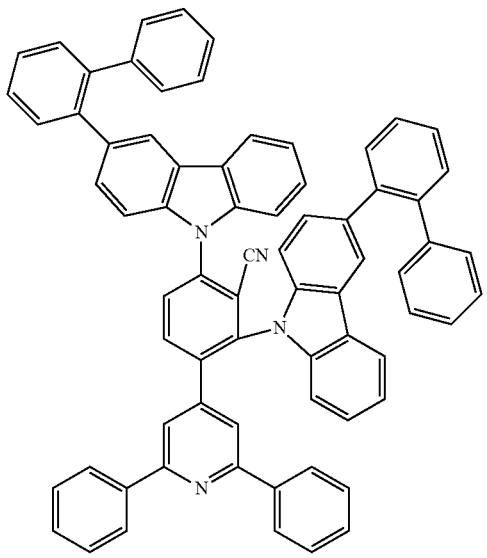

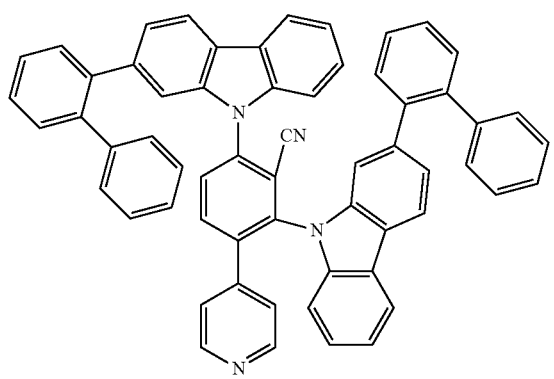
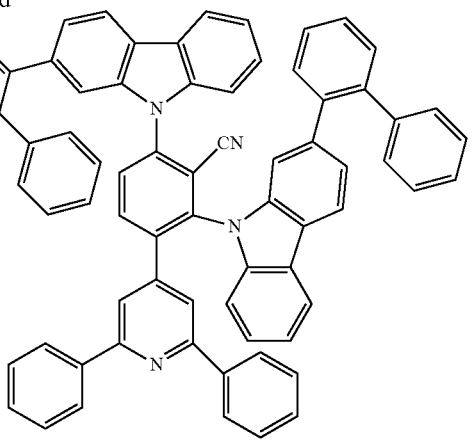

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

The invention claimed is:
1. A composition comprising:
   (a) at least one light emitting organic molecule in the form of an emitter;
   (b) one or more host materials other than the at least one light emitting organic molecule of component (a); and
   (c) optionally one or more dyes and/or one or more solvents;
wherein the at least one light emitting organic molecule of component (a) comprises a structure of formula VI:

(VI)
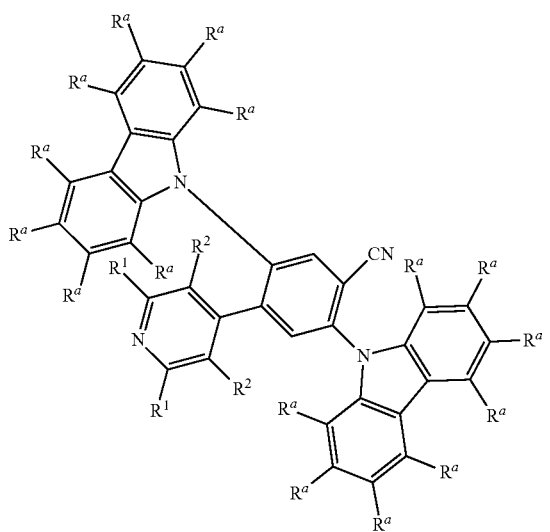

where
R$^1$ and R$^2$ are the same or different at each instance and are selected from the group consisting of:
  H, deuterium;
  a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium; and
  an aromatic or heteroaromatic ring system which has 5 to 15 aromatic ring atoms and may be substituted in each case by one or more R$^6$ radicals;
R$^a$ is the same or different at each instance and is selected from the group consisting of:
  H, deuterium, N(R$^5$)$_2$, OH, Si(R$^5$)$_3$, B(OR$^5$)$_2$, OSO$_7$R$^5$ CF$_3$, CN, F, Br, I;
  a linear alkyl, alkoxy or thioalkoxy group which has 1 to 40 carbon atoms and may be substituted in each case by one or more R$^5$ radicals, where one or more nonadjacent CH$_2$ groups may be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and where one or more hydrogen atoms may be replaced by deuterium, CN, CF$_3$ or NO$_2$;
  a linear alkenyl or alkynyl group which has 2 to 40 carbon atoms and may be substituted in each case by one or more R$^5$ radicals, where one or more nonadjacent CH$_2$ groups may be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and where one or more hydrogen atoms may be replaced by deuterium, CN, CF$_3$ or NO$_2$;
  a branched or cyclic alkyl, alkenyl, alkynyl, alkoxy or thioalkoxy group which has 3 to 40 carbon atoms and may be substituted in each case by one or more R$^5$ radicals, where one or more nonadjacent CH$_2$ groups may be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and where one or more hydrogen atoms may be replaced by deuterium, CN, CF$_3$ or NO$_2$;
  an aromatic or heteroaromatic ring system which has 5 to 60 aromatic ring atoms and may be substituted in each case by one or more R$^5$ radicals;
  an aryloxy or heteroaryloxy group which has 5 to 60 aromatic ring atoms and may be substituted in each case by one or more R$^5$ radicals; and
  a diarylamino group, diheteroarylamino group or arylheteroarylamino group which has 10 to 40 aromatic ring atoms and may be substituted in each case by one or more R$^5$ radicals;
R$^5$ is the same or different at each instance and is selected from the group consisting of:

H, deuterium, N(R$^6$)$_2$, OH, Si(R$^6$)$_3$, B(OR$^6$)$_2$, OSO$_7$R$^6$ CF$_3$, CN, F, Br, I;

a linear alkyl, alkoxy or thioalkoxy group which has 1 to 40 carbon atoms and may be substituted in each case by one or more R$^6$ radicals, where one or more nonadjacent CH$_2$ groups may be replaced by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$ and where one or more hydrogen atoms may be replaced by deuterium, CN, CF$_3$ or NO$_2$;

a linear alkenyl or alkynyl group which has 2 to 40 carbon atoms and may be substituted in each case by one or more R$^6$ radicals, where one or more nonadjacent CH$_2$ groups may be replaced by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$ and where one or more hydrogen atoms may be replaced by deuterium, CN, CF$_3$ or NO$_2$;

a branched or cyclic alkyl, alkenyl, alkynyl, alkoxy or thioalkoxy group which has 3 to 40 carbon atoms and may be substituted in each case by one or more R$^6$ radicals, where one or more nonadjacent CH$_2$ groups may be replaced by R$^6$C=CR$^6$, C≡C, Si(R$^6$)$_2$, Ge(R$^6$)$_2$, Sn(R$^6$)$_2$, C=O, C=S, C=Se, C=NR$^6$, P(=O)(R$^6$), SO, SO$_2$, NR$^6$, O, S or CONR$^6$ and where one or more hydrogen atoms may be replaced by deuterium, CN, CF$_3$ or NO$_2$;

an aromatic or heteroaromatic ring system which has 5 to 60 aromatic ring atoms and may be substituted in each case by one or more R$^6$ radicals;

an aryloxy or heteroaryloxy group which has 5 to 60 aromatic ring atoms and may be substituted in each case by one or more R$^6$ radicals; and a diarylamino group, diheteroarylamino group or arylheteroarylamino group which has 10 to 40 aromatic ring atoms and may be substituted in each case by one or more R$^6$ radicals; and R$^6$ is the same or different at each instance and is selected from the group consisting of:

H, deuterium, OH, CF$_3$ CN, F;

a linear alkyl, alkoxy or thioalkoxy group having 1 to 5 carbon atoms, where one or more hydrogen atoms may be replaced by deuterium, CN, CF$_3$ or NO$_2$;

a linear alkenyl or alkynyl group having 2 to 5 carbon atoms, where one or more hydrogen atoms may be replaced by deuterium, CN, CF$_3$ or NO$_2$;

a branched or cyclic alkyl, alkenyl, alkynyl, alkoxy or thioalkoxy group having 3 to 5 carbon atoms, where one or more hydrogen atoms may be replaced by deuterium, CN, CF$_3$ or NO$_2$;

an aromatic or heteroaromatic ring system having 5 to 60 aromatic ring atoms;

an aryloxy or heteroaryloxy group having 5 to 60 aromatic ring atoms; and a diarylamino group, diheteroarylamino group or arylheteroarylamino group having 10 to 40 aromatic ring atoms;

where each of the R$^a$, R$^3$, R$^4$ or R$^5$ radicals together with one or more further R$^a$, R$^3$, R$^4$ or R$^5$ radicals may form a mono- or polycyclic, aliphatic, aromatic and/or benzofused ring system.

2. The composition according to claim 1, wherein R$^1$ and R$^2$ of the at least one light emitting organic molecule are the same or different at each instance and are H, methyl or phenyl.

3. An optoelectronic device comprising a composition comprising:
(a) at least one light emitting organic molecule in the form of an emitter;
(b) one or more host materials other than the at least one light emitting organic molecule of component (a); and
(c) optionally one or more dyes and/or one or more solvents;

wherein the at least one light emitting organic molecule of component (a) comprises a structure of formula VI:

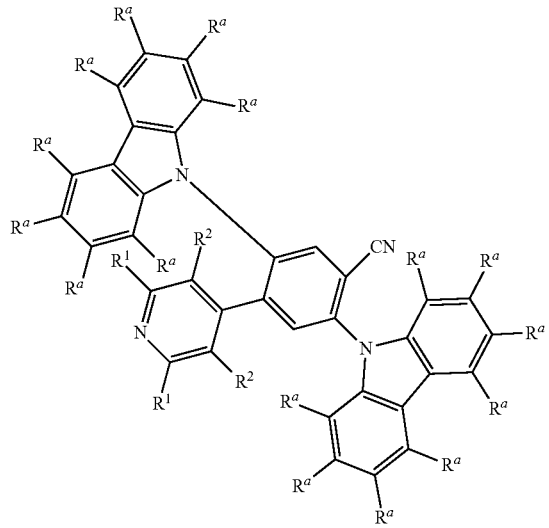

(VI)

where
R$^1$ and R$^2$ are the same or different at each instance and are selected from the group consisting of:
H, deuterium;
a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium; and
an aromatic or heteroaromatic ring system which has 5 to 15 aromatic ring atoms and may be substituted in each case by one or more R$^6$ radicals;

R$^a$ is the same or different at each instance and is selected from the group consisting of:
H, deuterium, N(R$^5$)$_2$, OH, Si(R$^5$)$_3$, B(OR$^5$)$_2$, OSO$_2$R$^5$ CF$_3$, CN, F, Br, I;

a linear alkyl, alkoxy or thioalkoxy group which has 1 to 40 carbon atoms and may be substituted in each case by one or more R$^5$ radicals, where one or more nonadjacent CH$_2$ groups may be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and where one or more hydrogen atoms may be replaced by deuterium, CN, CF$_3$ or NO$_2$;

a linear alkenyl or alkynyl group which has 2 to 40 carbon atoms and may be substituted in each case by one or more R$^5$ radicals, where one or more nonadjacent CH$_2$ groups may be replaced by R$^5$C=CR$^5$, C≡C, Si(R$^5$)$_2$, Ge(R$^5$)$_2$, Sn(R$^5$)$_2$, C=O, C=S, C=Se, C=NR$^5$, P(=O)(R$^5$), SO, SO$_2$, NR$^5$, O, S or CONR$^5$ and where one or more hydrogen atoms may be replaced by deuterium, CN, CF$_3$ or NO$_2$;

a branched or cyclic alkyl, alkenyl, alkynyl, alkoxy or thioalkoxy group which has 3 to 40 carbon atoms and may be substituted in each case by one or more R⁵ radicals, where one or more nonadjacent CH₂ groups may be replaced by R⁵C=CR⁵, C≡C, Si(R⁵)₂, Ge(R⁵)₂, Sn(R⁵)₂, C=O, C=S, C=Se, C=NR⁵, P(=O)(R⁵), SO, SO₂, NR⁵, O, S or CONR⁵ and where one or more hydrogen atoms may be replaced by deuterium, CN, CF₃ or NO₂;

an aromatic or heteroaromatic ring system which has 5 to 60 aromatic ring atoms and may be substituted in each case by one or more R⁵ radicals;

an aryloxy or heteroaryloxy group which has 5 to 60 aromatic ring atoms and may be substituted in each case by one or more R⁵ radicals; and a diarylamino group, diheteroarylamino group or aryl-heteroarylamino group which has 10 to 40 aromatic ring atoms and may be substituted in each case by one or more R⁵ radicals;

R⁵ is the same or different at each instance and is selected from the group consisting of:
H, deuterium, N(R⁶)₂, OH, Si(R⁶)₃, B(OR⁶)₂, OSO₇R⁶ CF₃, CN, F, Br, I;

a linear alkyl, alkoxy or thioalkoxy group which has 1 to 40 carbon atoms and may be substituted in each case by one or more R⁶ radicals, where one or more nonadjacent CH₂ groups may be replaced by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶ and where one or more hydrogen atoms may be replaced by deuterium, CN, CF₃ or NO₂;

a linear alkenyl or alkynyl group which has 2 to 40 carbon atoms and may be substituted in each case by one or more R⁶ radicals, where one or more nonadjacent CH₂ groups may be replaced by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶ and where one or more hydrogen atoms may be replaced by deuterium, CN, CF₃ or NO₂;

a branched or cyclic alkyl, alkenyl, alkynyl, alkoxy or thioalkoxy group which has 3 to 40 carbon atoms and may be substituted in each case by one or more R⁶ radicals, where one or more nonadjacent CH₂ groups may be replaced by R⁶C=CR⁶, C≡C, Si(R⁶)₂, Ge(R⁶)₂, Sn(R⁶)₂, C=O, C=S, C=Se, C=NR⁶, P(=O)(R⁶), SO, SO₂, NR⁶, O, S or CONR⁶ and where one or more hydrogen atoms may be replaced by deuterium, CN, CF₃ or NO₂;

an aromatic or heteroaromatic ring system which has 5 to 60 aromatic ring atoms and may be substituted in each case by one or more R⁶ radicals;

an aryloxy or heteroaryloxy group which has 5 to 60 aromatic ring atoms and may be substituted in each case by one or more R⁶ radicals; and a diarylamino group, diheteroarylamino group or aryl-heteroarylamino group which has 10 to 40 aromatic ring atoms and may be substituted in each case by one or more R⁶ radicals; and R⁶ is the same or different at each instance and is selected from the group consisting of:
H, deuterium, OH, CF₃ CN, F;

a linear alkyl, alkoxy or thioalkoxy group having 1 to 5 carbon atoms, where one or more hydrogen atoms may be replaced by deuterium, CN, CF₃ or NO₂;

a linear alkenyl or alkynyl group having 2 to 5 carbon atoms, where one or more hydrogen atoms may be replaced by deuterium, CN, CF₃ or NO₂;

a branched or cyclic alkyl, alkenyl, alkynyl, alkoxy or thioalkoxy group having 3 to 5 carbon atoms, where one or more hydrogen atoms may be replaced by deuterium, CN, CF₃ or NO₂;

an aromatic or heteroaromatic ring system having 5 to 60 aromatic ring atoms;

an aryloxy or heteroaryloxy group having 5 to 60 aromatic ring atoms; and a diarylamino group, diheteroarylamino group or aryl-heteroarylamino group having 10 to 40 aromatic ring atoms;

where each of the Rᵃ, R³, R⁴ or R⁵ radicals together with one or more further Rᵃ, R³, R⁴ or R⁵ radicals may form a mono- or polycyclic, aliphatic, aromatic and/or benzofused ring system.

4. The optoelectronic device according to claim 3, comprising:
a substrate;
an anode;
a cathode, where the anode or the cathode has been applied to the substrate; and
at least one light-emitting layer which is arranged between the anode and the cathode and comprises the composition according to claim 1.

5. The optoelectronic device according to claim 3, wherein the optoelectronic device is an organic light-emitting diode (OLEDs), a light-emitting electrochemical cell, an OLED sensor, an organic diode, an organic solar cell, an organic transistor, an organic field-effect transistor, an organic laser and a down-conversion element.

6. The optoelectronic device according to claim 3, wherein R¹ and R² of the at least one light emitting organic molecule are the same or different at each instance and are H, methyl or phenyl.

7. An optoelectronic device, comprising:
a substrate;
an anode;
a cathode, where the anode or the cathode has been applied to the substrate; and
at least one light-emitting layer which is arranged between the anode and the cathode and comprises a light emitting organic molecule and a host material; wherein the light emitting organic molecule comprises a structure of formula VI:

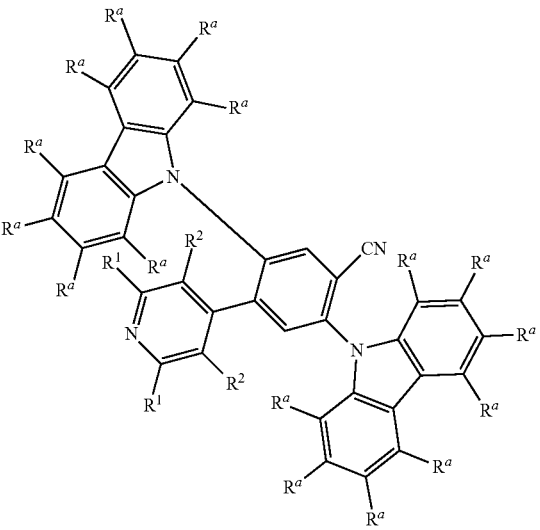

(VI)

where
R¹ and R² are the same or different at each instance and are selected from the group consisting of:
H, deuterium;
a linear alkyl group having 1 to 5 carbon atoms, a linear alkenyl or alkynyl group having 2 to 8 carbon atoms, a branched or cyclic alkyl, alkenyl or alkynyl group having 3 to 10 carbon atoms, where one or more hydrogen atoms may be replaced by deuterium; and an aromatic or heteroaromatic ring system which has 5 to 15 aromatic ring atoms and may be substituted in each case by one or more $R^6$ radicals;

$R^a$ is the same or different at each instance and is selected from the group consisting of:

H, deuterium, $N(R^5)_2$, OH, $Si(R^5)_3$, $B(OR^5)_2$, $OSO_2R^5$ $CF_3$, CN, F, Br, I;

a linear alkyl, alkoxy or thioalkoxy group which has 1 to 40 carbon atoms and may be substituted in each case by one or more $R^5$ radicals, where one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and where one or more hydrogen atoms may be replaced by deuterium, CN, $CF_3$ or $NO_2$;

a linear alkenyl or alkynyl group which has 2 to 40 carbon atoms and may be substituted in each case by one or more $R^5$ radicals, where one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and where one or more hydrogen atoms may be replaced by deuterium, CN, $CF_3$ or $NO_2$;

a branched or cyclic alkyl, alkenyl, alkynyl, alkoxy or thioalkoxy group which has 3 to 40 carbon atoms and may be substituted in each case by one or more $R^5$ radicals, where one or more nonadjacent $CH_2$ groups may be replaced by $R^5C=CR^5$, $C\equiv C$, $Si(R^5)_2$, $Ge(R^5)_2$, $Sn(R^5)_2$, $C=O$, $C=S$, $C=Se$, $C=NR^5$, $P(=O)(R^5)$, SO, $SO_2$, $NR^5$, O, S or $CONR^5$ and where one or more hydrogen atoms may be replaced by deuterium, CN, $CF_3$ or $NO_2$;

an aromatic or heteroaromatic ring system which has 5 to 60 aromatic ring atoms and may be substituted in each case by one or more $R^5$ radicals;

an aryloxy or heteroaryloxy group which has 5 to 60 aromatic ring atoms and may be substituted in each case by one or more $R^5$ radicals; and a diarylamino group, diheteroarylamino group or arylheteroarylamino group which has 10 to 40 aromatic ring atoms and may be substituted in each case by one or more $R^5$ radicals;

$R^5$ is the same or different at each instance and is selected from the group consisting of:

H, deuterium, $N(R^6)_2$, OH, $Si(R^6)_3$, $B(OR^6)_2$, $OSO_2R^6$ $CF_3$, CN, F, Br, I;

a linear alkyl, alkoxy or thioalkoxy group which has 1 to 40 carbon atoms and may be substituted in each case by one or more $R^6$ radicals, where one or more nonadjacent $CH_2$ groups may be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and where one or more hydrogen atoms may be replaced by deuterium, CN, $CF_3$ or $NO_2$;

a linear alkenyl or alkynyl group which has 2 to 40 carbon atoms and may be substituted in each case by one or more $R^6$ radicals, where one or more nonadjacent $CH_2$ groups may be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and where one or more hydrogen atoms may be replaced by deuterium, CN, $CF_3$ or $NO_2$;

a branched or cyclic alkyl, alkenyl, alkynyl, alkoxy or thioalkoxy group which has 3 to 40 carbon atoms and may be substituted in each case by one or more $R^6$ radicals, where one or more nonadjacent $CH_2$ groups may be replaced by $R^6C=CR^6$, $C\equiv C$, $Si(R^6)_2$, $Ge(R^6)_2$, $Sn(R^6)_2$, $C=O$, $C=S$, $C=Se$, $C=NR^6$, $P(=O)(R^6)$, SO, $SO_2$, $NR^6$, O, S or $CONR^6$ and where one or more hydrogen atoms may be replaced by deuterium, CN, $CF_3$ or $NO_2$;

an aromatic or heteroaromatic ring system which has 5 to 60 aromatic ring atoms and may be substituted in each case by one or more $R^6$ radicals;

an aryloxy or heteroaryloxy group which has 5 to 60 aromatic ring atoms and may be substituted in each case by one or more $R^6$ radicals; and a diarylamino group, diheteroarylamino group or arylheteroarylamino group which has 10 to 40 aromatic ring atoms and may be substituted in each case by one or more $R^6$ radicals; and $R^6$ is the same or different at each instance and is selected from the group consisting of:

H, deuterium, OH, $CF_3$, CN, F;

a linear alkyl, alkoxy or thioalkoxy group having 1 to 5 carbon atoms, where one or more hydrogen atoms may be replaced by deuterium, CN, $CF_3$ or $NO_2$;

a linear alkenyl or alkynyl group having 2 to 5 carbon atoms, where one or more hydrogen atoms may be replaced by deuterium, CN, $CF_3$ or $NO_2$;

a branched or cyclic alkyl, alkenyl, alkynyl, alkoxy or thioalkoxy group having 3 to 5 carbon atoms, where one or more hydrogen atoms may be replaced by deuterium, CN, $CF_3$ or $NO_2$;

an aromatic or heteroaromatic ring system having 5 to 60 aromatic ring atoms;

an aryloxy or heteroaryloxy group having 5 to 60 aromatic ring atoms; and a diarylamino group, diheteroarylamino group or arylheteroarylamino group having 10 to 40 aromatic ring atoms;

where each of the $R^a$, $R^3$, $R^4$ or $R^5$ radicals together with one or more further $R^a$, $R^3$, $R^4$ or $R^5$ radicals may form a mono- or polycyclic, aliphatic, aromatic and/or benzofused ring system.

8. The optoelectronic device according to claim 7, wherein $R^1$ and $R^2$ of the light emitting organic molecule are the same or different at each instance and are H, methyl or phenyl.

* * * * *